US008097440B1

(12) United States Patent
Buelter et al.

(10) Patent No.: US 8,097,440 B1
(45) Date of Patent: Jan. 17, 2012

(54) ENGINEERED MICROORGANISMS CAPABLE OF PRODUCING TARGET COMPOUNDS UNDER ANAEROBIC CONDITIONS

(75) Inventors: Thomas Buelter, Denver, CO (US); Peter Meinhold, Denver, CO (US); Reid M. Renny Feldman, San Francisco, CA (US); Andrew C. Hawkins, Parker, CO (US); Jun Urano, Irvine, CA (US); Sabine Bastian, Pasadena, CA (US); Frances Arnold, La Canada, CA (US)

(73) Assignees: Gevo, Inc., Englewood, CO (US); California Institute of Technology, Pasadena, CA (US)

( * ) Notice: Subject to any disclaimer, the term of this patent is extended or adjusted under 35 U.S.C. 154(b) by 0 days.

(21) Appl. No.: 13/269,937

(22) Filed: Oct. 10, 2011

Related U.S. Application Data

(62) Division of application No. 12/610,784, filed on Nov. 2, 2009.

(60) Provisional application No. 61/110,543, filed on Oct. 31, 2008, provisional application No. 61/121,830, filed on Dec. 11, 2008, provisional application No. 61/184,580, filed on Jun. 5, 2009, provisional application No. 61/184,605, filed on Jun. 5, 2009, provisional application No. 61/239,618, filed on Sep. 3, 2009.

(51) Int. Cl.

| | |
|---|---|
| ***C12P 7/16*** | (2006.01) |
| ***C12N 15/53*** | (2006.01) |
| ***C12N 1/15*** | (2006.01) |
| *C12N 9/02* | (2006.01) |

(52) U.S. Cl. .................. 435/160; 435/252.3; 435/254.2; 435/189; 536/23.2

(58) Field of Classification Search ........................ None
See application file for complete search history.

(56) References Cited

U.S. PATENT DOCUMENTS

| | | | | |
|---|---|---|---|---|
| 5,830,716 | A | 11/1998 | Kojima et al. | |
| 2005/0208558 | A1 | 9/2005 | Venter et al. | |
| 2007/0087403 | A1 | 4/2007 | Bestel-Corre et al. | |
| 2007/0092957 | A1 | 4/2007 | Donaldson et al. | |
| 2008/0148432 | A1 | 6/2008 | Abad et al. | |
| 2008/0261230 | A1 | 10/2008 | Liao et al. | |
| 2008/0274526 | A1 | 11/2008 | Bramucci et al. | |
| 2009/0081746 | A1 | 3/2009 | Liao et al. | |
| 2009/0155869 | A1 | 6/2009 | Buelter et al. | |
| 2009/0163376 | A1 * | 6/2009 | Li et al. | 506/9 |
| 2009/0305369 | A1 | 12/2009 | Donaldson et al. | |
| 2010/0120105 | A1 | 5/2010 | Anthony et al. | |
| 2010/0197519 | A1 | 8/2010 | Li et al. | |

FOREIGN PATENT DOCUMENTS

| | | | |
|---|---|---|---|
| EP | 0733712 | B1 | 12/2001 |
| WO | WO 99/46363 | A1 | 9/1999 |
| WO | WO 00/03020 | A1 | 1/2000 |
| WO | WO 00/03021 | A2 | 1/2000 |
| WO | WO 2004/048559 | A1 | 6/2004 |
| WO | WO 2007/120423 | A2 | 10/2007 |
| WO | WO 2008/013996 | A2 | 1/2008 |
| WO | WO 2008/042338 | A2 | 4/2008 |
| WO | WO 2008/080124 | A2 | 7/2008 |
| WO | WO 2008/121701 | A1 | 9/2008 |
| WO | WO 2008/130372 | A2 | 10/2008 |
| WO | WO 2008/131286 | A1 | 10/2008 |
| WO | WO 2008/144791 | A2 | 12/2008 |
| WO | WO 2008/028002 | A9 | 4/2009 |
| WO | WO 2009/059254 | A2 | 5/2009 |
| WO | WO 2009/085953 | A2 | 7/2009 |
| WO | WO 2009/086423 | A2 | 7/2009 |

OTHER PUBLICATIONS

M.J. Rane et al.. "Reversal of the Nucleotide Specificity of Ketol Acid Reductoisomerase by Site Directed Mutagenesis Identifies the NADPH Binding Site", Archives of Biochemistry and Biophysics 338(1):83-89 (1997).*

Anderlund, M., et al., Expression of the *Escherichia coli* pntA and pntB genes, encoding nicotinamide nucleotide transhydrogenase, in *Saccharomyces cerevisiae* and its effect on product formation during anaerobic glucose fermentation, Applied and Environmental Microbiology 1999 65(6):2333-2340.

Atsumi et al., Metabolic engineering of *Escherichia coli* for 1-butanolproduction. Metab Eng. 2007, 10(6):305-311; p. 308, col. 1; p. 309, col. 1; p. 311, col. 1.

Atsumi et al., Metabolic engineering for advanced biofuels production from *Escherichia coli.* Curr. Opin. Biotechnol. 2008, 19(5):414-419.

Atsumi et al., Engineering the isobutanol biosynthetic pathway in *Escherichia coli* by comparison of three aldehyde reductase/alcohol dehydrogenase genes, Appl. Microbiol. Biotechnol. 2009 85(3):651-657.

Benyajati, et al., Alcohol dehydrogenase gene of *Drosophila melanogaster*: relationship of intervening sequences to functional domains in the protein. Proc. Natl. Acad. Sci. USA 1981, 78(5):2717-2721; abstract.

(Continued)

*Primary Examiner* — Rebecca Prouty

(74) *Attorney, Agent, or Firm* — Cooley LLP

(57) ABSTRACT

The present invention is generally provides recombinant microorganisms comprising engineered metabolic pathways capable of producing C3-C5 alcohols under aerobic and anaerobic conditions. The invention further provides ketol-acid reductoisomerase enzymes which have been mutated or modified to increase their NADH-dependent activity or to switch the cofactor preference from NADPH to NADH and are expressed in the modified microorganisms. In addition, the invention provides isobutyraldehyde dehydrogenase enzymes expressed in modified microorganisms. Also provided are methods of producing beneficial metabolites under aerobic and anaerobic conditions by contacting a suitable substrate with the modified microorganisms of the present invention.

19 Claims, 54 Drawing Sheets

OTHER PUBLICATIONS

Boonstra, B., et al., Cofactor regeneration by a soluble pyridine nucleotide transhydrogenase for biological production of hydromorphone, Applied and Environmental Microbiology 2000 66(12):5161-5166.

Bro, C., et al., In silico aided metabolic engineering of *Saccharomyces cerevisiae* for improved bioethanol production, Metabolic Engineering 2006 8:102-111.

Calvo, K. and Rane, M. Use of site directed mutagenesis to reverse the nucleotide specificity of ketol acid reductoisomerase from *Escherichia coli*, Faseb Journal, 1995 9(6):A1484, abs. No. 1319.

Canonaco, F., et al., Metabolic flux response to phosphoglucose isomerase knock-out in *Escherichia coli* and impact of overexpression of the soluble transhydrogenase UdhA, FEMS Microbiology Letters 2001 204:247-252.

Dos Santos, M., et al., Manipulation of malic enzyme in *Saccharomyces cerevisiae* for increasing NADPH production capacity aerobically in different compartments, Metabolic Engineering 2004 6:352-363.

Echave et al., Novel antioxidant role of alcohol dehydrogenase E from *Escherichia coli*. J. Biol. Chem. 2003, 278(32):30193-30198; abstract.

Jeppsson, M., et al., The expression of a *Pichia stipitis xylose* reductase mutant with higher $K_m$ for NADPH increases ethanol production from xylose in recombinant *Saccharomyces cerevisiae*, Biotechnology and Bioengineering 2006 93(4):665-673.

Jeun, Y.-S., et al., Expression of *Azotobacter vinelandii* soluble transhydrogenase perturbs xylose reductase-mediated conversion of xylose to xylitol by recombinant *Saccharomyces cerevisiae*, Journal of Molecular Catalysis B: Enzymatic 2003 26:251-256.

Lee et al., Metabolic engineering of microorganisms for biofuels production: from bugs to synthetic biology to fuels. Curr. Opin. Biotechnol. 2008, 19(6):556-563.

Martinez, I., et al., Replacing *Escherichia coli* NAD-dependent glyceraldehyde 3-phosphate dehydrogenase (GAPDH) with a NADP-dependent enzyme from *Clostridium acetobutylicum* facilitates NADPH dependent pathways. Metabolic Engineering 2008 10(6):352-359.

Matsushika, A., et al., Bioethanol production from xylose by recombinant *Saccharomyces cerevisiae* expressing xylose reductase, NADP(+)-dependent xylitol dehydrogenase, and xylulokinase, Journal of Bioscience and Bioengineering 2008 105(3):296-299.

Matsushika, A., et al., Expression of protein engineered NADP—dependent xylitol dehydrogenase increases ethanol production from xylose in recombinant *Saccharomyces cerevisiae*, Applied Microbiology and Biotechnology 2008 81(2):243-255.

Nissen, T.L., et al., Expression of a cytoplasmic transhydrogenase in *Saccharomyces cerevisiae* results in formation of 2-oxoglutarate due to depletion of the NADPH pool, Yeast 2001 18:19-32.

Ostergaard, S., et al., Metabolic Engineering of *Saccharomyces cerevisiae*, Microbiology and Molecular Biology Reviews 2000 64(1):34-50.

Petschacher, B. and B. Nidetzky, Altering the coenzyme preference of xylose reductase to favor utilization of NADH enhances ethanol yield from xylose in a metabolically engineered strain of *Saccharomyces cerevisiae*, Microbial Cell Factories 2008 7:9.

Rosell, A., et al., Complete reversal of coenzyme specificity by concerted mutation of three consecutive residues in alcohol dehydrogenase. Journal of Biological Chemistry 2003 278(42):40573-40580.

Sauer, U., et al., The soluble and membrane-bound transhydrogenases UdhA and PntAB have divergent functions in NADPH metabolism of *Escherichia coli*, Journal of Biological Chemistry 2004 279(8):6613-6619.

Scrutton, N.S., A. Berry, and R.N. Perham, Redesign of the Coenzyme Specificity of a Dehydrogenase by Protein Engineering, Nature 1990 343(6253):38-43.

Shen et al., Metabolic engineering of *Escherichia coli* for I-butanol and I-propanol production via the keto-acid pathways. Metab. Eng. 2008 10(6):312-320.

Verho, R., et al., Engineering redox cofactor regeneration for improved pentose fermentation in *Saccharomyces cerevisiae*. Applied and Environmental Microbiology 2003 69(10):5892-5897.

Watanabe, S., et al., Ethanol production from xylose by recombinant *Saccharomyces cerevisiae* expressing protein-engineered $NADP^+$-dependent xylitol dehydrogenase, Journal of Biotehcnology 2007 130:316-319.

Watanabe, S., et al., Ethanol production from xylose by recombinant *Saccharomyces cerevisiae* expressing protein-engineered NADH-preferring xylose reductase from *Pichia stipitis*, Microbiology 2007 153:3044-3054.

Weckbecker, A. and W. Hummel, Improved synthesis of chiral alcohols with *Escherichia coli* cells co-expressing pyridine nucleotide transhydrogenase, $NADP^+$-dependent alcohol dehydrogenase and $NAD^+$-dependent formate dehydrogenase. Biotechnology Letters 2004 26(22):1739.

International Search Report and Written Opinion mailed Nov. 5, 2010 in the International (PCT) Application No. PCT/US09/62952, 15 pages.

* cited by examiner

| | | |
|---|---|---|
| Ignicoccus hospitalis KARI | (344) | -------------------------------------------------- |
| Picrophilus torridus KARI | (330) | -------------------------------------------------- |
| Acidiphilium cryptum KARI | (340) | -------------------------------------------------- |
| Rice KARI | (469) | [illegible] |
| Spinach KARI | (487) | [illegible] |
| Chlamydomonas reinhardtii KARI | (436) | [illegible] |
| Neurospora crassa KARI | (403) | -------------------------------------------------- |
| S. cerevisiae ILV5 | (396) | -------------------------------------------------- |
| S. pombe KARI | (405) | -------------------------------------------------- |
| Laccaria bicolor KARI | (416) | -------------------------------------------------- |
| Piromyces sp. KARI | (353) | -------------------------------------------------- |
| Consensus | (501) | |
| | | 551 600 |
| E. coli ilvC | (433) | [illegible] |
| Vibrio fischeri KARI | (433) | [illegible] |
| Gramella forsetii KARI | (433) | [illegible] |
| Cytophaga hutchinsonii KARI | (433) | [illegible] |
| Buchnera aphidicola KARI | (433) | [illegible] |
| Zymomonas mobilis KARI | (340) | -------------------------------------------------- |
| Bacteroides thetaiotaomicron KARI | (360) | -------------------------------------------------- |
| Shewanella sp. KARI | (433) | [illegible] |
| Psychromonas ingrahamii KARI | (433) | [illegible] |
| Cyanobacteria sp. KARI | (331) | -------------------------------------------------- |
| Methanococcus maripaludis KARI | (331) | -------------------------------------------------- |
| Ignicoccus hospitalis KARI | (344) | -------------------------------------------------- |
| Picrophilus torridus KARI | (330) | -------------------------------------------------- |
| Acidiphilium cryptum KARI | (340) | -------------------------------------------------- |
| Rice KARI | (519) | [illegible] |
| Spinach KARI | (537) | [illegible] |
| Chlamydomonas reinhardtii KARI | (486) | [illegible] |
| Neurospora crassa KARI | (403) | -------------------------------------------------- |
| S. cerevisiae ILV5 | (396) | -------------------------------------------------- |
| S. pombe KARI | (405) | -------------------------------------------------- |
| Laccaria bicolor KARI | (416) | -------------------------------------------------- |
| Piromyces sp. KARI | (353) | -------------------------------------------------- |
| Consensus | (551) | |
| | | 601 620 |
| E. coli ilvC | (479) | [illegible] |
| Vibrio fischeri KARI | (482) | [illegible] |
| Gramella forsetii KARI | (481) | [illegible] |
| Cytophaga hutchinsonii KARI | (482) | [illegible] |
| Buchnera aphidicola KARI | (479) | [illegible] |
| Zymomonas mobilis KARI | (340) | -------------------- |
| Bacteroides thetaiotaomicron KARI | (360) | -------------------- |
| Shewanella sp. KARI | (481) | [illegible] |
| Psychromonas ingrahamii KARI | (481) | [illegible] |
| Cyanobacteria sp. KARI | (331) | -------------------- |
| Methanococcus maripaludis KARI | (331) | -------------------- |
| Ignicoccus hospitalis KARI | (344) | -------------------- |
| Picrophilus torridus KARI | (330) | -------------------- |
| Acidiphilium cryptum KARI | (340) | -------------------- |
| Rice KARI | (567) | [illegible] |
| Spinach KARI | (585) | [illegible] |
| Chlamydomonas reinhardtii KARI | (536) | [illegible] |
| Neurospora crassa KARI | (403) | -------------------- |
| S. cerevisiae ILV5 | (396) | -------------------- |
| S. pombe KARI | (405) | -------------------- |
| Laccaria bicolor KARI | (416) | -------------------- |
| Piromyces sp. KARI | (353) | -------------------- |
| Consensus | (601) | |

Figure 6 (CONT.)

ENGINEERED MICROORGANISMS CAPABLE OF PRODUCING TARGET COMPOUNDS UNDER ANAEROBIC CONDITIONS

CROSS-REFERENCE TO RELATED APPLICATIONS

This application is a divisional appliation of U.S. application Ser. No. 12/610,784, filed Nov. 2, 2009, which claims priority to U.S. Provisional Application Ser. No. 61/110,543, filed Oct. 31, 2008; U.S. Provisional Application Ser. No. 61/121,830, filed Dec. 11, 2008; U.S. Provisional Application Ser. No. 61/184,580, filed Jun. 5, 2009; U.S. Provisional Application Ser. No. 61/184,605, filed Jun. 5, 2009; and U.S. Provisional Application Ser. No. 61/239,618, filed Sep. 3, 2009, all of which are herein incorporated by reference in their entireties for all purposes.

STATEMENT REGARDING FEDERALLY FUNDED RESEARCH

This invention was made with government support under contract DE-FG02-07ER84893, awarded by the Department of Energy. The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: GEVO_018_02US_SeqList.txt, date recorded: Oct. 10, 2011, file size: 527 kilobytes).

FIELD OF THE INVENTION

The present invention is generally related to genetically engineered microorganisms, methods of producing such organisms, and methods of using such organisms for the production of beneficial metabolites, including C3-C5 alcohols such as isobutanol.

BACKGROUND

Biofuels have a long history ranging back to the beginning of the 20th century. As early as 1900, Rudolf Diesel demonstrated at the World Exhibition in Paris, France, an engine running on peanut oil. Soon thereafter, Henry Ford demonstrated his Model T running on ethanol derived from corn. Petroleum-derived fuels displaced biofuels in the 1930s and 1940s due to increased supply, and efficiency at a lower cost.

Market fluctuations in the 1970s coupled to the decrease in US oil production led to an increase in crude oil prices and a renewed interest in biofuels. Today, many interest groups, including policy makers, industry planners, aware citizens, and the financial community, are interested in substituting petroleum-derived fuels with biomass-derived biofuels. The leading motivations for developing biofuels are of economical, political, and environmental nature.

One is the threat of ‘peak oil’, the point at which the consumption rate of crude oil exceeds the supply rate, thus leading to significantly increased fuel cost results in an increased demand for alternative fuels. In addition, instability in the Middle East and other oil-rich regions has increased the demand for domestically produced biofuels. Also, environmental concerns relating to the possibility of carbon dioxide related climate change is an important social and ethical driving force which is starting to result in government regulations and policies such as caps on carbon dioxide emissions from automobiles, taxes on carbon dioxide emissions, and tax incentives for the use of biofuels.

Ethanol is the most abundant biofuel today but has several drawbacks when compared to gasoline. Butanol, in comparison, has several advantages over ethanol as a fuel: it can be made from the same feedstocks as ethanol but, unlike ethanol, it is compatible with gasoline at any ratio and can also be used as a pure fuel in existing combustion engines without modifications. Unlike ethanol, butanol does not absorb water and can thus be stored and distributed in the existing petrochemical infrastructure. Due to its higher energy content which is close to that of gasoline, the fuel economy (miles per gallon) is better than that of ethanol. Also, butanol-gasoline blends have lower vapor pressure than ethanol-gasoline blends, which is important in reducing evaporative hydrocarbon emissions.

Isobutanol has the same advantages as butanol with the additional advantage of having a higher octane number due to its branched carbon chain. Isobutanol is also useful as a commodity chemical. For example, it is used as the starting material in the manufacture of isobutyl acetate, which is primarily used for the production of lacquer and similar coatings. In addition, isobutanol finds utility in the industrial synthesis of derivative esters. Isobutyl esters such as diisobutyl phthalate (DIBP) are used as plasticizer agents in plastics, rubbers, and other dispersions.

A number of recent publications have described methods for the production of industrial chemicals such as isobutanol using engineered microorganisms. See, e.g., WO/2007/050671 to Donaldson et al., and WO/2008/098227 to Liao et al., which are herein incorporated by reference in their entireties. These publications disclose recombinant microorganisms that utilize a series of heterologously expressed enzymes to convert sugars into isobutanol. However, the production of isobutanol using these microorganisms is feasible only under aerobic conditions and the maximum yield that can be achieved is limited.

There is a need, therefore, to provide modified microorganisms capable of producing isobutanol under anaerobic conditions and at close to theoretical yield. The present invention addresses this need by providing modified microorganisms capable of producing isobutanol under anaerobic conditions and at high yields.

SUMMARY OF THE INVENTION

The present invention provides recombinant microorganisms comprising an engineered metabolic pathway capable of producing one or more C3-C5 alcohols under aerobic and anaerobic conditions. In a preferred embodiment, the recombinant microorganism produces the C3-C5 alcohol under anaerobic conditions at a rate higher than a parental microorganism comprising a native or unmodified metabolic pathway. In another preferred embodiment, the recombinant microorganism produces the C3-C5 alcohol under anaerobic conditions at a rate of at least about 2-fold higher than a parental microorganism comprising a native or unmodified metabolic pathway. In another preferred embodiment, the recombinant microorganism produces the C3-C5 alcohol under anaerobic conditions at a rate of at least about 10-fold, of at least about 50-fold, or of at least about 100-fold higher than a parental microorganism comprising a native or unmodified metabolic pathway.

In various embodiments described herein, the C3-C5 alcohol may be selected from 1-propanol, 2-propanol, 1-butanol, 2-butanol, isobutanol, 2-methyl-1-butanol, 3-methyl-1-butanol, and 1-pentanol. In a preferred embodiment, the C3-C5 alcohol is isobutanol. In another preferred embodiment, isobutanol is produced at a specific productivity of at least about 0.025 g $l^{-1}$ $h^{-1}$ $OD^{-1}$.

In one aspect, there are provided recombinant microorganisms comprising an engineered metabolic pathway for producing one or more C3-C5 alcohols under anaerobic and aerobic conditions that comprises an overexpressed transhydrogenase that converts NADH to NADPH. In one embodiment, the transhydrogenase is a membrane-bound transhydrogenase. In a specific embodiment, the membrane-bound transhydrogenase is encoded by the *E. coli* pntAB genes or homologues thereof.

In another aspect, there are provided recombinant microorganisms comprising an engineered metabolic pathway for producing one or more C3-C5 alcohols under anaerobic and aerobic conditions that comprises an NADPH-dependent glyceraldehyde-3-phosphate dehydrogenase. In one embodiment, the NADPH-dependent glyceraldehyde-3-phosphate dehydrogenase is encoded by the *Clostridium acetobutylicum* gapC gene. In another embodiment, the NADPH-dependent glyceraldehyde-3-phosphate dehydrogenase is encoded by the *Kluyveromyces lactis* GDP1 gene.

In yet another aspect, there are provided recombinant microorganisms comprising an engineered metabolic pathway for producing one or more C3-C5 alcohols under anaerobic and aerobic conditions that comprises one or more enzymes catalyzing conversions in said engineered metabolic pathway that are not catalyzed by glyceraldehyde-3-phosphate dehydrogenase, and wherein said one or more enzymes have increased activity using NADH as a cofactor. In one embodiment, said one or more enzymes are selected from an NADH-dependent ketol-acid reductoisomerase (KARI) and an NADH-dependent alcohol dehydrogenase (ADH). In various embodiments described herein, the KARI and/or ADH enzymes may be engineered to have increased activity with NADH as the cofactor as compared to the wild-type *E. coli* KARI llvC and a native *E. coli* ADH YqhD, respectively. In some embodiments, the KARI and/or the ADH are modified or mutated to be NADH-dependent. In other embodiments, the KARI and/or ADH enzymes are identified in nature with increased activity with NADH as the cofactor as compared to the wild-type *E. coli* KARI llvC and a native *E. coli* ADH YqhD, respectively.

In various embodiments described herein, the KARI and/or ADH may show at least a 10-fold higher catalytic efficiency using NADH as a cofactor as compared to the wild-type *E. coli* KARI llvC and the native ADH YqhD, respectively. In a preferred embodiment, the KARI enhances the recombinant microorganism's ability to convert acetolactate to 2,3-dihydroxyisovalerate under anaerobic conditions. In another embodiment, the KARI enhances the recombinant microorganism's ability to utilize NADH from the conversion of acetolactate to 2,3-dihydroxyisovalerate.

The present invention also provides modified or mutated KARI enzymes that preferentially utilize NADH rather than NADPH, and recombinant microorganisms comprising said modified or mutated KARI enzymes. In general, these modified or mutated KARI enzymes may enhance the cell's ability to produce beneficial metabolites such as isobutanol and enable the production of beneficial metabolites such as isobutanol under anaerobic conditions.

In certain aspects, the invention includes KARIs which have been modified or mutated to increase the ability to utilize NADH. Examples of such KARIs include enzymes having one or more modifications or mutations at positions corresponding to amino acids selected from the group consisting of: (a) alanine 71 of the wild-type *E. coli* llvC (SEQ ID NO: 13); (b) arginine 76 of the wild-type *E. coli* llvC; (c) serine 78 of the wild-type *E. coli* llvC; and (d) glutamine 110 of the wild-type *E. coli* llvC, wherein llvC (SEQ ID NO: 13) is encoded by codon optimized *E. coli* ketol-acid reductoisomerase (KARI) genes Ec_ilvC_coEc (SEQ ID NO: 11) or Ec_ilvC_coSc (SEQ ID NO: 12).

In one embodiment, the KARI enzyme contains a modification or mutation at the amino acid corresponding to position 71 of the wild-type *E. coli* llvC (SEQ ID NO: 13). In another embodiment, the KARI enzyme contains a modification or mutation at the amino acid corresponding to position 76 of the wild-type *E. coli* llvC (SEQ ID NO: 13). In yet another embodiment, the KARI enzyme contains a modification or mutation at the amino acid corresponding to position 78 of the wild-type *E. coli* llvC (SEQ ID NO: 13). In yet another embodiment, the KARI enzyme contains a modification or mutation at the amino acid corresponding to position 110 of the wild-type *E. coli* llvC (SEQ ID NO: 13).

In one embodiment, the KARI enzyme contains two or more modifications or mutations at the amino acids corresponding to the positions described above. In another embodiment, the KARI enzyme contains three or more modifications or mutations at the amino acids corresponding to the positions described above. In yet another embodiment, the KARI enzyme contains four modifications or mutations at the amino acids corresponding to the positions described above.

In one specific embodiment, the invention is directed to KARI enzymes wherein the alanine at position 71 is replaced with serine. In another specific embodiment, the invention is directed to KARI enzymes wherein the arginine at position 76 is replaced with aspartic acid. In yet another specific embodiment, the invention is directed to KARI enzymes wherein the serine at position 78 is replaced with aspartic acid. In yet another specific embodiment, the invention is directed to KARI enzymes wherein the glutamine at position 110 is replaced with valine. In yet another specific embodiment, the invention is directed to KARI enzymes wherein the glutamine at position 110 is replaced with alanine. In certain embodiments, the KARI enzyme contains two or more modifications or mutations at the amino acids corresponding to the positions described in these specific embodiments. In certain other embodiments, the KARI enzyme contains three or more modifications or mutations at the amino acids corresponding to the positions described in these specific embodiments. In an exemplary embodiment, the KARI enzyme contains four modifications or mutations at the amino acids corresponding to the positions described in these specific embodiments. In additional embodiments described herein, the KARI may further comprise an amino acid substitution at position 68 of the wild-type *E. coli* llvC (SEQ ID NO: 13).

In one embodiment, the modified or mutated KARI is selected from group consisting of SEQ ID NO: 17, SEQ ID NO: 19, SEQ ID NO: 23, SEQ ID NO: 25, SEQ ID NO: 34, SEQ ID NO: 36, SEQ ID NO: 38, SEQ ID NO: 40, SEQ ID NO: 42 and SEQ ID NO: 44.

Further included within the scope of the invention are KARI enzymes, other than the *E. coli* llvC (SEQ ID NO: 13), which contain alterations corresponding to those set out above. Such KARI enzymes may include, but are not limited to, the KARI enzymes encoded by the *S. cerevisiae* ILV5 gene, the KARI enzyme encoded by the *E. coli* ilvC gene and the KARI enzymes from *Piromyces* sp., *Buchnera aphidicola, Spinacia oleracea, Oryza sativa, Chlamydomonas rein-*

*hardtii, Neurospora crassa, Schizosaccharomyces pombe, Laccaria bicolor, Ignicoccus hospitalis, Picrophilus torridus, Acidiphilium cryptum, Cyanobacteria/Synechococcus* sp., *Zymomonas mobilis, Bacteroides thetaiotaomicron, Methanococcus maripaludis, Vibrio fischeri, Shewanella* sp, *Gramella forsetti, Psychromonas ingrhamaii*, and *Cytophaga hutchinsonii*.

In certain exemplary embodiments, the KARI to be modified or mutated is a KARI selected from the group consisting of *Escherichia coli* (GenBank No: NP_418222, SEQ ID NO 13), *Saccharomyces cerevisiae* (GenBank No: NP_013459, SEQ ID NO: 70), *Methanococcus maripaludis* (GenBank No: YP_001097443, SEQ ID NO: 71), *Bacillus subtilis* (GenBank Nos: CAB14789, SEQ ID NO: 72), *Piromyces* sp (GenBank No: CAA76356, SEQ ID NO: 73), *Buchnera aphidicola* (GenBank No: AAF13807, SEQ ID NO: 74), *Spinacia oleracea* (GenBank Nos: □01292 and CAA40356, SEQ ID NO: 75), *Oryza sativa* (GenBank No: NP_001056384, SEQ ID NO: 76) *Chlamydomonas reinhardtii* (GenBank No: XP_001702649, SEQ ID NO: 77), *Neurospora crassa* (GenBank No: XP_961335, SEQ ID NO: 78), *Schizosaccharomyces pombe* (GenBank No: NP_001018845, SEQ ID NO: 79), *Laccaria bicolor* (GenBank No: XP_001880867, SEQ ID NO: 80), *Ignicoccus hospitalis* (GenBank No: YP_001435197, SEQ ID NO: 81), *Picrophilus torridus* (GenBank No: YP_023851, SEQ ID NO: 82), *Acidiphilium cryptum* (GenBank No: YP_001235669, SEQ ID NO: 83), *Cyanobacteria/Synechococcus* sp. (GenBank No: YP_473733, SEQ ID NO: 84), *Zymomonas mobilis* (GenBank No: YP_162876, SEQ ID NO: 85), *Bacteroides thetaiotaomicron* (GenBank No: NP_810987, SEQ ID NO: 86), *Vibrio fischeri* (GenBank No: YP_205911, SEQ ID NO: 87), *Shewanella* sp (GenBank No: YP_732498, SEQ ID NO: 88), *Gramella forsetti* (GenBank No: YP_862142, SEQ ID NO: 89), *Psychromonas ingrhamaii* (GenBank No: YP_942294, SEQ ID NO: 90), and *Cytophaga hutchinsonii* (GenBank No: YP_677763, SEQ ID NO: 91).

In various embodiments described herein, the modified or mutated KARI may exhibit an increased catalytic efficiency with NADH as compared to the wild-type KARI. In one embodiment, the KARI has at least about a 5% increased catalytic efficiency with NADH as compared to the wild-type KARI. In another embodiment, the KARI has at least about a 25%, at least about a 50%, at least about a 75%, or at least about a 100% increased catalytic efficiency with NADH as compared to the wild-type KARI.

In some embodiments described herein, the catalytic efficiency of the modified or mutated KARI with NADH is increased with respect to the catalytic efficiency with NADPH of the wild-type KARI. In one embodiment, the catalytic efficiency of said KARI with NADH is at least about 10% of the catalytic efficiency with NADPH of the wild-type KARI. In another embodiment, the catalytic efficiency of said KARI with NADH is at least about 25%, at least about 50%, or at least about 75% of the catalytic efficiency with NADPH of the wild-type KARI. In some embodiments, the modified or mutated KARI preferentially utilizes NADH rather than NADPH.

In one embodiments, the invention is directed to modified or mutated KARI enzymes that demonstrate a switch in cofactor preference from NADPH to NADH. In one embodiment, the modified or mutated KARI has at least about a 2:1 ratio of $k_{cat}$ with NADH over $k_{cat}$ with NADPH. In an exemplary embodiment, the modified or mutated KARI has at least about a 10:1 ratio of $k_{cat}$ with NADH over $k_{cat}$ with NADPH.

In one embodiments, the invention is directed to a modified or mutated KARI enzyme that exhibits at least about a 1:10 ratio of catalytic efficiency ($k_{cat}/K_M$) with NADH over catalytic efficiency with NADPH. In another embodiment, the modified or mutated KARI enzyme exhibits at least about a 1:1 ratio of catalytic efficiency ($k_{cat}/K_M$) with NADH over catalytic efficiency with NADPH. In yet another embodiment, the modified or mutated KARI enzyme exhibits at least about a ratio of catalytic efficiency ($k_{cat}/K_M$) with NADH over catalytic efficiency with NADPH. In an exemplary embodiment, the modified or mutated KARI enzyme exhibits at least about a 100:1 ratio of catalytic efficiency ($k_{cat}/K_M$) with NADH over catalytic efficiency with NADPH.

In some embodiments, the modified or mutated KARI has been modified to be NADH-dependent. In one embodiment, the KARI exhibits at least about a 1:10 ratio of $K_M$ for NADH over $K_M$ for NADPH.

In additional embodiments, the invention is directed to modified or mutated KARI enzymes that have been codon optimized for expression in certain desirable host organisms, such as yeast and *E. coli*. In other aspects, the present invention is directed to recombinant host cells (e.g. recombinant microorganisms) comprising a modified or mutated KARI enzyme of the invention. According to this aspect, the present invention is also directed to methods of using the modified or mutated KARI enzymes in any fermentation process where the conversion of acetolactate to 2,3-dihydroxyisovalerate is desired. In one embodiment according to this aspect, the modified or mutated KARI enzymes may be suitable for enhancing a host cell's ability to produce isobutanol and enable the production of isobutanol under anaerobic conditions. In another embodiment according to this aspect, the modified or mutated KARI enzymes may be suitable for enhancing a host cell's ability to produce 3-methyl-1-butanol.

According to this aspect, the present invention is also directed to methods of using the modified or mutated KARI enzymes in any fermentation process where the conversion of 2-aceto-2-hydroxy-butyrate to 2,3-dihydroxy-3-methylvalerate is desired. In one embodiment according to this aspect, the modified or mutated KARI enzymes may be suitable for enhancing a host cell's ability to produce 2-methyl-1-butanol and enable the production of 2-methyl-1-butanol under anaerobic conditions.

In another aspect, there are provided recombinant microorganisms comprising an engineered metabolic pathway for producing one or more C3-C5 alcohols under anaerobic conditions, wherein said engineered metabolic pathway comprises a first dehydrogenase and a second dehydrogenase that catalyze the same reaction, and wherein the first dehydrogenase is NADH-dependent and wherein the second dehydrogenase is NADPH dependent. In an exemplary embodiment, the first dehydrogenase is encoded by the *E. coli* gene maeA and the second dehydrogenase is encoded by the *E. coli* gene maeB.

In another aspect, there are provided recombinant microorganisms comprising an engineered metabolic pathway for producing one or more C3-C5 alcohols under anaerobic conditions, wherein said engineered metabolic pathway comprises a replacement of a gene encoding for pyk or homologs thereof with a gene encoding for ppc or pck or homologs thereof. In another embodiment, the engineered metabolic pathway may further comprise the overexpression of the genes mdh and maeB.

In various embodiments described herein, the recombinant microorganisms may further be engineered to express an isobutanol producing metabolic pathway comprising at least one exogenous gene that catalyzes a step in the conversion of pyruvate to isobutanol. In one embodiment, the recombinant microorganism may be engineered to express an isobutanol producing metabolic pathway comprising at least two exogenous genes. In another embodiment, the recombinant microorganism may be engineered to express an isobutanol producing metabolic pathway comprising at least three exogenous genes. In another embodiment, the recombinant microorganism may be engineered to express an isobutanol producing metabolic pathway comprising at least four exogenous genes. In another embodiment, the recombinant microorganism may be engineered to express an isobutanol producing metabolic pathway comprising five exogenous genes.

In various embodiments described herein, the isobutanol pathway enzyme(s) may be selected from the group consisting of acetolactate synthase (ALS), ketol-acid reductoisomerase (KARI), dihydroxyacid dehydratase (DHAD), 2-keto-acid decarboxylase (KIVD), and alcohol dehydrogenase (ADH).

In another embodiment, the recombinant microorganism further comprises a pathway for the fermentation of isobutanol from a pentose sugar. In one embodiment, the pentose sugar is xylose. In one embodiment, the recombinant microorganism is engineered to express a functional xylose isomerase (XI). In another embodiment, the recombinant microorganism further comprises a deletion or disruption of a native gene encoding for an enzyme that catalyzes the conversion of xylose to xylitol. In one embodiment, the native gene is xylose reductase (XR). In another embodiment, the native gene is xylitol dehydrogenase (XDH). In yet another embodiment, both native genes are deleted or disrupted. In yet another embodiment, the recombinant microorganism is engineered to express a xylulose kinase enzyme.

In another embodiment, the recombinant microorganisms of the present invention may further be engineered to include reduced pyruvate decarboxylase (PDC) activity as compared to a parental microorganism. In one embodiment, PDC activity is eliminated. PDC catalyzes the decarboxylation of pyruvate to acetaldehyde, which is reduced to ethanol by alcohol dehydrogenases via the oxidation of NADH to NAD+. In one embodiment, the recombinant microorganism includes a mutation in at least one PDC gene resulting in a reduction of PDC activity of a polypeptide encoded by said gene. In another embodiment, the recombinant microorganism includes a partial deletion of a PDC gene resulting in a reduction of PDC activity of a polypeptide encoded by said gene. In another embodiment, the recombinant microorganism comprises a complete deletion of a PDC gene resulting in a reduction of PDC activity of a polypeptide encoded by said gene. In yet another embodiment, the recombinant microorganism includes a modification of the regulatory region associated with at least one PDC gene resulting in a reduction of PDC activity of a polypeptide encoded by said gene. In yet another embodiment, the recombinant microorganism comprises a modification of the transcriptional regulator resulting in a reduction of PDC gene transcription. In yet another embodiment, the recombinant microorganism comprises mutations in all PDC genes resulting in a reduction of PDC activity of the polypeptides encoded by said genes.

In another embodiment, the recombinant microorganisms of the present invention may further be engineered to include reduced glycerol-3-phosphate dehydrogenase (GPD) activity as compared to a parental microorganism. In one embodiment, GPD activity is eliminated. GPD catalyzes the reduction of dihydroxyacetone phosphate (DHAP) to glycerol-3-phosphate (G3P) via the oxidation of NADH to $NAD^+$. Glycerol is produced from G3P by Glycerol-3-phosphatase (GPP). In one embodiment, the recombinant microorganism includes a mutation in at least one GPD gene resulting in a reduction of GPD activity of a polypeptide encoded by said gene. In another embodiment, the recombinant microorganism includes a partial deletion of a GPD gene resulting in a reduction of GPD activity of a polypeptide encoded by the gene. In another embodiment, the recombinant microorganism comprises a complete deletion of a GPD gene resulting in a reduction of GPD activity of a polypeptide encoded by the gene. In yet another embodiment, the recombinant microorganism includes a modification of the regulatory region associated with at least one GPD gene resulting in a reduction of GPD activity of a polypeptide encoded by said gene. In yet another embodiment, the recombinant microorganism comprises a modification of the transcriptional regulator resulting in a reduction of GPD gene transcription. In yet another embodiment, the recombinant microorganism comprises mutations in all GPD genes resulting in a reduction of GPD activity of a polypeptide encoded by the gene.

In various embodiments described herein, the recombinant microorganisms of the invention may produce one or more C3-C5 alcohols under anaerobic conditions at a yield which is at least about the same yield as under aerobic conditions. In additional embodiments described herein, the recombinant microorganisms of the invention may produce one or more C3-C5 alcohols at substantially the same rate under anaerobic conditions as the parental microorganism produces under aerobic conditions. In the various embodiments described herein, the engineered metabolic pathway may be balanced with respect to NADH and NADPH as compared to a native or unmodified metabolic pathway from a corresponding parental microorganism, wherein the native or unmodified metabolic pathway is not balanced with respect to NADH and NADPH.

In another aspect, the present invention provides a method of producing a C3-C5 alcohol, comprising (a) providing a recombinant microorganism comprising an engineered metabolic pathway capable of producing one or more C3-C5 alcohols under aerobic and anaerobic conditions; (b) cultivating the recombinant microorganism in a culture medium containing a feedstock providing the carbon source, until a recoverable quantity of the C3-C5 alcohol is produced; and (c) recovering the C3-C5 alcohol. In one embodiment, the recombinant microorganism is cultured under anaerobic conditions. In a preferred embodiment, the C3-C5 alcohol is produced under anaerobic conditions at a yield which is at least about the same yield as under aerobic conditions.

In various embodiments described herein, a preferred C3-C5 alcohol is isobutanol. In one embodiment, the microorganism produces isobutanol from a carbon source at a yield of at least about 5 percent theoretical. In another embodiment, the microorganism is selected to produce isobutanol at a yield of at least about 10 percent, at least about 15 percent, about least about 20 percent, at least about 25 percent, at least about 30 percent, at least about 35 percent, at least about 40 percent, at least about 45 percent, at least about 50 percent, at least about 55 percent, at least about 60 percent, at least about 65 percent, at least about 70 percent, at least about 75 percent, at least about 80 percent theoretical, at least about 85 percent theoretical, at least about 90 percent theoretical, or at least about 95 percent theoretical. In one embodiment, the C3-C5 alcohol, such as isobutanol, is produced under anaerobic conditions at about the same yield as under aerobic conditions.

In another aspect, the present invention provides a recombinant microorganism comprising a metabolic pathway for producing a C3-C5 alcohol from a carbon source, wherein said recombinant microorganism comprises a modification that leads to the regeneration of redox co-factors within said recombinant microorganism. In one embodiment according to this aspect, the modification increases the production of a C3-C5 alcohol under anaerobic conditions as compared to the parental or wild-type microorganism. In a preferred embodiment, the fermentation product is isobutanol. In one embodiment, the re-oxidation or re-reduction of said redox co-factors does not require the pentose phosphate pathway, the TCA cycle, or the generation of additional fermentation products. In another embodiment, the re-oxidation or re-reduction of said redox co-factors does not require the production of byproducts or co-products. In yet another embodiment, additional fermentation products are not required for the regeneration of said redox co-factors.

In another aspect, the present invention provides a method of producing a C3-C5 alcohol, comprising providing a recombinant microorganism comprising a metabolic pathway for producing a C3-C5 alcohol, wherein said recombinant microorganism comprises a modification that leads to the regeneration of redox co-factors within said recombinant microorganism; cultivating the microorganism in a culture medium containing a feedstock providing the carbon source, until a recoverable quantity of said C3-C5 alcohol is produced; and optionally, recovering the C3-C5 alcohol. In one embodiment, said microorganism is cultivated under anaerobic conditions. In another embodiment, the C3-C5 alcohol is produced under anaerobic conditions at about the same yield as under aerobic conditions. In a preferred embodiment, the C3-C5 alcohol is isobutanol.

In various embodiments described herein, the recombinant microorganisms may be microorganisms of the *Saccharomyces* clade, *Saccharomyces* sensu stricto microorganisms, Crabtree-negative yeast microorganisms, Crabtree-positive yeast microorganisms, post-WGD (whole genome duplication) yeast microorganisms, pre-WGD (whole genome duplication) yeast microorganisms, and non-fermenting yeast microorganisms.

In some embodiments, the recombinant microorganisms may be yeast recombinant microorganisms of the *Saccharomyces* clade.

In some embodiments, the recombinant microorganisms may be *Saccharomyces* sensu stricto microorganisms. In one embodiment, the *Saccharomyces* sensu stricto is selected from the group consisting of *S. cerevisiae, S. kudriavzevii, S. mikatae, S. bayanus, S. uvarum. S. carocanis* and hybrids thereof.

In some embodiments, the recombinant microorganisms may be Crabtree-negative recombinant yeast microorganisms. In one embodiment, the Crabtree-negative yeast microorganism is classified into a genera selected from the group consisting of *Kluyveromyces, Pichia, Hansenula*, or *Candida*. In additional embodiments, the Crabtree-negative yeast microorganism is selected from *Kluyveromyces lactis, Kluyveromyces marxianus, Pichia anomala, Pichia stipitis, Hansenula anomala, Candida utilis, Issatchenkia orientalis* and *Kluyveromyces waltii.*

In some embodiments, the recombinant microorganisms may be Crabtree-positive recombinant yeast microorganisms. In one embodiment, the Crabtree-positive yeast microorganism is classified into a genera selected from the group consisting of *Saccharomyces, Kluyveromyces, Zygosaccharomyces, Debaryomyces, Candida, Pichia* and *Schizosaccharomyces*. In additional embodiments, the Crabtree-positive yeast microorganism is selected from the group consisting of *Saccharomyces cerevisiae, Saccharomyces uvarum, Saccharomyces bayanus, Saccharomyces paradoxus, Saccharomyces castelli, Saccharomyces kluyveri, Kluyveromyces thermotolerans, Candida glabrata, Z. baiffi, Z. rouxii, Debaryomyces hansenii, Pichia pastorius, Schizosaccharomyces pombe*, and *Saccharomyces uvarum.*

In some embodiments, the recombinant microorganisms may be post-WGD (whole genome duplication) yeast recombinant microorganisms. In one embodiment, the post-WGD yeast recombinant microorganism is classified into a genera selected from the group consisting of *Saccharomyces* or *Candida*. In additional embodiments, the post-WGD yeast is selected from the group consisting of *Saccharomyces cerevisiae, Saccharomyces uvarum, Saccharomyces bayanus, Saccharomyces paradoxus, Saccharomyces casteffi*, and *Candida glabrata.*

In some embodiments, the recombinant microorganisms may be pre-WGD (whole genome duplication) yeast recombinant microorganisms. In one embodiment, the pre-WGD yeast recombinant microorganism is classified into a genera selected from the group consisting of *Saccharomyces, Kluyveromyces, Candida, Pichia, Debaryomyces, Hansenula, Pachysolen, Issatchenkia, Yarrowia* and *Schizosaccharomyces*. In additional embodiments, the pre-WGD yeast is selected from the group consisting of *Saccharomyces kluyveri, Kluyveromyces thermotolerans, Kluyveromyces marxianus, Kluyveromyces waltii, Kluyveromyces lactis, Candida tropicalis, Pichia pastoris, Pichia anomala, Pichia stipitis, Debaryomyces hansenii, Hansenula anomala, Pachysolen tannophilis, Yarrowia lipolytica, Issatchenkia orientalis*, and *Schizosaccharomyces pombe.*

In some embodiments, the recombinant microorganisms may be microorganisms that are non-fermenting yeast microorganisms, including, but not limited to those, classified into a genera selected from the group consisting of *Tricosporon, Rhodotorula*, or *Myxozyma.*

In certain specific embodiments, there are provided recombinant microorganisms comprising an engineered metabolic pathway for producing one or more C3-C5 alcohols under anaerobic conditions, wherein the recombinant microorganism is selected from GEVO1846, GEVO1886, GEVO1993, GEVO2158, GEVO2302, GEVO1803, GEVO2107, GEVO2710, GEVO2711, GEVO2712, GEVO2799, GEVO2847, GEVO2848, GEVO2849, GEVO2851, GEVO2852, GEVO2854, GEVO2855 and GEVO2856. In another specific embodiment, the present invention provides a plasmid is selected from the group consisting of pGV1698 (SEQ ID NO: 112), pGV1720 (SEQ ID NO: 115), pGV1745 (SEQ ID NO: 117), pGV1655 (SEQ ID NO: 109), pGV1609 (SEQ ID NO: 108), pGV1685 (SEQ ID NO: 111), and pGV1490 (SEQ ID NO: 104).

In yet another aspect, the present invention provides methods for the conversion of an aldehyde with three to five carbon atoms to the corresponding alcohol is provided. The method includes providing a microorganism comprising a heterologous polynucleotide encoding a polypeptide having NADH-dependent aldehyde reduction activity that is greater than its NADPH-dependent aldehyde reduction activity and having NADH-dependent aldehyde reduction activity that is greater than the endogenous NADPH-dependent aldehyde reduction activity of the microorganism; and contacting the microorganism with the aldehyde.

In another embodiment, a method for the conversion of an aldehyde derived from the conversion of a 2-ketoacid by a 2-ketoacid decarboxylase is provided. The method includes providing a microorganism comprising a heterologous polynucleotide encoding a polypeptide having NADH-dependent aldehyde reduction activity that is greater than its NADPH-dependent aldehyde reduction activity and having NADH-dependent aldehyde reduction activity that is greater than the endogenous NADPH-dependent aldehyde reduction activity of the microorganism; and contacting the microorganism with the aldehyde. In various embodiments described herein, the aldehyde may be selected from 1-propanal, 1-butanal, isobutyraldehyde, 2-methyl-1-butanal, or 3-methyl-1-butanal. In a preferred embodiment, the aldehyde is isobutyraldehyde.

In another embodiment, an microorganism include a heterologous polynucleotide encoding a polypeptide having NADH-dependent aldehyde reduction activity that is greater than its NADPH-dependent aldehyde reduction activity and having NADH-dependent aldehyde reduction activity that is greater than the endogenous NADPH-dependent aldehyde reduction activity of the microorganism is provided. The microorganism converts an aldehyde comprising three to five carbon atoms to the corresponding alcohol.

In another embodiment, an isolated microorganism is provided. The microorganism includes a heterologous polynucleotide encoding a polypeptide having NADH-dependent aldehyde reduction activity that is greater than its NADPH-dependent aldehyde reduction activity and having NADH-dependent aldehyde reduction activity that is greater than the endogenous NADPH-dependent aldehyde reduction activity of the microorganism. The microorganism converts an aldehyde derived from a 2-ketoacid by a 2-ketoacid decarboxylase. In one embodiment, the polypeptide is encoded by the *Drosophila melanogaster* ADH gene or homologs thereof. In a preferred embodiment, the *Drosophila melanogaster* ADH gene is set forth in SEQ ID NO: 60. In an alternative embodiment, the *Drosophila melanogaster* alcohol dehydrogenase is set forth in SEQ ID NO: 61. In another embodiment, the polypeptide possesses 1,2 propanediol dehydrogenase activity and is encoded by a 1,2 propanediol dehydrogenase gene. In a preferred embodiment, the 1,2-propanediol dehydrogenase gene is the *Klebsiella pneumoniae* dhaT gene as set forth in SEQ ID NO: 62. In an alternative embodiment, the 1,2-propanediol dehydrogenase is set forth in SEQ ID NO: 63. In another embodiment, the polypeptide possesses is encoded by a 1,3-propanediol dehydrogenase gene. In a preferred embodiment, the 1,3-propanediol dehydrogenase gene is the *Escherichia coli* fucO gene as set forth in SEQ ID NO: 64. In an alternative embodiment, the 1,3-propanediol dehydrogenase is set forth in SEQ ID NO: 65.

In yet another aspect, the present invention provides a recombinant microorganism producing isobutanol, wherein said recombinant microorganism i) does not overexpress an alcohol dehydrogenase; and ii) produces isobutanol at a higher rate, titer, and productivity as compared to recombinant microorganism expressing the *S. cerevisiae* alcohol dehydrogenase ADH2.

BRIEF DESCRIPTION OF THE DRAWINGS

Illustrative embodiments of the invention are illustrated in the drawings, in which.

DETAILED DESCRIPTION

Definitions

Figure 1:
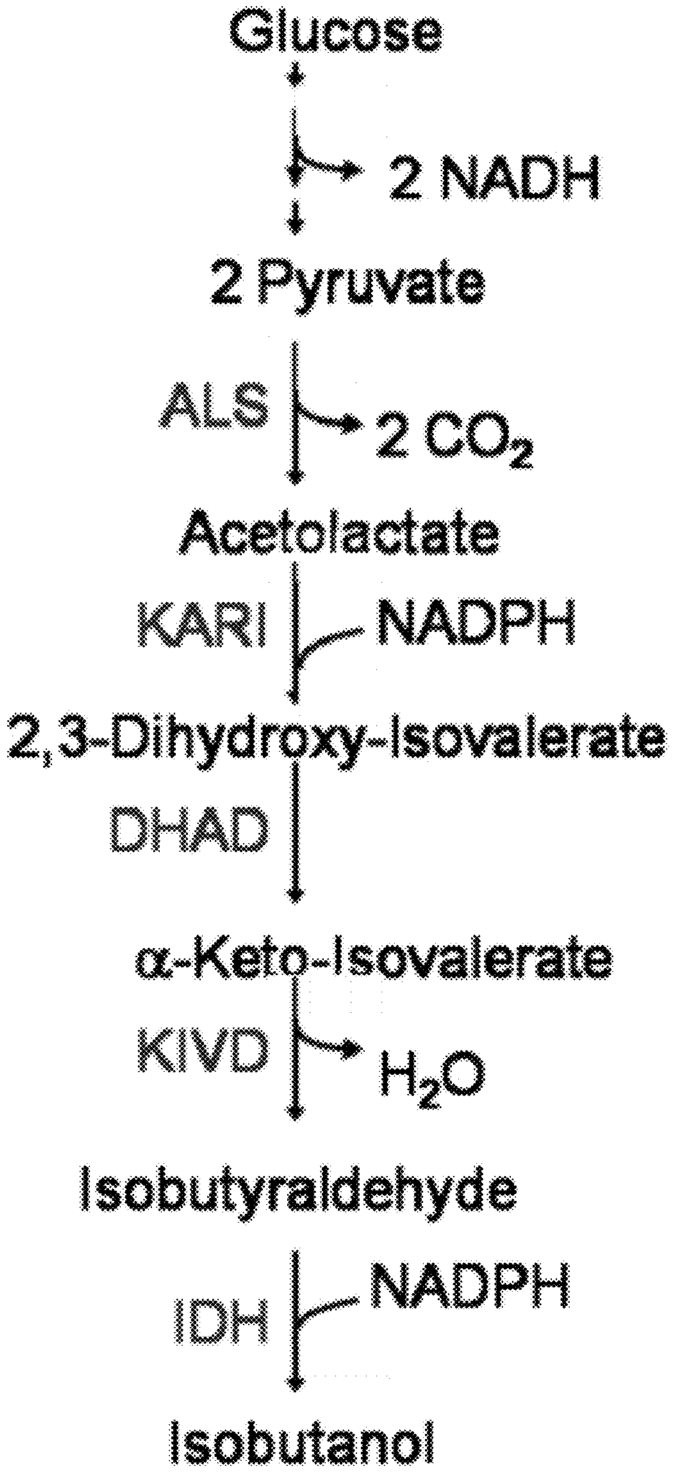
FIG. 1 illustrates an exemplary metabolic pathway for the conversion of glucose to isobutanol via pyruvate.

As used herein and in the appended claims, the singular forms "a," "an," and "the" include plural referents unless the context clearly dictates otherwise. Thus, for example, reference to "a polynucleotide" includes a plurality of such polynucleotides and reference to "the microorganism" includes reference to one or more microorganisms, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Any publications discussed above and throughout the text are provided solely for their disclosure prior to the filing date of the present application. Nothing herein is to be construed as an admission that the inventors are not entitled to antedate such disclosure by virtue of prior disclosure.

The term "microorganism" includes prokaryotic and eukaryotic microbial species from the Domains Archaea, Bacteria and Eukarya, the latter including yeast and filamentous fungi, protozoa, algae, or higher Protista. The terms "microbial cells" and "microbes" are used interchangeably with the term microorganism.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl); and extreme (hyper) thermophiles (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consist mainly of hyperthermophilic sulfur-dependent prokaryotes and the Euryarchaeota contain the methanogens and extreme halophiles.

"Bacteria", or "eubacteria", refers to a domain of prokaryotic organisms. Bacteria include at least 11 distinct groups as follows: (1) Gram-positive (gram$^+$) bacteria, of which there are two major subdivisions: (1) high G+C group (Actinomycetes, *Mycobacteria, Micrococcus*, others) (2) low G+C group (Bacillus, Clostridia, *Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides, Flavobacteria;* (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho* thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium.*

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces.*

The term "genus" is defined as a taxonomic group of related species according to the Taxonomic Outline of Bacteria and Archaea (Garrity, G. M., Lilburn, T. G., Cole, J. R., Harrison, S. H., Euzeby, J., and Tindall, B. J. (2007) The Taxonomic Outline of Bacteria and Archaea. TOBA Release 7.7, March 2007. Michigan State University Board of Trustees.

The term "species" is defined as a collection of closely related organisms with greater than 97% 16S ribosomal RNA sequence homology and greater than 70% genomic hybridization and sufficiently different from all other organisms so as to be recognized as a distinct unit.

The terms "modified microorganism," "recombinant microorganism" and "recombinant host cell" are used by inserting, expressing or overexpressing endogenous polynucleotides, by expressing or overexpressing heterologous polynucleotides, such as those included in a vector, by introducing a mutations into the microorganism or by altering the expression of an endogenous gene. The polynucleotide generally encodes a target enzyme involved in a metabolic pathway for producing a desired metabolite. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

The term "wild-type microorganism" describes a cell that occurs in nature, i.e. a cell that has not been genetically modified. A wild-type microorganism can be genetically modified to express or overexpress a first target enzyme. This microorganism can act as a parental microorganism in the generation of a microorganism modified to express or overexpress a second target enzyme. In turn, the microorganism modified to express or overexpress a first and a second target enzyme can be modified to express or overexpress a third target enzyme.

Accordingly, a "parental microorganism" functions as a reference cell for successive genetic modification events. Each modification event can be accomplished by introducing a nucleic acid molecule into the reference cell. The introduction facilitates the expression or overexpression of a target enzyme. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of heterologous polynucleotides encoding a target enzyme in to a parental microorganism.

The term "mutation" as used herein indicates any modification of a nucleic acid and/or polypeptide which results in an altered nucleic acid or polypeptide. Mutations include, for example, point mutations, deletions, or insertions of single or multiple residues in a polynucleotide, which includes alterations arising within a protein-encoding region of a gene as well as alterations in regions outside of a protein-encoding sequence, such as, but not limited to, regulatory or promoter sequences. A genetic alteration may be a mutation of any type. For instance, the mutation may constitute a point mutation, a frame-shift mutation, an insertion, or a deletion of part or all of a gene. In addition, in some embodiments of the modified microorganism, a portion of the microorganism genome has been replaced with a heterologous polynucleotide. In some embodiments, the mutations are naturally-occurring. In other embodiments, the mutations are the results of artificial mutation pressure. In still other embodiments, the mutations in the microorganism genome are the result of genetic engineering.

The term "biosynthetic pathway", also referred to as "metabolic pathway", refers to a set of anabolic or catabolic biochemical reactions for converting one chemical species into another. Gene products belong to the same "metabolic pathway" if they, in parallel or in series, act on the same substrate, produce the same product, or act on or produce a metabolic intermediate (i.e., metabolite) between the same substrate and metabolite end product.

The term "heterologous" as used herein with reference to molecules and in particular enzymes and polynucleotides, indicates molecules that are expressed in an organism other than the organism from which they originated or are found in nature, independently on the level of expression that can be lower, equal or higher than the level of expression of the molecule in the native microorganism.

On the other hand, the term "native" or "endogenous" as used herein with reference to molecules, and in particular enzymes and polynucleotides, indicates molecules that are expressed in the organism in which they originated or are found in nature, independently on the level of expression that can be lower equal or higher than the level of expression of the molecule in the native microorganism. It is understood that expression of native enzymes or polynucleotides may be modified in recombinant microorganisms.

The term "carbon source" generally refers to a substance suitable to be used as a source of carbon for prokaryotic or eukaryotic cell growth. Carbon sources include, but are not limited to, biomass hydrolysates, starch, sucrose, cellulose, hemicellulose, xylose, and lignin, as well as monomeric components of these substrates. Carbon sources can comprise various organic compounds in various forms, including, but not limited to polymers, carbohydrates, acids, alcohols, aldehydes, ketones, amino acids, peptides, etc. These include, for example, various monosaccharides such as glucose, dextrose (D-glucose), maltose, oligosaccharides, polysaccharides, saturated or unsaturated fatty acids, succinate, lactate, acetate, ethanol, etc., or mixtures thereof. Photosynthetic organisms can additionally produce a carbon source as a product of photosynthesis. In some embodiments, carbon sources may be selected from biomass hydrolysates and glucose. The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, such as any biomass derived sugar, but also intermediate and end product metabolites used in a pathway associated with a modified microorganism as described herein.

The term "volumetric productivity" or "production rate" is defined as the amount of product formed per volume of medium per unit of time. Volumetric productivity is reported in gram per liter per hour (g/L/h).

The term "specific productivity" is defined as the rate of formation of the product. To describe productivity as an inherent parameter of the microorganism or microorganism and not of the fermentation process, productivity is herein further defined as the specific productivity in gram product per unit of cells, typically measured spectroscopically as absorbance units at 600 nm ($OD_{600}$ or OD) per hour (g/L/h/OD).

The term "yield" is defined as the amount of product obtained per unit weight of raw material and may be expressed as g product per g substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product. For example, the theoretical yield for one typical conversion of glucose to isobutanol is 0.41 g/g. As such, a yield of butanol from glucose of 0.39 g/g would be expressed as 95% of theoretical or 95% theoretical yield.

The term "titre" or "titer" is defined as the strength of a solution or the concentration of a substance in solution. For example, the titre of a biofuel in a fermentation broth is described as g of biofuel in solution per liter of fermentation broth (g/L).

The term "total titer" is defined as the sum of all biofuel produced in a process, including but not limited to the biofuel in solution, the biofuel in gas phase, and any biofuel removed from the process and recovered relative to the initial volume in the process or the operating volume in the process.

A "facultative anaerobic organism" or a "facultative anaerobic microorganism" is defined as an organism that can grow in either the presence or in the absence of oxygen.

A "strictly anaerobic organism" or a "strictly anaerobic microorganism" is defined as an organism that cannot grow in the presence of oxygen and which does not survive exposure to any concentration of oxygen.

An "anaerobic organism" or an "anaerobic microorganism" is defined as an organism that cannot grow in the presence of oxygen.

"Aerobic conditions" are defined as conditions under which the oxygen concentration in the fermentation medium is sufficiently high for an aerobic or facultative anaerobic microorganism to use as a terminal electron acceptor.

In contrast, "Anaerobic conditions" are defined as conditions under which the oxygen concentration in the fermentation medium is too low for the microorganism to use as a terminal electron acceptor. Anaerobic conditions may be achieved by sparging a fermentation medium with an inert gas such as nitrogen until oxygen is no longer available to the microorganism as a terminal electron acceptor. Alternatively, anaerobic conditions may be achieved by the microorganism consuming the available oxygen of the fermentation until oxygen is unavailable to the microorganism as a terminal electron acceptor. "Anaerobic conditions" are further defined as conditions under which no or small amounts of oxygen are added to the medium at rates of $<3$ mmol/L/h, preferably $<2.5$ mmol/L/h, more preferably $<2$ mmol/L/h and most preferably $<1.5$ mmol/L/h. "Anaerobic conditions" means in particular completely oxygen-free ($=0$ mmol/L/h oxygen) or with small amounts of oxygen added to the medium at rates of e.g. $<0.5$ to $<1$ mmol/L/h.

"Dissolved oxygen," abbreviated as "DO" is expressed throughout as the percentage of saturating concentration of oxygen in water.

"Aerobic metabolism" refers to a biochemical process in which oxygen is used as a terminal electron acceptor to make energy, typically in the form of ATP, from carbohydrates. Aerobic metabolism occurs e.g. via glycolysis and the TCA cycle, wherein a single glucose molecule is metabolized completely into carbon dioxide in the presence of oxygen.

In contrast, "anaerobic metabolism" refers to a biochemical process in which oxygen is not the final acceptor of electrons contained in NADH. Anaerobic metabolism can be divided into anaerobic respiration, in which compounds other than oxygen serve as the terminal electron acceptor, and substrate level phosphorylation, in which the electrons from NADH are utilized to generate a reduced product via a "fermentative pathway."

In "fermentative pathways," NAD(P)H donates its electrons to a molecule produced by the same metabolic pathway that produced the electrons carried in NAD(P)H. For example, in one of the fermentative pathways of certain yeast strains, NAD(P)H generated through glycolysis transfers its electrons to pyruvate, yielding lactate. Fermentative pathways are usually active under anaerobic conditions but may also occur under aerobic conditions, under conditions where NADH is not fully oxidized via the respiratory chain. For example, above certain glucose concentrations, crabtree positive yeasts produce large amounts of ethanol under aerobic conditions.

The term "fermentation product" means any main product plus its coupled product. A "coupled product" is produced as part of the stoichiometric conversion of the carbon source to the main fermentation product. An example for a coupled product is the two molecules of $CO_2$ that are produced with every molecule of isobutanol during production of isobutanol from glucose according the biosynthetic pathway described herein.

The term "byproduct" means an undesired product related to the production of a biofuel. Byproducts are generally disposed as waste, adding cost to a biofuel process.

The term "co-product" means a secondary or incidental product related to the production of biofuel. Co-products have potential commercial value that increases the overall value of biofuel production, and may be the deciding factor as to the viability of a particular biofuel production process.

The term "non-fermenting yeast" is a yeast species that fails to demonstrate an anaerobic metabolism in which the electrons from NADH are utilized to generate a reduced product via a fermentative pathway such as the production of ethanol and $CO_2$ from glucose. Non-fermentative yeast can be identified by the "Durham Tube Test" (J. A. Barnett, R. W. Payne, and D. Yarrow. 2000. Yeasts Characteristics and Identification. 3$^{rd}$ edition. p. 28-29. Cambridge University Press, Cambridge, UK.) or by monitoring the production of fermentation productions such as ethanol and $CO_2$ The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, DNA, RNA, analogs and fragments thereof. A polynucleotide of three or more nucleotides is also called nucleotidic oligomer or oligonucleotide.

It is understood that the polynucleotides described herein include "genes" and that the nucleic acid molecules described herein include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence.

The term "operon" refers two or more genes which are transcribed as a single transcriptional unit from a common promoter. In some embodiments, the genes comprising the operon are contiguous genes. It is understood that transcription of an entire operon can be modified (i.e., increased, decreased, or eliminated) by modifying the common promoter. Alternatively, any gene or combination of genes in an operon can be modified to alter the function or activity of the encoded polypeptide. The modification can result in an increase in the activity of the encoded polypeptide. Further, the modification can impart new activities on the encoded polypeptide. Exemplary new activities include the use of alternative substrates and/or the ability to function in alternative environmental conditions.

A "vector" is any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

"Transformation" refers to the process by which a vector is introduced into a host cell. Transformation (or transduction, or transfection), can be achieved by any one of a number of means including electroporation, microinjection, biolistics (or particle bombardment-mediated delivery), or *agrobacterium* mediated transformation.

The term "enzyme" as used herein refers to any substance that catalyzes or promotes one or more chemical or biochemical reactions, which usually includes enzymes totally or partially composed of a polypeptide, but can include enzymes composed of a different molecule including polynucleotides.

The term "protein" or "polypeptide" as used herein indicates an organic polymer composed of two or more amino acidic monomers and/or analogs thereof. As used herein, the term "amino acid" or "amino acidic monomer" refers to any natural and/or synthetic amino acids including glycine and both D or L optical isomers. The term "amino acid analog" refers to an amino acid in which one or more individual atoms have been replaced, either with a different atom, or with a different functional group. Accordingly, the term polypeptide includes amino acidic polymer of any length including full length proteins, and peptides as well as analogs and fragments thereof. A polypeptide of three or more amino acids is also called a protein oligomer or oligopeptide The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

The term "analog" or "analogous" refers to nucleic acid or protein sequences or protein structures that are related to one another in function only and are not from common descent or do not share a common ancestral sequence. Analogs may differ in sequence but may share a similar structure, due to convergent evolution. For example, two enzymes are analogs or analogous if the enzymes catalyze the same reaction of conversion of a substrate to a product, are unrelated in sequence, and irrespective of whether the two enzymes are related in structure.

The Microorganism in General

Microorganism Characterized by Producing C3-C5 Alcohols from Pyruvate Via an Overexpressed Metabolic Pathway Native producers of butanol, and more specifically 1-butaanol, such as *Clostridium acetobutylicum*, are known, but these organisms generate byproducts such as acetone, ethanol, and butyrate during fermentations. Furthermore, these microorganisms are relatively difficult to manipulate, with significantly fewer tools available than in more commonly used production hosts such as *E. coli*. Additionally, the physiology and metabolic regulation of these native producers are much less well understood, impeding rapid progress towards high-efficiency production. Furthermore, no native microorganisms have been identified that can metabolize glucose into isobutanol in industrially relevant quantities or yields.

The production of isobutanol and other fusel alcohols by various yeast species, including *Saccharomyces cerevisiae* is of special interest to the distillers of alcoholic beverages, for whom fusel alcohols constitute often undesirable off-notes. Production of isobutanol in wild-type yeasts has been documented on various growth media, ranging from grape must from winemaking (Romano, et al., Metabolic diversity of *Saccharomyces cerevisiae* strains from spontaneously fermented grape musts, 19:311-315, 2003), in which 12-219 mg/L isobutanol were produced, supplemented to minimal media (Oliviera, et al. (2005) World Journal of Microbiology and Biotechnology 21:1569-1576), producing 16-34 mg/L isobutanol. Work from Dickinson, et al. (J Biol. Chem. 272 (43):26871-8, 1997) has identified the enzymatic steps utilized in an endogenous *S. cerevisiae* pathway converting branch-chain amino acids (e.g., valine or leucine) to isobutanol.

A number of recent publications have described methods for the production of industrial chemicals such as C3-C5 alcohols such as isobutanol using engineered microorganisms. See, e.g., WO/2007/050671 to Donaldson et al., and WO/2008/098227 to Liao et al., which are herein incorporated by reference in their entireties. These publications disclose recombinant microorganisms that utilize a series of heterologously expressed enzymes to convert sugars into isobutanol. However, the production of isobutanol using these microorganisms is feasible only under aerobic conditions and the maximum yield that can be achieved is limited.

Recombinant microorganisms provided herein can express a plurality of target enzymes involved in pathways for the production isobutanol from a suitable carbon source under anaerobic conditions.

Accordingly, "engineered" or "modified" microorganisms are produced via the introduction of genetic material into a host or parental microorganism of choice thereby modifying or altering the cellular physiology and biochemistry of the microorganism. Through the introduction of genetic material the parental microorganism acquires new properties, e.g. the ability to produce a new, or greater quantities of, an intracellular metabolite under anaerobic conditions. As described herein, the introduction of genetic material into a parental microorganism results in a new or modified ability to produce isobutanol under anaerobic conditions. The genetic material introduced into the parental microorganism contains gene(s), or parts of genes, coding for one or more of the enzymes involved in a biosynthetic pathway for the production of isobutanol under anaerobic conditions and may also include additional elements for the expression and/or regulation of expression of these genes, e.g. promoter sequences.

An engineered or modified microorganism can also include in the alternative or in addition to the introduction of a genetic material into a host or parental microorganism, the disruption, deletion or knocking out of a gene or polynucleotide to alter the cellular physiology and biochemistry of the microorganism. Through the reduction, disruption or knocking out of a gene or polynucleotide the microorganism acquires new or improved properties (e.g., the ability to produce a new metabolite or greater quantities of an intracellular metabolite, improve the flux of a metabolite down a desired pathway, and/or reduce the production of undesirable byproducts).

Microorganisms provided herein are modified to produce under anaerobic conditions metabolites in quantities not available in the parental microorganism. A "metabolite" refers to any substance produced by metabolism or a substance necessary for or taking part in a particular metabolic process. A metabolite can be an organic compound that is a starting material (e.g., glucose or pyruvate), an intermediate (e.g., 2-ketoisovalerate), or an end product (e.g., isobutanol) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

Exemplary metabolites include glucose, pyruvate, and C3-C5 alcohols, including isobutanol. The metabolite isobutanol can be produced by a recombinant microorganism engineered to express or over-express metabolic pathway that converts pyruvate to isobutanol. An exemplary metabolic pathway that converts pyruvate to isobutanol may be comprised of a acetohydroxy acid synthase (ALS) enzyme encoded by, for example, alsS from *B. subtilis*, a ketolacid reductoisomerase (KARI) encoded by, for example ilvC from *E. coli*, a dihyroxy-acid dehydratase (DHAD), encoded by, for example ilvD from *E. coli*, a 2-keto-acid decarboxylase (KIVD) encoded by, for example kivd from *L. lactis*, and an alcohol dehydrogenase (ADH), encoded by, for example, by a native *E. coli* alcohol dehydrogenase gene, like Ec_yqhD.

Accordingly, provided herein are recombinant microorganisms that produce isobutanol and in some aspects may include the elevated expression of target enzymes such as ALS (encoded e.g. by the ilvIH operon from *E. coli* or by alsS from *Bacillus subtilis*), KARI (encoded e.g. by ilvC from *E. coli*), DHAD (encoded, e.g. by ilvD from *E. coli*, or by ILV3 from *S. cerevisiae*, and KIVD (encoded, e.g. by, AR010 from *S. cerevisiae*, THI3 from *S. cerevisiae*, kivd from *L. lactis*).

The recombinant microorganism may further include the deletion or reduction of the activity of enzymes that (a) directly consume a precursor of the product, e.g. an isobutanol precursor, (b) indirectly consume a precursor of the product, e.g. of isobutanol, or (c) repress the expression or function of a pathway that supplies a precursor of the product, e.g. of isobutanol. These enzymes include pyruvate decarboxylase (encoded, e.g. by PDC1, PDC2, PDC3, PDC5, or PDC6 of *S. cerevisiae*), glycerol-3-phosphate dehydrogenase (encoded, e.g. by GPD1 or GPD2 of *S. cerevisiae*) an alcohol dehydrogenase (encoded, e.g., by adhE of *E. coli* or ADH1, ADH2, ADH3, ADH4, ADH5, ADH6, or ADH7 of *S. cerevisiae*), lacate dehydrogenase (encoded, e.g., by IdhA of *E. coli*), fumarate reductase (encoded, e.g., by frdB, frdC or frdBC of *E. coli*), FNR (encoded, e.g. by fnr of *E. coli*), 2-isopropylmalate synthase (encoded, e.g. by leuA of *E. coli* or by LEU4 or LEU9 of *S. cerevisiae*), valine transaminase (encoded, e.g. by ilvE of *E. coli* or by BAT1 or BAT2 of *S. cerevisiae*), pyruvate oxidase (e.g. encoded by poxB of *E. coli*), Threonine deaminase (encoded, e.g. by i/vA of *E. coli* or CHA1 or ILV1 of *S. cerevisiae*), pyruvate-formate-lyase (encoded, e.g. by pflB of *E. coli*), or phosphate acetyltransferase (encoded, e.g. by pta of *E. coli*), or any combination thereof, to increase the availability of pyruvate or reduce enzymes that compete for a metabolite in a desired biosynthetic pathway.

In yeast microorganisms, pyruvate decarboxylase (PDC) is a major competitor for pyruvate. During anaerobic fermentation, the main pathway to oxidize the NADH from glycolysis is through the production of ethanol. Ethanol is produced by alcohol dehydrogenase (ADH) via the reduction of acetaldehyde, which is generated from pyruvate by pyruvate decarboxylase (PDC). Thus, most of the pyruvate produced by glycolysis is consumed by PDC and is not available for the isobutanol pathway. Another pathway for NADH oxidation is through the production of glycerol. Dihydroxyacetone-phospate, an intermediate of glycolysis is reduced to glycerol 3-phosphate by glycerol 3-phosphate dehydrogenase (GPD). Glycerol 3-phosphatase (GPP) converts glycerol 3-phosphate to glycerol. This pathway consumes carbon from glucose as well as reducing equivalents (NADH) resulting in less pyruvate and reducing equivalents available for the isobutanol pathway. These pathways contribute to low yield and low productivity of C3-C5 alcohols, including isobutanol. Accordingly, deletion or reduction of the activity of PDC and GPD may increase yield and productivity of C3-C5 alcohols, including isobutanol.

Reduction of PDC activity can be accomplished by 1) mutation or deletion of a positive transcriptional regulator for the structural genes encoding for PDC or 2) mutation or deletion of all PDC genes in a given organism. The term "transcriptional regulator" can specify a protein or nucleic acid that works in trans to increase or to decrease the transcription of a different locus in the genome. For example, in *S. cerevisiae*, the PDC2 gene, which encodes for a positive transcriptional regulator of PDC1,5,6 genes can be deleted; a *S. cerevisiae* in which the PDC2 gene is deleted is reported to have only ~10% of wildtype PDC activity (Hohmann, *Mol Gen Genet,* 241:657-666 (1993)). Alternatively, for example, all structural genes for PDC (e.g. in *S. cerevisiae*, PDC1, PDC5, and PDC6, or in *K. lactis*, PDC1) are deleted.

Crabtree-positive yeast strains such as *Saccharomyces. cerevisiae* strain that contains disruptions in all three of the PDC alleles no longer produce ethanol by fermentation. However, a downstream product of the reaction catalyzed by PDC, acetyl-CoA, is needed for anabolic production of necessary molecules. Therefore, the Pdc-mutant is unable to grow solely on glucose, and requires a two-carbon carbon source, either ethanol or acetate, to synthesize acetyl-CoA. (Flikweert M T, de Swaaf M, van Dijken J P, Pronk J T. FEMS Microbiol Lett. 1999 May 1; 174(1):73-9. PMID:10234824 and van Maris A J, Geertman J M, Vermeulen A, Groothuizen M K, Winkler A A, Piper M D, van Dijken J P, Pronk J T. Appl Environ Microbiol. 2004 January; 70(1):159-66. PMID: 14711638).

Thus, in an embodiment, such a Crabtree-positive yeast strain may be evolved to generate variants of the PDC mutant yeast that do not have the requirement for a two-carbon molecule and has a growth rate similar to wild type on glucose. Any method, including chemostat evolution or serial dilution may be utilized to generate variants of strains with deletion of three PDC alleles that can grow on glucose as the sole carbon source at a rate similar to wild type (van Maris et al., Directed Evolution of Pyruvate Decarboxylase-Negative *Saccharomyces cerevisiae, Yielding a C*2-Independent, Glucose-Tolerant, and Pyruvate-Hyperproducing Yeast, Applied and Environmental Microbiology, 2004, 70(1), 159-166).

Another byproduct that would decrease yield of isobutanol is glycerol. Glycerol is produced by 1) the reduction of the glycolysis intermediate, dihydroxyacetone phosphate (DHAP), to glycerol-3-phosphate (G3P) via the oxidation of NADH to $NAD^+$ by Glycerol-3-phosphate dehydrogenase (GPD) followed by 2) the dephosphorylation of glycerol-3-phophate to glycerol by glycerol-3-phosphatase (GPP). Production of glycerol results in loss of carbons as well as reducing equivalents. Reduction of GPD activity would increase yield of isobutanol. Reduction of GPD activity in addition to PDC activity would further increase yield of isobutanol. Reduction of glycerol production has been reported to increase yield of ethanol production (Nissen et al., Anaerobic and aerobic batch cultivation of *Saccharomyces cerevisiae* mutants impaired in glycerol synthesis, Yeast, 2000, 16, 463-474; Nevoigt et al., Method of modifying a yeast cell for the production of ethanol, WO 2009/056984). Disruption of this pathway has also been reported to increase yield of lactate in a yeast engineered to produce lactate instead of ethanol (Dundon et al., Yeast cells having disrupted pathway from dihydroxyacetone phosphate to glycerol, US 2009/0053782).

In one embodiment, the microorganism is a crab-tree positive yeast with reduced or no GPD activity. In another embodiment, the microorganism is a crab-tree positive yeast with reduced or no GPD activity, and expresses an isobutanol biosynthetic pathway and produces isobutanol. In yet another embodiment, the microorganism is a crab-tree positive yeast with reduced or no GPD activity and with reduced or no PDC activity. In another embodiment, the microorganism is a crab-tree positive yeast with reduced or no GPD activity, with reduced or no PDC activity, and expresses an isobutanol biosynthetic pathway and produces isobutanol.

In another embodiment, the microorganism is a crab-tree negative yeast with reduced or no GPD activity. In another embodiment, the microorganism is a crab-tree negative yeast with reduced or no GPD activity, expresses the isobutanol biosynthetic pathway and produces isobutanol. In yet another embodiment, the microorganism is a crab-tree negative yeast with reduced or no GPD activity and with reduced or no PDC activity. In another embodiment, the microorganism is a crab-tree negative yeast with reduced or no GPD activity, with reduced or no PDC activity, expresses an an isobutanol biosynthetic pathway and produces isobutanol.

Any method can be used to identify genes that encode for enzymes with pyruvate decarboxylase (PDC) activity. PDC catalyzes the decarboxylation of pyruvate to form acetaldehyde. Generally, homologous or similar PDC genes and/or homologous or similar PDC enzymes can be identified by functional, structural, and/or genetic analysis. In most cases, homologous or similar PDC genes and/or homologous or similar PDC enzymes will have functional, structural, or genetic similarities. Techniques known to those skilled in the art may be suitable to identify homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous genes, proteins, or enzymes, techniques may include, but not limited to, cloning a PDC gene by PCR using primers based on a published sequence of a gene/enzyme or by degenerate PCR using degenerate primers designed to amplify a conserved region among PDC genes. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity, then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above mentioned databases in accordance with the teachings herein. Furthermore, PDC activity can be determined phenotypically. For example, ethanol production under fermentative conditions can be assessed. A lack of ethanol production may be indicative of a yeast microorganism with no PDC activity.

Any method can be used to identify genes that encode for enzymes with glycerol-3-phosphate dehydrogenase (GPD) activity. GPD catalyzes the reduction of dihydroxyacetone phosphate (DHAP) to glycerol-3-phosphate (G3P) with the corresponding oxidation of NADH to NAD+. Generally, homologous or similar GPD genes and/or homologous or similar GPD enzymes can be identified by functional, structural, and/or genetic analysis. In most cases, homologous or similar GPD genes and/or homologous or similar GPD enzymes will have functional, structural, or genetic similarities. Techniques known to those skilled in the art may be suitable to identify homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous genes, proteins, or enzymes, techniques may include, but not limited to, cloning a GPD gene by PCR using primers based on a published sequence of a gene/enzyme or by degenerate PCR using degenerate primers designed to amplify a conserved region among GPD genes. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity, then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above mentioned databases in accordance with the teachings herein. Furthermore, GPD activity can be determined phenotypically. For example, glycerol production under fermentative conditions can be assessed. A lack of glycerol production may be indicative of a yeast microorganism with no GPD activity.

The recombinant microorganism may further include metabolic pathways for the fermentation of a C3-C5 alcohols from five-carbon (pentose) sugars including xylose. Most yeast species metabolize xylose via a complex route, in which xylose is first reduced to xylitol via a xylose reductase (XR) enzyme. The xylitol is then oxidized to xylulose via a xylitol dehydrogenase (XDH) enzyme. The xylulose is then phosphorylated via an xylulokinase (XK) enzyme. This pathway operates inefficiently in yeast species because it introduces a redox imbalance in the cell. The xylose-to-xylitol step uses NADH as a cofactor, whereas the xylitol-to-xylulose step uses NADPH as a cofactor. Other processes must operate to restore the redox imbalance within the cell. This often means that the organism cannot grow anaerobically on xylose or other pentose sugar. Accordingly, a yeast species that can efficiently ferment xylose and other pentose sugars into a desired fermentation product is therefore very desirable.

Thus, in one aspect, the recombinant microorganism is engineered to express a functional exogenous xylose isomerase. Exogenous xylose isomerases functional in yeast are known in the art. See, e.g., Rajgarhia et al, US20060234364, which is herein incorporated by reference in its entirety. In an embodiment according to this aspect, the exogenous xylose isomerase gene is operatively linked to promoter and terminator sequences that are functional in the yeast cell. In a preferred embodiment, the recombinant microorganism further has a deletion or disruption of a native gene that encodes for an enzyme (e.g. XR and/or XDH) that catalyzes the conversion of xylose to xylitol. In a further preferred embodiment, the recombinant microorganism also contains a functional, exogenous xylulokinase (XK) gene operatively linked to promoter and terminator sequences that are functional in the yeast cell. In one embodiment, the xylulokinase (XK) gene is overexpressed.

The disclosure identifies specific genes useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutation and silent mutations. Such modified or mutated polynucleotides and polypeptides can be screened for expression of a functional enzyme using methods known in the art.

Due to the inherent degeneracy of the genetic code, other polynucleotides which encode substantially the same or a functionally equivalent polypeptide can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

Those of skill in the art will recognize that, due to the degenerate nature of the genetic code, a variety of DNA compounds differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as they modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for generating metabolites are encompassed by the microorganisms and methods provided herein.

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, hereby incorporated herein by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A typical algorithm used comparing a molecule sequence to a database containing a large number of sequences from different organisms is the computer program BLAST (Altschul, S. F., et al. (1990) "Basic local alignment search tool." J. Mol. Biol. 215:403-410; Gish, W. and States, D. J. (1993) "Identification of protein coding regions by database similarity search." Nature Genet. 3:266-272; Madden, T. L., et al. (1996) "Applications of network BLAST server" Meth. Enzymol. 266:131-141; Altschul, S. F., et al. (1997) "Gapped BLAST and PSI-BLAST: a new generation of protein database search programs." Nucleic Acids Res. 25:3389-3402; Zhang, J. and Madden, T. L. (1997) "PowerBLAST: A new network BLAST application for interactive or automated sequence analysis and annotation." Genome Res. 7:649-656), especially blastp or tblastn (Altschul, S. F., et al. (1997) "Gapped BLAST and PSI-BLAST: a new generation of protein database search programs." Nucleic Acids Res. 25:3389-3402). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, W. R. (1990) "Rapid and Sensitive Sequence Comparison with FASTP and FASTA" Meth. Enzymol. 183:63-98). For example, percent sequence identity between amino acid sequences can be determined using FASTA with its default parameters (a word size of 2 and the PAM250 scoring matrix), as provided in GCG Version 6.1, hereby incorporated herein by reference.

It is understood that a range of microorganisms can be modified to include recombinant metabolic pathways suitable for the production of C3-C5 alcohols, including isobutanol. In various embodiments, microorganisms may be selected from bacterial or yeast microorganisms. Microorganisms for the production of C3-C5 alcohols, including isobutanol may be selected based on certain characteristics:

One characteristic may include the ability to metabolize a carbon source in the presence of a C3-C5 alcohol, including isobutanol. A microorganism capable of metabolizing a carbon source at a high isobutanol concentration is more suitable as a production microorganism compared to a microorganism capable of metabolizing a carbon source at a low isobutanol concentration. Another characteristic may include the property that the microorganism is selected to convert various carbon sources into C3-C5 alcohols, including isobutanol. Accordingly, in one embodiment, the recombinant microorganism herein disclosed can convert a variety of carbon sources to products, including but not limited to glucose, galactose, mannose, xylose, arabinose, lactose, sucrose, and mixtures thereof.

Another characteristic specific to a yeast microorganism may include the property that the microorganism is able to metabolize a carbon source in the absence of pyruvate decarboxylase (PDC). In an embodiment, it is preferable that the yeast microorganism is able to metabolize 5- and 6-carbon sugar in the absence of PDC. In one embodiment, it is even more preferred that a yeast microorganism is able to grow on 5- and 6-carbon sugars in the absence of PDC.

Another characteristic may include the property that the wild-type or parental microorganism is non-fermenting. In other words, it cannot metabolize a carbon source anaerobically while the yeast is able to metabolize a carbon source in the presence of oxygen. Non-fermenting yeast refers to both naturally occurring yeasts as well as genetically modified yeast. During anaerobic fermentation with fermentative yeast, the main pathway to oxidize the NADH from glycolysis is through the production of ethanol. Ethanol is produced by alcohol dehydrogenase (ADH) via the reduction of acetaldehyde, which is generated from pyruvate by pyruvate decarboxylase (PDC).

Thus, in one embodiment, a fermentative yeast can be engineered to be non-fermentative by the reduction or elimination of the native PDC activity. Thus, most of the pyruvate produced by glycolysis is not consumed by PDC and is available for the isobutanol pathway. Deletion of this pathway increases the pyruvate and the reducing equivalents available for the isobutanol pathway. Fermentative pathways contribute to low yield and low productivity of isobutanol. Accordingly, deletion of PDC may increase yield and productivity of isobutanol. In one embodiment, the yeast microorganisms may be selected from the "*Saccharomyces* Yeast Clade", defined as an ascomycetous yeast taxonomic class by Kurtzman and Robnett in 1998 ("Identification and phylogeny of ascomycetous yeast from analysis of nuclear large subunit (26S) ribosomal DNA partial sequences." Antonie van Leeuwenhoek 73: 331-371, see FIG. 2 of Leeuwenhook reference). They were able to determine the relatedness of yeast of approximately 500 yeast species by comparing the nucleotide sequence of the D1/D2 domain at the 5' end of the gene encoding the large ribosomal subunit 26S. In pair-wise comparisons of the D1/D2 nucleotide sequence of *S. cerevisiae* and the two most distant yeast in the *Saccharomyces* clade: *K. lactis* and *K. marxianus*, yeast from this clade share greater than 80% identity.

An ancient whole genome duplication (WGD) event occurred during the evolution of hemiascomycete yeast was discovered using comparative genomics tools (Kellis et al 2004 "Proof and evolutionary analysis of ancient genome duplication in the yeast *S. cerevisiae.*" *Nature* 428:617-624. Dujon et al 2004 "Genome evolution in yeasts." *Nature* 430: 35-44. Langkjaer et al 2003 "Yeast genome duplication was followed by asynchronous differentiation of duplicated genes." *Nature* 428:848-852. Wolfe and Shields 1997 "Molecular evidence for an ancient duplication of the entire yeast genome." *Nature* 387:708-713.) Using this major evolutionary event, yeast can be divided into species that diverged from a common ancestor following the WGD event (termed "post-WGD yeast" herein) and species that diverged from the yeast lineage prior to the WGD event (termed "pre-WGD yeast" herein).

Accordingly, in one embodiment, the yeast microorganism may be selected from a post-WGD yeast genus, including but not limited to *Saccharomyces* and *Candida*. The favored post-WGD yeast species include: *S. cerevisiae, S. uvarum, S. bayanus, S. paradoxus, S. casteffi*, and *C. glabrata.*

In another embodiment, a method provided herein includes a recombinant organism that is a *Saccharomyces* sensu stricto yeast microorganism. In one aspect, a *Saccharomyces* sensu stricto yeast microorganism is selected from one of the species: *S. cerevisiae, S. cerevisiae, S. kudriavzevii, S. mikatae, S. bayanus, S. uvarum, S. carocanis* or hybrids thereof.

In another embodiment, the yeast microorganism may be selected from a pre-whole genome duplication (pre-WBD) yeast genus including but not limited to *Saccharomyces, Kluyveromyces, Issatchenkia, Candida, Pichia, Debaryomyces, Hansenula, Pachysolen, Yarrowia* and, *Schizosaccharomyces*. Representative pre-WGD yeast species include: *S. kluyveri, K. thermotolerans, K. marxianus, K. waltii, K. lactis, C. tropicalis, P. pastoris*, P. anomala, P. stipitis, D. hansenii, H. anomala, P. tannophilis, I. orientalis, Y. lipolytica, and *S. pombe.*

A yeast microorganism may be either Crabtree-negative or Crabtree-positive. A yeast cell having a Crabtree-negative phenotype is any yeast cell that does not exhibit the Crabtree effect. The term "Crabtree-negative" refers to both naturally occurring and genetically modified organisms. Briefly, the Crabtree effect is defined as the inhibition of oxygen consumption by a microorganism when cultured under aerobic conditions due to the presence of a high concentration of glucose (e.g., 50 g-glucose $L^{-1}$). In other words, a yeast cell having a Crabtree-positive phenotype continues to ferment irrespective of oxygen availability due to the presence of glucose, while a yeast cell having a Crabtree-negative phenotype does not exhibit glucose mediated inhibition of oxygen consumption.

Accordingly, in one embodiment the yeast microorgnanism may be selected from a yeast with a Crabtree-negative phenotype including but not limited to the following genera: *Kluyveromyces, Pichia, Issatchenkia, Hansenula*, and *Candida*. Crabtree-negative species include but are not limited to: *K. lactis, K. marxianus, P. anomala, P. stipitis, H. anomala, I. orientalis*, and *C. utilis.*

In another embodiment, the yeast microorganism may be selected from a yeast with a Crabtree-positive phenotype, including but not limited to *Saccharomyces, Kluyveromyces, Zygosaccharomyces, Debaryomyces, Pichia* and *Schizosaccharomyces*. Crabtree-positive yeast species include but are not limited to: *S. cerevisiae, S. uvarum, S. bayanus, S. paradoxus, S. casteffi, S. kluyveri, K. thermotolerans, C. glabrata, Z. bailli, Z. rouxii, D. hansenii, P. pastorius*, and *S. pombe.*

Bacterial Microorganisms may be selected from a number of genera, including but not limited to *Arthrobacter, Bacillus, Brevibacterium, Clostridium, Corynebacterium, Cyanobacterium, Escherichia, Gluconobacter, Lactobacillus, Nocardia, Pseudomonas, Rhodococcus, Saccharomyces, Shewanella, Streptomyces, Xanthomonas*, and *Zymomonas*. In another embodiment, such hosts are *Corynebacterium, Cyanobacterium, E. coli* or *Pseudomonas*. In another embodiment, such hosts are *E. coli* W3110, *E. coli* B, *Pseudomonas oleovorans, Pseudomonas fluorescens*, or *Pseudomonas putida.*

One exemplary metabolic pathway for the conversion of a carbon source to a C3-C5 alcohol via pyruvate begins with the conversion of glucose to pyruvate via glycolysis. Glycolysis also produces 2 moles of NADH and 2 moles of ATP. Two moles of pyruvate are then used to produce one mole of isobutanol (PCT/US2006/041602, PCT/US2008/053514). Alternative isobutanol pathways have been described in International Patent Application No PCT/US2006/041602 and in Dickinson et al., *Journal of Biological Chemistry* 273:25751-15756 (1998).

Accordingly, the engineered isobutanol pathway to convert pyruvate to isobutanol can be, but is not limited to, the following reactions:

$$2\ \text{pyruvate} \rightarrow \text{acetolactate} + CO_2 \quad 1.$$

$$\text{acetolactate} + \text{NADPH} \rightarrow \text{2,3-dihydroxyisovalerate} + \text{NADP+} \quad 2.$$

$$\text{2,3-dihydroxyisovalerate} \rightarrow \text{alpha-ketoisovalerate} \quad 3.$$

$$\text{alpha-ketoisovalerate} \rightarrow \text{isobutyraldehyde} + CO_2 \quad 4.$$

$$\text{isobutyraldehyde} + \text{NADPH} \rightarrow \text{isobutanol} + \text{NADP}^+ \quad 5.$$

These reactions are carried out by the enzymes 1) Acetolactate Synthase (ALS), 2) Ketol-acid Reducto-Isomerase (KARI), 3) Dihydroxy-acid dehydratase (DHAD), 4) Keto-isovalerate decarboxylase (KIVD), and 5) an Alcohol Dehydrogenase (ADH).

In another embodiment, the microorganism is engineered to overexpress these enzymes. For example, ALS can be encoded by the aisS gene of *B. subtilis*, aisS of *L. lactis*, or the ilvK gene of *K. pneumonia*. For example, KARI can be encoded by the ilvC genes of *E. coli, C. glutamicum*, M. maripaludis, or *Piromyces* sp E2. For example, DHAD can be encoded by the ilvD genes of *E. coli, L. lactis*, or *C. glutamicum*, or by the ILV3 gene from *S. cerevisiae*. KIVD can be encoded by the kivd gene of *L. lactis*. ADH can be encoded by ADH2, ADH6, or ADH7 of *S. cerevisiae*, by the adhA gene product of *L. lactis*, or by an ADH from *D. melanogaster.*

The microorganism of the invention may be engineered to have increased ability to convert pyruvate to a C3-C5 alcohol, including isobutanol. In one embodiment, the microorganism may be engineered to have increased ability to convert pyruvate to isobutyraldehyde. In another embodiment, the microorganism may be engineered to have increased ability to convert pyruvate to keto-isovalerate. In another embodiment, the microorganism may be engineered to have increased ability to convert pyruvate to 2,3-dihydroxyisovalerate. In another embodiment, the microorganism may be engineered to have increased ability to convert pyruvate to acetolactate.

Furthermore, any of the genes encoding the foregoing enzymes (or any others mentioned herein (or any of the regulatory elements that control or modulate expression thereof)) may be optimized by genetic/protein engineering techniques, such as directed evolution or rational mutagenesis.

It is understood that various microorganisms can act as "sources" for genetic material encoding target enzymes suitable for use in a recombinant microorganism provided herein. For example, In addition, genes encoding these enzymes can be identified from other fungal and bacterial species and can be expressed for the modulation of this pathway. A variety of eukaryotic organisms could serve as sources for these enzymes, including, but not limited to, *Drosophila* spp., including *D. melanogaster, Saccharomyces* spp., including *S. cerevisiae* and S. uvarum, *Kluyveromyces* spp., including *K. thermotolerans, K. lactis*, and *K. marxianus, Pichia* spp., *Hansenula* spp., including *H. polymorpha, Candida* spp., *Trichosporon* spp., *Yamadazyma* spp., including *Y. stipitis, Torulaspora pretoriensis, Schizosaccharomyces* spp., including *S. pombe, Cryptococcus* spp., *Aspergillus* spp., *Neurospora* spp., or *Ustilago* spp. Sources of genes from anaerobic fungi include, but not limited to, *Piromyces* spp., *Orpinomyces* spp., or *Neocallimastix* spp. Sources of prokaryotic enzymes that are useful include, but not limited to, *Escherichia. coli, Klebsiella* spp., including *K. pneumoniae, Zymomonas mobilis, Staphylococcus aureus, Bacillus* spp., *Clostridium* spp., *Corynebacterium* spp., *Pseudomonas* spp., *Lactococcus* spp., *Enterobacter* spp., and *Salmonella* spp.

Methods in General

Gene Expression

In another embodiment a method of producing a recombinant microorganism that converts a suitable carbon substrate to C3-C5 alcohols such as isobutanol is provided. The method includes transforming a microorganism with one or more recombinant polynucleotides encoding polypeptides that include but are not limited to, for example, ALS, KARI, DHAD, KIVD, ADH and a transhydrogenase. Polynucleotides that encode enzymes useful for generating metabolites including homologs, variants, fragments, related fusion proteins, or functional equivalents thereof, are used in recombinant nucleic acid molecules that direct the expression of such polypeptides in appropriate host cells, such as bacterial or yeast cells. It is understood that the addition of sequences which do not alter the encoded activity of a polynucleotide, such as the addition of a non-functional or non-coding sequence, is a conservative variation of the basic nucleic acid. The "activity" of an enzyme is a measure of its ability to catalyze a reaction resulting in a metabolite, i.e., to "function", and may be expressed as the rate at which the metabolite of the reaction is produced. For example, enzyme activity can be represented as the amount of metabolite produced per unit of time or per unit of enzyme (e.g., concentration or weight), or in terms of affinity or dissociation constants.

Those of skill in the art will recognize that, due to the degenerate nature of the genetic code, a variety of DNA compounds differing in their nucleotide sequences can be used to encode a given amino acid sequence of the disclosure. The native DNA sequence encoding the biosynthetic enzymes described herein are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with alternate amino acid sequences, and the amino acid sequences encoded by the DNA sequences shown herein merely illustrate embodiments of the disclosure.

The disclosure provides nucleic acid molecules in the form of recombinant DNA expression vectors or plasmids, as described in more detail below, that encode one or more target enzymes. Generally, such vectors can either replicate in the cytoplasm of the host microorganism or integrate into the chromosomal DNA of the host microorganism. In either case, the vector can be a stable vector (i.e., the vector remains present over many cell divisions, even if only with selective pressure) or a transient vector (i.e., the vector is gradually lost by host microorganisms with increasing numbers of cell divisions). The disclosure provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) forms.

Provided herein are methods for the expression of one or more of the genes involved in the production of beneficial metabolites and recombinant DNA expression vectors useful in the method. Thus, included within the scope of the disclosure are recombinant expression vectors that include such nucleic acids. The term expression vector refers to a nucleic acid that can be introduced into a host microorganism or cell-free transcription and translation system. An expression vector can be maintained permanently or transiently in a microorganism, whether as part of the chromosomal or other DNA in the microorganism or in any cellular compartment, such as a replicating vector in the cytoplasm. An expression vector also comprises a promoter that drives expression of an RNA, which typically is translated into a polypeptide in the microorganism or cell extract. For efficient translation of RNA into protein, the expression vector also typically contains a ribosome-binding site sequence positioned upstream of the start codon of the coding sequence of the gene to be expressed. Other elements, such as enhancers, secretion signal sequences, transcription termination sequences, and one or more marker genes by which host microorganisms containing the vector can be identified and/or selected, may also be present in an expression vector. Selectable markers, i.e., genes that confer antibiotic resistance or sensitivity, are used and confer a selectable phenotype on transformed cells when the cells are grown in an appropriate selective medium.

The various components of an expression vector can vary widely, depending on the intended use of the vector and the host cell(s) in which the vector is intended to replicate or drive expression. Expression vector components suitable for the expression of genes and maintenance of vectors in *E. coli*, yeast, *Streptomyces*, and other commonly used cells are widely known and commercially available. For example, suitable promoters for inclusion in the expression vectors of the disclosure include those that function in eukaryotic or prokaryotic host microorganisms. Promoters can comprise regulatory sequences that allow for regulation of expression relative to the growth of the host microorganism or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433), can also be used. For *E. coli* expression vectors, it is useful to include an *E. coli* origin of replication, such as from pUC, p1 P, p1, and pBR.

Thus, recombinant expression vectors contain at least one expression system, which, in turn, is composed of at least a portion of PKS and/or other biosynthetic gene coding sequences operably linked to a promoter and optionally termination sequences that operate to effect expression of the coding sequence in compatible host cells. The host cells are modified by transformation with the recombinant DNA expression vectors of the disclosure to contain the expression system sequences either as extrachromosomal elements or integrated into the chromosome.

Moreover, methods for expressing a polypeptide from a nucleic acid molecule that are specific to yeast microorganisms are well known. For example, nucleic acid constructs that are used for the expression of heterologous polypeptides within *Kluyveromyces* and *Saccharomyces* are well known (see, e.g., U.S. Pat. Nos. 4,859,596 and 4,943,529, each of which is incorporated by reference herein in its entirety for *Kluyveromyces* and, e.g., Gellissen et al., Gene 190(1):87-97 (1997) for *Saccharomyces*. Yeast plasmids have a selectable marker and an origin of replication, also known as Autonomously Replicating Sequences (ARS). In addition certain plasmids may also contain a centromeric sequence. These centromeric plasmids are generally a single or low copy plasmid. Plasmids without a centromeric sequence and utilizing either a 2 micron (*S. cerevisiae*) or 1.6 micron (*K. lactis*) replication origin are high copy plasmids. The selectable marker can be either prototrophic, such as HIS3, TRP1, LEU2, URA3 or ADE2, or antibiotic resistance, such as, bar, ble, hph, or kan.

A nucleic acid of the disclosure can be amplified using cDNA, mRNA or alternatively, genomic DNA, as a template and appropriate oligonucleotide primers according to standard PCR amplification techniques and those procedures described in the Examples section below. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

It is also understood that an isolated nucleic acid molecule encoding a polypeptide homologous to the enzymes described herein can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the polynucleotide by standard techniques, such as site-directed mutagenesis and PCR-mediated mutagenesis. In contrast to those positions where it may be desirable to make a non-conservative amino acid substitutions (see above), in some positions it is preferable to make conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Although the effect of an amino acid change varies depending upon factors such as phosphorylation, glycosylation, intra-chain linkages, tertiary structure, and the role of the amino acid in the active site or a possible allosteric site, it is generally preferred that the substituted amino acid is from the same group as the amino acid being replaced. To some extent the following groups contain amino acids which are interchangeable: the basic amino acids lysine, arginine, and histidine; the acidic amino acids aspartic and glutamic acids; the neutral polar amino acids serine, threonine, cysteine, glutamine, asparagine and, to a lesser extent, methionine; the nonpolar aliphatic amino acids glycine, alanine, valine, isoleucine, and leucine (however, because of size, glycine and alanine are more closely related and valine, isoleucine and leucine are more closely related); and the aromatic amino acids phenylalanine, tryptophan, and tyrosine. In addition, although classified in different categories, alanine, glycine, and serine seem to be interchangeable to some extent, and cysteine additionally fits into this group, or may be classified with the polar neutral amino acids.

Overexpression of Heterologous Genes

Methods for overexpressing a polypeptide from a native or heterologous nucleic acid molecule are well known. Such methods include, without limitation, constructing a nucleic acid sequence such that a regulatory element promotes the expression of a nucleic acid sequence that encodes the desired polypeptide. Typically, regulatory elements are DNA sequences that regulate the expression of other DNA sequences at the level of transcription. Thus, regulatory elements include, without limitation, promoters, enhancers, and the like. For example, the exogenous genes can be under the control of an inducible promoter or a constitutive promoter. Moreover, methods for expressing a polypeptide from an exogenous nucleic acid molecule in yeast are well known. For example, nucleic acid constructs that are used for the expression of exogenous polypeptides within *Kluyveromyces* and *Saccharomyces* are well known (see, e.g., U.S. Pat. Nos. 4,859,596 and 4,943,529, for *Kluyveromyces* and, e.g., Gellissen et al., Gene 190(1):87-97 (1997) for *Saccharomyces*). Yeast plasmids have a selectable marker and an origin of replication. In addition certain plasmids may also contain a centromeric sequence. These centromeric plasmids are generally a single or low copy plasmid. Plasmids without a centromeric sequence and utilizing either a 2 micron (*S. cerevisiae*) or 1.6 micron (*K. lactis*) replication origin are high copy plasmids. The selectable marker can be either prototrophic, such as HIS3, TRP1, LEU2, URA3 or ADE2, or antibiotic resistance, such as, bar, ble, hph, or kan.

In another embodiment, heterologous control elements can be used to activate or repress expression of endogenous genes. Additionally, when expression is to be repressed or eliminated, the gene for the relevant enzyme, protein or RNA can be eliminated by known deletion techniques.

As described herein, any microorganism within the scope of the disclosure can be identified by selection techniques specific to the particular enzyme being expressed, over-expressed or repressed. Methods of identifying the strains with the desired phenotype are well known to those skilled in the art. Such methods include, without limitation, PCR, RT-PCR, and nucleic acid hybridization techniques such as Northern and Southern analysis, altered growth capabilities on a particular substrate or in the presence of a particular substrate, a chemical compound, a selection agent and the like. In some cases, immunohistochemistry and biochemical techniques can be used to determine if a cell contains a particular nucleic acid by detecting the expression of the encoded polypeptide. For example, an antibody having specificity for an encoded enzyme can be used to determine whether or not a particular microorganism contains that encoded enzyme. Further, biochemical techniques can be used to determine if a cell contains a particular nucleic acid molecule encoding an enzymatic polypeptide by detecting a product produced as a result of the expression of the enzymatic polypeptide. For example, transforming a cell with a vector encoding acetolactate synthase and detecting increased cytosolic acetolactate concentrations compared to a cell without the vector indicates that the vector is both present and that the gene product is active. Methods for detecting specific enzymatic activities or the presence of particular products are well known to those skilled in the art. For example, the presence of acetolactate can be determined as described by Hugenholtz and Starrenburg, *Appl. Microbiol. Biotechnol.* 38:17-22 (1992).

Identification of Genes in a Host Microorganism

Any method can be used to identify genes that encode for enzymes with a specific activity. Generally, homologous or analogous genes with similar activity can be identified by functional, structural, and/or genetic analysis. In most cases, homologous or analogous genes with similar activity will have functional, structural, or genetic similarities. Techniques known to those skilled in the art may be suitable to identify homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous genes, proteins, or enzymes, techniques may include, but not limited to, cloning a gene by PCR using primers based on a published sequence of a gene/enzyme or by degenerate PCR using degenerate primers designed to amplify a conserved region among a gene. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity, then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or analogous genes with similar activity, techniques also include comparison of data concerning a candidate gene or enzyme with databases such as BRENDA, KEGG, or MetaCYC. The candidate gene or enzyme may be identified within the above mentioned databases in accordance with the teachings herein. Furthermore, enzymatic activity can be determined phenotypically. For example, ethanol production under fermentative conditions can be assessed. A lack of ethanol production may be indicative of a microorganism lacking an alcohol dehydrogenase capable of reducing acetaldehyde to ethanol.

Genetic Insertions and Deletions

Any method can be used to introduce a nucleic acid molecule into the chromosomal DNA of a microorganism and many such methods are well known. For example, lithium acetate transformation and electroporation are common methods for introducing nucleic acid into yeast microorganisms. See, e.g., Gietz et al., *Nucleic Acids Res.* 27:69-74 (1992); Ito et al., *J. Bacterol.* 153:163-168 (1983); and Becker and Guarente, *Methods in Enzymology* 194:182-187 (1991).

In an embodiment, the deletion of a gene of interest in a bacterial microorganism, including an *E. coli* microorganism occurs according to the principle of homologous recombination. According to this embodiment, an integration cassette containing a module comprising at least one marker gene is flanked on either side by DNA fragments homologous to those of the ends of the targeted integration site. After transforming the host microorganism with the cassette by appropriate methods, homologous recombination between the flanking sequences may result in the marker replacing the chromosomal region in between the two sites of the genome corresponding to flanking sequences of the integration cassette. The homologous recombination event may be facilitated by a recombinase enzyme that may be native to the host microorganism or may be heterologous and transiently overexpressed (Datsenko and Wanner, Proc. Natl. Acad. Sci. USA 97, 6640-6645, 2000).

In an embodiment, the integration of a gene of interest into a DNA fragment or target gene of a yeast microorganism occurs according to the principle of homologous recombination. According to this embodiment, an integration cassette containing a module comprising at least one yeast marker gene and/or the gene to be integrated (internal module) is flanked on either side by DNA fragments homologous to those of the ends of the targeted integration site (recombinogenic sequences). After transforming the yeast with the cassette by appropriate methods, a homologous recombination between the recombinogenic sequences may result in the internal module replacing the chromosomal region in between the two sites of the genome corresponding to the recombinogenic sequences of the integration cassette. (Orr-Weaver et al., *Proc Natl Acad Sci USA* 78:6354-6358 (1981))

In an embodiment, the integration cassette for integration of a gene of interest into a yeast microorganism includes the heterologous gene under the control of an appropriate promoter and terminator together with the selectable marker flanked by recombinogenic sequences for integration of a heterologous gene into the yeast chromosome. In an embodiment, the heterologous gene includes an appropriate native gene desired to increase the copy number of a native gene(s). The selectable marker gene can be any marker gene used in yeast, including but not limited to, HIS3, TRP1, LEU2, URA3, bar, ble, hph, and kan. The recombinogenic sequences can be chosen at will, depending on the desired integration site suitable for the desired application.

Additionally, in an embodiment pertaining to yeast microorganisms, certain introduced marker genes are removed from the genome using techniques well known to those skilled in the art. For example, URA3 marker loss can be obtained by plating URA3 containing cells in FOA (5-fluoro-orotic acid) containing medium and selecting for FOA resistant colonies (Boeke, J. et al, 1984, *Mol. Gen. Genet,* 197, 345-47).

Integration of all the genes of a metabolic pathway that lead to a product into the genome of the production strain eliminates the need of a plasmid expression system, as the enzymes are produced from the chromosome. The integration of pathway genes avoids loss of productivity over time due to plasmid loss. This is important for long fermentation times and for fermentations in large scale where the seed train is long and the production strain has to go through many doublings from the first inoculation to the end of the large scale fermentation.

Integrated genes are maintained in the strain without selection. This allows the construction of production strains that are free of marker genes which are commonly used for maintenance of plasmids. Production strains with integrated pathway genes can contain minimal amounts of foreign DNA since there are no origins of replication and other non coding DNA necessary that have to be in plasmid based systems. The biocatalyst with integrated pathway genes improves the performance of a production process because it avoids energy and carbon requiring processes. These processes are the replication of many copies of plasmids and the production of non-pathway active proteins like marker proteins in the production strain.

The expression of pathway genes on multi-copy plasmids can lead to overexpression phenotypes for certain genes. These phenotypes can be growth retardation, inclusion bodies, and cell death. Therefore the expression levels of genes on multi copy plasmids has to be controlled effectively by using inducible expression systems, optimizing the time of induction of said expression system, and optimizing the amount of inducer provided. The time of induction has to be correlated to the growth phase of the biocatalyst, which can be followed by measuring of optical density in the fermentation broth.

A biocatalyst that has all pathway genes integrated on its chromosome is far more likely to allow constitutive expression since the lower number of gene copies may avoid overexpression phenotypes.

Plasmids disclosed herein were generally based upon parental plasmids described previously (Lutz, R. & Bujard, H. (1997) Nucleic Acids Research 25(6):1203-1210). Plasmids pGV1698 (SEQ ID NO: 112) and pGV1655 (SEQ ID NO: 109) produce optimized levels of isobutanol pathway enzymes in a production host when compared to other expression systems in the art. Compared to the expression of the isobutanol pathway from pSA55 and pSA69 as described in (WO 2008/098227) BIOFUEL PRODUCTION BY RECOMBINANT MICROORGANISMS, pGV1698 and pGV1655 lead to higher expression of *E. coli* IlvC and *Bacillus subtilis* AlsS and lower expression levels for *Lactococcus* lactis Kivd and *E. coli* ilvD. These changes are the result of differences in plasmid copy numbers. Also the genes coding for *E. coli* IlvD and *E. coli* IlvC were codon optimized for *E. coli*. This leads to optimized expression of the genes and it also avoids recombination of these genes with their native copies on the *E. coli* chromosome, thus stabilizing the production strain. The combination of two plasmids with the pSC101 and the ColE1 origin of replication in one cell as realized in a production strain carrying pGV1698 and pGV1655 is known to be more stable than the combination of two plasmids with p15A and ColE1 origins respectively as was used in the prior art (WO 2008/098227—BIOFUEL PRODUCTION BY RECOMBINANT MICROORGANISMS).

Reduction of Enzymatic Activity

Host microorganisms within the scope of the invention may have reduced enzymatic activity such as reduced alcohol dehydrogenase activity. The term "reduced" as used herein with respect to a particular enzymatic activity refers to a lower level of enzymatic activity than that measured in a comparable host cell of the same species. Thus, host cells lacking alcohol dehydrogenase activity are considered to have reduced alcohol dehydrogenase activity since most, if not all, comparable host cells of the same species have at least some alcohol dehydrogenase activity. Such reduced enzymatic activities can be the result of lower enzyme expression level, lower specific activity of an enzyme, or a combination thereof. Many different methods can be used to make host cells having reduced enzymatic activity. For example, a host cell can be engineered to have a disrupted enzyme-encoding locus using common mutagenesis or knock-out technology. See, e.g., Methods in Yeast Genetics (1997 edition), Adams, Gottschling, Kaiser, and Stems, Cold Spring Harbor Press (1998), Datsenko and Wanner, Proc. Natl. Acad. Sci. USA 97, 6640-6645, 2000.

In addition, certain point-mutation(s) can be introduced which results in an enzyme with reduced activity.

Alternatively, antisense technology can be used to reduce enzymatic activity. For example, host cells can be engineered to contain a cDNA that encodes an antisense molecule that prevents an enzyme from being made. The term "antisense molecule" as used herein encompasses any nucleic acid molecule that contains sequences that correspond to the coding strand of an endogenous polypeptide. An antisense molecule also can have flanking sequences (e.g., regulatory sequences). Thus antisense molecules can be ribozymes or antisense oligonucleotides. A ribozyme can have any general structure including, without limitation, hairpin, hammerhead, or axhead structures, provided the molecule cleaves RNA.

Host cells having a reduced enzymatic activity can be identified using many methods. For example, host cells having reduced alcohol dehydrogenase activity can be easily identified using common methods, which may include, for example, measuring ethanol formation via gas chromatography.

Increase of Enzymatic Activity

Host microorganisms of the invention may be further engineered to have increased activity of enzymes. The term "increased" as used herein with respect to a particular enzymatic activity refers to a higher level of enzymatic activity than that measured in a comparable yeast cell of the same species. For example, overexpression of a specific enzyme can lead to an increased level of activity in the cells for that enzyme. Increased activities for enzymes involved in glycolysis or the isobutanol pathway would result in increased productivity and yield of isobutanol.

Methods to increase enzymatic activity are known to those skilled in the art. Such techniques may include increasing the expression of the enzyme by increasing plasmid copy number and/or use of a stronger promoter and/or use of activating riboswitches, introduction of mutations to relieve negative regulation of the enzyme, introduction of specific mutations to increase specific activity and/or decrease the $K_M$ for the substrate, or by directed evolution. See, e.g., Methods in Molecular Biology (vol. 231), ed. Arnold and Georgiou, Humana Press (2003).

Microorganism in Detail

Microorganism Characterized by the Ability to Produce Isobutanol Under Anaerobic Conditions Economic studies indicate that the aeration of a fermentation process leads to increased operating and capital expenses and thus makes such a fermentation process less desirable compared to a fermentation process that operates under anaerobic conditions. In addition, yield and aeration conditions are closely related. For example, oxygen used as the terminal electron acceptor in respiration leads to undesired loss of carbon in the form of carbon dioxide, resulting in a reduced yield of the target compound.

As exemplified in the examples below, the present inventors have overcome the problem of an oxygen requirement for the production of a fermentation product. For example isobutanol was produced anaerobically at rates, titers and yields comparable to those achieved under micro-aerobic conditions.

Thus, in one embodiment, a modified microorganism may produce said fermentation product under anaerobic conditions, conditions at higher rates, and yields, as compared to a the wild-type or parental microorganism.

In one embodiment, said modified microorganism may be engineered to balance cofactor usage during the production of said fermentation product under anaerobic conditions.

In a specific aspect, a modified microorganism in which cofactor usage is balanced during the production of isobutanol may allow the microorganism to produce said isobutanol under anaerobic conditions at higher rates and yields as compared to a modified microorganism in which the cofactor usage in not balanced during production of isobutanol. One compound to be produced by the recombinant microorganism according to the present invention is isobutanol. However, the present invention is not limited to isobutanol. The invention may be applicable to any metabolic pathway that is imbalanced with respect to cofactor usage. One of skill in the art is able identify pathways that are imbalanced with respect to cofactor usage and apply this invention to provide recombinant microorganisms in which the same pathway is balanced with respect to cofactor usage.

Any method, including the methods described herein may be used to provide a modified microorganism with a metabolic pathway for the production of a target compound in which the cofactor usage is balanced; i.e. said metabolic pathway utilizes the same cofactor that is produced during glycolysis.

In one embodiment, the microorganism may converts glucose, which can be derived from biomass into a target compound under anaerobic conditions with a yield of greater than 75% of theoretical. In another embodiment, the yield is greater than 80% of theoretical. In another embodiment the yield is greater than 85% of theoretical. In another embodiment, the yield is greater than 90% of theoretical. In another embodiment, the yield is greater than 95% of theoretical. In another embodiment, the yield is greater than 97% of theoretical. In another embodiment the yield is greater than 98% of theoretical. In yet another embodiment, the yield is greater than 99% of theoretical. In still another embodiment, the yield is approximately 100% of theoretical In one aspect, the microorganism may convert glucose, which can be derived from biomass into isobutanol under anaerobic conditions with a yield of greater than 50% of theoretical. In one embodiment, the yield is greater than 60% theoretical. In another embodiment, the yield is greater than 70% of theoretical. In yet another embodiment the yield is greater than 80% of theoretical. In yet another embodiment, the yield is greater than 85% of theoretical. In another embodiment, the yield is greater than 90% of theoretical. In yet another embodiment, the yield is greater than 95% of theoretical. In yet another embodiment, the yield is greater than 97% of theoretical. In yet another embodiment the yield is greater than 98% of theoretical. In yet another embodiment, the yield is greater than 99% of theoretical. In still another embodiment, the yield is approximately 100% of theoretical.

It is understood that while in the present disclosure the yield is exemplified for glucose as a carbon source, the invention can be applied to other carbon sources and the yield may vary depending on the carbon source used. One skilled in the art can calculate yields on various carbon sources. Other carbon sources, such as including but not limited to galactose, mannose, xylose, arabinose, sucrose, lactose, may be used. Further, oligomers or polymers of these and other sugars may be used as a carbon source.

Microorganism Characterized by an Increased Product Yield

Economic studies indicate that the predominant factor accounting for the production cost for commodity chemicals and fuels from fermentation processes is attributed to the feedstock cost. In fact, as much as 60% of the variable cash operating costs or more may be attributable to feedstock costs. An important measure of the process economics is therefore the product yield. For a biocatalyst to produce a biofuel most economically, a single product is desired. Extra products reduce primary product yield increasing capital and operating costs, particularly if those extra, undesired products, or byproducts have little or no value. Extra products or byproducts also require additional capital and operating costs to separate these products from the product or biofuel of interest or may require additional cost for disposal.

As exemplified in the examples below, the present inventors have shown that, achieving cofactor balance increases the yield of fermentation products as compared to wild-type or parental organisms.

In an embodiment, a microorganism is provided in which cofactor usage is balanced during the production of a fermentation product and the microorganism produces the fermentation product at a higher yield compared to a modified microorganism in which the cofactor usage in not balanced.

In a specific aspect of the present invention, a microorganism is provided in which cofactor usage is balanced during the production of isobutanol and the microorganism produces isobutanol at a higher yield compared to a modified microorganism in which the cofactor usage in not balanced.

One compound to be produced by the recombinant microorganism according to the present invention is isobutanol. However, the present invention is not limited to isobutanol. The invention may be applicable to any microorganism comprising a metabolic pathway that leads to an imbalance with respect to cofactor usage. One of skill in the art is able to identify microorganisms comprising metabolic pathways that lead to an imbalance with respect to cofactor usage and apply this invention to provide recombinant microorganisms in which the microorganism comprising the same metabolic pathway is balanced with respect to cofactor usage.

Any method, including the methods described herein may be used to provide a modified microorganism with a metabolic pathway for the production of a target compound in which the cofactor usage is balanced; i.e. said metabolic pathway utilizes the same cofactor that is produced during glycolysis.

In one embodiment, the microorganism may convert glucose, which can be derived from biomass into a target compound with a yield of greater than 75% of theoretical. In another embodiment, the yield is greater than 80% of theoretical. In another embodiment the yield is greater than 85% of theoretical. In another embodiment, the yield is greater than 90% of theoretical. In another embodiment, the yield is greater than 95% of theoretical. In another embodiment, the yield is greater than 97% of theoretical. In another embodiment the yield is greater than 98% of theoretical. In yet another embodiment, the yield is greater than 99% of theoretical. In still another embodiment, the yield is approximately 100% of theoretical In one aspect, the microorganism may convert glucose, which can be derived from biomass into isobutanol with a yield of greater than 75% of theoretical. In one embodiment, the yield is greater than 80% of theoretical. In one embodiment the yield is greater than 85% of theoretical. In another embodiment, the yield is greater than 90% of theoretical. In yet another embodiment, the yield is greater than 95% of theoretical. In yet another embodiment, the yield is greater than 97% of theoretical. In yet another embodiment the yield is greater than 98% of theoretical. In yet another embodiment, the yield is greater than 99% of theoretical. In still another embodiment, the yield is approximately 100% of theoretical.

It is understood that while in the present disclosure the yield is exemplified for glucose as a carbon source, the invention can be applied to other carbon sources and the yield may vary depending on the carbon source used. One skilled in the art can calculate yields on various carbon sources. Other carbon sources, such as including but not limited to galactose, mannose, xylose, arabinose, sucrose, lactose, may be used. Further, oligomers or polymers of these and other sugars may be used as a carbon source.

Microorganism Characterized by Balancing Cofactor Usage

The ideal production microorganism produces a desirable product at close to theoretical yield. For example the ideal isobutanol producing organism produces isobutanol according to the following equation:

$$1\ \text{glucose} \rightarrow \text{isobutanol} + 2\ CO_2 + H_2O$$

Accordingly, 66% of the glucose carbon results in isobutanol, while 33% is lost as $CO_2$. In exemplary metabolic pathways for the conversion of pyruvate to isobutanol described by Atsumi et al. (Atsumi et al., Nature, 2008 Jan. 3; 451(7174):86-9, which is herein incorporated by reference; International Patent Application No PCT/US2008/053514, which is herein incorporated by reference) two of the five enzymes used to convert pyruvate into isobutanol according to the metabolic pathway outlined in FIG. 1 require the reduced cofactor nicotinamide adenine dinucleotide phosphate (NADPH). NADPH is produced only sparingly by the cell—the reduced cofactor nicotinamide adenine dinucleotide (NADH) is the preferred equivalent. Respiration is required to produce NADPH in the large quantities required to support high-level production of isobutanol.

Even If competing pathways can be eliminated or reduced in activity by metabolic engineering, yield is limited to about 83% of theoretical. Carbon loss to carbon dioxide ($CO_2$) remains the main limitation on yield in the aforementioned metabolic pathway for the production of isobutanol. Reducing the oxygen uptake rate (OUR) of the cells should decrease the loss of carbon to $CO_2$ because it decreases the metabolic flux through the $CO_2$-generating tricarboxylic acid (TCA) cycle and/or pentose phosphate pathway (PPP). However, a modified microorganism utilizing the aforementioned metabolic pathway for the production of isobutanol exhibits drastically decreased specific productivity under conditions where the OUR is decreased and isobutanol production under anaerobic conditions may not be possible.

The decreased yield and the loss of productivity upon $O_2$ limitation indicate that the strain uses one or more metabolic pathways to generate the NADPH needed to support isobutanol production. In a modified cell utilizing the aforementioned metabolic pathway the production of isobutanol from glucose results in an imbalance between the cofactors reduced during glycolysis and the cofactors oxidized during the conversion of pyruvate to isobutanol. While glycolysis produces two moles of NADH, the isobutanol pathway consumes two moles of NADPH. This leads to a deficit of two moles of NADPH and overproduction of two moles of NADH per isobutanol molecule produced, a state described henceforth as cofactor imbalance.

The terms “cofactor balance” or “balanced with respect to cofactor usage” refer to a recombinant microorganism comprising a metabolic pathway converting a carbon source to a fermentation product and a modification that leads to the regeneration of all redox cofactors within the recombinant microorganism producing said fermentation product from a carbon source and wherein the re-oxidation or re-reduction of said redox cofactors does not require the pentose phosphate pathway, the TCA cycle or the generation of additional fermentation products.

Stated another way, the terms “cofactor balance” or “balanced with respect to cofactor usage” can refer to an advantageous modification that leads to the regeneration of all redox cofactors within the recombinant microorganism producing a fermentation product from a carbon source and wherein said re-oxidation or re-reduction of all redox cofactors does not require the production of byproducts or co-products.

Stated another way, the terms “cofactor balance” or “balanced with respect to cofactor usage” can refer to an advantageous modification that leads to the regeneration of all redox cofactors within the recombinant microorganism producing a fermentation product from a carbon source under anaerobic conditions and wherein the production of additional fermentation products is not required for re-oxidation or re-reduction of redox cofactors.

Stated another way, the terms “cofactor balance” or “balanced with respect to cofactor usage” can refer to an advantageous modification that leads to the regeneration of all redox cofactors within the recombinant microorganism producing a fermentation product from a carbon source and wherein said modification increases production of said fermentation product under anaerobic conditions compared to the parental or wild type microorganism and wherein additional fermentation products are not required for the regeneration of said redox cofactors.

The cell has several options for resolving a cofactor imbalance. One is to change the relative fluxes going from glucose through glycolysis and through the pentose phosphate pathway (PPP). For each glucose molecule metabolized through the PPP, two moles of NADPH are generated in addition to the two moles of NADH that are generated through glycolysis (a total of 4 reducing equivalents). Therefore, use of the PPP results in the generation of excess reducing equivalents since only two moles are consumed during the production of isobutanol. Under anaerobic conditions, and without an alternate electron acceptor, the cell has no way to reoxidize or regenerate these extra cofactors to $NADP^+$ and metabolism thus stops. The excess reducing equivalents must instead be utilized for energy production through aerobic respiration which is only possible under aerobic conditions or for the production of byproducts. Another result of the flux through the PPP is that one additional molecule of $CO_2$ is lost per molecule of glucose consumed, which limits the yield of isobutanol that can be achieved under aerobic conditions.

Another way the cell can generate NADPH is via the TCA cycle. Flux through the TCA cycle results in carbon loss through $CO_2$ and in production of NADH in addition to the NADPH required for the isobutanol pathway. The NADH would have to be utilized for energy production through respiration under aerobic conditions (and without an alternate electron acceptor) or for the production of byproducts. In addition, the TCA cycle likely is not functional under anaerobic conditions and is therefore unsuitable for the production of stoichiometric amounts of NADPH in an anaerobic isobutanol process.

An economically competitive isobutanol process requires a high yield from a carbon source. Lower yield means that more feedstock is required to produce the same amount of isobutanol. Feedstock cost is the major component of the overall operating cost, regardless of the nature of the feedstock and its current market price. From an economical perspective, this is important because the cost of isobutanol is dependent on the cost of the biomass-derived sugars. An increase in feedstock cost results in an increase in isobutanol cost. Thus, it is desirable to utilize NADH-dependent enzymes for the conversion of pyruvate to isobutanol.

An enzyme is "NADH-dependent" if it catalyzes the reduction of a substrate coupled to the oxidation of NADH with a catalytic efficiency that is greater than the reduction of the same substrate coupled to the oxidation of NADPH at equal substrate and cofactor concentrations.

Thus, in one embodiment of the invention, a microorganism is provided in which cofactor usage is balanced during the production of a fermentation product.

In a specific aspect, a microorganism is provided in which cofactor usage is balanced during the production of isobutanol, in this case, production of isobutanol from pyruvate utilizes the same cofactor that is produced during glycolysis.

In another embodiment, a microorganism is provided in which cofactor usage is balanced during the production of a fermentation product and the microorganism produces the fermentation product at a higher yield compared to a modified microorganism in which the cofactor usage in not balanced.

In a specific aspect, a microorganism is provided in which cofactor usage is balanced during the production of isobutanol and the microorganism produces isobutanol at a higher yield compared to a modified microorganism in which the cofactor usage in not balanced.

In yet another embodiment, a modified microorganism in which cofactor usage is balanced during the production of a fermentation product may allow the microorganism to produce said fermentation product under anaerobic conditions at higher rates, and yields as compared to a modified microorganism in which the cofactor usage in not balanced during production of a fermentation product.

In a specific aspect, a modified microorganism in which cofactor usage is balanced during the production of isobutanol may allow the microorganism to produce isobutanol under anaerobic conditions at higher rates, and yields as compared to a modified microorganism in which the cofactor usage is not balanced during production of isobutanol.

One compound to be produced by the recombinant microorganism according to the present invention is isobutanol. However, the present invention is not limited to isobutanol. The invention may be applicable to any metabolic pathway that is imbalanced with respect to cofactor usage. One skilled in the art is able to identify pathways that are imbalanced with respect to cofactor usage and apply this invention to provide recombinant microorganisms in which the same pathway is balanced with respect to cofactor usage. One skilled in the art will recognize that the identified pathways may be of longer or shorter length, contain more or fewer genes or proteins, and require more or fewer cofactors than the exemplary isobutanol pathway. Further, one skilled in the art will recognize that in certain embodiments, such as a recombinant microbial host that produces an excess of NADPH, certain embodiments of the present invention may be adapted to convert NADPH to NADH.

Microorganism Characterized by Providing Cofactor Balance Via Overexpression of a Transhydrogenase Conversion of glucose to pyruvate via glycolysis in *E. coli* leads to the production of two moles of NADH. A metabolic pathway that converts pyruvate to a target product that consumes either two moles of NADPH or one mole of NADH and one mole of NADPH leads to cofactor imbalance. For example, the isobutanol metabolic pathway that converts glucose to two moles of pyruvate via glycolysis to 1 mole of isobutanol generates two moles of NADH and consumes two moles of NADPH and thus is imbalanced with respect to cofactor usage.

The different ways in which the cell can provide NADPH to the isobutanol pathway show that utilization of the TCA cycle as well as the PPP has to be avoided to maximize the yield of the isobutanol process. Loss of $CO_2$ as a byproduct in isobutanol producing microorganism described in the prior art (Atsumi et al., Nature, 2008 Jan. 3; 451(7174):86-9; International Patent Application No PCT/US2008/053514; International Patent Application No PCT/US2006/041602) indicates that either or both of these two yield-limiting pathways are currently active.

Figure 2:
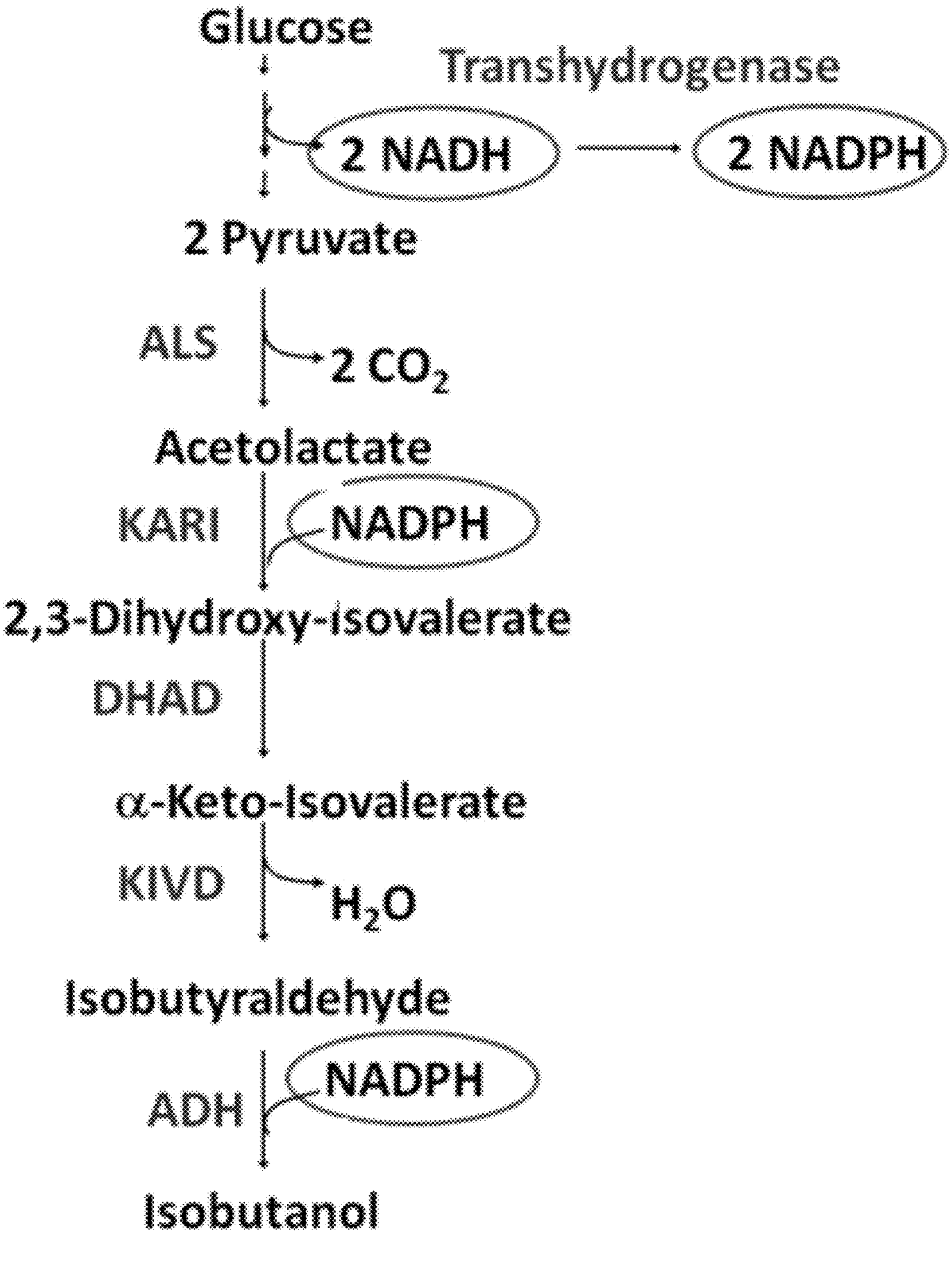
FIG. 2 illustrates a metabolic pathway for the conversion of glucose to isobutanol via pyruvate in which a transhydrogenase converts NADH from glycolysis to NADPH

A Nicotinamide dinucleotide transhydrogenase (hereinafter may be referred to simply as "transhydrogenase") that catalyzes the interconversion of NADH and NADPH as disclosed herein may be used to provide cofactor balance in a metabolic pathway for the production of a target compound that is otherwise imbalanced with respect to cofactor usage and thus decrease the yield loss to $CO_2$ in such a pathway (FIG. 2)

A preferred transhydrogenase under conditions in which the reduced cofactor NADPH is limiting is one that preferentially catalyzes the conversion of NADH to NADPH. For example, membrane-bound transhydrogenases have been described in bacteria that catalyze this reaction. Membrane bound transhydrogenases require energy in form of proton translocation to catalyze the reaction. As long as there is enough energy available to maintain the proton gradient across the cell membrane a transhydrogenase may thus be used to balance an otherwise imbalanced metabolic pathway. However, in some circumstances, a transhydrogenase that catalyzes the conversion of NADPH to NADH may be preferred. However, a preferred transhydrogenase under conditions in which the reduced cofactor NADH is limiting is one that preferentially catalyzes the conversion of NADPH to NADH.

The expression and specific activity of an endogenously expressed membrane-bound transhydrogenase might not be sufficient to maintain the high metabolic flux through the metabolic pathway for the production of a fermentation product (e.g. for isobutanol) that is required in a commercial process.

Thus, in one embodiment, the insufficient activity of the membrane-bound transhydrogenase may be compensated by overexpression of the coding genes of a membrane bound transhydrogenase.

In a preferred embodiment, the *E. coli* pntA (SEQ ID NO: 1) and pntB genes (SEQ ID NO: 3), encoding for the PntA (SEQ ID NO: 2) and PntB (SEQ ID NO: 4) enzymes respectively or homologs thereof may be overexpressed. These genes have been overexpressed in *E. coli* before for characterization of the enzyme (Clarke, D. M. and P. D. Bragg, Journal of Bacteriology, 1985. 162(1): p. 367-373) and have been used to regenerate NADPH cofactor in the production of chiral alcohols from ketones using a whole cell biocatalyst (Weckbecker, A. and W. Hummel, Biotechnology Letters, 2004. 26(22): p. 1739-1744.) or to increase production of biosynthesized products that rely on NADPH-dependent biosynthetic pathways (U.S. Pat. No. 5,830,716).

In one embodiment, the *E. coli* pntAB operon (SEQ ID NO: 1 and SEQ ID NO: 3) is expressed in the presence of the isobutanol pathway. The *E. coli* pntAB operon may be cloned on a medium copy plasmid (p15A origin of replication) under the control of the LtetOl promoter, for example pGV1685 (SEQ ID NO: 111). The high level expression of membrane proteins can lead to the buildup of toxic intermediates and to inclusion bodies. Thus, in another embodiment, different copy numbers of the *E. coli* pntAB operons may be tested to find the optimum expression level of this membrane transhydrogenase.

In another embodiment, the *E. coli* pntAB operon may be integrated into the chromosome of the microorganism. For example, *E. coli* pntAB may be integrated into the *E. coli* genome.

In one aspect of the present invention, the pntAB operon may be integrated into the sthA locus of *E. coli* or the corresponding locus in another microorganism. The sthA gene codes for the soluble transhydrogenase of *E. coli* and has previously been shown to be utilized by the cell for the conversion of NADPH to NADH. To avoid the generation of a futile cycle *E. coli* pntAB may be integrated at the sthA site, thus removing the sthA gene and eliminating this reverse reaction.

The *E. coli* pntAB operon may be integrated into a wild-type *E. coli* W3110 and then transduced into a recombinant microorganism that produces a product via a metabolic pathway that is imbalanced with respect to cofactor usage. For example, the *E. coli* pntAB operon may be integrated into an isobutanol producing strain in which the isobutanol pathway is integrated into the chromosome.

For example the *E. coli* pntAB operon may be integrated into the isobutanol pathway strain GEVO1859 which has the pathway genes Bs_alsS1 and Ec_ilvC_coEc integrated into the pflB site and has Ll_kivd1 and Ec_ilvD_coEc genes integrated into the adhE site. All genes may be under the control of the LlacOl promoter.

The soluble *E. coli* transhydrogenase coded by sthA has been shown to be utilized by the cell for the conversion of NADPH to NADH. However overexpression of sthA was demonstrated to increase the yield of poly(3-hydroxybutyrate) production in *E. coli*. These results indicate that if a pathway is present in *E. coli* that consumes NADPH effectively, the soluble transhydrogenase can function in the direction of NADPH production. The advantages of using SthA as opposed to *E. coli* PntAB are that the soluble protein might be easier to overexpress and that this enzyme is energy independent. The sthA gene may be cloned into pGV1685, replacing *E. coli* pntAB. Decisive for the success of this approach is the affinity of *E. coli* IlvC (KARI enzyme) for its cofactor and the steady state concentrations of NADH and NADPH in the cell that allow SthA to run “backwards” or in the direction of converting NADH to NADPH. It is to be expected that the concentration of the reduced cofactor NADPH has to be low in order for SthA to supply this cofactor. If this concentration is low enough to limit the activity of *E. coli* IlvC and therefore the flux through the isobutanol pathway then this approach is not suitable for the isobutanol production strain without further modifications. These modifications could be identification of a KARI with a lower $K_M$ for NADPH, or mutagenesis and directed evolution to increase the affinity of *E. coli* IlvC for its cofactor.

This approach may be used to provide cofactor balance in a metabolic pathway otherwise imbalanced with respect to cofactor usage if the steady state concentrations of NADH and NADPH in the cell are appropriate to allow SthA to run “backwards” or in the direction of converting NADH to NADPH. It is to be expected that the concentration of the reduced cofactor NADPH has to be low in order for SthA to supply this cofactor.

This embodiment may enable higher yields of a fermentation product in a microorganism. Further, this embodiment may enable economical anaerobic production of a fermentation product, which was not possible without the teachings of this embodiment. Further, this embodiment may enable aerobic production of a fermentation product at higher yield, which was not possible without the teachings of this embodiment.

Microorganism Characterized by Providing Cofactor Balance Via Overexpression of an NADPH-Dependent GAPDH Conversion of glucose to pyruvate via glycolysis in *E. coli* leads to the production of two moles of NADH. A metabolic pathway that converts pyruvate to a target product that consumes either two moles of NADPH or one mole of NADH and one mole of NADPH leads to cofactor imbalance. For example, the isobutanol metabolic pathway that converts glucose to two moles of pyruvate via glycolysis to 1 mole of isobutanol generates two moles of NADH and consumes two moles of NADPH and thus is imbalanced with respect to cofactor usage.

GAPDH catalyzes the conversion of glyceraldehyde 3-phosphate (GAP) to 1,3-diphosphate glycerate as part of glycolysis. For example, in *E. coli* GAPDH is encoded by gapA which is NADH-dependent and is active in glycolysis as well as in gluconeogenesis [DellaSeta, F., et al., *Characterization of Escherichia coli strains with gapA and gapB genes deleted*. Journal of Bacteriology, 1997. 179(16): p. 5218-5221.]. GAPDH proteins from other organisms vary in their cofactor requirements.

Figure 3:
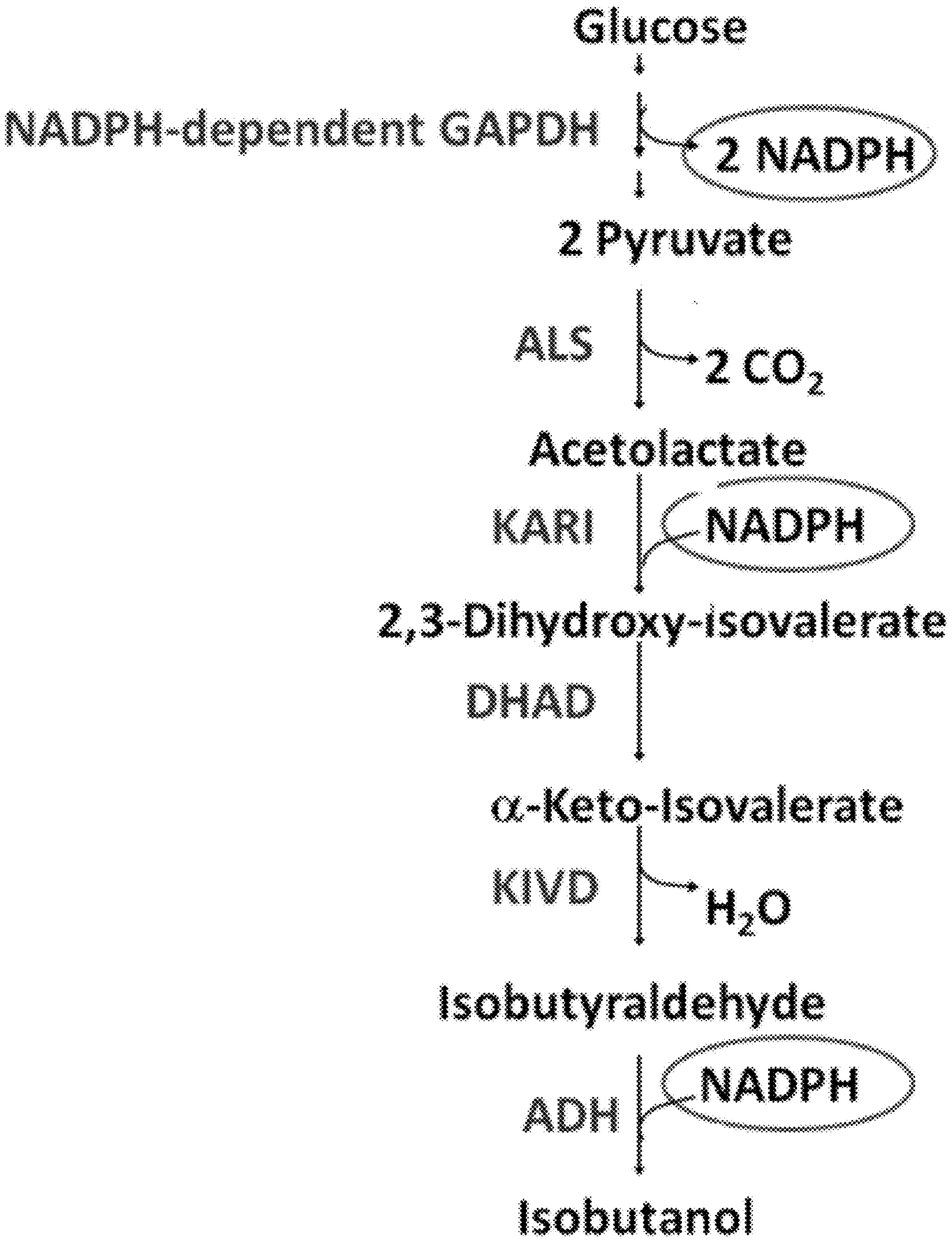
FIG. 3 illustrates a metabolic pathway for the conversion of glucose to isobutanol via pyruvate in which an NADPH-dependent glyceraldehyde-3-phosphate dehydrogenase converts generates NADPH during glycolysis.

Thus in an embodiment, a recombinant microorganism that produces a compound may express a GAPDH is that uses the same cofactor as the fermentative pathway for the production of said compound. For example, in case of an isobutanol biosynthetic pathway that consumes two moles of NADPH per mole of pyruvate an NADPH-dependent GAPDH may be utilized to provide a metabolic pathway that is balanced with respect to cofactor usage (FIG. 3). In such an embodiment, it may also be desirable to increase the concentration of NADPH in the cell by overexpression of other enzymes for the metabolic synthesis of NADPH cofactor. In other embodiments, it may also be desirable to increase the concentration of NADPH in the cell by overexpression of other enzymes for the metabolic synthesis of NADPH cofactor.

Thus, such an NADPH-dependent GAPDH may be expressed in a recombinant microorganism. NADPH-dependent GAPDH enzymes may be identified by analysis with an in vitro enzyme assay. Further, some NADPH-dependent GAPDH enzymes may be identified by analysis of protein identity, similarity, or homology. Further, genes that encode NADPH-dependent GAPDH enzymes may be identified by analysis of gene identity, similarity, or homology.

One NADPH-dependent GAPDH according to the present invention with reported high activity with NADPH is Gdp1 from *Kluyveromyces lactis* [Verho, R., et al., *Identification of the first fungal NADP-GAPDH from Kluyveromyces lactis*. Biochemistry, 2002. 41(46): p. 13833-13838.]. Gdp1 has been expressed in *Saccharomyces cerevisiae* to improve ethanol fermentations on xylose as a substrate [Verho, R., et al., *Engineering redox cofactor regeneration for improved pentose fermentation in Saccharomyces cerevisiae*. Applied and Environmental Microbiology, 2003. 69(10): p. 5892-5897.] Expression of Gdp1 improved the yield of the fermentation from 18 to 23% and from 24 to 41% when it was coupled to a zwf1 deletion which forces more flux through glycolysis. Purified Gdp1 was shown in the literature to be as active with NAD+ as it is with NADP+. Thus, the intracellular concentrations and more importantly the redox ratio of the cofactors in a recombinant microorganism according to the present invention will dictate which cofactor is used in glycolysis.

Another NADPH accepting GAPDH is found in *Clostridium acetobutylicum* and is coded by the gene gap C. Additional homologs of NADPH-dependent GAPDH enzymes may be found in thermotolerant bacteria. Other alternatives of such GAPDH enzymes are those found in cyanobacteria.

A different class of enzymes that can be used to generate NADPH from glucose during glycolysis is comprised of the NADP+-dependent GAPDH (non-phosphorylating). Such enzymes are designated as GapN. However, use of this enzyme results in a loss of one ATP per pyruvate produced. Thus, the production of one NADPH is coupled to a reduction of ATP yield by 1 ATP.

To provide cofactor balance in a recombinant microorganism via an NADPH-dependent GAPDH, it may be necessary to deactivate the native NADH-dependent GAPDH. For example, in the host strain *E. coli* the gapA gene may be deleted.

Another way to force the cell to produce NADPH with GDP1 is the elimination of flux through the PPP. This can be accomplished by deletion of the gene that encodes 6-Phosphogluconate dehydrogenase or decreasing the activity of 6-Phosphogluconate dehydrogenase. For example, in *E. coli* 6-Phosphogluconate dehydrogenase is encoded by zwf. The mutation of zwf eliminates flux through the PPP and may force the microorganism to utilize glycolysis in which the heterologously expressed GAPDH will utilize the cofactor NADP+instead of NADH.

Alternatively, cofactor imbalance in a recombinant microorganism Alternatively, cofactor imbalance in a recombinant microorganism that produces a fermentation product may be alleviated by engineering the native GAPDH to accept NADPH as cofactor. A crystal structure is available from the *Palinurus versicolor* GAPDH which can be used to model the structures of GDP1, GapA (*E. coli*) and other GAPDH enzymes with different cofactor specificities. It is known that an aspartate residue in the NAD binding site is conserved among the NAD dependent GAPDHs. This residue is replaced by asparagine in GDP1.

Additional target amino acids may be found using sequence alignments and structure modeling for site directed mutagenesis. The gapA gene can be mutated using saturation mutagenesis or random mutagenesis according to protein engineering methods known to those skilled in the art. The library of mutant genes may be transformed into microorganisms carrying a zwf deletion and expressing a metabolic pathway that is imbalanced with respect to cofactor usage pathway genes. Mutant enzymes that are NADPH-dependent may be identified in those microorganism that grow on a growth medium. In certain embodiments, it may not be necessary to delete the zwf gene. Alternate genes known to one skilled in the art may be deleted from the organism that in effect inhibits flux through the pentose phosphate pathway.

This embodiment may enable higher yields of a fermentation product in a microorganism. Further, this embodiment may enable anaerobic production of a fermentation product, which was not possible without the teachings of this embodiment. Further, this embodiment may enable anaerobic production of a fermentation product at higher yield, which was not possible without the teachings of this embodiment.

Microorganism Characterized by Providing Cofactor Balance Via a Transhydrogenase Cycle Conversion of glucose to pyruvate via glycolysis in *E. coli* leads to the production of two moles of NADH. A metabolic pathway that converts pyruvate to a target product that consumes either two moles of NADPH or one mole of NADH and one mole of NADPH leads to cofactor imbalance. For example, the isobutanol metabolic pathway that converts glucose to two moles of pyruvate via glycolysis to 1 mole of isobutanol generates two moles of NADH and consumes two moles of NADPH and thus is imbalanced with respect to cofactor usage.

Figure 4:
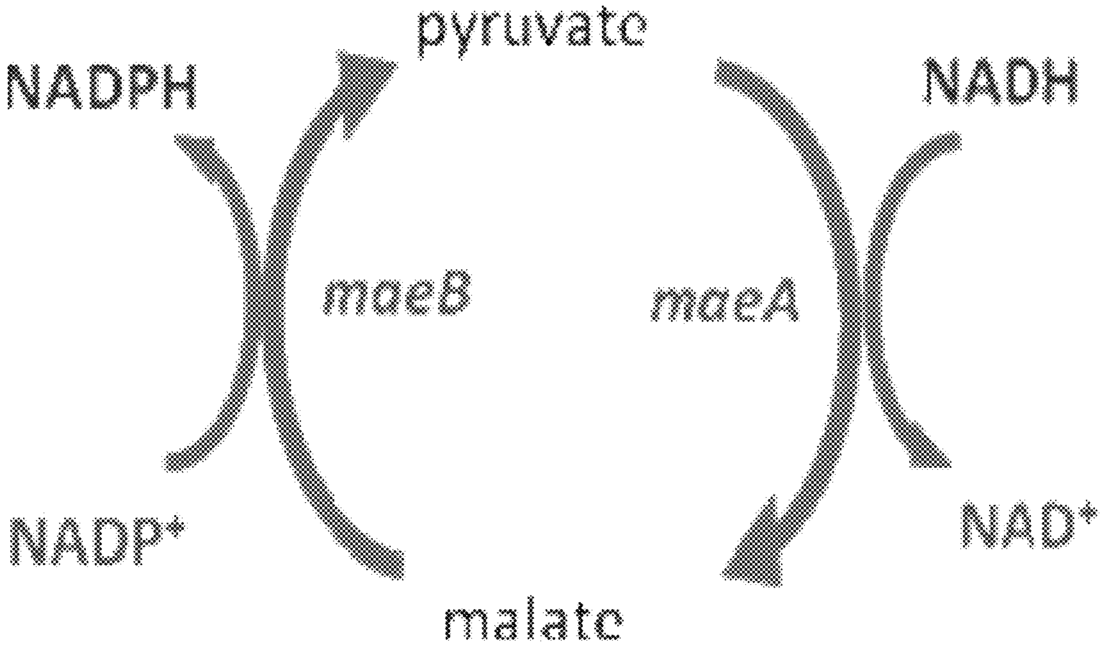
FIG. 4 illustrates a Transhydrogenase cycle converting NADH to NADPH

This cofactor imbalance may be resolved using two dehydrogenase enzymes that catalyze the same reaction but use different cofactors. One example for such a pair of enzymes are the malic enzymes MaeA and MaeB. MaeA is NADH-dependent and MaeB is NADPH-dependent and both catalyze the conversion of malate to pyruvate [Bologna, F. P., C. S. Andreo, and M. F. Drincovich, *Escherichia coli* malic enzymes: Two isoforms with substantial differences in kinetic properties, metabolic regulation, and structure. Journal of Bacteriology, 2007. 189(16): p. 5937-5946.]. The reaction catalyzed by each of these two enzymes is reversible. The kinetics of the two malic enzymes and the different concentrations and redox ratios of the cofactors they use might allow the NADH-dependent enzyme to run in the oxidative direction while the NADPH-dependent enzyme catalyses the reductive direction of the same conversion. In effect the enzymes would catalyze the interconversion of pyruvate and malate coupled to the consumption of NADH and the generation of NADPH (FIG. 4).

Thus the two malic enzymes may function like a transhydrogenase. This cofactor conversion cycle is dependent on the redox ratios of the cofactors which depends on the kinetics of the enzymes in an metabolic pathway that is imbalanced with respect to cofactor, for example the isobutanol pathway enzyme *E. coli* llvc as well as GapA and the malic enzymes. Homologs of malic enzymes can be identified by those skilled in the art. Those enzymes may be used which show kinetic properties favoring the oxidative conversion with NAD+ as cofactor and the reductive conversion with NADPH. The *E. coli* enzymes may to perform these reactions but enzymes with more favorable kinetics may increase the performance of the cofactor conversion.

This embodiment may enable higher yields of a fermentation product in a microorganism. Further, this embodiment may enable anaerobic production of a fermentation product, which was not possible without the teachings of this embodiment. Further, this embodiment may enable anaerobic production of a fermentation product at higher yield, which was not possible without the teachings of this embodiment.

Microorganism Characterized by Providing Cofactor Balance Via Metabolic Transhydrogenation via Ppc or Pyc Conversion of glucose to pyruvate via glycolysis in *E. coli* leads to the production of two moles of NADH. A metabolic pathway that converts pyruvate to a target product that consumes either two moles of NADPH or one mole of NADH and one mole of NADPH leads to cofactor imbalance. For example, the isobutanol metabolic pathway that converts glucose to two moles of pyruvate via glycolysis to 1 mole of isobutanol generates two moles of NADH and consumes two moles of NADPH and thus is imbalanced with respect to cofactor usage.

Figure 5:
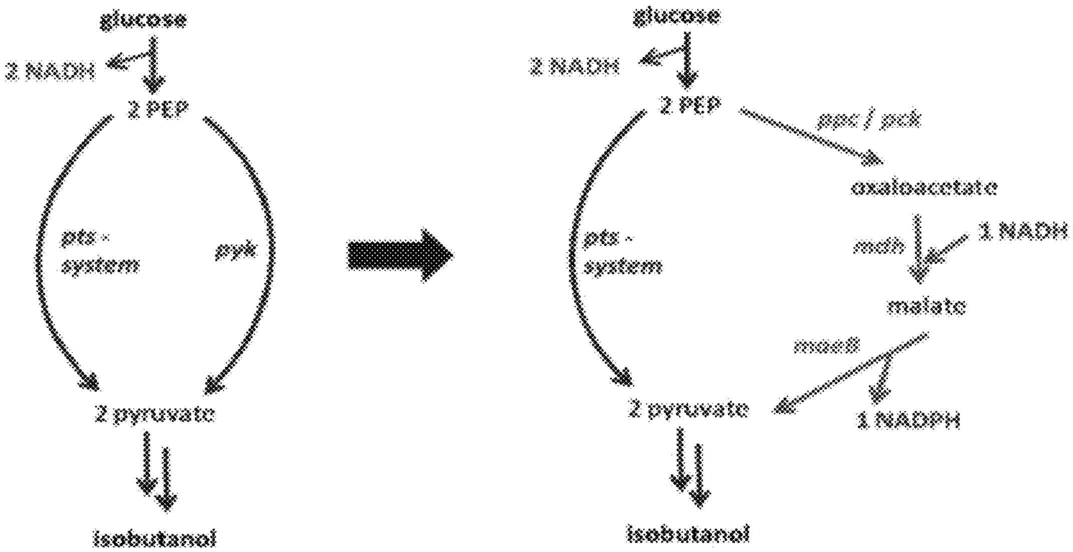
FIG. 5 illustrates an exemplary isobutanol pathway; on the left native conversion of PEP to pyruvate; on the right bypass of pyruvate kinase.

To resolve this cofactor imbalance the metabolic flux may be diverted to allow the conversion of at least one mole of NADH into NADPH. Looking at the stoichiometric network in *E. coli* points to a pathway that allows such a conversion of cofactors (FIG. 5).

Flux from PEP to pyruvate can be replaced by flux from PEP to oxaloacetate, to malate, to pyruvate. To redirect the flux in such a way the native conversion from PEP to pyruvate has to be removed from the network by deletion of the genes coding for pyruvate kinase (pykA, pykF). The other enzymes required are phosphoenolpyruvate carboxylase (Ppc) or phosphoenolpyruvate carboxykinase (Pck) for the conversion of PEP to oxaloacetate, malate dehydrogenase (mdh) for the conversion of oxaloacetate to malate and MaeB for the conversion of malate to pyruvate. The choice whether to use ppc or pck for the conversion of PEP to oxaloacetate depends on the energy load of the isobutanol production strain. With the deletion of Pyk the ATP yield of the strain is reduced if Ppc is used. If Pck is used instead the ATP yield is the same as when the flux goes from PEP to pyruvate using Pyk. Under production condition the strain will only need limited amounts of ATP for cell maintenance. This energy requirement might be lower than the two ATP per glucose generated by glycolysis. By overexpressing ppc, pck or both enzymes the energy yield of the conversion of PEP to pyruvate can be varied between one and two moles of ATP.

The native expression levels of some or all of the enzymes used in the above described conversion from PEP to pyruvate is expected to be insufficient to sustain the high glycolytic flux necessary in the isobutanol production strain. As an example the expression level of mdh is reduced in the presence of glucose and it is further reduced two-fold under anaerobic conditions. Therefore these enzymes may be overexpressed. To allow conversion of 50% of the NADH generated through glycolysis to NADPH the NADH-dependent malic enzyme MaeA may be deleted. Further the enzyme Mqo was reported to catalyze the conversion of malate to oxaloacetate and may be deleted to allow maximum flux in the opposite direction. The thermodynamic equilibrium of the conversion of malate to oxaloacetate lies on the malate side and Mdh catalyzes the reduction of oxaloacetate under anaerobic respiration and under fermentative conditions.

Flux through the PPP may be avoided by adding the deletion of zwf to the strain which eliminates glucose 6-phosphate 1-dehydrogenase the first committed step of the oxidative PPP.

This embodiment may enable higher yields of a fermentation product in a microorganism. Further, this embodiment may enable anaerobic production of a fermentation product, which was not possible without the teachings of this embodiment. Further, this embodiment may enable anaerobic production of a fermentation product at higher yield, which was not possible without the teachings of this embodiment.

Yeast Microorganism Characterized by Providing Cofactor Balance

The aforementioned methods to provide cofactor balance are generally applicable to many microorganisms, including yeast microorganisms. Specifically, however, in yeast, metabolic transhydrogenation may accomplished by introduction of NADPH dependent malic enzyme into yeast. If the conversion of phosphoenol pyruvate to pyruvate by pyruvate kinase is disrupted then the carbon flux can go through a pyruvate kinase bypass that goes from PEP to oxaloacetate to malate and from there to pyruvate. The conversion of oxaloacetate to malate by Mdh consumes one NADH and the conversion of malate to pyruvate by the heterologous malic enzyme produces one NADPH. NADPH dependent malic enzymes are common in bacteria and one example is *E. coli* MaeB. If the NADPH cofactor is needed in the mitochondria the malic enzyme expression can be directed into this organelle instead of the cytoplasm by addition of mitochondrial targeting sequence to the N-terminus or C-terminus of the gene. Also, the yeast enzyme Mae1, which is physiologically localized in the mitochondria can be overexpressed. Malate as well as pyruvate is shuttled across the mitochondrial membranes enabling the pyruvate bypass to effectively convert one cytoplasmic NADH into a mitochondrial NADPH. In yeast the complete carbon flux can be diverted in this way since there is no phosphotransferase (pts) system for glucose import and all PEP generated by glycolysis is available. However, one ATP is lost per NADPH produced through the yeast pyruvate kinase bypass.

Yeast do not have transhydrogenases. The heterologous expression of bacterial, plant or other eukaryotic transhydrogenases in yeast can be used to provide cofactor balance. The transhydrogenases that natively convert NADH to NADPH are generally membrane proteins that use the proton motive force to drive the reaction they are catalyzing. Bacterial transhydrogenases are in the cell membrane while plant and mammalian transhydrogenases are located in the inner mitochondrial membrane. For the heterologous transhydrogenase expression these enzymes can be targeted either to the cytoplasmic membrane or to the mitochondrial membrane in yeast. To achieve this leader sequences have to be added to the heterologous proteins. The mechanisms of membrane targeting are well understood and the direction of normally cytosolic proteins to the mitochondrium has been demonstrated. These targeting mechanisms are well conserved throughout the eukaryotes, which was demonstrated by the use of plant mitochondrial targeting sequences in yeast. Eukaryotic transhydrogenases are expressed in yeast with their native targeting and sorting sequences. Bacterial transhydrogenases are fused to mitochondrial targeting and membrane sorting sequences that have been characterized in yeast membrane proteins.

An alternative approach for the production of NADPH is the use of biosynthetic pathway enzymes. An NADH kinase could phosphorylate NADH to NADPH. Then the NADP+ needs to be dephosphorylated to NAD+ to maintain NAD+ pool. This can be carried out by an NADP phosphatase.

Microorganisms Characterized by Providing Cofactor Balance Via Engineered Enzymes Conversion of one mole of glucose to two moles of pyruvate via glycolysis leads to the production of two moles of NADH. A metabolic pathway that converts pyruvate to a target product that consumes either two moles of NADPH or one mole of NADH and one mole of NADPH leads to cofactor imbalance. One example of such a metabolic pathway is the isobutanol metabolic pathway described by Atsumi et al. (Atsumi et al., 2008, *Nature* 451(7174): 86-9) which converts two moles of pyruvate to one mole of isobutanol. In this five enzyme pathway, two enzymes are dependent upon NADPH: (1) KARI and (2) ADH, encoded by the *E. coli* ilvC and *E. coli* yqhD, respectively.

To resolve this cofactor imbalance, the present invention provides a recombinant microorganism in which the NADPH-dependent enzymes KARI and ADH are replaced with enzymes that preferentially depend on NADH (i.e. KARI and ADH enzymes that are NADH-dependent).

To further resolve this cofactor imbalance, the present invention in another embodiment provides recombinant microorganisms wherein the NADH-dependent KARI and ADH enzymes are overexpressed.

In one aspect, such enzymes may be identified in nature. In an alternative aspect, such enzymes may be generated by protein engineering techniques including but not limited to directed evolution or site-directed mutagenesis.

In one embodiment, the two NADPH-dependent enzymes within an isobutanol biosynthetic pathway that converts pyruvate to isobutanol may be replaced with ones that utilize NADH. These two enzymes may be KARI and an alcohol dehydrogenase (ADH).

In another embodiment, two NADH-dependent enzymes that catalyze the same reaction as the NADH-dependent enzymes are overexpressed. These two enzymes may be KARI and an alcohol dehydrogenase.

In one aspect, NADH-dependent KARI and ADH enzymes are identified in nature. In another aspect, the NADPH-dependent KARI and ADH enzymes may be engineered using protein engineering techniques including but not limited to directed evolution and site-directed mutagenesis.

There exist two basic options for engineering NADH-dependent isobutyraldehyde dehydrogenases or ketol-acid reductoisomerases: (1) increase the NADH-dependent activity of an NADPH-dependent enzyme that is active towards the substrate of interest and/or (2) increase the activity of an NADH-dependent enzyme that is not sufficiently active towards the substrate of interest.

NADH-Dependent KARI Enzymes

As shown in FIG. 1, the ketol-acid reductoisomerase (KARI) enzyme of the isobutanol biosynthetic pathway as disclosed by Atsumi et al (Atsumi et al., 2008, Nature 451 (7174): 86-9, herein incorporated by reference in its entirety), requires the cofactor nicotinamide dinucleotide phosphate (NADPH) to convert acetolactate to 2,3-dihydroxyisovalerate. However, under anaerobic conditions, NADPH is produced only sparingly by the cell—nicotinamide adenine dinucleotide (NADH) is the preferred equivalent. Therefore, oxygen is required to produce NADPH in the large quantities to support high-level production of isobutanol. Thus, the production of isobutanol is feasible only under aerobic conditions and the maximum yield that can be achieved with this pathway is limited. Accordingly, KARI enzymes that preferentially utilize NADH rather than NADPH are desirable.

Other biosynthetic pathways utilize KARI enzymes for the conversion of acetolactate to 2-3-dihydroxyisovalerate. For example, KARI enzymes convert acetolactate to 2-3-dihydroxyisovalerate as part of the biosynthetic pathway for the production of 3-methyl-1-butanol (Atsumi et al., 2008, Nature 451(7174): 86-9, herein incorporated by reference in its entirety).

Yet other biosynthetic pathways utilize KARI to convert 2-aceto-2-hydroxy-butyrate to 2,3-dihydroxy-3-methylvalerate. This reaction is part of the biosynthetic pathway for the production of 2-methyl-1-butanol. (Atsumi et al., 2008, Nature 451(7174): 86-9, herein incorporated by reference in its entirety).

As used herein, the term "KARI" or "KARI enzyme" or "ketol-acid reductoisomerase" are used interchangeably herein to refer to an enzyme that catalyzes the conversion of acetolactate to 2,3-dihydroxyisovalerate and/or the conversion of 2-aceto-2-hydroxy-butyrate to 2,3-dihydroxy-3-methylvalerate. Moreover, these terms can be used interchangeably herein with the terms "acetohydroxy acid isomeroreductase" and "acetohydroxy acid reductoisomerase."

Enzymes for use in the compositions and methods of the invention include any enzyme having the ability to convert acetolactate to 2,3-dihydroxyisovalerate and/or the ability to convert 2-aceto-2-hydroxy-butyrate to 2,3-dihydroxy-3-methylvalerate. Such enzymes include, but are not limited to, the *E. coli* ilvC gene product and the *S. cerevisiae* ilv5 gene product, and the KARI enzyme from *Piromyces* sp, *Buchnera aphidicola, Spinacia oleracea, Oryza sativa, Chlamydomonas reinhardtii, Neurospora crassa, Schizosaccharomyces pombe, Laccaria bicolor, Ignicoccus hospitalis, Picrophilus torridus, Acidiphilium cryptum, Cyanobacteria/Synechococcus* sp., *Zymomonas mobilis, Bacteroides thetaiotaomicron, Methanococcus maripaludis, Vibrio fischeri, Shewanella* sp, *Gramella forsetti, Psychromonas ingrhamaii*, and *Cytophaga hutchinsonii.*

Preferred KARI enzymes are known by the EC number 1.1.1.86 and sequences are available from a vast array of microorganisms, including, but not limited to, *Escherichia coli* (GenBank Nos: NP_418222 and NC_000913, *Saccharomyces cerevisiae* (GenBank Nos: NP_013459 and NC_001144, *Methanococcus maripaludis* (GenBank Nos: CAF30210 and BX957220, and *Bacillus subtilis* (GenBank Nos: CAB14789 and Z99118) and the KARI enzymes from *Piromyces* sp (GenBank No: CAA76356), *Buchnera aphidicola* (GenBank No: AAF13807), *Spinacia oleracea* (GenBank Nos: □01292 and CAA40356), *Oryza sativa* (GenBank No: NP_001056384) *Chlamydomonas reinhardtii* (GenBank No: XP_001702649), *Neurospora crassa* (GenBank No: XP_961335), *Schizosaccharomyces pombe* (GenBank No: NP_001018845), *Laccaria bicolor* (GenBank No: XP_001880867), *Ignicoccus hospitalis* (GenBank No: YP_001435197), *Picrophilus torridus* (GenBank No: YP_023851), *Acidiphilium cryptum* (GenBank No: YP_001235669), *Cyanobacteria/Synechococcus* sp. (GenBank No: YP_473733), *Zymomonas mobilis* (GenBank No: YP_162876), *Bacteroides thetaiotaomicron* (GenBank No: NP_810987), *Methanococcus maripaludis* (GenBank No: YP_001097443), *Vibrio fischeri* (GenBank No: YP_205911), *Shewanella* sp (GenBank No: YP_732498), *Gramella forsetti* (GenBank No: YP_862142), *Psychromonas ingrhamaii* (GenBank No: YP_942294), and *Cytophaga hutchinsonii* (GenBank No: YP_677763).

As will be understood by one of ordinary skill in the art, modified KARI enzymes may be obtained by recombinant or genetic engineering techniques that are routine and well-known in the art. Mutant KARI enzymes can, for example, be obtained by mutating the gene or genes encoding the KARI enzyme of interest by site-directed or random mutagenesis. Such mutations may include point mutations, deletion mutations and insertional mutations. For example, one or more point mutations (e.g., substitution of one or more amino acids with one or more different amino acids) may be used to construct mutant KARI enzymes of the invention.

Ketol-acid reductoisomerase (KARI; EC 1.1.1.86) catalyzes the reduction of acetolactate to 2,3-dihydroxyisovalerate. The two-step reaction involves an alkyl migration and a ketone reduction that occurs at a single active site on the enzyme without dissociation of any reaction intermediates. The enzyme is NADPH-dependent. The cofactor specificity may be expanded or switched so that it will utilize both cofactors and preferentially NADH during the production of isobutanol. A study published in 1997 (Rane, M. J. and K. C. Calvo, Archives of Biochemistry and Biophysics, 1997. 338 (1): p. 83-89) describes a supposed cofactor-switched KARI quadruplet variant of the *E. coli* ilvC gene product with mutations R68D, K69L, K75V and R76D). However, in-house studies indicate that although the ratio NADH/NADPH was 2.5, the specific activity of this variant on NADH was actually worse than wild-type (Table 25), rendering this enzyme not suited for the purpose of this disclosure.

Modified or Mutated KARI Enzymes

In accordance with the invention, any number of mutations can be made to the KARI enzymes, and in a preferred aspect, multiple mutations can be made to result in an increased ability to utilize NADH for the conversion of acetolactate to 2,3-dihydroxyisovalerate. Such mutations include point mutations, frame shift mutations, deletions, and insertions, with one or more (e.g., one, two, three, or four, etc.) point mutations preferred.

Mutations may be introduced into the KARI enzymes of the present invention using any methodology known to those skilled in the art. Mutations may be introduced randomly by, for example, conducting a PCR reaction in the presence of manganese as a divalent metal ion cofactor. Alternatively, oligonucleotide directed mutagenesis may be used to create the mutant KARI enzymes which allows for all possible classes of base pair changes at any determined site along the encoding DNA molecule. In general, this technique involves annealing an oligonucleotide complementary (except for one or more mismatches) to a single stranded nucleotide sequence coding for the KARI enzyme of interest. The mismatched oligonucleotide is then extended by DNA polymerase, generating a double-stranded DNA molecule which contains the desired change in sequence in one strand. The changes in sequence can, for example, result in the deletion, substitution, or insertion of an amino acid. The double-stranded polynucleotide can then be inserted into an appropriate expression vector, and a mutant or modified polypeptide can thus be produced. The above-described oligonucleotide directed mutagenesis can, for example, be carried out via PCR.

The invention further includes homologous KARI enzymes which are 5%, 10%, 20%, 30%, 40%, 50%, 60%, 70%, 75%, 80%, 85%, 90%, 95%, 96%, 97%, 98%, or 99% identical at the amino acid level to a wild-type KARI enzyme (e.g., encoded by the Ec_ilvC gene or *S. cerevisiae* ilv5 gene) and exhibit an increased ability to utilize NADH for the conversion of acetolactate to 2,3-dihydroxyisovalerate. Also included within the invention are KARI enzymes which are 50%, 60%, 70%, 75%, 80%, 85%, 90%, 95%, 96%, 97%, 98%, or 99% identical at the amino acid level to a KARI enzyme comprising the amino acid sequence set out in SEQ ID NO: 13 and exhibit an increased ability to utilize NADH for the conversion of acetolactate to 2,3-dihydroxyisovalerate. The invention also includes nucleic acid molecules which encode the above described KARI enzymes.

The invention also includes fragments of KARI enzymes which comprise at least 50, 100, 150, 200, 250, 300, 350, 400, 450, 500, 550, or 600 amino acid residues and retain one or more activities associated with KARI enzymes. Such fragments may be obtained by deletion mutation, by recombinant techniques that are routine and well-known in the art, or by enzymatic digestion of the KARI enzyme(s) of interest using any of a number of well-known proteolytic enzymes. The invention further includes nucleic acid molecules which encode the above described mutant KARI enzymes and KARI enzyme fragments.

By a protein or protein fragment having an amino acid sequence at least, for example, 50% "identical" to a reference amino acid sequence it is intended that the amino acid sequence of the protein is identical to the reference sequence except that the protein sequence may include up to 50 amino acid alterations per each 100 amino acids of the amino acid sequence of the reference protein. In other words, to obtain a protein having an amino acid sequence at least 50% identical to a reference amino acid sequence, up to 50% of the amino acid residues in the reference sequence may be deleted or substituted with another amino acid, or a number of amino acids up to 50% of the total amino acid residues in the reference sequence may be inserted into the reference sequence. These alterations of the reference sequence may occur at the amino (N-) and/or carboxy (C-) terminal positions of the reference amino acid sequence and/or anywhere between those terminal positions, interspersed either individually among residues in the reference sequence and/or in one or more contiguous groups within the reference sequence. As a practical matter, whether a given amino acid sequence is, for example, at least 50% identical to the amino acid sequence of a reference protein can be determined conventionally using known computer programs such as those described above for nucleic acid sequence identity determinations, or using the CLUSTAL W program (Thompson, J. D., et al., *Nucleic Acids Res.* 22:4673 4680 (1994)).

In one aspect, amino acid substitutions are made at one or more of the above identified positions (i.e., amino acid positions equivalent or corresponding to A71, R76, S78, or Q110 of *E. coli* llvC). Thus, the amino acids at these positions may be substituted with any other amino acid including Ala, Asn, Arg, Asp, Cys, Gln, Glu, Gly, His, Ile, Leu, Lys, Met, Phe, Pro, Ser, Thr, Trp, Tyr, and Val. A specific example of a KARI enzyme which exhibits an increased ability to utilize NADH includes an *E. coli* llvC KARI enzyme in which (1) the alanine at position 71 has been replaced with a serine, (2) the arginine at position 76 has been replaced with an aspartic acid, (3) the serine at position 78 has been replaced with an aspartic acid, and/or (4) the glutamine at position 110 has been replaced with valine.

Polypeptides having the ability to convert acetolactate to 2,3-dihydroxyisovalerate and/or 2-aceto-2-hydroxy-butyrate to 2,3-dihydroxy-3-methylvalerate for use in the invention may be isolated from their natural prokaryotic or eukaryotic sources according to standard procedures for isolating and purifying natural proteins that are well-known to one of ordinary skill in the art (see, e.g., Houts, G. E., et al., J. Virol. 29:517 (1979)). In addition, polypeptides having the ability to convert acetolactate to 2,3-di hydroxyisovalerate and/or 2-aceto-2-hydroxy-butyrate to 2,3-dihydroxy-3-methylvalerate may be prepared by recombinant DNA techniques that are familiar to one of ordinary skill in the art (see, e.g., Kotewicz, M. L., et al., *Nucl. Acids Res.* 16:265 (1988); Soltis, D. A., and Skalka, A. M., *Proc. Natl. Acad. Sci. USA* 85:3372 3376 (1988)).

In accordance with the invention, one or more mutations may be made in any KARI enzyme of interest in order to increase the ability of the enzyme to utilize NADH, or confer other properties described herein upon the enzyme, in accordance with the invention. Such mutations include point mutations, frame shift mutations, deletions and insertions. Preferably, one or more point mutations, resulting in one or more amino acid substitutions, are used to produce KARI enzymes having an enhanced or increased ability to utilize NADH, particularly to facilitate the conversion of acetolactate to 2,3-dihydroxyisovalerate and/or the conversion of 2-aceto-2-hydroxy-butyrate to 2,3-dihydroxy-3-methylvalerate. In a preferred aspect of the invention, one or more mutations at positions equivalent or corresponding to position A71 (e.g., A71S), R76 (e.g., R76D), S78 (e.g. S78D), and/or Q110 (e.g. Q110V) and/or D146 (e.g. D146G), and/or G185 (e.g. G185R) and/or K433 (e.g. K433E) of the *E. coli* llvC KARI enzyme may be made to produce the desired result in other KARI enzymes of interest.

The corresponding positions of the KARI enzymes identified herein (e.g. *E. coli* llvC may be readily identified for other KARI enzymes by one of skill in the art. Thus, given the defined region and the assays described in the present application, one with skill in the art can make one or a number of modifications which would result in an increased ability to utilize NADH, particularly for the conversion of acetolactate to 2,3-dihydroxyisovalerate, in any KARI enzyme of interest. Residues to be modified in accordance with the present invention may include those described in Examples 14, 15, and 16.

In a preferred embodiment, the modified or mutated KARI enzymes have from 1 to 4 amino acid substitutions in amino acid regions involved in cofactor specificity as compared to the wild-type KARI enzyme proteins. In other embodiments, the modified or mutated KARI enzymes have additional amino acid substitutions at other positions as compared to the respective wild-type KARI enzymes. Thus, modified or mutated KARI enzymes may have at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 different residues in other positions as compared to the respective wild-type KARI enzymes. As will be appreciated by those of skill in the art, the number of additional positions that may have amino acid substitutions will depend on the wild-type KARI enzyme used to generate the variants. Thus, in some instances, up to 50 different positions may have amino acid substitutions.

The nucleotide sequences for several KARI enzymes are known. For instance, the sequences of KARI enzymes are available from a vast array of microorganisms, including, but not limited to, *Escherichia coli* (GenBank No: NP_418222), *Saccharomyces cerevisiae* (GenBank Nos: NP_013459, *Methanococcus maripaludis* (GenBank No: YP_001097443), *Bacillus subtilis* (GenBank Nos: CAB14789), and the KARI enzymes from *Piromyces* sp (GenBank No: CAA76356), *Buchnera aphidicola* (GenBank No: AAF13807), *Spinacia oleracea* (GenBank Nos: Q01292 and CAA40356), *Oryza sativa* (GenBank No: NP_001056384) *Chlamydomonas reinhardtii* (GenBank No: XP_001702649), *Neurospora crassa* (GenBank No: XP_961335), *Schizosaccharomyces pombe* (GenBank No: NP_001018845), *Laccaria bicolor* (GenBank No: XP_001880867), *Ignicoccus hospitalis* (GenBank No: YP_001435197), *Picrophilus torridus* (GenBank No: YP_023851), *Acidiphilium cryptum* (GenBank No: YP_001235669), *Cyanobacteria/Synechococcus* sp. (GenBank No: YP_473733), *Zymomonas mobilis* (GenBank No: YP_162876), *Bacteroides thetaiotaomicron* (GenBank No: NP_810987), *Methanococcus maripaludis* (GenBank No: YP_001097443), *Vibrio fischeri* (GenBank No: YP_205911), *Shewanella* sp (GenBank No: YP_732498), *Gramella forsetti* (GenBank No: YP_862142), *Psychromonas ingrhamaii* (GenBank No: YP_942294), and *Cytophaga hutchinsonii* (GenBank No: YP_677763).

Improved NADH-Dependent Activity

In one aspect, the NADH-dependent activity of the modified or mutated KARI enzyme is increased.

In a preferred embodiment, the catalytic efficiency of the modified or mutated KARI enzyme is improved for the cofactor NADH. Preferably, the catalytic efficiency of the modified or mutated KARI enzyme is improved by at least about 5% as compared to the wild-type or parental KARI for NADH. More preferably the catalytic efficiency of the modified or mutated KARI enzyme is improved by at least about 15% as compared to the wild-type or parental KARI for NADH. More preferably, the catalytic efficiency of the modified or mutated KARI enzyme is improved by at least about 25% as compared to the wild-type or parental KARI for NADH. More preferably, the catalytic efficiency of the modified or mutated KARI enzyme is improved by at least about 50% as compared to the wild-type or parental KARI for NADH. More preferably, the catalytic efficiency of the modified or mutated KARI enzyme is improved by at least about 75% as compared to the wild-type or parental KARI for NADH. More preferably, the catalytic efficiency of the modified or mutated KARI enzyme is improved by at least about 100% as compared to the wild-type or parental KARI for NADH. More preferably, the catalytic efficiency of the modified or mutated KARI enzyme is improved by at least about 300% as compared to the wild-type or parental KARI for NADH. More preferably, the catalytic efficiency of the modified or mutated KARI enzyme is improved by at least about 500% as compared to the wild-type or parental KARI for NADH. More preferably, the catalytic efficiency of the modified or mutated KARI enzyme is improved by at least about 1000% as compared to the wild-type or parental KARI for NADH. More preferably, the catalytic efficiency of the modified or mutated KARI enzyme is improved by at least about 5000% as compared to the wild-type or parental KARI for NADH.

In a preferred embodiment, the catalytic efficiency of the modified or mutated KARI enzyme with NADH is increased with respect to the catalytic efficiency of the wild-type or parental enzyme with NADPH. Preferably, the catalytic efficiency of the modified or mutated KARI enzyme is at least about 10% of the catalytic efficiency of the wild-type or parental KARI enzyme for NADPH. More preferably, the catalytic efficiency of the modified or mutated KARI enzyme is at least about 25% of the catalytic efficiency of the wild-type or parental KARI enzyme for NADPH. More preferably, the catalytic efficiency of the modified or mutated KARI enzyme is at least about 50% of the catalytic efficiency of the wild-type or parental KARI enzyme for NADPH. More preferably, the catalytic efficiency of the modified or mutated KARI enzyme is at least about 75%, 85%, 95% of the catalytic efficiency of the wild-type or parental KARI enzyme for NADPH.

In a preferred embodiment, the $K_M$ of the KARI enzyme for NADH is decreased relative to the wild-type or parental enzyme. A change in $K_M$ is evidenced by at least a 5% or greater increase or decrease in $K_M$ compared to the wild-type KARI enzyme. In certain embodiments, modified or mutated KARI enzymes of the present invention may show greater than 10 times decreased $K_M$ for NADH compared to the wild-type or parental KARI enzyme. In certain embodiments, modified or mutated KARI enzymes of the present invention may show greater than 30 times decreased $K_M$ for NADH compared to the wild-type or parental KARI enzyme.

In a preferred embodiment, the $k_{cat}$ of the KARI enzyme with NADH is increased relative to the wild-type or parental enzyme. A change in $k_{cat}$ is evidenced by at least a 5% or greater increase or decrease in $K_M$ compared to the wild-type KARI enzyme. In certain embodiments, modified or mutated KARI enzymes of the present invention may show greater than 50% increased $k_{cat}$ for NADH compared to the wild-type or parental KARI enzyme. In certain embodiments, modified or mutated KARI enzymes of the present invention may show greater than 100% increased $k_{cat}$ for NADH compared to the wild-type or parental KARI enzyme. In certain embodiments, modified or mutated KARI enzymes of the present invention may show greater than 200% increased $k_{cat}$ for NADH compared to the wild-type or parental KARI enzyme.

Cofactor Switch

In preferred embodiments, the cofactor specificity of the modified or mutated KARI enzyme is altered such that there is a cofactor switch from NADPH to NADH. In other words, these modified or mutated KARI enzymes will have an increase in NADH-dependent activity and a substantially simultaneous decrease in NADPH dependent activity. Thus, the methods of the present invention can be used to change the cofactor preference from NADPH to NADH.

"Cofactor specificity" is a measure of the specificity of an enzyme for one cofactor over another. Thus, the methods of the present invention may be used to alter the cofactor preference of the target enzyme, such that the preference for the less favored cofactor is increased by 20%, 50%, 100%, 300%, 500%, 1000%, up to 2000%. For example, a number of reductase enzymes have been described that favor NADPH over NADH (see WO 02/22526; WO 02.29019; Mittl, P R., et al., (1994) Protein Sci., 3: 1504 14; Banta, S., et al., (2002) Protein Eng., 15:131 140; all of which are hereby incorporated by reference in their entirety). As the availability of NADPH is often limiting, both in vivo and in vitro, the overall activity of the target protein is often limited. For target proteins that prefer NADPH as a cofactor, it would be desirable to alter the cofactor specificity of the target protein (e.g. a KARI enzyme) to a cofactor that is more readily available, such as NADH.

In a preferred embodiment, the cofactor specificity of the KARI enzyme is switched. By "switched" herein is meant, that the cofactor preference (in terms of catalytic efficiency ($k_{cat}/K_M$) of the KARI enzyme is changed to another cofactor Preferably, in one embodiment, by switching cofactor specificity, activity in terms of catalytic efficiency ($k_{cat}/K_M$) with the cofactor preferred by the wild-type KARI enzyme is reduced, while the activity with the less preferred cofactor is increased. This can be achieved, for example by increasing the $k_{cat}$ for less preferred cofactor over the preferred cofactor or by decreasing $K_M$ for the less preferred cofactor over the preferred cofactor or both.

In a preferred embodiment, the KARI enzyme is modified or a mutated to become NADH-dependent. The term "NADH-dependent" refers to the property of an enzyme to preferentially use NADH as the redox cofactor. An NADH-dependent enzyme has a higher catalytic efficiency ($k_{cat}/K_M$) with the cofactor NADH than with the cofactor NADPH as determined by in vitro enzyme activity assays. Accordingly, the term "NADPH-dependent" refers to the property of an enzyme to preferentially use NADPH as the redox cofactor. An NADPH dependent enzyme has a higher catalytic efficiency ($k_{cat}/K_M$) with the cofactor NADPH than with the cofactor NADH as determined by in vitro enzyme activity assays.

In a preferred embodiment, the catalytic efficiency of the KARI enzyme for NADH is enhanced relative to the catalytic efficiency with NADPH. The term "catalytic efficiency" describes the ratio of the rate constant $k_{cat}$ over the Michaelis-Menten constant $K_M$. In one embodiment, the invention is directed to a modified or mutated KARI enzyme that exhibits at least about a 1:10 ratio of catalytic efficiency ($k_{cat}/K_M$) with NADH over catalytic efficiency with NADPH. In another embodiment, the modified or mutated KARI enzyme exhibits at least about a 1:1 ratio of catalytic efficiency ($k_{cat}/K_M$) with NADH over catalytic efficiency with NADPH. In yet another embodiment, the modified or mutated KARI enzyme exhibits at least about a 10:1 ratio of catalytic efficiency ($k_{cat}/K_M$) with NADH over catalytic efficiency with NADPH. In yet another embodiment, the modified or mutated KARI enzyme exhibits at least about a 100:1 ratio of catalytic efficiency ($k_{cat}/K_M$) with NADH over catalytic efficiency with NADPH. In an exemplary embodiment, the modified or mutated KARI enzyme exhibits at least about a 100:1 ratio of catalytic efficiency ($k_{cat}/K_M$) with NADH over catalytic efficiency with NADPH.

In a preferred embodiment, the $K_M$ of the KARI enzyme for NADH is decreased relative to the $K_M$ of the KARI enzyme for NADPH. In one embodiment, the invention is directed to a modified or mutated KARI enzyme that exhibits at least about a 10:1 ratio of $K_M$ for NADH over $K_M$ for NADPH. In one embodiment, the invention is directed to a modified or mutated KARI enzyme that exhibits at least about a 1:1 ratio of $K_M$ for NADH over $K_M$ for NADPH. In a preferred embodiment, the invention is directed to a modified or mutated KARI enzyme that exhibits at least about a 1:10 ratio of $K_M$ for NADH over $K_M$ for NADPH. In yet another embodiment, the invention is directed to a modified or mutated KARI enzyme that exhibits at least about a 1:20, 1:100, 1:1000 ratio of $K_M$ for NADH over $K_M$ for NADPH.

Figure 6:
FIG. 6 illustrates an amino acid sequence alignment among various members of the KARI enzyme family.
Figure 6:
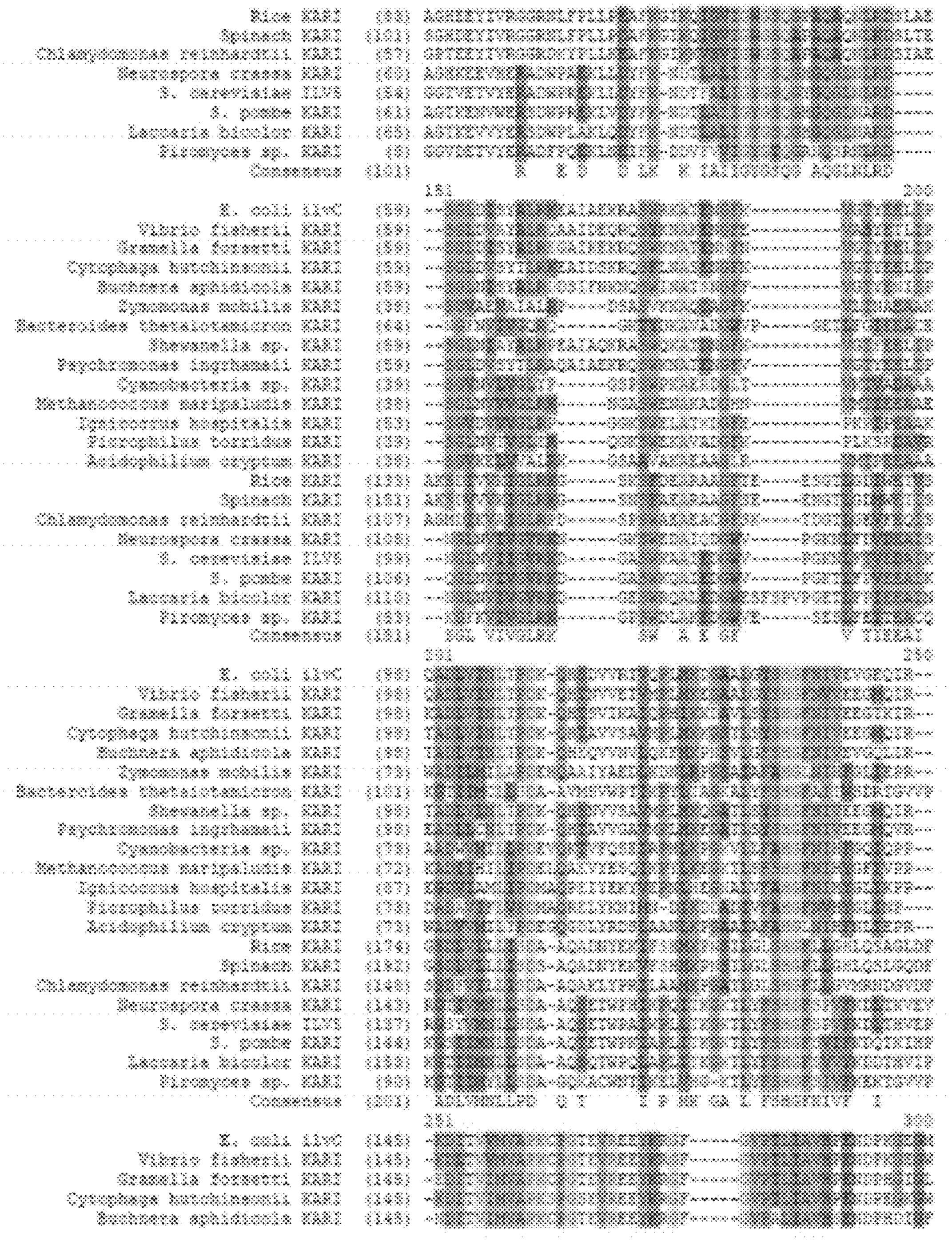
Figure 6:
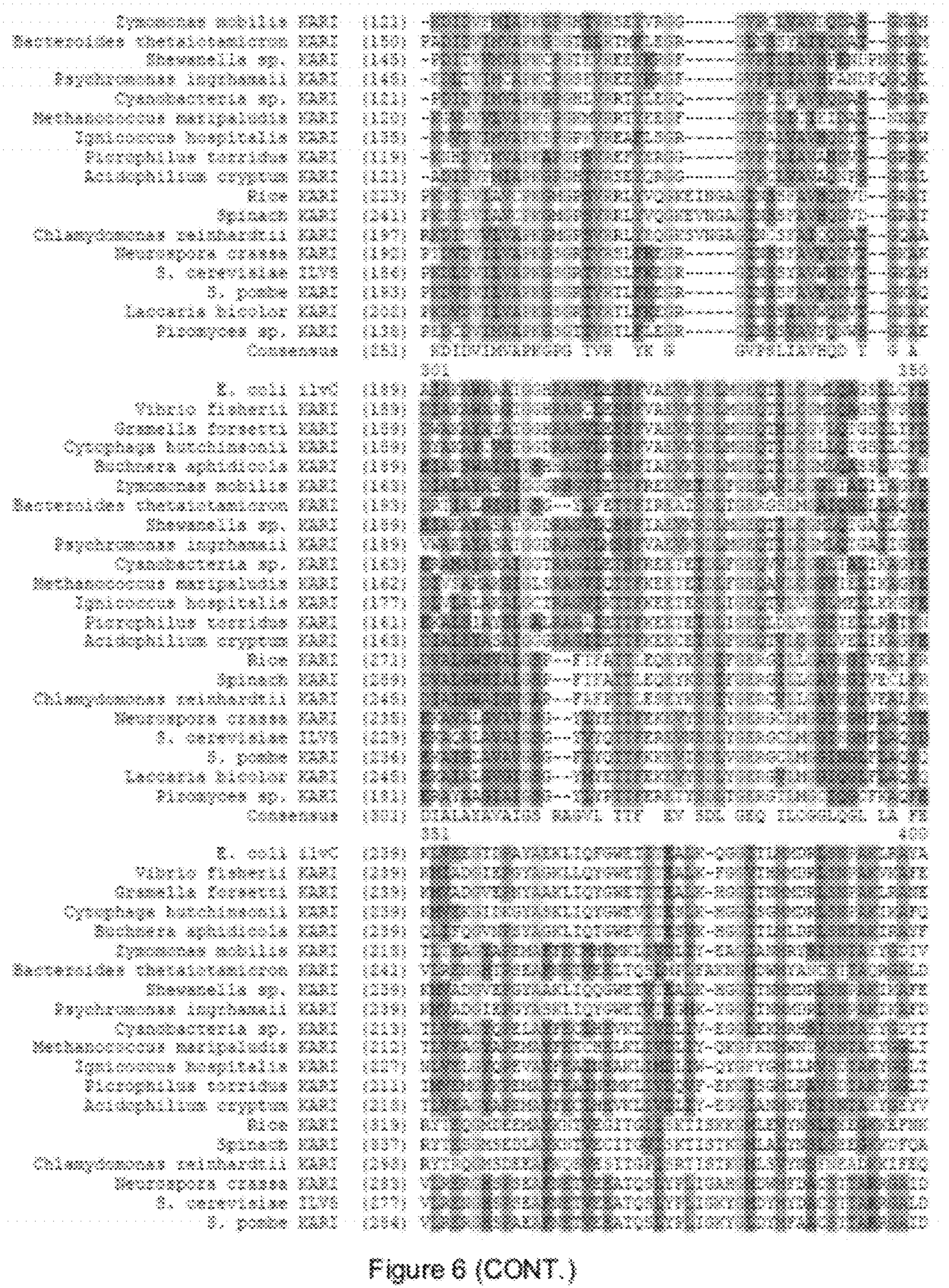
Figure 6:
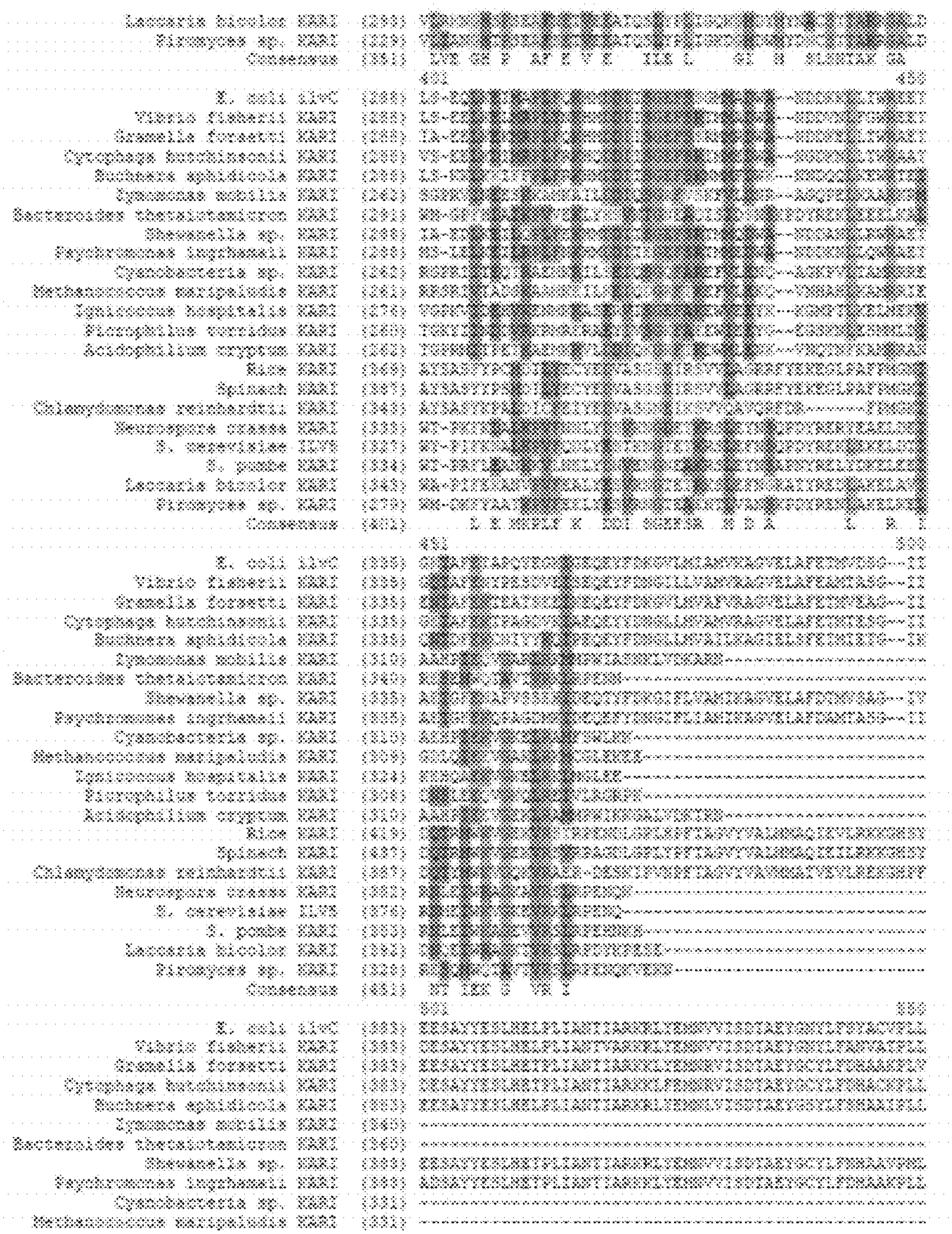

In another preferred embodiment, the $k_{cat}$ of the KARI enzyme with NADH is increased relative to $k_{cat}$ with NADPH. In certain embodiments, modified or mutated KARI enzymes of the present invention may show greater than 0.8:1 ratio of $k_{cat}$ with NADH over $k_{cat}$ with NADPH. In certain embodiments, modified or mutated KARI enzymes of the present invention may show greater than 1:1 ratio of $k_{cat}$ with NADH over $k_{cat}$ with NADPH. In a preferred embodiments, modified or mutated KARI enzymes of the present invention may show greater than 10:1 ratio of $k_{cat}$ with NADH over $k_{cat}$ with NADPH. In certain embodiments, modified or mutated KARI enzymes of the present invention may show greater than 100:1 ratio of $k_{cat}$ with NADH over $k_{cat}$ with NADPH Identification of Corresponding Amino Acid Substitutions in Homologous Enzymes An amino acid sequence alignment of 22 KARIs (including *E. coli* llvC, spinach KARI and rice KARI) was performed (FIG. 6). Some KARIs aligned with the *E. coli* KARI sequence at amino acid positions 71, 76, 78, and 110 and this allows to conclude that the beneficial mutations found for *E. coli* KARI confer the same effects in these KARI enzymes. Other sequences show deletions at about these positions and the sequence alignment is not sufficient to make any predictions.

Figure 7:
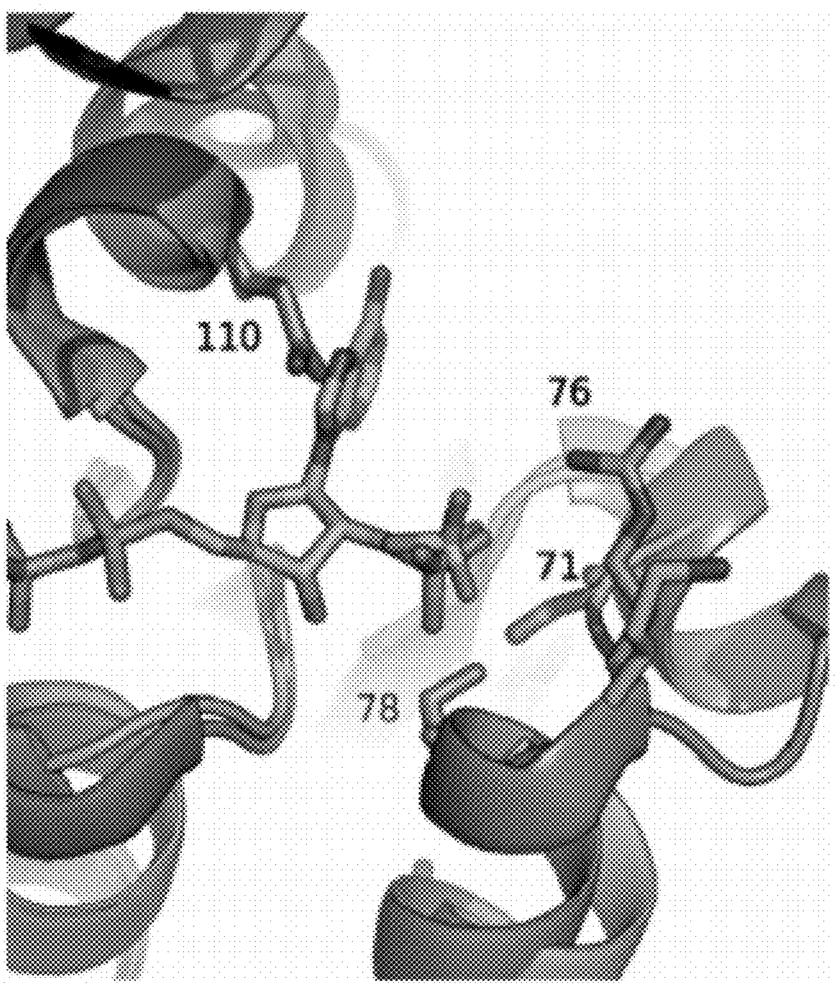
FIG. 7 illustrates the structure alignment of *E. coli* KARI with rice KARI.

A structure alignment of *E. coli* KARI (PDB ID NO. 1YRL) with rice KARI (PDB ID NO. 3FR8) as a representative of the shorter loop group was performed (FIG. 7). The sites of useful mutations in the *E. coli* context corresponded reasonably well with specific residues in the context of the shorter loop: Ser165, Lys166, and Ser167. Ser165 of (corresponding to A71 in *E. coli*) therefore may be substituted with aspartate. A charge reversal at position K166 (corresponding to position R76D) may yield the same result. Ser167 may correspond to Ser78 and a mutation to aspartate may be beneficial Mutations at Q110 may be transferable in all 22 KARIs aligned.

In the case of D146 (e.g. D146G), G185 (e.g. G185R), and $K_{433}$ (e.g. K433E), surface charge changes took place. Glycine at position 185 and Lysine at position 433 are highly conserved among other KARIs. These mutations may therefore be transferable to other KARIs with a similar effect. Aspartate at position 146 is not as highly conserved.

NADH-Dependent ADH Enzymes

Several alcohol dehydrogenases may be suitable candidates for conversion into an NADH-dependent isobutyraldehyde dehydrogenase. Among the preferred enzymes for conversion are *S. cerevisiae* ADH1, *Zymomonas mobilis* ADHII, *E. coli* YqhD, herein referred to as Ec_YqhD, and *S. cerevisiae* ADH7.

As described in the prior art in PCT/US2008/053514, the *S. cerevisiae* ADH2 gene is expected to be functionally expressed from pSA55 and required for catalyzing the final step of the isobutanol biosynthetic pathway, namely the conversion of isobutyraldehyde to isobutanol. Thus, no isobutanol should be produced with the plasmid combination lacking ADH2 as adhE is deleted in JCL260. However, as exemplified in Example 10, the results of a fermentation using a strain without overexpression of any gene encoding an enzyme with ADH activity for the conversion of isobutyraldehyde to isobutanol showed that overexpression of an ADH enzyme is not required for isobutanol production in *E. coli*. In fact, isobutanol production for the system lacking ADH2 was higher than for the system with ADH2 expression. Volumetric productivity and titer showed 42% increase, specific productivity showed 18% increase and yield 12% increase. This suggests strongly that a native *E. coli* dehydrogenase is responsible for the conversion of isobutyraldehyde to isobutanol.

Surprisingly, this last step of the isobutanol biosynthetic pathway was found to be carried out by a native *E. coli* dehydrogenase in the aforementioned strains, as exemplified in Example 11: Approximately ~80% of the isobutyraldehyde reduction activity is due to Ec_YqhD under certain culture conditions. Available literature on Ec_YqhD suggests that while it does prefer long-chain alcohols, it also utilizes NADPH (versus NADH) (Perez, J. M., et al., Journal of Biological Chemistry, 2008. 283(12): p. 7346-7353).

Switching the cofactor specificity of an NADPH-dependent alcohol dehydrogenase may be complicated by the fact that cofactor binding induces a conformational change, resulting in an anhydrous binding pocket that facilitates hydride transfer from the reduced cofactor to the aldehyde (Leskovac, V., S. Trivic, and D. Pricin, Fems Yeast Research, 2002. 2: p. 481-494; Reid, M. F. and C. A. Fewson, Critical Reviews in Microbiology, 1994. 20(1): p. 13-56). Mutations that are beneficial for binding NADH may have deleterious effects with respect to this conformational change.

Alternatively, isobutyraldehyde reduction activity of an NADH-dependent enzyme with little native activity towards this substrate may be increased. This approach has the advantages that (1) several specialized enzymes exist in nature that are highly active under fermentative conditions, (2) the binding sites of several of these enzymes are known, (3) mutational studies indicate that substrate specificity can easily be altered to achieve high activity on a new substrate.

Several alcohol dehydrogenase enzymes may be suitable candidates for conversion into an NADH-dependent isobutyraldehyde dehydrogenase: *S. cerevisiae* ADH1 and *Zymomonas mobilis* ADHII are NADH-dependent enzymes responsible for the conversion of acetaldehyde to ethanol under anaerobic conditions. These enzymes are highly active. The substrate specificity for these enzymes has been analyzed (Leskovac, V., S. Trivic, and D. Pricin, Fems Yeast Research, 2002. 2: p. 481-494; Rellos, P., J. Ma, and R. K. Scopes, Protein Expression and Purification, 1997. 9: p. 89-90), the amino acid residues comprising the substrate binding pocket are known (Leskovac, V., S. Trivic, and D. Pricin, Fems Yeast Research, 2002. 2: p. 481-494; Rellos, P., J. Ma, and R. K. Scopes, Protein Expression and Purification, 1997. 9: p. 89-90), and attempts to alter the substrate specificity by mutation have revealed that the substrate specificity can be altered (Rellos, P., J. Ma, and R. K. Scopes, Protein Expression and Purification, 1997. 9: p. 89-90; Green, D. W., H. Suns, and B. V. Plapp, Journal of Biological Chemistry, 1993. 268(11): p. 7792-7798). Ec_YqhD and *S. cerevisiae* ADH7 are NADPH-dependent enzymes whose physiological functions are not as well understood. Ec_YqhD has been implicated in the protection of the cell from peroxide-derived aldehydes (Perez, J. M., et al., Journal of Biological Chemistry, 2008. 283(12): p. 7346-7353). The substrate specificity of both enzymes is understood, and amino acids lining the substrate binding pocket are known (Perez, J. M., et al., Journal of Biological Chemistry, 2008. 283(12): p. 7346-7353). Based on the known amino acid residues implicated in substrate binding (*S. cerevisiae* ADH1, *Z. mobilis* ADHII) or the cofactor binding site (Ec_yqhD), sites with the highest likelihood of affecting desired enzyme features such as substrate specificity or cofactor specificity may be mutated to generate the desired function.

One approach to increase activity of enzymes with NADH as the cofactor may be saturation mutagenesis with NNK libraries at each of the residues that interact with the cofactor. These libraries may be screened for activity in the presence of NADPH and NADH in order to identify which single mutations contribute to increased activity on NADH and altered specificity for NADH over NADPH. Combinations of mutations at aforementioned residues may be investigated by any method. For example, a combinatorial library of mutants may be designed based on the results of the saturation mutagenesis studies. For example, a combinatorial library of mutants may be designed including only those mutations that do not lead to decrease in NADH-dependent activity.

Another approach to increase the NADH-dependent activity of the enzyme is to perform saturation mutagenesis of a first amino acid that interacts with the cofactor, then isolate the mutant with the highest activity using NADH as the cofactor, then perform saturation mutagenesis of a second amino acid that interacts with the cofactor, and so on. Similarly, a limited number of amino acids that interact with the cofactor may be targeted for randomization simultaneously and then be screened for improved activity with NADH as the cofactor. The selected, best mutant can then be subjected to the same procedure again and this approach may be repeated iteratively until the desired result is achieved.

Another approach is to use random oligonucleotide mutagenesis to generate diversity by incorporating random mutations, encoded on a synthetic oligonucleotide, into the cofactor binding region of the enzyme. The number of mutations in individual enzymes within the population may be controlled by varying the length of the target sequence and the degree of randomization during synthesis of the oligonucleotides. The advantages of this more defined approach are that all possible amino acid mutations and also coupled mutations can be found.

If the best variants from the experiments described above are not sufficiently active with NADH as the cofactor, directed evolution via error-prone PCR may be used to obtain further improvements. Error-prone PCR mutagenesis of the first domain containing the cofactor binding pocket may be performed followed by screening for ADH activity with NADH and/or increased specificity for NADH over NADPH as the cofactor.

Surprisingly, alcohol dehydrogenase enzymes that are not known to catalyze the reduction of isobutyraldehyde to isobutanol were identified that catalyze this reaction. Thus, in another aspect, such an alcohol dehydrogenase may be encoded by an NADH-dependent 1,3-propanediol dehydrogenase. In yet another aspect, such an alcohol dehydrogenase may be encoded by an NADH-dependent 1,2-propanediol dehydrogenase. Preferred enzymes of this disclosure include enzymes listed in Table 1. These enzymes exhibit NADH-dependent isobutyraldehyde reduction activity, measured as Unit per minute per mg of crude cell lysate (U $min^{-1}$ $mg^{-1}$) that is approximately six-fold to seven-fold greater than the corresponding NADPH-dependent isobutyraldehyde reduction activity (Tables 2 and 23).

In addition to exhibiting increased activity with NADH as the cofactor as compared to the NADPH, alcohol dehydrogenases of the present invention may further be more active as compared to the native *E. coli* alcohol dehydrogenase Ec_YqhD. In particular, alcohol dehydrogenases of the present invention may exhibit increased activity and/or decreased $K_M$ values with NADH as the cofactor as compared to Ec_YqhD with NADPH as the cofactor. Exemplary enzymes that exhibit greater NADH-dependent alcohol dehydrogenase activity than the NADPH-dependent alcohol dehydrogenase activity are listed in Table 1; activity values are listed in Table 2 and Table 23.

TABLE 1

ADH genes tested in the following fermentations, and rationale for inclusion of each

| GENE NAME | SEQ ID NO | Accession Number | Rationale for inclusion |
|---|---|---|---|
| *Drosophila melanogaster* ADH | 60 (nucleotide sequence) 61 (amino acid sequence) | NT_033779, REGION: 14615555.. 14618902 | NADH-dependent, broad substrate specificity, well-expressed in bacterial expression systems. Different class of enzyme versus others tested (short-chain, non-metal binding) |
| *Lactococcus lactis* adhA | 66 (nucleotide sequence) 67 (amino acid sequence) | | NADH-dependent alcohol dehydrogenase with activity using isobutyraldehyde as the substrate (Atsumi et al., Appl. Microbiol. Biotechnol., 2009, DOI 10.1007/s00253-009-2085-6) |
| *Klebsiella pneumoniae* dhaT | 62 (nucleotide sequence) 63( amino acid sequence) | NC_011283 | NADH-utilizing 1,2-propanediol dehydrogenase |
| *Escherichia coli* fucO | 64 (nucleotide sequence) 65 (amino acid sequence) | NC_000913.2 (2929887.. 2931038, complement) | Homolog of *K. pneumoniae* dhaT, NADH-dependent 1,3-propanediol dehydrogenase |

TABLE 2

Kinetic parameters for the conversion of isobutyraldehyde to isobutanol by Ec_YqhD, Ec_FucO, Dm_Adh, and Kp_DhaT

| | | NADH | | NADPH | |
|---|---|---|---|---|---|
| Plasmid | Adh | $K_M$ (mM) | Activity (U/min$^{-1}$ mg$^{-1}$ crude lysate) | $K_M$ (mM) | Activity (U/min$^{-1}$ mg$^{-1}$ crude lysate) |
| pGV1705-A | Ec_YqhD | n.d. | n.d. | 0.25 | 0.09 |
| pGV1748-A | Ec_FucO | 0.8 | 0.23 | 0.2 | 0.04 |
| pGV1749-A | Dm_Adh | 0.9 | 6.60 | 2.7 | 1.70 |
| pGV1778-A | Kp_DhaT | 1.3 | 0.56 | 0.6 | 0.08 |

Alcohol dehydrogenases of the present disclosure may also be utilized in metabolically-modified microorganisms that include recombinant biochemical pathways useful for producing additional alcohols such as 2-methyl-1-butanol, 3-methyl-1-butanol, 2-phenylethanol, 1-propanol, or 1-butanol via conversion of a suitable substrate by a modified microorganism.

Microorganisms producing such compounds have been described (PCT/US2008/053514). For example, these alcohols can be 1-propanol, 1-butanol, 2-methyl-1-butanol, 3-methyl-1-butanol or 2-phenylethanol and are generally produced from a metabolite comprising a 2-keto acid. In some aspects, the 2-keto acid includes 2-ketobutyrate, 2-ketovalerate, 2-keto-3-methylvalerate, 2-keto-4-methyl-pentanoate, or phenylpyruvate. The 2-ketoacid is converted to the respective aldehyde by a 2-ketoacid decarboxylase. For example, 2-ketobutyrate is converted to 1-propanal, 2-ketovalerate is converted to 1-butanal, 2-keto-3-methylvalerate is converted to 2-methyl-1-butanol, 2-keto-4-methyl-pentanoate is converted to 3-methyl-1-butanal, and phenylpyruvate is converted to phenylethanal by a 2-ketoacid decarboxylase. Thus, the recombinant microorganism includes elevated expression or activity of a 2-keto-acid decarboxylase, as compared to a parental microorganism. The 2-keto-acid decarboxylase may be encoded by kivd from *Lactococcus lactis*, or homologs thereof. The 2-keto-acid decarboxylase can be encoded by a polynucleotide derived from a gene selected from kivd from *L. lactis*, or homologs thereof.

In earlier publications (PCT/US2008/053514, Atsumi et al., Nature, 2008 Jan. 3; 451(7174):86-9), only NADPH-dependent alcohol dehydrogenases are described that convert the aforementioned aldehyde to an alcohol. In particular, *S. cerevisiae* Adh2p is described that converts the aldehyde to the respective aldehyde.

Thus, in one embodiment of this disclosure, a microorganism is provided in which the cofactor dependent final step for the conversion of the aldehyde to the respective alcohol is catalyzed by an NADH-dependent alcohol dehydrogenase. In particular, NADH-dependent alcohol dehydrogenases are disclosed that catalyze the reduction aldehydes to alcohols, for example, of 1-propanal to 1propanol, 1-butanal to 1-butanol, 2-methyl-1-butanal to 2-methyl-1-butanol, 3-methyl-1-butanal to 3-methyl-1-butanol, or phenylethanal to phenylethanol.

In a specific aspect, such an alcohol dehydrogenase may be encoded by the *Drosophila melanogaster* alcohol dehydrogenase Dm_Adh or homologs thereof. In another specific aspect, such an alcohol dehydrogenase may be encoded by the *Lactococcus* lactis alcohol dehydrogenase LI AdhA (SEQ ID NO: 67), as described by Atsumi et al. (Atsumi et al., Appl. Microbiol. Biotechnol., 2009, DOI 10.1007/s00253-009-2085-6) or homologs thereof.

Surprisingly, alcohol dehydrogenase enzymes that are not known to catalyze the reduction of isobutyraldehyde to isobutanol were identified that catalyze this reaction. Thus, in another aspect, such an alcohol dehydrogenase may be encoded by an NADH-dependent 1,3-propanediol dehydrogenase. In yet another aspect, such an alcohol dehydrogenase may be encoded by an NADH-dependent 1,2-propanediol dehydrogenase. Preferred enzymes of this disclosure include enzymes listed in Table 1.

In another embodiment, a method of producing an alcohol is provided. The method includes providing a recombinant microorganism provided herein; culturing the microorganism of in the presence of a suitable substrate or metabolic intermediate and under conditions suitable for the conversion of the substrate to an alcohol; and detecting the production of the alcohol. In various aspects, the alcohol is selected from 1-propanol, 1-butanol, 2-methyl 1-butanol, 3-methyl 1-butanol, and 2-phenylethanol. In another aspect, the substrate or metabolic intermediate includes a 2-keto acid-derived aldehyde, such as 1-propanal, 1-butanal, 2-methyl-1-butanal, 3-methyl-1-butanal, or phenylethanal.

Recombinant Host Cells Comprising a NADH-dependent KARI and/or ADH Enzymes

In an additional aspect, the present invention is directed to recombinant host cells (i.e. metabolically "engineered" or "modified" microorganisms) comprising NADH-dependent KARI and/or ADH enzymes of the invention. Recombinant microorganisms provided herein can express a plurality of additional heterologous and/or native target enzymes involved in pathways for the production of beneficial metabolites such as isobutanol from a suitable carbon source.

Accordingly, metabolically "engineered" or "modified" microorganisms are produced via the introduction of genetic material (i.e. a NADH-dependent KARI and/or ADH enzymes) into a host or parental microorganism of choice, thereby modifying or altering the cellular physiology and biochemistry of the microorganism. Through the introduction of genetic material and/or the modification of the expression of native genes the parental microorganism acquires new properties, e.g. the ability to produce a new, or greater quantities of, an intracellular metabolite. As described herein, the introduction of genetic material and/or the modification of the expression of native genes into a parental microorganism results in a new or modified ability to produce beneficial metabolites such as isobutanol. The genetic material introduced into and/or the genes modified for expression in the parental microorganism contains gene(s), or parts of genes, coding for one or more of the enzymes involved in a biosynthetic pathway for the production of isobutanol and may also include additional elements for the expression and/or regulation of expression of these genes, e.g. promoter sequences.

Recombinant microorganisms provided herein may also produce metabolites in quantities not available in the parental microorganism. A "metabolite" refers to any substance produced by metabolism or a substance necessary for or taking part in a particular metabolic process. A metabolite can be an organic compound that is a starting material (e.g., glucose or pyruvate), an intermediate (e.g., 2-ketoisovalerate), or an end product (e.g., 1-propanol, 1-butanol, isobutanol, 2-methyl-1-butanol, 3-methyl-1-butanol) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

Exemplary metabolites include glucose, pyruvate, 1-propanol, 1-butanol, isobutanol, 2-methyl-1-butanol, and 3-methyl-1-butanol.

The metabolite 1-propanol can be produced by a recombinant microorganism engineered to express or over-express a metabolic pathway that converts pyruvate to 1-propanol. An exemplary metabolic pathway that converts pyruvate to 1-propanol has been described in WO/2008/098227 and by Atsumi et al. (Atsumi et al., 2008, *Nature* 451(7174): 86-9), the disclosures of which are herein incorporated by reference in their entireties. In a preferred embodiment, metabolic pathway comprises a KARI and/or an ADH enzyme of the present invention.

The metabolite 1-butanol can be produced by a recombinant microorganism engineered to express or over-express a metabolic pathway that converts pyruvate to 3-methyl-1-butanol. An exemplary metabolic pathway that converts pyruvate to 3-methyl-1-butanol has been described in WO/2008/098227 and by Atsumi et al. (Atsumi et al., 2008, *Nature* 451(7174): 86-9), the disclosures of which are herein incorporated by reference in their entireties. In a preferred embodiment, metabolic pathway comprises a KARI and/or an ADH enzyme of the present invention.

The metabolite isobutanol can be produced by a recombinant microorganism engineered to express or over-express a metabolic pathway that converts pyruvate to isobutanol. An exemplary metabolic pathway that converts pyruvate to isobutanol may be comprised of a acetohydroxy acid synthase (ALS) enzyme encoded by, for example, alsS from *B. subtilis*, a ketolacid reductoisomerase (KARI) of the present invention, a dihydroxy-acid dehydratase (DHAD), encoded by, for example ilvD from *E. coli*, a 2-keto-acid decarboxylase (KIVD) encoded by, for example kivd from *L. lactis*, and an alcohol dehydrogenase (ADH) of the present invention.

The metabolite 3-methyl-1-butanol can be produced by a recombinant microorganism engineered to express or over-express a metabolic pathway that converts pyruvate to 3-methyl-1-butanol. An exemplary metabolic pathway that converts pyruvate to 3-methyl-1-butanol has been described in WO/2008/098227 and by Atsumi et al. (Atsumi et al., 2008, *Nature* 451(7174): 86-9), the disclosures of which are herein incorporated by reference in their entireties. In a preferred embodiment, metabolic pathway comprises a KARI and/or an ADH enzyme of the present invention.

The metabolite 2-methyl-1-butanol can be produced by a recombinant microorganism engineered to express or over-express a metabolic pathway that converts pyruvate to 2-methyl-1-butanol. An exemplary metabolic pathway that converts pyruvate to 2-methyl-1-butanol has been described in WO/2008/098227 and by Atsumi et al. (Atsumi et al., 2008, *Nature* 451(7174): 86-9), the disclosures of which are herein incorporated by reference in their entireties. In a preferred embodiment, metabolic pathway comprises a KARI and/or an ADH enzyme of the present invention.

The disclosure identifies specific genes useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutation and silent mutations. Such modified or mutated polynucleotides and polypeptides can be screened for expression of a functional enzyme using methods known in the art. In addition, homologs of enzymes useful for generating metabolites are encompassed by the microorganisms and methods provided herein.

Method of Using Microorganism for Anaerobic Isobutanol Fermentation

In a method to produce a target compound from a carbon source at high yield a modified microorganism subject to this invention is cultured in an appropriate culture medium containing a carbon source.

An exemplary embodiment provide a method for producing isobutanol comprising a modified microorganism of the invention in a suitable culture medium containing a carbon source that can be converted to isobutanol by the microorganism of the invention.

In certain embodiments, the method further includes isolating said target compound from the culture medium. For example, isobutanol may be isolated from the culture medium by any method, in particular a method known to those skilled in the art, such as distillation, pervaporation, or liquid-liquid extraction.

This invention is further illustrated by the following examples that should not be construed as limiting. The contents of all references, patents, and published patent applications cited throughout this application, as well as the Figures and the Sequence Listing, are incorporated herein by reference for all purposes.

EXAMPLES

The following provides examples that demonstrate that microorganisms modified to resolve a cofactor imbalance produce a target compound at higher yield under conditions that include anaerobic conditions. One compound to be produced by the recombinant microorganism according to the present invention is isobutanol. The present invention is not limited to isobutanol. The invention may be applicable to any metabolic pathway that is imbalanced with respect to cofactor usage. One skilled in the art is able identify pathways that are imbalanced with respect to cofactor usage and apply this invention to provide recombinant microorganisms in which the same pathway is balanced with respect to cofactor usage.

Sample Preparation

Generally, samples (2 mL) from fermentation experiments performed in shake flasks were stored at 4° C. for later substrate and product analysis. Prior to analysis, samples were centrifuged at 14,000×g for 10 min. The supernatant was filtered through a 0.2 μm filter. Analysis of substrates and products was performed using authentic standards (>99%, obtained from Sigma-Aldrich), and a 5-point calibration curve (with 1-pentanol as an internal standard for analysis by gas chromatography).

Determination of Optical Density

The optical density of the yeast cultures was determined at 600 nm using a DU 800 spectrophotometer (Beckman-Coulter, Fullerton, Calif., USA). Samples were diluted as necessary to yield an optical density of between 0.1 and 0.8.

Gas Chromatography

Analysis of volatile organic compounds, including ethanol and isobutanol was performed on a HP 5890 gas chromatograph fitted with an HP 7673 Autosampler, a DB-FFAP column (J&W; 30 m length, 0.32 mm ID, 0.25 μM film thickness) or equivalent connected to a flame ionization detector (FID). The temperature program was as follows: 200° C. for the injector, 300° C. for the detector, 100° C. oven for 1 minute, 70° C./minute gradient to 235° C., and then hold for 2.5 min.

Analysis was performed using authentic standards (>99%, obtained from Sigma-Aldrich), and a 5-point calibration curve with 1-pentanol as the internal standard.

High Performance Liquid Chromatography

Analysis of glucose and organic acids was performed on a HP-1100 High Performance Liquid Chromatography system equipped with an Aminex HPX-87H Ion Exclusion column (Bio-Rad, 300×7.8 mm) or equivalent and an $H^+$ cation guard column (Bio-Rad) or equivalent. Organic acids were detected using an HP-1100 UV detector (210 nm, 8 nm 360 nm reference) while glucose was detected using an HP-1100 refractive index detector. The column temperature was 60° C. This method was Isocratic with 0.008N sulfuric acid in water as mobile phase. Flow was set at 0.6 mL/min. Injection size was 20 μL and the run time was 30 minutes.

Molecular Biology and Bacterial Cell Culture

Standard molecular biology methods for cloning and plasmid construction were generally used, unless otherwise noted (Sambrook, J., Russel, D. W. *Molecular Cloning, A Laboratory Manual.* 3 ed. 2001, Cold Spring Harbor, N.Y.: Cold Spring Harbor Laboratory Press).

Standard recombinant DNA and molecular biology techniques used in the Examples are well known in the art and are described by Sambrook, J., Russel, D. W. *Molecular Cloning, A Laboratory Manual.* 3 ed. 2001, Cold Spring Harbor, N.Y.: Cold Spring Harbor Laboratory Press; and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., *Current Protocols in Molecular Biology*, pub. by Greene Publishing Assoc. and Wiley-Interscience (1987).

General materials and methods suitable for the routine maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds.), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989).

Preparation of Electrocompetent *E. Coli* Cells and Transformation

The acceptor strain culture was grown in SOB-medium (Sambrook, J., Russel, D. W. *Molecular Cloning, A Laboratory Manual.* 3 ed. 2001, Cold Spring Harbor, N.Y.: Cold Spring Harbor Laboratory Press) to an $OD_{600}$ of about 0.6 to 0.8. The culture was concentrated 100-fold, washed once with ice cold water and 3 times with ice cold 10% glycerol. The cells were then resuspended in 150 μL of ice-cold 10% glycerol and aliquoted into 50 μL portions. These aliquots were used immediately for standard transformation or stored at −80° C. These cells were transformed with the desired plasmid(s) via electroporation. After electroporation, SOC medium (Sambrook, J., Russel, D. W. *Molecular Cloning, A Laboratory Manual.* 3 ed. 2001, Cold Spring Harbor, N.Y.: Cold Spring Harbor Laboratory Press) was immediately added to the cells. After incubation for an hour at 37° C. the cells were plated onto LB-plates containing the appropriate antibiotics and incubated overnight at 37° C.

Transformation of *S. cerevisiae* Cells

*S. cerevisiae* strains were transformed by the Lithium Acetate method (Gietz et al., *Nucleic Acids Res.* 27:69-74 (1992): Cells from 50 mL YPD cultures (YPGal for valine auxotrophs) were collected by centrifugation (2700 rcf, 2 minutes, 25° C.) once the cultures reached an $OD_{600}$ of 1.0. The cells were washed cells with 50 mL sterile water and collected by centrifugation at 2700 rcf for 2 minutes at 25° C. The cells were washed again with 25 mL sterile water and collected cells by centrifugation at 2700 rcf for 2 minutes at 25° C. The cells were resuspended in 1 mL of 100 mM lithium acetate and transferred to a 1.5 mL eppendorf tube. The cells were collected cells by centrifugation for 20 sec at 18,000 rcf, 25° C. The cells were resuspended cells in a volume of 100 mM lithium acetate that was approximately 4× the volume of the cell pellet. A mixture of DNA (final volume of 15 μl with sterile water), 72 μl 50% PEG, 10 μl 1 M lithium acetate, and 3 μl denatured salmon sperm DNA was prepared for each transformation. In a 1.5 mL tube, 15 μl of the cell suspension was added to the DNA mixture (85 μl), and the transformation suspension was vortexed with 5 short pulses. The transformation was incubated at 30 minutes at 30° C., followed by incubation for 22 minutes at 42° C. The cells were collected by centrifugation for 20 sec at 18,000 rcf, 25° C. The cells were resuspended in 100 μl SOS (1 M sorbitol, 34% (v/v) YP (1% yeast extract, 2% peptone), 6.5 mM $CaCl_2$) or 100 μl YP (1% yeast extract, 2% peptone) and spread over an appropriate selective plate.

Sporulation of Diploid *S. Cerevisiae* and Germination to Obtain Haploids

Random spore analysis was used to identify desired haploid segregants of relevant diploid strains. Diploid strains were sporulated by pre-culturing in YPD for 24 hrs and then transferring the cells into 5 mL of sporulation medium (1% wt/vol potassium acetate). After 4-5 days, the culture was examined microscopically for the presence of visible spore-containing asci. To the 5 mL sporulation culture, 0.5 mL of 1 mg/mL Zymolyase-T (Seikagaku Biobusiness, Tokyo, Japan) and 10 μL of β-mercaptoethanol were added, and the cells were incubated overnight at 30° C. while shaking slowly (60 rpm). The next day, 5 mL of 1.5% IGEPAL-CA-630 [reference] were added and the mixture incubated on ice for 15 minutes. The cell suspension was then sonicated (3 rounds, 30 seconds per round, 50% power) with 2 minutes on ice between sonications. The suspension was centrifuged (1200× g, 10 min), the liquid poured off, 5 mL of 1.5% IGEPAL-CA-630 (Sigma-Aldrich Co., St. Louis, Mo.) were added, and the centrifugation and resuspension step repeated once more. The cell suspension was again sonicated as described above, after which it was centrifuged and washed as described above except that instead of IGEPAL, sterile water was used to resuspend the cells. The cells were finally resuspended in 1 mL of sterile water, and 0.1 mL of a 1:10, 1:100, 1:100, and 1:10,000 dilution of the initial 1 mL cell suspension were plated onto SCE-Trp, Leu, Ura (for full-pathway integrants strains) or SCD-Trp, Ura (for partial-pathway integrant strains) media and the plates incubated at 30° C. until colonies appeared (typically, 4-5 days).

Yeast Colony PCR

Colony PCR was carried out using the FailSafe mix (Epicentre Biotechnologies, Madison, Wis.). Specifically, 15 L of FailSafe Mix "E" were combined with 13 µL sterile water, 0.35 µL of each primer (from a 100 µM solution), and 0.6 µL FailSafe polymerase. For template, a small dab of yeast cells sufficient to just turn the solution turbid was swirled into each individual reaction mixture. The PCR reactions were incubated as follows: 1 cycle of 94° C.×2 min; 40 cycles of 94° C.×15 sec, 53° C.×15 sec, 72° C.×1 min; 1 cycle of 72° C.×8 min.

qRT-PCR

Performed by isolating RNA, synthesizing cDNA by reverse transcription and performing qPCR using protocols described below.

RNA isolation for Reverse Transcription (RT)

3 ml YPD cell cultures were incubated at 30° C., 250 RPM until they reached $OD_{600}$'s of 0.7 to 1.5. $2OD_{600}$'s (e.g. 1 mL of a culture at $20D_{600}$) of cells were then harvested from each culture in 1.5 ml tubes by centrifugation at full speed in a microfuge for 2 minutes. The cell pellet was stored overnight at −20° C. RNA was isolated using the YeaStar RNAKit™ (Zymo Research Corp. Orange, Calif. 92867 USA). Following the protocol provided with the kit, cells were resuspended in 80 µl of YR Digestion Buffer and 5 µl of Zymolyase™. The pellet was completely resuspended by repeated pipetting. The suspension was incubated at 37° C. for 60 minutes. 160 µl of YR Lysis Buffer was added to the suspension, which was then mixed thoroughly by vortexing. The mixture was centrifuged at >4,000×g for 2 minutes in the microfuge, and the supernatant was transferred to a Zymo-Spin Column in a Collection Tube. The column was centrifuged at >10,000×g for 1 minute in the microfuge. To the column, 200 µl RNA Wash Buffer was added, and the column was centrifuged for 1 minute at 14,000 RPM in the microfuge. The flow-through was discarded and 200 µl RNA Wash Buffer was added to the column. The column was centrifuged for 1 minute at >10,000×g. The Zymo-Spin Column was transferred to a new RNase-free 1.5 ml centrifuge tube, and 60 µl of DNase/RNase-Free Water was added directly to the column membrane. The RNA was eluted by centrifugation for 30 seconds at >10,000×g in the microfuge.

cDNA Synthesis (Reverse Transcription) for qPCR

Using the gScript™ cDNA SuperMix kit provided by Quanta Biosciences™ (Gaithersburg, Md.), cDNA was prepared following the protocol provided with the kit. First, the concentration of RNA was measured for the preparations from each transformant candidate and control strain. A final solution of 300 ng of RNA in sterile water was prepared in a volume of 16 µl in 0.2 ml PCR tube (RNase-free). To each sample, 4 µl of qScript cDNA Supermix was added. The reactions were incubated on a thermocycler for 5 minutes at 25° C., 30 minutes at 42° C., and 5 minutes at 85° C.

qPCR:

Each reaction contained: 10 µL of PerfeCTa™ SYBR® Green SuperMix kit (Quanta Biosciences™ Gaithersburg, Md.), 1 µl of cDNA, 1 µl of a 5 µM (each) mix of forward and reverse primers and 8 µl of sterile water. Each reaction was assembled in a well of a 0.2 ml 96-well plate, and a clear plastic sheet was carefully (to avoid the introduction of warped surface or fingerprints or smudges) and firmly placed over the 96-well plate. The reactions were incubated in an Eppendorf Mastercycler ep thermocycler (Eppendorf, Hamburg, Germany) using the following conditions: 95° C. for 2 minutes, 40 cycles of 95° C. for 15 seconds and 60° C. for 45 seconds, 95° C. for 15 seconds, 60° C. for 15 seconds, and a 20 minute slow ramping up of the temperature until it reaches 95° C. Finally, it was incubated at 95° for 15 seconds. The fluorescence emitted by the SYBR dye was measured at the 60° C. incubation step during each of the 40 cycles, as well as during the ramping up to 95° C. for melting curve analysis of the primer sets.

Construction of *E. coli* Strains

GEVO1385 was constructed by integrating the Z1 module into the chromosome of JCL260 by P1 transduction from the strain *E. coli* W3110, Z1 (Lutz, R, Bujard, H Nucleic Acids Research (1997) 25, 1203-1210).

GEVO1399: The gene zwf was deleted according to the standard protocol for gene deletion using the Wanner method (Datsenko, K. and Wanner, B. One-step Inactivation of chromosomal genes in *Escherichia coli* K-12 using PCR products. PNAS 2000). Primers 73 and 74 were used to amplify the Kan resistance cassette from pKD13. The linear PCR product was transformed into *E. coli* W3110 pKD46 electro competent cells and the knock-out of zwf was verified by PCR. Lysate of the new strain (*E. coli* W3110, Δzwf::FRT::Kan::FRT) was prepared and the knock-out was transferred into JCL260 by P1 transduction. Removal of the Kan resistance cassette from this strain using transient expression of FLP recombinase yielded GEVO1399.

GEVO1608: The gene Ec_yqhD (SEQ ID NO: 68) was deleted according to the standard protocol for gene deletion using the Wanner method (Datsenko, K and Wanner, B, "One-step Inactivation of chromosomal genes in *Escherichia coli* K-12 using PCR products," PNAS 2000, 97:6640-6645). Primers 1155 and 1156 were used to amplify the Kan resistance cassette from pKD13. The linear PCR product was transformed into *E. coli* W3110 pKD46 electro competent cells and the knock-out of Ec_yqhD was verified by PCR. A lysate of the new strain (*E. coli* W3110, ΔyqhD::FRT::Kan::FRT) was prepared and the knock-out was transferred into JCL260 by P1 transduction yielding GEVO1608.

GEVO1745: Removal of the Kan resistance cassette from GEVO1608 using transient expression of FLP recombinase yielded GEVO1745.

GEVO1748 and GEVO1749 are derivatives of JCL260. For the construction of GEVO1748, PLlacO1::L1_kivd1::Ec_ilvD_coEc was integrated into the ilvC locus on the *E. coli* chromosome. In particular primers 869 and 1030 were used to amplify the kanamycin resistance cassette (Kan) from pKD13, and primers 1031 and 1032 were used to amplify PLlacO1::L1_kivd1::Ec_ilvD_coEc from pGV1655 (SEQ ID NO: 109). For the construction of GEVO1749 PLlacO1::L1_kivd1::Ec_ilvD_coEc was integrated into the adhE locus on the *E. coli* chromosome. In particular primers 50 and 1030 were used to amplify the kanamycin resistance cassette from pKD13, and primers 1031 and 1205 were used to amplify PLlacO1::L1_kivd1::Ec_ilvD_coEc from pGV1655 (SEQ ID NO: 109). Afterwards, SOE (splicing by overlap extension) (Horton, R M, Cai, Z L, Ho, S N, et al. Biotechniques Vol. 8 (1990) pp 528) reactions were done to connect the gene expression cassettes to the resistance cassette using primers 1032 and 869 for the ilvC locus and primers 1205 and 50 for the adhE locus. The linear PCR products were transformed into W3110 pKD46 electro competent cells and the knock ins of PLlacO1::L1_kivd1::Ec_ilvD_coEc::FRT::Kan::FRT were verified by PCR. The knock ins were further verified by sequencing. Lysates of the new strains *E. coli* W3110, ΔilvC::

PLlacO1::Ll_kivd1::Ec_ilvD_coEc::FRT::Kan::FRT) and *E. coli* W3110, ΔadhE::PLlacO1::Ll_kivd1:: Ec_ilvD_coEc::FRT::Kan::FRT) were prepared and the knock ins were transferred to JCL260 by P1 transduction. Removal of the Kan resistance cassette from this strain using expression of FLP recombinase yielded GEVO1748 and GEVO1749.

GEVO1725, GEVO1750, GEVO1751: The gene maeA was deleted according to the standard protocol for gene deletion using the Wanner method (Datsenko, K. and Wanner, B. One-step Inactivation of chromosomal genes in *Escherichia coli* K-12 using PCR products. PNAS 2000). Primers 116 and 117 were used to amplify the Kan resistance cassette from pKD13. The linear PCR product was transformed into *E. coli* W3110 pKD46 electro competent cells and the knock-out of maeA was verified by PCR. Lysate of the new strain (*E. coli* W3110, ΔmaeA::FRT::Kan::FRT) was prepared and the knock-out was transferred into JCL260 by P1 transduction. The Kan resistance cassette was removed from this strain using transient expression of FLP recombinase. The resulting strain was transduced with the Z1 cassette yielding GEVO1750, and the same strain was transduced with a lysate conferring a pykA deletion. The pykA deletion lysate was prepared from W3110, ΔpykA::FRT::Kan::FRT, which was created using homologous recombination according to the Wanner method using primers 1187 and 1188 for the amplification of the Kan cassette from pKD13. The Kan resistance cassette was removed from this strain using transient expression of FLP recombinase. The resulting strain was transduced with a lysate conferring a pykF deletion. The pykF deletion lysate was prepared from W3110, ΔpykF::FRT::Kan::FRT, which was created using homologous recombination according to the Wanner method using primers 1191 and 1192 for the amplification of the Kan cassette from pKD13. Removal of the Kan resistance cassette from this strain using transient expression of FLP recombinase yielded GEVO1725. For the construction of GEVO1751 strain GEVO1725 was transduced with a lysate of W3110Z1. The resulting strain was GEVO1751.

For the construction of GEVO1777 ilvC was deleted according to the standard protocol for gene deletion using the Wanner method. Primers 868 and 869 were used to amplify the Kan resistance cassette from pKD13. The linear PCR product was transformed into *E. coli* W3110 pKD46 electro competent cells and the knock-out of ilvC was verified by PCR. The Kan resistance cassette was removed from this strain using transient expression of FLP recombinase. The resulting strain was transduced with the Z1 cassette yielding GEVO1777.

GEVO1780 was constructed by transforming JCL260 with plasmids pGV1655 (SEQ ID NO: 109) and pGV1698 (SEQ ID NO: 112).

GEVO1844: An *E. coli* sthA deletion strain was obtained from the Keio collection and the deletion of sthA was verified. The sthA deletion was transferred to GEVO1748 by P1 phage transduction and after removal of the Kan resistance cassette by transient expression of FLP recombinase the resulting strain GEVO1844 was verified for the sthA deletion.

GEVO1846 was constructed by transforming strain GEVO1748 with plasmids pGV1745 (SEQ ID NO: 117) and pGV1698 (SEQ ID NO: 112).

GEVO1859 was constructed according to the standard protocol for gene integration using the Wanner method (Datsenko, K. and Wanner, B. One-step Inactivation of chromosomal genes in *Escherichia coli* K-12 using PCR products. PNAS 2000). Primers 1219 and 1485 were used to amplify PLlacO1::Bs_alsS1::Ec_ilvC_coEc from pGV1698 (SEQ ID NO: 112). Primers 1218 and 1486 were used to amplify the Kan resistance cassette from pKD13. SOE (splicing by overlap extension) was used to combine the two pieces to one integration cassette. The linear PCR product was transformed into *E. coli* W3110 pKD46 electro competent cells and the knock-in of PLlacO1::Bs_alsS1::Ec_ilvC_coEc::FRT::Kan::FRT into the pflB locus was verified by PCR. The knock-in was further verified by sequencing. Lysate of the new strain (*E. coli* W3110, ΔpflB:: PLlacO1::Bs_alsS1::Ec_ilvC_coEc::FRT::Kan::FRT) was prepared and the knock-in was transferred into GEVO1749 by P1 transduction. Removal of the Kan resistance cassette from this strain using transient expression of FLP recombinase yielded GEVO1859.

GEVO1886 was constructed according to the standard protocol for gene integration using the Wanner method (Datsenko, K. and Wanner, B. One-step Inactivation of chromosomal genes in *Escherichia coli* K-12 using PCR products. PNAS 2000). Primers 1562 and 1539 were used to amplify PLlacO1::pntAB from pGV1745 (SEQ ID NO: 117). Primers 1479 and 1561 were used to amplify the Kan resistance cassette from pKD13. SOE was used to combine the two pieces to one integration cassette. The linear PCR product was transformed into *E. coli* W3110 pKD46 electro competent cells and the knock-in of PLlacO1::pntAB::FRT::Kan::FRT into the sthA locus was verified by PCR. The knock-in was further verified by sequencing. Lysate of the new strain (*E. coli* W3110, AsthA:: PLlacO1::pntAB::FRT::Kan::FRT) was prepared and the knock-in was transferred into GEVO1859 by P1 transduction. Removal of the Kan resistance cassette from this strain using transient expression of FLP recombinase yielded GEVO1886.

GEVO1993 is a derivative of GEVO1748. For the construction of GEVO1993, PLlacO1::Bs_alsS1 was integrated into the pta locus on the *E. coli* chromosome. In particular primers 1526 and 474 were used to amplify the kanamycin resistance cassette (Kan) from pKD13, and primers 1563 and 1527 were used to amplify PLlacO1:: Bs_alsS1 from pGV1698. Afterwards, SOE (splicing by overlap extension) reactions were done to connect the gene expression cassette to the resistance cassette using primers 1563 and 474. The linear PCR products were transformed into *E. coli* W3110 pKD46 electro competent cells and the knock-ins of PLlacO1::Bs_alsS1::FRT::Kan::FRT were verified by PCR. The knock-ins were further verified by sequencing. Lysate of the new strain *E. coli* W3110, Δpta::PLlacO1::Bs_alsS1::FRT::Kan::FRT was prepared and the knock-in was transferred to GEVO1748 by P1 transduction yielding GEVO1993. The integration into the pta locus in GEVO1993 was verified by PCR.

Construction of *Saccharomyces cerevisiae* Strains

A PDC deletion variant *S. cerevisiae*, GEVO2302, was evolved so that it does not have the requirement for a two-carbon molecule and has a growth rate similar to the parental strain on glucose.

GEVO1186 is *S. cerevisiae* CEN.PK2

GEVO1803 was made by transforming GEVO1186 with the 6.7 kb pGV1730 (SEQ ID NO: 116) (contains *S. cerevisiae* TRP1 marker and the CUP1 promoter-driven Bs_alsS2) that had been linearized by digestion with NruI. Completion of the digest was confirmed by running a small sample on a gel. The digested DNA was then purified using Zymo Research DNA Clean and Concentrator and used in the transformation. Trp+ clones were confirmed for the correct integration into the PDC1 locus by colony PCR using primer pairs 1440+1441 and 1442+1443 for the 5' and 3' junctions, respectively. Expression of Bs_alsS2 was confirmed by qRT-PCR using primer pairs 1323+1324.

GEVO2107 was made by transforming GEVO1803 with linearized, HpaI-digested pGV1914 (SEQ ID NO: 119). Correct integration of pGV1914 at the PDC6 locus was confirmed by analyzing candidate Ura+colonies by colony PCR using primers 1440 plus 1441, or 1443 plus 1633, to detect the 5' and 3' junctions of the integrated construct, respectively. Expression of all transgenes were confirmed by qRT-PCR using primer pairs 1321 plus 1322, 1587 plus 1588, and 1633 plus 1634 to examine Bs_alsS2, Ll_kivd2_coEc, and Dm_ADH transcript levels, respectively.

GEVO2158 was made by transforming GEVO2107 with NruI-digested pGV1936 (SEQ ID NO: 120). Correct integration of pGV1936 at the PDC5 locus was confirmed by analyzing candidate Ura+, Leu+ colonies by colony PCR using primers primers 1436 plus 1437, or 1595 plus 1439, to detect the 5' and 3' junctions of the integrated construct, respectively. Expression of all transgenes were confirmed by qRT-PCR using primer pairs 1321 plus 1322, 1597 plus 1598, 1566 plus 1567, 1587 plus 1588, 1633 plus 1634, and 1341 plus 1342 to examine levels of Bs_alsS2, Ec_ilvC_coSc$^{Q110V}$, Sc_ilv3ΔN, Ll_kivd2 coEc, Dm_ADH, and ACT1, respectively.

GEVO2302 was constructed by sporulating GEVO2158. Haploid spores were prepared for random spores analysis (as described above), and the spores were plated onto SCE-Trp, Leu,Ura medium (14 g/L Sigma™ Synthetic Dropout Media supplement (includes amino acids and nutrients excluding histidine, tryptophan, uracil, and leucine), 6.7 g/L Difco™ Yeast Nitrogen Base without amino acids. 0.076 g/L histidine and 25 mL/L 100% ethanol). Candidate colonies were patched onto SCE-Trp, Leu, Ura plates (Plate version of the above medium was prepared using 20 g/L agar) and then replica plated onto YPD (10 g/L yeast extract, 20 g/L peptone, 20 g/L glucose) and YPE (10 g/L yeast extract, 20 g/L peptone, 25 mL/L 100% ethanol) plates. Patches that grew on YPE but failed to grow on YPD were further analyzed by colony PCR to confirm mating type (and, hence, their status as haploid). Several verified haploid candidates were further analyzed for transgene expression by qRT-PCR. GEVO2302 contains the full isobutanol pathway with ALS, KARI, DHAD, KIVD, and ADH being encoded by Bs_alsS2, Ec_ilvC_coSc$^{Q110V}$, Sc_ilv3ΔN, Ll_kivd2_coEc, Dm_ADH, respectively.

GEVO2710, GEVO2711, GEVO2712 and GEVO2799 are C2-independent, glucose de-repressed derivatives of GEVO2302, which were constructed via chemostat evolution: A DasGip fermentor vessel was sterilized and filled with 1 L of YNB+histidine medium (Yeast Nitrogen Base+histidine, containing per liter of distilled water: 6.7 g YNB without amino acids from Difco and 0.076 g histidine; the medium was adjusted to pH 5 by adding a few drops of HCL or KOH) and contained 2% w/v ethanol. The vessel was installed and all probes were calibrated according to DasGip instructions. The vessel was also attached to an off-gas analyzer of the DasGip system, as well as to a mass spectrometer. Online measurements of oxygen, carbon dioxide, isobutanol, and ethanol were taken throughout the experiment. The two probes that were inside the vessel measured pH and dissolved oxygen levels at all times. A medium inlet and an outlet were also set up on the vessel. The outlet tube was placed at a height just above the 1 L level, and the pump rate was set to maximum. This arrangement helped maintain the volume in the vessel at 1 L. Air was sparged into the fermentor at 12 standard liters per hour (slph) at all times. The temperature of the vessel was held constant at 30.0° C. and the agitation rate was set at a minimum of 500 rpm, with a cascade control to adjust the agitation to maintain 50% dissolved oxygen in the culture. The off-gas was analyzed for $CO_2$, $O_2$, ethanol and isobutanol concentrations. The amount of carbon dioxide ($X_{CO2}$) and oxygen ($X_{O2}$) levels in the off-gas were used to assess the metabolic state of the cells. An increase in $X_{CO2}$ levels and decrease in $X_{O2}$ levels indicated an increase in growth rate and glucose consumption rate. The ethanol levels were monitored to ensure that there was no contamination, either from other yeast cells or from potential revertants of the mutant strain because the *S. cerevisiae* PDC triple-mutant (GEVO2302) does not produce ethanol. The minimum pH in the vessel was set to 5, and a base control was set up to pump in potassium hydroxide into the vessel when the pH dropped below 5.

GEVO2302 was inoculated into 10 ml of YNB+histidine medium with 2% w/v ethanol as the carbon source. The culture was incubated at 30° C. overnight with shaking. The overnight culture was used to inoculate the DasGip vessel. Initially, the vessel was run in batch mode, to build up a high cell density. When about a cell biomass of $OD_{600}$=8 was reached, the vessel was switched to chemostat mode and the dilution of the culture began. The medium pumped into the vessel was YNB+histidine with 6.357 g/L glucose and 0.364 g/L of acetate (5% carbon equivalent). The initial dilution rate was set to 0.06 $h^{-1}$ to avoid washout.

After the culture in the chemostat was stabilized at the 0.06 $h^{-1}$ dilution rate, the concentration of acetate was slowly decreased. This was achieved by using a two pump system, effectively producing a gradient pumping scheme. Initially pump A was pumping YNB+histidine medium with 10 g/L glucose at a rate of 35.5 mL/h and pump B was pumping YNB+histidine medium with only 1 g/L acetate at a rate of 20.3 mL/h. The total acetate going into the vessel was 0.364 g/L. Then, over a period of 5 days, the rate of pump B was slowly decreased and the rate of pump A was increased so that the combined rate of feeding increased from 56 mL/h to 74 ml/h. Over this period, the rate of pump B was finally reduced to 0, resulting in no (0 g/L) acetate addition to the chemostat. The glucose feed to the chemostat over this period was increased from 6.4 g/L to 10 g/L and the evolved strain was able to grow on glucose only.

Evolution of the strain for growth on increased glucose concentration was performed by slowly increasing the concentration of glucose in the chemostat with the evolved strain that no longer required a 2-carbon supplement. The concentration of glucose in the feed medium was increased from 10 g/L to 38 g/L over a period of 31 days. This was achieved by using a two pump system, effectively producing a gradient pumping scheme. Initially pump A was pumping YNB+histidine medium with 10 g/L glucose at a rate of 35.2 mL/h and pump B was pumping YNB+histidine medium with 15 g/L glucose at a rate of 32.9 mL/h. The total glucose going into the vessel was 12.4 g/L. Then, over a period of 18 days, the medium reservoirs for pump A and pump B were replaced with reservoirs containing increased concentrations of glucose until the reservoir for pump A contained 80 g/L glucose and the reservoir for pump B contained 100 g/L glucose. During this period, the combined rate of feeding maintained a dilution rate of 0.04 $h^{-1}$. At the end of this period, the rate of pump A was finally reduced to 0, resulting in a feed of 100 g/L glucose. This dilution rate resulted in a biomass of $OD_{600}$=4.8 at this glucose concentration and increasing the dilution rate to 0.09 $h^{-1}$ over a period of 4 days lowered the biomass to an $OD_{600}$=2.6. The dilution rate was lowered to 0.03 $h^{-1}$ and gradually raised to 0.04 $h^{-1}$ at 100 g/L glucose feed to raise the biomass to an $OD_{600}$=4.4 over a period of 5 days. The glucose feed was then lowered by replacing the medium reservoir for pump A with a reservoir containing 0 g/L glucose, pumping initially at a rate of 33.4 ml/h, and pumping the 100 g/L glucose feed from pump B at 2.4 ml/h. This resulted in a dilution rate of 0.04 $h^{-1}$, a glucose feed of 6.7 g/L and a biomass of $OD_{600}$=6.0. Over a period of 4 days, the glucose concentration in the feed was gradually increased to 37.8 g/L by increasing the rate of pump B and decreasing the rate of pump A while maintaining a dilution rate of 0.04 $h^{-1}$ and resulting in a biomass under these conditions of an $OD_{600}$=6.6 and a glucose level in the chemostat of 18.8 g/L.

Evolution of the strain for increased growth rate was performed by slowly increasing the dilution rate in the chemostat with the evolved strain that no longer required a 2-carbon supplement and could grow with a feed of 37.8 g/L glucose with a glucose level in the chemostat of 18.8 g/L. Over a period of 13 days, the dilution rate was gradually increased from 0.04 $h^{-1}$ to 0.14 $h^{-1}$ by alternately increasing the rates of pump A and pump B to maintain a glucose feed concentration of 21-24 g/L glucose. A biomass of $OD_{600}$=1.6 to an $OD_{600}$=2.0 was maintained at dilution rates of 0.13 $h^{-1}$ to 0.14 $h^{-1}$.

Over the period of evolution, a sample was occasionally removed from the vessel directly. Samples were analyzed for glucose, acetate, and pyruvate using HPLC. Samples were plated onto YNB+histidine medium with 2% w/v ethanol as carbon source, YNB+histidine medium with different glucose concentrations (5 g/L, 10 g/L, 15 g/L, 20 g/L, 25 g/L and 50 g/L glucose), and YPD medium (containing 10 g/L yeast extract, 20 g/L peptone and 20 g/L dextrose) agar plates (plates contain the indicated medium+20 g/L agar). $OD_{600}$ measurements were taken regularly to make sure the chemostat did not wash out. Freezer stocks of samples of the culture were made regularly for future characterization of the strains.

The chemostat with the evolved strain that no longer required a 2-carbon supplement and could grow with a feed of 37.8 g/L glucose with a glucose level in the chemostat of 18.8 g/L and could grow at a dilution rate >0.13 $h^{-1}$ was maintained for another 23 days with varying dilution rates from 0.07 $h^{-1}$ to 0.11 $h^{-1}$ to allow further evolution for improved growth rate. At the end of this period, a sample from the chemostat was plated onto YNB+histidine medium with 50 g/L glucose agar plates and allowed to form colonies at 30° C. Ten colonies were picked for further characterization and re-streaked onto YNB+histidine medium with 50 g/L glucose agar plates for purification. None of these 10 evolved strains isolated from the chemostat sample grew when streaked onto SC-histidine medium (Synthetic complete medium lacking histidine, containing per liter of distilled water: 6.7 g YNB without amino acids from Difco, 100 ml of a solution of 14 g Yeast Synthetic Drop-out Medium Supplements without histidine, leucine, tryptophan and uracil from Sigma dissolved in 1 L water, 20 ml of a solution of 3.8 g/L tryptophan, 20 ml of a solution of 19 g/L leucine and 40 ml of a solution of 1.9 g/L uracil) containing 20 g/L glucose plates but did grow on SC-leucine medium (Synthetic complete medium lacking leucine, containing per liter of distilled water: 6.7 g YNB without amino acids from Difco, 100 ml of a solution of 14 g Yeast Synthetic prop-out Medium Supplements without histidine, leucine, tryptophan and uracil from Sigma dissolved in 1 L water, 20 ml of a solution of 3.8 g/L tryptophan, 20 ml of a solution of 3.8 g/L histidine and 40 ml of a solution of 1.9 g/L uracil) containing 20 g/L glucose plates, indicating that they were still auxotrophic for histidine.

To characterize growth of the evolved strains, single colonies from each of the 10 evolved isolates purified on YNB+histidine medium with 50 g/L glucose agar plates were inoculated into 3 ml of YNB+histidine medium with 50 g/L glucose and YPD medium in 14 ml round-bottom snap-cap tubes and incubated overnight at 30° C. as a pre-culture. The next day the pre-cultures were used to inoculate 5 ml of the same medium as the pre-cultures in 50 ml conical plastic screw-cap centrifuge tubes to an $OD_{600}$ of 0.01. The cultures were incubated shaking upright at 250 rpm at 30° C. and sampled periodically for $OD_{600}$ measurement. Growth rates were calculated from plots of the $OD_{600}$ measurements vs. time of incubation. Evolved isolates GEVO2710, GEVO2711, GEVO2712 and GEVO2799 were selected because of high growth rates in both YNB+histidine medium with 50 g/L glucose and YPD medium.

GEVO2792 is a C2-independent, PDC-minus *S. cerevisiae* strain carrying a control plasmid encoding no genes for an isobutanol metabolic pathway. To generate this strain, GEVO2710 was transformed with plasmid pGV2020 (SEQ ID NO: 121).

GEVO2844 is a C2-independent, PDC-minus *S. cerevisiae* strain carrying a control plasmid encoding no genes for an isobutanol metabolic pathway. To generate this strain, GEVO2799 was transformed with plasmid pGV2020 (SEQ ID NO: 121).

GEVO2847 is a C2-independent, PDC-minus *S. cerevisiae* strain carrying a partially NADH-utilizing isobutanol metabolic pathway. To generate this strain, GEVO2799 was transformed with plasmid pGV2082 (SEQ ID NO: 122), carrying the genes encoding NADPH-dependent KARI and the NADH-dependent ADH, Ec_ilvC_coSc$^{Q110V}$ (SEQ ID NO: 24), and Dm_ADH (SEQ ID NO: 60), respectively.

GEVO2848 is a C2-independent, PDC-minus *S. cerevisiae* strain carrying a partially NADH-utilizing isobutanol metabolic pathway. To generate this strain, GEVO2799 was transformed with plasmid pGV2227 (SEQ ID NO: 123), carrying the genes encoding NADPH-dependent KARI and the NADH-dependent ADH, Ec_ilvC_coSc$^{Q110V}$ (SEQ ID NO: 24), and Ll_adhA (SEQ ID NO: 66), respectively.

GEVO2849 is a C2-independent, PDC-minus *S. cerevisiae* strain carrying an NADH-utilizing isobutanol metabolic pathway. To generate this strain, GEVO2799 was transformed with plasmid pGV2242 (SEQ ID NO: 125), carrying the genes encoding NADH-dependent KARI and ADH, Ec_ilvC_coSc$^{P2D1}$ (SEQ ID NO: 39) and Ll_adhA (SEQ ID NO: 66), respectively.

GEVO2851 is a C2-independent, PDC-minus *S. cerevisiae* strain carrying a partially NADH-utilizing isobutanol metabolic pathway. To generate this strain, GEVO2711 was transformed with plasmid pGV2227 (SEQ ID NO: 123), carrying the genes encoding NADPH-dependent KARI and the NADH-dependent ADH, Ec_ilvC_coSc$^{Q110V}$ (SEQ ID NO: 24), and Ll adhA (SEQ ID NO: 66), respectively.

GEVO2852 is a C2-independent, PDC-minus *S. cerevisiae* strain carrying an NADH-utilizing isobutanol metabolic pathway. To generate this strain, GEVO2711 was transformed with plasmid pGV2242 (SEQ ID NO: 125), carrying the genes encoding NADH-dependent KARI and ADH, Ec_ilvC_coSc$^{P2D1}$ (SEQ ID NO: 39) and Ll_adhA (SEQ ID NO: 66), respectively.

GEVO2854 is a C2-independent, PDC-minus *S. cerevisiae* strain carrying a partially NADH-utilizing isobutanol metabolic pathway. To generate this strain, GEVO2710 was transformed with plasmid pGV2082 (SEQ ID NO: 122), carrying the genes encoding NADPH-dependent KARI and the NADH-dependent ADH, Ec_ilvC_coSc$^{Q110V}$, and Dm_ADH (SEQ ID NO: 60), respectively.

GEVO2855 is a C2-independent, PDC-minus *S. cerevisiae* strain carrying a partially NADH-utilizing isobutanol metabolic pathway. To generate this strain, GEVO2710 was transformed with plasmid pGV2227 (SEQ ID NO: 123), carrying the genes encoding NADPH-dependent KARI and the NADH-dependent ADH Ec_ilvC_coSc$^{Q110V}$, and Ll_adhA (SEQ ID NO: 66), respectively.

GEVO2856 is a C2-independent, PDC-minus *S. cerevisiae* strain carrying an NADH-utilizing isobutanol metabolic pathway. To generate this strain, GEVO2710 was transformed with plasmid pGV2242 (SEQ ID NO: 125), carrying the genes encoding NADH-dependent KARI and ADH, Ec_ilvC_coSc$^{P2D1}$ (SEQ ID NO: 39) and Ll_adhA (SEQ ID NO: 66), respectively.

Construction of *E. coli* Expression Plasmids pGV1631: The adh2 gene was cut out of plasmid pSA55 using appropriate restriction enzymes. Re-ligation yielded plasmid pGV1631 featuring only Ll_kivd1 (SEQ ID NO: 45) under the control of the PLlacO1 promoter. The plasmid was verified by sequencing prior to its use.

pGV1705A: The Ec_yqhD gene (SEQ ID NO: 68) contained on plasmid pGV1705 was cloned into plasmid pGV1711 (SEQ ID NO: 113) using the primers XX3 and XX4. These primers added additional sequences surrounding the ADH coding sequence. Specifically, the 5'-end of the PCR product contains an EcoRI site, a BamHI site, a RBS (aggaga), a 7 nucleotide space sequence, and the initiating ATG codon. The 3' end of the product, following the stop codon, contains a NotI site followed by an AvrII site. The amplified product was digested with EcoRI and NotI and ligated into pGV1711 (SEQ ID NO: 113) which had been cut with both EcoRI and AwlI and gel purified to generate plasmid pGV1705-A, ADH genes, whether PCR amplified or ordered as synthetic DNA sequences were cloned into plasmid pGV1716 (SEQ ID NO: 114), a derivative of plasmid pGV1698 carrying an in vitro-synthesized gene for *S. cerevisiae* ADH2, codon-optimized for expression in *E. coli* (="ADH2co"). ADH2co gene was amplified from plasmid pGV1527 in a PCR reaction using KOD polymerase (Novagen, Gibbstown, N.J.) and primers 1296 and 1297. These primers add additional sequences surrounding the ADH2co coding sequence. Specifically, the 5'-end of the PCR product contains a SalI site, a BamHI site, an RBS (aggaga), a 7 nucleotide space sequence, and the initiating ATG codon. The 3' end of the product, following the stop codon, contains a NotI site followed by a SalI site. The amplified product was digested SalI and was ligated into pGV1698 (SEQ ID NO: 112) which had been cut with SalI and gel purified. DNA constructs were analyzed by multiple restriction digests, and also by DNA sequencing to confirm integrity and to correct construction. Oligonucleotides 1220 and 1365 were used as primers in standard DNA sequencing reactions to sequence all of the aforementioned clones.

Plasmid pGV1748, which contains the ORF for Ec_fucO (SEQ ID NO: 64) expressed under the control of the IPTG-inducible promoter PLlacO1, was generated by amplifying the Ec_fucO gene in a PCR reaction, using primers 1470 and 1471 and *E. coli* genomic DNA as a template. The ~1.2 kb PCR product so generated was digested with BamHI plus NotI, purified using a Zymo Research DNA Gel Extraction kit (Zymo Research, Orange, Calif.) according to manufacturer's protocol, and ligated into the vector pGV1716 (SEQ ID NO: 114) which had been digested with BamHI plus NotI and purified using a Zymo Research DNA Gel Extraction kit (Zymo Research, Orange, Calif.).

Plasmid pGV1748-A: The Ec_fuc0 gene contained on plasmid pGV1748 was cloned into plasmid pGV1711 (SEQ ID NO: 113) using the primers XX1 and XX2. These primers add additional sequences into the vector backbone upstream of the AwlI restriction site and downstream of the EcoRI restriction site. Specifically, the 5'-end of the PCR product contains a NotI site followed by an AwlI site and the 3' end of the product, contains an AgeI site followed by an EcoRI site. The amplified product was digested with AgeI and NotI and ligated with the similarly digested pGV1711 to generate plasmid 1748-A.

Plasmid pGV1749, which contains the ORF for Dm_ADH (SEQ ID NO: 60) expressed under the control of the IPTG-inducible promoter PLlacO1, was generated by amplifying the Dm_ADH gene in a PCR reaction, using primers 1469 and 1364 and the clone RH54514 (Drosophila Genome Resource Center) as a template. The ~0.8 kb PCR product was digested with BglII plus NotI, was purified using a Zymo Research DNA Gel Extraction kit according to manufacturer's protocol, and was ligated into the vector pGV1716 (SEQ ID NO: 114) which had been digested with BamHI plus NotI and purified using a Zymo Research DNA Gel Extraction kit.

Plasmid pGV1749-A: The Dm_ADH gene (SEQ ID NO: 60) contained on plasmid pGV1749 was cloned into plasmid pGV1711 (SEQ ID NO: 113) using the primers XX1 and XX2. These primers add additional sequences into the vector backbone 5' of the AwlI restriction site and 3' of the EcoRI restriction site. Specifically, the 5'-end of the PCR product contains a NotI site followed by an AwlI site and the 3' end of the product, contains an AgeI site followed by an EcorI site. The amplified product was digested with AgeI and NotI and ligated with the product of the ADH gene similarly digested with AgeI and NotI to generate plasmid pGV1749-A.

Plasmid pGV1778, which contains the ORF for Kp_dhaT (SEQ ID NO: 62) expressed under the control of the IPTG-inducible promoter PLlacO1, was generated by excising the Kp_dhaT gene from an in vitro synthesized plasmid (generated by DNA2.0, Menlo Park, Calif.) by digestion with BamHI plus NotI. The released 1.16 kb fragment was purified using a Zymo Research DNA Gel Extraction kit according to manufacturer's protocol, and was ligated into the vector pGV1716 (SEQ ID NO: 114) which had been digested with BamHI plus NotI and purified using a Zymo Research DNA Gel Extraction kit.

Plasmid pGV1778-A: The Kp_dhaT gene (SEQ ID NO: 62) contained on plasmid pGV1778 was cloned into plasmid pGV1711 (SEQ ID NO: 113) using the primers XX1 and XX2. These primers add additional sequences into the vector backbone 5' of the AwlI restriction site and 3' of the EcoRI restriction site. Specifically, the 5'-end of the PCR product contains a NotI site followed by an AwlI site and the 3' end of the product, contains an AgeI site followed by an EcoRI site. The amplified product was digested with AgeI and NotI and ligated with the product of the ADH gene similarly digested with AgeI and NotI to generate plasmid pGV1778-A.

Plasmids pGV1655 (SEQ ID NO: 109) and pGV1711 (SEQ ID NO: 113) have been described previously. Briefly, pGV1655 is a low-copy, Kan$^{R}$-selected plasmid that expresses *E. coli* Ec_ilvD_coEc (SEQ ID NO: 51) and Ll_kivd1 (SEQ ID NO: 41) under the control of the PLIac promoter.

Plasmid pGV1938 was constructed by inserting the gene coding for Ec_llvC_coEc$^{S78D}$ into pGV1711 (SEQ ID NO: 113). The KARI variant gene was amplified with primers Not_in_for and AvrII_in_rev introducing the 5' NotI and the 3' AvrII restriction sites, DpnI digested for 1 h at 37° C., and then cleaned up using the Zymo PCR clean up kit. The fragment and the vector pGV1711 were restriction digested with NotI and AwII and run out on a 1% agarose gel. After cutting out the fragments, they were cleaned up using the Freeze'n'Squeeze and pellet paint procedure. Ligation was performed with the rapid ligation kit from Roche according to the manufacturer's instructions.

Plasmid pGV1939 was generated using primers XX3 and XX4 to amplify the Ec_fucO gene from plasmid pGV1748-A. The forward primer adds a new RBS (aggaga), a 7 nucleotide space sequence, and the initiating ATG codon. The amplified product was digested with EcoRI and NotI and ligated with the similarly digested pGV1711 (SEQ ID NO: 113) to generate plasmid pGV1939 containing the modified RBS.

The genes coding for KARI variants Ec_ilvC_coEc$^{his6}$ (SEQ ID NO: 14), Ec_ilvC_coEc$^{S78D-his6}$ (SEQ ID NO: 16), Ec_ilvC_coEc$^{6E6-his6}$ (SEQ ID NO: 32) and Ec_ilvC_coEc$^{2H10-his6}$ (SEQ ID NO: 30) were cloned into pGV1939 generating plasmids pGV1925, pGV1927, pGV1975 and pGV1976, respectively using primers NotI_in_for and AvrII_in_rev. The PCR products were DpnI digested for 1 h and cleaned over a 1% agarose gel. After a sequential restriction digestion of vector and insert with NotI for 1 h followed by 1 h with AvrII, ligation was performed using rapid ligase (Roche). Ligation mixture was desalted using the Zymo PCR clean up kit and used to transform *E. coli* DH5α. DNA constructs were analyzed by restriction digests, and also by DNA sequencing to confirm integrity and correct construction. Primers pETup and KARIpETrev were used as primers in standard DNA sequencing reactions to sequence pET22b(+) derivatives, primer seq_ilvc_pGV was used to sequence pGV1925, pGV1927, pGV1975 and pGV1976.

Construction of *Saccharomyces cerevisiae* Expression Plasmids pGV1824: The gene coding for Ec_llvC (SEQ ID NO: 13) was codon optimized for *S. cerevisiae* and synthesized (DNA2.0, Menlo Park, Calif.), resulting in Ec_ilvC_coSc (SEQ ID NO: 12). To generate pGV1824, the Ec_ilvC_coSc gene was excised from plasmid pGV1774 using Bg/II and XhoI. Plasmid pGV1662 was digested with SalI and BamHI. The pGV1662 vector backbone and Ec_ilvC_coSc insert were ligated using standard methods resulting in plasmid pGV1824 containing the gene Ec_ilvC_coSc.

pGV1914 (SEQ ID NO: 119) is a yeast integrating vector (Ylp) that utilizes the *S. cerevisiae* URA3 gene as a selection marker and contains homologous sequence for targeting the HpaI-digested, linearized plasmid for integration at the PDC6 locus of *S. cerevisiae*. This plasmid does not carry a yeast replication origin, thus is unable to replicate episomally. This plasmid carries the Dm_ADH (SEQ ID NO: 60) and Ll_kivd2_coEc (SEQ ID NO: 48) genes, expressed under the control of the *S. cerevisiae* TDH3 and TEF1 promoters, respectively. pGV1914 was generated in two steps. First, the Dm_ADH-containing *E. coli* expression plasmid pGV1749 was digested with SalI plus NotI, and the 0.78 kb fragment containing the Dm_ADH ORF released by digestion was gel purified and ligated into pGV1635, which had been digested with XhoI plus NotI and gel purified. Plasmid pGV1635 is a yeast expression plasmid which has as its salient feature a TDH3 promoter followed by several restriction enzyme recognition sites, into which the Dm_ADH sequence was cloned as described above. A correct recombinant plasmid was named pGV1913. In the second step of pGV1914 construction, pGV1913 was digested with BamHI plus NotI and the 1.45 kb fragment, containing the TDH3 promoter-Dm_ADH ORF sequence was gel purified and ligated into pGV1733, which had been digested with BamHI plus NotI and similarly gel purified, yielding pGV1914. Thus, the ScADH7 ORF in pGV1733 is replaced by the Dm_ADH ORF in the pGV1914, both under the control of the TDH3 promoter; both plasmids also contain the $P_{TEF1}$-Ll_kivd2_coEc cassette as well as the URA3 selection marker and ScPDC6 5' and 3' regions suitable for homologous recombination targeting following linearization of the plasmid with HpaI.

pGV1936 (SEQ ID NO: 120) is a yeast integrating vector (Ylp) that utilizes the *S. cerevisiae* LEU2 gene as a selection marker and contains homologous sequence for targeting the linearized (by HpaI digestion) plasmid for integration at the PDC5 locus of *S. cerevisiae*. This plasmid does not carry a yeast replication origin, thus is unable to replicate episomally. This plasmid carries the Ec_ilvC_coSc$^{Q116V}$ (SEQ ID NO: 24) mutant (i.e. codon optimized for expression in *S. cerevisiae*) and *S. cerevisiae* ILV3ΔN genes, expressed under the control of the *S. cerevisiae* TDH3 and TEF1 promoters, respectively. pGV1936 was constructed using an SOE PCR method that amplified the Ec_ilvC_coSc gene while simultaneously introducing the nucleotide changes coding for a Q110V mutation. Specifically, primers 1624 and 1814 were used to amplify a portion of plasmid pGV1774 containing the Ec_ilvC_coSc gene; primers 1813 and 1798 were used to amplify a portion of plasmid pGV1824 that also contained the Ec_ilvC_coSc gene. The two separate PCR products were gel purified, eluted in 15 μL, and 3 μL of each were used as a template along with primers 1624 and 1798. The resulting PCR product was digested with XhoI plus NotI and ligated into pGV1765 that had been digested with XhoI plus NotI, yielding pGV1936. Candidate clones of pGV1936 were confirmed by sequencing, using primers 350, 1595, and 1597.

pGV1994: Mutations found in variant Ec_llvC$^{6E6-his6}$ were introduced into pGV1824 by SOE PCR. The 5' PCR used primers 1898 and 2037 and the 3' PCR used primers 1893 and 2036. Each of these primer pairs were used with pGV1894 as the template in two separate PCR reactions. The product was used in a second PCR with the end primers 1898 and 1893 to yield a final PCR product. This final PCR product has a 5' SalI restriction site and 3' BglII followed by NotI restriction sites. These were cloned into pGV1662 using the SalI and NotI site and yielding plasmid pGV1994 which carries Ec_ilvC_coSc$^{6E6}$ (SEQ ID NO: 35).

pGV2020 (SEQ ID NO: 121) is an empty G418 resistant 2-micron yeast vector that was generated by removing the Ll_kivd2_coEc sequence from pGV2017. This was carried out by amplifying the TDH3 promoter from pGV2017 using primers 1926 and 1927, digesting with SalI and NotI and cloning into the same sites of pGV2017.

pGV2082 (SEQ ID NO: 122) is a G418 resistant yeast 2-micron plasmid for the expressions of Ec_ilvC_coSc$^{Q110V}$ (SEQ ID NO: 24), Ll_ilvD_coSc (SEQ ID NO: 54), Ll_kivd2_coEc (SEQ ID NO: 48), and Dm_ADH (SEQ ID NO: 60). A fragment carrying the PGK1 promoter, Ll_kivd2_coEc and a short region of the PDC1 terminator sequence was obtained by cutting pGV2047 with AvrII and NcoI. This fragment was treated with Klenow to generate blunt ends then cloned into pGV2044 that had been digested with EcoRI and SbfI and the overhangs filled in with Klenow. This construction replaced the CUP1 promoter and the Bs_alsS1_coSc (SEQ ID NO: 6) in pGV2044 with the PGK1 promoter and Ll_kivd2_coEc.

pGV2193: The Ec_llvC variant encoded by Ec_ilvC_coSc$^{6E6-his6}$ (SEQ ID NO: 33) encoded on pGV2241 (SEQ ID NO: 124) served as template for error-prone PCR using primers pGV1994ep_for and pGV1994ep_rev yielding variant Ec_llvC$^{P2D1-his6}$ (SEQ ID NO: 38) which is encoded by Ec_ilvC_coSc$^{P291-his6}$ (SEQ ID NO: 37) on construct pGV2193.

pGV2227 (SEQ ID NO: 123) is a G418 resistant yeast 2-micron plasmid for the expressions of Ec_ilvC_coSc$^{Q110V}$ (SEQ ID NO: 24), Ll_ilvD_coSc (SEQ ID NO: 54), Ll_kivd2_coEc (SEQ ID NO: 48), and Ll_adhA (SEQ ID NO: 66). pGV2227 is a derivative of pGV2201 where the BamHI and XhoI sites at the 3' end of the Ll_adhA were removed and replaced with an AvrII site. This construction was carried out by cloning into the NheI-MluI sites of pGV2202 a fragment carrying the 3' end of the Ll_adhA sequence, an AvrII site, and the 5' part of the CYC1 terminator. This fragment was generated by SOE PCR combining a PCR product using primers 2091 and 2352 with pGV2201 as template and a PCR product using primers 2353 and 772 with pGV2201 as template. The sequences of primers 2352 and 2353 overlap and introduce an AvrII site. This SOE PCR product was digested with NheI and MluI for cloning into pGV2201.

pGV2238: The Ec_IlvC variant encoded by Ec_ilvC_coSc$^{P2D1\text{-}his6}$ (SEQ ID NO: 37) encoded on pGV2193 served as parent for an additional error-prone PCR round using the same primers as described before on template DNA pGV2193 yielding an improved KARI variant named Ec_IlvC$^{P2D1\text{-}A1\text{-}his6}$ (SEQ ID NO: 42) which is encoded by the gene Ec_ilvC_coSc$^{P2D1\text{-}A1\text{-}his6}$ (SEQ ID NO: 41) on plasmid pGV2238.

pGV2241 (SEQ ID NO: 124): The gene Ec_ilvC_coSc$^{6E6}$ (SEQ ID NO: 35) was his-tagged using primers pGV1994_ep_for and 1994hisrev, cleaned with the Zymo PCR clean up kit (Zymo Research), NotI and SalI digested, and ligated into similarly digested pGV1994, resulting in construct pGV2241 coding for Ec_ilvC_coSc$^{6E6\text{-}his6}$(SEQ ID NO: 33).

pGV2242 (SEQ ID NO: 125) is a G418 resistant yeast 2-micron plasmid for the expressions of Ec iivC coSc$^{P}$2D1 (SEQ ID NO: 39), Ll_ilvD_coSc (SEQ ID NO: 54), Ll_kivd2_coEc (SEQ ID NO: 48), and Ll_adhA (SEQ ID NO: 66). This plasmid was generated by cloning the SalI-BspEI fragment of pGV2193 carrying the region encoding for Ec_IlvC with the relevant mutations for the Ec_ilvC_coSc$^{P2D1}$ allele into the XhoI-BspEI sites of pGV2227 (SEQ ID NO: 123).

TABLE 3

Strains disclosed herein

| Strain No. | Description |
|---|---|
| GEVO1186 | *S. cerevisiae* CEN.PK2 (MATa/α ura3/ura3 leu2/leu2 his3/his3 trp1/trp1 PDC1/PDC1 PDC5/PDC5 PDC6/PDC6) |
| GEVO1385 | *E. coli* BW25113, ΔldhA-fnr::FRT, ΔadhE::FRT, Δfrd::FRT, Δpta::FRT, ΔpflB::FRT, F' (lacIq+), attB::(Sp$^+$ lacIq$^+$ tetR$^+$) |
| GEVO1399 | *E. coli* BW25113, ΔldhA-fnr::FRT, ΔadhE::FRT, Δfrd::FRT, Δpta::FRT, pflB::FRT, Δzwf::FRT F' (lacIq+) |
| GEVO1608 | *E. coli* BW25113, ΔldhA-fnr::FRT, ΔadhE::FRT, Δfrd::FRT, ΔpflB::FRT, Δpta::FRT, ΔyqhD::FRT-Kan-FRT, F' (lacIq+) |
| GEVO1725 | *E. coli* BW25113, ΔldhA-fnr::FRT, ΔadhE::FRT, Δfrd::FRT, Δpta::FRT, ΔpflB::FRT, ΔmaeA::FRT, ΔpykA::FRT, ΔpykF::FRT, F' (lacIq+) |
| GEVO1745 | *E. coli* BW25113, ΔldhA-fnr::FRT, ΔadhE::FRT, Δfrd::FRT, ΔpflB::FRT, Δpta::FRT, ΔyqhD::FRT |
| GEVO1748 | *E. coli* BW25113, ΔldhA-fnr::FRT, ΔadhE::FRT, Δfrd::FRT, Δpta::FRT, pflB::FRT, F' (lacIq+), ΔilvC::PLlacO1::Ll_kivd1::Ec_ilvD_coEc::FRT |
| GEVO1749 | *E. coli* BW25113, ΔldhA-fnr::FRT, Δfrd::FRT, Δpta::FRT, pflB::FRT, F' (lacIq+), ΔadhE::[PLlacO1::Ll_kivd1::Ec_ilvD_coEc::FRT] |
| GEVO1750 | *E. coli* BW25113, ΔldhA-fnr::FRT, ΔadhE::FRT, Δfrd::FRT, Δpta::FRT, ΔpflB::FRT, ΔmaeA::FRT, F' (lacIq+), attB::(Sp+ lacIq+ tetR+) |
| GEVO1751 | *E. coli* BW25113, ΔldhA-fnr::FRT, ΔadhE::FRT, Δfrd::FRT, Δpta::FRT, ΔpflB::FRT, ΔmaeA::FRT, ΔpykA::FRT, ΔpykF::FRT, F' (lacIq+), attB::(Sp+ lacIq+ tetR+) |
| GEVO1777 | *E. coli* W3110, ΔilvC::FRT, attB::(Sp+ lacIq+ tetR+) |
| GEVO1780 | JCL260 transformed with pGV1655 and pGV1698 |
| GEVO1803 | *S. cerevisiae* CEN.PK2, MATa/alpha ura3/ura3 leu2/leu2 his3/his3 trp1/trp1 pdc1::Bs_alsS2, TRP1/PDC1 |
| GEVO1844 | *E. coli* BW25113, Δ(ldhA-fnr::FRT) ΔadhE::FRT Δfrd::FRT Δpta::FRT ΔpflB::FRT ΔilvC::$P_{LlacO1}$::Ll_kivd1::Ec_ilvD_coEc::FRT ΔsthA::FRT |
| GEVO1846 | *E. coli* BW25113, ΔldhA- fnr::FRT, ΔadhE::FRT, Δfrd::FRT, Δpta::FRT, pflB::FRT, F' (lacIq+), ΔilvC::PLlacO1:Ll_kivd1::Ec_ilvD_coEc::FRT, pGV1745, pGV1698 |
| GEVO1859 | *E. coli* BW25113, ΔldhA-fnr::FRT, Δfrd::FRT, Δpta::FRT, F' (lacIq+), ΔadhE::[pLlacO1::Ll_kivd1::Ec_ilvD_coEc::FRT], pflB::[pLlacO1::Bs_alsS1::Ec_ilvC_coEc::FRT] |
| GEVO1886 | *E. coli* BW25113, ΔldhA-fnr::FRT, Δfrd::FRT, Δpta::FRT, F' (lacIq+), ΔadhE::[pLlacO1:Ll_kivd1::Ec_ilvD_coEc::FRT], ΔpflB::[pLlacO1::Bs_alsS1::Ec_ilvC_coEc::FRT] ΔsthA::[pLlacO1::pntA::pntB::FRT] |
| GEVO1993 | *E. coli* BW25113, ΔldhA-fnr::FRT, ΔadhE::FRT, Δfrd::FRT, DpflB::FRT, F' (lacIq+), ΔilvC::PLlacO1::Ll_kivd1::Ec_ilvD_coEc::FRT, Δpta::PLlacO1::Bs_alsS1, FRT::KAN::FRT |
| GEVO2107 | *S. cerevisiae* CEN.PK2, MATa/alpha ura3/ura3 leu2/leu2 his3/his3 trp1/trp1 pdc1::Bs_alsS2, TRP1/PDC1 pdc6::{ScTEF1p- Ll_kivd2_coEc ScTDH3p-Dm_ADH URA3}/PDC6 |
| GEVO2158 | *S. cerevisiae* CEN. PK2; MATa/α ura3/ura3 leu2/leu2 his3/his3 trp1/trp1 pdc1::Bs_alsS2, TRP1/PDC1 pdc5::{ScTEF1prom-Sc_ILV3ΔN ScTDH3prom-Ec_ilvC_coSc$^{Q110V}$LEU2}/PDC5 pdc6::{ScTEF1p- Ll_kivd2_coEc ScTDH3p-Dm_ADH URA3}/PDC6 |
| GEVO2302 | *S. cerevisiae* CEN.PK2; MATa ura3 leu2 his3 trp1 pdc1::Bs_alsS2, TRP1 pdc5::{$P_{TEF1}$:Sc_ILV3ΔN $P_{TDH3}$:Ec_ilvC_coSc$^{Q110V}$LEU2} pdc6::{$P_{TEF1}$: Ll_kivd2_coEc $P_{TDH3}$:Dm_ADH URA3} |
| GEVO2710 | *S. cerevisiae* CEN.PK2; MATa ura3 leu2 his3 trp1 pdc1::{$P_{CUP1}$- Bs_alsS2, TRP1} pdc5::{$P_{TEF1}$:Sc_ILV3ΔN $P_{TDH3}$:Ec_ilvC_coSc$^{Q110V}$, LEU2} pdc6::{$P_{TEF1}$: Ll_kivd2_coEc $P_{TDH3}$:Dm_ADH, URA3}, evolved for C2 supplement-independence, glucose tolerance and faster growth |
| GEVO2711 | *S. cerevisiae* CEN.PK2; MATa ura3 leu2 his3 trp1 pdc1::{$P_{CUP1}$- Bs_alsS2, TRP1} pdc5::{$P_{TEF1}$:Sc_ILV3ΔN $P_{TDH3}$:Ec_ilvC_coSc $^{Q110V}$, LEU2} pdc6::{$P_{TEF1}$: Ll_kivd2_coEc $P_{TDH3}$:Dm_ADH, URA3}, evolved for C2 supplement-independence, glucose tolerance and faster growth |
| GEVO2712 | *S. cerevisiae* CEN.PK2; MATa ura3 leu2 his3 trp1 pdc1::{$P_{CUP1}$- Bs_alsS2, TRP1} pdc5::{$P_{TEF1}$:Sc_ILV3ΔN $P_{TDH3}$:Ec_ilvC_coSc $^{Q110V}$, LEU2} pdc6::{$P_{TEF1}$: Ll_kivd2_coEc $P_{TDH3}$:Dm_ADH, URA3}, evolved for C2 supplement-independence, glucose tolerance and faster growth |
| GEVO2799 | *S. cerevisiae* CEN.PK2; MATa ura3 leu2 his3 trp1 pdc1::{$P_{CUP1}$- Bs_alsS2, TRP1} pdc5::{$P_{TEF1}$:Sc_ILV3ΔN $P_{TDH3}$:Ec_ilvC_coSc $^{Q110V}$, LEU2} pdc6::{$P_{TEF1}$: Ll_kivd2_coEc $P_{TDH3}$:Dm_ADH, URA3}, evolved for C2 supplement-independence, glucose tolerance and faster growth |
| GEVO2792 | GEVO2710 transformed with pGV2020 |
| GEVO2844 | GEVO2799 transformed with pGV2020 |
| GEVO2847 | GEVO2799 transformed with pGV2082 |
| GEVO2848 | GEVO2799 transformed with pGV2227 |
| GEVO2849 | GEVO2799 transformed with pGV2242 |
| GEVO2851 | GEVO2711 transformed with pGV2227 |
| GEVO2052 | GEVO2711 transformed with pGV2242 |
| GEVO2854 | GEVO2710 transformed with pGV2082 |

TABLE 3-continued

| Strains disclosed herein | |
|---|---|
| Strain No. | Description |
| GEVO2855 | GEVO2710 transformed with pGV2227 |
| GEVO2856 | GEVO2710 transformed with pGV2242 |
| GEVO5001 | *S. cerevisiae* CEN.PK2, Δpdc1 Δpdc5 Δpdc6 expressing an isobutanol pathway (ALS, KARI, DHAD, KIVD, ADH) |
| GEVO5002 | GEVO5001 $P_{TEF1}$:NADH kinase $P_{TDH3}$:$NADP^+$ phosphatase HPH |
| GEVO5003 | GEVO5001, $P_{TDH3}$:Kl_GDP1 HPH |
| GEVO5004 | GEVO5001 $P_{TEF1}$:ess:pntA $P_{TDH3}$:ess:pntB HPH |
| GEVO5005 | GEVO5001 $P_{TEF1}$:mts:pntA $P_{TDH3}$:mts:pntB HPH |
| GEVO5006 | GEVO5001 $P_{ADH1}$:PYC1 $P_{TEF1}$:MDH2 $P_{TDH3}$:maeB HPH |
| *E. coli* BL21 (DE3) | Lucigen Corporation (Middleton, WI) |
| *E. coli* DH5αZ1 | Lutz, R. and Bujard, H, Nucleic Acids Research (1997) 25 1203-1210 |
| JCL260* | *E. coli* BW25113, ΔldhA-fnr::FRT, ΔadhE::FRT, Δfrd::FRT, ΔpflB::FRT, Δpta::FRT, F' (laclq+) |

*These strains are described in PCT/US2008/053514

TABLE 4

| Plasmids disclosed herein | | | |
|---|---|---|---|
| GEVO No. | Figure | SEQ ID NO | Genotype or Reference |
| pKD13 | n/a | | Datsenko, K and Wanner, B. PNAS 2000, 97:6640-5 |
| pKD46 | n/a | | Datsenko, K and Wanner, B. PNAS 2000, 97:6640-5 |
| pSA55* | n/a | | pLlacO1::Ll_kivd1::ADH2, ColE1, Amp |
| pSA69* | n/a | | pLlacO1::Bs_alsS1::Ec_ilvC::Ec_ilvD, p15A, Kan |
| pET22b(+) | n/a | | Novagen, Gibbstown, NJ |
| pET22b[ilv Cco] | n/a | | Novagen, Gibbstown, NJ |
| pGV1102 | | 101 | $P_{TEF1}$-HA-tag-MCS-$T_{CYC1}$, URA3, 2-micron, bla, pUC-ori |
| pGV1323 | | 102 | |
| pGV1485 | | 103 | PLlacO1::Ll_kivd1::ADH2, pSC101, Km |
| pGV1490 | | 104 | pLtetO1:: p15A, Cm |
| pGV1527 | | | PLtetO1::Ll_kivd1_coEc::*S. cerevisiae* ADH2 ColE1, bla |
| pGV1572 | | 105 | PLlacO1::empty, p15A, $Cm^R$ |
| pGV1573 | | 106 | PLlacO1::GDP1, p15A, $Cm^R$ |
| pGV1575 | | 107 | PLlacO1::gapC, p15A, $Cm^R$ |
| pGV1609 | | 108 | PLlacO1::Bs_alsS1::ilvC::Ec_ilvD, p15A, Cm |
| pGV1631 | | | PLlacO1::Ll_kivd1, ColE1, Amp |
| pGV1655 | | 109 | PLlacO1::Ll_kivd1::Ec_ilvD_coEc,, pSC101, Km |
| pGV1661 | | 110 | pLtetO1::maeB::ppc::mdh, p15A, Cm |
| pGV1662 | | | |
| pGV1685 | | 111 | PLtetO1::pntAB, p15A, Cm |
| pGV1698 | | 112 | PLlacO1::Bs_alsS1::ilvC, bla, ColE1 ORI |
| pGV1705-A | | | PLlacO1::Ec_yqhD bla, ColE1 ORI |
| pGV1711 | | 113 | PLlacO1::(no ORF) bla, ColE1 ORI |
| pGV1716 | | 114 | PLlacO1::Bs_alsS1::*Saccharomyces cerevisiae* ADH2::ilvC bla, ColE1 ORI |
| pGV1720 | | 115 | pLlacO1::empty, pSC101, Km |
| pGV1730 | | 116 | $P_{CUP1}$- Bs_alsS2-PDC1 3' region-PDC1 5' region, TRP1, bla, pUC ori |
| pGV1745 | | 117 | pLlacO1::pntAB, pSC101, Km |
| pGV1748 | | | PLlacO1::Bs_alsS1::Ec_fucO::Ec_ ilvC_coEc bla, ColE1 ORI |
| pGV1748-A | | | PLlacO1::Ec_fucO:: bla, ColE1 ORI |
| pGV1749 | | | PLlacO1:: Bs_alsS1::Dm_ADH: Ec_ilvC_coEc bla, ColE1 ORI |
| pGV1749-A | | | PLlacO1::Dm_ADH:: bla, ColE1 ORI |
| pGV1772 | | | pLtetO1::maeB::pck::mdh, p15A, Cm |
| pGV1777 | | 118 | PLlacO1::Ec_ilvC_coEc, bla, ColE1 ORI |

TABLE 4-continued

| Plasmids disclosed herein | | | |
|---|---|---|---|
| GEVO No. | Figure | SEQ ID NO | Genotype or Reference |
| pGV1778 | | | PLlacO1:: Bs_alsS1::Kp_dhaT::Ec_ilvC_coEc bla, ColE1 ORI |
| pGV1778-A | | | PLlacO1::Kp_dhaT::bla, ColE1 ORI |
| pGV1824 | | | $P_{TEF1}$::Ec_ilvC_coSc:$T_{CYC1}$, pUC ORI, URA3, 2μ ORI, bla |
| pGV1914 | | 119 | $P_{TEF1}$:Ll_kivd2: $P_{TDH3}$:Dm_ADH PDC6 5',3' targeting homology URA3 pUC ori bla(ampR) |
| pGV1925 | | | pLlacO1::Ec_fucO ::Ec_ilvC_coEc::bla, ColE1 ORI |
| pGV1927 | | | pLlacO1::Ec_fucO::Ec_ilvC_coEc$^{S78D}$ bla, ColE1 ORI |
| pGV1936 | | 120 | $P_{TEF1}$:Sc_ILV3ΔN $P_{TDH3}$: Ec_ilvC_coSc$^{Q110V}$ PDC5 5',3' targeting homology LEU2 |
| pGV1938 | | | pLlac01::ilvC_coS78D bla, ColE1 ORI |
| pGV1939 | | | pLlacO1::*E. coli* fucO bla, ColE1 ORI |
| pGV1975 | | | pLlacO1::Ec_fucO::Ec_ilvC_coEc$^{6E6}$ bla, ColE1 ORI |
| pGV1976 | | | pLlacO1::Ec_fucO::Ec_ilvC_coEc$^{2H10}$ bla, ColE1 ORI |
| pGV1994 | | | $P_{TEF1}$::Ec_ ilvC_coSc$^{6E6}$:$T_{CYC1}$, bla, pUC ORI, URA3, 2μ ORI |
| pGV2020 | | 121 | $P_{Sc\_TEF1}$, $P_{Sc_TPI1}$, $P_{Sc_TPI1}$G418$^R$, AP$^r$, 2μ -- Vector Control |
| pGV2082 | | 122 | $P_{TEF1}$-Ll_ilvD_coSc-$P_{TDH3}$-Ec_ilvC_coSc$^{Q110V}$-$P_{TPI1}$-G418R-$P_{PGK1}$-Ll_kivd2_coEc-PDC1-3'region-$P_{ENO2}$-Dm_ADH 2μ bla, pUC-ori |
| pGV2193 | | | $P_{TEF1}$::EC_ ilvC_coSc$^{P2D1\text{-}his6}$:$T_{CYC1}$, bla, pUC ORI, URA3, 2μ ORI |
| pGV2227 | | 123 | $P_{TEF1}$-Ll_ilvD_coSc-$P_{TDH3}$-Ec_ilvC_coSc$^{Q110V}$-$P_{TPI1}$-G418R-$P_{PGK1}$-Ll_kivd2_coEc-PDC1-3'region-$P_{ENO2}$-Ll_adhA 2μ bla, pUC-ori |
| pGV2238 | | | $P_{TEF1}$::Ec_ ilvC_coSc$^{P2D1\text{-}A1\text{-}his6}$:$T_{CYC1}$, bla, pUC ORI, URA3, 2μ ORI. |
| pGV2241 | | 124 | $P_{TEF1}$::EC_ ilvC_coSc$^{6E6\text{-}his6}$:$T_{CYC1}$, bla, pUC ORI, URA3, 2μ ORI. |
| pGV2242 | | 125 | $P_{TEF1}$-Ll_ilvD_coSc-$P_{TDH3}$-Ec_ilvC_coSc$^{P2D1}$-$P_{TPI1}$-G418R-$P_{PGK1}$-Ll_kivd2_coEc-PDC1-3'region-$P_{ENO2}$-Ll_adhA 2μ bla, pUC-ori |
| pGV6000 | | | $P_{TEF1}$:NADH kinase $P_{TDH3}$:$NADP^+$ phosphatase HPH |
| pGV6001 | | | $P_{TDH3}$:Kl_GDP1 HPH |
| pGV6002 | | | $P_{TEF1}$:ess:pntA $P_{TDH3}$:ess:pntB HPH |
| pGV6003 | | | $P_{TEF1}$:mts:pntA $P_{TDH3}$:mts:pntB HPH |
| pGV6004 | | | $P_{ADH1}$:PYC1 $P_{TEF1}$:MDH2 $P_{TDH3}$:maeB HPH |

*These plasmids are described in PCT/US2008/053514

TABLE 5

| Amino acid and nucleotide sequences of enzymes and genes disclosed herein | | | |
|---|---|---|---|
| Enz. | Source | Gene (SEQ ID NO) | Corresponding Protein (SEQ ID NO) |
| pntA | *E. coli* | *E. coli* pntA (SEQ ID NO: 1) | *E. coli* PntA (SEQ ID NO: 2) |
| pntB | *E. coli* | *E. coli* pntB (SEQ ID NO: 3) | *E. coli* PntB (SEQ ID NO: 4) |
| ALS | *B. subtilis* | Bs_alsS1 (SEQ ID NO: 5) | BsAlsS1 (SEQ ID NO: 7) |
| | | Bs_alsS1_coSc (SEQ ID NO: 6) | |
| | | Bs_alsS2 (SEQ ID NO: 8) | Bs_AlsS2 (SEQ ID NO: 9) |

TABLE 5-continued

| Amino acid and nucleotide sequences of enzymes and genes disclosed herein | | | |
|---|---|---|---|
| Enz. | Source | Gene (SEQ ID NO) | Corresponding Protein (SEQ ID NO) |
| KARI | *E. coli* | Ec_ilvC<br>(SEQ ID NO: 10)<br>Ec_ilvC_coEc<br>(SEQ ID NO: 11)<br>Ec_ilvC_coSc<br>(SEQ ID NO: 12) | Ec_IlvC<br>(SEQ ID NO: 13) |
| | | Ec_ilvC_coEc$^{his6}$<br>(SEQ ID NO: 14) | Ec_IlvC$^{his6}$<br>(SEQ ID NO: 15) |
| | | Ec_ilvC_coEc$^{S78D-his6}$<br>(SEQ ID NO: 16) | Ec_IlvC$^{S78D-his6}$<br>(SEQ ID NO: 17) |
| | | Ec_ilvC_coEc$^{S78D}$<br>(SEQ ID NO: 18) | Ec_IlvC$^{S78D}$<br>(SEQ ID NO: 19) |
| | | Ec_ilvC_coEc$^{Q110A-his6}$<br>(SEQ ID NO: 20) | Ec_IlvC$^{Q110A-his6}$<br>(SEQ ID NO: 21) |
| | | Ec_ilvC_coEc$^{Q110V-his6}$<br>(SEQ ID NO: 22) | Ec_IlvC$^{Q110V-his6}$<br>(SEQ ID NO: 23) |
| | | Ec_ilvC_coSc$^{Q110V}$<br>(SEQ ID NO: 24) | Ec_IlvC$^{Q110V}$<br>(SEQ ID NO: 25) |
| | | Ec_ilvC_coEc$^{B8-his6}$<br>(SEQ ID NO: 26) | Ec_IlvC$^{B8-his6}$<br>(SEQ ID NO: 27) |
| | | Ec_ilvC_coEc$^{B8A71S-his6}$<br>(SEQ ID NO: 28) | Ec_IlvC$^{B8A71S-his6}$<br>(SEQ ID NO: 29) |
| | | Ec_ilvC_coEc$^{2H10-his6}$<br>(SEQ ID NO: 30) | Ec_IlvC$^{2H10-his6}$<br>(SEQ ID NO: 31) |
| | | Ec_ilvC_coEc$^{6E6-his6}$<br>(SEQ ID NO: 32)<br>Ec_ilvC_coSc$^{6E6-his6}$<br>(SEQ ID NO: 33) | Ec_IlvC$^{6E6-his6}$<br>(SEQ ID NO: 34) |
| | | Ec_ilvC_coSc$^{6E6}$<br>(SEQ ID NO: 35) | Ec_IlvC$^{6E6}$<br>(SEQ ID NO: 36) |
| | | Ec_ilvC_coSc$^{P2D1-his6}$<br>(SEQ ID NO: 37) | Ec_IlvC$^{P2D1-his6}$<br>(SEQ ID NO: 38) |
| | | Ec_ilvC_coSc$^{P2D1}$<br>(SEQ ID NO: 39) | Ec_IlvC$^{P2D1}$<br>(SEQ ID NO: 40) |
| | | Ec_ilvC_coSc$^{P2D1-A1-his6}$<br>(SEQ ID NO: 41) | Ec_IlvC$^{P2D1-A1-his6}$<br>(SEQ ID NO: 42) |
| | | Ec_ilvC_coSc$^{P2D1-A1}$<br>(SEQ ID NO: 43) | Ec_IlvC$^{P2D1-A1}$<br>(SEQ ID NO: 44) |
| KIVD | *L. lactis* | Ll_kivd1<br>(SEQ ID NO: 45)<br>Ll_kivd1_coEc<br>(SEQ ID NO: 46) | Ll_Kivd1<br>(SEQ ID NO: 47) |
| | | Ll_kivd2_coEc<br>(SEQ ID NO: 48) | Ll_Kivd2<br>(SEQ ID NO: 49) |
| DHAD | *E. coli* | Ec_ilvD<br>(SEQ ID NO: 50)<br>Ec_ilvD_coEc<br>(SEQ ID NO: 51) | Ec_IlvD<br>(SEQ ID NO: 52) |
| | *L. lactis* | Ll_ilvD_coSc<br>(SEQ ID NO: 54) | Ll_IlvD<br>(SEQ ID NO: 55) |
| | *S. cerevisiae* | Sc_ILV3<br>(SEQ ID NO: 56) | Sc_Ilv3<br>(SEQ ID NO: 57) |
| | | Sc_ILV3ΔN<br>(SEQ ID NO: 58) | Sc_Ilv3ΔN<br>(SEQ ID NO: 59) |
| ADH | *D. melanogaster* | Dm_ADH<br>(SEQ ID NO: 60) | Dm_Adh<br>(SEQ ID NO: 61) |
| | *K. pneumoniae* | Kp_dhaT<br>(SEQ ID NO: 62) | Kp_DhaT<br>(SEQ ID NO: 63) |
| | *E. coli* | Ec_fucO<br>(SEQ ID NO: 64) | Ec_FucO<br>(SEQ ID NO: 65) |
| | *L. lactis* | Ll_adhA<br>(SEQ ID NO: 66) | Ll_AdhA<br>(SEQ ID NO: 67) |
| | *E. coli* | Ec_yqhD<br>(SEQ ID NO: 68) | Ec_YqhD<br>(SEQ ID NO: 69) |

TABLE 6

| Primers sequences disclosed herein | |
|---|---|
| No. (SEQ ID NO) | Sequence (listed as 5' to 3') |
| XX1 (SEQ ID NO: 201) | CGCACCGGTTTTCTCCTCTTTAATGAATTCGGTCAGTGCGTCC TGC |
| XX2 (SEQ ID NO: 202) | GCGGCCGCCCTAGGGCGTTCGGCTGCGGCGAGCGGT |
| XX3 (SEQ ID NO: 203) | CGCGAATTCGGATCCGAGGAGAAAATAGTTATGAACAACTTTA ATCTGCACACCCC |
| XX4 (SEQ ID NO: 204) | GCGCCTAGGGCGGCCGCTTAGCGGGCGGCTTCGTATATACGG |
| 50 (SEQ ID NO: 205) | GCAGTTTCACCTTCTACATAATCACGACCGTAGTAGGTATCATT CCGGGGATCCGTCGACC |
| 73 (SEQ ID NO: 206) | CTGGCTTAAGTACCGGGTTAGTTAACTTAAGGAGAATGACGTG TAGGCTGGAGCTGCTTC |
| 74 (SEQ ID NO: 207) | CTCAAACTCATTCCAGGAACGACCATCACGGGTAATCATCATT CCGGGGATCCGTCGACC |
| 116 (SEQ ID NO: 208) | CAGCGTTCGCTTTATATCCCTTACGCTGGCCCTGTACTGCTGG AAGTGTAGGCTGGAGCTGCTTC |
| 117 (SEQ ID NO: 209) | TTCGGCTTGCCAGAAATTATCGTCAATGGCCTGTTGCAGGGCT TCATTCCGGGGATCCGTCGACC |
| 350 (SEQ ID NO: 210) | CTTAAATTCTACTTTTATAGTTAGTC |
| 474 (SEQ ID NO: 211) | CAAAGCTGCGGATGATGACGAGATTACTGCTGCTGTGCAGACT GAATTCCGGGGATCCGTCGACC |
| 772 (SEQ ID NO: 212) | AGGAAGGAGCACAGACTTAG |
| 868 (SEQ ID NO: 213) | CACAACATCACGAGGAATCACCATGGCTAACTACTTCAATACA CGTGTAGGCTGGAGCTGCTTC |
| 869 (SEQ ID NO: 214) | CTTAACCCGCAACAGCAATACGTTTCATATCTGTCATATAGCCG CATTCCGGGGATCCGTCGACC |
| 1030 (SEQ ID NO: 215) | GTCGGTGAACGCTCTCCTGAGTAGGGTGTAGGCTGGAGCTGC TTC |
| 1031 (SEQ ID NO: 216) | GAAGCAGCTCCAGCCTACACCCTACTCAGGAGAGCGTTCACC GAC |
| 1032 (SEQ ID NO: 217) | CACAACATCACGAGGAATCACCATGGCTAACTACTTCAATACA CCACGAGGCCCTTTCGTCTTCACCTC |

TABLE 6-continued

Primers sequences disclosed herein

| No. (SEQ ID NO) | Sequence (listed as 5' to 3') |
|---|---|
| 1155 (SEQ ID NO: 218) | CCCAACCCGCATTCTGTTTGGTAAAGGCGCAATCGCTGGTTTACGGTGTAGGCTGGAGCTGCTTC |
| 1156 (SEQ ID NO: 219) | CAATCGCGGCGTCAATACGCTCATCATCGGAACCTTCAGTGATGTATTCCGGGGATCCGTCGACC |
| 1187 (SEQ ID NO: 220) | CGGATAAAGTTCGTGAGATTGCCGCAAAACTGGGGCGTCATGTGGGTGTAGGCTGGAGCTGCTTC |
| 1188 (SEQ ID NO: 221) | CAGACATCAAGTAACCTTTATCGCGCAGCAGATTAACCGCTTCGCATTCCGGGGATCCGTCGACC |
| 1191 (SEQ ID NO: 222) | GGCACTCACGTTGGGCTGAGACACAAGCACACATTCCTCTGCACGGTGTAGGCTGGAGCTGCTTC |
| 1192 (SEQ ID NO: 223) | GCACCAGAAACCATAACTACAACGTCACCTTTGTGTGCCAGACCGATTCCGGGGATCCGTCGACC |
| 1205 (SEQ ID NO: 224) | GTTATCTAGTTGTGCAAAACATGCTAATGTAGCCACCAAATCCACGAGGCCCTTTCGTCTTCACCTC |
| 1218 (SEQ ID NO: 225) | GCTCACTCAAAGGCGGTAATACGTGTAGGCTGGAGCTGCTTC |
| 1219 (SEQ ID NO: 226) | GAAGCAGCTCCAGCCTACACGTATTACCGCCTTTGAGTGAGC |
| 1220 (SEQ ID NO: 227) | CGTAGAATCACCAGACCAGC |
| 1296 (SEQ ID NO: 228) | TTTTGTCGACGGATCCAGGAGACAACATTATGTCTATTCCAGAAACTCAAAAAGCG |
| 1297 (SEQ ID NO: 229) | TTTTGTCGACGCGGCCGCTTATTTAGAGGTGTCCACCACGTAACGG |
| 1321 (SEQ ID NO: 230) | AATCATATCGAACACGATGC |
| 1322 (SEQ ID NO: 231) | TCAGAAAGGATCTTCTGCTC |
| 1323 (SEQ ID NO: 232) | ATCGATATCGTGAAATACGC |
| 1324 (SEQ ID NO: 233) | AGCTGGTCTGGTGATTCTAC |
| 1341 (SEQ ID NO: 234) | TGCTGAAAGAGAAATTGTCC |
| 1342 (SEQ ID NO: 235) | TTTCTTGTTCGAAGTCCAAG |
| 1364 (SEQ ID NO: 236) | TTTTGCGGCCGCTTAGATGCCGGAGTCCCAGTGCTTG |
| 1365 (SEQ ID NO: 237) | AGTTGTTGACGCAGGTTCAGAG |
| 1436 (SEQ ID NO: 238) | AAATGACGACGAGCCTGAAG |
| 1437 (SEQ ID NO: 239) | GACCTGACCATTTGATGGAG |
| 1439 (SEQ ID NO: 240) | CAATTGGCGAAGCAGAACAAG |
| 1469 (SEQ ID NO: 241) | TTTTAGATCTAGGAGATACCGGTATGTCGTTTACTTTGACCAACAAG |
| 1440 (SEQ ID NO: 242) | ATCGTACATCTTCCAAGCATC |
| 1441 (SEQ ID NO: 243) | AATCGGAACCCTAAAGGGAG |
| 1442 (SEQ ID NO: 244) | AATGGGCAAGCTGTTTGCTG |
| 1443 (SEQ ID NO: 245) | TGCAGATGCAGATGTGAGAC |
| 1470 (SEQ ID NO: 246) | TTTTGGATCCAGGAAATAGATCTATGATGGCTAACAGAATGATTCTGAACG |
| 1471 (SEQ ID NO: 247) | TTTTGCGGCCGCTTACCAGGCGGTATGGTAAAGCTC |
| 1479 (SEQ ID NO: 248) | CCGATAGGCTTCCGCCATCGTCGGGTAGTTAAAGGTGGTGTTGAGTGTAGGCTGGAGCTGCTTC |
| 1485 (SEQ ID NO: 249) | GCCTTTATTGTACGCTTTTTACTGTACGATTTCAGTCAAATCTAACACGAGGCCCTTTCGTCTTCACCTC |
| 1486 (SEQ ID NO: 250) | AAGTACGCAGTAAATAAAAAATCCACTTAAGAAGGTAGGTGTTACATTCCGGGGATCCGTCGACC |
| 1526 (SEQ ID NO: 251) | TCGACGAGGAGACAACATTGTGTAGGCTGGAGCTGCTTC |
| 1527 (SEQ ID NO: 252) | GAAGCAGCTCCAGCCTACACAATGTTGTCTCCTCGTCGA |
| 1539 (SEQ ID NO: 253) | CCATTCTGTTGCTTTTATGTATAAGAACAGGTAAGCCCTACCATGGAGAATTGTGAGCGGATAAC |
| 1561 (SEQ ID NO: 254) | GCAATCCTGAAAGCTCTGTAACATTCCGGGGATCCGTCGACC |
| 1562 (SEQ ID NO: 255) | GGTCGACGGATCCCCGGAATGTTACAGAGCTTTCAGGATTGC |
| 1563 (SEQ ID NO: 256) | CAAATCGGCGGTAACGAAAGAGGATAAACCGTGTCCCGTATTATTCACGAGGCCCTTTCGTCTTCACCTC |
| 1566 (SEQ ID NO: 257) | TCCCACCCAATCAAGGCCAACG |
| 1567 (SEQ ID NO: 258) | TCCACCTGGTGCCAATGAACCG |
| 1587 (SEQ ID NO: 259) | CGGCTGCCAGAACTCTACTAACTG |
| 1588 (SEQ ID NO: 260) | GCGACGTCTACTGGCAGGTTAAT |
| 1595 (SEQ ID NO: 261) | CAACCTGGTGATTTGGGGAAG |
| 1597 (SEQ ID NO: 262) | GAATGATGGCAGATTGGGCA |
| 1598 (SEQ ID NO: 263) | TATTGTGGGGCTGTCTCGAATG |
| 1624 (SEQ ID NO: 264) | CCCTCATGTTGTCTAACGG |
| 1633 (SEQ ID NO: 265) | TCCGTCACTGGATTCAATGCCATC |
| 1634 (SEQ ID NO: 266) | TTCGCCAGGGAGCTGGTGAA |
| 1798 (SEQ ID NO: 267) | GCAAATTAAAGCCTTCGAGCG |
| 1926 (SEQ ID NO: 268) | TTTTTGTCGACGGATCCAGTTTATCATTATCAATACTCG |
| 1927 (SEQ ID NO: 269) | TTTTGCGGCCGCAGATCTCTCGAGTCGAAACTAAGTTCTGGTGTT |
| 2091 (SEQ ID NO: 270) | CTTTTCTTCCCTTGTCTCAATC |
| 2352 (SEQ ID NO: 271) | GACTCGACCTAGGTTATTTAGTAAAATCAATGACCATTC |
| 2353 (SEQ ID NO: 272) | CTAAATAACCTAGGTCGAGTCATGTAATTAGTTATGTC |
| KARIpETfor (SEQ ID NO: 273) | ATTCATATGGCGAATTATTTCAACACTCTG |
| KARIpETrev (SEQ ID NO: 274) | TAATCTCGAGGCCAGCCACCGCGATGCG |
| pETup (SEQ ID NO: 275) | ATGCGTCCGGCGTAGA |
| seq_ilvC_pGV (SEQ ID NO: 276) | GCGGCCGCGTCGACGAGGAGACAACATTATGGCGA |

TABLE 6-continued

Primers sequences disclosed herein

| No. (SEQ ID NO) | Sequence (listed as 5' to 3') |
|---|---|
| pGV1994ep_for (SEQ ID NO: 277) | CGGTCTTCAATTTCTCAAGTTTCAGTTTCATTTTTCTTGTTCTATTACAAC |
| pGV1994ep_rev (SEQ ID NO: 278) | CTAACTCCTTCCTTTTCGGTTAGAGCGGATGTGGG |
| Not_in_for (SEQ ID NO: 279) | CCTCTAGAAATAATTTGCGGCCGCGTTAAGAAGGAGATATACATATG |
| AvrII_in_rev (SEQ ID NO: 280) | CCGAACGCCCTAGGTCAGTGGTGGTGGTGGTGGTGCTCGAG |
| R68DK69Lfor (SEQ ID NO: 281) | TAGCTATGCGCTGGACCTGGAGGCTATC |
| R68DK69Lrev (SEQ ID NO: 282) | GATAGCCTCCAGGTCCAGCGCATAGCTA |
| K75VR76Dfor (SEQ ID NO: 283) | AGGCTATCGCGGAAGTTGACGCTAGCTG |
| K75VR76Drev (SEQ ID NO: 284) | CAGCTAGCGTCAACTTCCGCGATAGCCT |
| R69NNKfor (SEQ ID NO: 285) | TAGCTATGCGCTGCGCNNKGAGGCTATC |
| R69NNKrev (SEQ ID NO: 286) | GATAGCCTCMNNGCGCAGCGCATAGCTA |
| K75NNKfor (SEQ ID NO: 287) | AGGCTATCGCGGAANNKCGTGCTAGCTG |
| K75NNKrev (SEQ ID NO: 288) | CAGCTAGCACGMNNTTCCGCGATAGCCT |
| R76NNKfor (SEQ ID NO: 289) | AGGCTATCGCGGAAAAANNKGCTAGCTGGC |
| R76NNKrev (SEQ ID NO: 290) | GCCAGCTAGCMNNTTTTCCGCGATAGCCT |
| R68NNK_for (SEQ ID NO: 291) | TAGCTATGCGCTGNNKAAGGAGGCTATC |
| R68NNK_rev (SEQ ID NO: 292) | GATAGCCTCCTTMNNCAGCGCATAGCTA |
| S78NNK_for (SEQ ID NO: 293) | GCGGAAAAACGTGCTNNKTGGCGCAAGGCTACT |
| S78NNK_rev (SEQ ID NO: 294) | AGTAGCCTTGCGCCAMNNAGCACGTTTTTCCGC |
| A71NNK_for (SEQ ID NO: 295) | GCGCTGCGCAAGGAGNNKATCGCGGAAAAAC |
| A71NNK_rev (SEQ ID NO: 296) | GTTTTTCCGCGATMNNCTCCTTGCGCAGCGC |
| Gln110NNK_for (SEQ ID NO: 297) | CTGACCCCAGATAAANNKCATAGCGACGTTG |
| Gln110NNK_rev (SEQ ID NO: 298) | CAACGTCGCTATGMNNTTTATCTGGGGTCAG |
| seq_ilvC_pGV (SEQ ID NO: 299) | GCGGCCGCGTCGACGAGGAGACAACATTATGGCGA |
| Q110Qfor (SEQ ID NO: 300) | GACCCCAGATAAACAACATAGCGACGTTGTT |
| Q110Qrev (SEQ ID NO: 301) | AACAACGTCGCTATGTTGTTTATCTGGGGTC |
| Q110Afor (SEQ ID NO: 302) | GACCCCAGATAAAGCACATAGCGACGTTGTT |
| Q110Arev (SEQ ID NO: 303) | AACAACGTCGCTATGTGCTTTATCTGGGGTC |
| Q110Vfor (SEQ ID NO: 304) | GACCCCAGATAAAGTACATAGCGACGTTGTT |
| Q110Vrev (SEQ ID NO: 305) | AACAACGTCGCTATGTACTTTATCTGGGGTC |
| R68A71recombfor (SEQ ID NO: 306) | GCTATGCGCTGCKAAAGGAGDCAATCGCGG |
| R68A71recombrev (SEQ ID NO: 307) | CCGCGATTGHCTCCTTTMGCAGCGCATAGC |
| R76S78recombfor (SEQ ID NO: 308) | GAAAAACGTGCTAGCTGGCGCAAGGCTACT |
| R76S78recombrev (SEQ ID NO: 309) | AGTAGCCTTGCGCCAGCTAGCACGTTTTTC |
| G76S78recombfor (SEQ ID NO: 310) | GAAAAAGGTGCTAGCTGGCGCAAGGCTACT |
| G76S78recombrev (SEQ ID NO: 311) | AGTAGCCTTGCGCCAGCTAGCACCTTTTTC |
| S76S78recombfor (SEQ ID NO: 312) | GAAAAAAGTGCTAGCTGGCGCAAGGCTACT |
| S76S78recombrev (SEQ ID NO: 313) | AGTAGCCTTGCGCCAGCTAGCACTTTTTTC |
| T76S78recombfor (SEQ ID NO: 314) | GAAAAAACTGCTAGCTGGCGCAAGGCTACT |
| T76S78recombrev (SEQ ID NO: 315) | AGTAGCCTTGCGCCAGCTAGCAGTTTTTTC |
| D76S78recombfor (SEQ ID NO: 316) | GAAAAAGATGCTAGCTGGCGCAAGGCTACT |
| D76S78recombrev (SEQ ID NO: 317) | AGTAGCCTTGCGCCAGCTAGCATCTTTTTC |
| R76D78recombfor (SEQ ID NO: 318) | GAAAAACGTGCTGACTGGCGCAAGGCTACT |
| R76D78recombrev (SEQ ID NO: 319) | AGTAGCCTTGCGCCAGTCAGCACGTTTTTC |
| G76D78recombfor (SEQ ID NO: 320) | GAAAAAGGTGCTGACTGGCGCAAGGCTACT |
| G76D78recombrev (SEQ ID NO: 321) | AGTAGCCTTGCGCCAGTCAGCACCTTTTTC |
| S76D78recombfor (SEQ ID NO: 322) | GAAAAAAGTGCTGACTGGCGCAAGGCTACT |
| S76D78recombrev (SEQ ID NO: 323) | AGTAGCCTTGCGCCAGTCAGCACTTTTTTC |
| T76D78recombfor (SEQ ID NO: 324) | GAAAAAACTGCTGACTGGCGCAAGGCTACT |
| T76D78recombrev (SEQ ID NO: 325) | AGTAGCCTTGCGCCAGTCAGCAGTTTTTTC |
| D76D78recombfor (SEQ ID NO: 326) | GAAAAAGATGCTGACTGGCGCAAGGCTACT |
| D76D78recombrev (SEQ ID NO: 327) | AGTAGCCTTGCGCCAGTCAGCATCTTTTTC |
| 1994hisrev (SEQ ID NO: 328) | TGACTCGAGCGGCCGCGGATCCTTAGTGGTGGTGGTGGTGGTGTCCTGCCACTGCA |
| pGV1994ep_for (SEQ ID NO: 329) | CGGTCTTCAATTTCTCAAGTTTCAGTTTCATTTTTCTTGTTCTATTACAAC |
| pGV1994ep_rev (SEQ ID NO: 330) | CTAACTCCTTCCTTTTCGGTTAGAGCGGATGTGGG |

Example 1

Low-Level Anaerobic Production of Isobutanol

This example illustrates that a modified microorganism which is engineered to overexpress an isobutanol producing pathway produces a low amount of isobutanol under anaerobic conditions.

Overnight cultures of GEVO1859 were started from glycerol stocks stored at −80° C. of previously transformed strains. These cultures were started in 3 mL M9 minimal medium (Miller, J. H. A Short Course in Bacterial Genetics: A laboratory manual and handbook for *Escherichia coli* and related bacteria. 1992. Cold Spring Harbor Laboratory Press, Cold Spring Harbor, N.Y.), supplemented with 10 g/L yeast extract, 10 μM ferric citrate and trace metals, containing 8.5% glucose and the appropriate antibiotics in snap cap tubes about 14 h prior to the start of the fermentation. Isobutanol fermentations were then carried out in screw cap flasks containing 20 mL of the same medium that was inoculated with 0.2 mL of the overnight culture. The cells were incubated at 37° C./250 rpm until the strains had grown to an $OD_{600}$ of 0.6-0.8 and were then induced with Isopropyl β-D-1-thiogalactopyranoside at 1 mM final concentration.

Three hours after induction the cultures were either kept under the current conditions (micro-aerobic conditions) or shifted to anaerobic conditions by loosening the cap of the flasks and placing the flasks into to a Coy Laboratory Products Type B Vinyl anaerobic chamber (Coy Laboratory Products, Grass Lakes, Mich.) through an airlock in which the flasks were cycled three times with nitrogen and vacuum, and then filled with the a hydrogen gas mix (95% Nitrogen, 5% Hydrogen).

Once the flasks were inside the anaerobic chamber, the flasks were closed again and incubated without shaking at 30° C. The flasks in the anaerobic chamber were swirled twice a day. Samples (2 mL) were taken at the time of the shift and at 24 h and 48 h after inoculation, spun down at 22,000 g for 1 min to separate the cell pellet from the supernatant and stored frozen at −20° C. until analysis. The samples were analyzed using High performance liquid chromatography (HPLC) and gas chromatography (GC).

Figure 8:
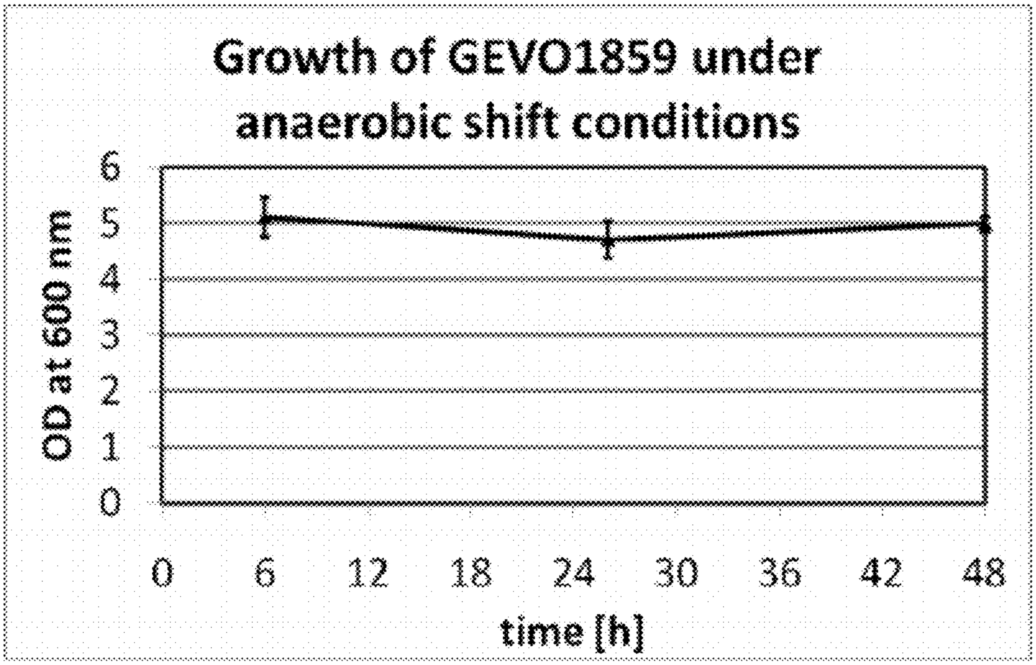
FIG. 8 illustrates growth of GEVO1859 under anaerobic shift conditions over the course of the fermentation.
Figure 9:
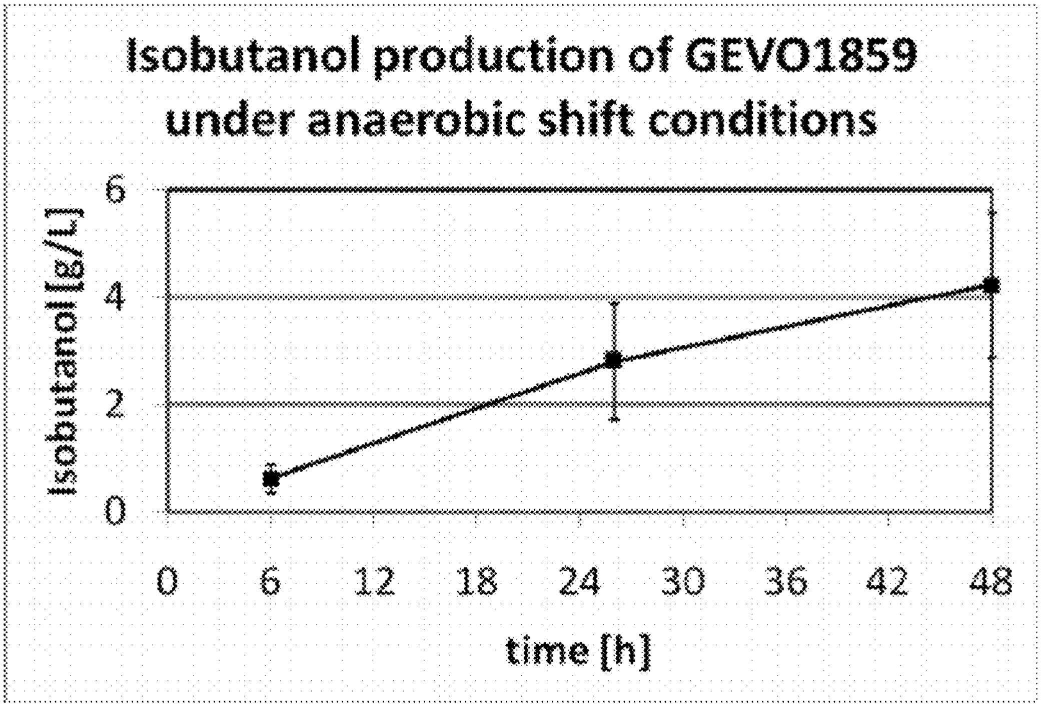
FIG. 9 illustrates isobutanol production of GEVO1859 under under anaerobic shift conditions over the course of the fermentation.

GEVO1859 was run in triplicate. Stable OD values can be observed for all strains under anaerobic shift conditions over the course of the fermentation (FIG. 8). The complete pathway integrant strain showed low-level anaerobic isobutanol production over the course of the fermentation (FIG. 9, Table 7).

GEVO1385 was transformed with pGV1698, pGV1655, and either pGV1685 or pGV1490. Transformed cells were plated on LB-plates containing the appropriate antibiotics and the plates were incubated overnight at 37° C. Overnight cultures were started in 3 mL EZ-Rich Defined Medium (Neidhardt, F. C., P. L. Bloch, and D. F. Smith. 1974, Culture medium for enterobacteria, *J. Bacteriol.* 119:736-47) containing 5% glucose and the appropriate antibiotics in snap cap tubes about 14 h prior to the start of the fermentation. Isobutanol fermentations were then carried out in EZ-Rich containing 5% glucose and the appropriate antibiotics. 250 mL screw cap flasks with 20 mL EZ-Rich containing 5% glucose and the appropriate antibiotics were inoculated with 1% of the grown overnight culture. The cells were incubated at 37° C./250 rpm until the strains were grown to an $OD_{600}$ of 0.6-0.8 and these strains were then induced with Isopropyl β-D-1-thiogalactopyranoside (IPTG (Gold BioTechnology, Inc, 12481C100) 1 mM) and anhydrotetracycline (aTc (Sigma, 37919-100 mg) 100 ng/mL). Samples were taken of the medium 48 h after inoculation. 15 mL of cell culture from each flask were centrifuged at 5,000×g for 5 min to separate the cell pellet from the supernatant. The cell pellets were stored frozen at −80° C. until analysis. The cultures grew to a comparable OD in this experiment.

TABLE 7

Volumetric productivity, specific productivity titer and yield reached in an anaerobic fermentation for the tested strains and plasmid systems

| | Volumetric Productivity | | Specific Productivity | | Titer | | Yield | |
|---|---|---|---|---|---|---|---|---|
| Samples | [g/L/h] | ± | [g/L/h/OD] | ± | [g/L] | ± | [g/g] | ± |
| GEVO1859 | 0.088 | 0.028 | 0.019 | 0.005 | 4.22 | 1.35 | 0.140 | 0.029 |

In the period from 6 h to 48 h, i.e. under anaerobic conditions GEVO1859 demonstrated limited production of isobutanol (Table 8).

TABLE 8

Volumetric productivity, specific productivity titer and yield reached in the period from 6 to 48 h for the tested strain

| | | Volumetric Productivity | | Specific Productivity | | Titer | | Yield | |
|---|---|---|---|---|---|---|---|---|---|
| Samples | Condition | [g/L/h] | ± | [g/L/h/OD] | ± | [g/L] | ± | [g/g] | ± |
| GEVO1859 | Micro-aerobic | 0.266 | 0.010 | 0.040 | 0.004 | 11.2 | 0.4 | 0.33 | 0.016 |
| GEVO1859 | Anaerobic | 0.086 | 0.026 | 0.019 | 0.005 | 3.60 | 1.1 | 0.14 | 0.032 |

Example 2

Determination of Transhydrogenase Activity

This example illustrates that an isobutanol producing microorganism which carries a plasmid for the expression of the *E. coli* PntAB transhydrogenase (SEQ ID NO: 2 and SEQ ID NO: 4) contains increased transhydrogenase activity.

A fermentation was performed with a strain expressing the tet repressor (GEVO1385) and carrying the plasmids pGV1655 (SEQ ID NO: 109) and pGV1698 (SEQ ID NO: 112) for expression of the isobutanol pathway. The *E. coli* transhydrogenase PntAB was expressed from a third plasmid pGV1685 (SEQ ID NO: 111), which contained the *E. coli* pntAB genes under control of the PLtet promoter. The appropriate empty vector control carries the plasmid pGV1490 (SEQ ID NO: 104).

To confirm that the transhydrogenase was actually expressed from the plasmids and to assess their enzymatic activity levels, enzyme assays were done with lysates prepared from the fermentation cultures. Frozen cell pellets were thawed on ice. The pellets were resuspended in 1.2 mL lysis buffer (50 mM potassium phosphate buffer at pH 7.5, $MgCl_2$ 2 mM). The suspensions were sonicated on ice for twice 2 min. The transhydrogenase enzyme assay was done in potassium phosphate buffer (50 mM pH 7.5, $MgCl_2$ 2 mM, 1 mM acetylpyridine-AD, 0.5 mM NADPH). The assay was run at 25° C. in a 96 well plate. Absorbance at 375 nm was followed in a kinetic assay format. To measure PntAB activity lysates were not cleared by centrifugation. The activity obtained for the samples featuring over-expressed *E. coli* pntAB show at least a 10 fold increase in transhydrogenase activity (Table 9).

TABLE 9

Shown are the enzymatic activities of the independent *E. coli* pntAB overexpressing strains and the amount of isobutanol production that would be supported by that activity calculated from $V_{max}$ values obtained from the enzyme assay

| Samples | average Vmax | stdev. Vmax | protein conc. [mg/mL] | units in reaction | specific activity [u/mg (total cell protein)] |
|---|---|---|---|---|---|
| pntAB-1 | 33.81 | 3.87 | 1.17 | 0.0010 | 0.1646 |
| pntAB-2 | 45.06 | 1.51 | 1.89 | 0.0013 | 0.1355 |
| empty vector-1 | 2.24 | 0.21 | 0.89 | 0.0001 | 0.0142 |
| empty vector-2 | −0.01 | 2.00 | 0.71 | 0.0000 | -0.0001 |

Example 3

Overexpression of Pntab Improves Isobutanol Fermentation Performance

This example illustrates that overexpression of a transhydrogenase, exemplified by the *E. coli* pntAB operon (SEQ ID NO: 1 and SEQ ID NO: 3) on a low copy plasmid improves isobutanol production under micro-aerobic conditions.

GEVO1748 was transformed with plasmids pGV1698 (SEQ ID NO: 112) and one of either pGV1720 (SEQ ID NO: 115) (control) or pGV1745 (SEQ ID NO: 117) (*E. coli* pntAB).

The aforementioned strains were plated on LB-plates containing the appropriate antibiotics and incubated overnight at 37° C. Overnight cultures were started in 3 mL EZ-Rich medium (Neidhardt, F. C., P. L. Bloch, and D. F. Smith. 1974. Culture medium for enterobacteria. J Bacteriol. 119:736-47) containing 5% glucose and the appropriate antibiotics in snap cap tubes about 14 h prior to the start of the fermentation. Isobutanol fermentations were then carried out in EZ-Rich Medium containing 5% glucose and the appropriate antibiotics. 250 mL screw cap flasks with 20 mL EZ-Rich medium containing 5% glucose and the appropriate antibiotics were inoculated with 1% of the grown overnight culture. The cells were incubated at 37° C./250 rpm until they reached an $OD_{600}$ of 0.6-0.8 followed by induction with Isopropyl β-D-1-thiogalactopyranoside (IPTG, 1 mM) and anhydrotetracycline (aTc, 100 ng/mL). Samples (2 mL) were taken 24 h and 48 h post inoculation, centrifuged at 22,000×g for 1 min and stored frozen at −20° C. until via Gas Chromatography (GC) and High Performance Liquid Chromatography (HPLC). Fermentations were run with two biological replicates.

All cultures grew to an OD of 5.5 to 6.5. Volumetric productivity and titer were improved by 45%, specific productivity even by 51%. Yield was improved by 8% (Table 10).

TABLE 10

Overexpression of *E. coli* pntAB improves isobutanol fermentation performance

| | Volumetric Productivity | | Specific Productivity | | Titer | | Yield | |
|---|---|---|---|---|---|---|---|---|
| Samples | [g/L/h] | ± | [g/L/h/OD] | ± | [g/L] | ± | [g/g] | ± |
| GEVO1748 +pGV1698 +pGV1720 | 0.205 | 0.001 | 0.035 | 0.001 | 9.86 | 0.04 | 0.311 | 0.001 |
| GEVO1748 +pGV1698 +pGV1745 | 0.298 | 0.006 | 0.053 | 0.003 | 14.29 | 0.28 | 0.337 | 0.001 |

Example 4

Overexpression of pntAB Enables Anaerobic Isobutanol Production

This example illustrates that overexpression of a transhydrogenase, exemplified by the *E. coli* pntAB operon product (SEQ ID NO: 2 and SEQ ID NO: 4), improves anaerobic isobutanol production. This is surprising because it was previously not known that isobutanol could be produced anaerobically. In addition, this result was achieved without modifying the isobutanol biosynthetic pathway itself.

GEVO1748 was transformed with plasmids pGV1698 (SEQ ID NO: 112) and pGV1720 (SEQ ID NO: 115) (control) or pGV1745 (SEQ ID NO: 117) (*E. coli* pntAB).

Overnight cultures of the aforementioned strains were started from glycerol stocks stored at −80° C. of previously transformed strains. These cultures were started in 3 mL M9 minimal medium (Miller, J.H. A Short Course in Bacterial Genetics: A laboratory manual and handbook for *Escherichia coli* and related bacteria. 1992. Cold Spring Harbor Laboratory Press, Cold Spring Harbor, N.Y.), supplemented with 10 g/L yeast extract, 10 μM ferric citrate and trace metals, containing 8.5% glucose and the appropriate antibiotics in snap cap tubes about 14 h prior to the start of the fermentation. Isobutanol fermentations were then carried out in 250 mL screw cap flasks containing 20 mL of the same medium that was inoculated with 0.2 mL of the overnight culture. The cells were incubated at 37° C./250 rpm until the strains had grown to an $OD_{600}$ of 0.6-0.8 and were then induced with Isopropyl 13-D-1-thiogalactopyranoside at 1 mM final concentration.

Three hours after induction the cultures were shifted to anaerobic fermentation conditions by loosening the cap of the flasks and placing the flasks into to a Coy Laboratory Products Type B Vinyl anaerobic chamber (Coy Laboratory Products, Grass Lakes, Mich.) through an airlock in which the flasks were cycled three times with nitrogen and vacuum, and then filled with the a hydrogen gas mix (95% Nitrogen, 5% Hydrogen). Once the flasks were inside the anaerobic chamber, the flasks were closed again and incubated without shaking at 30° C. Inside the chamber, an anaerobic atmosphere (<5 ppm oxygen) was maintained through the hydrogen gas mix (95% Nitrogen, 5% Hydrogen) reacting with a palladium catalyst to remove oxygen. The flasks in the anaerobic chamber were swirled twice a day. Samples (2 mL) were taken at the time of the shift and at 24 h and 48 h after inoculation, spun down at 22,000×g for 1 min to separate the cell pellet from the supernatant and stored frozen at −20° C. until analysis. The samples were analyzed using High performance liquid chromatography (HPLC) and gas chromatography (GC). All experiments for the *E. coli* pntAB-expressing strain were performed in duplicate while the control strain was only run in a single experiment.

Figure 10:
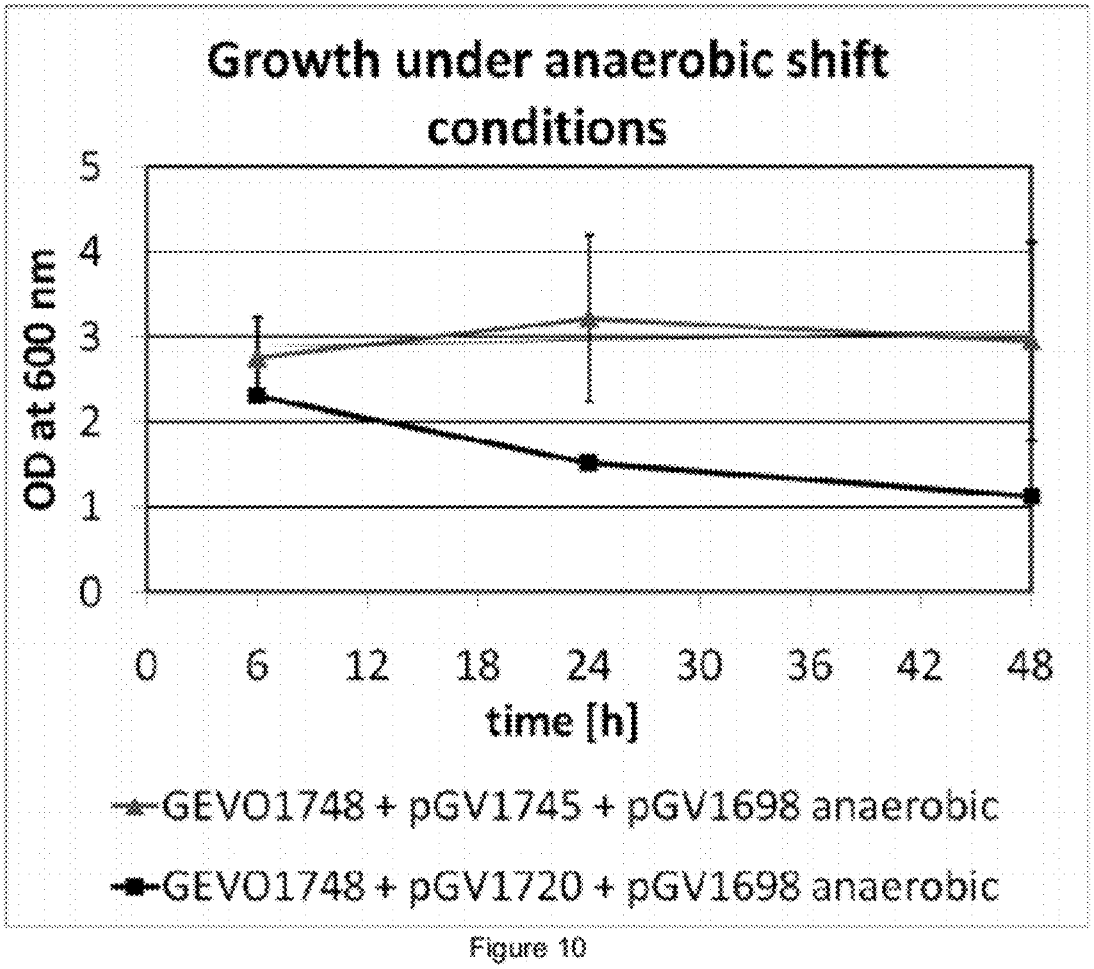
FIG. 10 illustrates that microorganisms featuring an overexpressed *E. coli* pntAB operon (pGV1745) increased in $OD_{600}$ from 6 h to 24 h by 0.2-1.1 under anaerobic conditions, while microorganisms lacking *E. coli* pntAB (pGV1720) decreased in $OD_{600}$ by 0.5-1.2.

At the time of shifting the cultures to anaerobic conditions all samples had an $OD_{600}$ ranging between 2.3 and 3.3. All samples featuring an overexpressed *E. coli* pntAB operon (pGV1745) increased in $OD_{600}$ from 6 h to 24 h by 0.2-1.1, all samples lacking pntAB (pGV1720) decreased in $OD_{600}$ by 0.5-1.2 (FIG. 10), indicating that overexpression of *E. coli* pntAB is beneficial under anaerobic conditions.

Figure 11:
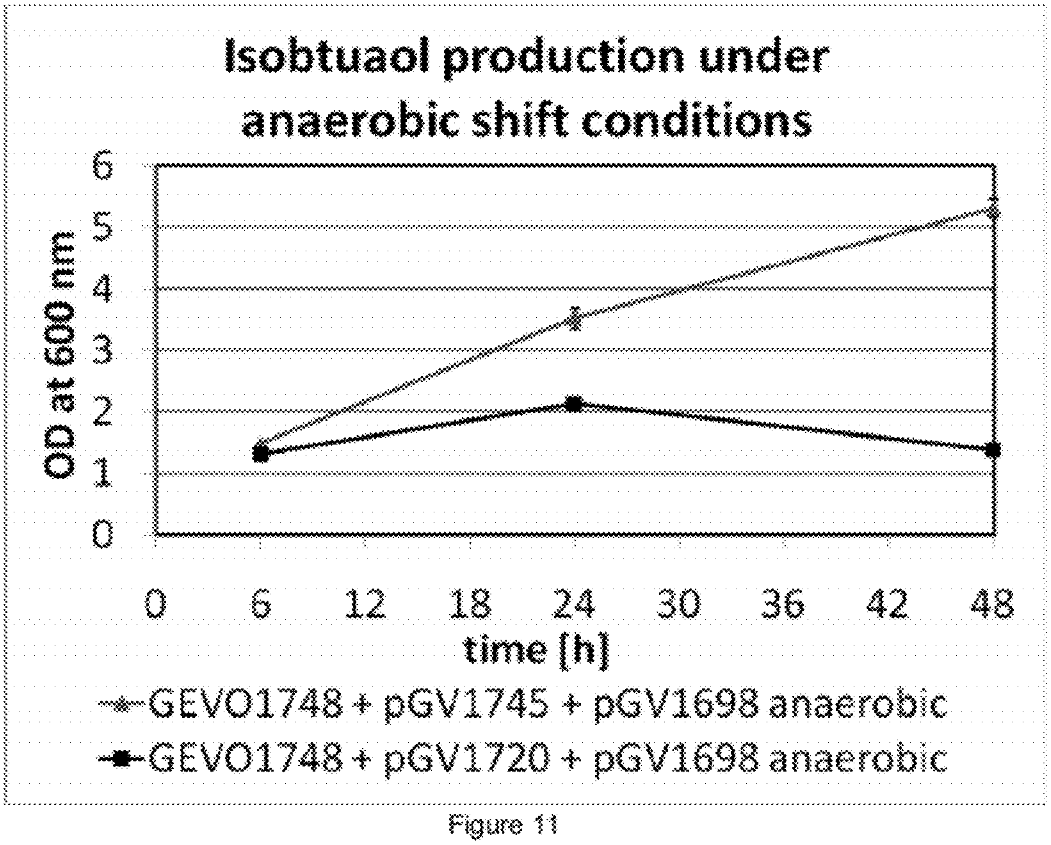
FIG. 11 illustrates that microorganisms featuring an overexpressed *E. coli* pntAB operon (pGV1745) continued isobutanol production under anaerobic conditions until the fermentation was stopped at 48 hours while microorganisms lacking *E. coli* pntAB (pGV1720) did not produce isobutanol between 24 and 48 hours

Furthermore, pntAB over-expression is beneficial for anaerobic isobutanol production. All samples featuring *E. coli* PntAB continued isobutanol production under anaerobic conditions until the fermentation was stopped at 48 hours whereas the samples lacking *E. coli* PntAB did not produce isobutanol between 24 and 48 hours (FIG. 11)

In the strain overexpressing *E. coli* pntAB, volumetric productivity and titer are increased 2.4-fold, specific productivity by 85% and yield by 9% (Table 11).

TABLE 11

Shown are the results for volumetric productivity, specific productivity titer and yield reached in an anaerobic fermentation for the tested strains and plasmid systems after 48 h

| | Volumetric Productivity | | Specific Productivity | | Titer | | Yield | |
|---|---|---|---|---|---|---|---|---|
| Samples | [g/L/h] | ± | [g/L/h/OD] | ± | [g/L] | ± | [g/g] | ± |
| GEVO1748 +pGV1720 +pGV1698 | 0.047 | | 0.022 | | 2.24 | | 0.279 | |
| GEVO1748 +pGV1745 +pGV1698 | 0.111 | 0.002 | 0.041 | 0.012 | 5.32 | 0.10 | 0.304 | 0.004 |

-

In the period from 6 h to 48 h, (i.e. under anaerobic conditions), GEVO1748 transformed with plasmids pGV1698 and pGV1745 (carrying *E. coli* pntAB) demonstrated significantly higher productivity, titer, and yield of isobutanol compared to the control strain carrying pGV1720 (without *E. coli* pntAB) (Table 12).

TABLE 12

Shown are the results for volumetric productivity, specific productivity titer and yield reached in the period from 6 to 48 h for the tested strains and plasmid systems

| | Volumetric Productivity | | Specific Productivity | | Titer | | Yield | |
|---|---|---|---|---|---|---|---|---|
| samples | [g/L/h] | ± | [g/L/h/OD] | ± | [g/L] | ± | [g/g] | ± |
| GEVO1748 +pGV1720 +pGV1698 | 0.029 | | 0.014 | | 1.21 | | 0.171 | |
| GEVO1748 +pGV1745 +pGV1698 | 0.096 | 0.003 | 0.035 | 0.015 | 4.01 | 0.15 | 0.246 | 0.002 |

Example 5

Chromosomal Integration of pntAB Improves Anaerobic Isobutanol Production

This example illustrates that overexpression of a transhydrogenase, exemplified by the *E. coli* pntAB operon product (SEQ ID NO: 2 and SEQ ID NO: 4), from the chromosome improves isobutanol production under anaerobic conditions compared to the case in which *E. coli* pntAB is expressed from a low copy plasmid. This strain reaches the same titer aerobically as anaerobically.

Overnight cultures of GEVO1846, GEVO1859, GEVO1886 were started from glycerol stocks stored at −80° C. of previously transformed strains. These cultures were started in 3 mL M9 minimal medium (Miller, J.H. A Short Course in Bacterial Genetics: A laboratory manual and handbook for *Escherichia coli* and related bacteria. 1992. Cold Spring Harbor Laboratory Press, Cold Spring Harbor, N.Y.), supplemented with 10 g/L yeast extract, 10 µM ferric citrate and trace metals, containing 8.5% glucose and the appropriate antibiotics in snap cap tubes about 14 h prior to the start of the fermentation. Isobutanol fermentations were then carried out in screw cap flasks containing 20 mL of the same medium that was inoculated with 0.2 mL of the overnight culture. The cells were incubated at 37° C./250 rpm until the strains had grown to an $OD_{600}$ of 0.6-0.8 and were then induced with Isopropyl 13-D-1-thiogalactopyranoside at 1 mM final concentration.

Three hours after induction the cultures were either kept under the current conditions (micro-aerobic conditions) or shifted to anaerobic conditions by loosening the cap of the flasks and placing the flasks into to a Coy Laboratory Products Type B Vinyl anaerobic chamber (Coy Laboratory Products, Grass Lakes, Mich.) through an airlock in which the flasks were cycled three times with nitrogen and vacuum, and then filled with the a hydrogen gas mix (95% Nitrogen, 5% Hydrogen). Once the flasks were inside the anaerobic chamber, the flasks were closed again and incubated without shaking at 30° C. The flasks in the anaerobic chamber were swirled twice a day. Samples (2 mL) were taken at the time of the shift and at 24 h and 48 h after inoculation, spun down at 22,000×g for 1 min to separate the cell pellet from the supernatant and stored frozen at −20° C. until analysis. The samples were analyzed using High performance liquid chromatography (HPLC) and gas chromatography (GC). All experiments were performed in duplicate.

Figure 12:
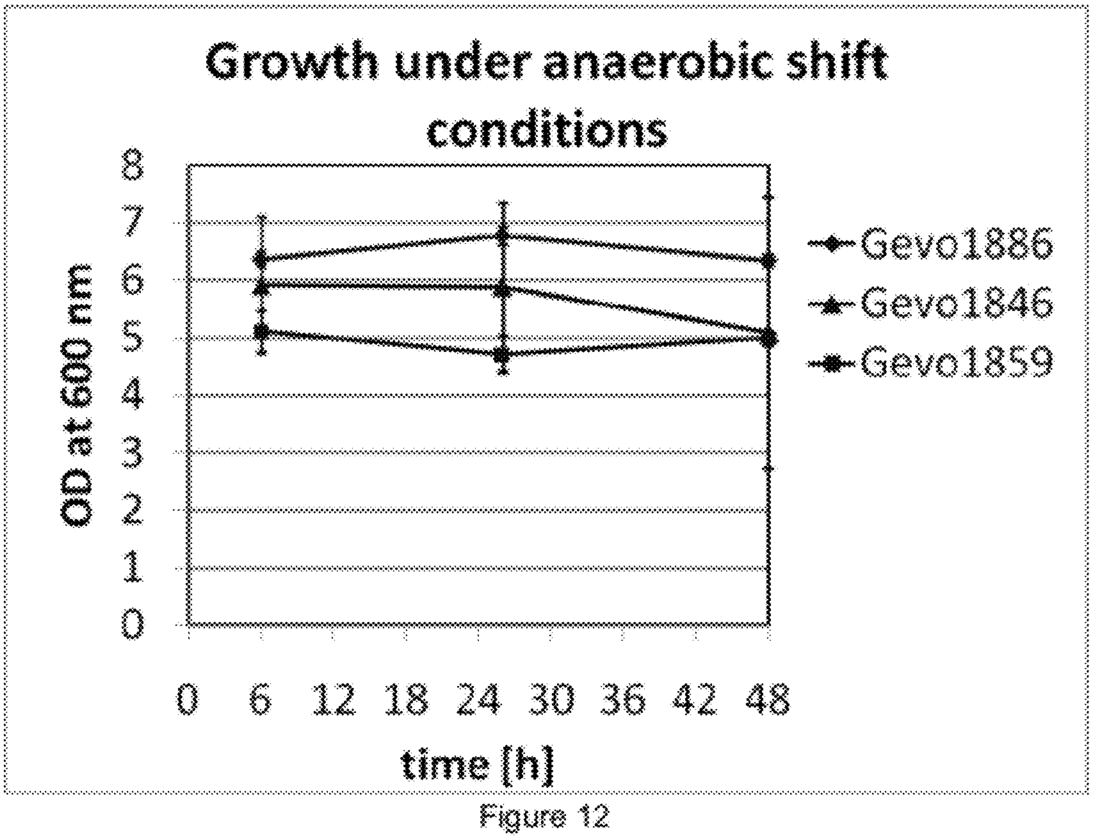
FIG. 12 illustrates that for strains GEVO1886, GEVO1859 and GEVO1846 stable OD values can be observed under anaerobic shift conditions over the course of the fermentation
Figure 13:
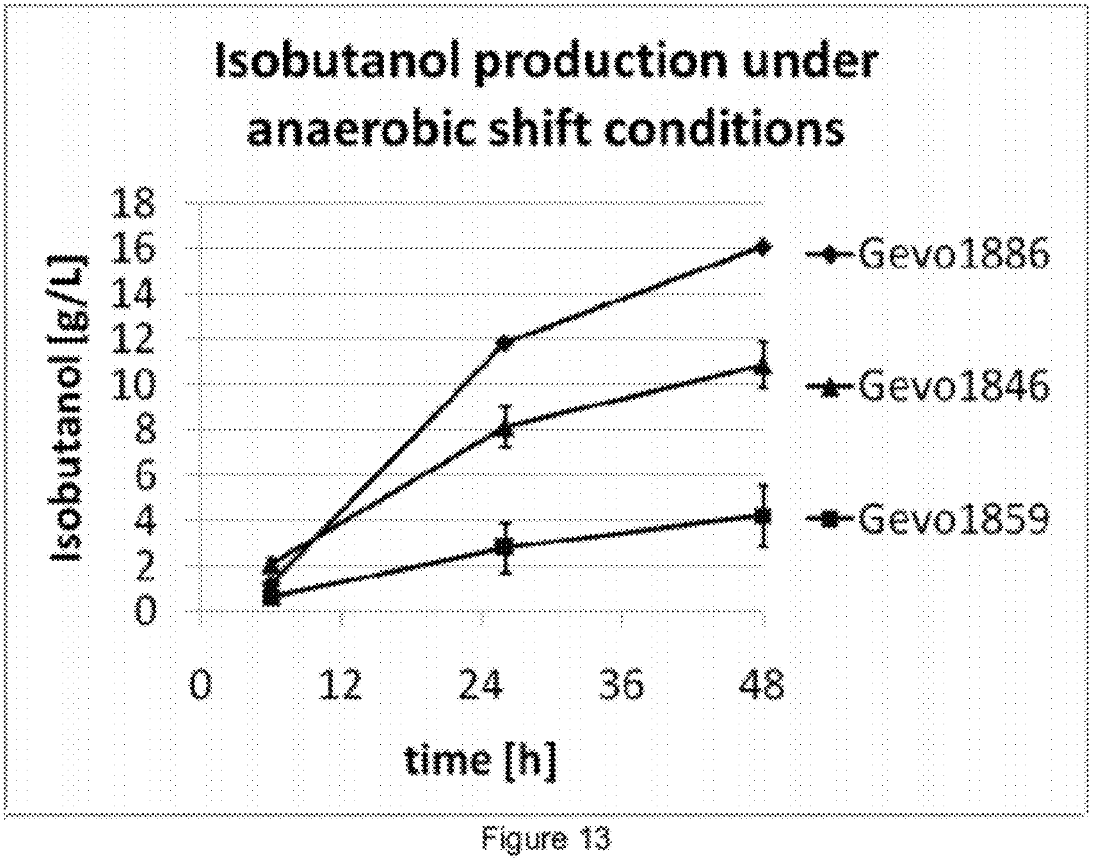
FIG. 13 illustrates that over-expression of *E. coli* pntAB in either strain GEVO1846 or GEVO1886 leads to an improvement in isobutanol production over the course of the fermentation compared to the control strain GEVO1859 which does not over-express *E. coli* pntAB.

GEVO1886, GEVO1859 and GEVO1846 were run in parallel. Each strain was run in triplicate. Stable OD values can be observed for all strains under anaerobic shift conditions over the course of the fermentation (FIG. 12). The overexpression of *E. coli* pntAB in the complete pathway integrant strain again showed improvement for isobutanol production over the course of the fermentation (FIG. 13).

Compared to the complete pathway integrant strain without *E. coli* pntAB knock-in (GEVO1859), volumetric productivity and titer are increased 3.8-fold, specific productivity is increased 2.8-fold and the yield is 2.2-fold higher in GEVO1886. In addition, GEVO1886 shows superior performance compared to the plasmid system strain (GEVO1846) under anaerobic conditions. Volumetric productivity and titer are increased by 48%, specific productivity is increased by 18% and yield is 12% higher (Table 13).

TABLE 13

Shown are the results for volumetric productivity, specific productivity titer and yield reached in an anaerobic fermentation for the tested strains and plasmid systems

| | Volumetric Productivity | | Specific Productivity | | Titer | | Yield | |
|---|---|---|---|---|---|---|---|---|
| Samples | [g/L/h] | ± | [g/L/h/OD] | ± | [g/L] | ± | [g/g] | ± |
| GEVO1886 | 0.335 | 0.002 | 0.053 | 0.001 | 16.08 | 0.08 | 0.307 | 0.004 |
| GEVO1859 | 0.088 | 0.028 | 0.019 | 0.005 | 4.22 | 1.35 | 0.140 | 0.029 |
| GEVO1846 | 0.227 | 0.021 | 0.045 | 0.005 | 10.88 | 1.01 | 0.274 | 0.003 |

The performance numbers in the period from 6 to 48 demonstrate that most of isobutanol production occurred under anaerobic conditions. Highest values for yield and specific productivity were reached by the strain featuring the complete pathway integration and the *E. coli* pntAB knock-in (GEVO1886) under anaerobic conditions. In addition this strain reached the highest values for volumetric productivity and titer under both conditions anaerobic and micro-aerobic (Table 14).

TABLE 14

Shown are the results for volumetric productivity, specific productivity titer and yield reached in the period from 6 to 48 h for the tested strains and plasmid systems

| | | Volumetric Productivity | | Specific Productivity | | Titer | | Yield | |
|---|---|---|---|---|---|---|---|---|---|
| Samples | Condition | [g/L/h] | ± | [g/L/h/OD] | ± | [g/L] | ± | [g/g] | ± |
| GEVO1886 | Micro-aerobic | 0.355 | 0.004 | 0.042 | 0.001 | 14.9 | 0.2 | 0.33 | 0.012 |
| GEVO1859 | Micro-aerobic | 0.266 | 0.010 | 0.040 | 0.004 | 11.2 | 0.4 | 0.33 | 0.016 |
| GEVO1846 | Micro-aerobic | 0.344 | 0.007 | 0.051 | 0.004 | 14.4 | 0.3 | 0.33 | 0.005 |
| GEVO1886 | Anaerobic | 0.355 | 0.008 | 0.056 | 0.001 | 14.9 | 0.1 | 0.35 | 0.004 |
| GEVO1859 | Anaerobic | 0.086 | 0.026 | 0.019 | 0.005 | 3.60 | 1.1 | 0.14 | 0.032 |
| GEVO1846 | Anaerobic | 0.209 | 0.019 | 0.041 | 0.004 | 8.79 | 0.8 | 0.27 | 0.006 |

The performance numbers in the period from 6 to 48 demonstrate that most of isobutanol production occurred under anaerobic conditions. Highest values for yield and specific productivity were reached by the strain featuring the complete pathway integration and the *E. coli* pntAB knock-in (GEVO1886) under anaerobic conditions.

Example 6

Anaerobic Batch Fermentation of GEVO1886 and GEVO1859

This example illustrates that an engineered microorganism which overexpresses a transhydrogenase, exemplified by the *E. coli* pntAB gene product (SEQ ID NO: 2 and SEQ ID NO: 4), from the chromosome produces isobutanol at a higher rate, titer and productivity compared to the a strain that does not overexpress a transhydrogenase. This is surprising because the increase in rate, titer, and productivity was achieved without modifying the isobutanol biosynthetic pathway itself.

Overnight cultures were started in 250 mL Erlenmeyer flasks with strain GEVO1886 and strain GEVO1859 cells from fresh streak plates with a 40 mL volume of M9 medium (Miller, J. H. A Short Course in Bacterial Genetics: A laboratory manual and handbook for *Escherichia coli* and related bacteria. 1992. Cold Spring Harbor Laboratory Press, Cold Spring Harbor, N.Y.) containing 85 g/L glucose, 20 g/L yeast extract, 20 μM ferric citrate, trace metals, an additional 1 g/L $NH_4Cl$, an additional 1 mM $MgSO_4$ and an additional 1 mM $CaCl_2$ and at a culture $OD_{600}$ of 0.02 to 0.05. The overnight cultures were grown for approximately 14 hours at 30° C. at 250 rpm.

Some of the overnight cultures were then transferred to 400 mL DasGip fermenter vessels containing about 200 mL of M9 medium (Miller, J. H. A Short Course in Bacterial Genetics: A laboratory manual and handbook for *Escherichia coli* and related bacteria. 1992. Cold Spring Harbor Laboratory Press, Cold Spring Harbor, N.Y.) containing 85 g/L glucose, 20 g/L yeast extract, 20 μM ferric citrate, trace metals, an additional 1 g/L $NH_4Cl$, an additional 1 mM $MgSO_4$ and an additional 1 mM $CaCl_2$ to achieve a starting cell concentration by optical density at 600 nm of 0.1. The vessels were attached to a computer control system to monitor and control pH at 6.5 through addition of base, temperature at 30° C., dissolved oxygen, and agitation. The vessels were agitated, with a minimum agitation of 200 rpm and agitation was varied to maintain a dissolved oxygen content of about 50% using a 12 sL/h air sparge until the $OD_{600}$ was about 1.0. The vessels were then induced with 1 mM IPTG.

After continuing growth for 3 hrs, the dissolved oxygen content was decreased to 0% with 200 rpm agitation and 2.5 sL/h sparge with nitrogen ($N_2$) gas. Measurement of the fermenter vessel off-gas for isobutanol and ethanol was performed throughout the experiment by passage of the off-gas stream through a mass spectrometer. Continuous measurement of off-gas concentrations of carbon dioxide and oxygen were also measured by a DasGip off-gas analyzer throughout the experiment. Samples were aseptically removed from the fermenter vessel throughout the experiment and used to measure $OD_{600}$, glucose concentration by HPLC, and isobutanol concentration in the broth by GC. Each strain was run in three independent fermentations.

Strain GEVO1886 reached an average isobutanol total titer of 21.6 g/L. The average yield of the fermentation, calculated when the titer of isobutanol was between 1 g/L and 15 g/L, was 88% of theoretical. The average productivity of the fermentation was 0.4 g/L/h. As described in Example 5, GEVO1886 performs at least equally well in terms of isobutanol productivity, titer, yield under anaerobic and aerobic conditions.

By comparison, strain GEVO1859 reached an average isobutanol total titer of 1.8 g/L. The average yield of the fermentation was 56% of theoretical, and the average productivity of the fermentation was 0.02 g/l/h.

Example 7

PntAB Overexpression Rescues a zwf-Deletion Phenotype

This example illustrates that a strain that has a growth defect and does not produce isobutanol because of the deletion in a native pathway that reduces the strains ability to produce the redox cofactor NADPH can surprisingly be rescued by overexpression of *E. coli* pntAB.

Overnight cultures of GEVO1399 transformed with plasmids pSA55, pGV1609 (SEQ ID NO: 108), and pGV1745 (SEQ ID NO: 117) and GEVO1399 transformed with plasmids pSA55, pGV1609, and pGV1720 (SEQ ID NO: 115) were started from glycerol stock cultures stored at −80° C. in 3 mL fermentation medium (M9 minimal medium according to Miller (Miller, J. H. A Short Course in Bacterial Genetics: A laboratory manual and handbook for *Escherichia coli* and related bacteria. 1992. Cold Spring Harbor Laboratory Press, Cold Spring Harbor, N.Y.), supplemented with 10 g/L yeast extract, 10 μM ferric citrate and trace metals) containing 8.5% glucose and the appropriate antibiotics in snap cap tubes about 14 h prior to the start of the fermentation.

Isobutanol fermentations were then carried out in fermentation medium containing 8.5% glucose and the appropriate antibiotics. Two 250 mL screw cap flasks with 20 mL fermentation medium containing 8.5% glucose and the appropriate antibiotics were inoculated with 1% of each grown overnight culture. The cells were incubated at 37° C./250 rpm until the strains were grown to an $OD_{600}$ of 0.6-0.8 and were then induced with Isopropyl β-D-1-thiogalactopyranoside at 1 mM final concentration. Three hours after induction one flask per overnight culture was shifted to anaerobic fermentation conditions. This was done by loosening the cap of the flasks and introducing the flasks into the anaerobic chamber. Once the flasks were flushed with oxygen free atmosphere (while going through the airlock), the flasks were closed again and incubated without shaking at 30° C. in the anaerobic chamber. The flasks in the anaerobic chamber were swirled twice a day. Samples were taken from the medium at the time of the shift and at 24 h and 48 h after inoculation, spun down at 22,000×g for 1 min to separate the cell pellet from the supernatant and stored frozen at −20° C. until analysis. The samples were analyzed using High performance liquid chromatography (HPLC) and gas chromatography (GC).

Figure 14:
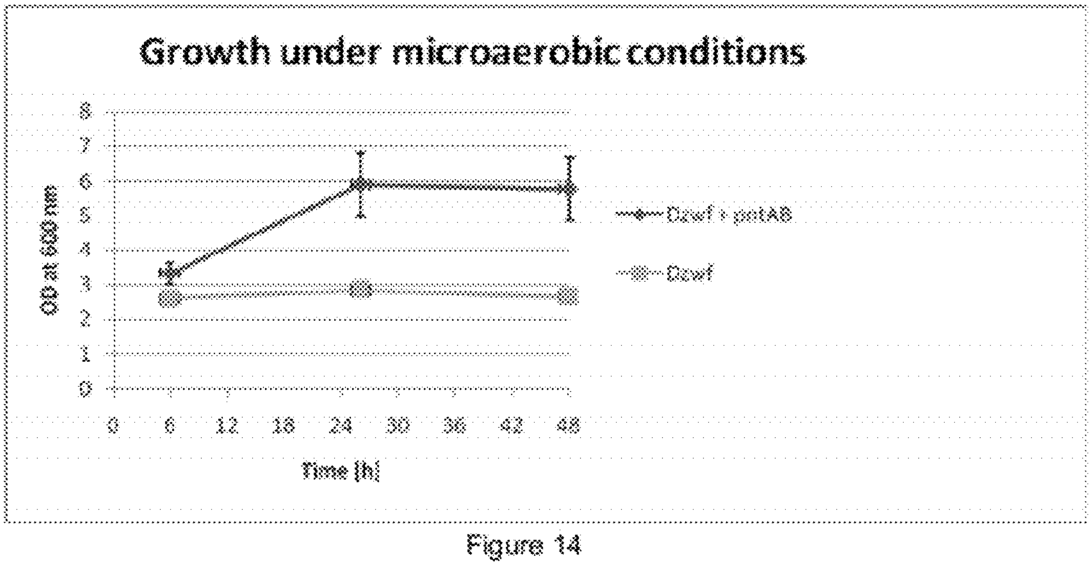
FIG. 14 illustrates that a strain lacking zwf without *E. coli* pntAB (Δzwf) grew to an OD of about 3, whereas the samples featuring *E. coli* pntAB (Δzwf+pntAB) reached OD values of about 5-6.

The strain lacking zwf without *E. coli* pntAB grew to an OD of about 3, whereas the samples featuring *E. coli* pntAB reached OD values of about 5-6. This OD was not significantly different from normal growth and thus the over-expression of *E. coli* pntAB rescues the zwf growth phenotype (FIG. 14).

Isobutanol production was rescued under micro-aerobic conditions by the overexpression of *E. coli* pntAB. Volumetric productivity and titer are improved 7.4 fold, specific productivity was improved 3.3 fold and yield 2.5 fold (Table 15).

TABLE 15

Volumetric productivity, specific productivity titer and yield in a micro-aerobic fermentation for the tested strains and plasmid systems

| Samples | Volumetric Productivity [g/L/h] | ± | Specific Productivity [g/L/h/OD] | ± | Titer [g/L] | ± | Yield [g/g] | ± |
|---|---|---|---|---|---|---|---|---|
| GEVO1399 + pGV1745 + pSA55 + pGV1609 | 0.170 | 0.001 | 0.030 | 0.003 | 8.18 | 0.02 | 0.248 | 0.012 |
| GEVO1399 + pGV1720 + pSA55 + pGV1609 | 0.023 | 0.004 | 0.009 | 0.002 | 1.10 | 0.18 | 0.100 | 0.013 |

For the anaerobic shift experiment the same trend was observed as under micro-aerobic conditions. Isobutanol production was rescued by the over-expression of *E. coli* pntAB. Volumetric productivity and titer are improved 3.4 fold, specific productivity was improved 2.1 fold and yield by 43% (Table 16).

TABLE 16

Volumetric productivity, specific productivity titer and yield in an anaerobic fermentation for the tested strains and plasmid systems

| Samples | Volumetric Productivity [g/L/h] | ± | Specific Productivity [g/L/h/OD] | ± | Titer [g/L] | ± | Yield [g/g] | ± |
|---|---|---|---|---|---|---|---|---|
| GEVO1399 + pGV1745 + pSA55 + pGV1609 | 0.125 | 0.038 | 0.035 | 0.003 | 6.00 | 1.84 | 0.297 | 0.008 |
| GEVO1399 + pGV1720 + pSA55 + pGV1609 | 0.037 | 0.001 | 0.017 | 0.001 | 1.78 | 0.04 | 0.207 | 0.005 |

Example 8 sthA does not Contribute to Improvement in Anaerobic Isobutanol Production

This example illustrates that an isobutanol production strain with a deletion of the soluble transhydrogenase sthA produces low amounts of isobutanol anaerobically. This shows that the introduction of the sthA deletion does not provide cofactor balance to the isobutanol production strain and does not enable anaerobic isobutanol production above the levels seen for strains without redox engineering. The deletion of sthA has no significant effect on anaerobic performance of a production strain that overexpresses *E. coli* pntAB.

GEVO1748 and GEVO1844 were transformed with plasmids pGV1698 (SEQ ID NO: 112) and one of either pGV1720 (SEQ ID NO: 115) (control) or pGV1745 (SEQ ID NO: 117) (*E. coli* pntAB).

Overnight cultures of the strains to be tested were started either using fresh transformants (for all combinations featuring strain GEVO1844) or using frozen stocks (all other samples). The cultures were started in 3 mL fermentation medium (M9 minimal medium according to Miller (Miller, J.H. A Short Course in Bacterial Genetics: A laboratory manual and handbook for *Escherichia coli* and related bacteria. 1992. Cold Spring Harbor Laboratory Press, Cold Spring Harbor, N.Y.), supplemented with 10 g/L yeast extract, 10 μM ferric citrate and trace metals) containing 8.5% glucose and the appropriate antibiotics in snap cap tubes about 14 h prior to the start of the fermentation.

Isobutanol fermentations were then carried out in fermentation medium containing 8.5% glucose and the appropriate antibiotics. Two 250 mL screw cap flasks with 20 mL fermentation medium containing 8.5% glucose and the appropriate antibiotics were inoculated with 1% of each grown overnight culture. The cells were incubated at 37° C./250 rpm until the strains were grown to an $OD_{600}$ of 0.6-0.8 and were then induced with Isopropyl β-D-1-thiogalactopyranoside at 1 mM final concentration. Three hours after induction the flasks were shifted to anaerobic fermentation conditions. This was done by loosening the cap of the flasks and introducing the flasks into the anaerobic chamber. Once the flasks were flushed with oxygen free atmosphere (while going through the airlock), the flasks were closed again and incubated without shaking at 30° C. in the anaerobic chamber. The flasks in the anaerobic chamber were swirled twice a day. Samples were taken of the medium at the time of the shift and at 24 h and 48 h after inoculation, spun down at 22,000×g for 1 min to separate the cell pellet from the supernatant and stored frozen at −20° C. until analysis. The samples were analyzed using High performance liquid chromatography (HPLC) and gas chromatography (GC).

Strain GEVO1844 showed similar isobutanol production compared to non redox cofactor engineered strain GEVO1748 (Table 17).

TABLE 17

Shown are the results for volumetric productivity, specific productivity titer and yield reached in an anaerobic fermentation for the tested strains and plasmid systems

| Samples | Volumetric Productivity [g/L/h] | ± | Specific Productivity [g/L/h/OD] | ± | Titer [g/L] | ± | Yield [g/g] | ± |
|---|---|---|---|---|---|---|---|---|
| GEVO1844 + pGV1720 + pGV1698 (i.e. ΔsthA without PntAB) | 0.039 | 0.004 | 0.036 | 0.006 | 1.89 | 0.20 | 0.236 | 0.025 |
| GEVO1748 + pGV1720 + pGV1698 (i.e. Control without PntAB) | 0.047 | | 0.022 | | 2.24 | | 0.279 | |

TABLE 17-continued

Shown are the results for volumetric productivity, specific productivity titer and yield reached in an anaerobic fermentation for the tested strains and plasmid systems

| | Volumetric Productivity | | Specific Productivity | | Titer | | Yield | |
|---|---|---|---|---|---|---|---|---|
| Samples | [g/L/h] | ± | [g/L/h/OD] | ± | [g/L] | ± | [g/g] | ± |
| GEVO1844 + pGV1745 + pGV1698 (i.e. ΔsthA with PntAB) | 0.127 | 0.004 | 0.033 | 0.002 | 6.11 | 0.19 | 0.310 | 0.007 |
| GEVO1748 + pGV1745 + pGV1698 (i.e. control with PntAB) | 0.111 | 0.002 | 0.041 | 0.012 | 5.32 | 0.10 | 0.304 | 0.004 |

The strains with the sthA deletion exhibited similar isobutanol production compared to the strains without the sthA deletion. This was independent on the presence or absence of overexpression of *E. coli* pntAB. It can thus be concluded that the sthA deletion has no significant effect on isobutanol production.

Example 9 pntAB in Yeast

This example illustrates an isobutanol producing yeast which is engineered to express a transhydrogenase.

Yeast strain, GEVO5001, which is deficient in pyruvate decarboxylase activity and expresses the isobutanol biosynthetic pathway is further engineered to express a transhydrogenase. The *E. coli* pntA (SEQ ID NO: 1) and pntB (SEQ ID NO: 3) genes are expressed in yeast with the modifications of (1) N-terminal addition of amino acids to target the proteins to the plasma membrane (export signal sequence (ess)) and (2) N-terminal modifications to target the proteins to the mitochondrial outer membrane (mitochondrial targeting sequence (mts)). pGV6002 is a yeast integration plasmid that carries versions of pntA and pntB with modifications to target them to the plasma membrane. pGV6003 is a yeast integration plasmid that carries versions of pntA and pntB with modifications to target them to the mitochondrial outer membrane. In both cases, the pntA and pntB genes are under the control of the strong constitutive promoters from TEF1 and TDH3, respectively. pGV6002 and pGV6003 are linearized and transformed into GEVO5001 to generate GEVO5004 and GEVO5005, respectively. Expression of pntA and pntB is confirmed by qRT-PCR and once confirmed; GEVO5004 and GEVO5005 are used in fermentations for the production of isobutanol.

Example 10

Native *E. Coli* Alcohol Dehydrogenase Activity Converts Isobutyraldehyde To Isobutanol This example illustrates that native *E. coli* alcohol dehydrogenase activity converts isobutyraldehyde to isobutanol.

Strain JCL260 transformed with pGV1631 and pSA69 (strain without *S. cerevisiae* ADH2) and JCL260 transformed with pSA55 and pSA69 (strain with *S. cerevisiae* ADH2) were plated onto LB-plates containing the appropriate antibiotics and incubated overnight at 37° C. Plates were taken out of the incubator and kept at room temperature until further use. Overnight cultures were started in 3 mL EZ-Rich medium containing 7.2% glucose and the appropriate antibiotics in snap cap tubes about 14 hours prior to the start of the fermentation. Isobutanol fermentations were then carried out in EZ-Rich defined medium containing 7.2% glucose and the appropriate antibiotics. Screw cap flasks with 20 mL EZ-Rich medium containing 7.2% glucose and the appropriate antibiotics were inoculated with 1% of the grown overnight culture. The cells were incubated at 37° C./250 rpm until they were grown to an $OD_{600}$ of 0.6-0.8 and induced with Isopropyl 13-D-1-thiogalactopyranoside (IPTG, 1 mM).

After induction the cells were incubated at 30° C./250 rpm. Samples were taken from the medium before induction, and 24 and 48 hours after inoculation, spun down at 22,000×g for 1 min to separate the cell pellet from the supernatant and stored frozen at −20° C. until analysis.

The ADH2 gene product is expected to be functionally expressed from pSA55 and required for isobutanol production. Thus, no isobutanol should be produced with the plasmid combination lacking ADH2 as adhE is deleted in JCL260. However, isobutanol production for the system lacking ADH2 was higher than for the system with ADH2 expression. Table 18 shows the results for the isobutanol fermentation comparing the pathway including Adh2 expression with the exact same system excluding Adh2 expression. Both systems feature Bs_AlsS1, Ec_IlvC and Ec_ilvD expressed from the same medium copy plasmid and Ll_Kivd1 expressed from a high copy plasmid. Volumetric productivity and titer showed 42% increase, specific productivity 18% and yield 12% increase. This suggests strongly that a native *E. coli* dehydrogenase is responsible for the conversion of isobutyraldehyde to isobutanol. and that Adh2 is not expressed and not necessary for isobutanol production in *E. coli*.

TABLE 18

Isobutanol fermentation with and without Adh2 expression

| | Volumetric Productivity | | Specific Productivity | | Titer | | Yield | |
|---|---|---|---|---|---|---|---|---|
| samples | [g/L/h] | ± | [g/L/h/OD] | ± | [g/L] | ± | [g/g] | ± |
| without Adh2 | 0.175 | 0.006 | 0.039 | 0.003 | 8.40 | 0.26 | 0.207 | 0.009 |
| with Adh2 | 0.123 | 0.004 | 0.033 | 0.001 | 5.88 | 0.17 | 0.185 | 0.004 |

Example 11

Identification of Native ADH

This example illustrates that the native *E. coli* alcohol dehydrogenase is encoded by the Ec_yqhD gene (SEQ ID NO: 68).

Several *E. coli* genes predicted or known to code for alcohol dehydrogenases were knocked out of strain JCL260 to determine whether any of them are involved in isobutyraldehyde reduction. Fermentations were carried out with GEVO1608 and with JCL260, each transformed with plasmids pGV1609 (SEQ ID NO: 108) and pGV1631 by electroporation. Single colonies were grown and two colonies from each strain were started in a 3 mL overnight culture, with appropriate antibiotics. Each 250 mL fermentation flask was filled with 20 mL of EZ-Rich medium (Neidhardt, F. C., P. L. Bloch, and D. F. Smith. 1974. Culture medium for enterobacteria. *J Bacteriol.* 119:736-47) supplemented with 5% glucose, Ampicillin (100 mg/mL), and Chloramphenical (100 mg/mL).

The cell densities of the overnight cultures were normalized and 2% inoculum was added to each fermentation flask and incubated at 270 rpm/37° C. The cultures were induced with 20 μL 0.1 M IPTG after they reached an $OD_{600}$ of 0.6-0.8 at which time the temperature was lowered to 30° C. Samples were taken from the medium before induction, and 24 hours after inoculation, spun down at 22,000×g for 1 min to separate the cell pellet from the supernatant and stored frozen at −20° C. until analysis. A second fermentation was performed in the same way with the best candidate, GEVO1608 containing the yqhD deletion, and samples were taken at 24 and 48 hours.

While both GEVO1608 and JCL260 grew to similar cell densities, GEVO1608 produced ~80% less isobutanol than the control strain (Table 19), indicating that the Ec_yqhD gene product is primarily responsible for isobutyraldehyde reduction.

TABLE 19

Specific Productivity and Titer of Fermentation

| Strain | Plasmids | Time | Titer (g/L) |
|---|---|---|---|
| GEVO1608 | pGV1609, pGV1631 | 24 h | 0.33 |
| JCL260 | pGV1609, pGV1631 | 24 h | 2.45 |
| GEVO1608 | pGV1609, pGV1631 | 48 h | 0.83 |
| JCL260 | pGV1609, pGV1631 | 48 h | 4.00 |

Example 12

Overexpression of NADH-Dependent Alcohol Dehydrogenase and Propanediol Dehydrogenases This example demonstrates that overexpression of an NADH-dependent alcohol dehydrogenase or propanediol dehydrogenases increases isobutanol production.

Relevant *E. coli* strains were transformed with the appropriate plasmids (Table 20).

TABLE 20

Plasmid and strain combinations used in isobutanol fermentations

| # | Plasmid 1 | Plasmid 2 | Strain | Comments |
|---|---|---|---|---|
| 1 | pGV1655 | pGV1698 | GEVO1745 | No ADH on plasmid |
| 2 | pGV1655 | pGV1698 | JCL260 | GEVO1780 |
| 3 | pGV1655 | pGV1748 | GEVO1745 | Ec_fucO |

TABLE 20-continued

Plasmid and strain combinations used in isobutanol fermentations

| # | Plasmid 1 | Plasmid 2 | Strain | Comments |
|---|---|---|---|---|
| 4 | pGV1655 | pGV1749 | GEVO1745 | Dm_ADH |
| 5 | pGV1655 | pGV1778 | GEVO1745 | Kp_dhaT |

Following transformation, the strains were plated on LB-plates containing the appropriate antibiotics and incubated overnight at 37° C. Overnight cultures were started in 3 mL EZ-Rich medium (Neidhardt, F. C., P. L. Bloch, and D. F. Smith. 1974. Culture medium for Enterobacteria. J Bacteriol. 119:736-47) containing 8% glucose and the appropriate antibiotics in snap cap tubes about 14 h prior to the start of the fermentation. Isobutanol fermentations were then carried out in EZ-Rich Medium containing 8% glucose and the appropriate antibiotics. Screw cap flasks with 25 mL EZ-Rich medium containing 8% glucose and the appropriate antibiotics were inoculated with a sufficient volume of the grown overnight culture to obtain a starting $OD_{600}$ of 0.1. The cells were incubated at 37° C./250 rpm until they reached an $OD_{600}$ of 0.6-0.8 followed by induction with Isopropyl β-D-1-thiogalactopyranoside (IPTG, 1 mM). After induction, cultures were capped, sealed and placed in 30° C. shaker, 225 rpm to start fermentation. Samples (2 mL) were taken 24 h and 48 h post induction, centrifuged at 22,000×g for 1 min and the supernatant stored at 4° C. until analyzed. Prior to analysis, the supernatants were filtered and then analyzed via Gas Chromatography and High Performance Liquid Chromatography. All experiments were carried out in triplicate.

Results are presented in Table 21, below. Expression of either 1,2-propanediol dehydrogenase Ec_fucO or 1,3-propanediol dehydrogenase Kp_dhaT significantly and reproducibly increases titer in the ΔyqhD background of strain GEVO1745. Expression of Dm_ADH enhances titer and yield of the fermentations in the ΔyqhD background of strain GEVO1745.

TABLE 21

Summary of isobutanol titer, and yield data from fermentations after 48 hours

| # | Comments | titer [g/L] | ± | Yield [% theor.] | ± |
|---|---|---|---|---|---|
| 1 | no ADH | 1.91 | 0.50 | 38.5 | 10.30 |
| 2 | GEVO1780 | 3.39 | 0.15 | 65.0 | 2.83 |
| 3 | Ec_FucO | 6.30 | 0.10 | 79.9 | 1.79 |
| 4 | Dm_Adh | 4.86 | 0.29 | 67.0 | 4.54 |
| 5 | Kp_DhaT | 6.22 | 0.16 | 75.3 | 2.04 |

Example 13

Characterization of Alcohol Dehydrogenases

This example demonstrates that the alcohol dehydrogenases Ec_FucO (SEQ ID NO: 65), Kp_DhaT (SEQ ID NO: 63), and Dm_Adh (SEQ ID NO: 61) catalyze the NADH-dependent reduction of isobutyraldehyde.

*E. coli* strain GEVO1745 was transformed by electroporation with one of plasmids pGV1705-A, pGV1748-A, pGV1749-A, or pGV1778-A. 50 mL of TB medium (23.1 g/L KH2PO4, 125.4 g/L K2HPO4, 12 g/L Bacto-tryptone, 24 g/L yeast extract, 4 ml/L glycerol) were inoculated to an initial $OD_{600}$ of 0.2 using a 3 mL overnight LB culture of a single colony. The 50 mL culture was allowed to grow for 3-4 hrs at 250 rpm and 37° C. Protein expression was induced at an $OD_{600}$ of 2-2.5 by the addition of IPTG to a final concentration of 1 mM. After the addition of IPTG, protein expression was allowed to continue for 20-24 hours at 225 rpm and 25° C.

Alcohol dehydrogenase (ADH) activity was assayed kinetically by monitoring the decrease in NAD(P)H concentration by measuring the absorbance at 340 nm. A reaction buffer was prepared containing 0.1 M potassium phosphate, 0.4 mM NAD(P)H, 10 mM isobutyraldehyde, 1 mM DTT, and 1 mM PMSF. Cell pellets were resuspended in 0.1 M potassium phosphate buffer containing 1 mM DTT and 1 mM PMSF at one fifth of the culture volume, i.e. 10 mL resuspension buffer for cell pellet from a 50 mL culture. The resuspended cells were lysed by sonication for 1 min with a 50% duty cycle. The reaction was initiated by the addition of 0.5 mL of the reaction buffer to 0.5 mL of clarified lysate in a cuvette. Dilution of the clarified lysate was necessary for ADHs that were highly active. A substrate free control was conducted using reaction buffer without the addition of aldehyde.

Kinetic parameters were determined for Ec_YghD, Ec_FucO, Dm_Adh, and Kp_DhaT (Table 22).

TABLE 22

Kinetic parameters for the conversion of isobutyraldehyde to isobutanol by Ec_YqhD, Ec_FucO, Dm_Adh, and Kp_DhaT

| | | NADH | | NADPH | |
|---|---|---|---|---|---|
| Plasmid | ADH | $K_M$ (mM) | Activity (U/ $min^{-1}$ $mg^{-1}$ crude lysate) | $K_M$ (mM) | Activity (U/ $min^{-1}$ $mg^{-1}$ crude lysate) |
| pGV1705-A | Ec_YqhD | n.d. | n.d. | 0.25 | 0.09 |
| pGV1748-A | Ec_FucO | 0.8 | 0.23 | 0.2 | 0.04 |
| pGV1749-A | Dm_Adh | 0.9 | 6.60 | 2.7 | 1.70 |
| pGV1778-A | Kp_DhaT | 1.3 | 0.56 | 0.6 | 0.08 |

The kinetic properties of the Ll_AdhA enzyme were described by Atsumi et al. (Atsumi et al., Appl. Microbiol. Biotechnol., 2009, DOI 10.1007/s00253-009-2085-6), and are shown in Table 23.

TABLE 23

Kinetic parameters for LI_AdhA (Atsumi et al., Appl. Microbiol. Biotechnol., 2009, DOI 10.1007/s00253-009-2085-6)

| | | NADH | | | NADPH | | |
|---|---|---|---|---|---|---|---|
| ADH | Substrate | $K_M$ (mM) | $k_{cat}$ ($s^{-1}$) | Kcat/ $K_M$ | $K_M$ (mM) | $k_{cat}$ ($s^{-1}$) | Kcat/ $K_M$ |
| LI_AdhA | Acetaldehyde | 0.5 | 10 | 20.9 | | n.d.[a] | |
| LI_AdhA | isobutyraldehyde | 9.1 | 6.6 | 0.8 | | | |

[a]did not show any detectably activity when tested with NADPH as a cofactor

Example 14

KARI Engineering by Saturation Mutagenesis

Construction of KARI-containing plasmids: Standard molecular biology procedures (Sambrook and Russell, Molecular Cloning, A Laboratory Manual, 3rd Edition, Vol. 3, 2001) were utilized to make plasmid pGV1711 (SEQ ID NO: 113) (pLlacO1::(no ORF) bla, ColE1 ORI). Plasmid pGV1711 is a high-copy, AmpR vector that serves as an "empty vector" control, i.e. it contains no open reading frames under the control of the PLlac promoter. The *E. coli* KARI gene Ec_ilvC (SEQ ID NO: 10) was codon optimized for *E. coli* resulting in gene Ec_ilvC_coEc (SEQ ID NO: 11)

The codon optimized gene Ec_ilvC_coEc was cloned into pET22b(+) using primers KARIpETfor and KARIpETrev introducing a 5' NdeI and a 3' XhoI restriction site and a C-terminal $his_6$-tag, resulting in plasmid pET22b[ilvCco] carrying Ec_ilvC_coEc$^{his6}$(SEQ ID NO: 14).

DNA constructs were analyzed by restriction digests, and also by DNA sequencing to confirm integrity and correct construction. Primers pETup and KARIpETrev were used as primers in standard DNA sequencing reactions to sequence pET22b(+) derivatives.

Construction of NNK libraries: NNK libraries were constructed using site directed mutagenesis overlap extension (SOE) PCR. First, the fragments containing the mutations were created allowing for at least 15 by of overlap using KARIpET_for and KARIpET_rev and the respective NNK primers listed in Table 6 (SEQ ID NO 285 through SEQ ID NO 298). After digesting traces of template DNA with Dpnl, the fragments were separated on a 1% TAE agarose gel, extracted, and the PCR products were precipitated using pellet paint (Novagen). The clean products were used as templates in a subsequent assembly PCR. The PCR product was cleaned up (Zymo Research, Orange, Calif.), restriction digested with NdeI and XhoI for 1.5 h at 37° C., cleaned on a 1% agarose gel, and ligated into pET22b(+).

Site directed mutagenesis mutants were generated as described above. The successful mutagenesis was confirmed by DNA sequencing.

Cell growth and protein expression in shake flasks: Flasks containing 25 mL of Luria-Bertani (LB) medium (10 g tryptone, 10 g NaCl, 5 g yeast extract) with ampicillin (final concentration 0.1 mg/mL) were inoculated to an initial $OD_{600}$ of 0.1 using 0.25 mL overnight LB culture of a single colony. The 25 mL LB expression culture was allowed to grow for 3-4 h at 250 rpm and 37° C. Protein expression was induced at $OD_{600}$ of 1 by the addition of IPTG to a final concentration of 0.5 mM. Protein expression was allowed to continue for 20-24 h at 225 rpm and 25° C. Cells were harvested at 5300×g and 4° C. for 10 min and the cell pellets were frozen at −20° C. until further use.

Cell growth and protein expression in microplates: In order to grow and express KARI variants in deep well plates, sterile toothpicks were used to pick single colonies into shallow 96 well plates filled with 300 µl $LB_{amp}$. 75 µl of these overnight cultures were used to inoculate deep well plates filled with 600 µl of $LB_{amp}$ per well. The plates were grown at 37° C. and 210 rpm for 4 h. One hour before induction with IPTG (final concentration 0.5 mM), the temperature of the incubator was reduced to 25° C. After induction, growth and expression continued for 20 h at 25° C. and 210 rpm. Cells were harvested at 5300×g and 4° C. and stored at −20° C.

KARI cuvette assay: KARI activity was assayed kinetically by monitoring the decrease in NAD(P)H concentration by measuring the absorbance at 340 nm. A reaction buffer was prepared containing 250 mM potassium phosphate pH 7, 1 mM DTT and 10 mM $MgCl_2$. Cell pellets were resuspended (0.25 g wet weight/mL buffer) in 250 mM potassium phosphate (KPi) buffer containing 1 mM DTT and 10 mM $MgCl_2$. The resuspended cells were lysed by sonication for 1 min with a 50% duty cycle and pelleted at 11000×g and 4° C. for 15 min. A reaction mixture consisting of 910 µl reaction buffer, 50 µl acetolactate, and 20 µl lysate was prepared in a cuvette. The reaction was initiated by addition of 20 µL of 10 mM NAD(P)H. A substrate free control was conducted using reaction buffer without the addition of acetolactate.

KARI high-throughput assay: Frozen cell pellets were thawed at room temperature for 20 min and then 100 μL of lysis buffer (250 mM Kpi, 750 mg/L lysozyme, 10 mg/L DNasel, pH 7) were added. Plates were vortexed to resuspend the cell pellets. After a 30 min incubation at 37° C., plates were centrifuged at 5300×g and 4° C. for 10 min. 20 μL of the resulting crude extract were transferred into assay plates (flat bottom, Rainin) using a liquid handling robot. 10 mL assay buffer per plate were prepared (250 mM Kpi, pH 7, 500 μL acetolactate, 1 mM DTT, 10 mM NAD(P)H, and 10 mM $MgCl_2$) and 90 μL thereof were added to each well to start the reaction. The depletion of NAD(P)H was monitored at 340 nm in a plate reader (TECAN) over 1.5 min.

Purification of KARI: Cell pellets used for purification were resuspended in purification buffer A (20 mM Tris, 20 mM imidazol, 100 mM NaCl, 10 mM $MgCl_2$, pH 7.4). KARI was purified by IMAC (Immobilized metal affinity chromatography) over a 1 ml Histrap High Performance (histrap HP) column pre-charged with Nickel (GE Healthcare) using an Akta FPLC system (GE Healthcare). The column was equilibrated with four column volumes (cv) of buffer A. After injecting the crude extract, the column was washed with buffer A for 2 cv, followed by a wash step with a mixture of 10% elution buffer B (20 mM Tris, 300 mM imidazol, 100 mM NaCl, 10 mM $MgCl_2$, pH 7.4) for 5 cv. KARI variants were eluted at 40% buffer B and stored at 4° C.

Homology modeling was performed with pymol and x-ray structures of *E. coli* KARI (PDB ID: 1YRL) and spinach KARI (PDB ID: 1YVE), the latter containing NADPH co-crystallized.

Figure 15:
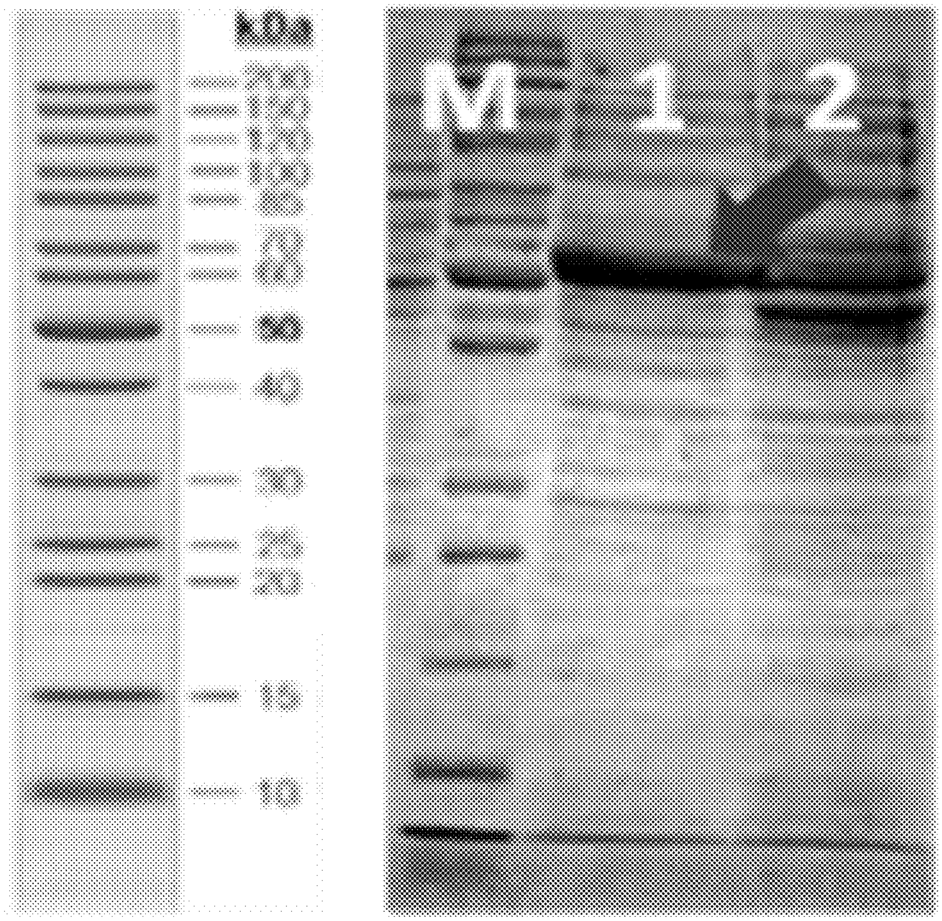
FIG. 15 illustrates an SDS PAGE of crude extracts of *E. coli* BL21(DE3) and GEVO1777 containing overexpressed KARI from plasmids pGV1777 and pET22-[ilvC_co], respectively. The arrow highlights the KARI band. The protein marker (M) was an unstained 200 kDa ladder from Fermentas.

A KARI expression construct (pGV1777 (SEQ ID NO: 118)) (pLlacO1::Ec_ilvC_coEc::bla, ColE1 ORI) was tested in *E. coli* strain GEVO1777 and yielded KARI activity in lysates. On this plasmid, the ilvC gene was not his-tagged and therefore no purification was attempted. In order to obtain higher expression levels for a high-throughput screen (HTS) in 96-well plate format, ilvC_co was sub-cloned into pET22b (+). This plasmid also ads a his-tag to the C-terminus of the protein to facilitate purification. *E. coli* BL21 (DE3) (Lucigen, Middleton, Wis.) cells were transformed with pET22-[ilvCco] and protein expression was performed in LB medium with ampicillin at 25° C. SDS PAGE analysis (FIG. 15) shows a comparison of crude extracts of BL21 (DE3) and GEVO1777 expressing KAR1.

Table 24 shows the specific activities in U/mg of KARI in lysates of GEVO1777 and BL21(DE3) being 15-fold higher in BL21 crude extract, mirroring the results shown in the SDS PAGE.

TABLE 24

Specific Activities of KARI in U/mg Expressed in GEVO1777 and BL21 (DE) measured with NADPH

| Strain/Construct | U/mg Crude Extract |
|---|---|
| pGV1777 in GEVO1777 | 0.03 |
| pET22b[ilvCco]in BL21 (DE3) | 0.45 |

Figure 16:
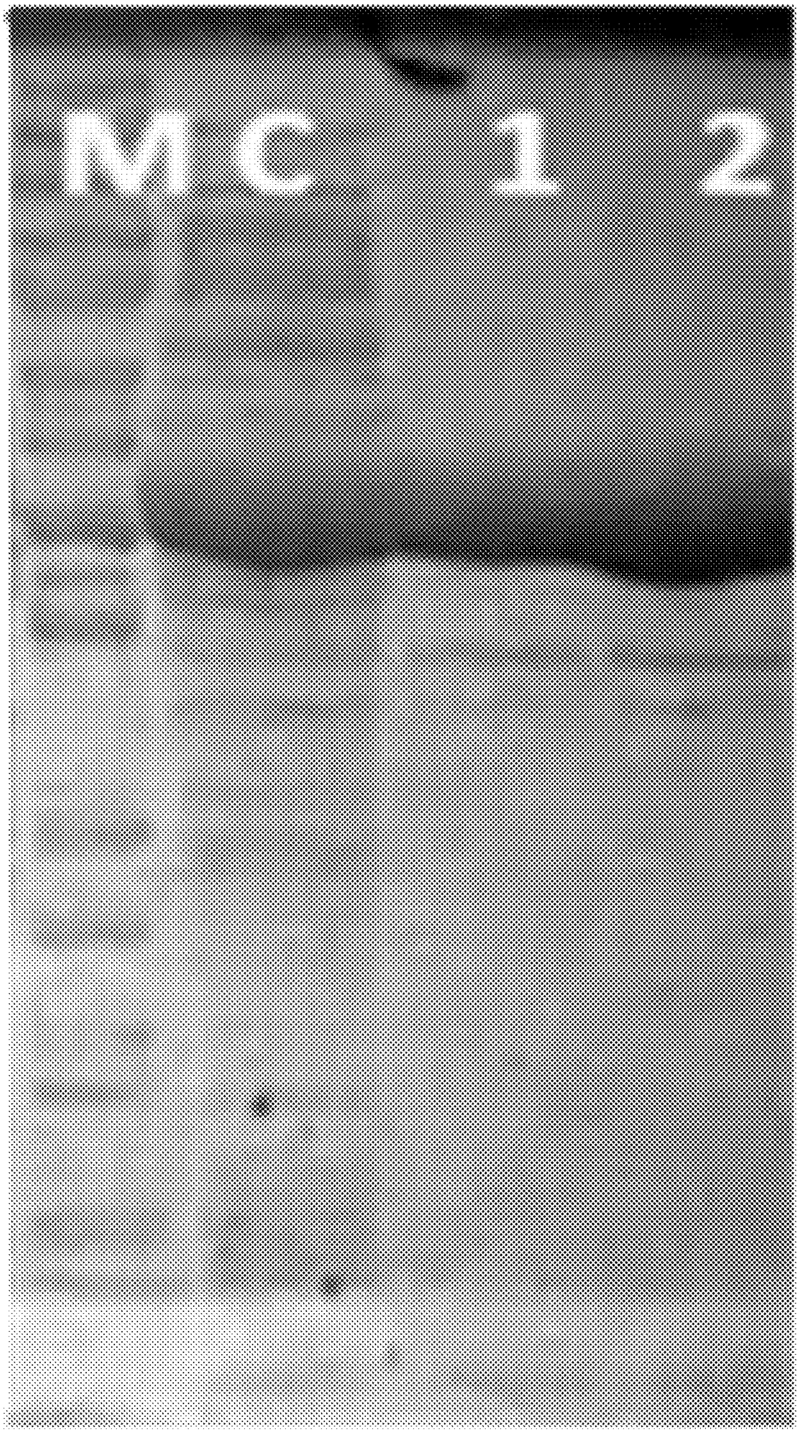
FIG. 16 illustrates an SDS PAGE of crude extract (C), purified KARI over a linear gradient (1), purified KARI over a step gradient (2), and PageRuler™ unstained protein ladder (M, Fermentas). KARI was enriched to high purity with just one purification step.

Purification of his-tagged KARI expressed from pET22 [ilvCco] in BL21(DE3) cells was first performed over a linear gradient to determine the proper amount of imidazol to elute KARI. Then, a step gradient was implemented and the protein was eluted at 40% elution buffer B (140 mM imidazol). A SDS PAGE documented the purity of the enriched protein (FIG. 16).

A quadruplet *E. coli* llvC mutant (R68D:K69L:K75V: R76D), which was described previously by Rane and coworkers (Rane et al., 1997, Arch Biochem Biophys 338: 83-89) was constructed using the respective primers listed in Table 6 (SEQ ID NO: 281 through SEQ ID NO 284) and cloned into pET22b(+) as described, but did not yield the cofactor switch that was described in the paper, although the ratio NADH/NADPH was 2.5 (wild-type 0.08). In fact, the specific activity of the quadruplet mutant on NADH was even worse than wild-type (Table 25), suggesting this mutant enzyme is not suited for the aforementioned aims.

TABLE 25

Comparison of specific activities from purified Ec_IlvC$^{his6}$ and purified IlvC$^{quadruplet\text{-}his6}$ quadruplet in U/mg measured on NAD(P)H

| Variant | U/mg with NADH | U/mg with NADPH | NADH/NADPH |
|---|---|---|---|
| Ec_IlvC$^{his6}$ | 0.03 | 1 | 0.08 |
| IlvC$^{quadruplet\text{-}his6}$ | 0.45 | 0.02 | 2.5 |

Figure 17:
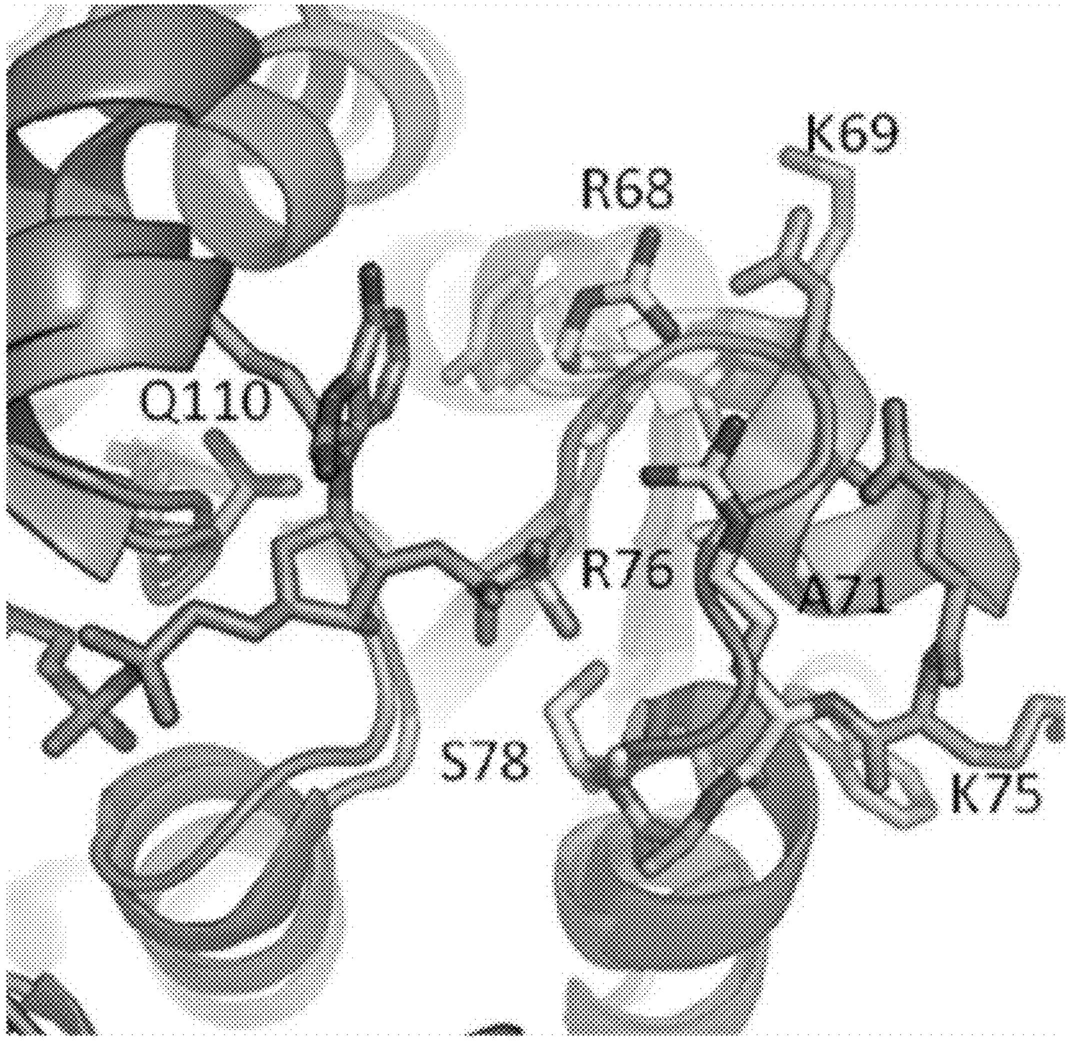
FIG. 17 illustrates the structure alignment of *E. coli* KARI with spinach KARI.

Since the quadruplet KARI mutant did not yield the promised activity, the Ec_ilvC_coEc$^{his6}$ gene (SEQ ID NO: 14) was used as starting point for engineering a cofactor switch. A structure alignment of *E. coli* KARI with spinach KARI was generated (FIG. 17) because spinach KARI was co-crystallized with NADPH. The position of the cofactor in the spinach KARI structure was in good agreement with the NADPH phosphate group in the *E. coli* KARI structure. Based on this, amino acid residues R68, A71, R76, S78, and Q110 seemed likely to be interacting with NADPH and therefore were chosen as targets in a site saturation mutagenesis experiment. Only residues R68 and R76 were found in the aforementioned quadruplet mutant. Residues K69 and K75 seemed less likely to be involved in cofactor binding.

Five individual site saturation libraries were generated and electro-competent *E. coli* BL21(DE3) cells were transformed with the desalted ligation mixtures. 88 clones of each library were screened for NAD(P)H depletion at 340 nm in microplates. Clones with an improved NADH/NADPH consumption ratio while maintaining or increasing their NADH activity were chosen for a rescreen. Variants that passed the rescreen were sequenced, expressed in shake flasks, purified, and characterized.

The first screening round resulted in several improved variants in terms of their specific activity on NADH (and NADPH for most of them) (Table 26). The first variant to favor NADH over NADPH was Ec_llvC$^{S78D\text{-}his6}$ which showed a specific activity for NADH that equals the specific activity of Ec_llvC$^{his6}$ for NAPDH (1 U/mg). Table 26 shows the variants resulting from the first round of site saturation mutagenesis compared to the parent Ec_llvC$^{his6}$. All proteins were purified over a histrap column.

TABLE 26

Specific Activities for NADH and NADPH in U/mg

| Variant | U/mg NADH | U/mg NADPH | NADH/NADPH |
|---|---|---|---|
| No mutation (Ec_IlvC$^{his6}$) | 0.08 | 1 | 0.08 |
| Ec_IlvC$^{R68L\text{-}his6}$ | 0.27 | 1.15 | 0.23 |
| Ec_IlvC$^{A71T\text{-}his6}$ | 0.48 | 1.81 | 0.27 |
| Ec_IlvC$^{A71S\text{-}his6}$ | 0.57 | 2.65 | 0.22 |
| Ec_IlvC$^{R76G\text{-}his6}$ | 0.64 | 2.73 | 0.23 |
| Ec_IlvC$^{R76S\text{-}his6}$ | 0.59 | 1.51 | 0.39 |
| Ec_IlvC$^{R76T\text{-}his6}$ | 0.25 | 1 | 0.25 |
| Ec_IlvC$^{R76D\text{-}his6}$ | 0.26 | 0.69 | 0.38 |
| Ec_IlvC$^{S78D\text{-}his6}$ | 1 | 0.61 | 1.64 |
| Ec_IlvC$^{Q110A\text{-}his6}$ | 0.85 | 2 | 0.43 |
| Ec_IlvC$^{Q110V\text{-}his6}$ | 0.93 | 2 | 0.47 |

The three best variants Ec_llvC$^{S78D\text{-}his6}$, Ec_llvC$^{Q110A\text{-}his6}$, and Ec_llvC$^{Q110V\text{-}his6}$ were characterized according to their specific activities [U/mg], $k_{cat}$ values [$s^{-1}$], catalytic efficiencies [$M^{-1}*s^{-1}$] (FIG. 18), and $K_M$ values (Table 27).

TABLE 27

$K_M$ values of Ec_IlvC$^{his6}$ compared to three variants resulting from the site saturation library

| Variant | $K_M$ [mM] NADPH | $K_M$ [mM] NADH |
|---|---|---|
| Ec_IlvC$^{his6}$ | 41 | 1075 |
| Ec_IlvC$^{S78D\text{-}his6}$ | 658 | 130 |
| Ec_IlvC$^{Q110V\text{-}his6}$ | 13 | 135 |
| Ec_IlvC$^{Q110A\text{-}his6}$ | 24 | 277 |

Figure 18:
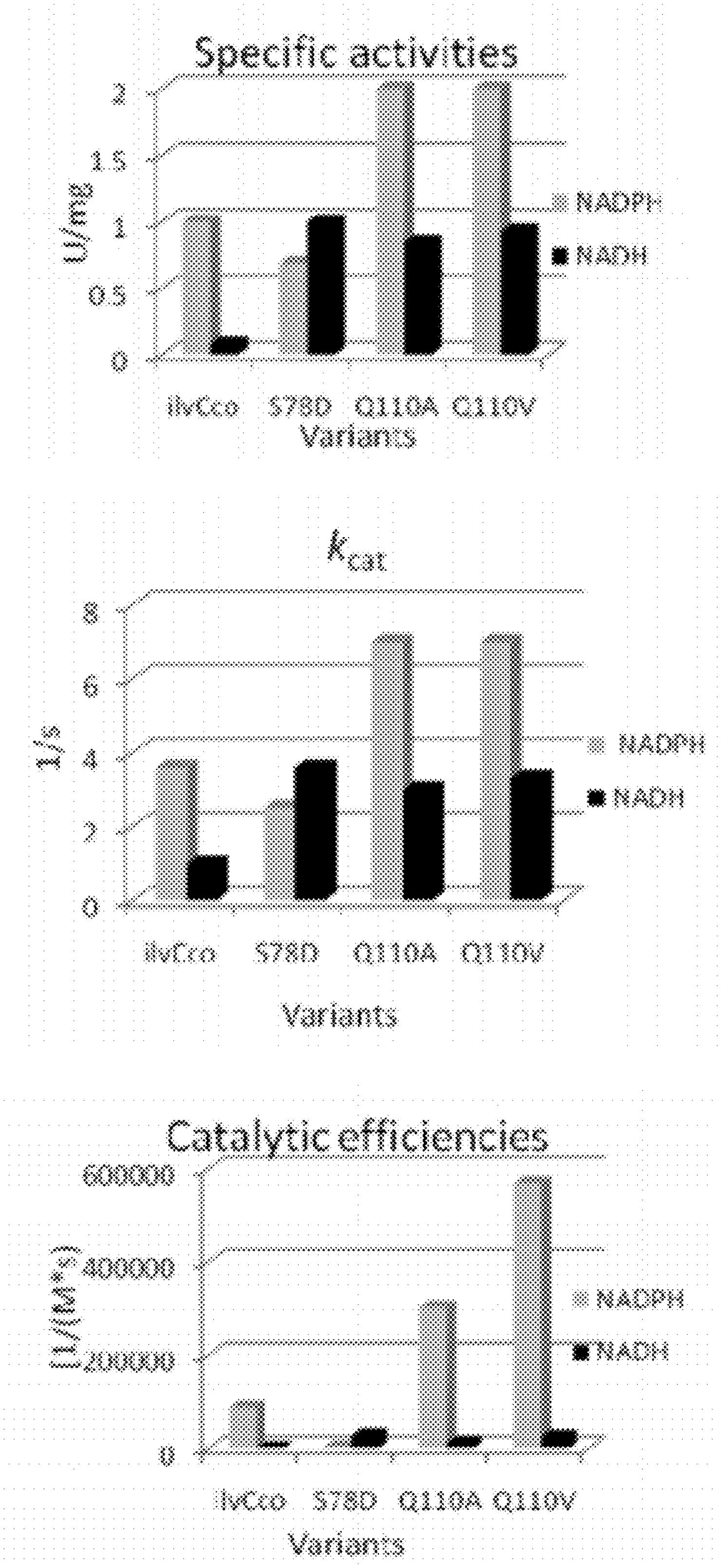
FIG. 18 illustrates the characterization of *E. coli* llvC and three variants resulting from the site saturation libraries: from top to bottom: Specific activities in U/mg, $k_{cat}$ in 1/s, and catalytic efficiencies in $M^{-1}*s^{-1}$. All proteins were purified over a nickel sepharose histrap column.

All three variants were improved compared to the parent Ec_llvC$^{his6}$. Ec_llvC$^{S78D\text{-}his6}$ was the first variant to show an actual preference of NADH over NADPH, while variants Ec_llvC$^{Q110A\text{-}his6}$ and Ec_llvC$^{Q110V\text{-}his6}$ showed drastic improvements in their overall catalytic efficiencies (FIG. 18). Table 28 contains a comparison of the $K_M$ values of Ec_llvC$^{his6}$ with the three best variants resulting from the site saturation mutagenesis library on both cofactors. All variants showed improved $K_M$ values on NADH. While Ec_llvC$^{Q110V\text{-}his6}$ and Ec_llvC$^{Q110A\text{-}his6}$ had improved $K_M$ values on NADPH compared to wild-type, the $K_M$ value of variant Ec_llvC$^{S78D\text{-}his6}$ on NADPH was decreased 16-fold from 1075 μM to 130 μM. The catalytic efficiencies on NADH were greatly improved as well. Ec_llvC$^{his6}$ showed 1,000 $M^{-1}*^{s-1}$ while Ec_llvC$^{S78D\text{-}his6}$ yielded 27,600 $M^{-1}*^{s-1}$.

TABLE 28

Catalytic efficiencies [$M^{-1}$ * $s^{-1}$] for Ec_IlvC$^{his6}$ and variants Ec_IlvC$^{Q110V\text{-}his6}$, Ec_IlvC$^{Q110A\text{-}his6}$ and Ec_IlvC$^{S78Dhis6}$ on NADPH

| Variant | $k_{cat}/K_M$ with NADH [$M^{-1}$ * $s^{-1}$] | $k_{cat}/K_M$ with NADH [$M^{-1}$ * $s^{-1}$] | ($k_{cat}/K_M$ with NADH)/($k_{cat}/K_M$ Of Ec_IlvC$^{his6}$ with NADPH) [%] |
|---|---|---|---|
| Ec_IlvC$^{his6}$ | 1000 | 87300 | 1% |
| Ec_IlvC$^{Q110V\text{-}his6}$ | 24800 | 569000 | 28% |
| Ec_IlvC$^{Q110A\text{-}his6}$ | 11063 | 301800 | 13% |
| Ec_IlvC$^{S78D\text{-}his6}$ | 27600 | 3770 | 32% |

Figure 19:
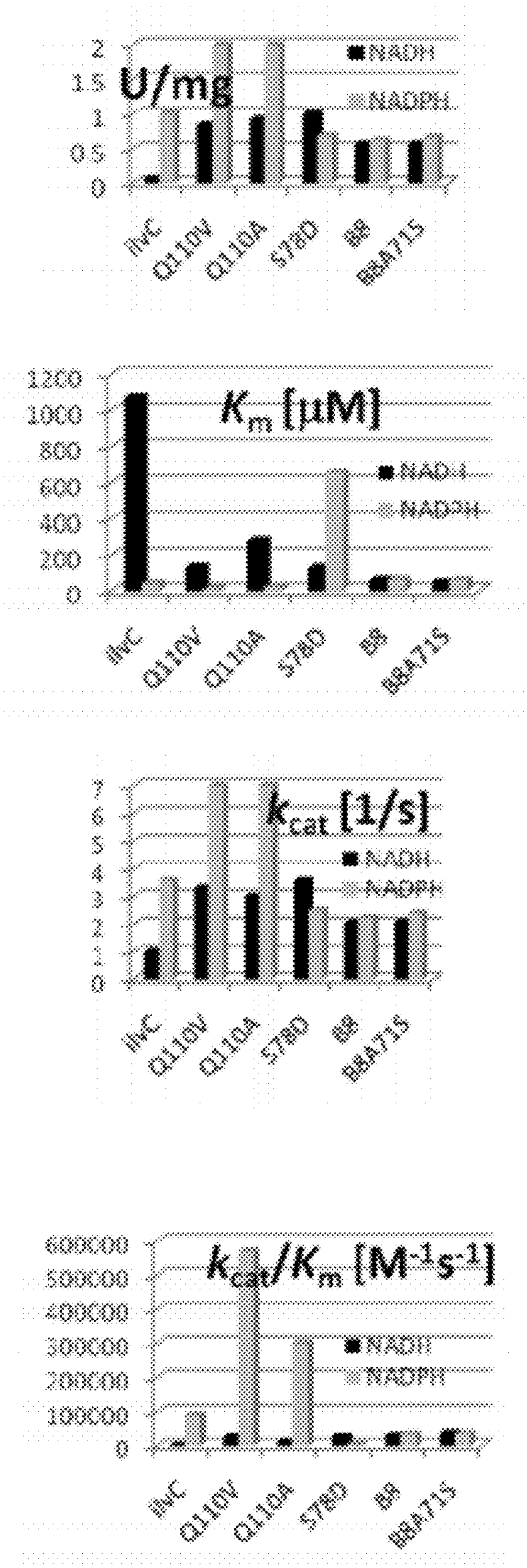
FIG. 19 illustrates the characterization of Ec_llvC$^{B8\text{-}his6}$ and Ec_llvC$^{B8A71S\text{-}his6}$ compared to Ec_llvC$^{his6}$, Ec_llvC$^{Q110V\text{-}his6}$, Ec_llvC$^{Q110A\text{-}his6}$, and Ec_llvC$^{S78D\text{-}his6}$.

As a next step, the gene encoding variant Ec_llvC$^{Q110V\text{-}his6}$ (SEQ ID NO: 23) was used as template to generate individual combinations of the mutation Q110V with other mutations: R68L, A71T, A71S, R76G, R76S, R76T, S78D, and R76D. After screening the variants as described above, the most promising ones were expressed, purified, and characterized. Table 29 lists the $K_M$ values in μM on NADPH and NADH for Ec_llvC$^{his6}$, Ec_llvC$^{Q110V\text{-}his6}$, and variants of Ec_llvC$^{Q110V\text{-}his6}$. Variant Ec_llvC$^{B8\text{-}his6}$ containing amino acid mutations Q110V and S78D, showed the same $K_M$ value for NADH and for NADPH with 65 μM. The A71S mutation was introduced into Ec_llvC$^{B8\text{-}his6}$ resulting in a variant Ec_llvC$^{B8A71S\text{-}his6}$, which yielded 44% catalytic efficiency on NADH compared to the catalytic efficiency of wild-type KARI on NADPH (FIG. 19 and Table 30).

TABLE 29

$K_M$ values for Ec_IlvC$^{his6}$, Ec_IlvC$^{Q110V\text{-}his6}$ and variants of Ec_IlvC$^{Q110V\text{-}his6}$ on NADPH and on NADH

| Variant | $K_M$ for NADPH [mM] | $K_M$ for NADH [mM] |
|---|---|---|
| Ec_IlvC$^{his6}$ | 41 | 1075 |
| Ec_IlvC$^{Q110V\text{-}his6}$ | 13 | 135 |
| Ec_IlvC$^{Q110VA71T\text{-}his6}$ | 37 | 80 |
| Ec_IlvC$^{Q110VA71S\text{-}his6}$ | 30 | 70 |
| Ec_IlvC$^{Q110VR76G\text{-}his6}$ | 47 | 87 |
| Ec_IlvC$^{Q110VR76S\text{-}his6}$ | n.d. | 223 |
| Ec_IlvC$^{B8\text{-}his6}$ | 65 | 65 |

TABLE 30

Catalytic efficiencies [$M^{-1}$ * $s^{-1}$] for wild-type Ec_IlvC$^{his6}$ and variants Ec_IlvC$^{Q110V\text{-}his6}$, Ec_IlvC$^{Q110A\text{-}his6}$, and Ec_IlvC$^{S78D\text{-}his6}$ on NAD(P)H compared to Ec_IlvC$^{B8\text{-}his6}$ and Ec_IlvC$^{B8A71S\text{-}his6}$

| Variant | $k_{cat}/K_M$ with NADH [$M^{-1}$ * $s^{-1}$] | $k_{cat}/K_M$ with NADH [$M^{-1}$ * $s^{-1}$] | ($k_{cat}/K_M$ with NADH)/($k_{cat}/K_M$ of Ec_IlvC$^{his6}$ with NADPH) [%] |
|---|---|---|---|
| Ec_IlvC$^{his6}$ | 1000 | 87300 | 1% |
| Ec_IlvC$^{Q110V\text{-}his6}$ | 24800 | 569000 | 28% |
| Ec_IlvC$^{Q110A\text{-}his6}$ | 11063 | 301800 | 13% |
| Ec_IlvC$^{S78D\text{-}his6}$ | 27600 | 3770 | 32% |
| Ec_IlvC$^{B8\text{-}his6}$ | 31775 | 34188 | 36% |
| Ec_IlvC$^{B8A71S\text{-}his6}$ | 38330 | 37459 | 44% |

Example 15

KARI Engineering by Recombination

The codon optimized gene Ec_ilvC_coEc$^{his6}$ (SEQ ID NO: 14) and libraries thereof were cloned into pET22b(+) using primers KARIpETfor and KARIpETrev (Table 6). DNA constructs were analyzed by restriction digests, and also by DNA sequencing to confirm integrity and correct construction. Primers pETup and KARIpETrev (Table 6) were used as primers in standard DNA sequencing reactions to sequence pET22b(+) derivatives.

The recombination library was constructed using SOE PCR introducing mutations found at the five targeted sites while allowing for wild-type sequence as well. The first fragments were generated using degenerate primers R68A71 recombfor and R68A71 recombrev which covered the gene sequence coding for the region at amino acid positions 68/71 (Table 6). After assembling the long and the short fragment, the assembly product was DpnI digested for 1 h, separated on an agarose gel, freeze'n'squeeze (BioRad, Hercules, Calif.) treated, and finally pellet painted (Novagen, Gibbstown, N.J.). The clean assembly product served as template for the second round of SOE PCR introducing mutations at amino acid positions 76/78 using the following primers: R68A71recombfor, R68A71recombrev, R76S78recombfor, R76S78recombrev, G76S78recombfor, G76S78recombrev, S76S78recombfor, S76S78recombrev, T76S78recombfor, T76S78recombrev, D76S78recombfor, D76S78recombrev, R76D78recombfor, R76D78recombrev, G76D78recombfor, G76D78recombrev, S76D78recombfor, S76D78recombrev, T76D78recombfor, T76D78recombrev, D76D78recombfor, D76D78recombrev (Table 6). The mixture of primers was used, since degenerate codons would have expanded the library size immensely. Again, the assembly product served as template to complete the recombination library with amino acid position 110. The same procedure was applied as described for the first two rounds of SOE PCR. Primers used were again a mixture prepared out of equimolar concentrations of Q110Qfor, Q110Qrev, Q110Afor, Q110Arev, Q110Vfor, and Q110Vrev. After all sites were recombined, the insert was restriction digested with NdeI and XhoI, ligated into pET22b(+), and electro-competent BL21(D3) (Lucigen, Middleton, Wis.) were transformed. In order to oversample the library by approximately five-fold, one thousand clones were picked and cultured as described below. In order to check for possible biases (i.e. certain mutations occurring more frequently than others), 20 clones were randomly chosen for DNA sequence analysis.

As described in Example 14, the first screening round identified several individual point mutations within the KARI cofactor binding region that either improved NADH-dependent activity or were at least neutral (i.e. had neither a beneficial nor deleterious effect). These mutations, along with the wild-type amino acid residue are listed in Table 31.

TABLE 31

Amino Acid Mutations Included in the Recombinatorial Library

| Amino Acid Position | Wild-type | Neutral or beneficial mutations identified | Total # (including wild-type) |
|---|---|---|---|
| 68 | R | L | 2 |
| 71 | A | T, S | 3 |
| 76 | R | G, S, T, D | 5 |
| 78 | S | D | 2 |
| 110 | Q | A, V | 3 |

A complete recombination library was constructed allowing for all beneficial and some neutral mutations (and including the wild-type residues) at each of the five sites. The total number of unique combinations was 180.

Generating all mutations using a single primer would result in a large library of ~4,000. Thus, the present inventors built the library stepwise in three SOE reactions using primers mixed in equimolar amounts for each of three SOE reactions:

SOE 1: R68/A71, R68/T71, R68/S71, L68/A71, L68/T71, L68/S71

SOE 2: A76/S78, G76/S78, S76/S78, T76/S78, D76/S78, A76/D78, G76/D78, S76/D78, T76/D78, D76/D78,

SOE 3: Q110,A110,V110

First, mutations at amino acid sites 68 and 71 were introduced into the Ec_ilvC_coEc$^{his6}$ gene, followed by mutations at site 76 and finally, by mutations at site 110. After the library had been generated, it was ligated into pET22b(+). The resulting plasmid library was used to transform *E. coli* BL21(DE3) electro-competent cells. Cells were grown in 96-well plates according to the protocol for cell growth and protein expression in microplates as described in Example 14. The KARI enzyme activity of each of 1,000 individual transformants was determined using the high-throughput assay as described in Example 14.

Only 20% of the enzymes of the recombination library were active on NADH. After screening 1,000 clones using the NADH depletion assay at 340 nm, 26 KARI variants were selected for a rescreen by the high-throughput assay described in Example 14 and eight thereof were expressed in 25 ml $LB_{amp}$ medium in shake flasks according to the protocol for cell growth and protein expression in shake flasks as described in Example 14, purified according to the protocol for purification of KARI enzymes as described in Example 14, and NAD(P)H depletion at 340 nm was measured again. Two candidates Ec_IlvC$^{2H10\text{-}his6}$ (containing the amino acid substitutions A71 S, R76D, S78D, and Q110A) and Ec_IlvC$^{6E6\text{-}his6}$ (containing the amino acid substitutions A71S, R76D, S78D, and Q110V) showed good specific activity on NADH and were only marginally active on NADPH. The other six variants showed lower specific activities on NADH (ranging from 0.44-0.55 U/mg) compared to the two favored variants Ec_IlvC$^{2H10\text{-}his6}$ and Ec_IlvC$^{6E6\text{-}his6}$ and higher specific activities on NADPH (0.72-2.62 U/mg). The $K_M$ values of variants Ec_IlvC$^{2H10\text{-}his6}$ and Ec_IlvC$^{6E6\text{-}his6}$ were measured and the catalytic efficiencies were calculated.

The kinetic parameters of the recombination variants and previously described KARI mutants are shown in Table 32. Both variants found in the recombination library showed an almost complete switch in cofactor preference from NADPH to NADH. The $K_M$ values of the mutants on NADH rival the $K_M$ value of KARI Ec_IlvC$^{his6}$ on NADPH (44.2 and 31.6 μM on NADH vs. 41 μM for Ec_IlvC$^{his6}$ on NADPH). The catalytic efficiencies of Ec_IlvC$^{2H10\text{-}his6}$ and Ec_IlvC$^{6E6\text{-}his6}$ on NADH (60322 and 74045 $M^{-1}*s^{-1}$, respectively) came very close to the catalytic efficiency of Ec_IlvC$^{his6}$ on NADPH (87300 $M^{-1}*s^{-1}$). The mutants described herein exhibit a complete reversal in cofactor specificity and the NADH-dependent activity approaches the NADPH-dependent activity of the wild-type enzyme. The best variant exhibited 85% activity (in terms of $k_{cat}/K_M$) on NADH compared to wild-type activity on NADPH.

TABLE 32

Kinetic parameters of Ec_IlvC$^{his6}$, two of the enzymes described previously (Ec_IlvC$^{B8\text{-}his6}$ and Ec_IlvC$^{B8A71S\text{-}his6}$), as well as the two mutants Ec_IlvC$^{2H10\text{-}his6}$ and Ec_IlvC$^{6E6\text{-}his6}$

| | U/mg | | $K_M$ [μM] | | $k_{cat}$ [$s^{-1}$] | | $k_{cat}/K_M$ [$M^{-1} * s^{-1}$] | |
|---|---|---|---|---|---|---|---|---|
| Variant | NADH | NADPH | NADH | NADPH | NADH | NADPH | NADH | NADPH |
| Ec_IlvC$^{his6}$ | 0.08 | 1.00 | 1,075 | 41 | 1.0 | 3.6 | 1,000 | 87,300 |
| Ec_IlvC$^{B8\text{-}his6}$ | 0.57 | 0.62 | 65 | 65 | 2.0 | 2.2 | 31,775 | 34,188 |
| Ec_IlvC$^{B8A71S\text{-}his6}$ | 0.57 | 0.66 | 53.5 | 63.4 | 2.0 | 2.4 | 38,330 | 37,459 |
| Ec_IlvC$^{2H10\text{-}his6}$ | 0.74 | 0.17 | 44.2 | 568 | 2.6 | 0.61 | 60,322 | 1,078 |
| Ec_IlvC$^{6E6\text{-}his6}$ | 0.65 | 0.07 | 31.6 | 653 | 2.3 | 0.2 | 74,045 | 386 |

The above data demonstrates the effects brought on by the beneficial mutations at positions 71 and 110. Moreover, aspartic acids at positions 76 and 78 electrostatically repel the phosphate of NADPH. It is noted that the electrostatic attraction of arginine to the NADPH phosphate is lost when R76 is mutated to an aspartic acid residue.

Example 16

KARI Engineering by Random Mutagenesis in Yeast

The following example demonstrates increases in specific, NADH-dependent KARI activity.

Methods: Plasmid pGV2241 (SEQ ID NO: 124) carrying the Ec_ilvC_coSc$^{6E6\text{-}his6}$ gene (SEQ ID NO: 33) served as template for generating the first error-prone PCR library using forward primer pGV1994ep_for and reverse primer pGV1994_rev. These primers are specific to the backbone pGV1102 (SEQ ID NO: 101) and bind 50 by upstream and downstream of the KARI insert to create an overlap for homologous recombination in yeast. Generally, three different $MnCl_2$ concentrations were tested (100, 200, and 300 μM $MnCl_2$) and the PCR compositions are summarized in Table 33.

TABLE 33

PCR set up for different concentrations of $MnCl_2$ that were tested. The final volumes were 100 μL and amounts of ingredients are in μL

| final $MnCl_2$ concentration [μM] | 100 | 150 | 200 | 250 | 300 |
|---|---|---|---|---|---|
| Template | 1 | 1 | 1 | 1 | 1 |
| primer forward | 2 | 2 | 2 | 2 | 2 |
| primer reverse | 2 | 2 | 2 | 2 | 2 |
| dNTP's | 4 | 4 | 4 | 4 | 4 |
| Taq buffer | 10 | 10 | 10 | 10 | 10 |
| $MgCl_2$ | 28 | 28 | 28 | 28 | 28 |
| Taq polymerase | 1.6 | 1.6 | 1.6 | 1.6 | 1.6 |
| $MnCl_2$ (1 mM stock) | 10 | 15 | 20 | 25 | 30 |
| PCR grade water | 41.4 | 36.4 | 31.4 | 26.4 | 21.4 |

The temperature profile was the following: 95° C. 3 min initial denaturation, 95° C. 30 s denaturation, 55° C. 30 s annealing, 72° C. 2 min elongation, 25 cycles, 5 min final elongation at 72° C.

The PCR products were checked on a 1% analytical TAE agarose gel, Dpnl digested for 1 h at 37° C. to remove traces of template DNA, and then cleaned up using a 1% preparative TAE agarose gel. The agarose pieces containing the PCR products were put into Freeze 'n' Squeeze tubes (BIORAD, catalog #732-6166) and frozen for 10 min at −20° C. Then, they were spun down at room temperature and 10,000 rpm to "squeeze" the buffer with the soluble DNA out of the agarose mesh. The volume of the eluted DNA/buffer mixture was estimated and then subjected to the pellet paint procedure (Novagen, catalog #69049-3), which was performed according to the manufacturer's manual. The dried pink DNA pellets were resuspended in 50 μL PCR grade water. In the meantime, the restriction digest of the backbone pGV1102 (SEQ ID NO: 101) was performed as follows: 10 μL of DNA, 32 μL PCR grade water, 5 μL NEB buffer 3 (10×), 2 μL NotI, and 1 μL SalI. After an incubation time of 3 h at 37° C., the digest was run out on an agarose gel and then pellet painted as described above. After determining the DNA concentration of cut vector and insert, 500 ng of each were mixed together, precipitated with pellet paint, and resuspended in 6 μL of PCR grade water. This mixture can be prepared a day before the transformation.

In the evening before the planned transformation, YPD medium (10 g/L yeast extract, 20 g/L peptone, 20 g/L glucose) was inoculated with a single colony of GEVO1186 and incubated at 30° C. and 250 rpm over night. The next morning, a 20 mL YPD culture was started in a 250 ml Erlenmeyer flask without baffles with the overnight culture at an $OD_{600}$ of 0.1. This culture was incubated at 30° C. and 250 rpm until it reached an $OD_{600}$ of 1.3-1.5. When the culture had reached the desired $OD_{600}$, 200 μL of freshly prepared sterile-filtered Tris-DTT (0.39 g 1,4-dithiothreitol per 1 mL of 1 M Tris, pH 8.0) were added and the culture was allowed to incubate at 30° C. and 250 rpm for another 15 min. The cells were then pelleted at 4° C. and 2,500×g for 3 min. After removing the supernatant, the pellet was resuspended in 10 mL of ice-cold buffer E and spun down again as described above. Then, the cell pellet was resuspended in 1 mL of sterile-filtered ice-cold buffer E (1.2 g Tris base, 92.4 g glucose, and 0.2 g $MgCl_2$ per 1 L deionized water, adjusted to pH 7.5) and spun down one more time as before. After removal of the supernatant with a pipette, 200 μL of ice-cold buffer E (1.2 g/L Tris, 92.4 g/L glucose, and 0.2 g/L $MgCl_2$, pH 7.5) were added and the pellet was gently resuspended. The 6 μL of insert/backbone mixture were split in half and added to 50 μL of electrocompetent GEVO1186 cells. The DNA/cell mixtures were transferred into 0.2 cm electroporation cuvettes (BioRad) and electroporated without a pulse controller at 0.54 kV and 25 pF. 1 mL of pre-warmed YPD medium was added immediately and the transformed cells were allowed to regenerate at 30° C. and 250 rpm in 15 mL round bottom culture tubes (Falcon). After 1 hour, the cells were spun down at 4° C. and 2,500×g for 3 min, and the pellets were resuspended in 1 mL pre-warmed SD-URA medium (1.7 g/L yeast nitrogen base, 5 g/L ammonium sulfate, 20 g/L glucose, with casamino acids but without uracil (CSM-URA). Different amounts of transformed cells were plated on SD-URA agar plats plates and incubated at 30° C. for 1.5 days or until the colonies were large enough to be picked with sterile toothpicks.

Single yeast colonies were picked with sterile toothpicks into shallow 96-well plates containing 300 μL of SC-URA medium (6.7 g/L Difco™ Yeast Nitrogen Base, 14 g/L Sigma™ Synthetic Dropout Media supplement (includes amino acids and nutrients excluding histidine, tryptophan, uracil, and leucine), 10 g/L casamino acids, 20 g/L glucose, 0.018 g/L adenine hemisulfate, and 0.076 g/L tryptophan) per well. Each plate encompassed 88 wells with variants, four wells with parent, three wells with GEVO1886 carrying pGV1102 as background control, and one well with medium only, which served as a sterility control. The plates were incubated at 250 rpm and 30° C. in a humidified plate shaker (Kuhner) over night. On the next morning, 50 μL of the overnight culture were transferred into 600 μL SC-URA medium in 96 well deep well plates (2 mL capacity per well). The cultures were allowed to grow for another 8 h at the same conditions, before they were spun down at 4° C. and 5000 rpm for 5 min. The supernatants were removed and the pellets were frozen at −20° C. until they were screened for activity as described in Example 14 above.

Improved variants were expressed and purified from GEVO1186. 20 mL SC-URA medium overnight cultures were grown at 30° C. and 250 rpm in 250 mL flasks and were then used to inoculate 96 well deep well plates on the next morning. 50 μL of the overnight cultures were transferred into 600 μL SC-URA medium per well. The plates were then grown at 30° C. and 250 rpm in a humidified plate shaker for 8 h. In order to the harvest, the cultures were transferred into 50 mL Falcon tubes and then spun down at 4° C. and 5,000 rpm for 10 min. The pellets were frozen until they were processed and purified as described in Example 14 above.

Results: Two rounds of error-prone PCR and screening were carried out. The libraries (~2400 clones per library) were screened using the KARI high-throughput assay. KARI variants that exhibited an improved activity compared to their parent (total of 88 variants) were picked and rescreened in triplicate and five clones were selected for sequencing and purification. In the first round variant Ec_llvC$^{P2D1\text{-}his6}$ (SEQ ID NO: 38), encoded by Ec_ilvC_coSc$^{P2D1\text{-}his6}$ (SEQ ID NO: 37) was identified carrying the following mutations: D146G and G185R. This variant served as parent for the second round of error-prone PCR and screening which yielded variant Ec_llvC$^{P2D1\text{-}A1\text{-}his6}$ (SEQ ID NO: 42), encoded by Ec_ilvC_coSc$^{P2D1\text{-}A1\text{-}his6}$ (SEQ ID NO: 41) with one additional mutation (K433E). The biochemical properties were determined and are summarized in Table 34. A two-fold improvement of the specific activity in lysate and in the purified enzyme was observed after two rounds of error-prone PCR.

TABLE 34

Comparison of the biochemical properties of the parent Ec_IlvC$^{6E6\text{-}his\text{-}6}$ with the variants found in round 1 (Ec_IlvC$^{P2D1\text{-}his6}$) and 2 (Ec_IlvC$^{P2D1\text{-}A1\text{-}his6}$). The variants were purified before characterization

| | U/mg | | $K_M$ [μM] | | $k_{cat}$ [$s^{-1}$] | | $k_{cat}/K_M$ [$M^{-1} * S^{-1}$] | |
|---|---|---|---|---|---|---|---|---|
| Variant | NADH | NADPH | NADH | NADPH | NADH | NADPH | NADH | NADPH |
| Ec_IlvC$^{6E6\text{-}his6}$ | 0.69 | | 39 | | 2.4 | | 63,000 | |
| Ec_IlvC$^{P2D1\text{-}his6}$ | 0.92 | 0.15 | 40 | 1432 | 3.3 | 0.54 | 82,650 | 377 |
| Ec_IlvC$^{P2D1\text{-}A1\text{-}his6}$ | 1.2 | 0.15 | 26 | >1432 | 4.3 | 0.54 | 167,687 | <377 |

Example 17

NADH-Dependent Anaerobic Isobutanol Production

This example illustrates that an isobutanol producing microorganism which is engineered to carry NADH-dependent KARI and ADH enzymes produces isobutanol at higher yield compared to strains engineered to carry NADPH-dependent KARI and ADH enzymes. These strains also acquire the ability to produce isobutanol anaerobically.

A first set of anaerobic fermentations with isobutanol producing strains according to Table 35 were performed. Strain GEVO1993 is an *E. coli* strain in which the native ilvC gene was deleted and the other three steps of the isobutanol pathway (Bs_alsS1, Ec_ilvD_coEc and Ll_kivd1) were integrated into the chromosome.

TABLE 35

Strain/Plasmid combinations described herein.

| Plasmid | Strain | KARI gene | ADH gene | Cofactor usage of the isobutanol pathway |
|---|---|---|---|---|
| pGV1777 | GEVO1993 | Ec_ilvC_coEc | Ec_yqhD (native) | NADPH/ NADPH |
| pGV1925 | GEVO1993 | Ec_ilvC_coEc | Ec_fucO | NADPH/NADH |
| pGV1938 | GEVO1993 | Ec_ilvC_coEc$^{S78D}$ | Ec_yqhD (native) | NADH/NADPH |
| pGV1927 | GEVO1993 | Ec_ilvC_coEc$^{S78D}$ | Ec_fucO | NADH/NADH |

Overnight cultures of the GEVO1993 transformed with pGV1777 (SEQ ID NO: 118), pGV1925, pGV1938, or pGV1927 were started from individual colonies of previously transformed strains. These cultures were started in 3 mL M9 minimal medium (Miller, J.H. A Short Course in Bacterial Genetics: A laboratory manual and handbook for *Escherichia coli* and related bacteria. 1992. Cold Spring Harbor Laboratory Press, Cold Spring Harbor, N.Y.), supplemented with 10 g/L yeast extract, 10 μM ferric citrate and trace metals, containing 8.5% glucose and the appropriate antibiotics in snap cap tubes about 14 h prior to the start of the fermentation.

Isobutanol fermentations were then carried out in screw cap flasks containing 20 mL of the same medium that was inoculated with 0.2 mL of the overnight culture. The cells were incubated at 37° C./250 rpm until the strains had grown to an $OD_{600}$ of 0.6-0.8 and were then induced with Isopropyl β-D-1-thiogalactopyranoside at 1 mM final concentration.

Three hours after induction the cultures were shifted to anaerobic fermentation conditions by loosening the cap of the flasks and placing the flasks into to a Coy Laboratory Products Type B Vinyl anaerobic chamber (Coy Laboratory Products, Grass Lakes, Mich.) through an airlock in which the flasks were cycled three times with nitrogen and vacuum, and then filled with the a hydrogen gas mix (95% Nitrogen, 5% Hydrogen). Once the flasks were inside the anaerobic chamber, the flasks were closed again and incubated without shaking at 30° C. Inside the chamber, an anaerobic atmosphere (<5 ppm oxygen) was maintained through the hydrogen gas mix (95% Nitrogen, 5% Hydrogen) reacting with a palladium catalyst to remove oxygen. The flasks in the anaerobic chamber were swirled twice a day. Samples (2 mL) were taken at the time of the shift and at 21 h and 45 h after shifting to anaerobic conditions, spun down at 22,000 g for 1 min to separate the cell pellet from the supernatant and stored frozen at −20° C. until analysis. The samples were analyzed using High performance liquid chromatography (HPLC) and gas chromatography GC. All experiments were performed in triplicate.

The $OD_{600}$ values of the cultures were similar amongst the three replicates. Notably, after 45 h, GEVO1993+pGV1927 (i.e. expressing NADH-dependent KARI and ADH) produced isobutanol at approximately twice the volumetric productivity, specific productivity, and titer. Surprisingly the theoretical yield increased from about 70% of theoretical to 96% of theoretical. Expressing only one NADH-dependent enzyme with the other enzyme being NADPH-dependent did not have an effect (Table 36).

TABLE 36

45 h performance parameters

| | | Vol. Productivity | | Spec. Productivity | | Anaerobic Yield[a] | | Titer | |
|---|---|---|---|---|---|---|---|---|---|
| Sample | KARI/ADH | [g/L/h] | ± | [g/L/h/OD] | ± | % theor. | ± | [g/L] | ± |
| GEVO1993 + pGV1777 | Ec_IlvC/ Ec_YqhD | 0.044 | 0.019 | 0.018 | 0.003 | 72 | 3 | 2.4 | 1.0 |

TABLE 36-continued 45 h performance parameters

| Sample | KARI/ADH | Vol. Productivity [g/L/h] | ± | Spec. Productivity [g/L/h/OD] | ± | Anaerobic Yield[a] % theor. | ± | Titer [g/L] | ± |
|---|---|---|---|---|---|---|---|---|---|
| GEVO1993 + pGV1925 | Ec_IlvC/ Ec_FucO | 0.031 | 0.002 | 0.017 | 0.003 | 55 | 4 | 1.9 | 0.1 |
| GEVO1993 + pGV1938 | Ec_IlvC$^{S78D}$/ Ec_YqhD | 0.040 | 0.015 | 0.021 | 0.002 | 78 | 10 | 2.1 | 0.9 |
| GEVO1993 + pGV1927 | Ec_IlvC$^{S78D}$/ Ec_FucO | 0.078 | 0.006 | 0.030 | 0.003 | 96 | 5 | 3.8 | 0.2 |

[a]The anaerobic yield is calculated by dividing the isobutanol produced from time of anaerobic shift until 45 hours after the shift by the amount of glucose consumed during this time period A second set of anaerobic fermentations with isobutanol producing strains according to Table 37 were performed to demonstrate that the of improved KARI variants correlates with an improvement of isobutanol production under anaerobic conditions.

TABLE 37

Strain/Plasmid combinations used for the second set of anaerobic fermentations.

| # | Plasmid | Strain | KARI gene | ADH gene | KARI $k_{cat}/K_{M,NADH}$ | KARI $(k_{cat}/K_{M,NADH})/(k_{cat}/K_{M,NADPH})$ |
|---|---|---|---|---|---|---|
| 1 | pGV1927 | GEVO1993 | Ec_ilvC_coEc$^{S78D}$ | Ec_fucO | 27,600 | 7 |
| 2 | pGV1976 | GEVO1993 | Ec_ilvC_coEc$^{2H10}$ | Ec_fucO | 60,300 | 56 |
| 3 | pGV1975 | GEVO1993 | Ec_ilvC_coEc$^{6E6}$ | Ec_fucO | 74,000 | 192 |

The experiment was carried out as described above except that the cell cultures were induced at an $OD_{600}$ of 0.8-1.0 instead of 0.6-0.8 and shifted to anaerobic conditions at and OD $OD_{600}$ of 4.0-6.0 instead of 3 hours after induction. In addition, samples were taken at the time of the anaerobic shift and 24 h and 48 h after induction (i.e. 20 h and 44 h after the anaerobic shift, respectively).

44 hours after shift to anaerobic fermentation conditions, the trend for volumetric and specific productivity is the same as observed 20 hours after shift to anaerobic conditions: strains carrying improved KARI variants Ec_llvC$^{2H10}$ and Ec_llvC$^{6E6}$ produced isobutanol at higher volumetric and specific productivity as well as yield compared to strains carrying KARI variant Ec_llvC$^{S78D}$ (Table 38).

TABLE 38

44 h performance parameters

| Sample | KARI/ ADH | Vol. Productivity [g/L/h] | ± | Spec. Productivity [g/L/h/OD] | ± | anaerobic Yield[a] % theor. | ± | Titer [g/L] | ± |
|---|---|---|---|---|---|---|---|---|---|
| GEVO1993 + pGV1927 | Ec_IlvC$^{S78D}$/ Ec_FucO | 0.215 | 0.005 | 0.037 | 0.002 | 79 | 12 | 10.9 | 0.3 |
| GEVO1993 + pGV1976 | Ec_IlvC$^{2H10}$/ Ec_FucO | 0.274 | 0.008 | 0.047 | 0.002 | 107 | 15 | 13.0 | 0.6 |
| GEVO1993 + pGV1975 | Ec_IlvC$^{6E6}$/ Ec_FucO | 0.270 | 0.032 | 0.047 | 0.005 | 97 | 2 | 12.5 | 1.5 |

[a]The anaerobic yield is calculated by dividing the isobutanol produced from time of anaerobic shift until 44 hours after the shift by the amount of glucose consumed during this time period

Example 18

NADH-Dependent Anaerobic Isobutanol Production in Yeast

This example illustrates that isobutanol producing yeast microorganisms engineered to carry NADH-dependent KARI and ADH enzymes produce isobutanol at higher yields compared to isobutanol producing yeast microorganisms engineered to carry NADPH-dependent KARI and/or ADH enzymes. These strains also produce isobutanol anaerobically.

Cultures of GEVO2710, GEVO2711 and GEVO2799 transformed with pGV2227 (SEQ ID NO: 123) or pGV2242 (SEQ ID NO: 125) and cultures of GEVO2710, and GEVO2799 transformed with pGV2020 (SEQ ID NO: 121) or pGV2082 (SEQ ID NO: 122) were started from individual colonies of previously transformed and purified strains. These cultures were started in 14 ml round-bottom snap-cap test tubes containing 3 ml of YPD medium supplemented with 0.2 g/L G418 antibiotic, and 1% (v/v) of a stock solution containing 3 g/L ergosterol and 66 g/L Tween 80 dissolved in ethanol. The snap-cap test tubes were not closed completely so that air would vent in/out of the tubes. After growth for about 10 hours at 30° C. shaking at 250 rpm, these cultures were added to 47 ml of the same medium in 250 ml non-baffled flasks with sleeve closures and incubated for about 14 hours at 30° C. shaking at 250 rpm. Isobutanol fermentations were then carried out after harvesting the cells from the 50 ml cultures by centrifugation, and resuspending the cell pellets in f 50 ml of the same medium in 250 ml non-baffled flasks to an initial optical density ($OD_{600}$) of 3-6.

Anaerobic fermentations were carried out by inoculating flasks with screw-cap closures as above and placing the flasks with loose caps into to a Coy Laboratory Products Type B Vinyl anaerobic chamber (Coy Laboratory Products, Grass Lakes, Mich.) through an airlock in which the flasks were cycled three times with nitrogen and vacuum, and then filled with a hydrogen gas mix (95% Nitrogen, 5% Hydrogen). The flasks were moved inside the anaerobic chamber from the airlock and the screw-caps on the flasks were closed inside the anaerobic chamber. Inside the chamber, an anaerobic atmosphere (<5 ppm oxygen) was maintained through the hydrogen gas mix (95% Nitrogen, 5% Hydrogen) reacting with a palladium catalyst to remove oxygen. The flasks were then removed from the anaerobic chamber and incubated outside the anaerobic chamber at 30° C. shaking at 75 rpm. Samples (2 ml) were taken at the beginning of the incubation of the anaerobic fermentations and after 24 hours, 48 hours and 72 hours of incubation. The samples taken at the beginning of the incubation were taken before moving the flasks into the anaerobic chamber. The 24 hour and 48 hour samples were taken by moving the flasks into the anaerobic chamber through the airlock as above, opening the flasks in the anaerobic chamber to remove the samples, re-closing the flasks in the anaerobic chamber and removing the flasks from the anaerobic chamber for continued incubation. The 72 hour samples were taken outside of the anaerobic chamber because these were the final samples from the flasks.

Samples from fermentations were centrifuged for 10 minutes at 18,000 g to separate the cells from the supernatant. The supernatant was removed and stored under refrigeration until analyzed by gas chromatography and high performance liquid chromatography as described above. All experiments were performed in triplicate.

In the anaerobic fermentations the $OD_{600}$ values of the cultures were similar amongst the three replicates. Notably, after 72 hours in anaerobic fermentations, GEVO2710+pGV2242, GEVO2711+pGV2242 and GEVO2799+pGV2242 (i.e. strains expressing an NADH-dependent KARI) produced isobutanol at an approximately 1.25- to 2-fold higher volumetric productivity, specific productivity, and titer than the same strains containing pGV2227 (i.e. strains expressing an NADPH-dependent KARI). The anaerobic yield increased from about 16-25% of theoretical to 22-35% of theoretical (Table 39).

TABLE 39

72 hour performance parameters from anaerobic fermentations

| Sample | KARI/ADH overexpressed from plasmid | Vol. Productivity [g/L/h] | ± | Spec. Productivity [g/L/h/OD] | ± | Yield % theor. | ± | Specific Titer [g/L/OD] | ± |
|---|---|---|---|---|---|---|---|---|---|
| GEVO2710 + pGV2020 | None/ None | 0.000 | 0.000 | 0.0001 | 0.0000 | 1 | 0 | 0.01 | 0.00 |
| GEVO2710 + pGV2082 | Ec_IlvC$^{Q110V}$/ Dm_Adh | 0.006 | 0.001 | 0.0014 | 0.0001 | 21 | 2 | 0.10 | 0.01 |
| GEVO2710 + pGV2227 | Ec_IlvC$^{Q110V}$/ LI_AdhA | 0.006 | 0.001 | 0.0017 | 0.0003 | 17 | 9 | 0.12 | 0.02 |
| GEVO2710 + pGV2242 | Ec_IlvC$^{P2D1}$/ LI_AdhA | 0.011 | 0.001 | 0.0029 | 0.0003 | 22 | 2 | 0.21 | 0.02 |
| GEVO2799 + pGV2020 | None/ None | 0.001 | 0.000 | 0.0002 | 0.0000 | 6 | 1 | 0.01 | 0.00 |
| GEVO2799 + pGV2082 | Ec_IlvC$^{Q110V}$/ Dm_Adh | 0.010 | 0.000 | 0.0019 | 0.0003 | 38 | 2 | 0.14 | 0.02 |
| GEVO2799 + pGV2227 | Ec_IlvC$^{Q110V}$/ LI_AdhA | 0.009 | 0.001 | 0.0014 | 0.0002 | 20 | 2 | 0.10 | 0.01 |
| GEVO2799 + pGV2242 | Ec_IlvC$^{P2D1}$/ LI_AdhA | 0.014 | 0.003 | 0.0026 | 0.0003 | 33 | 10 | 0.19 | 0.03 |
| GEVO2711 + pGV2227 | Ec_IlvC$^{Q110V}$/ LI_AdhA | 0.008 | 0.000 | 0.0020 | 0.0000 | 24 | 2 | 0.14 | 0.00 |
| GEVO2711 + pGV2242 | Ec_IlvC$^{P2D1}$/ LI_AdhA | 0.014 | 0.004 | 0.0025 | 0.0008 | 37 | 8 | 0.18 | 0.06 |

Example 19

Overexpression of an NADPH-Dependent GAPDH, GDP1

The purpose of this example is to describe how overexpression of an NADPH-dependent GAPDH can improve isobutanol production under anaerobic conditions.

GDP1 is expressed from plasmid pGV1573 (SEQ ID NO: 106) together with an isobutanol biosynthetic pathway expressed from pGV1485 (SEQ ID NO: 103) and pSA69. As a control the plasmid pGV1573 is replaced by the empty version of this plasmid pGV1572 (SEQ ID NO: 105). These plasmids are transformed into GEVO1859ΔgapA. Overnight cultures of Strain 1: GEVO1859 ΔgapA, pGV1573, pGV1485, pSA69 and Strain 2: GEVO1859ΔgapA, pGV1572, pGV1485, pSA69 are started from individual colonies of previously transformed strains. These cultures are started in 3 mL M9 minimal medium (Miller, J. H. A Short Course in Bacterial Genetics: A laboratory manual and handbook for *Escherichia coli* and related bacteria. 1992. Cold Spring Harbor Laboratory Press, Cold Spring Harbor, N.Y.), supplemented with 10 g/L yeast extract, 10 μM ferric citrate and trace metals, containing 8.5% glucose and the appropriate antibiotics in snap cap tubes about 14 h prior to the start of the fermentation. Isobutanol fermentations are then carried out in screw cap flasks containing 20 mL of the same medium that was inoculated with 0.2 mL of the overnight culture. The cells are incubated at 37° C./250 rpm until the strains had grown to an $OD_{600}$ of 0.6-0.8 and are then induced with Isopropyl β-D-1-thiogalactopyranoside at 1 mM final concentration.

Three hours after induction the cultures are shifted to anaerobic fermentation conditions by loosening the cap of the flasks and placing the flasks into to a Coy Laboratory Products Type B Vinyl anaerobic chamber (Coy Laboratory Products, Grass Lakes, Mich.) through an airlock in which the flasks are cycled three times with nitrogen and vacuum, and then filled with the a hydrogen gas mix (95% Nitrogen, 5% Hydrogen). Once the flasks are inside the anaerobic chamber, the flasks are closed again and incubated without shaking at 30° C. Inside the chamber, an anaerobic atmosphere (<5 ppm oxygen) was maintained through the hydrogen gas mix (95% Nitrogen, 5% Hydrogen) reacting with a palladium catalyst to remove oxygen. The flasks in the anaerobic chamber are swirled twice a day. Samples (2 mL) are taken at the time of the shift and at 24 h and 48 h after inoculation, spun down at 22,000 g for 1 min to separate the cell pellet from the supernatant and stored frozen at −20° C. until analysis. The samples are analyzed using High performance liquid chromatography (HPLC) and gas chromatography GC. All experiments are performed in duplicate.

Example 20

Overexpression of NADPH-Dependent GADPHs GDP1 and gapC pGV1572 (SEQ ID NO: 105) (PLlacO, p15A, $Cm^R$) was constructed as an empty vector compatible with the plasmids pGV1698 (SEQ ID NO: 112) and pGV1655 (SEQ ID NO: 109) for the expression of the isobutanol pathway. The GAPDHs from *Kluyveromyces lactis*, and *Clostridium acetobutylicum* were cloned into pGV1572 to make pGV1573 (SEQ ID NO: 106) (PLlacO1::GDP1, p15A, $Cm^R$), and pGV1573 (SEQ ID NO: 107) (PLlacO1::GapC, p15A, $Cm^R$) respectively. *K. lactis* GAPDH was subcloned from pGV1323 (SEQ ID NO: 102), which contains the GDP1 gene cloned from genomic DNA of *K. lactis*. GapC (*C. acetobutylicum*) was cloned from genomic DNA using primers 1049 and 1050.

*E. coli* DH5aZ1 (Lutz, R. and Bujard, H, Nucleic Acids Research (1997) 25 1203-1210) was chosen as the host strain. This strain contains the Z1 integration which provides overexpression of lacI from a lacIq expression cassette. DH5aZ1 was transformed with pGV1572, pGV1573, and pGV1575. Transformants were used to inoculate 5 mL cultures, which were incubated at 37° C., 250 rpm overnight. 50 mL cultures were inoculated with 1 mL overnight culture and incubated at 37° C., 250 rpm. The cultures were induced with IPTG when $OD_{600}$ was approximately 0.6 and incubated at 30° C., 250 rpm for 2 hours. The cultures were centrifuged at 2700×g at 4° C. for 10 min and the pellets were frozen at −80° C.

Pellets were resuspended with lysis buffer to 40% (w/v). (lysis buffer was the same as the reaction buffer but without substrate and cofactors). Cells were lysed in a bead mill using 3 times 1 min intervals, placing them on ice for 2 min in between each run. The lysate was centrifuged at 25000×g at 4° C. for 10 min, the supernatant was kept on ice and it was used as whole cell lysate for the enzyme assays.

The total reaction volume was 100 μL consisting of 90 μL of Reaction Buffer: 50 mM glycine buffer pH 9.5, 5 mM EDTA, 40 mM triethanolamine, 3 mM beta-mercaptoethanol, 6 mM NAD+ or NADP+, and 10 μL lysate. 10 μL of lysate were pipette into a UV permeable 96 well plate. 90 μL of reaction buffer was added to the lysate and mixed well by pipetting up and down. The plate was read for 5 min at 340 nm. Results are shown in Table 40.

TABLE 40

Volumetric and specific activity of various GAPDH with $NADP^+$

| Lysate Name | $NADP^+$ Volumetric Activity (mU/ml) | Sp. Activity (nmol/min/ μg total cell protein) | pGV# | organism |
|---|---|---|---|---|
| gapC | 10.022 | 0.010 | 1575 | *C. acetobutylicum* |
| GDP1 | 26.849 | 0.031 | 1573 | *K. lactis* |
| Control (DH5az1) | 3.819 | 0.005 | 1572 | |

DH5aZ1 was the host strain for all the plasmids and has its own indigenous GAPDH. The results show that the GAPDH enzymes are expressed and active in *E. coli*. The strain expressing GDP1 had more than 6 times higher in vitro GAPDH specific activity with the cofactor NADPH than the control strain not overexpressing GAPDH. The strain overexpressing gapC had twice the in vitro GAPDH specific activity with the cofactor NADPH than the control strain not overexpressing GAPDH.

Example 21

NADPH-Dependent GAPDH in Yeast

The purpose of this example is to describe how an isobutanol producing yeast which is engineered to express NADPH-dependent GAPDH and produce isobutanol anaerobically.

A yeast strain, GEVO5001, which expresses the isobutanol biosynthetic pathway and is deficient in pyruvate decarboxylase activity, is engineered to overproduce the *K. lactis* Gdp1. pGV6001 is a yeast integration plasmid carrying a hygromycin resistance marker and the GDP1 gene under the strong constitutive promoter from TDH3. This plasmid is linearized and transformed into GEVO5001 to generate GEVO5003. Expression of GDP1 is confirmed by qRT-PCR. Once confirmed, GEVO5003 and the parent strain GEVO5001 are used in fermentations for the production of isobutanol. Two fermentations are performed with the two strains. Fermentation 1 is an aerobic fermentation and Fermentation 2 is an anaerobic fermentation.

Example 22 pvk Bypass 1

This example illustrates that an isobutanol producing microorganism which is engineered to bypass the pyruvate kinase reaction shows increased productivity, titer and yield of isobutanol compared to the control strain without said engineering.

For the pyk bypass experiment, GEVO1385, GEVO1725 (triple deletion strain—tet repressor), and GEVO1751 were transformed with pGV1655 (SEQ ID NO: 109), pGV1698 (SEQ ID NO: 112), and pGV1490 (SEQ ID NO: 104) or pGV1661 (SEQ ID NO: 110). Strains GEVO1725 and GEVO1751 contain the deletions of pyruvate kinase and of the NADH dependent malic enzyme which are part of the pyruvate bypass engineering. All of these transformants were tested in isobutanol fermentations.

The aforementioned strains were grown overnight in two biological replicates for each strain in M9+A5 salts+FeCl3+10 g/L YE media and the appropriate antibiotics in 14 ml snap cap tubes and incubated at 37° C., 250 rpm. Screw cap flasks with 20 ml M9+A5 salts+FeCl3+10 g/L YE media and the appropriate antibiotics were inoculated with overnight culture to an $OD_{600}$ of 0.1. The cells were incubated at 37° C., 250 rpm until they were grown to an $OD_{600}$ of 0.6-0.8 and induced with IPTG [1 mM] and aTc [100 ng/ml]. Afterwards the cultures were incubated at 30° C., 250 rpm. Samples were taken of the medium, at 24 h and 48 h after inoculation. Samples were centrifuged at 15000 g for 1 min to separate the cell pellet from the supernatant and stored in −20° C. until sample submission. The samples were analyzed using High performance liquid chromatography (HPLC) and gas chromatography (GC).

The triple deletion strains GEVO1725 and GEVO1751 have a severe growth defect which is partially rescued by introduction of pGV1661.

The analysis of the fermentation data shows that the partial deletion strain, GEVO1750, with pGV1661 only has negative effects on isobutanol production (Tables 41, 42). However, at the 24 h time point the triple deletion strain with and without the tet repressor (GEVO1725 and GEVO1751 respectively) shows increased yield (Table 41). GEVO1725 shows a 20% increase in yield, with specific productivity similar to the control strain. GEVO1751 shows a 13% increase in yield and specific productivity.

TABLE 41

Analysis of the second pyk bypass fermentation from the 24 hour time point

| Samples 24 h | Volumetric Productivity [g/L/h] | ± | Specific Productivity [g/L/h/OD] | ± | Titer [g/L] | ± | Yield [g/g] | ± |
|---|---|---|---|---|---|---|---|---|
| GEVO1385 + pGV1655, pGV1698, pGV1490 (control) | 0.205 | 0.008 | 0.031 | 0.001 | 4.93 | 0.18 | 0.277 | 0.002 |
| GEVO1385 + pGV1655, pGV1698, pGV1661 (control) | 0.197 | 0.003 | 0.028 | 0.002 | 4.65 | 0.01 | 0.285 | 0.035 |
| GEVO1725 + pGV1655, pGV1698, pGV1490 | 0.125 | 0.009 | 0.034 | 0.005 | 2.83 | 0.19 | 0.331 | 0.029 |
| GEVO1725 + pGV1655, pGV1698, pGV1661 | 0.184 | 0.002 | 0.031 | 0.001 | 4.16 | 0.04 | 0.333 | 0.004 |
| GEVO1750 + pGV1655, pGV1698, pGV1490 | 0.144 | 0.004 | 0.022 | 0.001 | 3.30 | 0.14 | 0.267 | 0.001 |
| GEVO1750 + pGV1655, pGV1698, pGV1661 | 0.080 | 0.005 | 0.013 | 0.001 | 1.84 | 0.09 | 0.305 | |
| GEVO1751 + pGV1655, pGV1698, pGV1490 | 0.138 | 0.006 | 0.031 | 0.001 | 3.09 | 0.13 | 0.303 | 0.008 |
| GEVO1751 + pGV1655, pGV1698, pGV1661 | 0.204 | 0.004 | 0.035 | 0.001 | 4.55 | 0.08 | 0.318 | 0.006 |

TABLE 42

Analysis of the second pyk bypass fermentation from the 48 hour time point

| Samples 48 h | Volumetric Productivity [g/L/h] | ± | Specific Productivity [g/L/h/OD] | ± | Titer [g/L] | ± | Yield [g/g] | ± |
|---|---|---|---|---|---|---|---|---|
| GEVO1385 + pGV1655, pGV1698, pGV1490 (control) | 0.128 | 0.011 | 0.023 | 0.002 | 6.14 | 0.53 | 0.271 | 0.004 |
| GEVO1385 + pGV1655, pGV1698, pGV1661 (control) | 0.141 | 0.029 | 0.023 | 0.005 | 6.75 | 1.41 | 0.263 | 0.002 |
| GEVO1725 + pGV1655, pGV1698, pGV1490 | 0.070 | 0.002 | 0.024 | 0.002 | 3.25 | 0.10 | 0.299 | 0.009 |
| GEVO1725 + pGV1655, pGV1698, pGV1661 | 0.101 | 0.006 | 0.024 | 0.002 | 4.72 | 0.28 | 0.309 | 0.005 |
| GEVO1750 + pGV1655, pGV1698, pGV1490 | 0.102 | 0.013 | 0.018 | 0.002 | 4.77 | 0.54 | 0.277 | 0.013 |
| GEVO1750 + pGV1655, pGV1698, pGV1661 | 0.085 | 0.003 | 0.015 | 0.001 | 4.02 | 0.13 | 0.261 | 0.018 |
| GEVO1751 + pGV1655, pGV1698, pGV1490 | 0.093 | 0.004 | 0.029 | 0.001 | 4.29 | 0.16 | 0.267 | 0.006 |
| GEVO1751 + pGV1655, pGV1698, pGV1661 | 0.123 | 0.002 | 0.041 | 0.001 | 5.68 | 0.06 | 0.302 | 0.009 |

Figure 20:
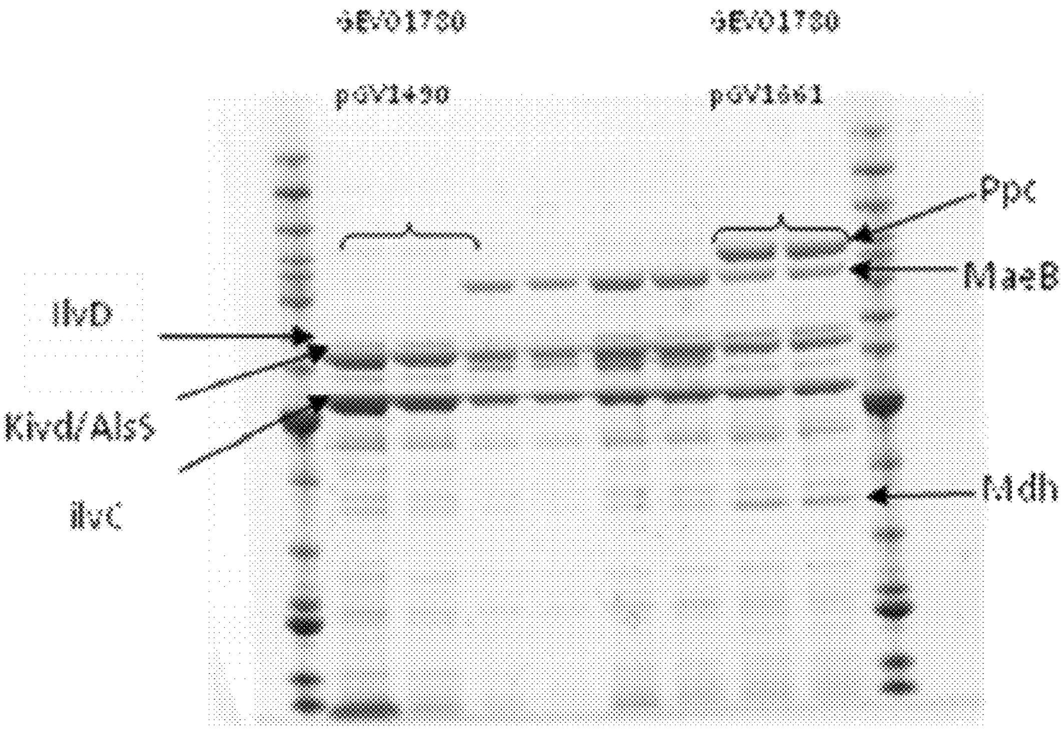
FIG. 20 illustrates a protein gel of cell lysates from the production strain GEVO1780 harboring the plasmids pGV1490, or pGV1661.
Figure 21:
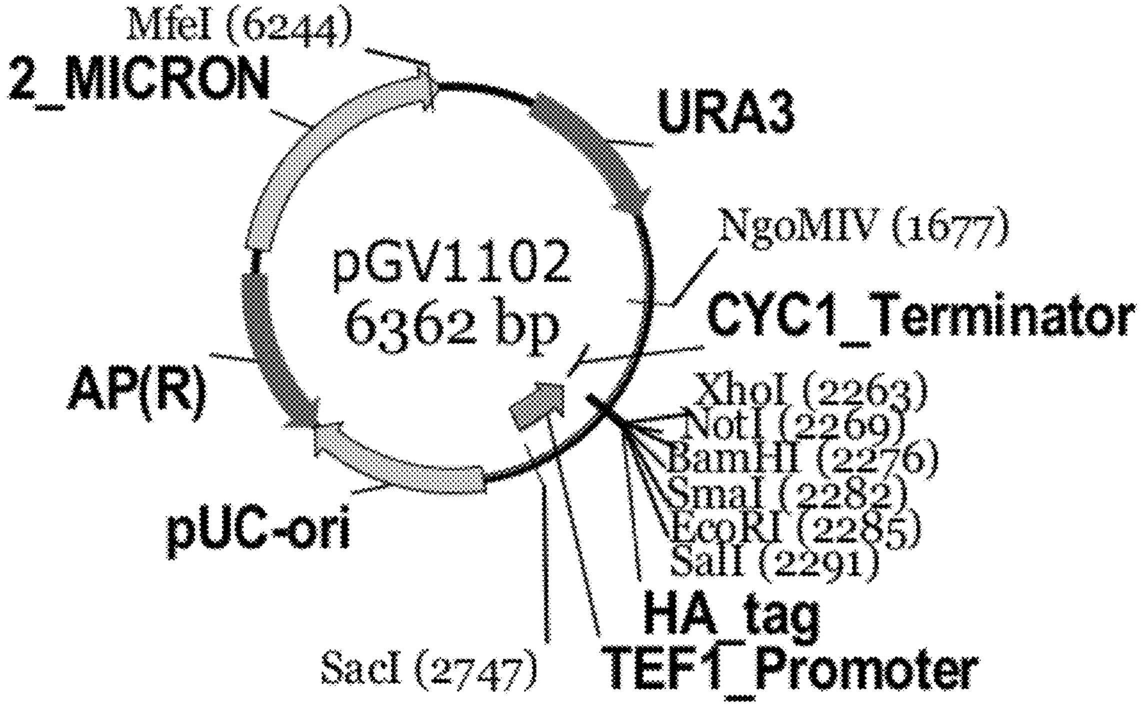
FIG. 21 illustrates plasmid pGV1102 (SEQ ID NO: 101).
Figure 22:
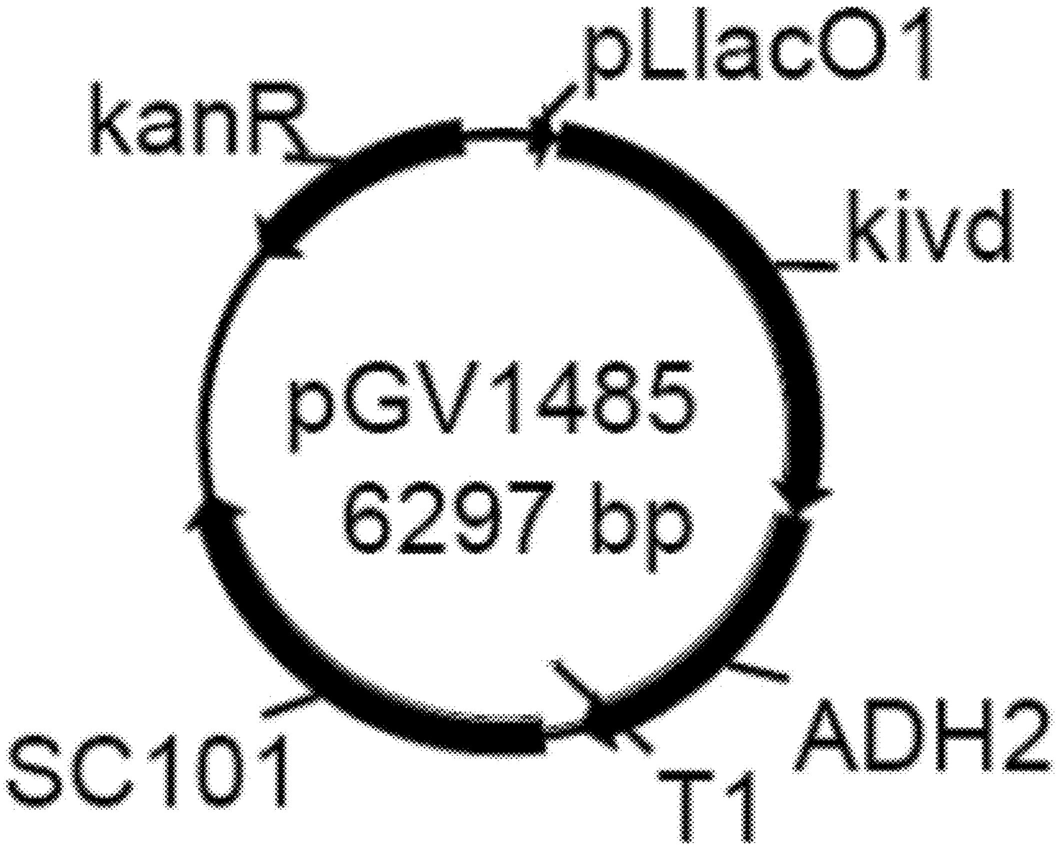
FIG. 22 illustrates plasmid pGV1485 (SEQ ID NO: 103).
Figure 23:
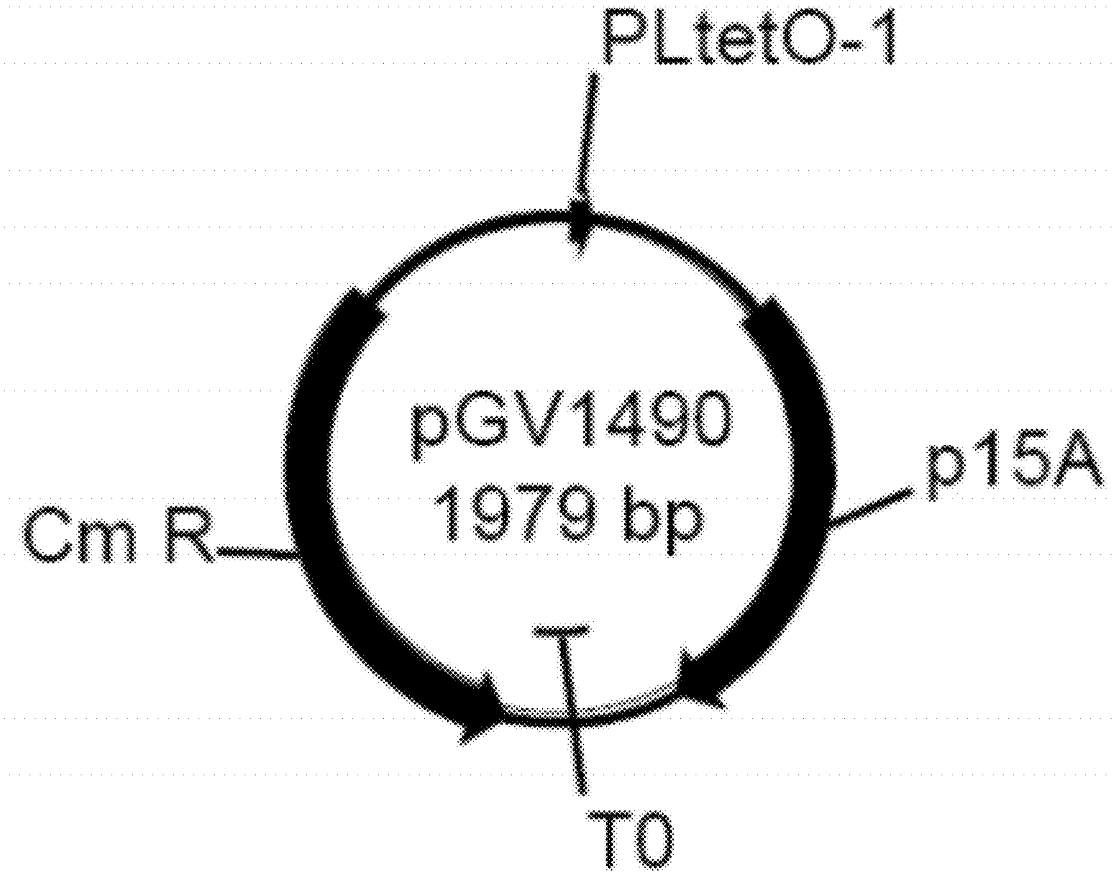
FIG. 23 illustrates plasmid pGV1490 (SEQ ID NO: 104).
Figure 24:
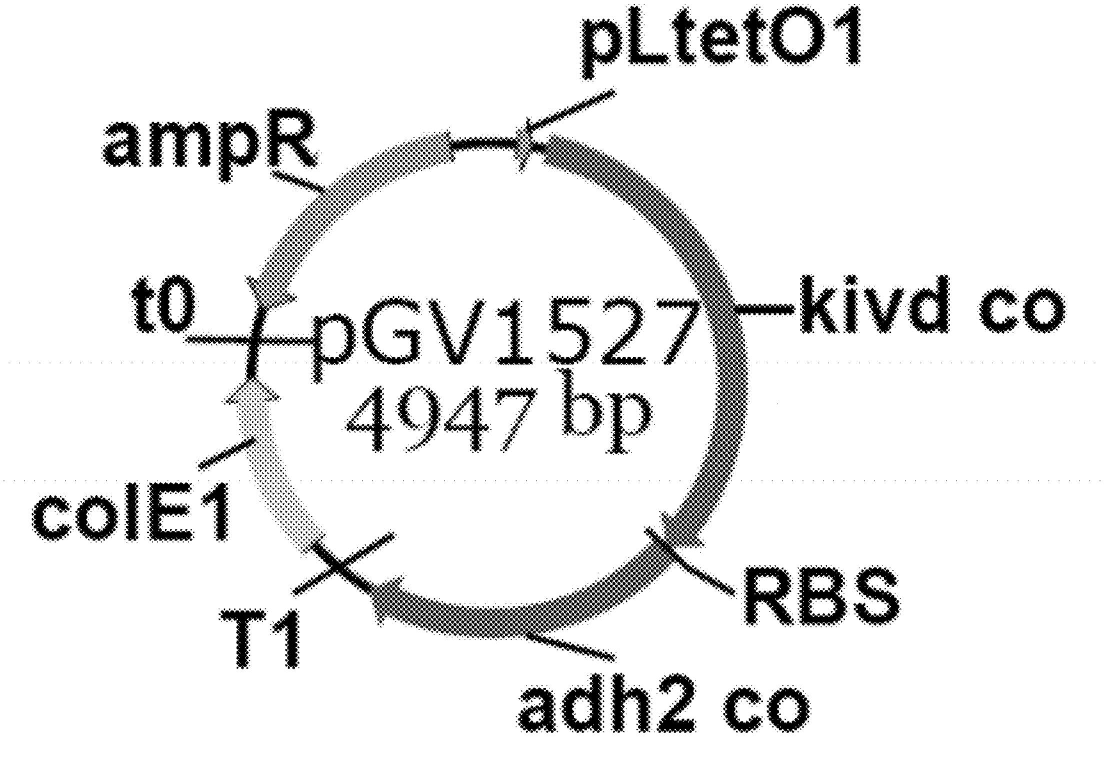
FIG. 24 illustrates plasmid pGV1527.
Figure 25:
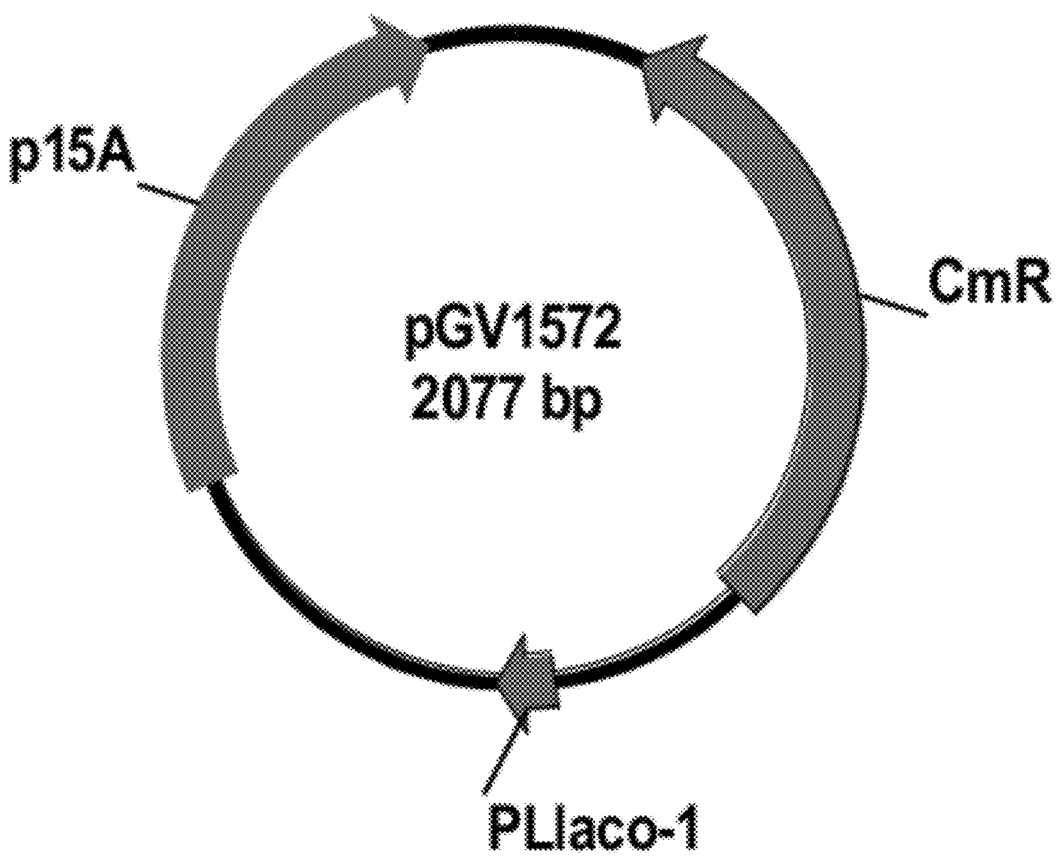
FIG. 25 illustrates plasmid pGV1572 (SEQ ID NO: 105).
Figure 26:
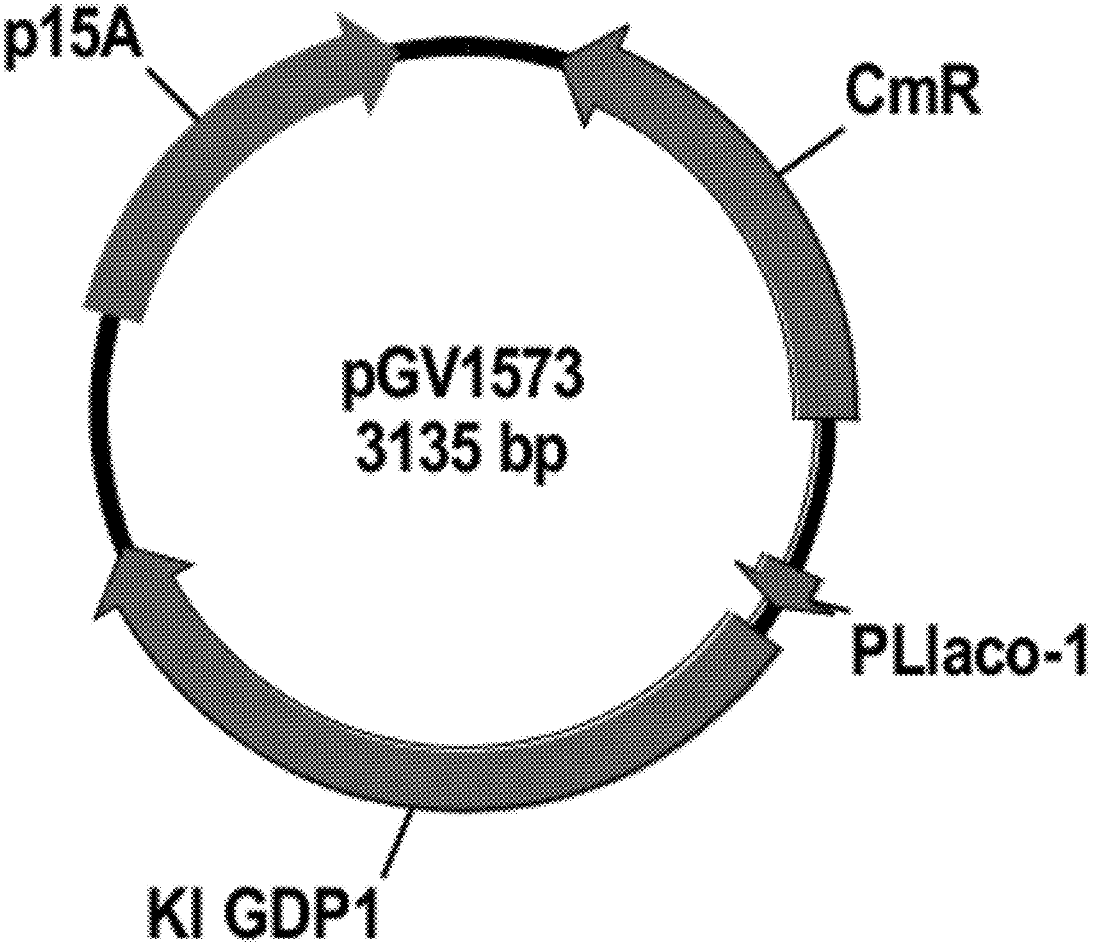
FIG. 26 illustrates plasmid pGV1573 (SEQ ID NO: 106).
Figure 27:
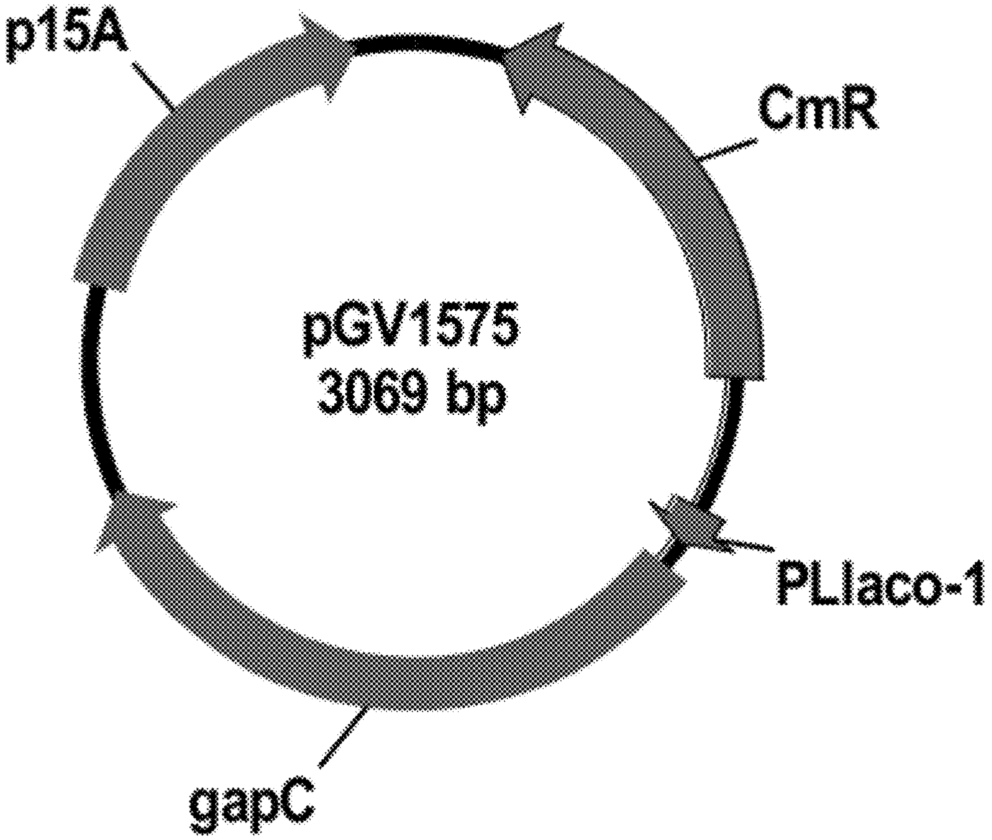
FIG. 27 illustrates plasmid pGV1575 (SEQ ID NO: 107).
Figure 28:
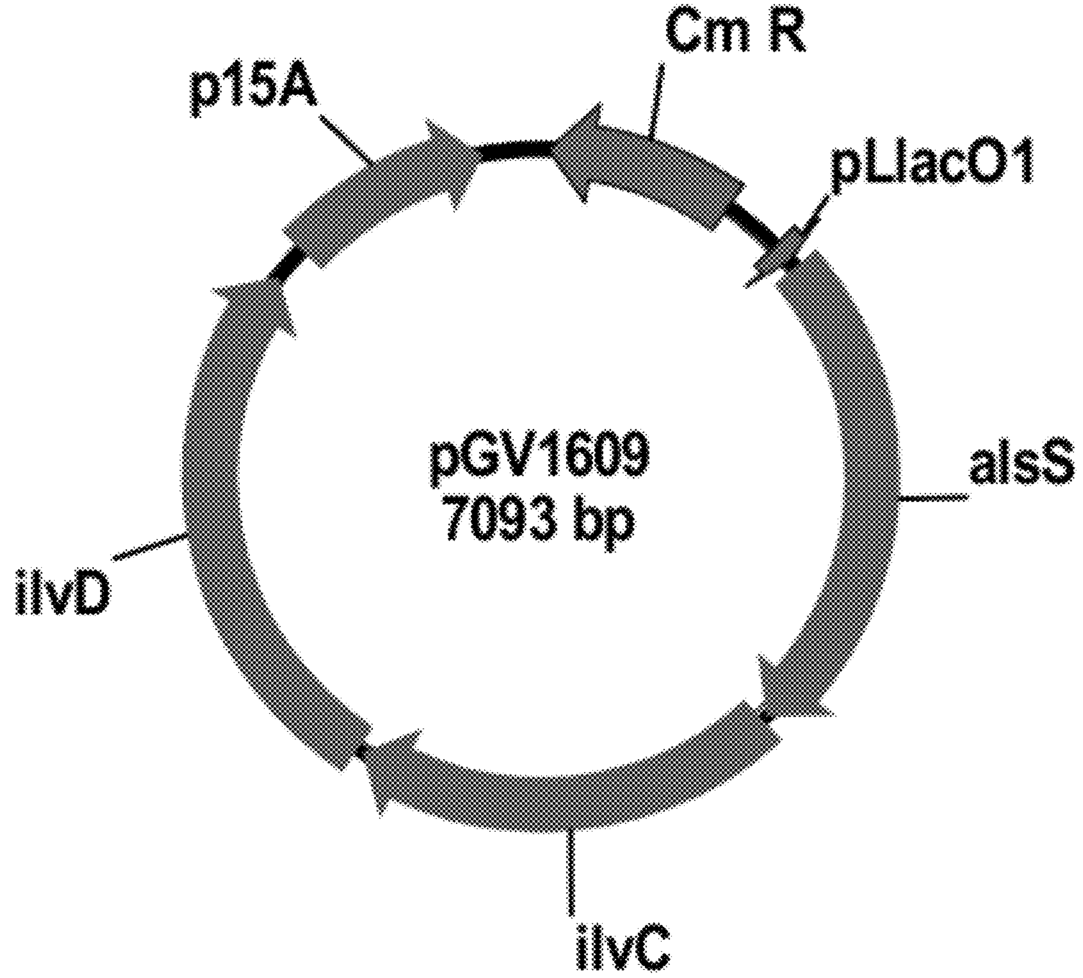
FIG. 28 illustrates plasmid pGV1609 (SEQ ID NO: 108).
Figure 29:
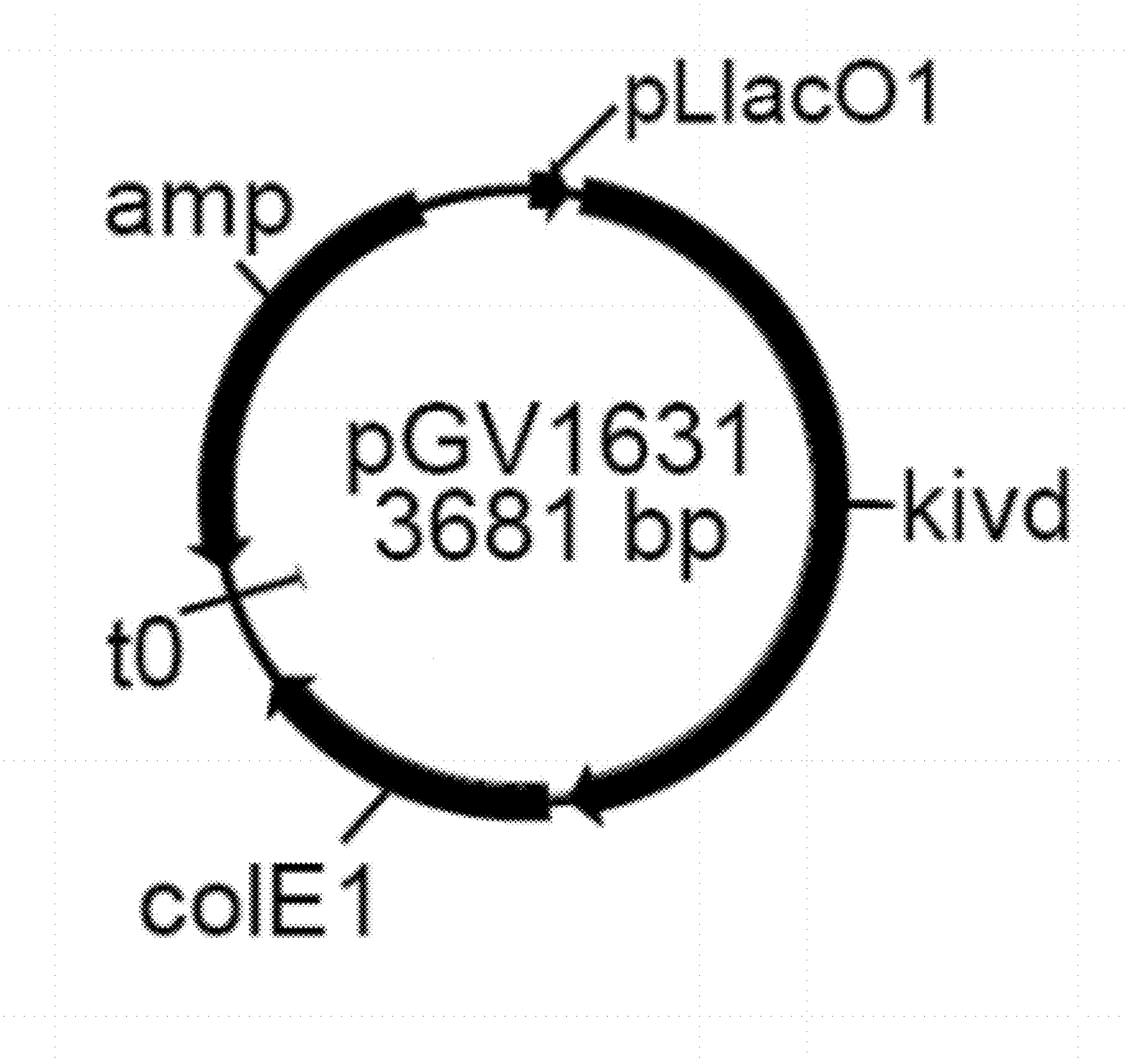
FIG. 29 illustrates plasmid pGV1631.
Figure 30:
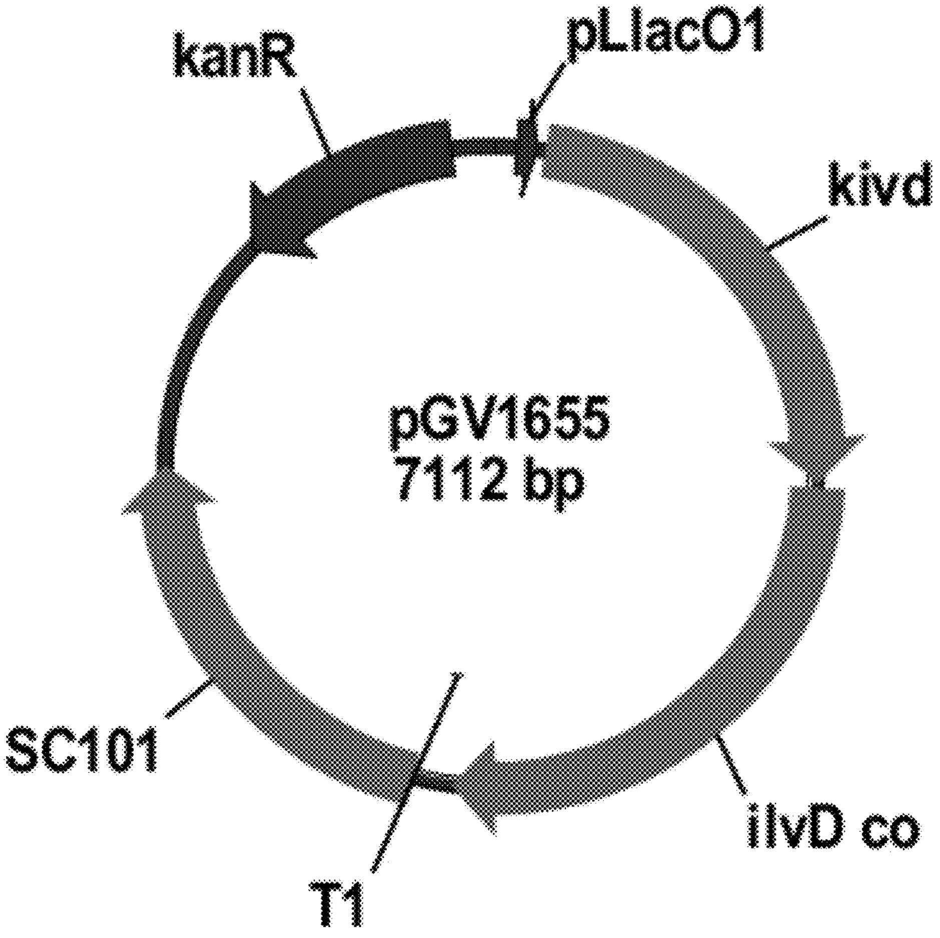
FIG. 30 illustrates plasmid pGV1655 (SEQ ID NO: 109).
Figure 31:
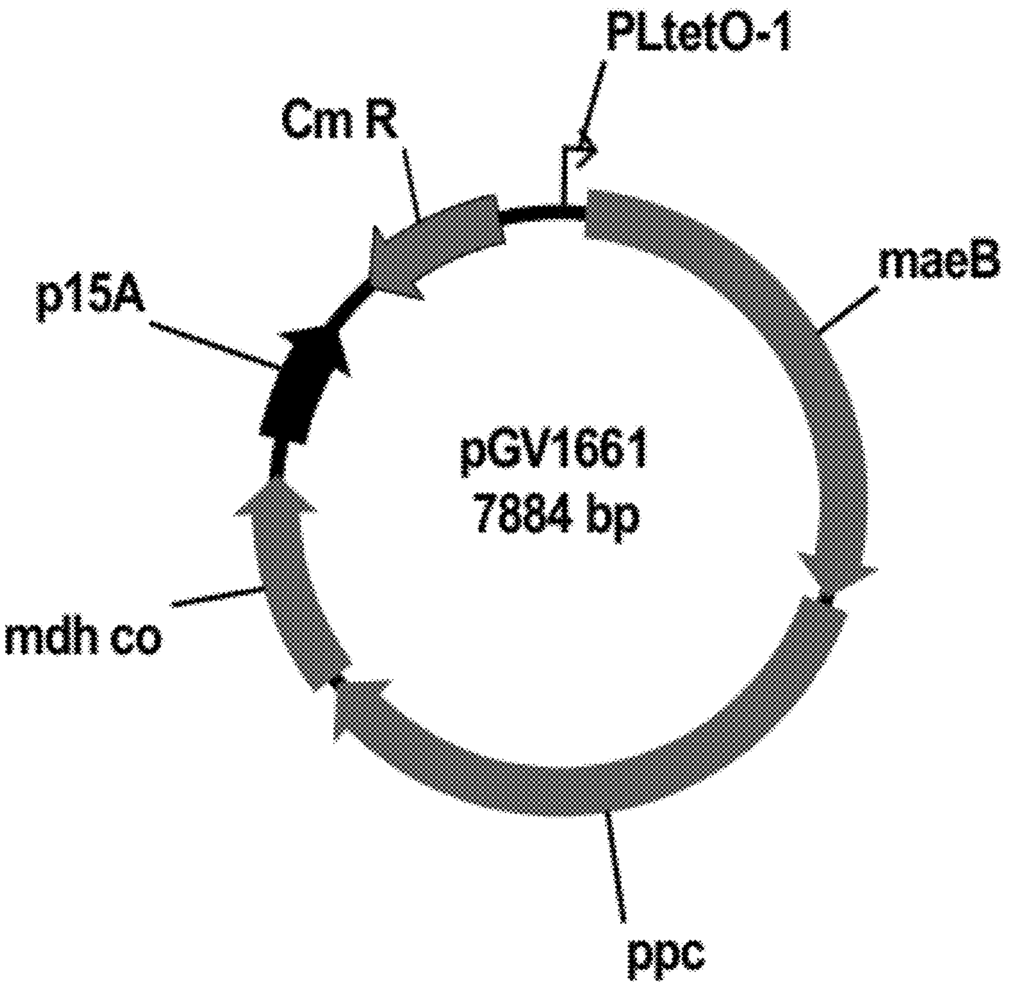
FIG. 31 illustrates plasmid pGV1661 (SEQ ID NO: 110).
Figure 32:
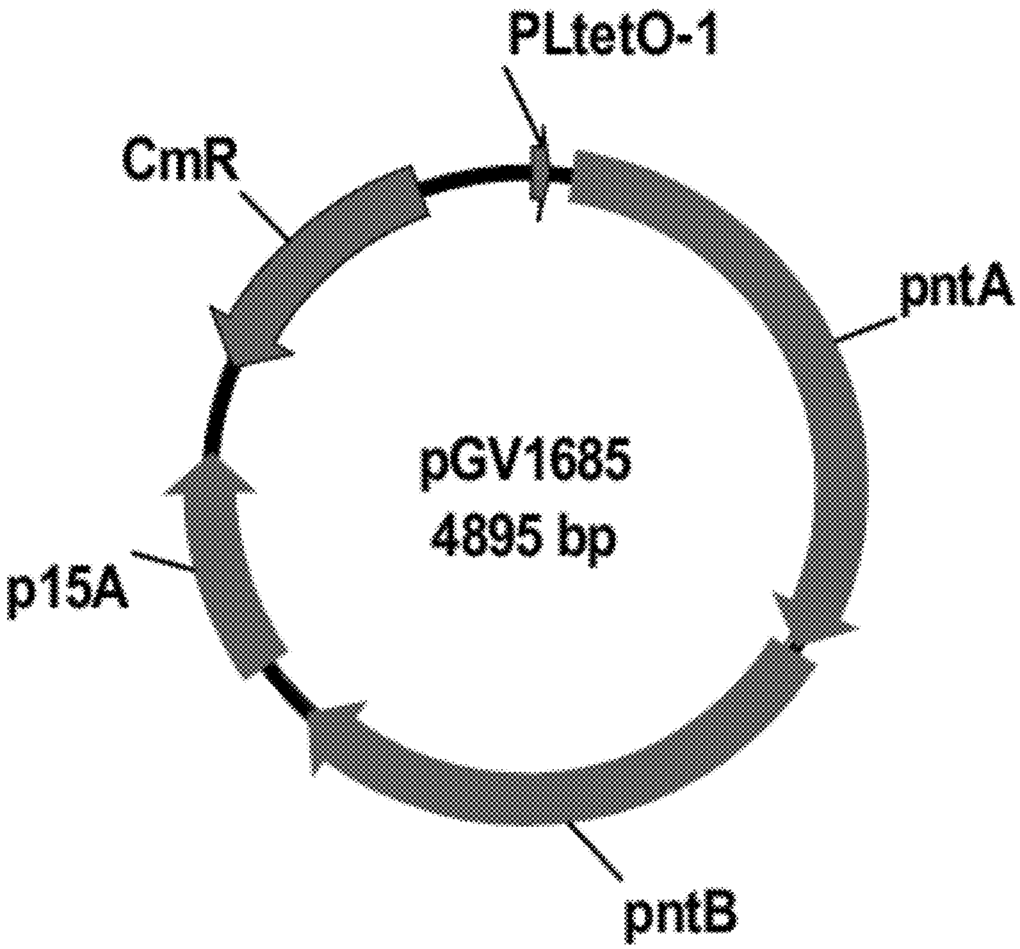
FIG. 32 illustrates plasmid pGV1685 (SEQ ID NO: 111).
Figure 33:
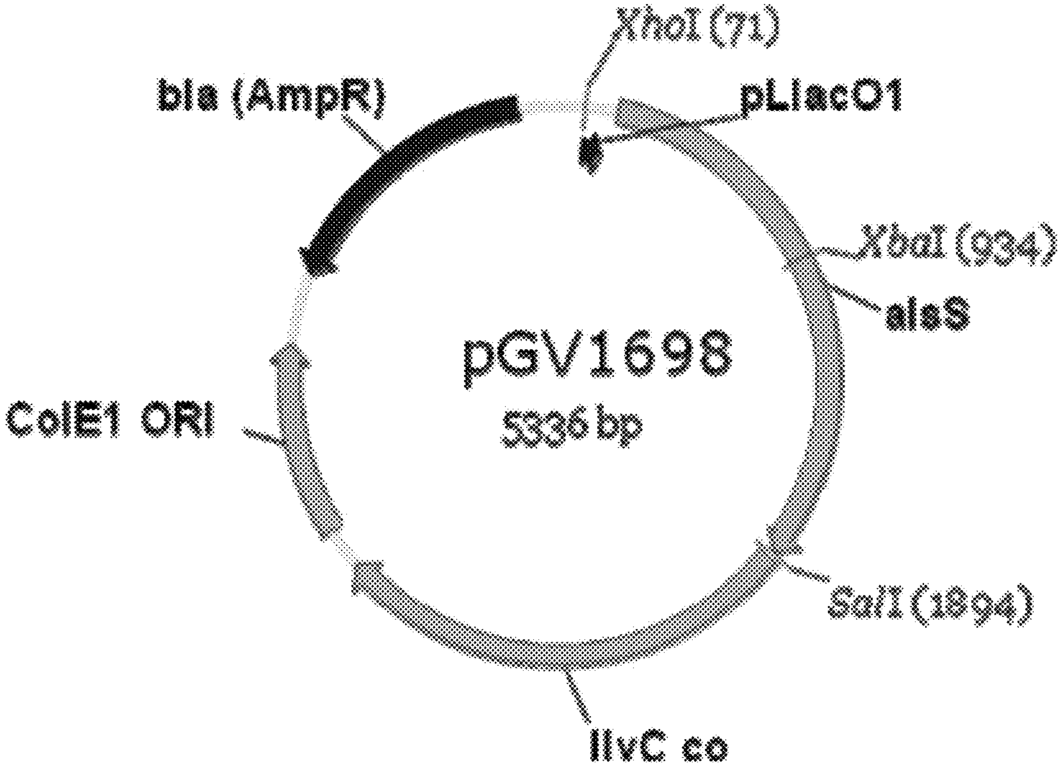
FIG. 33 illustrates plasmid pGV1698 (SEQ ID NO: 112).
Figure 34:
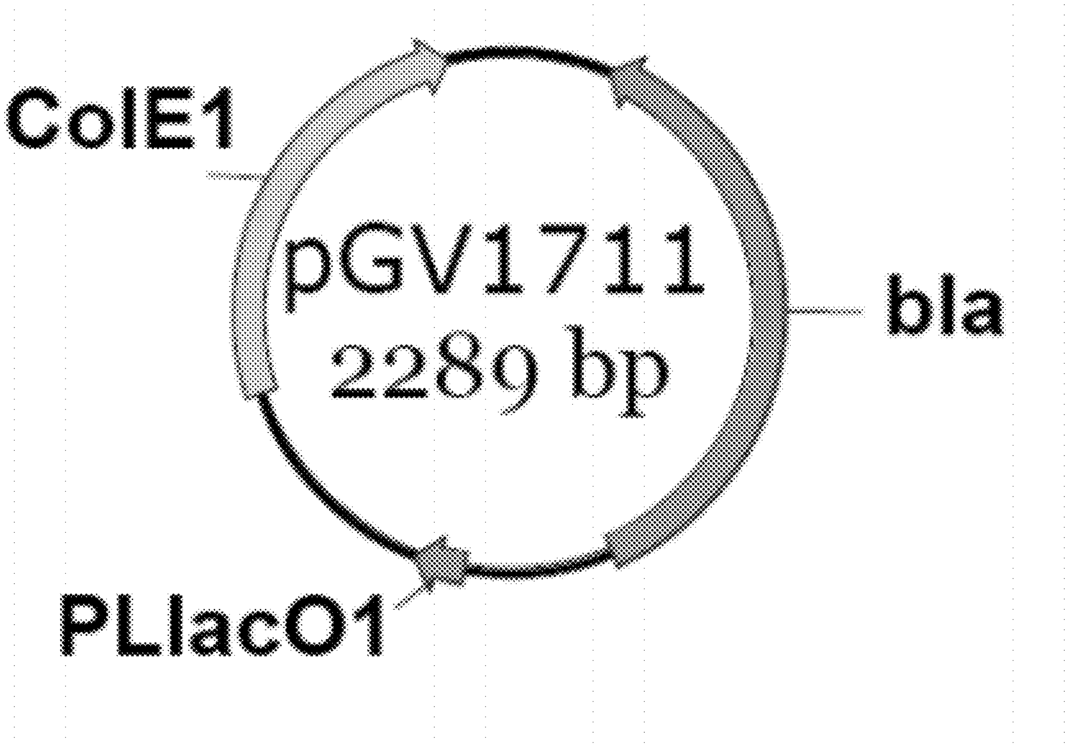
FIG. 34 illustrates plasmid pGV1711 (SEQ ID NO: 113).
Figure 35:
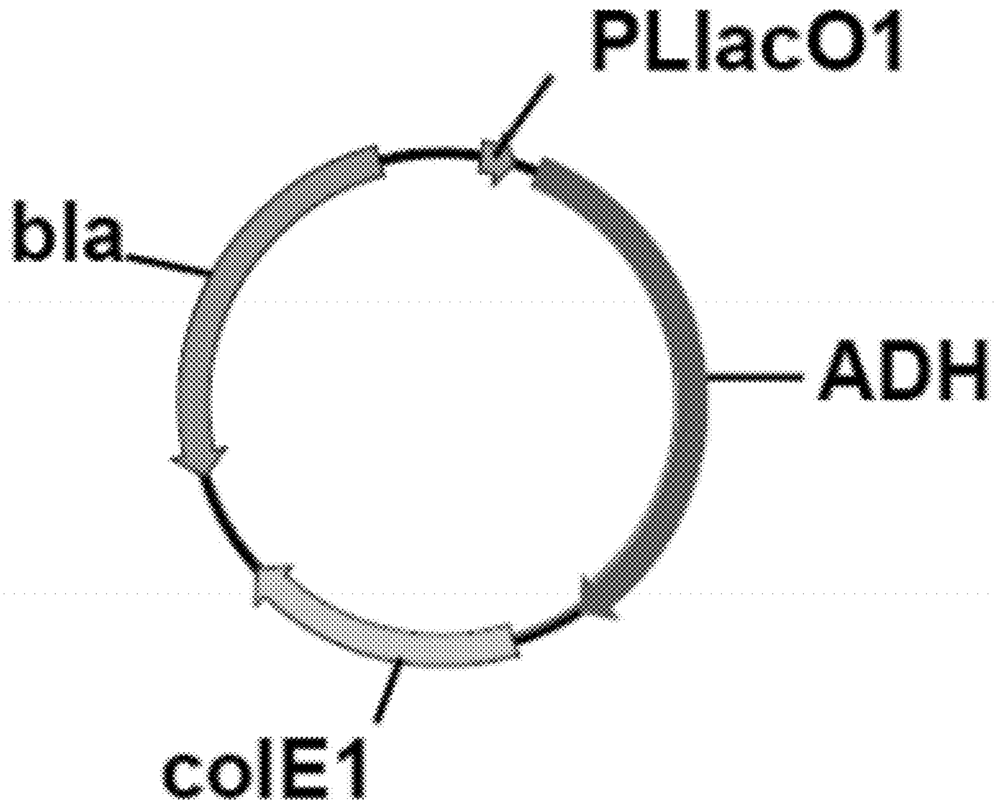
FIG. 35 illustrates plasmids pGV1705-A, pGV1748-A, pGV1749-A, and pGV1778-A carrying the ADH genes Ec_yqhD, Ec_fucO, Dm_ADH, and Kp_dhaT, respectively.
Figure 36:
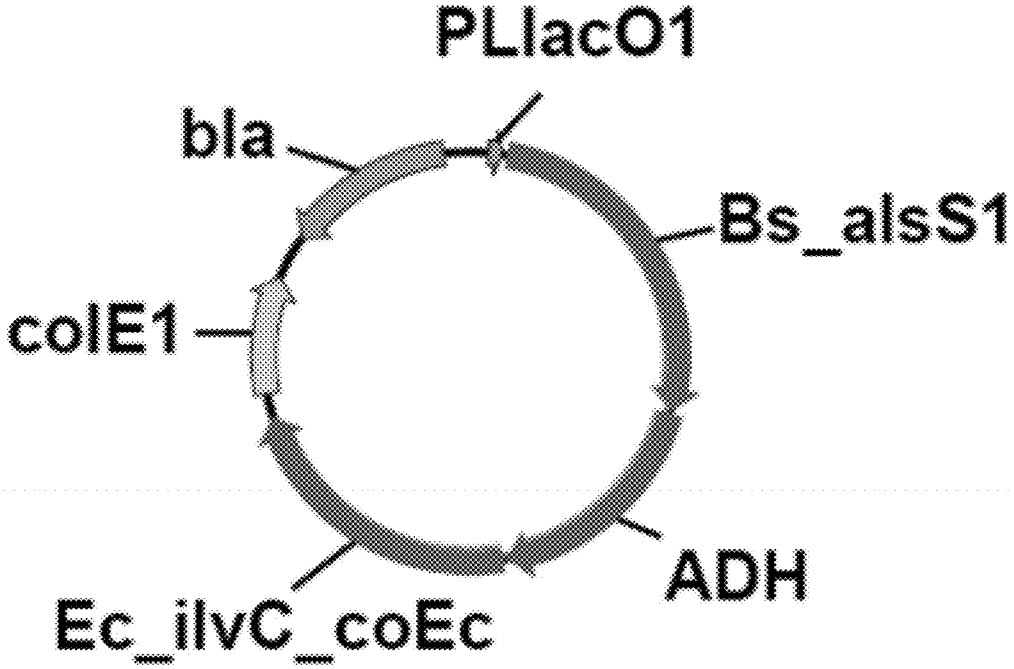
FIG. 36 illustrates plasmids pGV1748, pGV1749, and pGV1778 carrying the ADH genes Ec_fucO, Dm_ADH, and Kp_dhaT, respectively.
Figure 37:
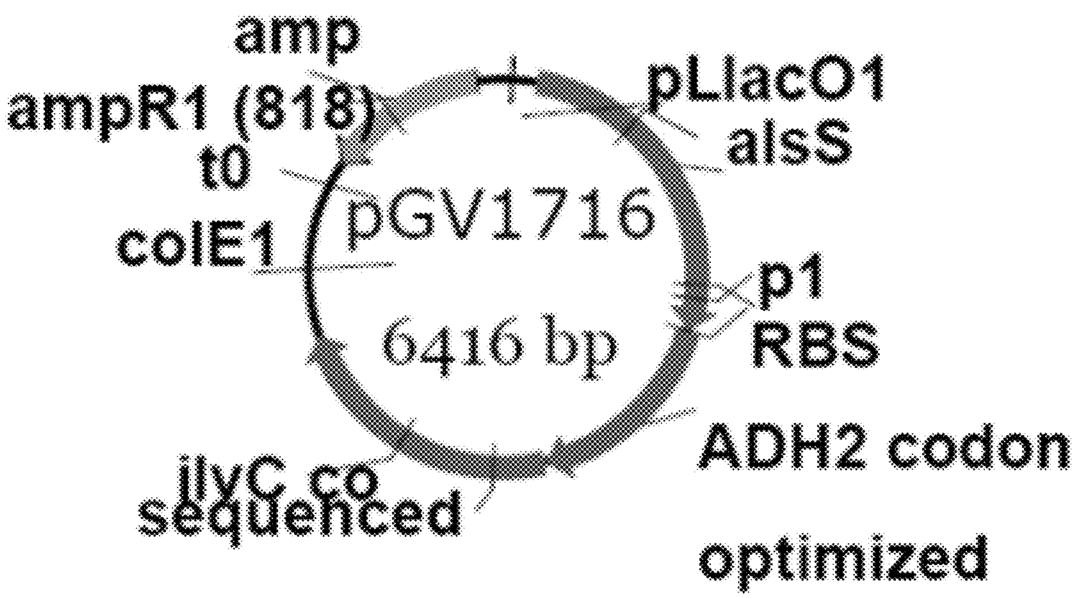
FIG. 37 illustrates plasmid pGV1716 (SEQ ID NO: 114).
Figure 38:
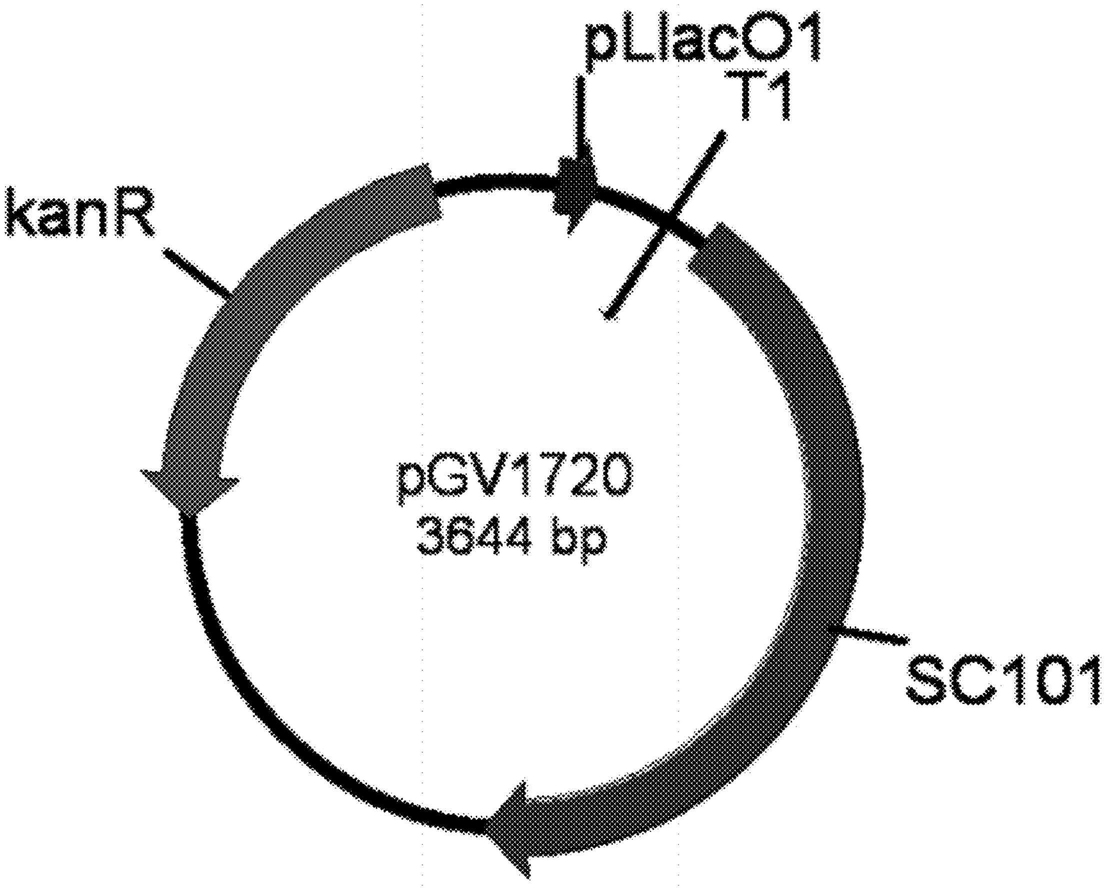
FIG. 38 illustrates plasmid pGV1720 (SEQ ID NO: 115).
Figure 39:
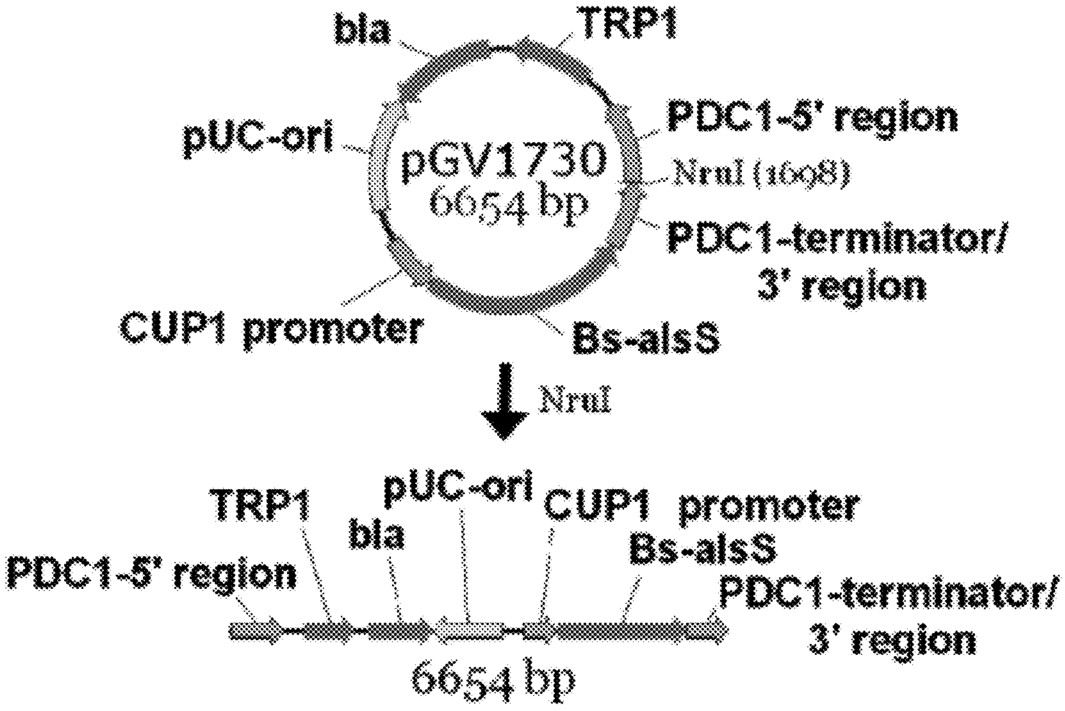
FIG. 39 illustrates plasmid pGV1730 (SEQ ID NO: 116) and linearization for integration by NruI digest (SEQ ID NO: 116).
Figure 40:
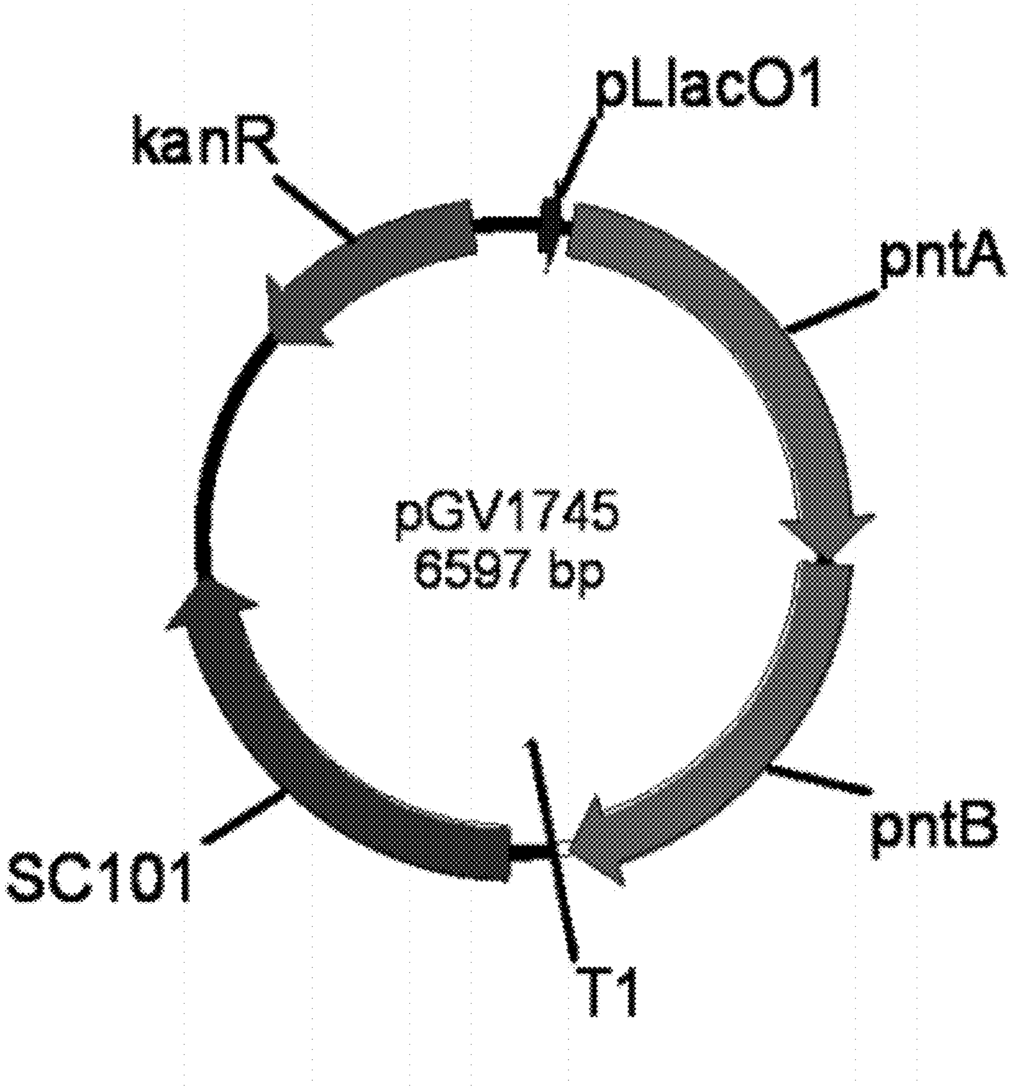
FIG. 40 illustrates plasmid pGV1745 (SEQ ID NO: 117).
Figure 41:
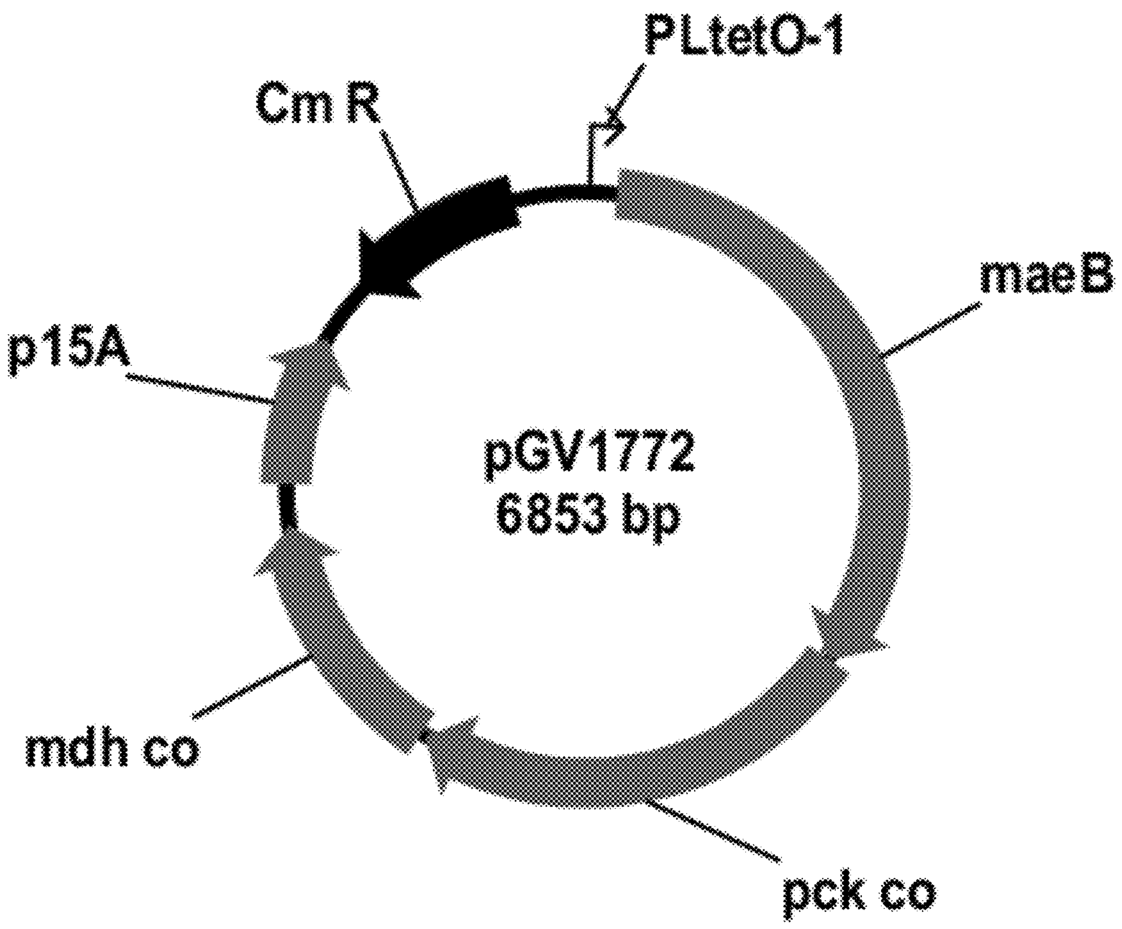
FIG. 41 illustrates plasmid pGV1772.
Figure 42:
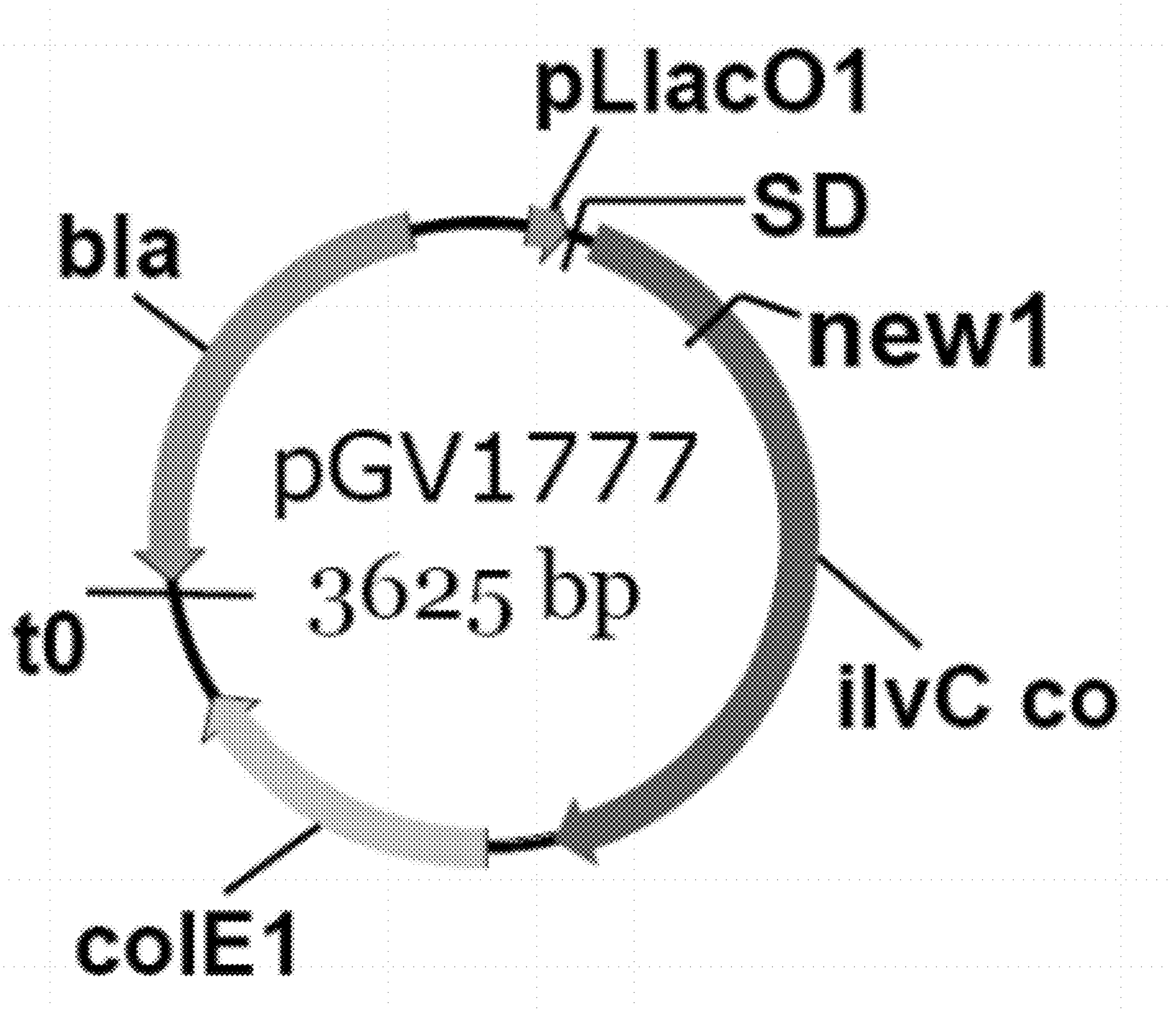
FIG. 42 illustrates plasmid pGV1777 (SEQ ID NO: 118).
Figure 43:
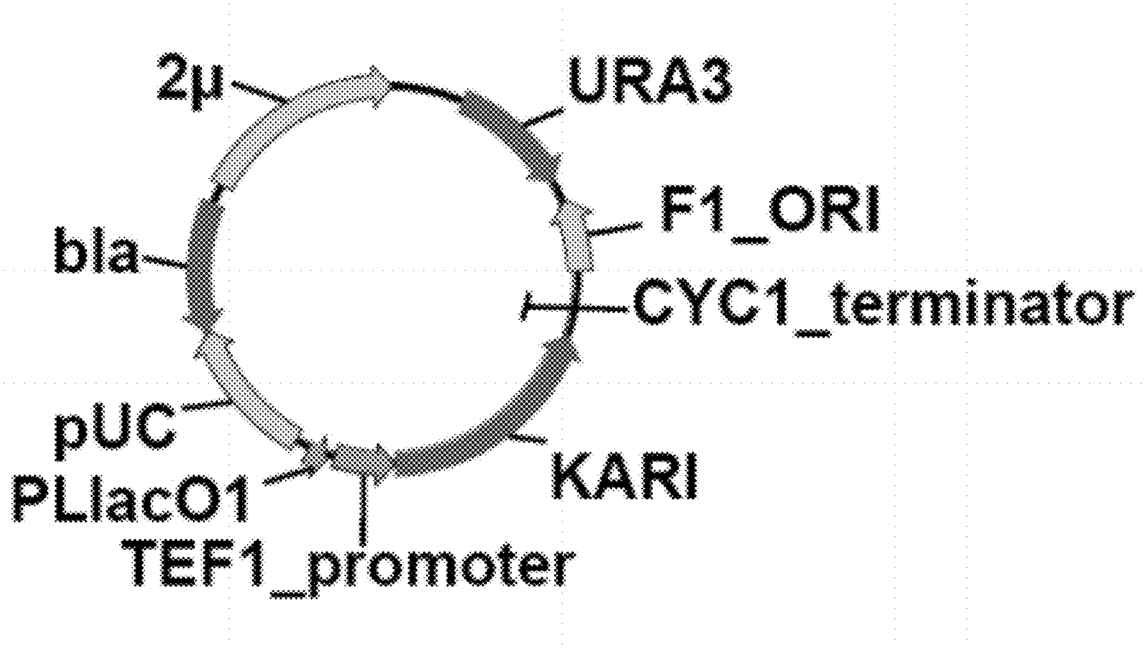
FIG. 43 illustrates plasmids pGV1824, pGV1994, pGV2193, pGV2238, and pGV2241 carrying the KARI genes Ec_ilvC_coSc, Ec_ilvC_coSc$^{6E6}$, Ec_ilvC_coSc$^{P2D1\text{-}his6}$, Ec_ilvC_coSc$^{P2D1\text{-}A1\text{-}his6}$, and Ec_ilvC_coSc$^{6E6\text{-}his6}$, respectively.
Figure 44:
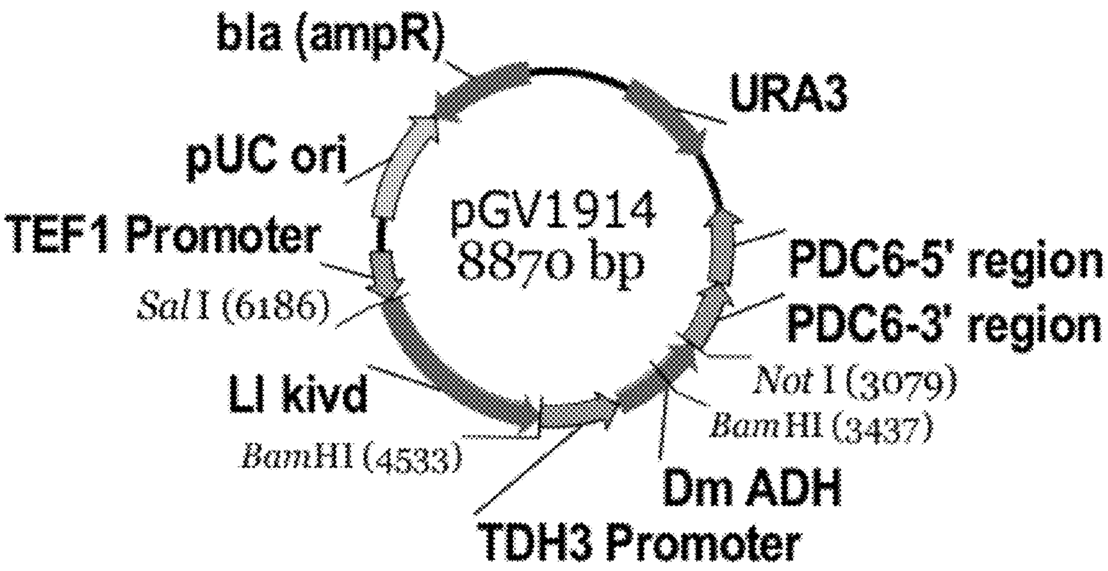
FIG. 44 illustrates plasmid pGV1914 (SEQ ID NO: 119).
Figure 45:
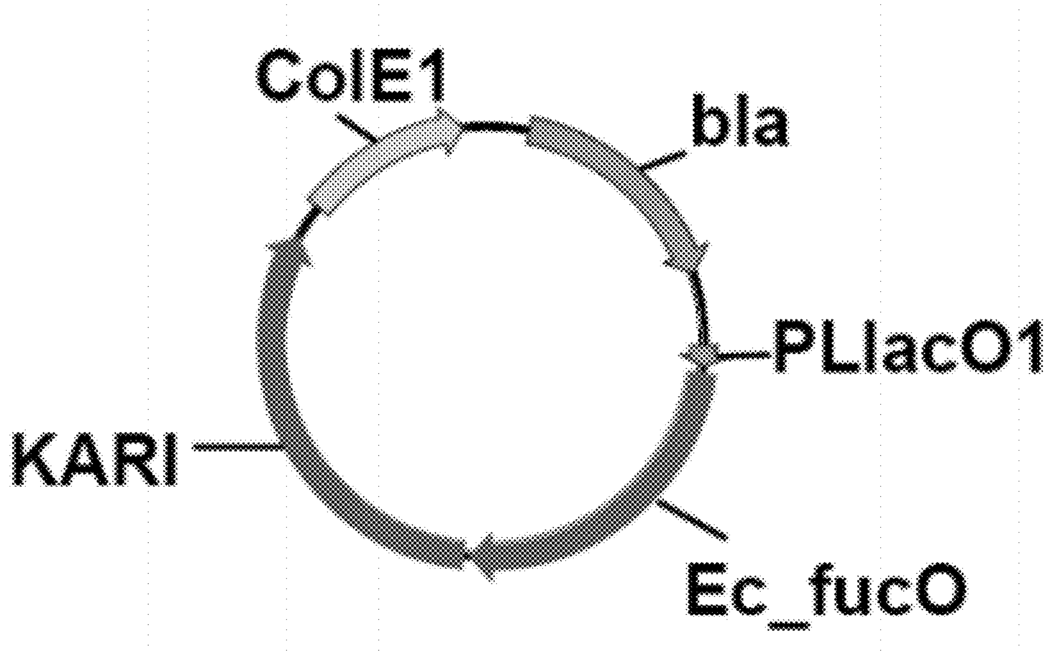
FIG. 45 illustrates plasmids pGV1925, pGV1927, pGV1975 and pGV1776 carrying the Ec_fucO in combination with KARI genes Ec_ilvC_coEc, Ec_ilvC_coEc$^{S78D}$, Ec_ilvC_coEc$^{6E6}$ and Ec_ilvC_coEc$^{2H10}$, respectively.
Figure 46:
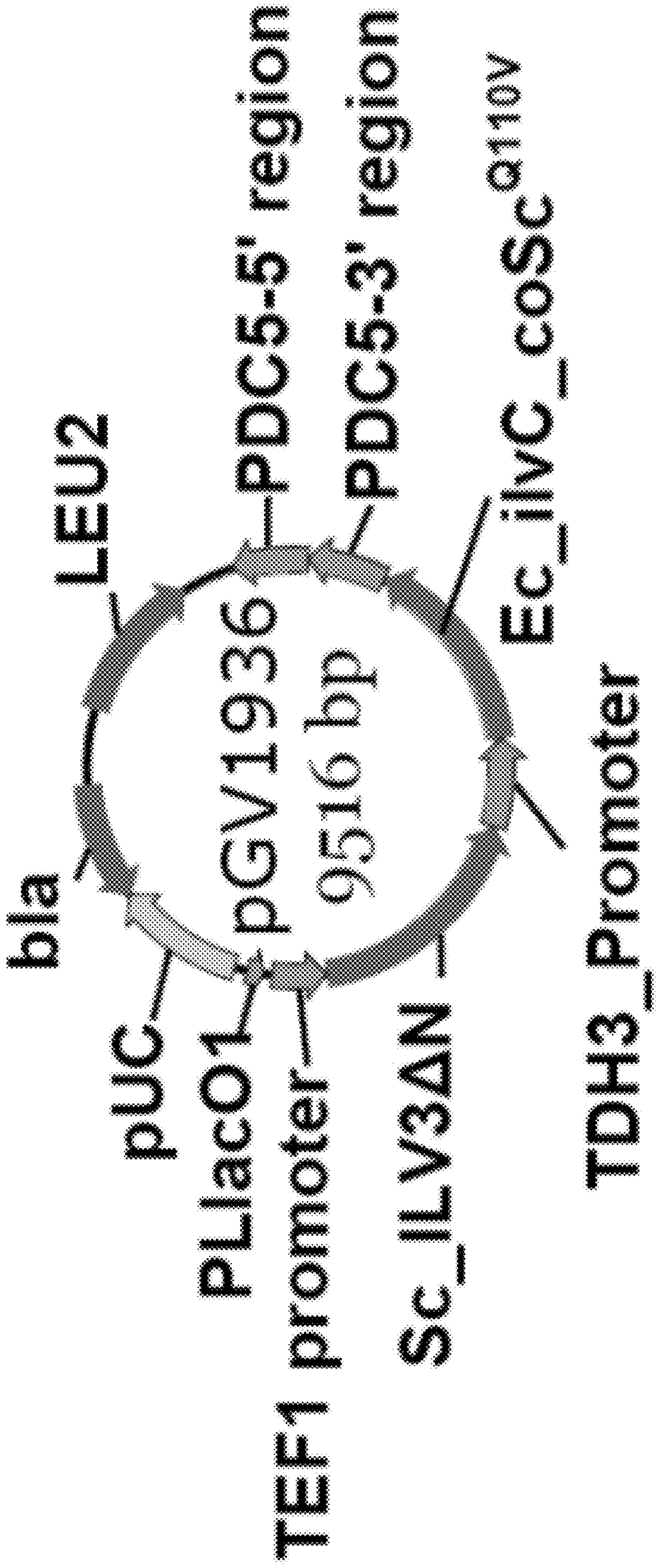
FIG. 46 illustrates plasmid pGV1936 (SEQ ID NO: 120).
Figure 47:
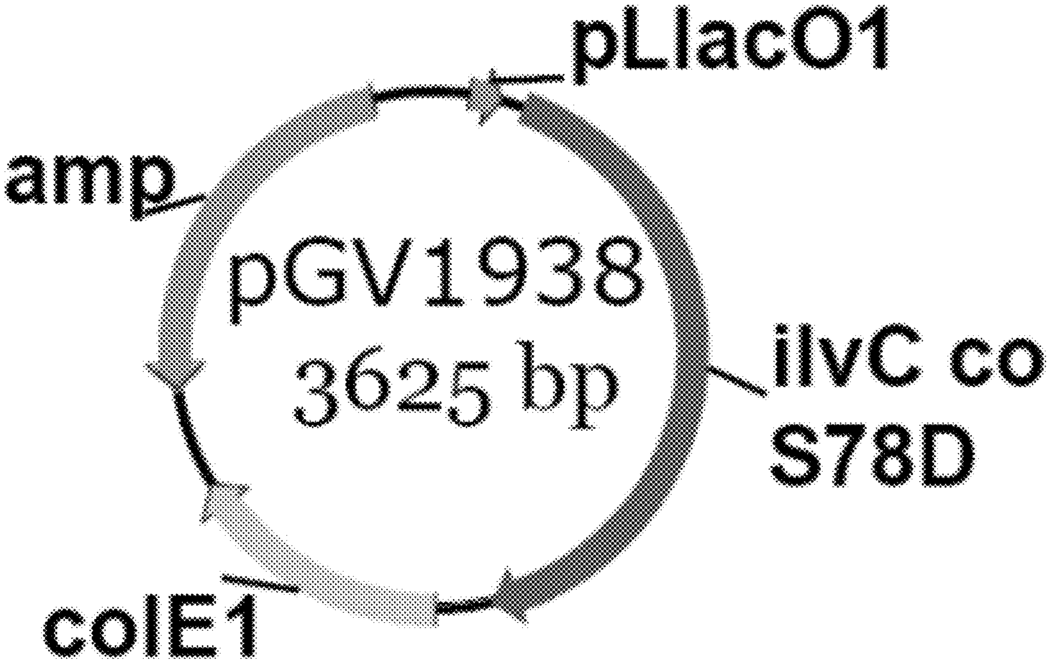
FIG. 47 illustrates plasmid pGV1938.
Figure 48:
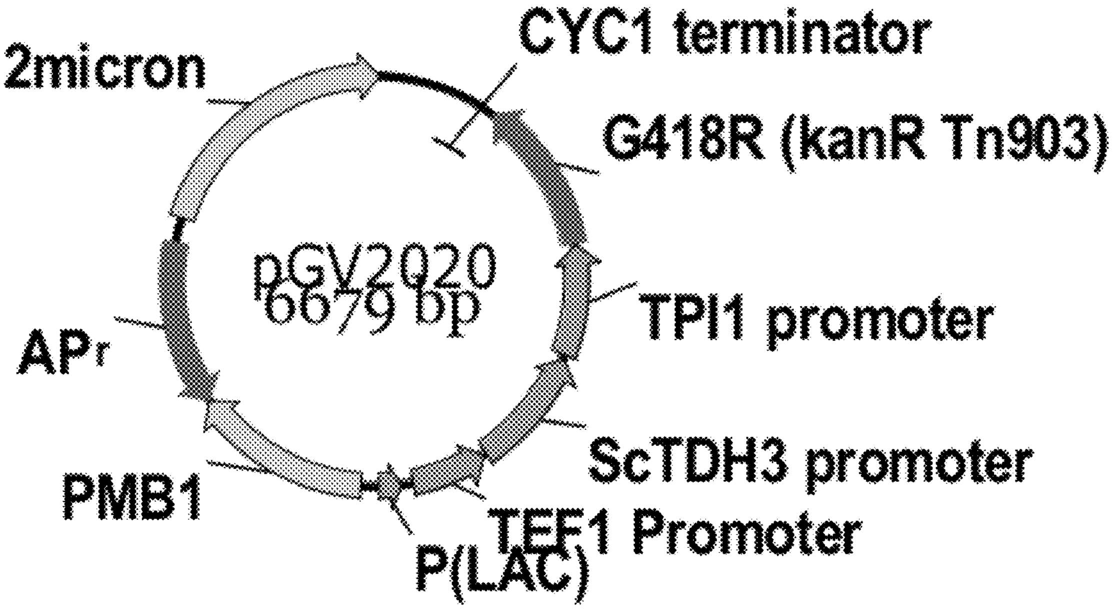
FIG. 48 illustrates plasmid pGV2020 (SEQ ID NO: 121).
Figure 49:
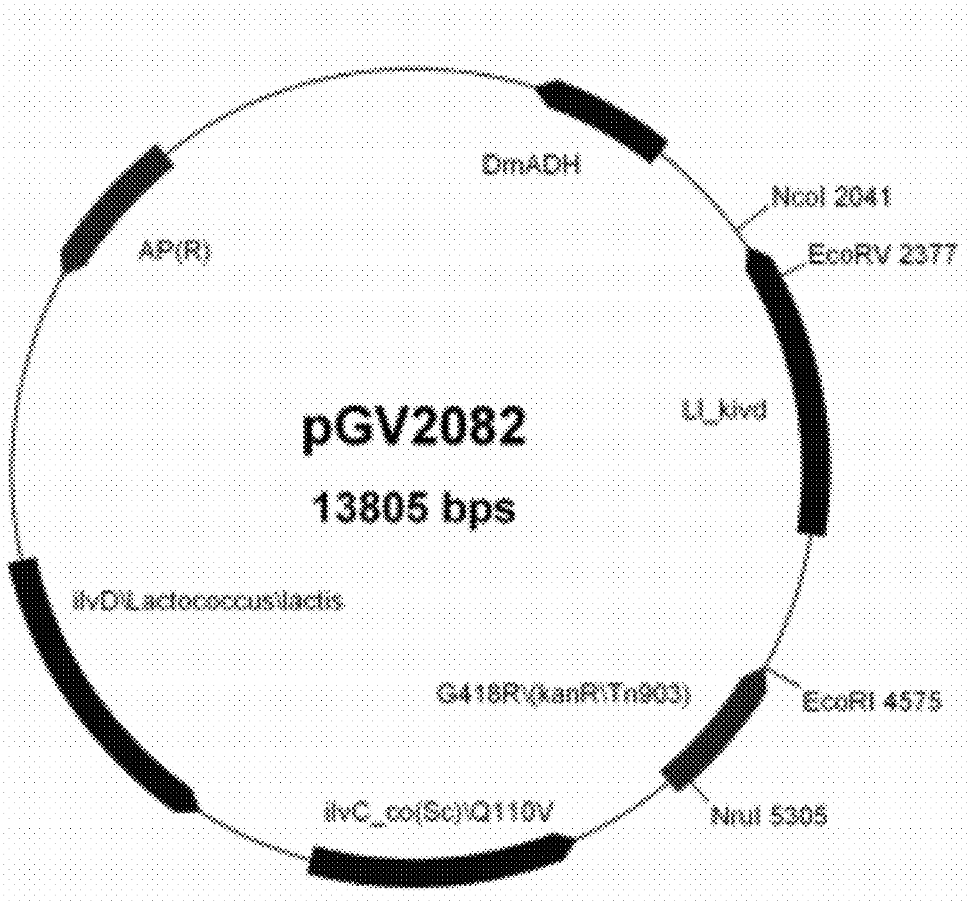
FIG. 49 illustrates plasmid pGV2082 (SEQ ID NO: 122).
Figure 50:
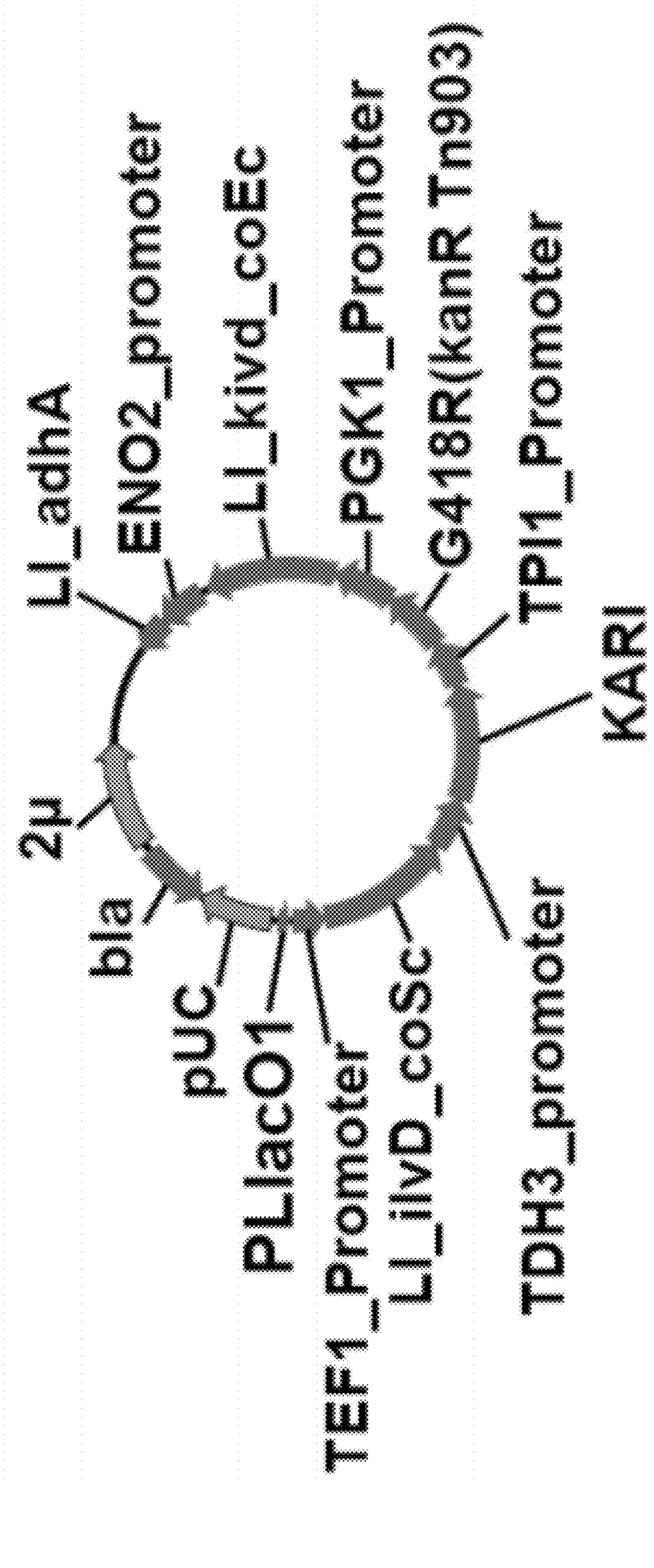
FIG. 50 illustrates plasmids pGV2227 (SEQ ID NO: 123), pGV2242 (SEQ ID NO: 125) carrying the KARI genes Ec_ilvC_coScQ110V and Ec_ilvC_coSc$^{P2D1}$, respectively.

To verify that maeB, ppc, and mdh were expressed, cell lysates were made from GEVO1780 transformed with the above plasmids and run on a protein gel (FIG. 20).

The gel shows that all pathway enzymes are expressed in GEVO1780 with pGV1490 (Ec_llvD=65.5 kD, Ll_Kivd1/Bs_AlsS1=60.9 kD, Ec_llvC=54.1 kD). The gel also shows that all pathway enzymes and Ppc (99 kD), MaeB (82 kD), and Mdh (32 kD) are expressed in GEVO1780 with pGV1661.

Example 23 pyk Bypass 2

This example illustrates that an isobutanol producing microorganism which is engineered to bypass the pyruvate kinase reaction shows increased productivity, titer and yield of isobutanol compared to the control strain without overexpression of ppc or pck.

Both plasmid constructs (pGV1661 (SEQ ID NO: 110) and pGV1772) were sequence verified. GEVO1725, and GEVO1751 were transformed with isobutanol pathway plasmids pGV1655 (SEQ ID NO: 109) and pGV1698 (SEQ ID NO: 112), and pyk bypass plasmids pGV1661 (ppc) or pGV1772 (pck). The controls were the same strains and pathway plasmids, but with the empty vector, pGV1490 (SEQ ID NO: 104), in place of pGV1661 or pGV1772. Strains GEVO1725 and GEVO1751 have deletions of pyruvate kinase (pykAF) and of the NADH dependent malic enzyme, maeA, which are part of the pyruvate kinase bypass engineering. The difference between GEVO1725 and GEVO1751 is that GEVO1725 does not have the tet repressor, and therefore, pGV1490, pGV1661, and pGV1772 are constitutively expressed in this strain.

All of these transformants were tested in isobutanol fermentations.

Overnight cultures were started in duplicate for each transformation in 3 mL M9+A5 salts+$FeCl_3$+10 g/L YE media and the appropriate antibiotics in 14 mL snap cap tubes and incubated at 37° C., 250 rpm. Screw cap flasks with 20 mL M9+A5 salts+$FeCl_3$+10 g/L YE media and the appropriate antibiotics were inoculated to a starting $OD_{600}$ of 0.1 with overnight culture. The cells were incubated at 37° C., 250 rpm until they reached an $OD_{600}$ of 0.6-0.8 and were then induced with IPTG [1 mM] and aTc [1 ng/mL]. After induction, the cultures were switched to incubation at 30° C., 250 rpm. Samples were taken of the cultures at 24 and 48 hours after inoculation and $OD_{600}$ and pH were measured. Samples were centrifuged at 22,000×g for 5 min and the supernatant was collected and stored at −20° C. until sample submission. After 48 hour samples were taken, the remainder of the culture was transferred to a 50 ml tube, centrifuged at 4000×g, for 10 min at 4° C. The supernatant was removed, and the cell pellet was stored at −80° C. The samples were analyzed using High performance liquid chromatography (HPLC) and gas chromatography (GC).

The deletion strains with pck (pGV1772) had greater specific productivities than the strains with ppc (pGV1661). When ppc is used in the pyk bypass system in GEVO1725 and GEVO1751, the specific productivity of these strains increased by 3% in GEVO1751 and by 13% in GEVO1725 compared to GEVO1385 with the empty vector. When pck is used instead of ppc, the specific productivity increased by 43% in GEVO1725 and by 50% in GEVO1751. Both of the deletion strains show improved volumetric and specific productivity, titer, and yield when pGV1661 and pGV1772 are expressed compared to the empty vector (Table 43).

TABLE 43

Isobutanol production at 24 hours for pyk bypass system with ppc or pck

| | Volumetric Productivity | | Specific Productivity | | Titer | | Yield | |
|---|---|---|---|---|---|---|---|---|
| samples 24 h | [g/L/h] | ± | [g/L/h/OD] | ± | [g/L] | ± | [g/g] | ± |
| GEVO1725 empty vector | 0.126 | 0.001 | 0.033 | 0.001 | 3.03 | 0.03 | 0.224 | 0.005 |
| GEVO1725 pGV1661 | 0.266 | 0.003 | 0.045 | 0.001 | 6.38 | 0.07 | 0.304 | 0.022 |
| GEVO1725 pGV1772 | 0.311 | 0.021 | 0.057 | 0.003 | 7.46 | 0.49 | 0.306 | 0.006 |
| GEVO1751 empty vector | 0.159 | 0.005 | 0.033 | 0.001 | 3.83 | 0.1 | 0.218 | 0.002 |
| GEVO1751 pGV1661 | 0.262 | 0.054 | 0.041 | 0.005 | 6.29 | 1.29 | 0.236 | 0.035 |
| GEVO1751 pGV1772 | 0.309 | 0.049 | 0.06 | 0.002 | 7.41 | 1.18 | 0.292 | 0.005 |

Example 24

NADH Kinase and NADP+Phosphatase in Yeast

The purpose of this example is to describe how an isobutanol producing yeast which is engineered to express NADPH biosynthesis enzymes to convert NADH into NADPH can produce isobutanol under anaerobic conditions.

A yeast strain GEVO5001 which expresses the isobutanol biosynthetic pathway and is deficient in pyruvate decarboxylase activity is engineered to express NADH kinase and NADP+phosphatase. pGV6000, which is a yeast integration plasmid carrying an hygromycin resistance marker, NADH kinase and NADP+phosphatase, is linearized by restriction digestion and transformed into GEVO5001. NADH kinase and NADP+phosphatase are expressed using the strong constitutive promoters from TEF1 and TDH3, respectively. Clones in which the NADH kinase and NADP+phosphatase are first identified by resistance to hygromycin. The clones are confirmed to be expressing NADH kinase and NADP+ phosphatase by qRT-PCR. The resulting strain, GEVO5002, along with the parent strain, GEVO5001, is used in fermentations for production of isobutanol.

Example 25

Metabolic Transhydrogenation in Yeast

This example describes an isobutanol producing yeast which is engineered to convert NADH into NADPH through the combination of two redox enzymes that are catalyzing a conversion that is part of the same pathway wherein one redox enzyme oxidizes NADH and the other redox enzyme reduces $NADP^+$.

The yeast strain, GEVO5001, is a yeast strain that has been engineered to be deficient in pyruvate decarboxylase activity and also to express the isobutanol pathway. A pyruvate bypass is generated by overexpressing in this yeast the genes for (a) pyruvate carboxylase (PYC1 or PYC2), (b) malate dehydrogenase, MDH2, and (c) malic enzyme (maeB). These genes are cloned to generate the yeast integration plasmid, pGV6004. This plasmid carries the hygromycin resistance marker and expresses PYC1, MDH2 and maeB under the strong promoters from ADH1, TEF1 and TDH3, respectively. pGV6004 is linearized and transformed into GEVO5001 to generate GEVO5006. Over-expressions of PYC1, MDH2 and maeB are confirmed by qRT-PCR.

The foregoing detailed description has been given for clearness of understanding only and no unnecessary limitations should be understood there from as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The disclosures, including the claims, figures and/or drawings, of each and every patent, patent application, and publication cited herein are hereby incorporated herein by reference in their entireties.

What is claimed is:

1. An isolated nucleic acid molecule encoding an NADH-dependent ketol-acid reductoisomerase, wherein said NADH-dependent ketol-acid reductoisomerase comprises SEQ ID NO: 44.

2. The isolated nucleic acid molecule of claim 1, wherein said isolated nucleic acid molecule has been codon-optimized for expression in yeast.

3. The isolated nucleic acid molecule of claim 1, wherein said NADH-dependent ketol-acid reductoisomerase exhibits at least a 10-fold higher catalytic efficiency using NADH as the co-factor as compared to the ketol-acid reductoisomerase comprised of SEQ ID NO: 13.

4. A recombinant microorganism comprising an isolated nucleic acid molecule encoding an NADH-dependent ketol-acid reductoisomerase, wherein said NADH-dependent ketol-acid reductoisomerase comprises SEQ ID NO: 44.

5. The recombinant microorganism of claim 4, wherein said isolated nucleic acid molecule has been codon-optimized for expression in yeast.

6. The recombinant microorganism of claim 4, wherein said recombinant microorganism comprises an isobutanol producing metabolic pathway, said isobutanol producing metabolic pathway comprising the following substrate to product conversions:

(a) pyruvate to acetolactate;

(b) acetolactate to 2,3-dihydroxyisovalerate;

(c) 2,3-dihydroxyisovalerate to α-ketoisovalerate;

(d) α-ketoisovalerate to isobutyraldehyde; and (e) isobutyraldehyde to isobutanol, and wherein said NADH-dependent ketol-acid reductoisomerase catalyzes the conversion of acetolactate to 2,3-dihydroxyisovalerate using NADH as an electron donor.

7. The recombinant microorganism of claim 6, wherein the enzyme that catalyzes the conversion of pyruvate to acetolactate is an acetolactate synthase.

8. The recombinant microorganism of claim 7, wherein said acetolactate synthase is derived from *Bacillus subtilis*.

9. The recombinant microorganism of claim 6, wherein the enzyme that catalyzes the conversion of 2,3-dihydroxyisovalerate to α-ketoisovalerate is a dihydroxy acid dehydratase.

10. The recombinant microorganism of claim 6, wherein the enzyme that catalyzes the conversion of α-ketoisovalerate to isobutyraldehyde is a 2-keto acid decarboxylase.

11. The recombinant microorganism of claim 10, wherein said 2-keto acid decarboxylase is derived from *Lactococcus lactis*.

12. The recombinant microorganism of claim 6, wherein the enzyme that catalyzes the conversion of isobutyraldehyde to isobutanol is an alcohol dehydrogenase.

13. The recombinant microorganism of claim 12, wherein said alcohol dehydrogenase is an NADH-dependent alcohol dehydrogenase.

14. The recombinant microorganism of claim 13, wherein said NADH-dependent alcohol dehydrogenase is derived from *Lactococcus* lactis.

15. The recombinant microorganism of claim 6, wherein said recombinant microorganism is a recombinant yeast microorganism.

16. The recombinant microorganism of claim 15, wherein said recombinant yeast microorganism has been engineered to reduce or eliminate pyruvate decarboxylase (PDC) activity.

17. The recombinant microorganism of claim 15, wherein said recombinant yeast microorganism has been engineered to reduce or eliminate glycerol-3-phosphate dehydrogenase (GPD) activity.

18. A method of producing isobutanol, said method comprising:

(a) providing a recombinant microorganism according to claim 6;

(b) cultivating the recombinant microorganism in a culture medium containing a feedstock providing a carbon source until the isobutanol is produced.

19. The method of claim 18, wherein said recombinant microorganism converts the carbon source to isobutanol under anaerobic conditions.

* * * * *

SEQUENCE LISTING

```
<160> NUMBER OF SEQ ID NOS: 330

<210> SEQ ID NO 1
<211> LENGTH: 1533
<212> TYPE: DNA
<213> ORGANISM: Escherichia coli

<400> SEQUENCE: 1

atgcgaattg gcataccaag agaacggtta accaatgaaa cccgtgttgc agcaacgcca     60

aaaacagtgg aacagctgct gaaactgggt tttaccgtcg cggtagagag cggcgcgggt    120

caactggcaa gttttgacga taaagcgttt gtgcaagcgg gcgctgaaat tgtagaaggg    180

aatagcgtct ggcagtcaga gatcattctg aaggtcaatg cgccgttaga tgatgaaatt    240

gcgttactga atcctgggac aacgctggtg agttttatct ggcctgcgca gaatccggaa    300

ttaatgcaaa aacttgcgga acgtaacgtg accgtgatgg cgatggactc tgtgccgcgt    360

atctcacgcg cacaatcgct ggacgcacta agctcgatgg cgaacatcgc cggttatcgc    420

gccattgttg aagcggcaca tgaatttggg cgcttcttta ccgggcaaat tactgcggcc    480

gggaaagtgc caccggcaaa agtgatggtg attggtgcgg gtgttgcagg tctggccgcc    540

attggcgcag caaacagtct cggcgcgatt gtgcgtgcat tcgacacccg cccggaagtg    600

aaagaacaag ttcaaagtat gggcgcggaa ttcctcgagc tggattttaa agaggaagct    660

ggcagcggcg atggctatgc caaagtgatg tcggacgcgt tcatcaaagc ggaaatggaa    720

ctctttgccg cccaggcaaa agaggtcgat atcattgtca ccaccgcgct tattccaggc    780

aaaccagcgc cgaagctaat tacccgtgaa atggttgact ccatgaaggc gggcagtgtg    840

attgtcgacc tggcagccca aaacggcggc aactgtgaat acaccgtgcc gggtgaaatc    900

ttcactacgg aaaatggtgt caaagtgatt ggttataccg atcttccggg ccgtctgccg    960

acgcaatcct cacagcttta cggcacaaac ctcgttaatc tgctgaaact gttgtgcaaa   1020

gagaaagacg gcaatatcac tgttgatttt gatgatgtgg tgattcgcgg cgtgaccgtg   1080

atccgtgcgg gcgaaattac ctggccggca ccgccgattc aggtatcagc tcagccgcag   1140

gcggcacaaa aagcggcacc ggaagtgaaa actgaggaaa aatgtacctg ctcaccgtgg   1200

cgtaaatacg cgttgatggc gctggcaatc attcttttg gctggatggc aagcgttgcg    1260

ccgaaagaat tccttgggca cttcaccgtt ttcgcgctgg cctgcgttgt cggttattac   1320

gtggtgtgga atgtatcgca cgcgctgcat acaccgttga tgtcggtcac caacgcgatt   1380

tcagggatta ttgttgtcgg agcactgttg cagattggcc agggcggctg ggttagcttc   1440

cttagtttta tcgcggtgct tatagccagc attaatattt tcggtggctt caccgtgact   1500
```

```
cagcgcatgc tgaaaatgtt ccgcaaaaat taa                             1533


<210> SEQ ID NO 2
<211> LENGTH: 510
<212> TYPE: PRT
<213> ORGANISM: Escherichia coli

<400> SEQUENCE: 2

Met Arg Ile Gly Ile Pro Arg Glu Arg Leu Thr Asn Glu Thr Arg Val
1               5                   10                  15

Ala Ala Thr Pro Lys Thr Val Glu Gln Leu Leu Lys Leu Gly Phe Thr
            20                  25                  30

Val Ala Val Glu Ser Gly Ala Gly Gln Leu Ala Ser Phe Asp Asp Lys
        35                  40                  45

Ala Phe Val Gln Ala Gly Ala Glu Ile Val Glu Gly Asn Ser Val Trp
    50                  55                  60

Gln Ser Glu Ile Ile Leu Lys Val Asn Ala Pro Leu Asp Asp Glu Ile
65                  70                  75                  80

Ala Leu Leu Asn Pro Gly Thr Thr Leu Val Ser Phe Ile Trp Pro Ala
                85                  90                  95

Gln Asn Pro Glu Leu Met Gln Lys Leu Ala Glu Arg Asn Val Thr Val
            100                 105                 110

Met Ala Met Asp Ser Val Pro Arg Ile Ser Arg Ala Gln Ser Leu Asp
        115                 120                 125

Ala Leu Ser Ser Met Ala Asn Ile Ala Gly Tyr Arg Ala Ile Val Glu
    130                 135                 140

Ala Ala His Glu Phe Gly Arg Phe Phe Thr Gly Gln Ile Thr Ala Ala
145                 150                 155                 160

Gly Lys Val Pro Pro Ala Lys Val Met Val Ile Gly Ala Gly Val Ala
                165                 170                 175

Gly Leu Ala Ala Ile Gly Ala Ala Asn Ser Leu Gly Ala Ile Val Arg
            180                 185                 190

Ala Phe Asp Thr Arg Pro Glu Val Lys Glu Gln Val Gln Ser Met Gly
        195                 200                 205

Ala Glu Phe Leu Glu Leu Asp Phe Lys Glu Glu Ala Gly Ser Gly Asp
    210                 215                 220

Gly Tyr Ala Lys Val Met Ser Asp Ala Phe Ile Lys Ala Glu Met Glu
225                 230                 235                 240

Leu Phe Ala Ala Gln Ala Lys Glu Val Asp Ile Ile Val Thr Thr Ala
                245                 250                 255

Leu Ile Pro Gly Lys Pro Ala Pro Lys Leu Ile Thr Arg Glu Met Val
            260                 265                 270

Asp Ser Met Lys Ala Gly Ser Val Ile Val Asp Leu Ala Ala Gln Asn
        275                 280                 285

Gly Gly Asn Cys Glu Tyr Thr Val Pro Gly Glu Ile Phe Thr Thr Glu
    290                 295                 300

Asn Gly Val Lys Val Ile Gly Tyr Thr Asp Leu Pro Gly Arg Leu Pro
305                 310                 315                 320

Thr Gln Ser Ser Gln Leu Tyr Gly Thr Asn Leu Val Asn Leu Leu Lys
                325                 330                 335

Leu Leu Cys Lys Glu Lys Asp Gly Asn Ile Thr Val Asp Phe Asp Asp
            340                 345                 350

Val Val Ile Arg Gly Val Thr Val Ile Arg Ala Gly Glu Ile Thr Trp
        355                 360                 365

Pro Ala Pro Pro Ile Gln Val Ser Ala Gln Pro Gln Ala Ala Gln Lys
```

-continued

```
    370                 375                 380

Ala Ala Pro Glu Val Lys Thr Glu Glu Lys Cys Thr Cys Ser Pro Trp
385                 390                 395                 400

Arg Lys Tyr Ala Leu Met Ala Leu Ala Ile Ile Leu Phe Gly Trp Met
                405                 410                 415

Ala Ser Val Ala Pro Lys Glu Phe Leu Gly His Phe Thr Val Phe Ala
            420                 425                 430

Leu Ala Cys Val Val Gly Tyr Tyr Val Val Trp Asn Val Ser His Ala
        435                 440                 445

Leu His Thr Pro Leu Met Ser Val Thr Asn Ala Ile Ser Gly Ile Ile
    450                 455                 460

Val Val Gly Ala Leu Leu Gln Ile Gly Gln Gly Gly Trp Val Ser Phe
465                 470                 475                 480

Leu Ser Phe Ile Ala Val Leu Ile Ala Ser Ile Asn Ile Phe Gly Gly
                485                 490                 495

Phe Thr Val Thr Gln Arg Met Leu Lys Met Phe Arg Lys Asn
            500                 505                 510


<210> SEQ ID NO 3
<211> LENGTH: 1389
<212> TYPE: DNA
<213> ORGANISM: Escherichia coli

<400> SEQUENCE: 3

atgtctggag gattagttac agctgcatac attgttgccg cgatcctgtt tatcttcagt      60

ctggccggtc tttcgaaaca tgaaacgtct cgccagggta acaacttcgg tatcgccggg     120

atggcgattg cgttaatcgc aaccattttt ggaccggata cgggtaatgt tggctggatc     180

ttgctggcga tggtcattgg tggggcaatt ggtatccgtc tggcgaagaa agttgaaatg     240

accgaaatgc cagaactggt ggcgatcctg catagcttcg tgggtctggc ggcagtgctg     300

gttggcttta acagctatct gcatcatgac gcgggaatgg caccgattct ggtcaatatt     360

cacctgacgg aagtgttcct cggtatcttc atcggggcgg taacgttcac gggttcggtg     420

gtggcgttcg gcaaactgtg tggcaagatt tcgtctaaac cattgatgct gccaaaccgt     480

cacaaaatga acctggcggc tctggtcgtt tccttcctgc tgctgattgt atttgttcgc     540

acggacagcg tcggcctgca agtgctggca ttgctgataa tgaccgcaat tgcgctggta     600

ttcggctggc atttagtcgc ctccatcggt ggtgcagata tgccagtggt ggtgtcgatg     660

ctgaactcgt actccggctg ggcggctgcg gctgcgggct ttatgctcag caacgacctg     720

ctgattgtga ccggtgcgct ggtcggttct tcgggggcta tcctttctta cattatgtgt     780

aaggcgatga accgttcctt tatcagcgtt attgcgggtg gtttcggcac cgacggctct     840

tctactggcg atgatcagga agtgggtgag caccgcgaaa tcaccgcaga agagacagcg     900

gaactgctga aaaactccca ttcagtgatc attactccgg ggtacggcat ggcagtcgcg     960

caggcgcaat atcctgtcgc tgaaattact gagaaattgc gcgctcgtgg tattaatgtg    1020

cgtttcggta tccacccggt cgcggggcgt ttgcctggac atatgaacgt attgctggct    1080

gaagcaaaag taccgtatga catcgtgctg gaaatggacg agatcaatga tgactttgct    1140

gataccgata ccgtactggt gattggtgct aacgatacgg ttaacccggc ggcgcaggat    1200

gatccgaaga gtccgattgc tggtatgcct gtgctggaag tgtggaaagc gcagaacgtg    1260

attgtcttta aacgttcgat gaacactggc tatgctggtg tgcaaaaccc gctgttcttc    1320

aaggaaaaca cccacatgct gtttggtgac gccaaagcca gcgtggatgc aatcctgaaa    1380
```

gctctgtaa 1389

<210> SEQ ID NO 4
<211> LENGTH: 462
<212> TYPE: PRT
<213> ORGANISM: Escherichia coli

<400> SEQUENCE: 4

Met Ser Gly Gly Leu Val Thr Ala Ala Tyr Ile Val Ala Ala Ile Leu
1 5 10 15

Phe Ile Phe Ser Leu Ala Gly Leu Ser Lys His Glu Thr Ser Arg Gln
20 25 30

Gly Asn Asn Phe Gly Ile Ala Gly Met Ala Ile Ala Leu Ile Ala Thr
35 40 45

Ile Phe Gly Pro Asp Thr Gly Asn Val Gly Trp Ile Leu Leu Ala Met
50 55 60

Val Ile Gly Gly Ala Ile Gly Ile Arg Leu Ala Lys Lys Val Glu Met
65 70 75 80

Thr Glu Met Pro Glu Leu Val Ala Ile Leu His Ser Phe Val Gly Leu
85 90 95

Ala Ala Val Leu Val Gly Phe Asn Ser Tyr Leu His His Asp Ala Gly
100 105 110

Met Ala Pro Ile Leu Val Asn Ile His Leu Thr Glu Val Phe Leu Gly
115 120 125

Ile Phe Ile Gly Ala Val Thr Phe Thr Gly Ser Val Val Ala Phe Gly
130 135 140

Lys Leu Cys Gly Lys Ile Ser Ser Lys Pro Leu Met Leu Pro Asn Arg
145 150 155 160

His Lys Met Asn Leu Ala Ala Leu Val Val Ser Phe Leu Leu Leu Ile
165 170 175

Val Phe Val Arg Thr Asp Ser Val Gly Leu Gln Val Leu Ala Leu Leu
180 185 190

Ile Met Thr Ala Ile Ala Leu Val Phe Gly Trp His Leu Val Ala Ser
195 200 205

Ile Gly Gly Ala Asp Met Pro Val Val Val Ser Met Leu Asn Ser Tyr
210 215 220

Ser Gly Trp Ala Ala Ala Ala Ala Gly Phe Met Leu Ser Asn Asp Leu
225 230 235 240

Leu Ile Val Thr Gly Ala Leu Val Gly Ser Ser Gly Ala Ile Leu Ser
245 250 255

Tyr Ile Met Cys Lys Ala Met Asn Arg Ser Phe Ile Ser Val Ile Ala
260 265 270

Gly Gly Phe Gly Thr Asp Gly Ser Ser Thr Gly Asp Asp Gln Glu Val
275 280 285

Gly Glu His Arg Glu Ile Thr Ala Glu Glu Thr Ala Glu Leu Leu Lys
290 295 300

Asn Ser His Ser Val Ile Ile Thr Pro Gly Tyr Gly Met Ala Val Ala
305 310 315 320

Gln Ala Gln Tyr Pro Val Ala Glu Ile Thr Glu Lys Leu Arg Ala Arg
325 330 335

Gly Ile Asn Val Arg Phe Gly Ile His Pro Val Ala Gly Arg Leu Pro
340 345 350

Gly His Met Asn Val Leu Leu Ala Glu Ala Lys Val Pro Tyr Asp Ile
355 360 365

Val Leu Glu Met Asp Glu Ile Asn Asp Asp Phe Ala Asp Thr Asp Thr

-continued

```
370                 375                 380

Val Leu Val Ile Gly Ala Asn Asp Thr Val Asn Pro Ala Ala Gln Asp
385                 390                 395                 400

Asp Pro Lys Ser Pro Ile Ala Gly Met Pro Val Leu Glu Val Trp Lys
                405                 410                 415

Ala Gln Asn Val Ile Val Phe Lys Arg Ser Met Asn Thr Gly Tyr Ala
            420                 425                 430

Gly Val Gln Asn Pro Leu Phe Phe Lys Glu Asn Thr His Met Leu Phe
        435                 440                 445

Gly Asp Ala Lys Ala Ser Val Asp Ala Ile Leu Lys Ala Leu
    450                 455                 460


<210> SEQ ID NO 5
<211> LENGTH: 1716
<212> TYPE: DNA
<213> ORGANISM: Bacillus subtilis

<400> SEQUENCE: 5

atgttgacaa aagcaacaaa agaacaaaaa tcccttgtga aaaacagagg ggcggagctt     60

gttgttgatt gcttagtgga gcaaggtgtc acacatgtat ttggcattcc aggtgcaaaa    120

attgatgcgg tatttgacgc tttacaagat aaaggacctg aaattatcgt tgcccggcac    180

gaacaaaacg cagcattcat ggcccaagca gtcggccgtt taactggaaa accgggagtc    240

gtgttagtca catcaggacc gggtgcctct aacttggcaa caggcctgct gacagcgaac    300

actgaaggag accctgtcgt tgcgcttgct ggaaacgtga tccgtgcaga tcgtttaaaa    360

cggacacatc aatctttgga taatgcggcg ctattccagc cgattacaaa atacagtgta    420

gaagttcaag atgtaaaaaa tataccggaa gctgttacaa atgcatttag gatagcgtca    480

gcagggcagg ctggggccgc ttttgtgagc tttccgcaag atgttgtgaa tgaagtcaca    540

aatacgaaaa acgtgcgtgc tgttgcagcg ccaaaactcg gtcctgcagc agatgatgca    600

atcagtgcgg ccatagcaaa aatccaaaca gcaaaacttc ctgtcgtttt ggtcggcatg    660

aaaggcggaa gaccggaagc aattaaagcg gttcgcaagc ttttgaaaaa ggttcagctt    720

ccatttgttg aaacatatca agctgccggt accctttcta gagatttaga ggatcaatat    780

tttggccgta tcggtttgtt ccgcaaccag cctggcgatt tactgctaga gcaggcagat    840

gttgttctga cgatcggcta tgacccgatt gaatatgatc cgaaattctg gaatatcaat    900

ggagaccgga caattatcca tttagacgag attatcgctg acattgatca tgcttaccag    960

cctgatcttg aattgatcgg tgacattccg tccacgatca atcatatcga acacgatgct   1020

gtgaaagtgg aatttgcaga gcgtgagcag aaaatccttt ctgatttaaa acaatatatg   1080

catgaaggtg agcaggtgcc tgcagattgg aaatcagaca gagcgcaccc tcttgaaatc   1140

gttaaagagt tgcgtaatgc agtcgatgat catgttacag taacttgcga tatcggttcg   1200

cacgccattt ggatgtcacg ttatttccgc agctacgagc cgttaacatt aatgatcagt   1260

aacggtatgc aaacactcgg cgttgcgctt ccttgggcaa tcggcgcttc attggtgaaa   1320

ccgggagaaa aagtggtttc tgtctctggt gacggcggtt tcttattctc agcaatggaa   1380

ttagagacag cagttcgact aaaagcacca attgtacaca ttgtatggaa cgacagcaca   1440

tatgacatgg ttgcattcca gcaattgaaa aaatataacc gtacatctgc ggtcgatttc   1500

ggaaatatcg atatcgtgaa atatgcggaa agcttcggag caactggctt gcgcgtagaa   1560

tcaccagacc agctggcaga tgttctgcgt caaggcatga acgctgaagg tcctgtcatc   1620

atcgatgtcc cggttgacta cagtgataac attaatttag caagtgacaa gcttccgaaa   1680
```

```
gaattcgggg aactcatgaa aacgaaagct ctctag                             1716


<210> SEQ ID NO 6
<211> LENGTH: 1716
<212> TYPE: DNA
<213> ORGANISM: Bacillus subtilis

<400> SEQUENCE: 6

atgttgacta aagctacaaa agagcagaaa tcattggtga aaaatagggg tgcagaactt     60

gttgtggact gtttggtaga acagggcgta acacatgttt ttggtatccc aggtgcaaaa    120

atcgacgccg tgtttgatgc attacaagac aagggtccag aaattattgt tgctagacat    180

gagcaaaatg ccgcatttat ggcgcaagct gtaggtaggc ttacaggtaa acctggtgtt    240

gtcctagtta cgtctggccc aggagcctcc aatttagcaa ctggtctatt gacagctaat    300

actgagggag atcctgtagt tgcgttagcc ggtaatgtaa ttagagctga taggcttaag    360

agaactcacc agtctctaga caacgctgct ttattccaac cgatcaccaa gtactcagta    420

gaggtacaag acgtaaagaa tatacctgaa gctgtgacaa acgcatttcg tatagcttct    480

gctggtcagg ctggtgccgc gtttgtttct tttcctcaag acgttgtcaa tgaagtgacc    540

aatactaaaa acgttagagc ggttgcagcc cctaaactag gtccagccgc agacgacgca    600

attagcgctg caattgctaa aattcagacg gcgaaactac cagtagtcct tgtcggtatg    660

aagggcggaa gaccagaagc aataaaagct gttcgtaagt tattgaagaa agtccaatta    720

cctttcgttg agacttacca agcagcaggt actttatcta gagatttaga ggatcagtat    780

tttggaagga taggtctatt tagaaaccaa ccaggagatt tactattaga acaagctgat    840

gttgtactta ctatcggtta tgatcctata gagtatgacc caaagttttg gaacataaat    900

ggggatagaa caattataca tctagacgag ataatcgccg acatcgatca cgcttatcaa    960

ccagatttag aactaatcgg agatatcccg tcaacaatca atcatattga acatgatgct   1020

gtaaaggttg agttcgctga acgtgagcag aaaatcttat ctgatctaaa gcaatatatg   1080

catgagggtg aacaagttcc agcagactgg aaatctgacc gtgcacatcc tttggaaatc   1140

gttaaggaac taagaaatgc ggtcgatgat catgtgactg ttacatgtga tatcggttca   1200

catgcaattt ggatgtcacg ttattttagg agctacgaac cattaacttt aatgatatct   1260

aacgggatgc aaactctggg ggttgcactt ccttgggcta ttggcgctag tttagttaag   1320

cccggtgaga aggtggtatc ggtatcaggt gatggtggct ttctgttttc ggctatggaa   1380

ttagaaactg cagtccgttt aaaagctccc attgtgcata ttgtctggaa tgattctact   1440

tacgacatgg ttgcttttca acagttgaag aaatacaata gaacttcggc tgtagacttt   1500

ggtaacatcg atattgtgaa atatgctgag tcttttggcg caacaggcct gagggtggaa   1560

agtccagatc agttagctga tgtgttgaga caagggatga atgccgaggg accggtaatc   1620

atagatgtgc cagttgacta ctcagacaat attaatttgg cttctgataa acttcctaaa   1680

gagtttggcg agctaatgaa gaccaaagcc ttataa                             1716


<210> SEQ ID NO 7
<211> LENGTH: 571
<212> TYPE: PRT
<213> ORGANISM: Bacillus subtilis

<400> SEQUENCE: 7

Met Leu Thr Lys Ala Thr Lys Glu Gln Lys Ser Leu Val Lys Asn Arg
1               5                   10                  15
```

-continued

```
Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
    370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445
```

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
    530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570

<210> SEQ ID NO 8
<211> LENGTH: 1716
<212> TYPE: DNA
<213> ORGANISM: Bacillus subtilis

<400> SEQUENCE: 8
atgttgacaa aagcaacaaa agaacaaaaa tcccttgtga aaagcagagg ggcggagctt 60
gttgttgatt gcttagcgga gcaaggtgtc acacatgtat ttggcattcc aggtgcaaaa 120
attgatgcgg tatttgacgc tttacaagat aaagggcctg aaattatcgt tgcccggcat 180
gaacaaaatg cagcatttat ggcgcaagca gtcggccgtt taactggaaa accgggagtc 240
gtgttagtca catcaggacc aggtgcttcg aacttggcaa caggactgct gacagcaaac 300
actgaaggtg accctgtcgt tgcgcttgct gggaacgtga tccgtgcaga tcgtttaaaa 360
cggacacatc aatctttgga taatgcggcg ctattccagc cgattacaaa atacagtgta 420
gaagttcaag atgtaaaaaa tataccggaa gctgttacaa atgcgtttag gatagcgtca 480
gcagggcagg ctggggccgc ttttgtgagt tttccgcaag atgttgtgaa tgaagtcaca 540
aatacaaaaa acgtacgtgc tgtcgcagcg ccaaaacttg gtcccgcagc agatgacgca 600
atcagtatgg ccattgcaaa aattcaaaca gcaaaacttc ctgtcgtttt agtcggcatg 660
aagggcggaa gaccggaagc gattaaagcg gttcgcaagc tattgaaaaa agtgcagctt 720
ccattcgttg aaacatatca agctgccggt actcttacga gagatttaga ggatcagtat 780
tttggccgga tcggtttatt ccgcaaccag cctggcgatc tgctgcttga gcaggctgat 840
gttgttctga caatcggcta tgacccaatt gaatatgatc cgaaattctg gaatgtcaat 900
ggagaccgga cgatcatcca tttagacgag attctggctg acattgatca tgcttaccag 960
ccggatcttg aactgatcgg tgatattcca tctacgatca atcatatcga acacgatgct 1020
gtgaaagtag actttgcgga acgtgagcag aagatccttt ctgatttaaa acaatatatg 1080
catgagggtg agcaggtgcc tgcagattgg aaatcagaca gagtgcatcc tcttgaaatc 1140
gttaaagaat tgcgaaacgc agtcgatgat catgttacag tgacttgcga tatcggttca 1200
cacgcgattt ggatgtcacg ttatttccgc agctacgagc cgttaacatt aatgattagt 1260
aacggtatgc aaacactcgg cgttgcgctt ccttgggcaa tcggcgcttc attggtgaaa 1320
ccgggagaaa aagtagtatc agtctccggt gatggcggtt tcttattctc agctatggaa 1380
ttagagacag cagttcgttt aaaagcacca attgtacaca ttgtatggaa cgacagcaca 1440

```
tatgacatgg ttgcattcca gcaattgaaa aaatataatc gtacatctgc ggtcgatttc   1500

ggaaatatcg atatcgtgaa atacgcggaa agcttcggag caactggctt acgcgtagaa   1560

tcaccagacc agctggcaga tgttctgcgt caaggcatga acgctgaggg gcctgtcatc   1620

attgatgtcc cggttgacta cagtgataac gttaatttag caagtgacaa gcttccgaaa   1680

gaattcgggg aactcatgaa aacgaaagct ctctag                             1716
```

<210> SEQ ID NO 9
<211> LENGTH: 571
<212> TYPE: PRT
<213> ORGANISM: Bacillus subtilis

<400> SEQUENCE: 9

```
Met Leu Thr Lys Ala Thr Lys Glu Gln Lys Ser Leu Val Lys Ser Arg
1               5                   10                  15

Gly Ala Glu Leu Val Val Asp Cys Leu Ala Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Met Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Thr Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Val Asn Gly Asp Arg Thr
    290                 295                 300

Ile Ile His Leu Asp Glu Ile Leu Ala Asp Ile Asp His Ala Tyr Gln
305                 310                 315                 320

Pro Asp Leu Glu Leu Ile Gly Asp Ile Pro Ser Thr Ile Asn His Ile
```

```
                325                 330                 335

Glu His Asp Ala Val Lys Val Asp Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Val His Pro Leu Glu Ile Val Lys Glu Leu
    370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
    530                 535                 540

Val Asp Tyr Ser Asp Asn Val Asn Leu Ala Ser Asp Lys Leu Pro Lys
545                 550                 555                 560

Glu Phe Gly Glu Leu Met Lys Thr Lys Ala Leu
                565                 570
```

<210> SEQ ID NO 10
<211> LENGTH: 1476
<212> TYPE: DNA
<213> ORGANISM: Escherichia coli

<400> SEQUENCE: 10

```
atggctaact acttcaatac actgaatctg cgccagcagc tggcacagct gggcaaatgt     60

cgctttatgg gccgcgatga attcgccgat ggcgcgagct accttcaggg taaaaaagta    120

gtcatcgtcg gctgtggcgc acagggtctg aaccagggcc tgaacatgcg tgattctggt    180

ctcgatatct cctacgctct gcgtaaagaa gcgattgccg agaagcgcgc gtcctggcgt    240

aaagcgaccg aaaatggttt taaagtgggt acttacgaag aactgatccc acaggcggat    300

ctggtgatta acctgacgcc ggacaagcag cactctgatg tagtgcgcac cgtacagcca    360

ctgatgaaag acggcgcggc gctgggctac tcgcacggtt tcaacatcgt cgaagtgggc    420

gagcagatcc gtaaagatat caccgtagtg atggttgcgc cgaaatgccc aggcaccgaa    480

gtgcgtgaag agtacaaacg tgggttcggc gtaccgacgc tgattgccgt tcacccggaa    540

aacgatccga aaggcgaagg catggcgatt gccaaagcct gggcggctgc aaccggtggt    600

caccgtgcgg gtgtgctgga atcgtccttc gttgcggaag tgaaatctga cctgatgggc    660

gagcaaacca tcctgtgcgg tatgttgcag gctggctctc tgctgtgctt cgacaagctg    720

gtggaagaag gtaccgatcc agcatacgca gaaaaactga ttcagttcgg ttgggaaacc    780
```

```
atcaccgaag cactgaaaca gggcggcatc accctgatga tggaccgtct ctctaacccg    840

gcgaaactgc gtgcttatgc gctttctgaa cagctgaaag agatcatggc acccctgttc    900

cagaaacata tggacgacat catctccggc gaattctctt ccggtatgat ggcggactgg    960

gccaacgatg ataagaaact gctgacctgg cgtgaagaga ccggcaaaac cgcgtttgaa   1020

accgcgccgc agtatgaagg caaaatcggc gagcaggagt acttcgataa aggcgtactg   1080

atgattgcga tggtgaaagc gggcgttgaa ctggcgttcg aaaccatggt cgattccggc   1140

atcattgaag agtctgcata ttatgaatca ctgcacgagc tgccgctgat tgccaacacc   1200

atcgcccgta agcgtctgta cgaaatgaac gtggttatct ctgataccgc tgagtacggt   1260

aactatctgt tctcttacgc ttgtgtgccg ttgctgaaac cgtttatggc agagctgcaa   1320

ccgggcgacc tgggtaaagc tattccggaa ggcgcggtag ataacgggca actgcgtgat   1380

gtgaacgaag cgattcgcag ccatgcgatt gagcaggtag gtaagaaact gcgcggctat   1440

atgacagata tgaaacgtat tgctgttgcg ggttaa                             1476
```

<210> SEQ ID NO 11
<211> LENGTH: 1476
<212> TYPE: DNA
<213> ORGANISM: Escherichia coli

<400> SEQUENCE: 11

```
atggcgaatt atttcaacac tctgaacctg cgtcaacaac tggcgcaact gggtaagtgc     60

cgtttcatgg gtcgtgacga gtttgcggac ggtgcttctt atctgcaagg caagaaggtt    120

gttattgttg gttgcggtgc gcaaggcctg aatcaaggtc tgaatatgcg cgacagcggc    180

ctggacatta gctatgcgct gcgcaaggag gctatcgcgg aaaaacgtgc tagctggcgc    240

aaggctactg agaacggctt caaggttggc acctatgagg agctgattcc gcaagctgac    300

ctggttatca atctgacccc agataaacaa catagcgacg ttgttcgtac tgttcaaccg    360

ctgatgaagg atggtgctgc tctgggttat agccacggct ttaacattgt tgaggtaggt    420

gaacaaattc gcaaggacat tactgttgtt atggtggctc caaagtgtcc gggtactgag    480

gttcgcgagg aatataagcg cggttttggt gttccaaccc tgatcgcggt gcatccagag    540

aatgacccaa agggtgaggg tatggctatc gcgaaggcgt gggctgcggc gactggcggc    600

catcgcgctg gcgttctgga gagcagcttt gtggctgagg ttaagagcga tctgatgggt    660

gaacagacta ttctgtgtgg tatgctgcaa gcgggtagcc tgctgtgttt tgataaactg    720

gttgaggagg gcactgaccc ggcgtatgcg gagaagctga tccaatttgg ctgggagact    780

attactgagg cgctgaagca aggtggtatt actctgatga tggatcgcct gagcaatcca    840

gctaagctgc gcgcgtacgc tctgagcgag caactgaagg aaattatggc accgctgttt    900

caaaagcaca tggatgatat cattagcggt gagtttagca gcggcatgat ggctgattgg    960

gcgaatgacg acaaaaagct gctgacttgg cgcgaggaaa ctggtaagac tgctttcgag   1020

actgctccac aatacgaggg taagattggt gaacaagaat attttgacaa gggtgttctg   1080

atgatcgcta tggttaaggc tggtgtggag ctggcttttg agactatggt tgacagcggt   1140

attatcgagg aaagcgcgta ctacgagagc ctgcatgaac tgccactgat cgcgaatact   1200

attgcgcgca aacgcctgta tgagatgaat gttgtgatta gcgacactgc ggaatatggc   1260

aattacctgt ttagctatgc gtgcgttcca ctgctgaagc cattcatggc ggaactgcag   1320

ccaggtgatc tgggcaaggc gatcccagag ggtgctgttg acaatggtca gctgcgcgac   1380

gttaatgagg ctatccgttc tcacgctatc gaacaagttg gcaaaaagct gcgtggttac   1440
```

atgaccgaca tgaagcgcat cgcggtggct ggctaa 1476

<210> SEQ ID NO 12
<211> LENGTH: 1476
<212> TYPE: DNA
<213> ORGANISM: Escherichia coli

<400> SEQUENCE: 12
atggccaact attttaacac attaaatttg agacaacaat tggctcaact gggtaagtgc 60
agatttatgg gaagggacga gtttgctgat ggtgcttctt atctgcaagg aaagaaagta 120
gtaattgttg gctgcggtgc tcagggtcta aaccaaggtt taaacatgag agattcaggt 180
ctggatattt cgtatgcatt gaggaaagag gcaattgcag aaaagagggc ctcctggcgt 240
aaagcgacgg aaaatgggtt caaagttggt acttacgaag aactgatccc tcaggcagat 300
ttagtgatta acctaacacc agataagcaa cactcagacg tagtaagaac agttcaaccg 360
ctgatgaagg atggggcagc tttaggttac tctcatggct ttaatatcgt tgaagtgggc 420
gagcagatca gaaaagatat aacagtcgta atggttgcac caaagtgccc aggtacggaa 480
gtcagagagg agtacaagag gggttttggt gtacctacat tgatcgccgt acatcctgaa 540
aatgacccca aaggtgaagg tatggcaatt gcgaaggcat gggcagccgc aaccggaggt 600
catagagcgg gtgtgttaga gagttctttc gtagctgagg tcaagagtga cttaatgggt 660
gaacaaacca ttctgtgcgg aatgttgcag gcagggtctt tactatgctt tgataaattg 720
gtcgaagagg gtacagatcc tgcctatgct gaaaagttga tacaatttgg ttgggagaca 780
atcaccgagg cacttaaaca aggtggcata acattgatga tggatagact ttcaaatccg 840
gccaagctaa gagcctacgc cttatctgag caactaaaag agatcatggc accattattc 900
caaaagcaca tggacgatat tatctccggt gagttttcct caggaatgat ggcagattgg 960
gcaaacgatg ataaaaagtt attgacgtgg agagaagaaa ccggcaagac ggcattcgag 1020
acagccccac aatacgaagg taaaattggt gaacaagaat actttgataa gggagtattg 1080
atgatagcta tggtgaaggc aggggtagaa cttgcattcg aaactatggt tgactccggt 1140
atcattgaag aatctgcata ctatgagtct ttgcatgaat tgcctttgat agcaaatact 1200
attgcaagaa aaagacttta cgagatgaat gttgtcatat cagacactgc agaatatggt 1260
aattacttat ttagctacgc atgtgtcccg ttgttaaagc ccttcatggc cgagttacaa 1320
cctggtgatt tggggaaggc tattccggaa ggagcggttg acaatggcca actgagagac 1380
gtaaatgaag ctattcgttc acatgctata gaacaggtgg gtaaaaagct gagaggatat 1440
atgaccgata tgaaaagaat tgcagtggca ggatga 1476

<210> SEQ ID NO 13
<211> LENGTH: 491
<212> TYPE: PRT
<213> ORGANISM: Escherichia coli

<400> SEQUENCE: 13

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65 70 75 80

Lys Ala Thr Glu Asn Gly Phe Lys Val Gly Thr Tyr Glu Glu Leu Ile
85 90 95

Pro Gln Ala Asp Leu Val Ile Asn Leu Thr Pro Asp Lys Gln His Ser
100 105 110

Asp Val Val Arg Thr Val Gln Pro Leu Met Lys Asp Gly Ala Ala Leu
115 120 125

Gly Tyr Ser His Gly Phe Asn Ile Val Glu Val Gly Glu Gln Ile Arg
130 135 140

Lys Asp Ile Thr Val Val Met Val Ala Pro Lys Cys Pro Gly Thr Glu
145 150 155 160

Val Arg Glu Glu Tyr Lys Arg Gly Phe Gly Val Pro Thr Leu Ile Ala
165 170 175

Val His Pro Glu Asn Asp Pro Lys Gly Glu Gly Met Ala Ile Ala Lys
180 185 190

Ala Trp Ala Ala Ala Thr Gly Gly His Arg Ala Gly Val Leu Glu Ser
195 200 205

Ser Phe Val Ala Glu Val Lys Ser Asp Leu Met Gly Glu Gln Thr Ile
210 215 220

Leu Cys Gly Met Leu Gln Ala Gly Ser Leu Leu Cys Phe Asp Lys Leu
225 230 235 240

Val Glu Glu Gly Thr Asp Pro Ala Tyr Ala Glu Lys Leu Ile Gln Phe
245 250 255

Gly Trp Glu Thr Ile Thr Glu Ala Leu Lys Gln Gly Gly Ile Thr Leu
260 265 270

Met Met Asp Arg Leu Ser Asn Pro Ala Lys Leu Arg Ala Tyr Ala Leu
275 280 285

Ser Glu Gln Leu Lys Glu Ile Met Ala Pro Leu Phe Gln Lys His Met
290 295 300

Asp Asp Ile Ile Ser Gly Glu Phe Ser Ser Gly Met Met Ala Asp Trp
305 310 315 320

Ala Asn Asp Asp Lys Lys Leu Leu Thr Trp Arg Glu Glu Thr Gly Lys
325 330 335

Thr Ala Phe Glu Thr Ala Pro Gln Tyr Glu Gly Lys Ile Gly Glu Gln
340 345 350

Glu Tyr Phe Asp Lys Gly Val Leu Met Ile Ala Met Val Lys Ala Gly
355 360 365

Val Glu Leu Ala Phe Glu Thr Met Val Asp Ser Gly Ile Ile Glu Glu
370 375 380

Ser Ala Tyr Tyr Glu Ser Leu His Glu Leu Pro Leu Ile Ala Asn Thr
385 390 395 400

Ile Ala Arg Lys Arg Leu Tyr Glu Met Asn Val Val Ile Ser Asp Thr
405 410 415

Ala Glu Tyr Gly Asn Tyr Leu Phe Ser Tyr Ala Cys Val Pro Leu Leu
420 425 430

Lys Pro Phe Met Ala Glu Leu Gln Pro Gly Asp Leu Gly Lys Ala Ile
435 440 445

Pro Glu Gly Ala Val Asp Asn Gly Gln Leu Arg Asp Val Asn Glu Ala
450 455 460

Ile Arg Ser His Ala Ile Glu Gln Val Gly Lys Lys Leu Arg Gly Tyr
465 470 475 480

Met Thr Asp Met Lys Arg Ile Ala Val Ala Gly

-continued 485 490

<210> SEQ ID NO 14
<211> LENGTH: 1500
<212> TYPE: DNA
<213> ORGANISM: Escherichia coli

<400> SEQUENCE: 14
atggcgaatt atttcaacac tctgaacctg cgtcaacaac tggcgcaact gggtaagtgc 60
cgtttcatgg gtcgtgacga gtttgcggac ggtgcttctt atctgcaagg caagaaggtt 120
gttattgttg gttgcggtgc gcaaggcctg aatcaaggtc tgaatatgcg cgacagcggc 180
ctggacatta gctatgcgct gcgcaaggag gctatcgcgg aaaaacgtgc tagctggcgc 240
aaggctactg agaacggctt caaggttggc acctatgagg agctgattcc gcaagctgac 300
ctggttatca atctgacccc agataaacaa catagcgacg ttgttcgtac tgttcaaccg 360
ctgatgaagg atggtgctgc tctgggttat agccacggct ttaacattgt tgaggtaggt 420
gaacaaattc gcaaggacat tactgttgtt atggtggctc caaagtgtcc gggtactgag 480
gttcgcgagg aatataagcg cggttttggt gttccaaccc tgatcgcggt gcatccagag 540
aatgacccaa agggtgaggg tatggctatc gcgaaggcgt gggctgcggc gactggcggc 600
catcgcgctg gcgttctgga gagcagcttt gtggctgagg ttaagagcga tctgatgggt 660
gaacagacta ttctgtgtgg tatgctgcaa gcgggtagcc tgctgtgttt tgataaactg 720
gttgaggagg gcactgaccc ggcgtatgcg gagaagctga tccaatttgg ctgggagact 780
attactgagg cgctgaagca aggtggtatt actctgatga tggatcgcct gagcaatcca 840
gctaagctgc gcgcgtacgc tctgagcgag caactgaagg aaattatggc accgctgttt 900
caaaagcaca tggatgatat cattagcggt gagtttagca gcggcatgat ggctgattgg 960
gcgaatgacg acaaaaagct gctgacttgg cgcgaggaaa ctggtaagac tgctttcgag 1020
actgctccac aatacgaggg taagattggt gaacaagaat attttgacaa gggtgttctg 1080
atgatcgcta tggttaaggc tggtgtggag ctggcttttg agactatggt tgacagcggt 1140
attatcgagg aaagcgcgta ctacgagagc ctgcatgaac tgccactgat cgcgaatact 1200
attgcgcgca aacgcctgta tgagatgaat gttgtgatta gcgacactgc ggaatatggc 1260
aattacctgt ttagctatgc gtgcgttcca ctgctgaagc cattcatggc ggaactgcag 1320
ccaggtgatc tgggcaaggc gatcccagag ggtgctgttg acaatggtca gctgcgcgac 1380
gttaatgagg ctatccgttc tcacgctatc gaacaagttg gcaaaaagct gcgtggttac 1440
atgaccgaca tgaagcgcat cgcggtggct ggcctcgagc accaccacca ccaccactga 1500

<210> SEQ ID NO 15
<211> LENGTH: 499
<212> TYPE: PRT
<213> ORGANISM: Escherichia coli

<400> SEQUENCE: 15

Met Ala Asn Tyr Phe Asn Thr Leu Asn Leu Arg Gln Gln Leu Ala Gln
1 5 10 15

Leu Gly Lys Cys Arg Phe Met Gly Arg Asp Glu Phe Ala Asp Gly Ala
20 25 30

Ser Tyr Leu Gln Gly Lys Lys Val Val Ile Val Gly Cys Gly Ala Gln
35 40 45

Gly Leu Asn Gln Gly Leu Asn Met Arg Asp Ser Gly Leu Asp Ile Ser
50 55 60

-continued

```
Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly Leu Glu His His His
                485                 490                 495
```

His His His

<210> SEQ ID NO 16
<211> LENGTH: 1494
<212> TYPE: DNA
<213> ORGANISM: Escherichia coli

<400> SEQUENCE: 16
atggcgaatt atttcaacac tctgaacctg cgtcaacaac tggcgcaact gggtaagtgc 60
cgtttcatgg gtcgtgacga gtttgcggac ggtgcttctt atctgcaagg caagaaggtt 120
gttattgttg gttgcggtgc gcaaggcctg aatcaaggtc tgaatatgcg cgacagcggc 180
ctggacatta gctatgcgct gcgcaaggag gctatcgcgg aaaaacgtgc tgactggcgc 240
aaggctactg agaacggctt caaggttggc acctatgagg agctgattcc gcaagctgac 300
ctggttatca atctgacccc agataaacaa catagcgacg ttgttcgtac tgttcaaccg 360
ctgatgaagg atggtgctgc tctgggttat agccacggct ttaacattgt tgaggtaggt 420
gaacaaattc gcaaggacat tactgttgtt atggtggctc caaagtgtcc gggtactgag 480
gttcgcgagg aatataagcg cggttttggt gttccaaccc tgatcgcggt gcatccagag 540
aatgacccaa agggtgaggg tatggctatc gcgaaggcgt gggctgcggc gactggcggc 600
catcgcgctg gcgttctgga gagcagcttt gtggctgagg ttaagagcga tctgatgggt 660
gaacagacta ttctgtgtgg tatgctgcaa gcgggtagcc tgctgtgttt tgataaactg 720
gttgaggagg gcactgaccc ggcgtatgcg gagaagctga tccaatttgg ctgggagact 780
attactgagg cgctgaagca aggtggtatt actctgatga tggatcgcct gagcaatcca 840
gctaagctgc gcgcgtacgc tctgagcgag caactgaagg aaattatggc accgctgttt 900
caaaagcaca tggatgatat cattagcggt gagtttagca gcggcatgat ggctgattgg 960
gcgaatgacg acaaaaagct gctgacttgg cgcgaggaaa ctggtaagac tgctttcgag 1020
actgctccac aatacgaggg taagattggt gaacaagaat attttgacaa gggtgttctg 1080
atgatcgcta tggttaaggc tggtgtggag ctggcttttg agactatggt tgacagcggt 1140
attatcgagg aaagcgcgta ctacgagagc ctgcatgaac tgccactgat cgcgaatact 1200
attgcgcgca aacgcctgta tgagatgaat gttgtgatta gcgacactgc ggaatatggc 1260
aattacctgt ttagctatgc gtgcgttcca ctgctgaagc cattcatggc ggaactgcag 1320
ccaggtgatc tgggcaaggc gatcccagag ggtgctgttg acaatggtca gctgcgcgac 1380
gttaatgagg ctatccgttc tcacgctatc gaacaagttg gcaaaaagct gcgtggttac 1440
atgaccgaca tgaagcgcat cgcggtggct ggccaccacc accaccacca ctaa 1494

<210> SEQ ID NO 17
<211> LENGTH: 499
<212> TYPE: PRT
<213> ORGANISM: Escherichia coli

<400> SEQUENCE: 17

Met Ala Asn Tyr Phe Asn Thr Leu Asn Leu Arg Gln Gln Leu Ala Gln
1 5 10 15

Leu Gly Lys Cys Arg Phe Met Gly Arg Asp Glu Phe Ala Asp Gly Ala
20 25 30

Ser Tyr Leu Gln Gly Lys Lys Val Val Ile Val Gly Cys Gly Ala Gln
35 40 45

Gly Leu Asn Gln Gly Leu Asn Met Arg Asp Ser Gly Leu Asp Ile Ser
50 55 60

Tyr Ala Leu Arg Lys Glu Ala Ile Ala Glu Lys Arg Ala Asp Trp Arg
65 70 75 80

Lys Ala Thr Glu Asn Gly Phe Lys Val Gly Thr Tyr Glu Glu Leu Ile
85 90 95

Pro Gln Ala Asp Leu Val Ile Asn Leu Thr Pro Asp Lys Gln His Ser
100 105 110

Asp Val Val Arg Thr Val Gln Pro Leu Met Lys Asp Gly Ala Ala Leu
115 120 125

Gly Tyr Ser His Gly Phe Asn Ile Val Glu Val Gly Glu Gln Ile Arg
130 135 140

Lys Asp Ile Thr Val Val Met Val Ala Pro Lys Cys Pro Gly Thr Glu
145 150 155 160

Val Arg Glu Glu Tyr Lys Arg Gly Phe Gly Val Pro Thr Leu Ile Ala
165 170 175

Val His Pro Glu Asn Asp Pro Lys Gly Glu Gly Met Ala Ile Ala Lys
180 185 190

Ala Trp Ala Ala Ala Thr Gly Gly His Arg Ala Gly Val Leu Glu Ser
195 200 205

Ser Phe Val Ala Glu Val Lys Ser Asp Leu Met Gly Glu Gln Thr Ile
210 215 220

Leu Cys Gly Met Leu Gln Ala Gly Ser Leu Leu Cys Phe Asp Lys Leu
225 230 235 240

Val Glu Glu Gly Thr Asp Pro Ala Tyr Ala Glu Lys Leu Ile Gln Phe
245 250 255

Gly Trp Glu Thr Ile Thr Glu Ala Leu Lys Gln Gly Gly Ile Thr Leu
260 265 270

Met Met Asp Arg Leu Ser Asn Pro Ala Lys Leu Arg Ala Tyr Ala Leu
275 280 285

Ser Glu Gln Leu Lys Glu Ile Met Ala Pro Leu Phe Gln Lys His Met
290 295 300

Asp Asp Ile Ile Ser Gly Glu Phe Ser Ser Gly Met Met Ala Asp Trp
305 310 315 320

Ala Asn Asp Asp Lys Lys Leu Leu Thr Trp Arg Glu Glu Thr Gly Lys
325 330 335

Thr Ala Phe Glu Thr Ala Pro Gln Tyr Glu Gly Lys Ile Gly Glu Gln
340 345 350

Glu Tyr Phe Asp Lys Gly Val Leu Met Ile Ala Met Val Lys Ala Gly
355 360 365

Val Glu Leu Ala Phe Glu Thr Met Val Asp Ser Gly Ile Ile Glu Glu
370 375 380

Ser Ala Tyr Tyr Glu Ser Leu His Glu Leu Pro Leu Ile Ala Asn Thr
385 390 395 400

Ile Ala Arg Lys Arg Leu Tyr Glu Met Asn Val Val Ile Ser Asp Thr
405 410 415

Ala Glu Tyr Gly Asn Tyr Leu Phe Ser Tyr Ala Cys Val Pro Leu Leu
420 425 430

Lys Pro Phe Met Ala Glu Leu Gln Pro Gly Asp Leu Gly Lys Ala Ile
435 440 445

Pro Glu Gly Ala Val Asp Asn Gly Gln Leu Arg Asp Val Asn Glu Ala
450 455 460

Ile Arg Ser His Ala Ile Glu Gln Val Gly Lys Lys Leu Arg Gly Tyr
465 470 475 480

Met Thr Asp Met Lys Arg Ile Ala Val Ala Gly Leu Glu His His His

-continued 485 490 495

His His His

<210> SEQ ID NO 18
<211> LENGTH: 1476
<212> TYPE: DNA
<213> ORGANISM: Escherichia coli

<400> SEQUENCE: 18
atggcgaatt atttcaacac tctgaacctg cgtcaacaac tggcgcaact gggtaagtgc 60
cgtttcatgg gtcgtgacga gtttgcggac ggtgcttctt atctgcaagg caagaaggtt 120
gttattgttg gttgcggtgc gcaaggcctg aatcaaggtc tgaatatgcg cgacagcggc 180
ctggacatta gctatgcgct gcgcaaggag gctatcgcgg aaaaacgtgc tgactggcgc 240
aaggctactg agaacggctt caaggttggc acctatgagg agctgattcc gcaagctgac 300
ctggttatca atctgacccc agataaacaa catagcgacg ttgttcgtac tgttcaaccg 360
ctgatgaagg atggtgctgc tctgggttat agccacggct ttaacattgt tgaggtaggt 420
gaacaaattc gcaaggacat tactgttgtt atggtggctc caaagtgtcc gggtactgag 480
gttcgcgagg aatataagcg cggttttggt gttccaaccc tgatcgcggt gcatccagag 540
aatgacccaa agggtgaggg tatggctatc gcgaaggcgt gggctgcggc gactggcggc 600
catcgcgctg gcgttctgga gagcagcttt gtggctgagg ttaagagcga tctgatgggt 660
gaacagacta ttctgtgtgg tatgctgcaa gcgggtagcc tgctgtgttt tgataaactg 720
gttgaggagg gcactgaccc ggcgtatgcg gagaagctga tccaatttgg ctgggagact 780
attactgagg cgctgaagca aggtggtatt actctgatga tggatcgcct gagcaatcca 840
gctaagctgc gcgcgtacgc tctgagcgag caactgaagg aaattatggc accgctgttt 900
caaaagcaca tggatgatat cattagcggt gagtttagca gcggcatgat ggctgattgg 960
gcgaatgacg acaaaaagct gctgacttgg cgcgaggaaa ctggtaagac tgctttcgag 1020
actgctccac aatacgaggg taagattggt gaacaagaat atttgacaa gggtgttctg 1080 atgatcgcta tggttaaggc tggtgtggag ctggcttttg agactatggt tgacagcggt 1140
attatcgagg aaagcgcgta ctacgagagc ctgcatgaac tgccactgat cgcgaatact 1200
attgcgcgca aacgcctgta tgagatgaat gttgtgatta gcgacactgc ggaatatggc 1260
aattacctgt ttagctatgc gtgcgttcca ctgctgaagc cattcatggc ggaactgcag 1320
ccaggtgatc tgggcaaggc gatcccagag ggtgctgttg acaatggtca gctgcgcgac 1380
gttaatgagg ctatccgttc tcacgctatc gaacaagttg gcaaaaagct gcgtggttac 1440
atgaccgaca tgaagcgcat cgcggtggct ggctaa 1476

<210> SEQ ID NO 19
<211> LENGTH: 493
<212> TYPE: PRT
<213> ORGANISM: Escherichia coli

<400> SEQUENCE: 19

Met Ala Asn Tyr Phe Asn Thr Leu Asn Leu Arg Gln Gln Leu Ala Gln
1 5 10 15

Leu Gly Lys Cys Arg Phe Met Gly Arg Asp Glu Phe Ala Asp Gly Ala
20 25 30

Ser Tyr Leu Gln Gly Lys Lys Val Val Ile Val Gly Cys Gly Ala Gln
35 40 45

Gly Leu Asn Gln Gly Leu Asn Met Arg Asp Ser Gly Leu Asp Ile Ser

-continued

```
    50                  55                  60

Tyr Ala Leu Arg Lys Glu Ala Ile Ala Glu Lys Arg Ala Asp Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480
```

-continued

Met Thr Asp Met Lys Arg Ile Ala Val Ala Gly Leu Glu
485 490

<210> SEQ ID NO 20
<211> LENGTH: 1476
<212> TYPE: DNA
<213> ORGANISM: Escherichia coli

<400> SEQUENCE: 20
atggcgaatt atttcaacac tctgaacctg cgtcaacaac tggcgcaact gggtaagtgc 60
cgtttcatgg gtcgtgacga gtttgcggac ggtgcttctt atctgcaagg caagaaggtt 120
gttattgttg gttgcggtgc gcaaggcctg aatcaaggtc tgaatatgcg cgacagcggc 180
ctggacatta gctatgcgct gcgcaaggag gctatcgcgg aaaaacgtgc tagctggcgc 240
aaggctactg agaacggctt caaggttggc acctatgagg agctgattcc gcaagctgac 300
ctggttatca atctgacccc agataaagca catagcgacg ttgttcgtac tgttcaaccg 360
ctgatgaagg atggtgctgc tctgggttat agccacggct ttaacattgt tgaggtaggt 420
gaacaaattc gcaaggacat tactgttgtt atggtggctc caaagtgtcc gggtactgag 480
gttcgcgagg aatataagcg cggttttggt gttccaaccc tgatcgcggt gcatccagag 540
aatgacccaa agggtgaggg tatggctatc gcgaaggcgt gggctgcggc gactggcggc 600
catcgcgctg gcgttctgga gagcagcttt gtggctgagg ttaagagcga tctgatgggt 660
gaacagacta ttctgtgtgg tatgctgcaa gcgggtagcc tgctgtgttt tgataaactg 720
gttgaggagg gcactgaccc ggcgtatgcg gagaagctga tccaatttgg ctgggagact 780
attactgagg cgctgaagca aggtggtatt actctgatga tggatcgcct gagcaatcca 840
gctaagctgc gcgcgtacgc tctgagcgag caactgaagg aaattatggc accgctgttt 900
caaaagcaca tggatgatat cattagcggt gagtttagca gcggcatgat ggctgattgg 960
gcgaatgacg acaaaaagct gctgacttgg cgcgaggaaa ctggtaagac tgctttcgag 1020
actgctccac aatacgaggg taagattggt gaacaagaat attttgacaa gggtgttctg 1080
atgatcgcta tggttaaggc tggtgtggag ctggcttttg agactatggt tgacagcggt 1140
attatcgagg aaagcgcgta ctacgagagc ctgcatgaac tgccactgat cgcgaatact 1200
attgcgcgca aacgcctgta tgagatgaat gttgtgatta gcgacactgc ggaatatggc 1260
aattacctgt ttagctatgc gtgcgttcca ctgctgaagc cattcatggc ggaactgcag 1320
ccaggtgatc tgggcaaggc gatcccagag ggtgctgttg acaatggtca gctgcgcgac 1380
gttaatgagg ctatccgttc tcacgctatc gaacaagttg gcaaaaagct gcgtggttac 1440
atgaccgaca tgaagcgcat cgcggtggct ggctaa 1476

<210> SEQ ID NO 21
<211> LENGTH: 498
<212> TYPE: PRT
<213> ORGANISM: Escherichia coli

<400> SEQUENCE: 21

Met Ala Asn Tyr Phe Asn Thr Leu Asn Leu Arg Gln Gln Leu Ala Gln
1 5 10 15

Leu Gly Lys Cys Arg Phe Met Gly Arg Asp Glu Phe Ala Asp Gly Ala
20 25 30

Ser Tyr Leu Gln Gly Lys Lys Val Val Ile Val Gly Cys Gly Ala Gln
35 40 45

Gly Leu Asn Gln Gly Leu Asn Met Arg Asp Ser Gly Leu Asp Ile Ser
50 55 60

-continued

```
Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Ala His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly Leu Glu His His His
```

-continued 485 490 495

His His

<210> SEQ ID NO 22
<211> LENGTH: 1500
<212> TYPE: DNA
<213> ORGANISM: Escherichia coli

<400> SEQUENCE: 22
atggcgaatt atttcaacac tctgaacctg cgtcaacaac tggcgcaact gggtaagtgc 60
cgtttcatgg gtcgtgacga gtttgcggac ggtgcttctt atctgcaagg caagaaggtt 120
gttattgttg gttgcggtgc gcaaggcctg aatcaaggtc tgaatatgcg cgacagcggc 180
ctggacatta gctatgcgct gcgcaaggag gctatcgcgg aaaaacgtgc tagctggcgc 240
aaggctactg agaacggctt caaggttggc acctatgagg agctgattcc gcaagctgac 300
ctggttatca atctgacccc agataaagtg catagcgacg ttgttcgtac tgttcaaccg 360
ctgatgaagg atggtgctgc tctgggttat agccacggct ttaacattgt tgaggtaggt 420
gaacaaattc gcaaggacat tactgttgtt atggtggctc caaagtgtcc gggtactgag 480
gttcgcgagg aatataagcg cggttttggt gttccaaccc tgatcgcggt gcatccagag 540
aatgacccaa agggtgaggg tatggctatc gcgaaggcgt gggctgcggc gactggcggc 600
catcgcgctg gcgttctgga gagcagcttt gtggctgagg ttaagagcga tctgatgggt 660
gaacagacta ttctgtgtgg tatgctgcaa gcgggtagcc tgctgtgttt tgataaactg 720
gttgaggagg gcactgaccc ggcgtatgcg gagaagctga tccaatttgg ctgggagact 780
attactgagg cgctgaagca aggtggtatt actctgatga tggatcgcct gagcaatcca 840
gctaagctgc gcgcgtacgc tctgagcgag caactgaagg aaattatggc accgctgttt 900
caaaagcaca tggatgatat cattagcggt gagtttagca gcggcatgat ggctgattgg 960
gcgaatgacg acaaaaagct gctgacttgg cgcgaggaaa ctggtaagac tgctttcgag 1020
actgctccac aatacgaggg taagattggt gaacaagaat atttgacaa gggtgttctg 1080 atgatcgcta tggttaaggc tggtgtggag ctggcttttg agactatggt tgacagcggt 1140
attatcgagg aaagcgcgta ctacgagagc ctgcatgaac tgccactgat cgcgaatact 1200
attgcgcgca aacgcctgta tgagatgaat gttgtgatta gcgacactgc ggaatatggc 1260
aattacctgt ttagctatgc gtgcgttcca ctgctgaagc cattcatggc ggaactgcag 1320
ccaggtgatc tgggcaaggc gatcccagag ggtgctgttg acaatggtca gctgcgcgac 1380
gttaatgagg ctatccgttc tcacgctatc gaacaagttg gcaaaaagct gcgtggttac 1440
atgaccgaca tgaagcgcat cgcggtggct ggcctcgagc accaccacca ccaccactaa 1500

<210> SEQ ID NO 23
<211> LENGTH: 499
<212> TYPE: PRT
<213> ORGANISM: Escherichia coli

<400> SEQUENCE: 23

Met Ala Asn Tyr Phe Asn Thr Leu Asn Leu Arg Gln Gln Leu Ala Gln
1 5 10 15

Leu Gly Lys Cys Arg Phe Met Gly Arg Asp Glu Phe Ala Asp Gly Ala
20 25 30

Ser Tyr Leu Gln Gly Lys Lys Val Val Ile Val Gly Cys Gly Ala Gln
35 40 45

Gly Leu Asn Gln Gly Leu Asn Met Arg Asp Ser Gly Leu Asp Ile Ser

-continued

```
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Val His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480
```

-continued

```
Met Thr Asp Met Lys Arg Ile Ala Val Ala Gly Leu Glu His His His
                485                 490                 495

His His His


<210> SEQ ID NO 24
<211> LENGTH: 1476
<212> TYPE: DNA
<213> ORGANISM: Escherichia coli

<400> SEQUENCE: 24

atggcgaatt atttcaacac tctgaacctg cgtcaacaac tggcgcaact gggtaagtgc      60

cgtttcatgg gtcgtgacga gtttgcggac ggtgcttctt atctgcaagg caagaaggtt     120

gttattgttg gttgcggtgc gcaaggcctg aatcaaggtc tgaatatgcg cgacagcggc     180

ctggacatta gctatgcgct gcgcaaggag gctatcgcgg aaaaacgtgc tagctggcgc     240

aaggctactg agaacggctt caaggttggc acctatgagg agctgattcc gcaagctgac     300

ctggttatca atctgacccc agataaagtg catagcgacg ttgttcgtac tgttcaaccg     360

ctgatgaagg atggtgctgc tctgggttat agccacggct ttaacattgt tgaggtaggt     420

gaacaaattc gcaaggacat tactgttgtt atggtggctc caaagtgtcc gggtactgag     480

gttcgcgagg aatataagcg cggttttggt gttccaaccc tgatcgcggt gcatccagag     540

aatgacccaa agggtgaggg tatggctatc gcgaaggcgt gggctgcggc gactggcggc     600

catcgcgctg gcgttctgga gagcagcttt gtggctgagg ttaagagcga tctgatgggt     660

gaacagacta ttctgtgtgg tatgctgcaa gcgggtagcc tgctgtgttt tgataaactg     720

gttgaggagg gcactgaccc ggcgtatgcg gagaagctga tccaatttgg ctgggagact     780

attactgagg cgctgaagca aggtggtatt actctgatga tggatcgcct gagcaatcca     840

gctaagctgc gcgcgtacgc tctgagcgag caactgaagg aaattatggc accgctgttt     900

caaaagcaca tggatgatat cattagcggt gagtttagca gcggcatgat ggctgattgg     960

gcgaatgacg acaaaaagct gctgacttgg cgcgaggaaa ctggtaagac tgctttcgag    1020

actgctccac aatacgaggg taagattggt gaacaagaat attttgacaa gggtgttctg    1080

atgatcgcta tggttaaggc tggtgtggag ctggcttttg agactatggt tgacagcggt    1140

attatcgagg aaagcgcgta ctacgagagc ctgcatgaac tgccactgat cgcgaatact    1200

attgcgcgca aacgcctgta tgagatgaat gttgtgatta gcgacactgc ggaatatggc    1260

aattacctgt ttagctatgc gtgcgttcca ctgctgaagc cattcatggc ggaactgcag    1320

ccaggtgatc tgggcaaggc gatcccagag ggtgctgttg acaatggtca gctgcgcgac    1380

gttaatgagg ctatccgttc tcacgctatc gaacaagttg gcaaaaagct gcgtggttac    1440

atgaccgaca tgaagcgcat cgcggtggct ggctaa                              1476


<210> SEQ ID NO 25
<211> LENGTH: 493
<212> TYPE: PRT
<213> ORGANISM: Escherichia coli

<400> SEQUENCE: 25

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45
```

```
Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Val His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480
```

```
Met Thr Asp Met Lys Arg Ile Ala Val Ala Gly Leu Glu
                485                 490


<210> SEQ ID NO 26
<211> LENGTH: 1494
<212> TYPE: DNA
<213> ORGANISM: Escherichia coli

<400> SEQUENCE: 26

atggcgaatt atttcaacac tctgaacctg cgtcaacaac tggcgcaact gggtaagtgc     60

cgtttcatgg gtcgtgacga gtttgcggac ggtgcttctt atctgcaagg caagaaggtt    120

gttattgttg gttgcggtgc gcaaggcctg aatcaaggtc tgaatatgcg cgacagcggc    180

ctggacatta gctatgcgct gcgcaaggag gctatcgcgg aaaaacgtgc tgactggcgc    240

aaggctactg agaacggctt caaggttggc acctatgagg agctgattcc gcaagctgac    300

ctggttatca atctgacccc agataaagtg catagcgacg ttgttcgtac tgttcaaccg    360

ctgatgaagg atggtgctgc tctgggttat agccacggct ttaacattgt tgaggtaggt    420

gaacaaattc gcaaggacat tactgttgtt atggtggctc caaagtgtcc gggtactgag    480

gttcgcgagg aatataagcg cggttttggt gttccaaccc tgatcgcggt gcatccagag    540

aatgacccaa agggtgaggg tatggctatc gcgaaggcgt gggctgcggc gactggcggc    600

catcgcgctg gcgttctgga gagcagcttt gtggctgagg ttaagagcga tctgatgggt    660

gaacagacta ttctgtgtgg tatgctgcaa gcgggtagcc tgctgtgttt tgataaactg    720

gttgaggagg gcactgaccc ggcgtatgcg gagaagctga tccaatttgg ctgggagact    780

attactgagg cgctgaagca aggtggtatt actctgatga tggatcgcct gagcaatcca    840

gctaagctgc gcgcgtacgc tctgagcgag caactgaagg aaattatggc accgctgttt    900

caaaagcaca tggatgatat cattagcggt gagtttagca gcggcatgat ggctgattgg    960

gcgaatgacg acaaaaagct gctgacttgg cgcgaggaaa ctggtaagac tgctttcgag   1020

actgctccac aatacgaggg taagattggt gaacaagaat atttgacaa gggtgttctg   1080

atgatcgcta tggttaaggc tggtgtggag ctggcttttg agactatggt tgacagcggt   1140

attatcgagg aaagcgcgta ctacgagagc ctgcatgaac tgccactgat cgcgaatact   1200

attgcgcgca aacgcctgta tgagatgaat gttgtgatta gcgacactgc ggaatatggc   1260

aattacctgt ttagctatgc gtgcgttcca ctgctgaagc cattcatggc ggaactgcag   1320

ccaggtgatc tgggcaaggc gatcccagag ggtgctgttg acaatggtca gctgcgcgac   1380

gttaatgagg ctatccgttc tcacgctatc gaacaagttg gcaaaaagct gcgtggttac   1440

atgaccgaca tgaagcgcat cgcggtggct ggccaccacc accaccacca ctaa         1494


<210> SEQ ID NO 27
<211> LENGTH: 499
<212> TYPE: PRT
<213> ORGANISM: Escherichia coli

<400> SEQUENCE: 27

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
```

```
    50                  55                  60

Tyr Ala Leu Arg Lys Glu Ala Ile Ala Glu Lys Arg Ala Asp Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Val His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480
```

```
Met Thr Asp Met Lys Arg Ile Ala Val Ala Gly Leu Glu His His His
                485                 490                 495

His His His


<210> SEQ ID NO 28
<211> LENGTH: 1494
<212> TYPE: DNA
<213> ORGANISM: Escherichia coli

<400> SEQUENCE: 28

atggcgaatt atttcaacac tctgaacctg cgtcaacaac tggcgcaact gggtaagtgc     60

cgtttcatgg gtcgtgacga gtttgcggac ggtgcttctt atctgcaagg caagaaggtt    120

gttattgttg gttgcggtgc gcaaggcctg aatcaaggtc tgaatatgcg cgacagcggc    180

ctggacatta gctatgcgct gcgcaaggag tctatcgcgg aaaaacgtgc tgactggcgc    240

aaggctactg agaacggctt caaggttggc acctatgagg agctgattcc gcaagctgac    300

ctggttatca atctgacccc agataaagtg catagcgacg ttgttcgtac tgttcaaccg    360

ctgatgaagg atggtgctgc tctgggttat agccacggct ttaacattgt tgaggtaggt    420

gaacaaattc gcaaggacat tactgttgtt atggtggctc caaagtgtcc gggtactgag    480

gttcgcgagg aatataagcg cggttttggt gttccaaccc tgatcgcggt gcatccagag    540

aatgacccaa agggtgaggg tatggctatc gcgaaggcgt gggctgcggc gactggcggc    600

catcgcgctg gcgttctgga gagcagcttt gtggctgagg ttaagagcga tctgatgggt    660

gaacagacta ttctgtgtgg tatgctgcaa gcgggtagcc tgctgtgttt tgataaactg    720

gttgaggagg gcactgaccc ggcgtatgcg gagaagctga tccaatttgg ctgggagact    780

attactgagg cgctgaagca aggtggtatt actctgatga tggatcgcct gagcaatcca    840

gctaagctgc gcgcgtacgc tctgagcgag caactgaagg aaattatggc accgctgttt    900

caaaagcaca tggatgatat cattagcggt gagtttagca gcggcatgat ggctgattgg    960

gcgaatgacg acaaaaagct gctgacttgg cgcgaggaaa ctggtaagac tgctttcgag   1020

actgctccac aatacgaggg taagattggt gaacaagaat attttgacaa gggtgttctg   1080

atgatcgcta tggttaaggc tggtgtggag ctggcttttg agactatggt tgacagcggt   1140

attatcgagg aaagcgcgta ctacgagagc ctgcatgaac tgccactgat cgcgaatact   1200

attgcgcgca aacgcctgta tgagatgaat gttgtgatta gcgacactgc ggaatatggc   1260

aattacctgt ttagctatgc gtgcgttcca ctgctgaagc cattcatggc ggaactgcag   1320

ccaggtgatc tgggcaaggc gatcccagag ggtgctgttg acaatggtca gctgcgcgac   1380

gttaatgagg ctatccgttc tcacgctatc gaacaagttg gcaaaaagct gcgtggttac   1440

atgaccgaca tgaagcgcat cgcggtggct ggccaccacc accaccacca ctaa         1494


<210> SEQ ID NO 29
<211> LENGTH: 499
<212> TYPE: PRT
<213> ORGANISM: Escherichia coli

<400> SEQUENCE: 29

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45
```

-continued

```
Gly Leu Asn Gln Gly Leu Asn Met Arg Asp Ser Gly Leu Asp Ile Ser
    50                  55                  60

Tyr Ala Leu Arg Lys Glu Ser Ile Ala Glu Lys Arg Ala Asp Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Val His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480
```

Met Thr Asp Met Lys Arg Ile Ala Val Ala Gly Leu Glu His His His
485 490 495

His His His

<210> SEQ ID NO 30
<211> LENGTH: 1494
<212> TYPE: DNA
<213> ORGANISM: Escherichia coli

<400> SEQUENCE: 30
atggcgaatt atttcaacac tctgaacctg cgtcaacaac tggcgcaact gggtaagtgc 60
cgtttcatgg gtcgtgacga gtttgcggac ggtgcttctt atctgcaagg caagaaggtt 120
gttattgttg gttgcggtgc gcaaggcctg aatcaaggtc tgaatatgcg cgacagcggc 180
ctggacatta gctatgcgct gcgcaaggag tctatcgcgg aaaaagatgc tgattggcgc 240
aaggctactg agaacggctt caaggttggc acctatgagg agctgattcc gcaagctgac 300
ctggttatca atctgacccc agataaagca catagcgacg ttgttcgtac tgttcaaccg 360
ctgatgaagg atggtgctgc tctgggttat agccacggct ttaacattgt tgaggtaggt 420
gaacaaattc gcaaggacat tactgttgtt atggtggctc caaagtgtcc gggtactgag 480
gttcgcgagg aatataagcg cggttttggt gttccaaccc tgatcgcggt gcatccagag 540
aatgacccaa agggtgaggg tatggctatc gcgaaggcgt gggctgcggc gactggcggc 600
catcgcgctg gcgttctgga gagcagcttt gtggctgagg ttaagagcga tctgatgggt 660
gaacagacta ttctgtgtgg tatgctgcaa gcgggtagcc tgctgtgttt tgataaactg 720
gttgaggagg gcactgaccc ggcgtatgcg gagaagctga tccaatttgg ctgggagact 780
attactgagg cgctgaagca aggtggtatt actctgatga tggatcgcct gagcaatcca 840
gctaagctgc gcgcgtacgc tctgagcgag caactgaagg aaattatggc accgctgttt 900
caaaagcaca tggatgatat cattagcggt gagtttagca gcggcatgat ggctgattgg 960
gcgaatgacg acaaaaagct gctgacttgg cgcgaggaaa ctggtaagac tgctttcgag 1020
actgctccac aatacgaggg taagattggt gaacaagaat attttgacaa gggtgttctg 1080
atgatcgcta tggttaaggc tggtgtggag ctggcttttg agactatggt tgacagcggt 1140
attatcgagg aaagcgcgta ctacgagagc ctgcatgaac tgccactgat cgcgaatact 1200
attgcgcgca aacgcctgta tgagatgaat gttgtgatta gcgacactgc ggaatatggc 1260
aattacctgt ttagctatgc gtgcgttcca ctgctgaagc cattcatggc ggaactgcag 1320
ccaggtgatc tgggcaaggc gatcccagag ggtgctgttg acaatggtca gctgcgcgac 1380
gttaatgagg ctatccgttc tcacgctatc gaacaagttg gcaaaaagct gcgtggttac 1440
atgaccgaca tgaagcgcat cgcggtggct ggccaccacc accaccacca ctaa 1494

<210> SEQ ID NO 31
<211> LENGTH: 499
<212> TYPE: PRT
<213> ORGANISM: Escherichia coli

<400> SEQUENCE: 31

Met Ala Asn Tyr Phe Asn Thr Leu Asn Leu Arg Gln Gln Leu Ala Gln
1 5 10 15

Leu Gly Lys Cys Arg Phe Met Gly Arg Asp Glu Phe Ala Asp Gly Ala
20 25 30

Ser Tyr Leu Gln Gly Lys Lys Val Val Ile Val Gly Cys Gly Ala Gln
35 40 45

```
Gly Leu Asn Gln Gly Leu Asn Met Arg Asp Ser Gly Leu Asp Ile Ser
    50                  55                  60

Tyr Ala Leu Arg Lys Glu Ser Ile Ala Glu Lys Asp Ala Asp Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Ala His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
```

-continued 465 470 475 480

Met Thr Asp Met Lys Arg Ile Ala Val Ala Gly Leu Glu His His His
485 490 495

His His His

<210> SEQ ID NO 32
<211> LENGTH: 1494
<212> TYPE: DNA
<213> ORGANISM: Escherichia coli

<400> SEQUENCE: 32
atggcgaatt atttcaacac tctgaacctg cgtcaacaac tggcgcaact gggtaagtgc 60
cgtttcatgg gtcgtgacga gtttgcggac ggtgcttctt atctgcaagg caagaaggtt 120
gttattgttg gttgcggtgc gcaaggcctg aatcaaggtc tgaatatgcg cgacagcggc 180
ctggacatta gctatgcgct gcgcaaggag tctatcgcgg aaaaagatgc tgattggcgc 240
aaggctactg agaacggctt caaggttggc acctatgagg agctgattcc gcaagctgac 300
ctggttatca atctgacccc agataaagta catagcgacg ttgttcgtac tgttcaaccg 360
ctgatgaagg atggtgctgc tctgggttat agccacggct ttaacattgt tgaggtaggt 420
gaacaaattc gcaaggacat tactgttgtt atggtggctc caaagtgtcc gggtactgag 480
gttcgcgagg aatataagcg cggttttggt gttccaaccc tgatcgcggt gcatccagag 540
aatgacccaa agggtgaggg tatggctatc gcgaaggcgt gggctgcggc gactggcggc 600
catcgcgctg gcgttctgga gagcagcttt gtggctgagg ttaagagcga tctgatgggt 660
gaacagacta ttctgtgtgg tatgctgcaa gcgggtagcc tgctgtgttt tgataaactg 720
gttgaggagg gcactgaccc ggcgtatgcg gagaagctga tccaatttgg ctgggagact 780
attactgagg cgctgaagca aggtggtatt actctgatga tggatcgcct gagcaatcca 840
gctaagctgc gcgcgtacgc tctgagcgag caactgaagg aaattatggc accgctgttt 900
caaaagcaca tggatgatat cattagcggt gagtttagca gcggcatgat ggctgattgg 960
gcgaatgacg acaaaaagct gctgacttgg cgcgaggaaa ctggtaagac tgctttcgag 1020
actgctccac aatacgaggg taagattggt gaacaagaat attttgacaa gggtgttctg 1080
atgatcgcta tggttaaggc tggtgtggag ctggcttttg agactatggt tgacagcggt 1140
attatcgagg aaagcgcgta ctacgagagc ctgcatgaac tgccactgat cgcgaatact 1200
attgcgcgca aacgcctgta tgagatgaat gttgtgatta gcgacactgc ggaatatggc 1260
aattacctgt ttagctatgc gtgcgttcca ctgctgaagc cattcatggc ggaactgcag 1320
ccaggtgatc tgggcaaggc gatcccagag ggtgctgttg acaatggtca gctgcgcgac 1380
gttaatgagg ctatccgttc tcacgctatc gaacaagttg gcaaaaagct gcgtggttac 1440
atgaccgaca tgaagcgcat cgcggtggct ggccaccacc accaccacca ctaa 1494

<210> SEQ ID NO 33
<211> LENGTH: 1494
<212> TYPE: DNA
<213> ORGANISM: Escherichia coli

<400> SEQUENCE: 33
atggccaact attttaacac attaaatttg agacaacaat tggctcaact gggtaagtgc 60
agatttatgg gaagggacga gtttgctgat ggtgcttctt atctgcaagg aaagaaagta 120
gtaattgttg gctgcggtgc tcagggtcta aaccaaggtt taaacatgag agattcaggt 180
ctggatattt cgtatgcatt gaggaaagag tctattgcag aaaaggatgc cgattggcgt 240

```
aaagcgacgg aaaatgggtt caaagttggt acttacgaag aactgatccc tcaggcagat    300

ttagtgatta acctaacacc agataaggtt cactcagacg tagtaagaac agttcaaccg    360

ctgatgaagg atggggcagc tttaggttac tctcatggct ttaatatcgt tgaagtgggc    420

gagcagatca gaaaagatat aacagtcgta atggttgcac caaagtgccc aggtacggaa    480

gtcagagagg agtacaagag gggttttggt gtacctacat tgatcgccgt acatcctgaa    540

aatgacccca aaggtgaagg tatggcaatt gcgaaggcat gggcagccgc aaccggaggt    600

catagagcgg gtgtgttaga gagttctttc gtagctgagg tcaagagtga cttaatgggt    660

gaacaaacca ttctgtgcgg aatgttgcag gcagggtctt tactatgctt tgataaattg    720

gtcgaagagg gtacagatcc tgcctatgct gaaaagttga tacaatttgg ttgggagaca    780

atcaccgagg cacttaaaca aggtggcata acattgatga tggatagact ttcaaatccg    840

gccaagctaa gagcctacgc cttatctgag caactaaaag agatcatggc accattattc    900

caaaagcaca tggacgatat tatctccggt gagttttcct caggaatgat ggcagattgg    960

gcaaacgatg ataaaaagtt attgacgtgg agagaagaaa ccggcaagac ggcattcgag   1020

acagccccac aatacgaagg taaaattggt gaacaagaat actttgataa gggagtattg   1080

atgatagcta tggtgaaggc aggggtagaa cttgcattcg aaactatggt tgactccggt   1140

atcattgaag aatctgcata ctatgagtct ttgcatgaat tgcctttgat agcaaatact   1200

attgcaagaa aaagacttta cgagatgaat gttgtcatat cagacactgc agaatatggt   1260

aattacttat ttagctacgc atgtgtcccg ttgttaaagc ccttcatggc cgagttacaa   1320

cctggtgatt tggggaaggc tattccggaa ggagcggttg acaatggcca actgagagac   1380

gtaaatgaag ctattcgttc acatgctata gaacaggtgg gtaaaaagct gagaggatat   1440

atgaccgata tgaaaagaat tgcagtggca ggacaccacc accaccacca ctga          1494
```

<210> SEQ ID NO 34
<211> LENGTH: 499
<212> TYPE: PRT
<213> ORGANISM: Escherichia coli

<400> SEQUENCE: 34

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ser Ile Ala Glu Lys Asp Ala Asp Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Val His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160
```

```
Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly Leu Glu His His His
                485                 490                 495

His His His
```

<210> SEQ ID NO 35
<211> LENGTH: 1476
<212> TYPE: DNA
<213> ORGANISM: Escherichia coli

<400> SEQUENCE: 35

```
atggccaact attttaacac attaaatttg agacaacaat tggctcaact gggtaagtgc      60

agatttatgg gaagggacga gtttgctgat ggtgcttctt atctgcaagg aaagaaagta     120

gtaattgttg gctgcggtgc tcagggtcta aaccaaggtt taaacatgag agattcaggt     180
```

```
ctggatattt cgtatgcatt gaggaaagag tctattgcag aaaaggatgc cgattggcgt    240

aaagcgacgg aaaatgggtt caaagttggt acttacgaag aactgatccc tcaggcagat    300

ttagtgatta acctaacacc agataaggtt cactcagacg tagtaagaac agttcaaccg    360

ctgatgaagg atggggcagc tttaggttac tctcatggct ttaatatcgt tgaagtgggc    420

gagcagatca gaaaagatat aacagtcgta atggttgcac caaagtgccc aggtacggaa    480

gtcagagagg agtacaagag ggttttggt gtacctacat tgatcgccgt acatcctgaa    540

aatgacccca aaggtgaagg tatggcaatt gcgaaggcat gggcagccgc aaccggaggt    600

catagagcgg gtgtgttaga gagttctttc gtagctgagg tcaagagtga cttaatgggt    660

gaacaaacca ttctgtgcgg aatgttgcag gcagggtctt tactatgctt tgataaattg    720

gtcgaagagg gtacagatcc tgcctatgct gaaaagttga tacaatttgg ttgggagaca    780

atcaccgagg cacttaaaca aggtggcata acattgatga tggatagact ttcaaatccg    840

gccaagctaa gagcctacgc cttatctgag caactaaaag agatcatggc accattattc    900

caaaagcaca tggacgatat tatctccggt gagttttcct caggaatgat ggcagattgg    960

gcaaacgatg ataaaaagtt attgacgtgg agagaagaaa ccggcaagac ggcattcgag   1020

acagccccac aatacgaagg taaaattggt gaacaagaat actttgataa gggagtattg   1080

atgatagcta tggtgaaggc aggggtagaa cttgcattcg aaactatggt tgactccggt   1140

atcattgaag aatctgcata ctatgagtct ttgcatgaat tgcctttgat agcaaatact   1200

attgcaagaa aaagacttta cgagatgaat gttgtcatat cagacactgc agaatatggt   1260

aattacttat ttagctacgc atgtgtcccg ttgttaaagc ccttcatggc cgagttacaa   1320

cctggtgatt tggggaaggc tattccggaa ggagcggttg acaatggcca actgagagac   1380

gtaaatgaag ctattcgttc acatgctata gaacaggtgg gtaaaaagct gagaggatat   1440

atgaccgata tgaaaagaat tgcagtggca ggatga                              1476
```

<210> SEQ ID NO 36
<211> LENGTH: 491
<212> TYPE: PRT
<213> ORGANISM: Escherichia coli

<400> SEQUENCE: 36

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ser Ile Ala Glu Lys Asp Ala Asp Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Val His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
```

```
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490
```

<210> SEQ ID NO 37
<211> LENGTH: 1494
<212> TYPE: DNA
<213> ORGANISM: Escherichia coli

<400> SEQUENCE: 37

```
atggccaact attttaacac attaaatttg agacaacaat tggctcaact gggtaagtgc      60

agatttatgg gaagggacga gtttgctgat ggtgcttctt atctgcaagg aaagaaagta     120

gtaattgttg gctgcggtgc tcagggtcta aaccaaggtt taaacatgag agattcaggt     180

ctggatattt cgtatgcatt gaggaaagag tctattgcag aaaaggatgc cgattggcgt     240
```

```
aaagcgacgg aaaatgggtt caaagttggt acttacgaag aactgatccc tcaggcagat    300

ttagtgatta acctaacacc agataaggtt cactcagacg tagtaagaac agttcaaccg    360

ctgatgaagg atggggcagc tttaggttac tctcatggct ttaatatcgt tgaagtgggc    420

gagcagatca gaaaaggtat aacagtcgta atggttgcgc caaagtgccc aggtacggaa    480

gtcagagagg agtacaagag gggttttggt gtacctacat tgatcgccgt acatcctgaa    540

aatgacccca aacgtgaagg tatggcaatt gcgaaggcat gggcagccgc aaccggaggt    600

catagagcgg gtgtgttaga gagttctttc gtagctgagg tcaagagtga cttaatgggt    660

gaacaaacca ttctgtgcgg aatgttgcag gcagggtctt tactatgctt tgataaattg    720

gtcgaagagg gtacagatcc tgcctatgct gaaaagttga tacaatttgg ttgggagaca    780

atcaccgagg cacttaaaca aggtggcata acattgatga tggatagact ttcaaatccg    840

gccaagctaa gagcctacgc cttatctgag caactaaaag agatcatggc accattattc    900

caaaagcaca tggacgatat tatctccggt gagttttcct caggaatgat ggcagattgg    960

gcaaacgatg ataaaaagtt attgacgtgg agagaagaaa ccggcaagac ggcattcgag   1020

acagccccac aatacgaagg taaaattggt gaacaagaat actttgataa gggagtattg   1080

atgatagcta tggtgaaggc aggggtagaa cttgcattcg aaactatggt tgactccggt   1140

atcattgaag aatctgcata ctatgagtct ttgcatgaat tgcctttgat agcaaatact   1200

attgcaagaa aaagacttta cgagatgaat gttgtcatat cagacactgc agaatatggt   1260

aattacttat ttagctacgc atgtgtcccg ttgttaaagc ccttcatggc cgagttacaa   1320

cctggtgatt tggggaaggc tattccggaa ggagcggttg acaatggcca actgagagac   1380

gtaaatgaag ctattcgttc acatgctata gaacaggtgg gtaaaaagct gagaggatat   1440

atgaccgata tgaaaagaat tgcagtggca ggacaccacc accaccacca ctga         1494
```

<210> SEQ ID NO 38
<211> LENGTH: 497
<212> TYPE: PRT
<213> ORGANISM: Escherichia coli

<400> SEQUENCE: 38

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ser Ile Ala Glu Lys Asp Ala Asp Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Val His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Gly Ile Thr Val Val Met Val Ala Pro Lys Cys Pro Gly Thr Glu
145                 150                 155                 160
```

```
Val Arg Glu Glu Tyr Lys Arg Gly Phe Gly Val Pro Thr Leu Ile Ala
                165                 170                 175

Val His Pro Glu Asn Asp Pro Lys Arg Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly His His His His His
                485                 490                 495

His

<210> SEQ ID NO 39
<211> LENGTH: 1476
<212> TYPE: DNA
<213> ORGANISM: Escherichia coli

<400> SEQUENCE: 39

atggccaact attttaacac attaaatttg agacaacaat tggctcaact gggtaagtgc      60

agatttatgg gaagggacga gtttgctgat ggtgcttctt atctgcaagg aaagaaagta     120

gtaattgttg gctgcggtgc tcagggtcta aaccaaggtt taaacatgag agattcaggt     180
```

```
ctggatattt cgtatgcatt gaggaaagag tctattgcag aaaaggatgc cgattggcgt    240

aaagcgacgg aaaatgggtt caaagttggt acttacgaag aactgatccc tcaggcagat    300

ttagtgatta acctaacacc agataaggtt cactcagacg tagtaagaac agttcaaccg    360

ctgatgaagg atggggcagc tttaggttac tctcatggct ttaatatcgt tgaagtgggc    420

gagcagatca gaaaaggtat aacagtcgta atggttgcgc caaagtgccc aggtacggaa    480

gtcagagagg agtacaagag ggttttggt gtacctacat tgatcgccgt acatcctgaa    540

aatgacccca aacgtgaagg tatggcaatt gcgaaggcat gggcagccgc aaccggaggt    600

catagagcgg gtgtgttaga gagttctttc gtagctgagg tcaagagtga cttaatgggt    660

gaacaaacca ttctgtgcgg aatgttgcag gcagggtctt tactatgctt tgataaattg    720

gtcgaagagg gtacagatcc tgcctatgct gaaaagttga tacaatttgg ttgggagaca    780

atcaccgagg cacttaaaca aggtggcata acattgatga tggatagact ttcaaatccg    840

gccaagctaa gagcctacgc cttatctgag caactaaaag agatcatggc accattattc    900

caaaagcaca tggacgatat tatctccggt gagttttcct caggaatgat ggcagattgg    960

gcaaacgatg ataaaaagtt attgacgtgg agagaagaaa ccggcaagac ggcattcgag   1020

acagccccac aatacgaagg taaaattggt gaacaagaat actttgataa gggagtattg   1080

atgatagcta tggtgaaggc aggggtagaa cttgcattcg aaactatggt tgactccggt   1140

atcattgaag aatctgcata ctatgagtct ttgcatgaat tgcctttgat agcaaatact   1200

attgcaagaa aaagacttta cgagatgaat gttgtcatat cagacactgc agaatatggt   1260

aattacttat ttagctacgc atgtgtcccg ttgttaaagc ccttcatggc cgagttacaa   1320

cctggtgatt tggggaaggc tattccggaa ggagcggttg acaatggcca actgagagac   1380

gtaaatgaag ctattcgttc acatgctata gaacaggtgg gtaaaaagct gagaggatat   1440

atgaccgata tgaaaagaat tgcagtggca ggatga                             1476
```

<210> SEQ ID NO 40
<211> LENGTH: 491
<212> TYPE: PRT
<213> ORGANISM: Escherichia coli

<400> SEQUENCE: 40

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ser Ile Ala Glu Lys Asp Ala Asp Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Val His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Gly Ile Thr Val Val Met Val Ala Pro Lys Cys Pro Gly Thr Glu
```

-continued 145 150 155 160

Val Arg Glu Glu Tyr Lys Arg Gly Phe Gly Val Pro Thr Leu Ile Ala
165 170 175

Val His Pro Glu Asn Asp Pro Lys Arg Glu Gly Met Ala Ile Ala Lys
180 185 190

Ala Trp Ala Ala Ala Thr Gly Gly His Arg Ala Gly Val Leu Glu Ser
195 200 205

Ser Phe Val Ala Glu Val Lys Ser Asp Leu Met Gly Glu Gln Thr Ile
210 215 220

Leu Cys Gly Met Leu Gln Ala Gly Ser Leu Leu Cys Phe Asp Lys Leu
225 230 235 240

Val Glu Glu Gly Thr Asp Pro Ala Tyr Ala Glu Lys Leu Ile Gln Phe
245 250 255

Gly Trp Glu Thr Ile Thr Glu Ala Leu Lys Gln Gly Gly Ile Thr Leu
260 265 270

Met Met Asp Arg Leu Ser Asn Pro Ala Lys Leu Arg Ala Tyr Ala Leu
275 280 285

Ser Glu Gln Leu Lys Glu Ile Met Ala Pro Leu Phe Gln Lys His Met
290 295 300

Asp Asp Ile Ile Ser Gly Glu Phe Ser Ser Gly Met Met Ala Asp Trp
305 310 315 320

Ala Asn Asp Asp Lys Lys Leu Leu Thr Trp Arg Glu Glu Thr Gly Lys
325 330 335

Thr Ala Phe Glu Thr Ala Pro Gln Tyr Glu Gly Lys Ile Gly Glu Gln
340 345 350

Glu Tyr Phe Asp Lys Gly Val Leu Met Ile Ala Met Val Lys Ala Gly
355 360 365

Val Glu Leu Ala Phe Glu Thr Met Val Asp Ser Gly Ile Ile Glu Glu
370 375 380

Ser Ala Tyr Tyr Glu Ser Leu His Glu Leu Pro Leu Ile Ala Asn Thr
385 390 395 400

Ile Ala Arg Lys Arg Leu Tyr Glu Met Asn Val Val Ile Ser Asp Thr
405 410 415

Ala Glu Tyr Gly Asn Tyr Leu Phe Ser Tyr Ala Cys Val Pro Leu Leu
420 425 430

Lys Pro Phe Met Ala Glu Leu Gln Pro Gly Asp Leu Gly Lys Ala Ile
435 440 445

Pro Glu Gly Ala Val Asp Asn Gly Gln Leu Arg Asp Val Asn Glu Ala
450 455 460

Ile Arg Ser His Ala Ile Glu Gln Val Gly Lys Lys Leu Arg Gly Tyr
465 470 475 480

Met Thr Asp Met Lys Arg Ile Ala Val Ala Gly
485 490

<210> SEQ ID NO 41
<211> LENGTH: 1494
<212> TYPE: DNA
<213> ORGANISM: Escherichia coli

<400> SEQUENCE: 41
atggccaact attttaacac attaaatttg agacaacaat tggctcaact gggtaagtgc 60
agatttatgg gaagggacga gtttgctgat ggtgcttctt atctgcaagg aaagaaagta 120
gtaattgttg gctgcggtgc tcagggtcta aaccaaggtt taaacatgag agattcaggt 180
ctggatattt cgtatgcatt gaggaaagag tctattgcag aaaaggatgc cgattggcgt 240

```
aaagcgacgg aaaatgggtt caaagttggt acttacgaag aactgatccc tcaggcagat    300
ttagtgatta acctaacacc agataaggtt cactcagacg tagtaagaac agttcaaccg    360
ctgatgaagg atggggcagc tttaggttac tctcatggct ttaatatcgt tgaagtgggc    420
gagcagatca gaaaaggtat aacagtcgta atggttgcgc caaagtgccc aggtacggaa    480
gtcagagagg agtacaagag gggttttggt gtacctacat tgatcgccgt acatcctgaa    540
aatgacccca aacgtgaagg tatggcaata gcgaaggcat gggcagccgc aaccggaggt    600
catagagcgg gtgtgttaga gagttctttc gtagctgagg tcaagagtga cttaatgggt    660
gaacaaacca ttctgtgcgg aatgttgcag gcagggtctt tactatgctt tgataaattg    720
gtcgaagagg gtacagatcc tgcctatgct gaaaagttga tacaatttgg ttgggagaca    780
atcaccgagg cacttaaaca aggtggcata acattgatga tggatagact ttcaaatccg    840
gccaagctaa gagcctacgc cttatctgag caactaaaag agatcatggc accattattc    900
caaaagcaca tggacgatat tatctccggt gagttttcct caggaatgat ggcagattgg    960
gcaaacgatg ataaaaagtt attgacgtgg agagaagaaa ccggcaagac ggcattcgag   1020
acagccccac aatacgaagg taaaattggt gaacaagaat actttgataa gggagtattg   1080
atgatagcta tggtgaaggc aggggtagaa cttgcattcg aaactatggt tgactccggt   1140
atcattgaag aatctgcata ctatgagtct ttgcatgaat tgcctttgat agcaaatact   1200
attgcaagaa aaagacttta cgagatgaat gttgtcatat cagacactgc agaatatggt   1260
aattacttat ttagctacgc gtgtgtcccg ttgttagagc ccttcatggc cgagttacaa   1320
cctggtgatt tggggaaggc tattccggaa ggagcggttg acaatggcca actgagagac   1380
gtaaatgaag ctattcgttc gcatgctata gaacaggtgg gtaaaaagct gagaggatat   1440
atgaccgata tgaaaagaat tgcagtggca ggacaccacc accaccacca ctga         1494
```

<210> SEQ ID NO 42
<211> LENGTH: 497
<212> TYPE: PRT
<213> ORGANISM: Escherichia coli

<400> SEQUENCE: 42

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ser Ile Ala Glu Lys Asp Ala Asp Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Val His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Gly Ile Thr Val Val Met Val Ala Pro Lys Cys Pro Gly Thr Glu
145                 150                 155                 160
```

```
Val Arg Glu Glu Tyr Lys Arg Gly Phe Gly Val Pro Thr Leu Ile Ala
                165                 170                 175

Val His Pro Glu Asn Asp Pro Lys Arg Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Glu Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly His His His His His
                485                 490                 495

His
```

<210> SEQ ID NO 43
<211> LENGTH: 1476
<212> TYPE: DNA
<213> ORGANISM: Escherichia coli

<400> SEQUENCE: 43

```
atggccaact attttaacac attaaatttg agacaacaat tggctcaact gggtaagtgc     60

agatttatgg gaagggacga gtttgctgat ggtgcttctt atctgcaagg aaagaaagta    120

gtaattgttg gctgcggtgc tcagggtcta aaccaaggtt taaacatgag agattcaggt    180
```

ctggatattt cgtatgcatt gaggaaagag tctattgcag aaaaggatgc cgattggcgt 240
aaagcgacgg aaaatgggtt caaagttggt acttacgaag aactgatccc tcaggcagat 300
ttagtgatta acctaacacc agataaggtt cactcagacg tagtaagaac agttcaaccg 360
ctgatgaagg atggggcagc tttaggttac tctcatggct ttaatatcgt tgaagtgggc 420
gagcagatca gaaaaggtat aacagtcgta atggttgcgc caaagtgccc aggtacggaa 480
gtcagagagg agtacaagag ggttttggt gtacctacat tgatcgccgt acatcctgaa 540
aatgacccca aacgtgaagg tatggcaata gcgaaggcat gggcagccgc aaccggaggt 600
catagagcgg gtgtgttaga gagttctttc gtagctgagg tcaagagtga cttaatgggt 660
gaacaaacca ttctgtgcgg aatgttgcag gcagggtctt tactatgctt tgataaattg 720
gtcgaagagg gtacagatcc tgcctatgct gaaaagttga tacaatttgg ttgggagaca 780
atcaccgagg cacttaaaca aggtggcata acattgatga tggatagact ttcaaatccg 840
gccaagctaa gagcctacgc cttatctgag caactaaaag agatcatggc accattattc 900
caaaagcaca tggacgatat tatctccggt gagttttcct caggaatgat ggcagattgg 960
gcaaacgatg ataaaaagtt attgacgtgg agagaagaaa ccggcaagac ggcattcgag 1020
acagccccac aatacgaagg taaaattggt gaacaagaat actttgataa gggagtattg 1080
atgatagcta tggtgaaggc aggggtagaa cttgcattcg aaactatggt tgactccggt 1140
atcattgaag aatctgcata ctatgagtct ttgcatgaat tgcctttgat agcaaatact 1200
attgcaagaa aaagacttta cgagatgaat gttgtcatat cagacactgc agaatatggt 1260
aattacttat ttagctacgc gtgtgtcccg ttgttagagc ccttcatggc cgagttacaa 1320
cctggtgatt tggggaaggc tattccggaa ggagcggttg acaatggcca actgagagac 1380
gtaaatgaag ctattcgttc gcatgctata gaacaggtgg gtaaaaagct gagaggatat 1440
atgaccgata tgaaaagaat tgcagtggca ggatga 1476

<210> SEQ ID NO 44
<211> LENGTH: 491
<212> TYPE: PRT
<213> ORGANISM: Escherichia coli

<400> SEQUENCE: 44

Met Ala Asn Tyr Phe Asn Thr Leu Asn Leu Arg Gln Gln Leu Ala Gln
1 5 10 15

Leu Gly Lys Cys Arg Phe Met Gly Arg Asp Glu Phe Ala Asp Gly Ala
20 25 30

Ser Tyr Leu Gln Gly Lys Lys Val Val Ile Val Gly Cys Gly Ala Gln
35 40 45

Gly Leu Asn Gln Gly Leu Asn Met Arg Asp Ser Gly Leu Asp Ile Ser
50 55 60

Tyr Ala Leu Arg Lys Glu Ser Ile Ala Glu Lys Asp Ala Asp Trp Arg
65 70 75 80

Lys Ala Thr Glu Asn Gly Phe Lys Val Gly Thr Tyr Glu Glu Leu Ile
85 90 95

Pro Gln Ala Asp Leu Val Ile Asn Leu Thr Pro Asp Lys Val His Ser
100 105 110

Asp Val Val Arg Thr Val Gln Pro Leu Met Lys Asp Gly Ala Ala Leu
115 120 125

Gly Tyr Ser His Gly Phe Asn Ile Val Glu Val Gly Glu Gln Ile Arg
130 135 140

Lys Gly Ile Thr Val Val Met Val Ala Pro Lys Cys Pro Gly Thr Glu 145 150 155 160

Val Arg Glu Glu Tyr Lys Arg Gly Phe Gly Val Pro Thr Leu Ile Ala
165 170 175

Val His Pro Glu Asn Asp Pro Lys Arg Glu Gly Met Ala Ile Ala Lys
180 185 190

Ala Trp Ala Ala Ala Thr Gly Gly His Arg Ala Gly Val Leu Glu Ser
195 200 205

Ser Phe Val Ala Glu Val Lys Ser Asp Leu Met Gly Glu Gln Thr Ile
210 215 220

Leu Cys Gly Met Leu Gln Ala Gly Ser Leu Leu Cys Phe Asp Lys Leu
225 230 235 240

Val Glu Glu Gly Thr Asp Pro Ala Tyr Ala Glu Lys Leu Ile Gln Phe
245 250 255

Gly Trp Glu Thr Ile Thr Glu Ala Leu Lys Gln Gly Gly Ile Thr Leu
260 265 270

Met Met Asp Arg Leu Ser Asn Pro Ala Lys Leu Arg Ala Tyr Ala Leu
275 280 285

Ser Glu Gln Leu Lys Glu Ile Met Ala Pro Leu Phe Gln Lys His Met
290 295 300

Asp Asp Ile Ile Ser Gly Glu Phe Ser Ser Gly Met Met Ala Asp Trp
305 310 315 320

Ala Asn Asp Asp Lys Lys Leu Leu Thr Trp Arg Glu Glu Thr Gly Lys
325 330 335

Thr Ala Phe Glu Thr Ala Pro Gln Tyr Glu Gly Lys Ile Gly Glu Gln
340 345 350

Glu Tyr Phe Asp Lys Gly Val Leu Met Ile Ala Met Val Lys Ala Gly
355 360 365

Val Glu Leu Ala Phe Glu Thr Met Val Asp Ser Gly Ile Ile Glu Glu
370 375 380

Ser Ala Tyr Tyr Glu Ser Leu His Glu Leu Pro Leu Ile Ala Asn Thr
385 390 395 400

Ile Ala Arg Lys Arg Leu Tyr Glu Met Asn Val Val Ile Ser Asp Thr
405 410 415

Ala Glu Tyr Gly Asn Tyr Leu Phe Ser Tyr Ala Cys Val Pro Leu Leu
420 425 430

Glu Pro Phe Met Ala Glu Leu Gln Pro Gly Asp Leu Gly Lys Ala Ile
435 440 445

Pro Glu Gly Ala Val Asp Asn Gly Gln Leu Arg Asp Val Asn Glu Ala
450 455 460

Ile Arg Ser His Ala Ile Glu Gln Val Gly Lys Lys Leu Arg Gly Tyr
465 470 475 480

Met Thr Asp Met Lys Arg Ile Ala Val Ala Gly
485 490

<210> SEQ ID NO 45
<211> LENGTH: 1647
<212> TYPE: DNA
<213> ORGANISM: Lactococcus lactis

<400> SEQUENCE: 45
atgtatacag taggagatta cctattagac cgattacacg agttaggaat tgaagaaatt 60
tttggagtcc ctggagacta taacttacaa tttttagatc aaattatttc ccgcaaggat 120
atgaaatggg tcggaaatgc taatgaatta aatgcttcat atatggctga tggctatgct 180
cgtactaaaa aagctgccgc atttcttaca acctttggag taggtgaatt gagtgcagtt 240

```
aatggattag caggaagtta cgccgaaaat ttaccagtag tagaaatagt gggatcacct    300
acatcaaaag ttcaaaatga aggaaaattt gttcatcata cgctggctga cggtgatttt    360
aaacacttta tgaaaatgca cgaacctgtt acagcagctc gaactttact gacagcagaa    420
aatgcaaccg ttgaaattga ccgagtactt tctgcactat taaaagaaag aaaacctgtc    480
tatatcaact taccagttga tgttgctgct gcaaaagcag agaaaccctc actccctttg    540
aaaaaagaaa actcaacttc aaatacaagt gaccaagaga tcttgaacaa aattcaagaa    600
agcttgaaaa atgccaaaaa accaatcgtg attacaggac atgaaataat tagttttggc    660
ttagaaaaaa cagtctctca atttatttca aagacaaaac tacctattac gacattaaac    720
tttggaaaaa gttcagttga tgaagctctc ccttcatttt taggaatcta taatggtaaa    780
ctctcagagc ctaatcttaa agaattcgtg gaatcagccg acttcatcct gatgcttgga    840
gttaaactca cagactcttc aacaggagcc ttcactcatc atttaaatga aaataaaatg    900
atttcactga atatagatga aggaaaaata tttaacgaaa gcatccaaaa ttttgatttt    960
gaatccctca tctcctctct cttagaccta agcgaaatag aatacaaagg aaaatatatc   1020
gataaaaagc aagaagactt tgttccatca aatgcgcttt tatcacaaga ccgcctatgg   1080
caagcagttg aaaacctaac tcaaagcaat gaaacaatcg ttgctgaaca agggacatca   1140
ttctttggcg cttcatcaat ttttcttaaa ccaaagagtc attttattgg tcaaccctta   1200
tggggatcaa ttggatatac attcccagca gcattaggaa gccaaattgc agataaagaa   1260
agcagacacc ttttatttat tggtgatggt tcacttcaac ttacggtgca agaattagga   1320
ttagcaatca gagaaaaaat taatccaatt tgctttatta tcaataatga tggttataca   1380
gtcgaaagag aaattcatgg accaaatcaa agctacaatg atattccaat gtggaattac   1440
tcaaaattac cagaatcatt tggagcaaca gaagaacgag tagtctcgaa aatcgttaga   1500
actgaaaatg aatttgtgtc tgtcatgaaa gaagctcaag cagatccaaa tagaatgtac   1560
tggattgagt taattttggc aaaagaagat gcaccaaaag tactgaaaaa aatgggcaaa   1620
ctatttgctg aacaaaataa atcataa                                        1647
```

<210> SEQ ID NO 46
<211> LENGTH: 1647
<212> TYPE: DNA
<213> ORGANISM: Lactococcus lactis

<400> SEQUENCE: 46

```
atgtatactg ttggtgatta tctgctggat cgtctgcatg aactgggtat tgaggagatc     60
tttggtgttc cgggcgacta caacctgcag ttcctggatc agatcatttc ccgtaaggat    120
atgaaatggg ttggcaacgc caacgagctg aatgctagct atatggctga tggttatgcg    180
cgtaccaaaa aggcggctgc cttcctgacc acgttcggtg ttggcgaact gtctgccgtc    240
aacggcctgg ctggtagcta tgctgagaac ctgccagtgg ttgaaattgt tggttctcct    300
acctctaaag ttcagaacga aggtaaattc gtgcatcaca ctctggctga cggtgatttc    360
aaacacttca tgaaaatgca cgagccggtg accgctgccc gtactctgct gacggctgag    420
aacgcgactg tggagatcga ccgtgtgctg tctgcactgc tgaaagagcg taaaccggtg    480
tacattaacc tgccggtgga tgtcgccgca gctaaagcag agaaaccgtc tctgccgctg    540
aaaaaggaga acagcacgtc taacacgtcc gatcaggaga tcctgaacaa aatccaggag    600
tccctgaaaa acgcgaagaa accgatcgta atcactggtc atgaaattat cagctttggc    660
ctggaaaaga ctgtaagcca gtttatctct aaaaccaaac tgccgatcac cactctgaat    720
```

```
ttcggcaaaa gcagcgttga tgaggcactg ccttccttcc tgggcattta taacggtaaa    780

ctgtccgagc cgaacctgaa agagttcgtt gagtccgccg atttcattct gatgctgggc    840

gtcaaactga ctgactcttc tactggtgcc ttcacccacc acctgaacga aaacaaaatg    900

atttccctga acattgatga gggtaaaatc ttcaacgaaa gcatccagaa cttcgacttc    960

gaatctctga tctcctctct gctggatctg agcgagatcg aatacaaggg caaatacatt   1020

gataagaaac aggaggactt cgttccgtct aacgctctgc tgagccagga ccgtctgtgg   1080

caggcagtcg aaaacctgac ccagtccaac gaaaccatcg ttgcagagca gggtacttcc   1140

ttcttcggtg cctcttctat cttcctgaaa ccgaagtccc acttcattgg ccagccgctg   1200

tggggtagca tcggctatac cttccctgca gctctgggtt ctcagattgc ggataaagaa   1260

tctcgccatc tgctgttcat cggcgacggc agcctgcagc tgaccgttca ggaactgggc   1320

ctggctatcc gtgaaaagat caacccaatt tgcttcatca tcaataacga cggttacact   1380

gtggaacgcg agatccacgg tccgaaccag tcttacaacg atatcccgat gtggaactac   1440

tccaagctgc cagagagctt cggtgctact gaggaacgtg tcgttagcaa gatcgtacgc   1500

accgaaaatg agttcgtaag cgttatgaaa gaagctcaag ctgatccgaa ccgcatgtat   1560

tggatcgagc tgatcctggc aaaagaggat gccccaaaag ttctgaagaa aatgggcaaa   1620

ctgttcgccg agcaaaacaa atcataa                                       1647
```

<210> SEQ ID NO 47
<211> LENGTH: 548
<212> TYPE: PRT
<213> ORGANISM: Lactococcus lactis

<400> SEQUENCE: 47

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205
```

```
Ile Val Ile Thr Gly His Glu Ile Ile Ser Phe Gly Leu Glu Lys Thr
    210                 215                 220

Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Lys Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Asp Ala Pro Lys Val Leu Lys Lys Met Gly Lys Leu Phe Ala Glu
    530                 535                 540

Gln Asn Lys Ser
545
```

<210> SEQ ID NO 48
<211> LENGTH: 1647
<212> TYPE: DNA
<213> ORGANISM: Lactococcus lactis

<400> SEQUENCE: 48

```
atgtatactg ttggtgatta tctgctggac cgtctgcatg aactgggtat cgaagaaatc      60

ttcggcgttc cgggtgatta caatctgcag ttcctggatc agatcatctc tcataaagac     120

atgaaatggg tgggtaacgc taacgaactg aacgcaagct acatggcaga tggttatgca     180
```

-continued

```
cgtaccaaga aagccgcggc atttctgacc actttcggtg ttggcgaact gagcgccgtc    240
aacggtctgg cgggctccta cgccgaaaac ctgccggtgg tggagatcgt aggcagccca    300
acgagcaaag ttcagaacga aggtaaattc gtccaccaca ctctggctga cggcgatttc    360
aaacacttca tgaaaatgca tgaacctgtg actgcggcac gtacgctgct gactgcagag    420
aacgctactg tggaaatcga ccgcgttctg tctgcgctgc tgaaagaacg caaaccagtt    480
tacatcaacc tgcctgtgga tgttgcggca gctaaagcgg aaaaaccgag cctgccgctg    540
aagaaagaaa actccacttc taacactagc gaccaggaaa tcctgaacaa aatccaggag    600
tctctgaaaa acgcaaagaa accaatcgtg atcaccggcc acgaaatcat ttcttttggt    660
ctggagaaga ccgtgaccca attcatcagc aaaaccaaac tgccgattac caccctgaac    720
ttcggcaagt cctctgttga cgaggctctg ccgtctttcc tgggcatcta caacggtact    780
ctgagcgaac cgaacctgaa agaatttgtt gaatctgcgg acttcatcct gatgctgggc    840
gttaaactga ccgactcttc taccggtgca ttcactcacc atctgaacga aaacaaaatg    900
attagcctga acatcgacga gggtaaaatc ttcaacgagc gtatccagaa cttcgacttc    960
gaaagcctga tcagctctct gctggacctg tccgaaatcg agtataaagg caaatacatt   1020
gacaaaaagc aagaagattt cgtaccatct aacgcactgc tgtcccagga tcgcctgtgg   1080
caggccgtgg agaacctgac ccagagcaat gaaaccatcg tggcggaaca aggtacgagc   1140
tttttcggcg cgtcttctat ctttctgaaa tccaaaagcc attttatcgg tcagccgctg   1200
tggggtagca ttggctatac tttcccggca gcgctgggct ctcagatcgc tgataaagaa   1260
tctcgtcatc tgctgttcat cggtgacggt tccctgcagc tgaccgtaca ggaactgggt   1320
ctggcaattc gtgaaaagat caacccgatt tgcttcatta ttaacaatga cggctacacc   1380
gttgagcgtg agatccacgg tccgaaccag tcttacaacg atatccctat gtggaactac   1440
tctaaactgc cggagtcctt cggcgcaact gaggaccgtg ttgtgtctaa aattgtgcgt   1500
accgaaaacg aatttgtgag cgtgatgaaa gaggcccagg ccgatccgaa ccgtatgtac   1560
tggatcgaac tgatcctggc gaaagaaggc gcaccgaagg tactgaagaa aatgggcaag   1620
ctgtttgctg aacagaataa atcctaa                                        1647
```

<210> SEQ ID NO 49
<211> LENGTH: 548
<212> TYPE: PRT
<213> ORGANISM: Lactococcus lactis

<400> SEQUENCE: 49

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
```

-continued

```
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540
```

Gln Asn Lys Ser
545

<210> SEQ ID NO 50
<211> LENGTH: 1851
<212> TYPE: DNA
<213> ORGANISM: Escherichia coli

<400> SEQUENCE: 50
atgcctaagt accgttccgc caccaccact catggtcgta atatggcggg tgctcgtgcg 60
ctgtggcgcg ccaccggaat gaccgacgcc gatttcggta agccgattat cgcggttgtg 120
aactcgttca cccaatttgt accgggtcac gtccatctgc gcgatctcgg taaactggtc 180
gccgaacaaa ttgaagcggc tggcggcgtt gccaaagagt tcaacaccat tgcggtggat 240
gatgggattg ccatgggcca cggggggatg ctttattcac tgccatctcg cgaactgatc 300
gctgattccg ttgagtatat ggtcaacgcc cactgcgccg acgccatggt ctgcatctct 360
aactgcgaca aaatcacccc ggggatgctg atggcttccc tgcgcctgaa tattccggtg 420
atctttgttt ccggcggccc gatggaggcc gggaaaacca aactttccga tcagatcatc 480
aagctcgatc tggttgatgc gatgatccag ggcgcagacc cgaaagtatc tgactcccag 540
agcgatcagg ttgaacgttc cgcgtgtccg acctgcggtt cctgctccgg gatgtttacc 600
gctaactcaa tgaactgcct gaccgaagcg ctgggcctgt cgcagccggg caacggctcg 660
ctgctggcaa cccacgccga ccgtaagcag ctgttcctta atgctggtaa acgcattgtt 720
gaattgacca aacgttatta cgagcaaaac gacgaaagtg cactgccgcg taatatcgcc 780
agtaaggcgg cgtttgaaaa cgccatgacg ctggatatcg cgatgggtgg atcgactaac 840
accgtacttc acctgctggc ggcggcgcag gaagcggaaa tcgacttcac catgagtgat 900
atcgataagc tttcccgcaa ggttccacag ctgtgtaaag ttgcgccgag cacccagaaa 960
taccatatgg aagatgttca ccgtgctggt ggtgttatcg gtattctcgg cgaactggat 1020
cgcgcggggt tactgaaccg tgatgtgaaa aacgtacttg gcctgacgtt gccgcaaacg 1080
ctggaacaat acgacgttat gctgacccag gatgacgcgg taaaaaatat gttccgcgca 1140
ggtcctgcag gcattcgtac cacacaggca ttctcgcaag attgccgttg ggatacgctg 1200
gacgacgatc gcgccaatgg ctgtatccgc tcgctggaac acgcctacag caaagacggc 1260
ggcctggcgg tgctctacgg taactttgcg gaaaacggct gcatcgtgaa aacggcaggc 1320
gtcgatgaca gcatcctcaa attcaccggc ccggcgaaag tgtacgaaag ccaggacgat 1380
gcggtagaag cgattctcgg cggtaaagtt gtcgccggag atgtggtagt aattcgctat 1440
gaaggcccga aaggcggtcc ggggatgcag gaaatgctct acccaaccag cttcctgaaa 1500
tcaatgggtc tcggcaaagc ctgtgcgctg atcaccgacg gtcgtttctc tggtggcacc 1560
tctggtcttt ccatcggcca cgtctcaccg gaagcggcaa gcggcggcag cattggcctg 1620
attgaagatg gtgacctgat cgctatcgac atcccgaacc gtggcattca gttacaggta 1680
agcgatgccg aactggcggc gcgtcgtgaa gcgcaggacg ctcgaggtga caaagcctgg 1740
acgccgaaaa atcgtgaacg tcaggtctcc tttgccctgc gtgcttatgc cagcctggca 1800
accagcgccg acaaaggcgc ggtgcgcgat aaatcgaaac tgggggggtta a 1851

<210> SEQ ID NO 51
<211> LENGTH: 1851
<212> TYPE: DNA
<213> ORGANISM: Escherichia coli

<400> SEQUENCE: 51

-continued

```
atgcctaaat atcgcagcgc aactactacc cacggccgca acatggcagg cgcgcgtgct     60
ctgtggcgtg cgactggtat gactgatgcg gactttggca aaccaatcat tgctgtggtt    120
aatagcttta ctcagttcgt tccaggccat gttcacctgc gtgacctggg caagctggtt    180
gcggagcaga tcgaggctgc gggtggtgtg gcgaaggaat ttaacaccat cgctgttgac    240
gacggtatcg cgatgggtca tggtggtatg ctgtacagcc tgccgagccg tgagctgatt    300
gcggacagcg tggaatacat ggttaatgcg cattgtgcgg atgcgatggt ttgtattagc    360
aactgtgata agattactcc aggtatgctg atggcgagcc tgcgtctgaa catcccagtt    420
attttcgtga gcggtggtcc aatggaagcg ggtaagacta agctgagcga ccagattatc    480
aaactggacc tggtggacgc tatgattcaa ggtgctgatc caaaggttag cgatagccaa    540
tctgaccaag tggagcgcag cgcttgccca acttgtggca gctgtagcgg tatgttcact    600
gcgaatagca tgaattgtct gactgaggct ctgggtctga gccaaccagg taatggtagc    660
ctgctggcga ctcatgcgga tcgcaaacaa ctgtttctga acgcgggcaa gcgtatcgtg    720
gagctgacta agcgctacta tgaacagaat gatgagtccg cgctgccacg caacattgcg    780
tccaaagctg ctttcgagaa tgcgatgacc ctggacattg ctatgggcgg tagcaccaat    840
actgttctgc atctgctggc tgctgctcaa gaggctgaga ttgattttac tatgtccgac    900
attgacaaac tgagccgtaa agtgccgcaa ctgtgcaagg tggctccatc tactcaaaag    960
tatcacatgg aggacgtgca tcgcgcgggt ggcgtgattg gcatcctggg tgagctggac   1020
cgtgctggtc tgctgaatcg cgacgttaag aatgttctgg gtctgaccct gccacagacc   1080
ctggagcagt atgatgtgat gctgactcaa gacgatgctg ttaagaacat gtttcgtgct   1140
ggtccggcgg gtatccgcac tacccaagcg tttagccagg actgtcgctg ggacaccctg   1200
gatgatgacc gtgcgaacgg ttgcattcgt agcctggaac atgcgtattc taaggatggt   1260
ggtctggctg ttctgtatgg caatttcgct gagaatggtt gtattgttaa gaccgcgggt   1320
gttgacgatt ctattctgaa gtttactggt ccagctaagg tttatgagtc tcaagatgac   1380
gctgttgagg ctatcctggg tggcaaggtg gttgcgggtg acgttgttgt tatccgttac   1440
gagggtccaa agggtggccc aggtatgcaa gagatgctgt atccgacttc ttttctgaag   1500
agcatgggcc tgggtaaggc gtgcgctctg attactgatg gccgctttag cggcggtact   1560
agcggcctga gcattggtca tgttagccca gaggctgcgt ctggtggttc tatcggtctg   1620
atcgaggacg gcgatctgat tgcgattgat attccaaatc gcggtatcca actgcaagtt   1680
tctgacgcgg agctggctgc tcgccgcgag gctcaagatg cgcgtggcga taaggcgtgg   1740
accccaaaga accgcgagcg ccaagttagc ttcgcgctgc gcgcgtacgc ctctctggcg   1800
acttctgcgg ataagggtgc tgttcgtgac aagagcaagc tgggtggcta a            1851
```

<210> SEQ ID NO 52
<211> LENGTH: 616
<212> TYPE: PRT
<213> ORGANISM: Escherichia coli

<400> SEQUENCE: 52

```
Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45
```

```
Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
            260                 265                 270

Ile Ala Met Gly Gly Ser Thr Asn Thr Val Leu His Leu Leu Ala Ala
        275                 280                 285

Ala Gln Glu Ala Glu Ile Asp Phe Thr Met Ser Asp Ile Asp Lys Leu
    290                 295                 300

Ser Arg Lys Val Pro Gln Leu Cys Lys Val Ala Pro Ser Thr Gln Lys
305                 310                 315                 320

Tyr His Met Glu Asp Val His Arg Ala Gly Gly Val Ile Gly Ile Leu
                325                 330                 335

Gly Glu Leu Asp Arg Ala Gly Leu Leu Asn Arg Asp Val Lys Asn Val
            340                 345                 350

Leu Gly Leu Thr Leu Pro Gln Thr Leu Glu Gln Tyr Asp Val Met Leu
        355                 360                 365

Thr Gln Asp Asp Ala Val Lys Asn Met Phe Arg Ala Gly Pro Ala Gly
    370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
            420                 425                 430

Gly Cys Ile Val Lys Thr Ala Gly Val Asp Asp Ser Ile Leu Lys Phe
        435                 440                 445

Thr Gly Pro Ala Lys Val Tyr Glu Ser Gln Asp Asp Ala Val Glu Ala
    450                 455                 460

Ile Leu Gly Gly Lys Val Val Ala Gly Asp Val Val Val Ile Arg Tyr
465                 470                 475                 480
```

```
Glu Gly Pro Lys Gly Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
            500                 505                 510

Asp Gly Arg Phe Ser Gly Gly Thr Ser Gly Leu Ser Ile Gly His Val
        515                 520                 525

Ser Pro Glu Ala Ala Ser Gly Gly Ser Ile Gly Leu Ile Glu Asp Gly
    530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
            580                 585                 590

Leu Arg Ala Tyr Ala Ser Leu Ala Thr Ser Ala Asp Lys Gly Ala Val
        595                 600                 605

Arg Asp Lys Ser Lys Leu Gly Gly
    610                 615
```

<210> SEQ ID NO 53

<400> SEQUENCE: 53

000

<210> SEQ ID NO 54
<211> LENGTH: 1713
<212> TYPE: DNA
<213> ORGANISM: Lactococcus lactis

<400> SEQUENCE: 54

```
atggagttta agtataacgg caaagttgaa tctgttgaac tgaataagta cagcaaaacg     60

ttgacacaag atcccacaca acccgccaca caggcaatgt attacggcat cgggtttaaa    120

gacgaagatt tcaagaaagc tcaagtgggt atagtgtcga tggactggga tggaaatcca    180

tgcaacatgc atttaggaac ccttggatca aagattaaaa gctcagtaaa tcagacagat    240

ggtctgatcg gcttacaatt tcatacgata ggagtttctg atgggatagc aaatggaaag    300

ttgggaatga gatactccct tgtttccaga gaagttatag ctgactctat tgaaaccaac    360

gctggcgctg aatactatga tgcaattgta gccatcccag gttgtgacaa aaatatgcca    420

ggttctatta ttggtatggc aagacttaat aggccaagca ttatggtgta tggaggaaca    480

atagaacacg gtgaatataa aggtgagaaa ttgaacatcg tatcggcttt tgaatctcta    540

ggccagaaaa ttaccggcaa tatctctgat gaagattatc acggtgttat ttgtaatgct    600

attcctggtc aaggggcatg tgggggggatg tacacagcta ataccttagc tgccgctatc    660

gaaacactag gtatgtcatt gccgtattct tcttcgaacc ctgcagtatc tcaagaaaaa    720

caagaagaat gtgatgagat tggattagcc attaagaatc ttttggaaaa agacatcaag    780

cctagtgata taatgactaa ggaggcgttc gagaacgcta ttaccattgt gatggtcttg    840

gggggtagta ctaatgctgt cttgcatatt attgcaatgg ctaacgcgat aggtgtcgaa    900

ataactcagg atgacttcca aagaattagt gacattactc cagtactagg tgattttaaa    960

ccttcaggta aatatatgat ggaagatttg cataaaattg gaggcttgcc agcagtgctt   1020

aagtaccttc taaaggaagg aaaattgcat ggtgactgcc ttactgtgac gggtaaaaca   1080

ttagccgaga atgtcgagac tgccctagac ttggatttcg actcacaaga tatcatgagg   1140
```

ccactaaaga atcctatcaa ggccaccggc cacttgcaga ttctgtacgg taatttagct 1200
caagggggtt ccgtagcaaa aattagcggt aaagaaggag agttcttcaa aggcactgcc 1260
agagtctttg atggtgaaca acattttatc gacggcatag aatctggtcg tttgcatgct 1320
ggagatgtag cggtaattag gaatataggt cccgtcggcg gacctggtat gcccgaaatg 1380
ctgaagccta catcagcatt aattggtgcg ggtttaggga aaagttgcgc gttaattacg 1440
gatggtagat tctccggtgg cactcacggt tttgttgtcg gccatattgt gcctgaagcc 1500
gttgagggtg gactaatcgg cttagttgaa gatgacgata taatagagat agatgcagtc 1560
aacaactcta tatccctgaa agtttccgat gaagaaatcg caaagagaag agctaattat 1620
cagaagccaa ctccgaaagc caccagggga gttttggcaa aattcgctaa attaacccgt 1680
cctgcatcgg aagggtgtgt tactgatctg taa 1713

<210> SEQ ID NO 55
<211> LENGTH: 570
<212> TYPE: PRT
<213> ORGANISM: Lactococcus lactis

<400> SEQUENCE: 55

Met Glu Phe Lys Tyr Asn Gly Lys Val Glu Ser Val Glu Leu Asn Lys
1 5 10 15

Tyr Ser Lys Thr Leu Thr Gln Asp Pro Thr Gln Pro Ala Thr Gln Ala
20 25 30

Met Tyr Tyr Gly Ile Gly Phe Lys Asp Glu Asp Phe Lys Lys Ala Gln
35 40 45

Val Gly Ile Val Ser Met Asp Trp Asp Gly Asn Pro Cys Asn Met His
50 55 60

Leu Gly Thr Leu Gly Ser Lys Ile Lys Ser Ser Val Asn Gln Thr Asp
65 70 75 80

Gly Leu Ile Gly Leu Gln Phe His Thr Ile Gly Val Ser Asp Gly Ile
85 90 95

Ala Asn Gly Lys Leu Gly Met Arg Tyr Ser Leu Val Ser Arg Glu Val
100 105 110

Ile Ala Asp Ser Ile Glu Thr Asn Ala Gly Ala Glu Tyr Tyr Asp Ala
115 120 125

Ile Val Ala Ile Pro Gly Cys Asp Lys Asn Met Pro Gly Ser Ile Ile
130 135 140

Gly Met Ala Arg Leu Asn Arg Pro Ser Ile Met Val Tyr Gly Gly Thr
145 150 155 160

Ile Glu His Gly Glu Tyr Lys Gly Glu Lys Leu Asn Ile Val Ser Ala
165 170 175

Phe Glu Ser Leu Gly Gln Lys Ile Thr Gly Asn Ile Ser Asp Glu Asp
180 185 190

Tyr His Gly Val Ile Cys Asn Ala Ile Pro Gly Gln Gly Ala Cys Gly
195 200 205

Gly Met Tyr Thr Ala Asn Thr Leu Ala Ala Ala Ile Glu Thr Leu Gly
210 215 220

Met Ser Leu Pro Tyr Ser Ser Ser Asn Pro Ala Val Ser Gln Glu Lys
225 230 235 240

Gln Glu Glu Cys Asp Glu Ile Gly Leu Ala Ile Lys Asn Leu Leu Glu
245 250 255

Lys Asp Ile Lys Pro Ser Asp Ile Met Thr Lys Glu Ala Phe Glu Asn
260 265 270

-continued

```
Ala Ile Thr Ile Val Met Val Leu Gly Gly Ser Thr Asn Ala Val Leu
        275                 280                 285

His Ile Ile Ala Met Ala Asn Ala Ile Gly Val Glu Ile Thr Gln Asp
    290                 295                 300

Asp Phe Gln Arg Ile Ser Asp Ile Thr Pro Val Leu Gly Asp Phe Lys
305                 310                 315                 320

Pro Ser Gly Lys Tyr Met Met Glu Asp Leu His Lys Ile Gly Gly Leu
                325                 330                 335

Pro Ala Val Leu Lys Tyr Leu Leu Lys Glu Gly Lys Leu His Gly Asp
            340                 345                 350

Cys Leu Thr Val Thr Gly Lys Thr Leu Ala Glu Asn Val Glu Thr Ala
        355                 360                 365

Leu Asp Leu Asp Phe Asp Ser Gln Asp Ile Met Arg Pro Leu Lys Asn
    370                 375                 380

Pro Ile Lys Ala Thr Gly His Leu Gln Ile Leu Tyr Gly Asn Leu Ala
385                 390                 395                 400

Gln Gly Gly Ser Val Ala Lys Ile Ser Gly Lys Glu Gly Glu Phe Phe
                405                 410                 415

Lys Gly Thr Ala Arg Val Phe Asp Gly Glu Gln His Phe Ile Asp Gly
            420                 425                 430

Ile Glu Ser Gly Arg Leu His Ala Gly Asp Val Ala Val Ile Arg Asn
        435                 440                 445

Ile Gly Pro Val Gly Gly Pro Gly Met Pro Glu Met Leu Lys Pro Thr
    450                 455                 460

Ser Ala Leu Ile Gly Ala Gly Leu Gly Lys Ser Cys Ala Leu Ile Thr
465                 470                 475                 480

Asp Gly Arg Phe Ser Gly Gly Thr His Gly Phe Val Val Gly His Ile
                485                 490                 495

Val Pro Glu Ala Val Glu Gly Gly Leu Ile Gly Leu Val Glu Asp Asp
            500                 505                 510

Asp Ile Ile Glu Ile Asp Ala Val Asn Asn Ser Ile Ser Leu Lys Val
        515                 520                 525

Ser Asp Glu Glu Ile Ala Lys Arg Arg Ala Asn Tyr Gln Lys Pro Thr
    530                 535                 540

Pro Lys Ala Thr Arg Gly Val Leu Ala Lys Phe Ala Lys Leu Thr Arg
545                 550                 555                 560

Pro Ala Ser Glu Gly Cys Val Thr Asp Leu
                565                 570
```

<210> SEQ ID NO 56
<211> LENGTH: 1758
<212> TYPE: DNA
<213> ORGANISM: Saccharomyces cerevisiae

<400> SEQUENCE: 56

```
atgggcttgt taacgaaagt tgctacatct agacaattct ctacaacgag atgcgttgca      60

aagaagctca acaagtactc gtatatcatc actgaaccta agggccaagg tgcgtcccag     120

gccatgcttt atgccaccgg tttcaagaag gaagatttca agaagcctca agtcggggtt     180

ggttcctgtt ggtggtccgg taacccatgt aacatgcatc tattggactt gaataacaga     240

tgttctcaat ccattgaaaa agcgggtttg aaagctatgc agttcaacac catcggtgtt     300

tcagacggta tctctatggg tactaaaggt atgagatact cgttacaaag tagagaaatc     360

attgcagact cctttgaaac catcatgatg gcacaacact acgatgctaa catcgccatc     420

ccatcatgtg acaaaaacat gcccggtgtc atgatggcca tgggtagaca taacagacct     480
```

```
tccatcatgg tatatggtgg tactatcttg cccggtcatc caacatgtgg ttcttcgaag    540

atctctaaaa acatcgatat cgtctctgcg ttccaatcct acggtgaata tatttccaag    600

caattcactg aagaagaaag agaagatgtt gtggaacatg catgcccagg tcctggttct    660

tgtggtggta tgtatactgc caacacaatg gcttctgccg ctgaagtgct aggtttgacc    720

attccaaact cctcttcctt cccagccgtt tccaaggaga agttagctga gtgtgacaac    780

attggtgaat acatcaagaa gacaatggaa ttgggtattt tacctcgtga tatcctcaca    840

aaagaggctt ttgaaaacgc cattacttat gtcgttgcaa ccggtgggtc cactaatgct    900

gttttgcatt tggtggctgt tgctcactct gcgggtgtca agttgtcacc agatgatttc    960

caaagaatca gtgatactac accattgatc ggtgacttca aaccttctgg taaatacgtc   1020

atggccgatt tgattaacgt tggtggtacc caatctgtga ttaagtatct atatgaaaac   1080

aacatgttgc acggtaacac aatgactgtt accggtgaca ctttggcaga acgtgcaaag   1140

aaagcaccaa gcctacctga aggacaagag attattaagc cactctccca cccaatcaag   1200

gccaacggtc acttgcaaat tctgtacggt tcattggcac caggtggagc tgtgggtaaa   1260

attaccggta aggaaggtac ttacttcaag ggtagagcac gtgtgttcga agaggaaggt   1320

gcctttattg aagccttgga aagaggtgaa atcaagaagg gtgaaaaaac cgttgttgtt   1380

atcagatatg aaggtccaag aggtgcacca ggtatgcctg aaatgctaaa gccttcctct   1440

gctctgatgg gttacggttt gggtaaagat gttgcattgt tgactgatgg tagattctct   1500

ggtggttctc acgggttctt aatcggccac attgttcccg aagccgctga aggtggtcct   1560

atcgggttgg tcagagacgg cgatgagatt atcattgatg ctgataataa caagattgac   1620

ctattagtct ctgataagga aatggctcaa cgtaaacaaa gttgggttgc acctccacct   1680

cgttacacaa gaggtactct atccaagtat gctaagttgg tttccaacgc ttccaacggt   1740

tgtgttttag atgcttga                                                 1758
```

<210> SEQ ID NO 57
<211> LENGTH: 585
<212> TYPE: PRT
<213> ORGANISM: Saccharomyces cerevisiae

<400> SEQUENCE: 57

```
Met Gly Leu Leu Thr Lys Val Ala Thr Ser Arg Gln Phe Ser Thr Thr
1               5                   10                  15

Arg Cys Val Ala Lys Lys Leu Asn Lys Tyr Ser Tyr Ile Ile Thr Glu
            20                  25                  30

Pro Lys Gly Gln Gly Ala Ser Gln Ala Met Leu Tyr Ala Thr Gly Phe
        35                  40                  45

Lys Lys Glu Asp Phe Lys Lys Pro Gln Val Gly Val Gly Ser Cys Trp
    50                  55                  60

Trp Ser Gly Asn Pro Cys Asn Met His Leu Leu Asp Leu Asn Asn Arg
65                  70                  75                  80

Cys Ser Gln Ser Ile Glu Lys Ala Gly Leu Lys Ala Met Gln Phe Asn
                85                  90                  95

Thr Ile Gly Val Ser Asp Gly Ile Ser Met Gly Thr Lys Gly Met Arg
            100                 105                 110

Tyr Ser Leu Gln Ser Arg Glu Ile Ile Ala Asp Ser Phe Glu Thr Ile
        115                 120                 125

Met Met Ala Gln His Tyr Asp Ala Asn Ile Ala Ile Pro Ser Cys Asp
    130                 135                 140
```

-continued

Lys Asn Met Pro Gly Val Met Met Ala Met Gly Arg His Asn Arg Pro
145 150 155 160

Ser Ile Met Val Tyr Gly Gly Thr Ile Leu Pro Gly His Pro Thr Cys
165 170 175

Gly Ser Ser Lys Ile Ser Lys Asn Ile Asp Ile Val Ser Ala Phe Gln
180 185 190

Ser Tyr Gly Glu Tyr Ile Ser Lys Gln Phe Thr Glu Glu Glu Arg Glu
195 200 205

Asp Val Val Glu His Ala Cys Pro Gly Pro Gly Ser Cys Gly Gly Met
210 215 220

Tyr Thr Ala Asn Thr Met Ala Ser Ala Ala Glu Val Leu Gly Leu Thr
225 230 235 240

Ile Pro Asn Ser Ser Ser Phe Pro Ala Val Ser Lys Glu Lys Leu Ala
245 250 255

Glu Cys Asp Asn Ile Gly Glu Tyr Ile Lys Lys Thr Met Glu Leu Gly
260 265 270

Ile Leu Pro Arg Asp Ile Leu Thr Lys Glu Ala Phe Glu Asn Ala Ile
275 280 285

Thr Tyr Val Val Ala Thr Gly Gly Ser Thr Asn Ala Val Leu His Leu
290 295 300

Val Ala Val Ala His Ser Ala Gly Val Lys Leu Ser Pro Asp Asp Phe
305 310 315 320

Gln Arg Ile Ser Asp Thr Thr Pro Leu Ile Gly Asp Phe Lys Pro Ser
325 330 335

Gly Lys Tyr Val Met Ala Asp Leu Ile Asn Val Gly Gly Thr Gln Ser
340 345 350

Val Ile Lys Tyr Leu Tyr Glu Asn Asn Met Leu His Gly Asn Thr Met
355 360 365

Thr Val Thr Gly Asp Thr Leu Ala Glu Arg Ala Lys Lys Ala Pro Ser
370 375 380

Leu Pro Glu Gly Gln Glu Ile Ile Lys Pro Leu Ser His Pro Ile Lys
385 390 395 400

Ala Asn Gly His Leu Gln Ile Leu Tyr Gly Ser Leu Ala Pro Gly Gly
405 410 415

Ala Val Gly Lys Ile Thr Gly Lys Glu Gly Thr Tyr Phe Lys Gly Arg
420 425 430

Ala Arg Val Phe Glu Glu Glu Gly Ala Phe Ile Glu Ala Leu Glu Arg
435 440 445

Gly Glu Ile Lys Lys Gly Glu Lys Thr Val Val Val Ile Arg Tyr Glu
450 455 460

Gly Pro Arg Gly Ala Pro Gly Met Pro Glu Met Leu Lys Pro Ser Ser
465 470 475 480

Ala Leu Met Gly Tyr Gly Leu Gly Lys Asp Val Ala Leu Leu Thr Asp
485 490 495

Gly Arg Phe Ser Gly Gly Ser His Gly Phe Leu Ile Gly His Ile Val
500 505 510

Pro Glu Ala Ala Glu Gly Gly Pro Ile Gly Leu Val Arg Asp Gly Asp
515 520 525

Glu Ile Ile Ile Asp Ala Asp Asn Asn Lys Ile Asp Leu Leu Val Ser
530 535 540

Asp Lys Glu Met Ala Gln Arg Lys Gln Ser Trp Val Ala Pro Pro Pro
545 550 555 560

Arg Tyr Thr Arg Gly Thr Leu Ser Lys Tyr Ala Lys Leu Val Ser Asn
565 570 575

Ala Ser Asn Gly Cys Val Leu Asp Ala
580 585

<210> SEQ ID NO 58
<211> LENGTH: 1701
<212> TYPE: DNA
<213> ORGANISM: Saccharomyces cerevisiae

<400> SEQUENCE: 58
atgaagaagc tcaacaagta ctcgtatatc atcactgaac ctaagggcca aggtgcgtcc 60
caggccatgc tttatgccac cggtttcaag aaggaagatt tcaagaagcc tcaagtcggg 120
gttggttcct gttggtggtc cggtaaccca tgtaacatgc atctattgga cttgaataac 180
agatgttctc aatccattga aaaagcgggt ttgaaagcta tgcagttcaa caccatcggt 240
gtttcagacg gtatctctat gggtactaaa ggtatgagat actcgttaca aagtagagaa 300
atcattgcag actcctttga aaccatcatg atggcacaac actacgatgc taacatcgcc 360
atcccatcat gtgacaaaaa catgcccggt gtcatgatgg ccatgggtag acataacaga 420
ccttccatca tggtatatgg tggtactatc ttgcccggtc atccaacatg tggttcttcg 480
aagatctcta aaaacatcga tatcgtctct gcgttccaat cctacggtga atatatttcc 540
aagcaattca ctgaagaaga aagagaagat gttgtggaac atgcatgccc aggtcctggt 600
tcttgtggtg gtatgtatac tgccaacaca atggcttctg ccgctgaagt gctaggtttg 660
accattccaa actcctcttc cttcccagcc gtttccaagg agaagttagc tgagtgtgac 720
aacattggtg aatacatcaa gaagacaatg gaattgggta ttttacctcg tgatatcctc 780
acaaaagagg cttttgaaaa cgccattact tatgtcgttg caaccggtgg gtccactaat 840
gctgttttgc atttggtggc tgttgctcac tctgcgggtg tcaagttgtc accagatgat 900
ttccaaagaa tcagtgatac tacaccattg atcggtgact tcaaaccttc tggtaaatac 960
gtcatggccg atttgattaa cgttggtggt acccaatctg tgattaagta tctatatgaa 1020
aacaacatgt tgcacggtaa cacaatgact gttaccggtg acactttggc agaacgtgca 1080
aagaaagcac caagcctacc tgaaggacaa gagattatta agccactctc ccacccaatc 1140
aaggccaacg gtcacttgca aattctgtac ggttcattgg caccaggtgg agctgtgggt 1200
aaaattaccg gtaaggaagg tacttacttc aagggtagag cacgtgtgtt cgaagaggaa 1260
ggtgccttta ttgaagcctt ggaaagaggt gaaatcaaga agggtgaaaa aaccgttgtt 1320
gttatcagat atgaaggtcc aagaggtgca ccaggtatgc ctgaaatgct aaagccttcc 1380
tctgctctga tgggttacgg tttgggtaaa gatgttgcat tgttgactga tggtagattc 1440
tctggtggtt ctcacgggtt cttaatcggc cacattgttc ccgaagccgc tgaaggtggt 1500
cctatcgggt tggtcagaga cggcgatgag attatcattg atgctgataa taacaagatt 1560
gacctattag tctctgataa ggaaatggct caacgtaaac aaagttgggt tgcacctcca 1620
cctcgttaca caagaggtac tctatccaag tatgctaagt tggtttccaa cgcttccaac 1680
ggttgtgttt tagatgcttg a 1701

<210> SEQ ID NO 59
<211> LENGTH: 566
<212> TYPE: PRT
<213> ORGANISM: Saccharomyces cerevisiae

<400> SEQUENCE: 59

Met Lys Lys Leu Asn Lys Tyr Ser Tyr Ile Ile Thr Glu Pro Lys Gly
1 5 10 15

```
Gln Gly Ala Ser Gln Ala Met Leu Tyr Ala Thr Gly Phe Lys Lys Glu
            20                  25                  30

Asp Phe Lys Lys Pro Gln Val Gly Val Gly Ser Cys Trp Trp Ser Gly
        35                  40                  45

Asn Pro Cys Asn Met His Leu Leu Asp Leu Asn Asn Arg Cys Ser Gln
    50                  55                  60

Ser Ile Glu Lys Ala Gly Leu Lys Ala Met Gln Phe Asn Thr Ile Gly
65                  70                  75                  80

Val Ser Asp Gly Ile Ser Met Gly Thr Lys Gly Met Arg Tyr Ser Leu
                85                  90                  95

Gln Ser Arg Glu Ile Ile Ala Asp Ser Phe Glu Thr Ile Met Met Ala
            100                 105                 110

Gln His Tyr Asp Ala Asn Ile Ala Ile Pro Ser Cys Asp Lys Asn Met
        115                 120                 125

Pro Gly Val Met Met Ala Met Gly Arg His Asn Arg Pro Ser Ile Met
    130                 135                 140

Val Tyr Gly Gly Thr Ile Leu Pro Gly His Pro Thr Cys Gly Ser Ser
145                 150                 155                 160

Lys Ile Ser Lys Asn Ile Asp Ile Val Ser Ala Phe Gln Ser Tyr Gly
                165                 170                 175

Glu Tyr Ile Ser Lys Gln Phe Thr Glu Glu Glu Arg Glu Asp Val Val
            180                 185                 190

Glu His Ala Cys Pro Gly Pro Gly Ser Cys Gly Gly Met Tyr Thr Ala
        195                 200                 205

Asn Thr Met Ala Ser Ala Ala Glu Val Leu Gly Leu Thr Ile Pro Asn
    210                 215                 220

Ser Ser Ser Phe Pro Ala Val Ser Lys Glu Lys Leu Ala Glu Cys Asp
225                 230                 235                 240

Asn Ile Gly Glu Tyr Ile Lys Lys Thr Met Glu Leu Gly Ile Leu Pro
                245                 250                 255

Arg Asp Ile Leu Thr Lys Glu Ala Phe Glu Asn Ala Ile Thr Tyr Val
            260                 265                 270

Val Ala Thr Gly Gly Ser Thr Asn Ala Val Leu His Leu Val Ala Val
        275                 280                 285

Ala His Ser Ala Gly Val Lys Leu Ser Pro Asp Asp Phe Gln Arg Ile
    290                 295                 300

Ser Asp Thr Thr Pro Leu Ile Gly Asp Phe Lys Pro Ser Gly Lys Tyr
305                 310                 315                 320

Val Met Ala Asp Leu Ile Asn Val Gly Gly Thr Gln Ser Val Ile Lys
                325                 330                 335

Tyr Leu Tyr Glu Asn Asn Met Leu His Gly Asn Thr Met Thr Val Thr
            340                 345                 350

Gly Asp Thr Leu Ala Glu Arg Ala Lys Lys Ala Pro Ser Leu Pro Glu
        355                 360                 365

Gly Gln Glu Ile Ile Lys Pro Leu Ser His Pro Ile Lys Ala Asn Gly
    370                 375                 380

His Leu Gln Ile Leu Tyr Gly Ser Leu Ala Pro Gly Gly Ala Val Gly
385                 390                 395                 400

Lys Ile Thr Gly Lys Glu Gly Thr Tyr Phe Lys Gly Arg Ala Arg Val
                405                 410                 415

Phe Glu Glu Glu Gly Ala Phe Ile Glu Ala Leu Glu Arg Gly Glu Ile
            420                 425                 430

Lys Lys Gly Glu Lys Thr Val Val Val Ile Arg Tyr Glu Gly Pro Arg
```

```
        435                 440                 445

Gly Ala Pro Gly Met Pro Glu Met Leu Lys Pro Ser Ser Ala Leu Met
    450                 455                 460

Gly Tyr Gly Leu Gly Lys Asp Val Ala Leu Leu Thr Asp Gly Arg Phe
465                 470                 475                 480

Ser Gly Gly Ser His Gly Phe Leu Ile Gly His Ile Val Pro Glu Ala
                485                 490                 495

Ala Glu Gly Gly Pro Ile Gly Leu Val Arg Asp Gly Asp Glu Ile Ile
            500                 505                 510

Ile Asp Ala Asp Asn Asn Lys Ile Asp Leu Leu Val Ser Asp Lys Glu
        515                 520                 525

Met Ala Gln Arg Lys Gln Ser Trp Val Ala Pro Pro Pro Arg Tyr Thr
    530                 535                 540

Arg Gly Thr Leu Ser Lys Tyr Ala Lys Leu Val Ser Asn Ala Ser Asn
545                 550                 555                 560

Gly Cys Val Leu Asp Ala
                565


<210> SEQ ID NO 60
<211> LENGTH: 771
<212> TYPE: DNA
<213> ORGANISM: Drosophila melanogaster

<400> SEQUENCE: 60

atgtcgttta ctttgaccaa caagaacgtg attttcgttg ccggtctggg aggcattggt      60

ctggacacca gcaaggagct gctcaagcgc gatctgaaga acctggtgat cctcgaccgc     120

attgagaacc cggctgccat tgccgagctg aaggcaatca atccaaaggt gaccgtcacc     180

ttctacccct atgatgtgac cgtgcccatt gccgagacca ccaagctgct gaagaccatc     240

ttcgcccagc tgaagaccgt cgatgtcctg atcaacggag ctggtatcct ggacgatcac     300

cagatcgagc gcaccattgc cgtcaactac actggcctgg tcaacaccac gacggccatt     360

ctggacttct gggacaagcg caagggcggt cccggtggta tcatctgcaa cattggatcc     420

gtcactggat tcaatgccat ctaccaggtg cccgtctact ccggcaccaa ggccgccgtg     480

gtcaacttca ccagctccct ggcgaaactg gcccccatta ccggcgtgac ggcttacact     540

gtgaaccccg gcatcacccg caccaccctg gtgcacacgt tcaactcctg gttggatgtt     600

gagcctcagg ttgccgagaa gctcctggct catcccaccc agccctcgtt ggcctgcgcc     660

gagaacttcg tcaaggctat cgagctgaac cagaacggag ccatctggaa actggacttg     720

ggcaccctgg aggccatcca gtggaccaag cactgggact ccggcatcta a              771


<210> SEQ ID NO 61
<211> LENGTH: 256
<212> TYPE: PRT
<213> ORGANISM: Drosophila melanogaster

<400> SEQUENCE: 61

Met Ser Phe Thr Leu Thr Asn Lys Asn Val Ile Phe Val Ala Gly Leu
1               5                   10                  15

Gly Gly Ile Gly Leu Asp Thr Ser Lys Glu Leu Leu Lys Arg Asp Leu
            20                  25                  30

Lys Asn Leu Val Ile Leu Asp Arg Ile Glu Asn Pro Ala Ala Ile Ala
        35                  40                  45

Glu Leu Lys Ala Ile Asn Pro Lys Val Thr Val Thr Phe Tyr Pro Tyr
    50                  55                  60
```

```
Asp Val Thr Val Pro Ile Ala Glu Thr Thr Lys Leu Leu Lys Thr Ile
65                  70                  75                  80

Phe Ala Gln Leu Lys Thr Val Asp Val Leu Ile Asn Gly Ala Gly Ile
                85                  90                  95

Leu Asp Asp His Gln Ile Glu Arg Thr Ile Ala Val Asn Tyr Thr Gly
            100                 105                 110

Leu Val Asn Thr Thr Thr Ala Ile Leu Asp Phe Trp Asp Lys Arg Lys
        115                 120                 125

Gly Gly Pro Gly Gly Ile Ile Cys Asn Ile Gly Ser Val Thr Gly Phe
    130                 135                 140

Asn Ala Ile Tyr Gln Val Pro Val Tyr Ser Gly Thr Lys Ala Ala Val
145                 150                 155                 160

Val Asn Phe Thr Ser Ser Leu Ala Lys Leu Ala Pro Ile Thr Gly Val
                165                 170                 175

Thr Ala Tyr Thr Val Asn Pro Gly Ile Thr Arg Thr Thr Leu Val His
            180                 185                 190

Thr Phe Asn Ser Trp Leu Asp Val Glu Pro Gln Val Ala Glu Lys Leu
        195                 200                 205

Leu Ala His Pro Thr Gln Pro Ser Leu Ala Cys Ala Glu Asn Phe Val
    210                 215                 220

Lys Ala Ile Glu Leu Asn Gln Asn Gly Ala Ile Trp Lys Leu Asp Leu
225                 230                 235                 240

Gly Thr Leu Glu Ala Ile Gln Trp Thr Lys His Trp Asp Ser Gly Ile
                245                 250                 255


<210> SEQ ID NO 62
<211> LENGTH: 1164
<212> TYPE: DNA
<213> ORGANISM: Klebsiella pneumoniae

<400> SEQUENCE: 62

atgagctacc gtatgtttga ctatctggtc cctaacgtga acttcttcgg cccgaatgca      60

atctctgtgg ttggcgaacg ttgccaactg ctgggtggta aaaaggcgct gctggtgacg     120

gataaaggtc tgcgtgcaat taaagacggt gccgttgata aaaccctgca ctatctgcgt     180

gaggccggca ttgaggttgc catcttcgat ggtgtagaac cgaacccgaa agatacgaac     240

gtgcgcgacg gtctggctgt tttccgtcgt gaacaatgtg acattatcgt taccgtgggt     300

ggtggctctc cgcatgattg cggtaaaggc atcggtatcg cggctaccca cgaaggtgat     360

ctgtaccagt atgcgggcat cgagactctg accaacccgc tgccgccgat cgttgctgta     420

aacaccacgg ccggcaccgc ctccgaagtt acccgtcatt gtgtgctgac taacaccgag     480

acgaaagtga aattcgttat tgtgtcctgg cgcaatctgc ctagcgtaag cattaacgat     540

ccgctgctga tgatcggcaa accagcggca ctgaccgctg caactggtat ggacgccctg     600

actcacgcag tcgaagcata tatctccaaa gatgctaacc cggtaaccga cgcggcagct     660

atgcaggcga ttcgtctgat tgcccgtaac ctgcgtcagg cagtggctct gggcagcaac     720

ctgcaggctc gtgagaacat ggcctacgcg agcctgctgg ccggcatggc attcaacaac     780

gctaacctgg gttacgttca tgcgatggct catcagctgg gcggcctgta cgacatgccg     840

cacggtgtag ctaacgcagt tctgctgcca catgttgctc gttataacct gatcgctaat     900

ccggaaaaat tcgcagacat cgcagaactg atgggcgaga acatcacggg tctgagcact     960

ctggatgccg cggaaaaagc gatcgcagcg attacgcgtc tgtctatgga cattggtatt    1020

ccgcaacacc tgcgtgacct gggtgtaaaa gaagctgatt tcccttacat ggcggaaatg    1080
```

gcactgaaag atggtaatgc gttttccaac ccacgtaaag gtaacgaaca ggagattgcg 1140
gctattttcc gtcaagcatt ctga 1164

<210> SEQ ID NO 63
<211> LENGTH: 387
<212> TYPE: PRT
<213> ORGANISM: Klebsiella pneumoniae

<400> SEQUENCE: 63

Met Ser Tyr Arg Met Phe Asp Tyr Leu Val Pro Asn Val Asn Phe Phe
1 5 10 15

Gly Pro Asn Ala Ile Ser Val Val Gly Glu Arg Cys Gln Leu Leu Gly
20 25 30

Gly Lys Lys Ala Leu Leu Val Thr Asp Lys Gly Leu Arg Ala Ile Lys
35 40 45

Asp Gly Ala Val Asp Lys Thr Leu His Tyr Leu Arg Glu Ala Gly Ile
50 55 60

Glu Val Ala Ile Phe Asp Gly Val Glu Pro Asn Pro Lys Asp Thr Asn
65 70 75 80

Val Arg Asp Gly Leu Ala Val Phe Arg Arg Glu Gln Cys Asp Ile Ile
85 90 95

Val Thr Val Gly Gly Gly Ser Pro His Asp Cys Gly Lys Gly Ile Gly
100 105 110

Ile Ala Ala Thr His Glu Gly Asp Leu Tyr Gln Tyr Ala Gly Ile Glu
115 120 125

Thr Leu Thr Asn Pro Leu Pro Pro Ile Val Ala Val Asn Thr Thr Ala
130 135 140

Gly Thr Ala Ser Glu Val Thr Arg His Cys Val Leu Thr Asn Thr Glu
145 150 155 160

Thr Lys Val Lys Phe Val Ile Val Ser Trp Arg Asn Leu Pro Ser Val
165 170 175

Ser Ile Asn Asp Pro Leu Leu Met Ile Gly Lys Pro Ala Ala Leu Thr
180 185 190

Ala Ala Thr Gly Met Asp Ala Leu Thr His Ala Val Glu Ala Tyr Ile
195 200 205

Ser Lys Asp Ala Asn Pro Val Thr Asp Ala Ala Ala Met Gln Ala Ile
210 215 220

Arg Leu Ile Ala Arg Asn Leu Arg Gln Ala Val Ala Leu Gly Ser Asn
225 230 235 240

Leu Gln Ala Arg Glu Asn Met Ala Tyr Ala Ser Leu Leu Ala Gly Met
245 250 255

Ala Phe Asn Asn Ala Asn Leu Gly Tyr Val His Ala Met Ala His Gln
260 265 270

Leu Gly Gly Leu Tyr Asp Met Pro His Gly Val Ala Asn Ala Val Leu
275 280 285

Leu Pro His Val Ala Arg Tyr Asn Leu Ile Ala Asn Pro Glu Lys Phe
290 295 300

Ala Asp Ile Ala Glu Leu Met Gly Glu Asn Ile Thr Gly Leu Ser Thr
305 310 315 320

Leu Asp Ala Ala Glu Lys Ala Ile Ala Ala Ile Thr Arg Leu Ser Met
325 330 335

Asp Ile Gly Ile Pro Gln His Leu Arg Asp Leu Gly Val Lys Glu Ala
340 345 350

Asp Phe Pro Tyr Met Ala Glu Met Ala Leu Lys Asp Gly Asn Ala Phe
355 360 365

Ser Asn Pro Arg Lys Gly Asn Glu Gln Glu Ile Ala Ala Ile Phe Arg
370 375 380

Gln Ala Phe
385

<210> SEQ ID NO 64
<211> LENGTH: 1152
<212> TYPE: DNA
<213> ORGANISM: Escherichia coli

<400> SEQUENCE: 64
atgatggcta acagaatgat tctgaacgaa acggcatggt ttggtcgggg tgctgttggg 60
gctttaaccg atgaggtgaa acgccgtggt tatcagaagg cgctgatcgt caccgataaa 120
acgctggtgc aatgcggcgt ggtggcgaaa gtgaccgata agatggatgc tgcagggctg 180
gcatgggcga tttacgacgg cgtagtgccc aacccaacaa ttactgtcgt caaagaaggg 240
ctcggtgtat tccagaatag cggcgcggat tacctgatcg ctattggtgg tggttctcca 300
caggatactt gtaaagcgat tggcattatc agcaacaacc cggagtttgc cgatgtgcgt 360
agcctggaag ggctttcccc gaccaataaa cccagtgtac cgattctggc aattcctacc 420
acagcaggta ctgcggcaga agtgaccatt aactacgtga tcactgacga agagaaacgg 480
cgcaagtttg tttgcgttga tccgcatgat atcccgcagg tggcgtttat tgacgctgac 540
atgatggatg gtatgcctcc agcgctgaaa gctgcgacgg gtgtcgatgc gctcactcat 600
gctattgagg ggtatattac ccgtggcgcg tgggcgctaa ccgatgcact gcacattaaa 660
gcgattgaaa tcattgctgg ggcgctgcga ggatcggttg ctggtgataa ggatgccgga 720
gaagaaatgg cgctcgggca gtatgttgcg ggtatgggct tctcgaatgt tgggttaggg 780
ttggtgcatg gtatggcgca tccactgggc gcgttttata acactccaca cggtgttgcg 840
aacgccatcc tgttaccgca tgtcatgcgt tataacgctg actttaccgg tgagaagtac 900
cgcgatatcg cgcgcgttat gggcgtgaaa gtggaaggta tgagcctgga agaggcgcgt 960
aatgccgctg ttgaagcggt gtttgctctc aaccgtgatg tcggtattcc gccacatttg 1020
cgtgatgttg gtgtacgcaa ggaagacatt ccggcactgg cgcaggcggc actggatgat 1080
gtttgtaccg gtggcaaccc gcgtgaagca acgcttgagg atattgtaga gctttaccat 1140
accgcctggt aa 1152

<210> SEQ ID NO 65
<211> LENGTH: 383
<212> TYPE: PRT
<213> ORGANISM: Escherichia coli

<400> SEQUENCE: 65

Met Met Ala Asn Arg Met Ile Leu Asn Glu Thr Ala Trp Phe Gly Arg
1 5 10 15

Gly Ala Val Gly Ala Leu Thr Asp Glu Val Lys Arg Arg Gly Tyr Gln
20 25 30

Lys Ala Leu Ile Val Thr Asp Lys Thr Leu Val Gln Cys Gly Val Val
35 40 45

Ala Lys Val Thr Asp Lys Met Asp Ala Ala Gly Leu Ala Trp Ala Ile
50 55 60

Tyr Asp Gly Val Val Pro Asn Pro Thr Ile Thr Val Val Lys Glu Gly
65 70 75 80

Leu Gly Val Phe Gln Asn Ser Gly Ala Asp Tyr Leu Ile Ala Ile Gly
85 90 95

```
Gly Gly Ser Pro Gln Asp Thr Cys Lys Ala Ile Gly Ile Ile Ser Asn
            100                 105                 110

Asn Pro Glu Phe Ala Asp Val Arg Ser Leu Glu Gly Leu Ser Pro Thr
        115                 120                 125

Asn Lys Pro Ser Val Pro Ile Leu Ala Ile Pro Thr Thr Ala Gly Thr
    130                 135                 140

Ala Ala Glu Val Thr Ile Asn Tyr Val Ile Thr Asp Glu Glu Lys Arg
145                 150                 155                 160

Arg Lys Phe Val Cys Val Asp Pro His Asp Ile Pro Gln Val Ala Phe
                165                 170                 175

Ile Asp Ala Asp Met Met Asp Gly Met Pro Pro Ala Leu Lys Ala Ala
            180                 185                 190

Thr Gly Val Asp Ala Leu Thr His Ala Ile Glu Gly Tyr Ile Thr Arg
        195                 200                 205

Gly Ala Trp Ala Leu Thr Asp Ala Leu His Ile Lys Ala Ile Glu Ile
    210                 215                 220

Ile Ala Gly Ala Leu Arg Gly Ser Val Ala Gly Asp Lys Asp Ala Gly
225                 230                 235                 240

Glu Glu Met Ala Leu Gly Gln Tyr Val Ala Gly Met Gly Phe Ser Asn
                245                 250                 255

Val Gly Leu Gly Leu Val His Gly Met Ala His Pro Leu Gly Ala Phe
            260                 265                 270

Tyr Asn Thr Pro His Gly Val Ala Asn Ala Ile Leu Leu Pro His Val
        275                 280                 285

Met Arg Tyr Asn Ala Asp Phe Thr Gly Glu Lys Tyr Arg Asp Ile Ala
    290                 295                 300

Arg Val Met Gly Val Lys Val Glu Gly Met Ser Leu Glu Glu Ala Arg
305                 310                 315                 320

Asn Ala Ala Val Glu Ala Val Phe Ala Leu Asn Arg Asp Val Gly Ile
                325                 330                 335

Pro Pro His Leu Arg Asp Val Gly Val Arg Lys Glu Asp Ile Pro Ala
            340                 345                 350

Leu Ala Gln Ala Ala Leu Asp Asp Val Cys Thr Gly Gly Asn Pro Arg
        355                 360                 365

Glu Ala Thr Leu Glu Asp Ile Val Glu Leu Tyr His Thr Ala Trp
    370                 375                 380


<210> SEQ ID NO 66
<211> LENGTH: 1023
<212> TYPE: DNA
<213> ORGANISM: Lactococcus lactis

<400> SEQUENCE: 66

atgaaagcag cagtagtaag acacaatcca gatggttatg cggaccttgt tgaaaaggaa      60

cttcgagcaa tcaaacctaa tgaagctttg cttgacatgg agtattgtgg agtctgtcat     120

accgatttgc acgttgcagc aggtgattat ggcaacaaag cagggactgt tcttggtcat     180

gaaggaattg gaattgtcaa agaaattgga gctgatgtaa gctcgcttca agttggtgat     240

cgggtttcag tggcttggtt ctttgaagga tgtggtcact gtgaatactg tgtatctggt     300

aatgaaactt tttgtcgaga agttaaaaat gcaggatatt cagttgatgg cggaatggct     360

gaagaagcaa ttgttgttgc cgattatgct gtcaaagttc ctgacggact tgacccaatt     420

gaagctagct caattacttg tgctggagta acaacttaca aagcaatcaa agtatcagga     480

gtaaaacctg gtgattggca agtaattttt ggtgctggag gacttggaaa tttagcaatt     540
```

```
caatatgcta aaaatgtttt tggagcaaaa gtaattgctg ttgatattaa tcaagataaa    600

ttaaatttag ctaaaaaaat tggagctgat gtgattatca attctggtga tgtaaatcca    660

gttgatgaaa ttaaaaaaat aactggcggc ttaggggtgc aaagtgcaat agtttgtgct    720

gttgcaagga ttgcttttga acaagcggtt gcttctttga aacctatggg caaaatggtt    780

gctgtggcac ttcccaatac tgagatgact ttatcagttc caacagttgt ttttgacgga    840

gtggaggttg caggttcact tgtcggaaca agacttgact tggcagaagc ttttcaattt    900

ggagcagaag gtaaggtaaa accaattgtt gcgacacgca aactggaaga aatcaatgat    960

attattgatg aaatgaaggc aggaaaaatt gaaggccgaa tggtcattga ttttactaaa   1020

taa                                                                 1023
```

<210> SEQ ID NO 67
<211> LENGTH: 340
<212> TYPE: PRT
<213> ORGANISM: Lactococcus lactis

<400> SEQUENCE: 67

```
Met Lys Ala Ala Val Val Arg His Asn Pro Asp Gly Tyr Ala Asp Leu
1               5                   10                  15

Val Glu Lys Glu Leu Arg Ala Ile Lys Pro Asn Glu Ala Leu Leu Asp
            20                  25                  30

Met Glu Tyr Cys Gly Val Cys His Thr Asp Leu His Val Ala Ala Gly
        35                  40                  45

Asp Tyr Gly Asn Lys Ala Gly Thr Val Leu Gly His Glu Gly Ile Gly
    50                  55                  60

Ile Val Lys Glu Ile Gly Ala Asp Val Ser Ser Leu Gln Val Gly Asp
65                  70                  75                  80

Arg Val Ser Val Ala Trp Phe Phe Glu Gly Cys Gly His Cys Glu Tyr
                85                  90                  95

Cys Val Ser Gly Asn Glu Thr Phe Cys Arg Glu Val Lys Asn Ala Gly
            100                 105                 110

Tyr Ser Val Asp Gly Gly Met Ala Glu Glu Ala Ile Val Val Ala Asp
        115                 120                 125

Tyr Ala Val Lys Val Pro Asp Gly Leu Asp Pro Ile Glu Ala Ser Ser
    130                 135                 140

Ile Thr Cys Ala Gly Val Thr Thr Tyr Lys Ala Ile Lys Val Ser Gly
145                 150                 155                 160

Val Lys Pro Gly Asp Trp Gln Val Ile Phe Gly Ala Gly Gly Leu Gly
                165                 170                 175

Asn Leu Ala Ile Gln Tyr Ala Lys Asn Val Phe Gly Ala Lys Val Ile
            180                 185                 190

Ala Val Asp Ile Asn Gln Asp Lys Leu Asn Leu Ala Lys Lys Ile Gly
        195                 200                 205

Ala Asp Val Ile Ile Asn Ser Gly Asp Val Asn Pro Val Asp Glu Ile
    210                 215                 220

Lys Lys Ile Thr Gly Gly Leu Gly Val Gln Ser Ala Ile Val Cys Ala
225                 230                 235                 240

Val Ala Arg Ile Ala Phe Glu Gln Ala Val Ala Ser Leu Lys Pro Met
                245                 250                 255

Gly Lys Met Val Ala Val Ala Leu Pro Asn Thr Glu Met Thr Leu Ser
            260                 265                 270

Val Pro Thr Val Val Phe Asp Gly Val Glu Val Ala Gly Ser Leu Val
        275                 280                 285
```

```
Gly Thr Arg Leu Asp Leu Ala Glu Ala Phe Gln Phe Gly Ala Glu Gly
    290                 295                 300

Lys Val Lys Pro Ile Val Ala Thr Arg Lys Leu Glu Glu Ile Asn Asp
305                 310                 315                 320

Ile Ile Asp Glu Met Lys Ala Gly Lys Ile Glu Gly Arg Met Val Ile
                325                 330                 335

Asp Phe Thr Lys
            340
```

<210> SEQ ID NO 68
<211> LENGTH: 1164
<212> TYPE: DNA
<213> ORGANISM: Escherichia coli

<400> SEQUENCE: 68

```
atgaacaact ttaatctgca caccccaacc cgcattctgt ttggtaaagg cgcaatcgct     60

ggtttacgcg aacaaattcc tcacgatgct cgcgtattga ttacctacgg cggcggcagc    120

gtgaaaaaaa ccggcgttct cgatcaagtt ctggatgccc tgaaaggcat ggacgtgctg    180

gaatttggcg gtattgagcc aaacccggct tatgaaacgc tgatgaacgc cgtgaaactg    240

gttcgcgaac agaaagtgac tttcctgctg gcggttggcg gcggttctgt actggacggc    300

accaaattta tcgccgcagc ggctaactat ccggaaaata tcgatccgtg gcacattctg    360

caaacgggcg gtaaagagat taaaagcgcc atcccgatgg gctgtgtgct gacgctgcca    420

gcaaccggtt cagaatccaa cgcaggcgcg gtgatctccc gtaaaaccac aggcgacaag    480

caggcgttcc attctgccca tgttcagccg gtatttgccg tgctcgatcc ggtttatacc    540

tacaccctgc cgccgcgtca ggtggctaac ggcgtagtgg acgcctttgt acacaccgtg    600

gaacagtatg ttaccaaacc ggttgatgcc aaaattcagg accgtttcgc agaaggcatt    660

ttgctgacgc taatcgaaga tggtccgaaa gccctgaaag agccagaaaa ctacgatgtg    720

cgcgccaacg tcatgtgggc ggcgactcag gcgctgaacg gtttgattgg cgctggcgta    780

ccgcaggact gggcaacgca tatgctgggc cacgaactga ctgcgatgca cggtctggat    840

cacgcgcaaa cactggctat cgtcctgcct gcactgtgga atgaaaaacg cgataccaag    900

cgcgctaagc tgctgcaata tgctgaacgc gtctggaaca tcactgaagg ttccgatgat    960

gagcgtattg acgccgcgat tgccgcaacc cgcaatttct ttgagcaatt aggcgtgccg   1020

acccacctct ccgactacgg tctggacggc agctccatcc cggctttgct gaaaaaactg   1080

gaagagcacg gcatgaccca actgggcgaa aatcatgaca ttacgttgga tgtcagccgc   1140

cgtatatacg aagccgcccg ctaa                                          1164
```

<210> SEQ ID NO 69
<211> LENGTH: 387
<212> TYPE: PRT
<213> ORGANISM: Escherichia coli

<400> SEQUENCE: 69

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60
```

Ile Glu Pro Asn Pro Ala Tyr Glu Thr Leu Met Asn Ala Val Lys Leu
65 70 75 80

Val Arg Glu Gln Lys Val Thr Phe Leu Leu Ala Val Gly Gly Gly Ser
85 90 95

Val Leu Asp Gly Thr Lys Phe Ile Ala Ala Ala Ala Asn Tyr Pro Glu
100 105 110

Asn Ile Asp Pro Trp His Ile Leu Gln Thr Gly Gly Lys Glu Ile Lys
115 120 125

Ser Ala Ile Pro Met Gly Cys Val Leu Thr Leu Pro Ala Thr Gly Ser
130 135 140

Glu Ser Asn Ala Gly Ala Val Ile Ser Arg Lys Thr Thr Gly Asp Lys
145 150 155 160

Gln Ala Phe His Ser Ala His Val Gln Pro Val Phe Ala Val Leu Asp
165 170 175

Pro Val Tyr Thr Tyr Thr Leu Pro Pro Arg Gln Val Ala Asn Gly Val
180 185 190

Val Asp Ala Phe Val His Thr Val Glu Gln Tyr Val Thr Lys Pro Val
195 200 205

Asp Ala Lys Ile Gln Asp Arg Phe Ala Glu Gly Ile Leu Leu Thr Leu
210 215 220

Ile Glu Asp Gly Pro Lys Ala Leu Lys Glu Pro Glu Asn Tyr Asp Val
225 230 235 240

Arg Ala Asn Val Met Trp Ala Ala Thr Gln Ala Leu Asn Gly Leu Ile
245 250 255

Gly Ala Gly Val Pro Gln Asp Trp Ala Thr His Met Leu Gly His Glu
260 265 270

Leu Thr Ala Met His Gly Leu Asp His Ala Gln Thr Leu Ala Ile Val
275 280 285

Leu Pro Ala Leu Trp Asn Glu Lys Arg Asp Thr Lys Arg Ala Lys Leu
290 295 300

Leu Gln Tyr Ala Glu Arg Val Trp Asn Ile Thr Glu Gly Ser Asp Asp
305 310 315 320

Glu Arg Ile Asp Ala Ala Ile Ala Ala Thr Arg Asn Phe Phe Glu Gln
325 330 335

Leu Gly Val Pro Thr His Leu Ser Asp Tyr Gly Leu Asp Gly Ser Ser
340 345 350

Ile Pro Ala Leu Leu Lys Lys Leu Glu Glu His Gly Met Thr Gln Leu
355 360 365

Gly Glu Asn His Asp Ile Thr Leu Asp Val Ser Arg Arg Ile Tyr Glu
370 375 380

Ala Ala Arg
385

<210> SEQ ID NO 70
<211> LENGTH: 395
<212> TYPE: PRT
<213> ORGANISM: Saccharomyces cerevisiae

<400> SEQUENCE: 70

Met Leu Arg Thr Gln Ala Ala Arg Leu Ile Cys Asn Ser Arg Val Ile
1 5 10 15

Thr Ala Lys Arg Thr Phe Ala Leu Ala Thr Arg Ala Ala Ala Tyr Ser
20 25 30

Arg Pro Ala Ala Arg Phe Val Lys Pro Met Ile Thr Thr Arg Gly Leu
35 40 45

Lys Gln Ile Asn Phe Gly Gly Thr Val Glu Thr Val Tyr Glu Arg Ala
    50                  55                  60

Asp Trp Pro Arg Glu Lys Leu Leu Asp Tyr Phe Lys Asn Asp Thr Phe
65                  70                  75                  80

Ala Leu Ile Gly Tyr Gly Ser Gln Gly Tyr Gly Gln Gly Leu Asn Leu
                85                  90                  95

Arg Asp Asn Gly Leu Asn Val Ile Ile Gly Val Arg Lys Asp Gly Ala
            100                 105                 110

Ser Trp Lys Ala Ala Ile Glu Asp Gly Trp Val Pro Gly Lys Asn Leu
        115                 120                 125

Phe Thr Val Glu Asp Ala Ile Lys Arg Gly Ser Tyr Val Met Asn Leu
    130                 135                 140

Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
                165                 170                 175

Phe Lys Asp Leu Thr His Val Glu Pro Pro Lys Asp Leu Asp Val Ile
            180                 185                 190

Leu Val Ala Pro Lys Gly Ser Gly Arg Thr Val Arg Ser Leu Phe Lys
        195                 200                 205

Glu Gly Arg Gly Ile Asn Ser Ser Tyr Ala Val Trp Asn Asp Val Thr
    210                 215                 220

Gly Lys Ala His Glu Lys Ala Gln Ala Leu Ala Val Ala Ile Gly Ser
225                 230                 235                 240

Gly Tyr Val Tyr Gln Thr Thr Phe Glu Arg Glu Val Asn Ser Asp Leu
                245                 250                 255

Tyr Gly Glu Arg Gly Cys Leu Met Gly Gly Ile His Gly Met Phe Leu
            260                 265                 270

Ala Gln Tyr Asp Val Leu Arg Glu Asn Gly His Ser Pro Ser Glu Ala
        275                 280                 285

Phe Asn Glu Thr Val Glu Glu Ala Thr Gln Ser Leu Tyr Pro Leu Ile
    290                 295                 300

Gly Lys Tyr Gly Met Asp Tyr Met Tyr Asp Ala Cys Ser Thr Thr Ala
305                 310                 315                 320

Arg Arg Gly Ala Leu Asp Trp Tyr Pro Ile Phe Lys Asn Ala Leu Lys
                325                 330                 335

Pro Val Phe Gln Asp Leu Tyr Glu Ser Thr Lys Asn Gly Thr Glu Thr
            340                 345                 350

Lys Arg Ser Leu Glu Phe Asn Ser Gln Pro Asp Tyr Arg Glu Lys Leu
        355                 360                 365

Glu Lys Glu Leu Asp Thr Ile Arg Asn Met Glu Ile Trp Lys Val Gly
    370                 375                 380

Lys Glu Val Arg Lys Leu Arg Pro Glu Asn Gln
385                 390                 395

<210> SEQ ID NO 71
<211> LENGTH: 330
<212> TYPE: PRT
<213> ORGANISM: Methanococcus maripaludis

<400> SEQUENCE: 71

Met Lys Val Phe Tyr Asp Ser Asp Phe Lys Leu Asp Ala Leu Lys Glu
1               5                   10                  15

Lys Thr Ile Ala Val Ile Gly Tyr Gly Ser Gln Gly Arg Ala Gln Ser
            20                  25                  30

Leu Asn Met Lys Asp Ser Gly Leu Asn Val Val Val Gly Leu Arg Lys
35 40 45

Asn Gly Ala Ser Trp Glu Asn Ala Lys Ala Asp Gly His Asn Val Met
50 55 60

Thr Ile Glu Glu Ala Ala Glu Lys Ala Asp Ile Ile His Ile Leu Ile
65 70 75 80

Pro Asp Glu Leu Gln Ala Glu Val Tyr Glu Ser Gln Ile Lys Pro Tyr
85 90 95

Leu Lys Glu Gly Lys Thr Leu Ser Phe Ser His Gly Phe Asn Ile His
100 105 110

Tyr Gly Phe Ile Val Pro Pro Lys Gly Val Asn Val Val Leu Val Ala
115 120 125

Pro Lys Ser Pro Gly Lys Met Val Arg Arg Thr Tyr Glu Glu Gly Phe
130 135 140

Gly Val Pro Gly Leu Ile Cys Ile Glu Ile Asp Ala Thr Asn Asn Ala
145 150 155 160

Phe Asp Ile Val Ser Ala Met Ala Lys Gly Ile Gly Leu Ser Arg Ala
165 170 175

Gly Val Ile Gln Thr Thr Phe Lys Glu Glu Thr Glu Thr Asp Leu Phe
180 185 190

Gly Glu Gln Ala Val Leu Cys Gly Gly Val Thr Glu Leu Ile Lys Ala
195 200 205

Gly Phe Glu Thr Leu Val Glu Ala Gly Tyr Ala Pro Glu Met Ala Tyr
210 215 220

Phe Glu Thr Cys His Glu Leu Lys Leu Ile Val Asp Leu Ile Tyr Gln
225 230 235 240

Lys Gly Phe Lys Asn Met Trp Asn Asp Val Ser Asn Thr Ala Glu Tyr
245 250 255

Gly Gly Leu Thr Arg Arg Ser Arg Ile Val Thr Ala Asp Ser Lys Ala
260 265 270

Ala Met Lys Glu Ile Leu Lys Glu Ile Gln Asp Gly Arg Phe Thr Lys
275 280 285

Glu Phe Val Leu Glu Lys Gln Val Asn His Ala His Leu Lys Ala Met
290 295 300

Arg Arg Ile Glu Gly Asp Leu Gln Ile Glu Glu Val Gly Ala Lys Leu
305 310 315 320

Arg Lys Met Cys Gly Leu Glu Lys Glu Glu
325 330

<210> SEQ ID NO 72
<211> LENGTH: 342
<212> TYPE: PRT
<213> ORGANISM: Bacillus subtilis

<400> SEQUENCE: 72

Met Val Lys Val Tyr Tyr Asn Gly Asp Ile Lys Glu Asn Val Leu Ala
1 5 10 15

Gly Lys Thr Val Ala Val Ile Gly Tyr Gly Ser Gln Gly His Ala His
20 25 30

Ala Leu Asn Leu Lys Glu Ser Gly Val Asp Val Ile Val Gly Val Arg
35 40 45

Gln Gly Lys Ser Phe Thr Gln Ala Gln Glu Asp Gly His Lys Val Phe
50 55 60

Ser Val Lys Glu Ala Ala Ala Gln Ala Glu Ile Ile Met Val Leu Leu
65 70 75 80

Pro Asp Glu Gln Gln Gln Lys Val Tyr Glu Ala Glu Ile Lys Asp Glu
85 90 95

Leu Thr Ala Gly Lys Ser Leu Val Phe Ala His Gly Phe Asn Val His
100 105 110

Phe His Gln Ile Val Pro Pro Ala Asp Val Asp Val Phe Leu Val Ala
115 120 125

Pro Lys Gly Pro Gly His Leu Val Arg Arg Thr Tyr Glu Gln Gly Ala
130 135 140

Gly Val Pro Ala Leu Phe Ala Ile Tyr Gln Asp Val Thr Gly Glu Ala
145 150 155 160

Arg Asp Lys Ala Leu Ala Tyr Ala Lys Gly Ile Gly Gly Ala Arg Ala
165 170 175

Gly Val Leu Glu Thr Thr Phe Lys Glu Glu Thr Glu Thr Asp Leu Phe
180 185 190

Gly Glu Gln Ala Val Leu Cys Gly Gly Leu Ser Ala Leu Val Lys Ala
195 200 205

Gly Phe Glu Thr Leu Thr Glu Ala Gly Tyr Gln Pro Glu Leu Ala Tyr
210 215 220

Phe Glu Cys Leu His Glu Leu Lys Leu Ile Val Asp Leu Met Tyr Glu
225 230 235 240

Glu Gly Leu Ala Gly Met Arg Tyr Ser Ile Ser Asp Thr Ala Gln Trp
245 250 255

Gly Asp Phe Val Ser Gly Pro Arg Val Val Asp Ala Lys Val Lys Glu
260 265 270

Ser Met Lys Glu Val Leu Lys Asp Ile Gln Asn Gly Thr Phe Ala Lys
275 280 285

Glu Trp Ile Val Glu Asn Gln Val Asn Arg Pro Arg Phe Asn Ala Ile
290 295 300

Asn Ala Ser Glu Asn Glu His Gln Ile Glu Val Val Gly Arg Lys Leu
305 310 315 320

Arg Glu Met Met Pro Phe Val Lys Gln Gly Lys Lys Lys Glu Ala Val
325 330 335

Val Ser Val Ala Gln Asn
340

<210> SEQ ID NO 73
<211> LENGTH: 352
<212> TYPE: PRT
<213> ORGANISM: Piromyces sp.

<400> SEQUENCE: 73

Met Val Lys Val Ile Asn Phe Gly Gly Val Asp Glu Thr Val Tyr Glu
1 5 10 15

Arg Ala Asp Phe Pro Gln Glu Lys Leu Asn Glu Ile Phe Lys Asp Asp
20 25 30

Val Phe Val Val Ile Gly Tyr Gly Thr Gln Gly Arg Asn Gln Ser Arg
35 40 45

Asn Leu Arg Asp Lys Gly Phe Lys Val Ile Val Gly Leu Arg Lys Gly
50 55 60

Pro Ser Trp Asp Leu Ala Lys Glu Asp Gly Trp Val Glu Ser Glu Ser
65 70 75 80

Leu Phe Glu Ile Thr Glu Ala Cys Gln Lys Gly Thr Ile Ile Met Tyr
85 90 95

Leu Leu Ser Asp Ala Gly Gln Lys Ala Cys Trp Asn Thr Ile Lys Glu
100 105 110

Leu Val His Gly Lys Thr Leu Tyr Phe Ser His Gly Phe Ser Ile Val
115 120 125

Phe Lys Glu Lys Thr Gly Val Val Pro Pro Glu Asp Cys Asp Val Ile
130 135 140

Met Val Ala Pro Lys Gly Ser Gly Thr Thr Val Arg Thr Leu Phe Leu
145 150 155 160

Glu Gly Arg Gly Ile Asn Ser Ser Val Ala Val Phe Gln Asn Trp Ser
165 170 175

Gly Lys Ala Glu Glu Arg Ala Tyr Ala Ala Gly Ile Ala Ile Gly Ser
180 185 190

Gly Tyr Leu Tyr Pro Thr Thr Phe Glu Arg Glu Thr Tyr Ser Asp Leu
195 200 205

Thr Gly Glu Arg Gly Thr Leu Met Gly Cys Ile Gln Gly Cys Phe Lys
210 215 220

Ala Gln Phe Glu Val Leu Ile Ala Asn Gly His Thr Pro Ser Glu Ala
225 230 235 240

Phe Ser Glu Thr Val Glu Glu Ala Thr Gln Ser Leu Tyr Pro Leu Ile
245 250 255

Gly Lys Asp Gly Met Asp Trp Met Tyr Asp Asn Cys Ser Thr Thr Ala
260 265 270

Arg Arg Gly Ala Leu Asp Trp Met Asp Lys Phe Tyr Ala Ala Thr Lys
275 280 285

Pro Val Phe Glu Glu Leu Tyr Glu Ser Val Arg Asn Gly Thr Glu Ala
290 295 300

Glu Asn Thr Leu Val Ala Asn Ser Lys Pro Asp Tyr Arg Glu Asn Leu
305 310 315 320

Ala Lys Glu Leu Lys Glu Leu Arg Glu Ser Gln Met Trp Gln Thr Ala
325 330 335

Val Thr Val Arg Ser Leu Arg Pro Glu Asn Gln Lys Val Glu Lys Asn
340 345 350

<210> SEQ ID NO 74
<211> LENGTH: 490
<212> TYPE: PRT
<213> ORGANISM: Buchnera aphidicola

<400> SEQUENCE: 74

Met Lys Asn Tyr Phe Asn Ser Leu Asn Phe Arg Gln Lys Leu Ile Asn
1 5 10 15

Leu Gln Lys Cys Lys Leu Ile Asp Asn Gln Phe Leu Ser Glu Lys Asn
20 25 30

Asn Val Leu Lys Gly Lys Asn Ile Val Ile Val Gly Cys Gly Ser Gln
35 40 45

Gly Leu Asn Gln Gly Leu Asn Met Arg Asp Ser Gly Leu Asn Ile Ser
50 55 60

Tyr Ala Leu Arg Asp Asp Ser Ile Phe Asn Lys Asn Gln Ser Trp Ile
65 70 75 80

Asn Ala Thr Ser Asn Gly Phe Phe Val Gly Thr Tyr Glu Asn Ile Ile
85 90 95

Pro Thr Ala Asp Leu Val Ile Asn Leu Thr Pro Asp Lys Gln His Glu
100 105 110

Gln Val Val Asn Val Leu Gln Lys Phe Met Lys Pro Asn Ser Val Leu
115 120 125

Gly Phe Ser His Gly Phe Asn Ile Val Glu Val Gly Gln Leu Ile Arg
130 135 140

Asn Asp Ile Thr Val Ile Met Val Ala Pro Lys Cys Pro Gly Thr Glu
145 150 155 160

Val Arg Glu Glu Tyr Lys Arg Gly Phe Gly Val Pro Ala Leu Ile Ala
165 170 175

Val His Ser Glu Asn Asp Pro His Asp Ile Gly Phe Glu Ile Ala Lys
180 185 190

Ser Trp Ala Ile Ser Ile Gly Ser His His Ala Gly Ile Leu His Ser
195 200 205

Ser Phe Ile Ala Glu Val Lys Ser Asp Leu Met Gly Glu Gln Thr Ile
210 215 220

Leu Cys Gly Met Leu Gln Ala Ser Ser Leu Val Cys Tyr Asn Gln Leu
225 230 235 240

Ile Phe Gln Gly Val Asn Pro Ser Tyr Ala Gly Lys Leu Ile Gln Thr
245 250 255

Gly Trp Glu Val Ile Thr Glu Ser Val Lys His Gly Gly Ile Thr Leu
260 265 270

Met Leu Asp Arg Leu Ser Asn Thr Ala Lys Ile Arg Ala Tyr Phe Leu
275 280 285

Ser Lys Lys Leu Lys Lys Ile Phe Phe Pro Leu Phe Arg Lys His Met
290 295 300

Asp Asp Ile Ile Ser Gly Glu Phe Ser Lys Asn Met Met Phe Asp Trp
305 310 315 320

Lys Asn Asn Asp Gln Gln Leu Lys Glu Trp Arg Thr Glu Ile Gln Asn
325 330 335

Thr Asp Phe Glu Lys Cys Asn Ile Tyr Tyr Lys Gln Ile Pro Glu Gln
340 345 350

Glu Tyr Phe Asp Asn Gly Leu Leu Met Val Ala Ile Leu Lys Ala Gly
355 360 365

Ile Glu Leu Ser Phe Glu Ile Met Ile Glu Thr Gly Ile Lys Glu Glu
370 375 380

Ser Ala Tyr Tyr Glu Ser Leu His Glu Leu Pro Leu Ile Ala Asn Thr
385 390 395 400

Ile Ala Arg Lys Arg Leu Tyr Glu Met Asn Leu Val Ile Ser Asp Thr
405 410 415

Ala Glu Tyr Gly Ser Tyr Leu Phe Ser His Ala Ala Ile Pro Leu Leu
420 425 430

Lys Lys Phe Met Asn Glu Leu Gln Pro Gly Asp Leu Gly Asn Lys Ile
435 440 445

Ser Thr Ser Glu Leu Asp Asn Ile Thr Leu Tyr Lys Val Asn Ala Lys
450 455 460

Ile Glu Ser His Pro Ile Glu Ile Ile Gly Lys Lys Leu Arg Leu Tyr
465 470 475 480

Met Thr Ser Met Val Pro Ile Lys Thr Lys
485 490

<210> SEQ ID NO 75
<211> LENGTH: 595
<212> TYPE: PRT
<213> ORGANISM: Spinacia oleracea

<400> SEQUENCE: 75

Met Ala Ala Thr Ala Ala Thr Thr Phe Ser Leu Ser Ser Ser Ser Ser
1 5 10 15

Thr Ser Ala Ala Ala Ser Lys Ala Leu Lys Gln Ser Pro Lys Pro Ser
20 25 30

```
Ala Leu Asn Leu Gly Phe Leu Gly Ser Ser Ser Thr Ile Lys Ala Cys
        35                  40                  45

Arg Ser Leu Lys Ala Ala Arg Val Leu Pro Ser Gly Ala Asn Gly Gly
    50                  55                  60

Gly Ser Ala Leu Ser Ala Gln Met Val Ser Ala Pro Ser Ile Asn Thr
65                  70                  75                  80

Pro Ser Ala Thr Thr Phe Asp Phe Asp Ser Ser Val Phe Lys Lys Glu
                85                  90                  95

Lys Val Thr Leu Ser Gly His Asp Glu Tyr Ile Val Arg Gly Gly Arg
            100                 105                 110

Asn Leu Phe Pro Leu Leu Pro Asp Ala Phe Lys Gly Ile Lys Gln Ile
        115                 120                 125

Gly Val Ile Gly Trp Gly Ser Gln Ala Pro Ala Gln Ala Gln Asn Leu
    130                 135                 140

Lys Asp Ser Leu Thr Glu Ala Lys Ser Asp Val Val Val Lys Ile Gly
145                 150                 155                 160

Leu Arg Lys Gly Ser Asn Ser Phe Ala Glu Ala Arg Ala Ala Gly Phe
                165                 170                 175

Ser Glu Glu Asn Gly Thr Leu Gly Asp Met Trp Glu Thr Ile Ser Gly
            180                 185                 190

Ser Asp Leu Val Leu Leu Leu Ile Ser Asp Ser Ala Gln Ala Asp Asn
        195                 200                 205

Tyr Glu Lys Val Phe Ser His Met Lys Pro Asn Ser Ile Leu Gly Leu
    210                 215                 220

Ser His Gly Phe Leu Leu Gly His Leu Gln Ser Leu Gly Gln Asp Phe
225                 230                 235                 240

Pro Lys Asn Ile Ser Val Ile Ala Val Cys Pro Lys Gly Met Gly Pro
                245                 250                 255

Ser Val Arg Arg Leu Tyr Val Gln Gly Lys Glu Val Asn Gly Ala Gly
            260                 265                 270

Ile Asn Ser Ser Phe Ala Val His Gln Asp Val Asp Gly Arg Ala Thr
        275                 280                 285

Asp Val Ala Leu Gly Trp Ser Ile Ala Leu Gly Ser Pro Phe Thr Phe
    290                 295                 300

Ala Thr Thr Leu Glu Gln Glu Tyr Lys Ser Asp Ile Phe Gly Glu Arg
305                 310                 315                 320

Gly Ile Leu Leu Gly Ala Val His Gly Ile Val Glu Cys Leu Phe Arg
                325                 330                 335

Arg Tyr Thr Glu Ser Gly Met Ser Glu Asp Leu Ala Tyr Lys Asn Thr
            340                 345                 350

Val Glu Cys Ile Thr Gly Val Ile Ser Lys Thr Ile Ser Thr Lys Gly
        355                 360                 365

Met Leu Ala Leu Tyr Asn Ser Leu Ser Glu Glu Gly Lys Lys Asp Phe
    370                 375                 380

Gln Ala Ala Tyr Ser Ala Ser Tyr Tyr Pro Ser Met Asp Ile Leu Tyr
385                 390                 395                 400

Glu Cys Tyr Glu Asp Val Ala Ser Gly Ser Glu Ile Arg Ser Val Val
                405                 410                 415

Leu Ala Gly Arg Arg Phe Tyr Glu Lys Glu Gly Leu Pro Ala Phe Pro
            420                 425                 430

Met Gly Lys Ile Asp Gln Thr Arg Met Trp Lys Val Gly Glu Lys Val
        435                 440                 445

Arg Ser Val Arg Pro Ala Gly Asp Leu Gly Pro Leu Tyr Pro Phe Thr
```

```
    450                 455                 460

Ala Gly Val Tyr Val Ala Leu Met Met Ala Gln Ile Glu Ile Leu Arg
465                 470                 475                 480

Lys Lys Gly His Ser Tyr Ser Glu Ile Ile Asn Glu Ser Val Ile Glu
                485                 490                 495

Ala Val Asp Ser Leu Asn Pro Phe Met His Ala Arg Gly Val Ser Phe
            500                 505                 510

Met Val Asp Asn Cys Ser Thr Thr Ala Arg Leu Gly Ser Arg Lys Trp
        515                 520                 525

Ala Pro Arg Phe Asp Tyr Ile Leu Ser Gln Gln Ala Leu Val Ala Val
    530                 535                 540

Asp Asn Gly Ala Pro Ile Asn Gln Asp Leu Ile Ser Asn Phe Leu Ser
545                 550                 555                 560

Asp Pro Val His Glu Ala Ile Gly Val Cys Ala Gln Leu Arg Pro Ser
                565                 570                 575

Val Asp Ile Ser Val Thr Ala Asp Ala Asp Phe Val Arg Pro Glu Leu
            580                 585                 590

Arg Gln Ala
        595


<210> SEQ ID NO 76
<211> LENGTH: 578
<212> TYPE: PRT
<213> ORGANISM: Oryza sativa

<400> SEQUENCE: 76

Met Ala Ala Ser Thr Thr Leu Ala Leu Ser His Pro Lys Thr Leu Ala
1               5                   10                  15

Ala Ala Ala Ala Ala Ala Pro Lys Ala Pro Thr Ala Pro Ala Ala Val
            20                  25                  30

Ser Phe Pro Val Ser His Ala Ala Cys Ala Pro Leu Ala Ala Arg Arg
        35                  40                  45

Arg Ala Val Thr Ala Met Val Ala Ala Pro Pro Ala Val Gly Ala Ala
    50                  55                  60

Met Pro Ser Leu Asp Phe Asp Thr Ser Val Phe Asn Lys Glu Lys Val
65                  70                  75                  80

Ser Leu Ala Gly His Glu Glu Tyr Ile Val Arg Gly Gly Arg Asn Leu
                85                  90                  95

Phe Pro Leu Leu Pro Glu Ala Phe Lys Gly Ile Lys Gln Ile Gly Val
            100                 105                 110

Ile Gly Trp Gly Ser Gln Gly Pro Ala Gln Ala Gln Asn Leu Arg Asp
        115                 120                 125

Ser Leu Ala Glu Ala Lys Ser Asp Ile Val Val Lys Ile Gly Leu Arg
    130                 135                 140

Lys Gly Ser Lys Ser Phe Asp Glu Ala Arg Ala Ala Gly Phe Thr Glu
145                 150                 155                 160

Glu Ser Gly Thr Leu Gly Asp Ile Trp Glu Thr Val Ser Gly Ser Asp
                165                 170                 175

Leu Val Leu Leu Leu Ile Ser Asp Ala Ala Gln Ala Asp Asn Tyr Glu
            180                 185                 190

Lys Ile Phe Ser His Met Lys Pro Asn Ser Ile Leu Gly Leu Ser His
        195                 200                 205

Gly Phe Leu Leu Gly His Leu Gln Ser Ala Gly Leu Asp Phe Pro Lys
    210                 215                 220

Asn Ile Ser Val Ile Ala Val Cys Pro Lys Gly Met Gly Pro Ser Val
```

-continued

```
225                 230                 235                 240

Arg Arg Leu Tyr Val Gln Gly Lys Glu Ile Asn Gly Ala Gly Ile Asn
                245                 250                 255

Ser Ser Phe Ala Val His Gln Asp Val Asp Gly Arg Ala Thr Asp Val
            260                 265                 270

Ala Leu Gly Trp Ser Val Ala Leu Gly Ser Pro Phe Thr Phe Ala Thr
        275                 280                 285

Thr Leu Glu Gln Glu Tyr Lys Ser Asp Ile Phe Gly Glu Arg Gly Ile
    290                 295                 300

Leu Leu Gly Ala Val His Gly Ile Val Glu Ala Leu Phe Arg Arg Tyr
305                 310                 315                 320

Thr Glu Gln Gly Met Asp Glu Glu Met Ala Tyr Lys Asn Thr Val Glu
                325                 330                 335

Gly Ile Thr Gly Ile Ile Ser Lys Thr Ile Ser Lys Lys Gly Met Leu
            340                 345                 350

Glu Val Tyr Asn Ser Leu Thr Glu Glu Gly Lys Lys Glu Phe Asn Lys
        355                 360                 365

Ala Tyr Ser Ala Ser Phe Tyr Pro Cys Met Asp Ile Leu Tyr Glu Cys
    370                 375                 380

Tyr Glu Asp Val Ala Ser Gly Ser Glu Ile Arg Ser Val Val Leu Ala
385                 390                 395                 400

Gly Arg Arg Phe Tyr Glu Lys Glu Gly Leu Pro Ala Phe Pro Met Gly
                405                 410                 415

Asn Ile Asp Gln Thr Arg Met Trp Lys Val Gly Glu Lys Val Arg Ser
            420                 425                 430

Thr Arg Pro Glu Asn Asp Leu Gly Pro Leu His Pro Phe Thr Ala Gly
        435                 440                 445

Val Tyr Val Ala Leu Met Met Ala Gln Ile Glu Val Leu Arg Lys Lys
    450                 455                 460

Gly His Ser Tyr Ser Glu Ile Ile Asn Glu Ser Val Ile Glu Ser Val
465                 470                 475                 480

Asp Ser Leu Asn Pro Phe Met His Ala Arg Gly Val Ala Phe Met Val
                485                 490                 495

Asp Asn Cys Ser Thr Thr Ala Arg Leu Gly Ser Arg Lys Trp Ala Pro
            500                 505                 510

Arg Phe Asp Tyr Ile Leu Thr Gln Gln Ala Phe Val Thr Val Asp Lys
        515                 520                 525

Asp Ala Pro Ile Asn Gln Asp Leu Ile Ser Asn Phe Met Ser Asp Pro
    530                 535                 540

Val His Gly Ala Ile Glu Val Cys Ala Glu Leu Arg Pro Thr Val Asp
545                 550                 555                 560

Ile Ser Val Pro Ala Asn Ala Asp Phe Val Arg Pro Glu Leu Arg Gln
                565                 570                 575

Ser Ser


<210> SEQ ID NO 77
<211> LENGTH: 555
<212> TYPE: PRT
<213> ORGANISM: Chlamydomonas reinhardtii

<400> SEQUENCE: 77

Met Gln Leu Leu Asn Ser Lys Ser Arg Val Leu Ser Gly Ser Arg Gln
1               5                   10                  15

Gln Ala Ala Ala Lys Ala Val Arg Val Ala Pro Ser Gly Arg Arg Ser
            20                  25                  30
```

```
Ala Val Arg Val Ser Ala Ala Val His Leu Asp Phe Asn Thr Lys Val
        35                  40                  45

Phe Gln Lys Glu His Ala Lys Phe Gly Pro Thr Glu Glu Tyr Ile Val
    50                  55                  60

Arg Gly Gly Arg Asp Lys Tyr Pro Leu Leu Lys Glu Ala Phe Lys Gly
65                  70                  75                  80

Ile Lys Lys Val Ser Val Ile Gly Trp Gly Ser Gln Ala Pro Ala Gln
                85                  90                  95

Ala Gln Asn Leu Arg Asp Ser Ile Ala Glu Ala Gly Met Asp Ile Lys
            100                 105                 110

Val Ala Ile Gly Leu Arg Pro Asp Ser Pro Ser Trp Ala Glu Ala Glu
        115                 120                 125

Ala Cys Gly Phe Ser Lys Thr Asp Gly Thr Leu Gly Glu Val Phe Glu
    130                 135                 140

Gln Ile Ser Ser Ser Asp Phe Val Ile Leu Leu Ile Ser Asp Ala Ala
145                 150                 155                 160

Gln Ala Lys Leu Tyr Pro Arg Ile Leu Ala Ala Met Lys Pro Gly Ala
                165                 170                 175

Thr Leu Gly Leu Ser His Gly Phe Leu Leu Gly Val Met Arg Asn Asp
            180                 185                 190

Gly Val Asp Phe Arg Lys Asp Ile Asn Val Val Leu Val Ala Pro Lys
        195                 200                 205

Gly Met Gly Pro Ser Val Arg Arg Leu Tyr Glu Gln Gly Lys Ser Val
    210                 215                 220

Asn Gly Ala Gly Ile Asn Cys Ser Phe Ala Ile Gln Gln Asp Ala Thr
225                 230                 235                 240

Gly Gln Ala Ala Asp Ile Ala Ile Gly Trp Ala Ile Gly Val Gly Ala
                245                 250                 255

Pro Phe Ala Phe Pro Thr Thr Leu Glu Ser Glu Tyr Lys Ser Asp Ile
            260                 265                 270

Tyr Gly Glu Arg Cys Val Leu Leu Gly Ala Val His Gly Ile Val Glu
        275                 280                 285

Ala Leu Phe Arg Arg Tyr Thr Arg Gln Gly Met Ser Asp Glu Glu Ala
    290                 295                 300

Phe Lys Gln Ser Val Glu Ser Ile Thr Gly Pro Ile Ser Arg Thr Ile
305                 310                 315                 320

Ser Thr Lys Gly Met Leu Ser Val Tyr Asn Ser Phe Asn Glu Ala Asp
                325                 330                 335

Lys Lys Ile Phe Glu Gln Ala Tyr Ser Ala Ser Tyr Lys Pro Ala Leu
            340                 345                 350

Asp Ile Cys Phe Glu Ile Tyr Glu Asp Val Ala Ser Gly Asn Glu Ile
        355                 360                 365

Lys Ser Val Val Gln Ala Val Gln Arg Phe Asp Arg Phe Pro Met Gly
    370                 375                 380

Lys Ile Asp Gln Thr Tyr Met Trp Lys Val Gly Gln Lys Val Arg Ala
385                 390                 395                 400

Glu Arg Asp Glu Ser Lys Ile Pro Val Asn Pro Phe Thr Ala Gly Val
                405                 410                 415

Tyr Val Ala Val Met Met Ala Thr Val Glu Val Leu Arg Glu Lys Gly
            420                 425                 430

His Pro Phe Ser Glu Ile Cys Asn Glu Ser Ile Ile Glu Ala Val Asp
        435                 440                 445

Ser Leu Asn Pro Tyr Met His Ala Arg Gly Val Ala Phe Met Val Asp
```

450 455 460

Asn Cys Ser Tyr Thr Ala Arg Leu Gly Ser Arg Lys Trp Ala Pro Arg
465 470 475 480

Phe Asp Tyr Ile Ile Glu Gln Gln Ala Phe Val Asp Ile Asp Ser Gly
485 490 495

Lys Ala Ala Asp Lys Glu Val Met Ala Glu Phe Leu Ala His Pro Val
500 505 510

His Ser Ala Leu Ala Thr Cys Ser Ser Met Arg Pro Ser Val Asp Ile
515 520 525

Ser Val Gly Gly Glu Asn Ser Ser Val Gly Val Gly Ala Gly Ala Ala
530 535 540

Arg Thr Glu Phe Arg Ser Thr Ala Ala Lys Val
545 550 555

<210> SEQ ID NO 78
<211> LENGTH: 402
<212> TYPE: PRT
<213> ORGANISM: Neurospora crassa

<400> SEQUENCE: 78

Met Ala Ala Arg Asn Cys Thr Lys Ala Leu Arg Pro Leu Ala Arg Gln
1 5 10 15

Leu Ala Thr Pro Ala Val Gln Arg Arg Thr Phe Val Ala Ala Ala Ser
20 25 30

Ala Val Arg Ala Ser Val Ala Val Lys Ala Val Ala Ala Pro Ala Arg
35 40 45

Gln Gln Val Arg Gly Val Lys Thr Met Asp Phe Ala Gly His Lys Glu
50 55 60

Glu Val His Glu Arg Ala Asp Trp Pro Ala Glu Lys Leu Leu Asp Tyr
65 70 75 80

Phe Lys Asn Asp Thr Leu Ala Leu Ile Gly Tyr Gly Ser Gln Gly His
85 90 95

Gly Gln Gly Leu Asn Leu Arg Asp Asn Gly Leu Asn Val Ile Val Gly
100 105 110

Val Arg Lys Asn Gly Lys Ser Trp Glu Asp Ala Ile Gln Asp Gly Trp
115 120 125

Val Pro Gly Lys Asn Leu Phe Asp Val Asp Glu Ala Ile Ser Arg Gly
130 135 140

Thr Ile Val Met Asn Leu Leu Ser Asp Ala Ala Gln Ser Glu Thr Trp
145 150 155 160

Pro His Ile Lys Pro Gln Ile Thr Lys Gly Lys Thr Leu Tyr Phe Ser
165 170 175

His Gly Phe Ser Pro Val Phe Lys Asp Leu Thr Lys Val Glu Val Pro
180 185 190

Thr Asp Val Asp Val Ile Leu Val Ala Pro Lys Gly Ser Gly Arg Thr
195 200 205

Val Arg Ser Leu Phe Arg Glu Gly Arg Gly Ile Asn Ser Ser Phe Ala
210 215 220

Val Tyr Gln Asp Val Thr Gly Lys Ala Lys Glu Lys Ala Val Ala Leu
225 230 235 240

Gly Val Ala Val Gly Ser Gly Tyr Leu Tyr Glu Thr Thr Phe Glu Lys
245 250 255

Glu Val Tyr Ser Asp Leu Tyr Gly Glu Arg Gly Cys Leu Met Gly Gly
260 265 270

Ile His Gly Met Phe Leu Ala Gln Tyr Glu Val Leu Arg Glu Arg Gly

```
        275                 280                 285

His Ser Pro Ser Glu Ala Phe Asn Glu Thr Val Glu Glu Ala Thr Gln
    290                 295                 300

Ser Leu Tyr Pro Leu Ile Gly Ala His Gly Met Asp Trp Met Phe Asp
305                 310                 315                 320

Ala Cys Ser Thr Thr Ala Arg Arg Gly Ala Ile Asp Trp Thr Pro Lys
                325                 330                 335

Phe Lys Asp Ala Leu Lys Pro Val Phe Asn Asn Leu Tyr Asp Ser Val
            340                 345                 350

Lys Asn Gly Asp Glu Thr Lys Arg Ser Leu Glu Tyr Asn Ser Gln Pro
        355                 360                 365

Asp Tyr Arg Glu Arg Tyr Glu Ala Glu Leu Asp Glu Ile Arg Asn Leu
    370                 375                 380

Glu Ile Trp Arg Ala Gly Lys Ala Val Arg Ser Leu Arg Pro Glu Asn
385                 390                 395                 400

Gln Lys


<210> SEQ ID NO 79
<211> LENGTH: 404
<212> TYPE: PRT
<213> ORGANISM: Schizosaccharomyces pombe

<400> SEQUENCE: 79

Met Ser Phe Arg Asn Ser Ser Arg Met Ala Met Lys Ala Leu Arg Thr
1               5                   10                  15

Met Gly Ser Arg Arg Leu Ala Thr Arg Ser Met Ser Val Met Ala Arg
            20                  25                  30

Thr Ile Ala Ala Pro Ser Met Arg Phe Ala Pro Arg Met Thr Ala Pro
        35                  40                  45

Leu Met Gln Thr Arg Gly Met Arg Val Met Asp Phe Ala Gly Thr Lys
    50                  55                  60

Glu Asn Val Trp Glu Arg Ser Asp Trp Pro Arg Glu Lys Leu Val Asp
65                  70                  75                  80

Tyr Phe Lys Asn Asp Thr Leu Ala Ile Ile Gly Tyr Gly Ser Gln Gly
                85                  90                  95

His Gly Gln Gly Leu Asn Ala Arg Asp Gln Gly Leu Asn Val Ile Val
            100                 105                 110

Gly Val Arg Lys Asp Gly Ala Ser Trp Lys Gln Ala Ile Glu Asp Gly
        115                 120                 125

Trp Val Pro Gly Lys Thr Leu Phe Pro Val Glu Glu Ala Ile Lys Lys
    130                 135                 140

Gly Ser Ile Ile Met Asn Leu Leu Ser Asp Ala Ala Gln Thr Glu Thr
145                 150                 155                 160

Trp Pro Lys Ile Ala Pro Leu Ile Thr Lys Gly Lys Thr Leu Tyr Phe
                165                 170                 175

Ser His Gly Phe Ser Val Ile Phe Lys Asp Gln Thr Lys Ile His Pro
            180                 185                 190

Pro Lys Asp Val Asp Val Ile Leu Val Ala Pro Lys Gly Ser Gly Arg
        195                 200                 205

Thr Val Arg Thr Leu Phe Lys Glu Gly Arg Gly Ile Asn Ser Ser Phe
    210                 215                 220

Ala Val Tyr Gln Asp Val Thr Gly Lys Ala Gln Glu Lys Ala Ile Gly
225                 230                 235                 240

Leu Ala Val Ala Val Gly Ser Gly Phe Ile Tyr Gln Thr Thr Phe Lys
                245                 250                 255
```

```
Lys Glu Val Ile Ser Asp Leu Val Gly Glu Arg Gly Cys Leu Met Gly
            260                 265                 270

Gly Ile Asn Gly Leu Phe Leu Ala Gln Tyr Gln Val Leu Arg Glu Arg
        275                 280                 285

Gly His Ser Pro Ala Glu Ala Phe Asn Glu Thr Val Glu Glu Ala Thr
    290                 295                 300

Gln Ser Leu Tyr Pro Leu Ile Gly Lys Tyr Gly Leu Asp Tyr Met Phe
305                 310                 315                 320

Ala Ala Cys Ser Thr Thr Ala Arg Arg Gly Ala Ile Asp Trp Thr Pro
                325                 330                 335

Arg Phe Leu Glu Ala Asn Lys Lys Val Leu Asn Glu Leu Tyr Asp Asn
            340                 345                 350

Val Glu Asn Gly Asn Glu Ala Lys Arg Ser Leu Glu Tyr Asn Ser Ala
        355                 360                 365

Pro Asn Tyr Arg Glu Leu Tyr Asp Lys Glu Leu Glu Glu Ile Arg Asn
    370                 375                 380

Leu Glu Ile Trp Lys Ala Gly Glu Val Val Arg Ser Leu Arg Pro Glu
385                 390                 395                 400

His Asn Lys His


<210> SEQ ID NO 80
<211> LENGTH: 415
<212> TYPE: PRT
<213> ORGANISM: Laccaria bicolor

<400> SEQUENCE: 80

Met Ala Ser Leu Ala Arg Ser Ala Ser Gln Ser Leu Arg Ala Ser Ala
1               5                   10                  15

Arg Arg Ala Pro Arg Ser Leu Ala Lys Ser Ala Val Arg Pro Thr Gln
            20                  25                  30

Ala Ala Ser Tyr Ser Leu Phe Ala Arg Ala Ala Ala Ala Lys Val Ala
        35                  40                  45

Gln Thr Ser Thr Ala Lys Gly Val Arg Gly Val Lys Thr Leu Asp Phe
    50                  55                  60

Ala Gly Thr Lys Glu Val Val Tyr Glu Arg Ser Asp Trp Pro Leu Ala
65                  70                  75                  80

Lys Leu Gln Asp Tyr Phe Lys Asn Asp Thr Leu Ala Leu Ile Gly Tyr
                85                  90                  95

Gly Ser Gln Gly His Gly Gln Gly Leu Asn Ala Arg Asp Asn Gly Leu
            100                 105                 110

Asn Val Ile Val Gly Val Arg Lys Asp Gly Glu Ser Trp Arg Gln Ala
        115                 120                 125

Leu Glu Asp Gly Trp Glu Ser Phe Ser Pro Val Pro Gly Glu Thr Leu
    130                 135                 140

Phe Pro Ile Glu Glu Ala Ile Asn Lys Gly Thr Ile Ile Met Asn Leu
145                 150                 155                 160

Leu Ser Asp Ala Ala Gln Ser Gln Thr Trp Pro Gln Leu Ala Pro Leu
                165                 170                 175

Ile Thr Lys Gly Lys Thr Leu Tyr Phe Ser His Gly Phe Ser Val Val
            180                 185                 190

Tyr Lys Asp Asp Thr His Val Ile Pro Pro Lys Asp Val Asp Val Ile
        195                 200                 205

Leu Val Ala Pro Lys Gly Ser Gly Arg Thr Val Arg Thr Leu Phe Lys
    210                 215                 220
```

-continued

Glu Gly Arg Gly Ile Asn Ser Ser Ile Ala Val Trp Gln Asp Val Thr
225 230 235 240

Gly Lys Ala Lys Glu Lys Ala Ile Ala Leu Gly Val Gly Ile Gly Ser
245 250 255

Gly Tyr Met Tyr Glu Thr Thr Phe Glu Lys Glu Val Tyr Ser Asp Leu
260 265 270

Tyr Gly Glu Arg Gly Val Leu Met Gly Gly Ile Gln Gly Leu Phe Leu
275 280 285

Ala Gln Tyr Gln Val Leu Arg Lys Asn Gly His Ser Pro Ser Glu Ala
290 295 300

Phe Asn Glu Thr Val Glu Glu Ala Thr Gln Ser Leu Tyr Pro Leu Ile
305 310 315 320

Gly Gln Lys Gly Met Asp Tyr Met Tyr Asn Ala Cys Ser Thr Thr Ala
325 330 335

Arg Arg Gly Ala Leu Asp Trp Ala Pro Ile Phe Glu Lys Ala Asn Val
340 345 350

Pro Val Phe Glu Ala Leu Tyr Glu Ser Val Arg Asn Gly Thr Glu Thr
355 360 365

Arg Lys Ser Leu Glu Phe Asn Gly Arg Ala Thr Tyr Arg Glu Asp Leu
370 375 380

Ala Lys Glu Leu Ala Val Ile Asp Asn Gln Glu Ile Trp Arg Ala Gly
385 390 395 400

Lys Thr Val Arg Ser Leu Arg Pro Asp Tyr Lys Pro Glu Ser Glu
405 410 415

<210> SEQ ID NO 81
<211> LENGTH: 343
<212> TYPE: PRT
<213> ORGANISM: Ignicoccus hospitalis

<400> SEQUENCE: 81

Met Gly Leu Asn Ala Gly Ala Leu Arg Arg Val Gly Val Thr Val Ala
1 5 10 15

Gln Ile Trp Lys Asp Ser Asp Val Ser Leu Glu Pro Leu Lys Gly Arg
20 25 30

Lys Val Ala Ile Ile Gly Tyr Gly Ser Gln Gly Arg Ala Trp Ala Leu
35 40 45

Asn Ile Arg Asp Ser Gly Val Asp Val Val Val Gly Leu Arg Pro Gly
50 55 60

Gly Lys Ser Trp Glu Leu Ala Thr Lys Asp Gly Phe Glu Pro Lys Pro
65 70 75 80

Ile Pro Glu Ala Ala Lys Glu Gly Asp Val Ile Ala Met Leu Ile Pro
85 90 95

Asp Met Ala Gln Pro Glu Ile Tyr Glu Lys Tyr Val Glu Pro Asn Leu
100 105 110

His Glu Gly Asn Ala Leu Val Phe Ala His Gly Phe Asn Ile His Tyr
115 120 125

Gly Leu Ile Lys Pro Pro Lys Asn Val Asp Val Ile Met Val Ala Pro
130 135 140

Lys Ser Pro Gly Pro Lys Val Arg Glu Ala Phe Leu Ser Gly Arg Gly
145 150 155 160

Val Pro Ala Leu Val Ala Val His Gln Asp Tyr Thr Gly Lys Ala Trp
165 170 175

Asp Leu Val Leu Ala Leu Ala Lys Ala Leu Gly Cys Thr Arg Ala Gly
180 185 190

```
Val Ile Lys Thr Thr Phe Lys Glu Glu Thr Glu Ser Asp Leu Ile Gly
        195                 200                 205

Glu Gln Thr Val Leu Val Gly Gly Leu Met Glu Leu Leu Lys Lys Gly
    210                 215                 220

Phe Glu Asn Leu Val Glu Leu Gly Tyr Gln Pro Glu Val Ala Tyr Phe
225                 230                 235                 240

Glu Ala Ile Asn Glu Ala Lys Leu Ile Met Asp Leu Ile Trp Gln Tyr
                245                 250                 255

Gly Phe Tyr Gly Met Leu Leu Arg Val Ser Asp Thr Ala Lys Tyr Gly
            260                 265                 270

Gly Leu Thr Val Gly Pro Lys Val Ile Asp Glu His Val Lys Glu Asn
        275                 280                 285

Met Lys Lys Ala Ser Glu Arg Val Ile Ser Gly Glu Phe Ala Lys Glu
    290                 295                 300

Trp Val Glu Glu Tyr Lys Lys Gly Met Pro Thr Leu Lys Glu Leu Met
305                 310                 315                 320

Glu Lys Val Lys Glu His Gln Ala Glu Lys Val Gly Lys Glu Leu Arg
                325                 330                 335

Lys Leu Met Gly Leu Glu Glu
            340
```

<210> SEQ ID NO 82
<211> LENGTH: 329
<212> TYPE: PRT
<213> ORGANISM: Picrophilus torridus

<400> SEQUENCE: 82

```
Met Glu Lys Val Tyr Thr Glu Asn Asp Leu Lys Glu Asn Leu Met Arg
1               5                   10                  15

Asn Lys Lys Ile Ala Val Leu Gly Tyr Gly Ser Gln Gly Arg Ala Trp
            20                  25                  30

Ala Leu Asn Met Arg Asp Ser Gly Leu Asn Val Thr Val Gly Leu Glu
        35                  40                  45

Arg Gln Gly Lys Ser Trp Glu Lys Ala Val Ala Asp Gly Phe Lys Pro
    50                  55                  60

Leu Lys Ser Arg Asp Ala Val Arg Asp Ala Asp Ala Val Ile Phe Leu
65                  70                  75                  80

Val Pro Asp Met Ala Gln Arg Glu Leu Tyr Lys Asn Ile Met Asn Asp
                85                  90                  95

Ile Lys Asp Asp Ala Asp Ile Val Phe Ala His Gly Phe Asn Val His
            100                 105                 110

Tyr Gly Leu Ile Asn Pro Lys Asn His Asp Val Tyr Met Val Ala Pro
        115                 120                 125

Lys Ala Pro Gly Pro Ser Val Arg Glu Phe Tyr Glu Arg Gly Gly Gly
    130                 135                 140

Val Pro Val Leu Ile Ala Val Ala Asn Asp Val Ser Gly Arg Ser Lys
145                 150                 155                 160

Glu Lys Ala Leu Ser Ile Ala Tyr Ser Leu Gly Ala Leu Arg Ala Gly
                165                 170                 175

Ala Ile Glu Thr Thr Phe Lys Glu Glu Thr Glu Thr Asp Leu Ile Gly
            180                 185                 190

Glu Gln Leu Asp Leu Val Gly Gly Ile Thr Glu Leu Leu Arg Ser Thr
        195                 200                 205

Phe Asn Ile Met Val Glu Met Gly Tyr Lys Pro Glu Met Ala Tyr Phe
    210                 215                 220
```

```
Glu Ala Ile Asn Glu Met Lys Leu Ile Val Asp Gln Val Phe Glu Lys
225                 230                 235                 240

Gly Ile Ser Gly Met Leu Arg Ala Val Ser Asp Thr Ala Lys Tyr Gly
                245                 250                 255

Gly Leu Thr Thr Gly Lys Tyr Ile Ile Asn Asp Asp Val Arg Lys Arg
            260                 265                 270

Met Arg Glu Arg Ala Glu Tyr Ile Val Ser Gly Lys Phe Ala Glu Glu
        275                 280                 285

Trp Ile Glu Glu Tyr Gly Glu Gly Ser Lys Asn Leu Glu Ser Met Met
    290                 295                 300

Leu Asp Ile Asp Asn Ser Leu Glu Glu Gln Val Gly Lys Gln Leu Arg
305                 310                 315                 320

Glu Ile Val Leu Arg Gly Arg Pro Lys
                325


<210> SEQ ID NO 83
<211> LENGTH: 339
<212> TYPE: PRT
<213> ORGANISM: Acidiphilium cryptum

<400> SEQUENCE: 83

Met Arg Val Tyr Tyr Asp Ser Asp Ala Asp Val Asn Leu Ile Lys Ala
1               5                   10                  15

Lys Lys Val Ala Val Val Gly Tyr Gly Ser Gln Gly His Ala His Ala
            20                  25                  30

Leu Asn Leu Lys Glu Ser Gly Val Lys Glu Leu Val Val Ala Leu Arg
        35                  40                  45

Lys Gly Ser Ala Ala Val Ala Lys Ala Glu Ala Ala Gly Leu Arg Val
    50                  55                  60

Met Thr Pro Glu Glu Ala Ala Ala Trp Ala Asp Val Val Met Ile Leu
65                  70                  75                  80

Thr Pro Asp Glu Gly Gln Gly Asp Leu Tyr Arg Asp Ser Leu Ala Ala
                85                  90                  95

Asn Leu Lys Pro Gly Ala Ala Ile Ala Phe Ala His Gly Leu Asn Ile
            100                 105                 110

His Phe Asn Leu Ile Glu Pro Arg Ala Asp Ile Asp Val Phe Met Ile
        115                 120                 125

Ala Pro Lys Gly Pro Gly His Thr Val Arg Ser Glu Tyr Gln Arg Gly
    130                 135                 140

Gly Gly Val Pro Cys Leu Val Ala Val Ala Gln Asn Pro Ser Gly Asn
145                 150                 155                 160

Ala Leu Asp Ile Ala Leu Ser Tyr Ala Ser Ala Ile Gly Gly Gly Arg
                165                 170                 175

Ala Gly Ile Ile Glu Thr Thr Phe Lys Glu Glu Cys Glu Thr Asp Leu
            180                 185                 190

Phe Gly Glu Gln Thr Val Leu Cys Gly Gly Leu Val Glu Leu Ile Lys
        195                 200                 205

Ala Gly Phe Glu Thr Leu Val Glu Ala Gly Tyr Ala Pro Glu Met Ala
    210                 215                 220

Tyr Phe Glu Cys Leu His Glu Val Lys Leu Ile Val Asp Leu Ile Tyr
225                 230                 235                 240

Glu Gly Gly Ile Ala Asn Met Asn Tyr Ser Ile Ser Asn Thr Ala Glu
                245                 250                 255

Tyr Gly Glu Tyr Val Thr Gly Pro Arg Met Ile Thr Pro Glu Thr Lys
            260                 265                 270
```

Ala Glu Met Lys Arg Val Leu Asp Asp Ile Gln Lys Gly Arg Phe Thr
275 280 285

Arg Asp Trp Met Leu Glu Asn Lys Val Asn Gln Thr Asn Phe Lys Ala
290 295 300

Met Arg Arg Ala Asn Ala Ala His Pro Ile Glu Glu Val Gly Glu Lys
305 310 315 320

Leu Arg Ala Met Met Pro Trp Ile Lys Lys Gly Ala Leu Val Asp Lys
325 330 335

Thr Arg Asn

<210> SEQ ID NO 84
<211> LENGTH: 330
<212> TYPE: PRT
<213> ORGANISM: Cyanobacteria/Synechococcus sp.

<400> SEQUENCE: 84

Met Ala Arg Leu Tyr Tyr Asp Thr Asp Ala Asn Leu Asp Leu Leu Asp
1 5 10 15

Gly Lys Thr Val Ala Ile Ile Gly Tyr Gly Ser Gln Gly His Ala His
20 25 30

Ala Leu Asn Leu Arg Asp Ser Gly Val Asn Val Leu Val Gly Leu Tyr
35 40 45

Pro Gly Ser Pro Ser Trp Pro Lys Ala Glu Arg Asp Gly Leu Thr Val
50 55 60

Lys Thr Val Ala Asp Ala Ala Ala Ala Ala Asp Trp Val Met Ile Leu
65 70 75 80

Leu Pro Asp Glu Val Gln Lys Thr Val Phe Gln Ser Glu Ile Arg Pro
85 90 95

His Leu Lys Pro Gly Lys Val Leu Leu Phe Ala His Gly Phe Asn Ile
100 105 110

His Phe Gly Gln Ile Gln Pro Pro Pro Asp Ile Asp Val Ile Met Val
115 120 125

Ala Pro Lys Gly Pro Gly His Leu Val Arg Arg Thr Tyr Leu Glu Gly
130 135 140

Gln Gly Val Pro Cys Leu Phe Ala Val Tyr Gln Asp Ala Ser Gly Met
145 150 155 160

Ala Arg Glu Arg Ala Met Ala Tyr Ala Lys Ala Ile Gly Gly Thr Arg
165 170 175

Ala Gly Ile Leu Glu Thr Ser Phe Arg Glu Glu Thr Glu Thr Asp Leu
180 185 190

Phe Gly Glu Gln Val Val Leu Cys Gly Gly Leu Thr Ala Leu Ile Lys
195 200 205

Ala Gly Phe Glu Thr Leu Val Glu Ala Gly Tyr Gln Pro Glu Leu Ala
210 215 220

Tyr Phe Glu Cys Leu His Glu Val Lys Leu Ile Val Asp Leu Ile Val
225 230 235 240

Glu Gly Gly Leu Glu Lys Met Arg His Ser Ile Ser Asn Thr Ala Glu
245 250 255

Tyr Gly Asp Tyr Thr Arg Gly Pro Arg Ile Ile Thr Glu Gln Thr Arg
260 265 270

Ala Glu Met Lys Arg Ile Leu Ser Glu Ile Gln Ser Gly Gln Phe Ala
275 280 285

Arg Glu Phe Val Leu Glu Asn Gln Ala Gly Lys Pro Val Leu Thr Ala
290 295 300

Met Arg Arg Arg Glu Ala Glu His Pro Ile Glu Lys Val Gly Lys Glu

```
305                 310                 315                 320

Leu Arg Ala Met Phe Ser Trp Leu Lys Lys
                325                 330


<210> SEQ ID NO 85
<211> LENGTH: 339
<212> TYPE: PRT
<213> ORGANISM: Zymomonas mobilis

<400> SEQUENCE: 85

Met Lys Val Tyr Tyr Asp Ser Asp Ala Asp Leu Gly Leu Ile Lys Ser
1               5                   10                  15

Lys Lys Ile Ala Ile Leu Gly Tyr Gly Ser Gln Gly His Ala His Ala
            20                  25                  30

Gln Asn Leu Arg Asp Ser Gly Val Ala Glu Val Ala Ile Ala Leu Arg
        35                  40                  45

Pro Asp Ser Ala Ser Val Lys Lys Ala Gln Asp Ala Gly Phe Lys Val
    50                  55                  60

Leu Thr Asn Ala Glu Ala Ala Lys Trp Ala Asp Ile Leu Met Ile Leu
65                  70                  75                  80

Ala Pro Asp Glu His Gln Ala Ala Ile Tyr Ala Glu Asp Leu Lys Asp
                85                  90                  95

Asn Leu Arg Pro Gly Ser Ala Ile Ala Phe Ala His Gly Leu Asn Ile
            100                 105                 110

His Phe Gly Leu Ile Glu Pro Arg Lys Asp Ile Asp Val Phe Met Ile
        115                 120                 125

Ala Pro Lys Gly Pro Gly His Thr Val Arg Ser Glu Tyr Val Arg Gly
    130                 135                 140

Gly Gly Val Pro Cys Leu Val Ala Val Asp Gln Asp Ala Ser Gly Asn
145                 150                 155                 160

Ala His Asp Ile Ala Leu Ala Tyr Ala Ser Gly Ile Gly Gly Gly Arg
                165                 170                 175

Ser Gly Val Ile Glu Thr Thr Phe Arg Glu Glu Val Glu Thr Asp Leu
            180                 185                 190

Phe Gly Glu Gln Ala Val Leu Cys Gly Gly Leu Thr Ala Leu Ile Thr
        195                 200                 205

Ala Gly Phe Glu Thr Leu Thr Glu Ala Gly Tyr Ala Pro Glu Met Ala
    210                 215                 220

Phe Phe Glu Cys Met His Glu Met Lys Leu Ile Val Asp Leu Ile Tyr
225                 230                 235                 240

Glu Ala Gly Ile Ala Asn Met Arg Tyr Ser Ile Ser Asn Thr Ala Glu
                245                 250                 255

Tyr Gly Asp Ile Val Ser Gly Pro Arg Val Ile Asn Glu Glu Ser Lys
            260                 265                 270

Lys Ala Met Lys Ala Ile Leu Asp Asp Ile Gln Ser Gly Arg Phe Val
        275                 280                 285

Ser Lys Phe Val Leu Asp Asn Arg Ala Gly Gln Pro Glu Leu Lys Ala
    290                 295                 300

Ala Arg Lys Arg Met Ala Ala His Pro Ile Glu Gln Val Gly Ala Arg
305                 310                 315                 320

Leu Arg Lys Met Met Pro Trp Ile Ala Ser Asn Lys Leu Val Asp Lys
                325                 330                 335

Ala Arg Asn


<210> SEQ ID NO 86
```

<211> LENGTH: 359
<212> TYPE: PRT
<213> ORGANISM: Bacteroides thetaiotaomicron

<400> SEQUENCE: 86

Met Ala Gln Val Ile Lys Thr Lys Lys Gln Lys Lys Met Ala Gln Leu
1 5 10 15

Asn Phe Gly Gly Thr Val Glu Asn Val Val Ile Arg Asp Glu Phe Pro
20 25 30

Leu Glu Lys Ala Arg Glu Val Leu Lys Asn Glu Thr Ile Ala Val Ile
35 40 45

Gly Tyr Gly Val Gln Gly Pro Gly Gln Ala Leu Asn Leu Arg Asp Asn
50 55 60

Gly Phe Asn Val Ile Val Gly Gln Arg Gln Gly Lys Thr Tyr Asp Lys
65 70 75 80

Ala Val Ala Asp Gly Trp Val Pro Gly Glu Thr Leu Phe Gly Ile Glu
85 90 95

Glu Ala Cys Glu Lys Gly Thr Ile Ile Met Cys Leu Leu Ser Asp Ala
100 105 110

Ala Val Met Ser Val Trp Pro Thr Ile Lys Pro Tyr Leu Thr Ala Gly
115 120 125

Lys Ala Leu Tyr Phe Ser His Gly Phe Ala Ile Thr Trp Ser Asp Arg
130 135 140

Thr Gly Val Val Pro Pro Ala Asp Ile Asp Val Ile Met Val Ala Pro
145 150 155 160

Lys Gly Ser Gly Thr Ser Leu Arg Thr Met Phe Leu Glu Gly Arg Gly
165 170 175

Leu Asn Ser Ser Tyr Ala Ile Tyr Gln Asp Ala Thr Gly Asn Ala Met
180 185 190

Asp Arg Thr Ile Ala Leu Gly Ile Gly Ile Gly Ser Gly Tyr Leu Phe
195 200 205

Glu Thr Thr Phe Ile Arg Glu Ala Thr Ser Asp Leu Thr Gly Glu Arg
210 215 220

Gly Ser Leu Met Gly Ala Ile Gln Gly Leu Leu Leu Ala Gln Tyr Glu
225 230 235 240

Val Leu Arg Glu Asn Gly His Thr Pro Ser Glu Ala Phe Asn Glu Thr
245 250 255

Val Glu Glu Leu Thr Gln Ser Leu Met Pro Leu Phe Ala Lys Asn Gly
260 265 270

Met Asp Trp Met Tyr Ala Asn Cys Ser Thr Thr Ala Gln Arg Gly Ala
275 280 285

Leu Asp Trp Met Gly Pro Phe His Asp Ala Ile Lys Pro Val Val Glu
290 295 300

Lys Leu Tyr His Ser Val Lys Thr Gly Asn Glu Ala Gln Ile Ser Ile
305 310 315 320

Asp Ser Asn Ser Lys Pro Asp Tyr Arg Glu Lys Leu Glu Glu Glu Leu
325 330 335

Lys Ala Leu Arg Glu Ser Glu Met Trp Gln Thr Ala Val Thr Val Arg
340 345 350

Lys Leu Arg Pro Glu Asn Asn
355

<210> SEQ ID NO 87
<211> LENGTH: 494
<212> TYPE: PRT
<213> ORGANISM: Vibrio fischeri

<400> SEQUENCE: 87

```
Met Ser Asn Tyr Phe Asn Thr Leu Asn Leu Arg Glu Gln Leu Asp Gln
1               5                   10                  15

Leu Gly Arg Cys Arg Phe Met Asp Arg Glu Glu Phe Ala Thr Glu Ala
            20                  25                  30

Asp Tyr Leu Lys Gly Lys Lys Val Val Ile Val Gly Cys Gly Ala Gln
        35                  40                  45

Gly Leu Asn Gln Gly Leu Asn Met Arg Asp Ser Gly Leu Asp Val Ala
    50                  55                  60

Tyr Ala Leu Arg Gln Ala Ala Ile Asp Glu Gln Arg Gln Ser Tyr Lys
65                  70                  75                  80

Asn Ala Lys Glu Asn Gly Phe Glu Val Ala Ser Tyr Glu Thr Leu Ile
                85                  90                  95

Pro Gln Ala Asp Leu Val Ile Asn Leu Thr Pro Asp Lys Gln His Thr
            100                 105                 110

Asn Val Val Glu Thr Val Met Pro Leu Met Lys Glu Gly Ala Ala Leu
        115                 120                 125

Gly Tyr Ser His Gly Phe Asn Val Val Glu Glu Gly Met Gln Ile Arg
    130                 135                 140

Lys Asp Leu Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Trp Asp Ile Ala Lys
            180                 185                 190

Ala Trp Ala Ala Gly Thr Gly Gly His Arg Ala Gly Cys Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Ile Val Ser Tyr Glu Lys Met
225                 230                 235                 240

Ile Ala Asp Gly Ile Glu Pro Gly Tyr Ala Gly Lys Leu Leu Gln Tyr
                245                 250                 255

Gly Trp Glu Thr Ile Thr Glu Ala Leu Lys Phe Gly Gly Val Thr His
            260                 265                 270

Met Met Asp Arg Leu Ser Asn Pro Ala Lys Val Lys Ala Phe Glu Leu
        275                 280                 285

Ser Glu Glu Leu Lys Glu Leu Met Arg Pro Leu Tyr Asn Lys His Met
    290                 295                 300

Asp Asp Ile Ile Ser Gly Glu Phe Ser Arg Thr Met Met Ala Asp Trp
305                 310                 315                 320

Ala Asn Asp Asp Val Asn Leu Phe Gly Trp Arg Glu Glu Thr Gly Gln
                325                 330                 335

Thr Ala Phe Glu Asn Tyr Pro Glu Ser Asp Val Glu Ile Ser Glu Gln
            340                 345                 350

Glu Tyr Phe Asp Asn Gly Ile Leu Leu Val Ala Met Val Arg Ala Gly
        355                 360                 365

Val Glu Leu Ala Phe Glu Ala Met Thr Ala Ser Gly Ile Ile Asp Glu
    370                 375                 380

Ser Ala Tyr Tyr Glu Ser Leu His Glu Leu Pro Leu Ile Ala Asn Thr
385                 390                 395                 400

Val Ala Arg Lys Arg Leu Tyr Glu Met Asn Val Val Ile Ser Asp Thr
                405                 410                 415
```

```
Ala Glu Tyr Gly Asn Tyr Leu Phe Ala Asn Val Ala Thr Pro Leu Leu
            420                 425                 430

Arg Glu Lys Phe Met Pro Ser Val Glu Thr Asp Val Ile Gly Arg Gly
        435                 440                 445

Leu Gly Glu Ala Ser Asn Gln Val Asp Asn Ala Thr Leu Ile Ala Val
    450                 455                 460

Asn Asp Ala Ile Arg Asn His Pro Val Glu Tyr Ile Gly Glu Glu Leu
465                 470                 475                 480

Arg Ser Tyr Met Ser Asp Met Lys Arg Ile Ala Val Gly Gly
                485                 490


<210> SEQ ID NO 88
<211> LENGTH: 492
<212> TYPE: PRT
<213> ORGANISM: Shewanella sp.

<400> SEQUENCE: 88

Met Ala Asn Tyr Phe Asn Ser Leu Asn Leu Arg Gln Gln Leu Glu Gln
1               5                   10                  15

Leu Gly Gln Cys Arg Phe Met Asp Arg Ser Glu Phe Ser Asp Gly Cys
            20                  25                  30

Asn Tyr Ile Lys Asp Trp Asn Ile Val Ile Leu Gly Cys Gly Ala Gln
        35                  40                  45

Gly Leu Asn Gln Gly Leu Asn Met Arg Asp Ser Gly Leu Asn Ile Ala
    50                  55                  60

Tyr Ala Leu Arg Pro Glu Ala Ile Ala Gln Lys Arg Ala Ser Trp Gln
65                  70                  75                  80

Lys Ala Thr Asp Asn Gly Phe Lys Val Gly Thr Phe Glu Glu Leu Ile
                85                  90                  95

Pro Thr Ala Asp Leu Val Leu Asn Leu Thr Pro Asp Lys Gln His Ser
            100                 105                 110

Asn Val Val Ser Ala Val Met Pro Leu Met Lys Gln Gly Ala Thr Leu
        115                 120                 125

Ser Tyr Ser His Gly Phe Asn Ile Val Glu Glu Gly Met Gln Ile Arg
    130                 135                 140

Pro Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Asn Gly Asp Gly Leu Glu Ile Ala Lys
            180                 185                 190

Ala Tyr Ala Ser Ala Thr Gly Gly Asp Arg Ala Gly Val Leu Gln Ser
        195                 200                 205

Ser Phe Ile Ala Glu Val Lys Ser Asp Leu Met Gly Glu Gln Thr Ile
    210                 215                 220

Leu Cys Gly Met Leu Gln Thr Gly Ala Ile Leu Gly Tyr Asp Lys Met
225                 230                 235                 240

Val Ala Asp Gly Val Glu Pro Gly Tyr Ala Ala Lys Leu Ile Gln Gln
                245                 250                 255

Gly Trp Glu Thr Val Thr Glu Ala Leu Lys His Gly Gly Ile Thr Asn
            260                 265                 270

Met Met Asp Arg Leu Ser Asn Pro Ala Lys Ile Lys Ala Phe Glu Ile
        275                 280                 285

Ala Glu Asp Leu Lys Glu Ile Leu Gln Pro Leu Phe Glu Lys His Met
    290                 295                 300
```

Asp Asp Ile Ile Ser Gly Glu Phe Ser Arg Thr Met Met Gln Asp Trp
305 310 315 320

Ala Asn Asp Asp Ala Asn Leu Leu Arg Trp Arg Ala Glu Thr Ala Glu
325 330 335

Thr Gly Phe Glu Asn Ala Pro Val Ser Ser Glu His Ile Asp Glu Gln
340 345 350

Thr Tyr Phe Asp Lys Gly Ile Phe Leu Val Ala Met Ile Lys Ala Gly
355 360 365

Val Glu Leu Ala Phe Asp Thr Met Val Ser Ala Gly Ile Val Glu Glu
370 375 380

Ser Ala Tyr Tyr Glu Ser Leu His Glu Thr Pro Leu Ile Ala Asn Thr
385 390 395 400

Ile Ala Arg Lys Arg Leu Tyr Glu Met Asn Val Val Ile Ser Asp Thr
405 410 415

Ala Glu Tyr Gly Cys Tyr Leu Phe Asn His Ala Ala Val Pro Met Leu
420 425 430

Arg Asp Tyr Val Asn Ala Met Ser Pro Glu Tyr Leu Gly Ala Gly Leu
435 440 445

Lys Asp Ser Ser Asn Asn Val Asp Asn Leu Gln Leu Ile Ala Ile Asn
450 455 460

Asp Ala Ile Arg His Thr Ser Val Glu Tyr Ile Gly Ala Glu Leu Arg
465 470 475 480

Gly Tyr Met Thr Asp Met Lys Ser Ile Val Gly Ala
485 490

<210> SEQ ID NO 89
<211> LENGTH: 491
<212> TYPE: PRT
<213> ORGANISM: Gramella forsetti

<400> SEQUENCE: 89

Met Thr Asn Tyr Phe Asn Ser Leu Ser Leu Arg Asp Gln Leu Ala Gln
1 5 10 15

Leu Gly Thr Cys Arg Phe Met Glu Leu Asp Glu Phe Ser Asn Glu Val
20 25 30

Ala Val Leu Lys Asp Lys Lys Ile Val Ile Val Gly Cys Gly Ala Gln
35 40 45

Gly Leu Asn Gln Gly Leu Asn Met Arg Asp Ser Gly Leu Asp Ile Ser
50 55 60

Tyr Ala Leu Arg Glu Gly Ala Ile Lys Glu Lys Arg Gln Ser Trp Lys
65 70 75 80

Asn Ala Thr Glu Asn Asn Phe Asn Val Gly Thr Tyr Glu Glu Leu Ile
85 90 95

Pro Lys Ala Asp Leu Val Ile Asn Leu Thr Pro Asp Lys Gln His Thr
100 105 110

Ser Val Ile Lys Ala Ile Gln Pro His Ile Lys Lys Asp Ala Val Leu
115 120 125

Ser Tyr Ser His Gly Phe Asn Ile Val Glu Glu Gly Thr Lys Ile Arg
130 135 140

Glu Asp Ile Thr Val Ile Met Val Ala Pro Lys Cys Pro Gly Thr Glu
145 150 155 160

Val Arg Glu Glu Tyr Lys Arg Gly Phe Gly Val Pro Thr Leu Ile Ala
165 170 175

Val His Pro Glu Asn Asp Pro His Gly Ile Gly Leu Asp Trp Ala Lys
180 185 190

```
Ala Tyr Ala Tyr Ala Thr Gly Gly His Arg Ala Gly Val Leu Glu Ser
        195                 200                 205

Ser Phe Val Ala Glu Val Lys Ser Asp Leu Met Gly Glu Gln Thr Met
    210                 215                 220

Leu Cys Gly Val Leu Gln Thr Gly Ser Ile Leu Thr Phe Asp Lys Met
225                 230                 235                 240

Val Ala Asp Gly Val Glu Pro Asn Tyr Ala Ala Lys Leu Ile Gln Tyr
                245                 250                 255

Gly Trp Glu Thr Ile Thr Glu Ala Leu Lys His Gly Gly Ile Thr Asn
            260                 265                 270

Met Met Asp Arg Leu Ser Asn Pro Ala Lys Leu Arg Ala Asn Glu Ile
        275                 280                 285

Ala Glu Glu Leu Lys Glu Lys Met Arg Pro Leu Phe Gln Lys His Met
    290                 295                 300

Asp Asp Ile Ile Ser Gly Glu Phe Ser Ser Arg Met Met Arg Asp Trp
305                 310                 315                 320

Ala Asn Asp Asp Lys Glu Leu Leu Thr Trp Arg Ala Glu Thr Glu Asn
                325                 330                 335

Thr Ala Phe Glu Lys Thr Glu Ala Thr Ser Glu Glu Ile Lys Glu Gln
            340                 345                 350

Glu Tyr Phe Asp Lys Gly Val Leu Met Val Ala Phe Val Arg Ala Gly
        355                 360                 365

Val Glu Leu Ala Phe Glu Thr Met Val Glu Ala Gly Ile Ile Glu Glu
    370                 375                 380

Ser Ala Tyr Tyr Glu Ser Leu His Glu Thr Pro Leu Ile Ala Asn Thr
385                 390                 395                 400

Ile Ala Arg Lys Lys Leu Tyr Glu Met Asn Arg Val Ile Ser Asp Thr
                405                 410                 415

Ala Glu Tyr Gly Cys Tyr Leu Phe Asp His Ala Ala Lys Pro Leu Val
            420                 425                 430

Lys Asp Tyr Val Asn Ser Leu Glu Pro Glu Val Ala Gly Lys Lys Phe
        435                 440                 445

Gly Thr Asp Cys Asn Gly Val Asp Asn Gln Lys Leu Ile His Val Asn
    450                 455                 460

Asp Asp Leu Arg Ser His Pro Val Glu Lys Val Gly Ala Arg Leu Arg
465                 470                 475                 480

Thr Ala Met Thr Ala Met Lys Lys Ile Tyr Ala
                485                 490


<210> SEQ ID NO 90
<211> LENGTH: 493
<212> TYPE: PRT
<213> ORGANISM: Psychromonas ingrhamaii

<400> SEQUENCE: 90

Met Ala Asn Tyr Phe Asn Thr Leu Ser Leu Arg Glu Lys Leu Asn Gln
1               5                   10                  15

Leu Gly Gln Cys Arg Phe Met Asp Arg Ser Glu Phe Thr Asp Gly Cys
            20                  25                  30

Asp Ala Leu Lys Gly Lys Lys Val Val Ile Ile Gly Cys Gly Ala Gln
        35                  40                  45

Gly Leu Asn Gln Gly Leu Asn Met Arg Asp Ser Gly Leu Asp Val Ser
    50                  55                  60

Tyr Thr Leu Arg Ala Gln Ala Ile Ala Glu Lys Arg Gln Ser Trp Lys
65                  70                  75                  80
```

```
Asn Ala Thr Glu Asn Gly Phe Val Val Gly Thr Tyr Glu Glu Leu Ile
                85                  90                  95

Pro Glu Ala Asp Leu Leu Cys Asn Leu Thr Pro Asp Lys Gln His Thr
            100                 105                 110

Ala Val Val Gly Ala Val Met Pro Leu Met Lys Glu Gly Ala Thr Leu
        115                 120                 125

Ser Tyr Ser His Gly Phe Asn Ile Val Glu Glu Gly Met Gln Val Arg
    130                 135                 140

Glu Asp Leu Thr Val Ile Met Cys Ala Pro Lys Cys Pro Gly Ser Glu
145                 150                 155                 160

Val Arg Glu Glu Tyr Lys Arg Gly Phe Gly Val Pro Thr Leu Ile Ala
                165                 170                 175

Val His Pro Ala Asn Asp Pro Gln Gly Gln Gly Leu Val Trp Ala Lys
            180                 185                 190

Ala Tyr Ala Ser Ala Thr Gly Gly Asp Arg Ala Gly Val Leu Met Ser
        195                 200                 205

Ser Phe Val Ala Glu Val Lys Ser Asp Leu Met Gly Glu Gln Thr Ile
    210                 215                 220

Leu Cys Gly Met Leu Gln Thr Gly Ala Ile Ile Gly Tyr Glu Lys Met
225                 230                 235                 240

Val Ala Asp Gly Ile Glu Pro Gly Tyr Ala Ser Lys Leu Ile Gln Tyr
                245                 250                 255

Gly Trp Glu Thr Val Thr Glu Gly Met Lys Tyr Gly Gly Ile Thr Asn
            260                 265                 270

Met Met Asp Arg Leu Ser Asn Pro Ala Lys Ile Lys Ala Phe Asp Met
        275                 280                 285

Ser Leu Glu Leu Lys Glu Ile Leu Arg Pro Leu Phe Asn Lys His Met
    290                 295                 300

Asp Asp Ile Ile Glu Gly Glu Phe Ser Arg Thr Met Met Glu Asp Trp
305                 310                 315                 320

Ala Asn Asp Asp Lys Asn Leu Leu Gln Trp Arg Ala Glu Thr Ala Glu
                325                 330                 335

Thr Gly Phe Glu Lys Gln Pro Ala Gly Asp Met Lys Ile Asp Glu Gln
            340                 345                 350

Glu Phe Tyr Asp Asn Gly Ile Phe Leu Ile Ala Met Ile Lys Ala Gly
        355                 360                 365

Val Glu Leu Ala Phe Asp Ala Met Thr Ala Ser Gly Ile Ile Ala Asp
    370                 375                 380

Ser Ala Tyr Tyr Glu Ser Leu His Glu Thr Pro Leu Ile Ala Asn Thr
385                 390                 395                 400

Ile Ala Arg Lys Lys Leu Tyr Glu Met Asn Val Val Ile Ser Asp Thr
                405                 410                 415

Ala Glu Tyr Gly Cys Tyr Leu Phe Asp His Ala Ala Lys Pro Leu Leu
            420                 425                 430

Ala Asp Phe Val Lys Ala Leu Asp Pro Glu Met Leu Gly Lys Pro Leu
        435                 440                 445

Thr Val Lys Asn Asn Ala Val Asp Asn Ala Arg Leu Ile Glu Val Asn
    450                 455                 460

Glu Ala Ile Arg Ser His Pro Val Glu Ile Val Gly Lys Lys Leu Arg
465                 470                 475                 480

Gly Tyr Met Thr Glu Met Lys Thr Ile Ile Thr Ala Ser
                485                 490
```

<210> SEQ ID NO 91
<211> LENGTH: 492
<212> TYPE: PRT
<213> ORGANISM: Cytophaga hutchinsonii

<400> SEQUENCE: 91

```
Met Ala Asn Tyr Phe Asn Thr Leu Ser Leu Arg Glu Lys Leu Asp Gln
1               5                   10                  15

Leu Gly Val Cys Glu Phe Met Asp Arg Ser Glu Phe Ser Asp Gly Val
            20                  25                  30

Ala Ala Leu Lys Gly Lys Lys Ile Val Ile Val Gly Cys Gly Ala Gln
        35                  40                  45

Gly Leu Asn Gln Gly Leu Asn Leu Arg Asp Ser Gly Leu Asp Val Ser
    50                  55                  60

Tyr Thr Leu Arg Lys Glu Ala Ile Asp Ser Lys Arg Gln Ser Phe Leu
65                  70                  75                  80

Asn Ala Ser Glu Asn Gly Phe Lys Val Gly Thr Tyr Glu Glu Leu Ile
                85                  90                  95

Pro Thr Ala Asp Leu Val Ile Asn Leu Thr Pro Asp Lys Gln His Thr
            100                 105                 110

Ala Val Val Ser Ala Val Met Pro Leu Met Lys Lys Gly Ser Thr Leu
        115                 120                 125

Ser Tyr Ser His Gly Phe Asn Ile Val Glu Glu Gly Met Gln Ile Arg
    130                 135                 140

Lys Asp Ile Thr Val Ile Met Val Ala Pro Lys Ser Pro Gly Ser Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Glu Gly Lys Gly Trp Asp Tyr Ala Lys
            180                 185                 190

Ala Tyr Cys Val Gly Thr Gly Gly Asp Arg Ala Gly Val Leu Lys Ser
        195                 200                 205

Ser Phe Val Ala Glu Val Lys Ser Asp Leu Met Gly Glu Gln Thr Ile
    210                 215                 220

Leu Cys Gly Leu Leu Gln Thr Gly Ser Ile Leu Cys Phe Asp Lys Met
225                 230                 235                 240

Val Glu Lys Gly Ile Asp Lys Gly Tyr Ala Ser Lys Leu Ile Gln Tyr
                245                 250                 255

Gly Trp Glu Val Ile Thr Glu Ser Leu Lys His Gly Gly Ile Ser Gly
            260                 265                 270

Met Met Asp Arg Leu Ser Asn Pro Ala Lys Ile Lys Ala Phe Gln Val
        275                 280                 285

Ser Glu Glu Leu Lys Asp Ile Met Arg Pro Leu Phe Arg Lys His Gln
    290                 295                 300

Asp Asp Ile Ile Ser Gly Glu Phe Ser Arg Ile Met Met Glu Asp Trp
305                 310                 315                 320

Ala Asn Gly Asp Lys Asn Leu Leu Thr Trp Arg Ala Ala Thr Gly Glu
                325                 330                 335

Thr Ala Phe Glu Lys Thr Pro Ala Gly Asp Val Lys Ile Ala Glu Gln
            340                 345                 350

Glu Tyr Tyr Asp Asn Gly Leu Leu Met Val Ala Met Val Arg Ala Gly
        355                 360                 365

Val Glu Leu Ala Phe Glu Thr Met Thr Glu Ser Gly Ile Ile Asp Glu
    370                 375                 380

Ser Ala Tyr Tyr Glu Ser Leu His Glu Thr Pro Leu Ile Ala Asn Thr
```

-continued

```
385                 390                 395                 400

Ile Ala Arg Lys Lys Leu Phe Glu Met Asn Arg Val Ile Ser Asp Thr
                405                 410                 415

Ala Glu Tyr Gly Cys Tyr Leu Phe Asp His Ala Cys Lys Pro Leu Leu
            420                 425                 430

Ala Asn Phe Met Lys Thr Val Asp Thr Asp Ile Ile Gly Lys Asn Phe
        435                 440                 445

Asn Ala Gly Lys Asp Asn Gly Val Asp Asn Gln Met Leu Ile Ala Val
    450                 455                 460

Asn Glu Val Leu Arg Ser His Pro Ile Glu Ile Val Gly Ala Glu Leu
465                 470                 475                 480

Arg Glu Ala Met Thr Glu Met Lys Ala Ile Val Ser
                485                 490


<210> SEQ ID NO 92

<400> SEQUENCE: 92

000


<210> SEQ ID NO 93

<400> SEQUENCE: 93

000


<210> SEQ ID NO 94

<400> SEQUENCE: 94

000


<210> SEQ ID NO 95

<400> SEQUENCE: 95

000


<210> SEQ ID NO 96

<400> SEQUENCE: 96

000


<210> SEQ ID NO 97

<400> SEQUENCE: 97

000


<210> SEQ ID NO 98

<400> SEQUENCE: 98

000


<210> SEQ ID NO 99

<400> SEQUENCE: 99

000


<210> SEQ ID NO 100

<400> SEQUENCE: 100
```

000

<210> SEQ ID NO 101
<211> LENGTH: 6362
<212> TYPE: DNA
<213> ORGANISM: Artificial Sequence
<220> FEATURE:
<223> OTHER INFORMATION: Plasmid pGV1102

<400> SEQUENCE: 101

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcggggctgg | cttaactatg | cggcatcaga | gcagattgta | ctgagagtgc | 180 |
| accataccac | agcttttcaa | ttcaattcat | catttttttt | ttattctttt | ttttgatttc | 240 |
| ggtttctttg | aaattttttt | gattcggtaa | tctccgaaca | gaaggaagaa | cgaaggaagg | 300 |
| agcacagact | tagattggta | tatatacgca | tatgtagtgt | tgaagaaaca | tgaaattgcc | 360 |
| cagtattctt | aacccaactg | cacagaacaa | aaacctgcag | gaaacgaaga | taaatcatgt | 420 |
| cgaaagctac | atataaggaa | cgtgctgcta | ctcatcctag | tcctgttgct | gccaagctat | 480 |
| ttaatatcat | gcacgaaaag | caaacaaact | tgtgtgcttc | attggatgtt | cgtaccacca | 540 |
| aggaattact | ggagttagtt | gaagcattag | gtcccaaaat | tgtttactaa | aaacacatg | 600 |
| tggatatctt | gactgatttt | tccatggagg | gcacagttaa | gccgctaaag | gcattatccg | 660 |
| ccaagtacaa | ttttttactc | ttcgaagaca | gaaaatttgc | tgacattggt | aatacagtca | 720 |
| aattgcagta | ctctgcgggt | gtatacagaa | tagcagaatg | ggcagacatt | acgaatgcac | 780 |
| acggtgtggt | gggcccaggt | attgttagcg | gtttgaagca | ggcggcagaa | gaagtaacaa | 840 |
| aggaacctag | aggccttttg | atgttagcag | aattgtcatg | caagggctcc | ctatctactg | 900 |
| gagaatatac | taagggtact | gttgacattg | cgaagagcga | caaagatttt | gttatcggct | 960 |
| ttattgctca | aagagacatg | ggtggaagag | atgaaggtta | cgattggttg | attatgacac | 1020 |
| ccggtgtggg | tttagatgac | aagggagacg | cattgggtca | acagtataga | accgtggatg | 1080 |
| atgtggtctc | tacaggatct | gacattatta | ttgttggaag | aggactattt | gcaaagggaa | 1140 |
| gggatgctaa | ggtagagggt | gaacgttaca | gaaaagcagg | ctgggaagca | tatttgagaa | 1200 |
| gatgcggcca | gcaaaactaa | aaaactgtat | tataagtaaa | tgcatgtata | ctaaactcac | 1260 |
| aaattagagc | ttcaatttaa | ttatatcagt | tattacccta | tgcggtgtga | aataccgcac | 1320 |
| agatgcgtaa | ggagaaaata | ccgcatcagg | aaattgtaaa | cgttaatatt | ttgttaaaat | 1380 |
| tcgcgttaaa | tttttgttaa | atcagctcat | tttttaacca | ataggccgaa | atcggcaaaa | 1440 |
| tcccttataa | atcaaaagaa | tagaccgaga | tagggttgag | tgttgttcca | gtttggaaca | 1500 |
| agagtccact | attaaagaac | gtggactcca | acgtcaaagg | gcgaaaaacc | gtctatcagg | 1560 |
| gcgatggccc | actacgtgaa | ccatcaccct | aatcaagttt | tttggggtcg | aggtgccgta | 1620 |
| aagcactaaa | tcggaaccct | aaagggagcc | cccgatttag | agcttgacgg | ggaaagccgg | 1680 |
| cgaacgtggc | gagaaaggaa | gggaagaaag | cgaaaggagc | gggcgctagg | gcgctggcaa | 1740 |
| gtgtagcggt | cacgctgcgc | gtaaccacca | cacccgccgc | gcttaatgcg | ccgctacagg | 1800 |
| gcgcgtcgcg | ccattcgcca | ttcaggctgc | gcaactgttg | ggaagggcga | tcggtgcggg | 1860 |
| cctcttcgct | attacgccag | ctggcgaaag | gggatgtgc | tgcaaggcga | ttaagttggg | 1920 |
| taacgccagg | gttttcccag | tcacgacgtt | gtaaaacgac | ggccagtgag | cgcgcgtaat | 1980 |
| acgactcact | atagggcgaa | ttgggtaccg | gccgcaaatt | aaagccttcg | agcgtcccaa | 2040 |

```
aaccttctca agcaaggttt tcagtataat gttacatgcg tacacgcgtc tgtacagaaa   2100
aaaaagaaaa atttgaaata taaataacgt tcttaatact aacataacta taaaaaaata   2160
aatagggacc tagacttcag gttgtctaac tccttccttt tcggttagag cggatgtggg   2220
gggagggcgt gaatgtaagc gtgacataac taattacatg actcgagcgg ccgcggatcc   2280
cgggaattcg tcgacacccg catagtcagg aacatcgtat gggtacatgc tagttctaga   2340
aaacttagat tagattgcta tgctttcttt ctaatgagca agaagtaaaa aaagttgtaa   2400
tagaacaaga aaaatgaaac tgaaacttga gaaattgaag accgtttatt aacttaaata   2460
tcaatgggag gtcatcgaaa gagaaaaaaa tcaaaaaaaa aattttcaag aaaaagaaac   2520
gtgataaaaa tttttattgc ctttttcgac gaagaaaaag aaacgaggcg gtctcttttt   2580
tcttttccaa acctttagta cgggtaatta acgacaccct agaggaagaa agaggggaaa   2640
tttagtatgc tgtgcttggg tgttttgaag tggtacggcg atgcgcggag tccgagaaaa   2700
tctggaagag taaaaaagga gtagaaacat tttgaagcta tgagctccag cttttgttcc   2760
ctttagtgag ggttaattgc gcgcttggcg taatcatggt catagctgtt tcctgtgtga   2820
aattgttatc cgctcacaat tccacacaac ataggagccg gaagcataaa gtgtaaagcc   2880
tggggtgcct aatgagtgag gtaactcaca ttaattgcgt tgcgctcact gcccgctttc   2940
cagtcgggaa acctgtcgtg ccagctgcat taatgaatcg gccaacgcgc ggggagaggc   3000
ggtttgcgta ttgggcgctc ttccgcttcc tcgctcactg actcgctgcg ctcggtcgtt   3060
cggctgcggc gagcggtatc agctcactca aaggcggtaa tacggttatc cacagaatca   3120
ggggataacg caggaaagaa catgtgagca aaaggccagc aaaaggccag gaaccgtaaa   3180
aaggccgcgt tgctggcgtt tttccatagg ctccgccccc ctgacgagca tcacaaaaat   3240
cgacgctcaa gtcagaggtg gcgaaacccg acaggactat aaagatacca ggcgtttccc   3300
cctggaagct ccctcgtgcg ctctcctgtt ccgaccctgc cgcttaccgg atacctgtcc   3360
gcctttctcc cttcgggaag cgtggcgctt tctcatagct cacgctgtag gtatctcagt   3420
tcggtgtagg tcgttcgctc caagctgggc tgtgtgcacg aaccccccgt tcagcccgac   3480
cgctgcgcct tatccggtaa ctatcgtctt gagtccaacc cggtaagaca cgacttatcg   3540
ccactggcag cagccactgg taacaggatt agcagagcga ggtatgtagg cggtgctaca   3600
gagttcttga agtggtggcc taactacggc tacactagaa ggacagtatt tggtatctgc   3660
gctctgctga agccagttac cttcggaaaa agagttggta gctcttgatc cggcaaacaa   3720
accaccgctg gtagcggtgg tttttttgtt tgcaagcagc agattacgcg cagaaaaaaa   3780
ggatctcaag aagatccttt gatcttttct acggggtctg acgctcagtg gaacgaaaac   3840
tcacgttaag ggattttggt catgagatta tcaaaaagga tcttcaccta gatcctttta   3900
aattaaaaat gaagttttaa atcaatctaa agtatatatg agtaaacttg gtctgacagt   3960
taccaatgct taatcagtga ggcacctatc tcagcgatct gtctatttcg ttcatccata   4020
gttgcctgac tccccgtcgt gtagataact acgatacggg agggcttacc atctggcccc   4080
agtgctgcaa tgataccgcg agacccacgc tcaccggctc cagatttatc agcaataaac   4140
cagccagccg gaagggccga gcgcagaagt ggtcctgcaa ctttatccgc ctccatccag   4200
tctattaatt gttgccggga agctagagta agtagttcgc cagttaatag tttgcgcaac   4260
gttgttgcca ttgctacagg catcgtggtg tcacgctcgt cgtttggtat ggcttcattc   4320
agctccggtt cccaacgatc aaggcgagtt acatgatccc ccatgttgtg caaaaaagcg   4380
gttagctcct tcggtcctcc gatcgttgtc agaagtaagt tggccgcagt gttatcactc   4440
```

atggttatgg cagcactgca taattctctt actgtcatgc catccgtaag atgcttttct 4500
gtgactggtg agtactcaac caagtcattc tgagaatagt gtatgcggcg accgagttgc 4560
tcttgcccgg cgtcaatacg ggataatacc gcgccacata gcagaacttt aaaagtgctc 4620
atcattggaa aacgttcttc ggggcgaaaa ctctcaagga tcttaccgct gttgagatcc 4680
agttcgatgt aacccactcg tgcacccaac tgatcttcag catcttttac tttcaccagc 4740
gtttctgggt gagcaaaaac aggaaggcaa aatgccgcaa aaaagggaat aagggcgaca 4800
cggaaatgtt gaatactcat actcttcctt tttcaatatt attgaagcat ttatcagggt 4860
tattgtctca tgagcggata catatttgaa tgtatttaga aaaataaaca aataggggtt 4920
ccgcgcacat ttccccgaaa agtgccacct gaacgaagca tctgtgcttc attttgtaga 4980
acaaaaatgc aacgcgagag cgctaatttt tcaaacaaag aatctgagct gcatttttac 5040
agaacagaaa tgcaacgcga aagcgctatt ttaccaacga agaatctgtg cttcattttt 5100
gtaaaacaaa aatgcaacgc gagagcgcta atttttcaaa caaagaatct gagctgcatt 5160
tttacagaac agaaatgcaa cgcgagagcg ctattttacc aacaaagaat ctatacttct 5220
tttttgttct acaaaaatgc atcccgagag cgctattttt ctaacaaagc atcttagatt 5280
actttttttc tcctttgtgc gctctataat gcagtctctt gataactttt tgcactgtag 5340
gtccgttaag gttagaagaa ggctactttg gtgtctattt tctcttccat aaaaaaagcc 5400
tgactccact tcccgcgttt actgattact agcgaagctg cgggtgcatt ttttcaagat 5460
aaaggcatcc ccgattatat tctataccga tgtggattgc gcatactttg tgaacagaaa 5520
gtgatagcgt tgatgattct tcattggtca gaaaattatg aacggtttct tctattttgt 5580
ctctatatac tacgtatagg aaatgtttac attttcgtat tgttttcgat tcactctatg 5640
aatagttctt actacaattt ttttgtctaa agagtaatac tagagataaa cataaaaaat 5700
gtagaggtcg agtttagatg caagttcaag gagcgaaagg tggatgggta ggttatatag 5760
ggatatagca cagagatata tagcaaagag atacttttga gcaatgtttg tggaagcggt 5820
attcgcaata ttttagtagc tcgttacagt ccggtgcgtt tttggttttt tgaaagtgcg 5880
tcttcagagc gcttttggtt ttcaaaagcg ctctgaagtt cctatacttt ctagagaata 5940
ggaacttcgg aataggaact tcaaagcgtt tccgaaaacg agcgcttccg aaaatgcaac 6000
gcgagctgcg cacatacagc tcactgttca cgtcgcacct atatctgcgt gttgcctgta 6060
tatatatata catgagaaga acggcatagt gcgtgtttat gcttaaatgc gtacttatat 6120
gcgtctattt atgtaggatg aaaggtagtc tagtacctcc tgtgatatta tcccattcca 6180
tgcggggtat cgtatgcttc cttcagcact accctttagc tgttctatat gctgccactc 6240
ctcaattgga ttagtctcat ccttcaatgc tatcatttcc tttgatattg gatcatacta 6300
agaaaccatt attatcatga cattaaccta taaaaatagg cgtatcacga ggccctttcg 6360
tc 6362

<210> SEQ ID NO 102
<211> LENGTH: 7314
<212> TYPE: DNA
<213> ORGANISM: Artificial Sequence
<220> FEATURE:
<223> OTHER INFORMATION: Plasmid pGV1323

<400> SEQUENCE: 102
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120

-continued

```
ttggcgggtg tcggggctgg cttaactatg cggcatcaga gcagattgta ctgagagtgc    180
accataaacg acattactat atatataata taggaagcat ttaatagaca gcatcgtaat    240
atatgtgtac tttgcagtta tgacgccaga tggcagtagt ggaagatatt ctttattgaa    300
aaatagcttg tcaccttacg tacaatcttg atccggagct tttctttttt tgccgattaa    360
gaattaattc ggtcgaaaaa agaaaaggag agggccaaga gggagggcat tggtgactat    420
tgagcacgtg agtatacgtg attaagcaca caaaggcagc ttggagtatg tctgttatta    480
atttcacagg tagttctggt ccattggtga aagtttgcgg cttgcagagc acagaggccg    540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa tttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctggcgaaag ggggatgtgc tgcaaggcga   1800
ttaagttggg taacgccagg gttttcccag tcacgacgtt gtaaaacgac ggccagtgag   1860
cgcgcgtaat acgactcact atagggcgaa ttgggtaccg gccgcaaatt aaagccttcg   1920
agcgtcccaa aaccttctca agcaaggttt tcagtataat gttacatgcg tacacgcgtc   1980
tgtacagaaa aaaaagaaaa atttgaaata taaataacgt tcttaatact aacataacta   2040
taaaaaaata aatagggacc tagacttcag gttgtctaac tccttccttt tcggttagag   2100
cggatgtggg gggagggcgt gaatgtaagc gtgacataac taattacatg actcgagcgg   2160
ccgcggatcc ttaaacacca gcttcgaagt ccttttgagc catgaaaatg gataaatcaa   2220
ccactcttga agagtaacca tattcattat cataccaaga aaggaccttg aaaaaatggt   2280
cgttcaattc aataccggcc ttggcatcaa caatagatga acgtgaatcg gatgtgaagt   2340
cagaggacac aacggcgtct ttggtaacac ccaaaacacc cttcatatcg ctgcgagatc   2400
tttgttctag ggccttcata atgtcatcgt aagaagtttt ctttgctgta cggaatgtca   2460
agtcaaccag ggaaatatta attgttggga ctcttataga cataccggtg atcttaccat   2520
```

```
taagttcagg caagattttc cctacagcct tagctgcacc agtagatgaa ggaatgatat   2580
ttccctggca agatctaccg cctctccagt ccttaccacc agaactggta ccatcgacag   2640
tcttttgaga agcagtagtt gcatgaatag ttgtcatcaa ggcttcttcg ataccgaact   2700
catcgtccaa agccttaacc aacggagcca aacagttggt agtacaggag gcattagaga   2760
ccacgtgatc cgtcaatggg ttgtatttaa cgtggttaac accatagacg tacattggcg   2820
cggtctttga tggagcagta atgataactt ttttgacacc tttatgtcta gaggctgtat   2880
cgacttcctt gaagacaccg gttgagtcaa ttacataatc gacgttgtag gaagcccatg   2940
ggatacgctc tggttcccta aaatgagata gagggatatg agccgaaaca tggtcatttt   3000
gaatgatgat acgttcatcg tcgaattcaa cttcaccacg atacttgccg tgagtagaat   3060
cgtatttgaa caaataagca gcgtattctg gtgttgtgga tggattattg attaatctga   3120
ccttaacttc tgggtgcgtc aaagcagcac gtagaaccaa tctaccgatt ctaccaaaac   3180
cattgatacc aatgttaatt tgagctggct tagaagaaga ttcgtttgtc atatcgggca   3240
tgtcgacacc cgcatagtca ggaacatcgt atgggtacat gctagttcta gaaaacttag   3300
attagattgc tatgctttct ttctaatgag caagaagtaa aaaaagttgt aatagaacaa   3360
gaaaaatgaa actgaaactt gagaaattga agaccgttta ttaacttaaa tatcaatggg   3420
aggtcatcga aagagaaaaa aatcaaaaaa aaaatttca agaaaaagaa acgtgataaa   3480
aatttttatt gcctttttcg acgaagaaaa agaaacgagg cggtctcttt tttcttttcc   3540
aaacctttag tacgggtaat taacgacacc ctagaggaag aaagagggga aatttagtat   3600
gctgtgcttg ggtgttttga agtggtacgg cgatgcgcgg agtccgagaa aatctggaag   3660
agtaaaaaag gagtagaaac attttgaagc tatgagctcc agcttttgtt ccctttagtg   3720
agggttaatt gcgcgcttgg cgtaatcatg gtcatagctg tttcctgtgt gaaattgtta   3780
tccgctcaca attccacaca acataggagc cggaagcata aagtgtaaag cctggggtgc   3840
ctaatgagtg aggtaactca cattaattgc gttgcgctca ctgcccgctt tccagtcggg   3900
aaacctgtcg tgccagctgc attaatgaat cggccaacgc gcggggagag gcggtttgcg   3960
tattgggcgc tcttccgctt cctcgctcac tgactcgctg cgctcggtcg ttcggctgcg   4020
gcgagcggta tcagctcact caaaggcggt aatacggtta tccacagaat caggggataa   4080
cgcaggaaag aacatgtgag caaaaggcca gcaaaaggcc aggaaccgta aaaaggccgc   4140
gttgctggcg tttttccata ggctccgccc ccctgacgag catcacaaaa atcgacgctc   4200
aagtcagagg tggcgaaacc cgacaggact ataaagatac caggcgtttc cccctggaag   4260
ctccctcgtg cgctctcctg ttccgaccct gccgcttacc ggatacctgt ccgcctttct   4320
cccttcggga agcgtggcgc tttctcatag ctcacgctgt aggtatctca gttcggtgta   4380
ggtcgttcgc tccaagctgg gctgtgtgca cgaacccccc gttcagcccg accgctgcgc   4440
cttatccggt aactatcgtc ttgagtccaa cccggtaaga cacgacttat cgccactggc   4500
agcagccact ggtaacagga ttagcagagc gaggtatgta ggcggtgcta cagagttctt   4560
gaagtggtgg cctaactacg gctacactag aaggacagta tttggtatct gcgctctgct   4620
gaagccagtt accttcggaa aaagagttgg tagctcttga tccggcaaac aaaccaccgc   4680
tggtagcggt ggtttttttg tttgcaagca gcagattacg cgcagaaaaa aaggatctca   4740
agaagatcct ttgatctttt ctacggggtc tgacgctcag tggaacgaaa actcacgtta   4800
agggattttg gtcatgagat tatcaaaaag gatcttcacc tagatccttt taaattaaaa   4860
atgaagtttt aaatcaatct aaagtatata tgagtaaact tggtctgaca gttaccaatg   4920
```

-continued

```
cttaatcagt gaggcaccta tctcagcgat ctgtctattt cgttcatcca tagttgcctg   4980
actccccgtc gtgtagataa ctacgatacg ggagggctta ccatctggcc ccagtgctgc   5040
aatgataccg cgagacccac gctcaccggc tccagattta tcagcaataa accagccagc   5100
cggaagggcc gagcgcagaa gtggtcctgc aactttatcc gcctccatcc agtctattaa   5160
ttgttgccgg gaagctagag taagtagttc gccagttaat agtttgcgca acgttgttgc   5220
cattgctaca ggcatcgtgg tgtcacgctc gtcgtttggt atggcttcat tcagctccgg   5280
ttcccaacga tcaaggcgag ttacatgatc ccccatgttg tgcaaaaaag cggttagctc   5340
cttcggtcct ccgatcgttg tcagaagtaa gttggccgca gtgttatcac tcatggttat   5400
ggcagcactg cataattctc ttactgtcat gccatccgta agatgctttt ctgtgactgg   5460
tgagtactca accaagtcat tctgagaata gtgtatgcgg cgaccgagtt gctcttgccc   5520
ggcgtcaata cgggataata ccgcgccaca tagcagaact ttaaaagtgc tcatcattgg   5580
aaaacgttct tcggggcgaa aactctcaag gatcttaccg ctgttgagat ccagttcgat   5640
gtaacccact cgtgcaccca actgatcttc agcatctttt actttcacca gcgtttctgg   5700
gtgagcaaaa acaggaaggc aaaatgccgc aaaaaaggga ataagggcga cacggaaatg   5760
ttgaatactc atactcttcc tttttcaata ttattgaagc atttatcagg gttattgtct   5820
catgagcgga tacatatttg aatgtattta gaaaaataaa caaatagggg ttccgcgcac   5880
atttccccga aaagtgccac ctgaacgaag catctgtgct tcattttgta gaacaaaaat   5940
gcaacgcgag agcgctaatt tttcaaacaa agaatctgag ctgcattttt acagaacaga   6000
aatgcaacgc gaaagcgcta ttttaccaac gaagaatctg tgcttcattt ttgtaaaaca   6060
aaaatgcaac gcgagagcgc taatttttca aacaaagaat ctgagctgca tttttacaga   6120
acagaaatgc aacgcgagag cgctatttta ccaacaaaga atctatactt cttttttgtt   6180
ctacaaaaat gcatcccgag agcgctattt ttctaacaaa gcatcttaga ttactttttt   6240
tctcctttgt gcgctctata atgcagtctc ttgataactt tttgcactgt aggtccgtta   6300
aggttagaag aaggctactt tggtgtctat tttctcttcc ataaaaaaag cctgactcca   6360
cttcccgcgt ttactgatta ctagcgaagc tgcgggtgca ttttttcaag ataaaggcat   6420
ccccgattat attctatacc gatgtggatt gcgcatactt tgtgaacaga aagtgatagc   6480
gttgatgatt cttcattggt cagaaaatta tgaacggttt cttctatttt gtctctatat   6540
actacgtata ggaaatgttt acattttcgt attgttttcg attcactcta tgaatagttc   6600
ttactacaat ttttttgtct aaagagtaat actagagata aacataaaaa atgtagaggt   6660
cgagtttaga tgcaagttca aggagcgaaa ggtggatggg taggttatat agggatatag   6720
cacagagata tatagcaaag agatactttt gagcaatgtt tgtggaagcg gtattcgcaa   6780
tattttagta gctcgttaca gtccggtgcg tttttggttt tttgaaagtg cgtcttcaga   6840
gcgcttttgg ttttcaaaag cgctctgaag ttcctatact ttctagagaa taggaacttc   6900
ggaataggaa cttcaaagcg tttccgaaaa cgagcgcttc cgaaaatgca acgcgagctg   6960
cgcacataca gctcactgtt cacgtcgcac ctatatctgc gtgttgcctg tatatatata   7020
tacatgagaa gaacggcata gtgcgtgttt atgcttaaat gcgtacttat atgcgtctat   7080
ttatgtagga tgaaaggtag tctagtacct cctgtgatat tatcccattc catgcggggt   7140
atcgtatgct tccttcagca ctacccttta gctgttctat atgctgccac tcctcaattg   7200
gattagtctc atccttcaat gctatcattt cctttgatat tggatcatat taagaaacca   7260
ttattatcat gacattaacc tataaaaata ggcgtatcac gaggcccttt cgtc         7314
```

<210> SEQ ID NO 103
<211> LENGTH: 6294
<212> TYPE: DNA
<213> ORGANISM: Artificial Sequence
<220> FEATURE:
<223> OTHER INFORMATION: Plasmid pGV1485

<400> SEQUENCE: 103
taagaaacca ttattatcat gacattaacc tataaaaata ggcgtatcac gaggcccttt 60
cgtcttcacc tcgagaattg tgagcggata acaattgaca ttgtgagcgg ataacaagat 120
actgagcaca tcagcaggac gcactgaccg aattcattaa agaggagaaa ggtaccatgt 180
atacagtagg agattaccta ttagaccgat tacacgagtt aggaattgaa gaaatttttg 240
gagtccctgg agactataac ttacaatttt tagatcaaat tatttcccgc aaggatatga 300
aatgggtcgg aaatgctaat gaattaaatg cttcatatat ggctgatggc tatgctcgta 360
ctaaaaaagc tgccgcattt cttacaacct ttggagtagg tgaattgagt gcagttaatg 420
gattagcagg aagttacgcc gaaaatttac cagtagtaga aatagtggga tcacctacat 480
caaaagttca aaatgaagga aaatttgttc atcatacgct ggctgacggt gattttaaac 540
actttatgaa aatgcacgaa cctgttacag cagctcgaac tttactgaca gcagaaaatg 600
caaccgttga aattgaccga gtactttctg cactattaaa agaaagaaaa cctgtctata 660
tcaacttacc agttgatgtt gctgctgcaa aagcagagaa accctcactc cctttgaaaa 720
aagaaaactc aacttcaaat acaagtgacc aagagatctt gaacaaaatt caagaaagct 780
tgaaaaatgc caaaaaacca atcgtgatta caggacatga aataattagt tttggcttag 840
aaaaaacagt ctctcaattt atttcaaaga caaaactacc tattacgaca ttaaactttg 900
gaaaaagttc agttgatgaa gctctccctt catttttagg aatctataat ggtaaactct 960
cagagcctaa tcttaaagaa ttcgtggaat cagccgactt catcctgatg cttggagtta 1020
aactcacaga ctcttcaaca ggagccttca ctcatcattt aaatgaaaat aaaatgattt 1080
cactgaatat agatgaagga aaaatattta acgaaagcat ccaaaatttt gatttttgaat 1140 ccctcatctc ctctctctta gacctaagcg aaatagaata caaaggaaaa tatatcgata 1200
aaaagcaaga agactttgtt ccatcaaatg cgcttttatc acaagaccgc ctatggcaag 1260
cagttgaaaa cctaactcaa agcaatgaaa caatcgttgc tgaacaaggg acatcattct 1320
ttggcgcttc atcaattttc ttaaaaccaa agagtcattt tattggtcaa cccttatggg 1380
gatcaattgg atatacattc ccagcagcat taggaagcca aattgcagat aaagaaagca 1440
gacacctttt atttattggt gatggttcac ttcaacttac ggtgcaagaa ttaggattag 1500
caatcagaga aaaaattaat ccaatttgct ttattatcaa taatgatggt tatacagtcg 1560
aaagagaaat tcatggacca aatcaaagct acaatgatat tccaatgtgg aattactcaa 1620
aattaccaga atcatttgga gcaacagaag aacgagtagt ctcgaaaatc gttagaactg 1680
aaaatgaatt tgtgtctgtc atgaaagaag ctcaagcaga tccaaataga atgtactgga 1740
ttgagttaat tttggcaaaa gaagatgcac caaaagtact gaaaaaaatg ggcaaactat 1800
ttgctgaaca aaataaatca taagcatgca ggagatatac catgtctatt ccagaaactc 1860
aaaaagccat tatcttctac gaatccaacg gcaagttgga gcataaggat atcccagttc 1920
caaagccaaa gcccaacgaa ttgttaatca acgtcaagta ctctggtgtc tgccacaccg 1980
atttgcacgc ttggcatggt gactggccat tgccaactaa gttaccatta gttggtggtc 2040
acgaaggtgc cggtgtcgtt gtcggcatgg gtgaaaacgt taagggctgg aagatcggtg 2100
actacgccgg tatcaaatgg ttgaacggtt cttgtatggc ctgtgaatac tgtgaattgg 2160
gtaacgaatc caactgtcct cacgctgact tgtctggtta cacccacgac ggttctttcc 2220
aagaatacgc taccgctgac gctgttcaag ccgctcacat tcctcaaggt actgacttgg 2280
ctgaagtcgc gccaatcttg tgtgctggta tcaccgtata caaggctttg aagtctgcca 2340
acttgagagc aggccactgg gcggccattt ctggtgctgc tggtggtcta ggttctttgg 2400
ctgttcaata tgctaaggcg atgggttaca gagtcttagg tattgatggt ggtccaggaa 2460
aggaagaatt gtttacctcg ctcggtggtg aagtattcat cgacttcacc aaagagaagg 2520
acattgttag cgcagtcgtt aaggctacca acggcggtgc ccacggtatc atcaatgttt 2580
ccgtttccga agccgctatc gaagcttcta ccagatactg tagggcgaac ggtactgttg 2640
tcttggttgg tttgccagcc ggtgcaaagt gctcctctga tgtcttcaac cacgttgtca 2700
agtctatctc cattgtcggc tcttacgtgg ggaacagagc tgataccaga gaagccttag 2760
atttctttgc cagaggtcta gtcaagtctc caataaaggt agttggctta tccagtttac 2820
cagaaattta cgaaaagatg gagaagggcc aaattgctgg tagatacgtt gttgacactt 2880
ctaaataatc tagaggcatc aaataaaacg aaaggctcag tcgaaagact gggcctttcg 2940
ttttatctgt tgtttgtcgg tgaacgctct cctgagtagg acaaatccgc cgccctagac 3000
ctagggtacg ggttttgctg cccgcaaacg ggctgttctg gtgttgctag tttgttatca 3060
gaatcgcaga tccggcttca ggtttgccgg ctgaaagcgc tatttcttcc agaattgcca 3120
tgattttttc cccacgggag gcgtcactgg ctcccgtgtt gtcggcagct ttgattcgat 3180
aagcagcatc gcctgtttca ggctgtctat gtgtgactgt tgagctgtaa caagttgtct 3240
caggtgttca atttcatgtt ctagttgctt tgttttactg gtttcacctg ttctattagg 3300
tgttacatgc tgttcatctg ttacattgtc gatctgttca tggtgaacag ctttaaatgc 3360
accaaaaact cgtaaaagct ctgatgtatc tatctttttt acaccgtttt catctgtgca 3420
tatggacagt tttccctttg atatctaacg gtgaacagtt gttctacttt tgtttgttag 3480
tcttgatgct tcactgatag atacaagagc cataagaacc tcagatcctt ccgtatttag 3540
ccagtatgtt ctctagtgtg gttcgttgtt tttgcgtgag ccatgagaac gaaccattga 3600
gatcatgctt actttgcatg tcactcaaaa attttgcctc aaaactggtg agctgaattt 3660
ttgcagttaa agcatcgtgt agtgtttttc ttagtccgtt acgtaggtag gaatctgatg 3720
taatggttgt tggtattttg tcaccattca tttttatctg gttgttctca agttcggtta 3780
cgagatccat ttgtctatct agttcaactt ggaaaatcaa cgtatcagtc gggcggcctc 3840
gcttatcaac caccaatttc atattgctgt aagtgtttaa atctttactt attggtttca 3900
aaacccattg gttaagcctt ttaaactcat ggtagttatt ttcaagcatt aacatgaact 3960
taaattcatc aaggctaatc tctatatttg ccttgtgagt tttcttttgt gttagttctt 4020
ttaataacca ctcataaatc ctcatagagt atttgttttc aaaagactta acatgttcca 4080
gattatattt tatgaatttt tttaactgga aaagataagg caatatctct tcactaaaaa 4140
ctaattctaa tttttcgctt gagaacttgg catagtttgt ccactggaaa atctcaaagc 4200
ctttaaccaa aggattcctg atttccacag ttctcgtcat cagctctctg gttgctttag 4260
ctaatacacc ataagcattt tccctactga tgttcatcat ctgagcgtat tggttataag 4320
tgaacgatac cgtccgttct ttccttgtag ggttttcaat cgtggggttg agtagtgcca 4380
cacagcataa aattagcttg gtttcatgct ccgttaagtc atagcgacta atcgctagtt 4440
catttgcttt gaaaacaact aattcagaca tacatctcaa ttggtctagg tgattttaat 4500

```
cactatacca attgagatgg gctagtcaat gataattact agtccttttc ccgggagatc   4560
tgggtatctg taaattctgc tagacctttg ctggaaaact tgtaaattct gctagaccct   4620
ctgtaaattc cgctagacct ttgtgtgttt tttttgttta tattcaagtg gttataattt   4680
atagaataaa gaaagaataa aaaaagataa aaagaataga tcccagccct gtgtataact   4740
cactacttta gtcagttccg cagtattaca aaaggatgtc gcaaacgctg tttgctcctc   4800
tacaaaacag accttaaaac cctaaaggct taagtagcac cctcgcaagc tcgggcaaat   4860
cgctgaatat tccttttgtc tccgaccatc aggcacctga gtcgctgtct ttttcgtgac   4920
attcagttcg ctgcgctcac ggctctggca gtgaatgggg gtaaatggca ctacaggcgc   4980
cttttatgga ttcatgcaag gaaactaccc ataatacaag aaaagcccgt cacgggcttc   5040
tcagggcgtt ttatggcggg tctgctatgt ggtgctatct gactttttgc tgttcagcag   5100
ttcctgccct ctgattttcc agtctgacca cttcggatta tcccgtgaca ggtcattcag   5160
actggctaat gcacccagta aggcagcggt atcatcaaca ggcttacccg tcttactgtc   5220
cctagtgctt ggattctcac caataaaaaa cgcccggcgg caaccgagcg ttctgaacaa   5280
atccagatgg agttctgagg tcattactgg atctatcaac aggagtccaa gcgagctctc   5340
gaaccccaga gtcccgctca gaagaactcg tcaagaaggc gatagaaggc gatgcgctgc   5400
gaatcgggag cggcgatacc gtaaagcacg aggaagcggt cagcccattc gccgccaagc   5460
tcttcagcaa tatcacgggt agccaacgct atgtcctgat agcggtccgc cacacccagc   5520
cggccacagt cgatgaatcc agaaaagcgg ccattttcca ccatgatatt cggcaagcag   5580
gcatcgccat gggtcacgac gagatcctcg ccgtcgggca tgcgcgcctt gagcctggcg   5640
aacagttcgg ctggcgcgag cccctgatgc tcttcgtcca gatcatcctg atcgacaaga   5700
ccggcttcca tccgagtacg tgctcgctcg atgcgatgtt tcgcttggtg gtcgaatggg   5760
caggtagccg gatcaagcgt atgcagccgc cgcattgcat cagccatgat ggatactttc   5820
tcggcaggag caaggtgaga tgacaggaga tcctgccccg gcacttcgcc caatagcagc   5880
cagtcccttc ccgcttcagt gacaacgtcg agcacagctg cgcaaggaac gcccgtcgtg   5940
gccagccacg atagccgcgc tgcctcgtcc tgcagttcat tcagggcacc ggacaggtcg   6000
gtcttgacaa aaagaaccgg gcgcccctgc gctgacagcc ggaacacggc ggcatcagag   6060
cagccgattg tctgttgtgc ccagtcatag ccgaatagcc tctccaccca agcggccgga   6120
gaacctgcgt gcaatccatc ttgttcaatc atgcgaaacg atcctcatcc tgtctcttga   6180
tcagatcttg atcccctgcg ccatcagatc cttggcggca agaaagccat ccagtttact   6240
ttgcagggct tcccaacctt accagagggc gccccagctg gcaattccga cgtc         6294
```

<210> SEQ ID NO 104
<211> LENGTH: 1980
<212> TYPE: DNA
<213> ORGANISM: Artificial Sequence
<220> FEATURE:
<223> OTHER INFORMATION: Plasmid pGV1490

<400> SEQUENCE: 104

```
ctcgagtccc tatcagtgat agagattgac atccctatca gtgatagaga tactgagcac     60
atcagcagga cgcactgacc gaattcatta aagaggagaa aggtacctgc acgtcgactc    120
cgtcctaggg gatatattcc gcttcctcgc tcactgactc gctacgctcg gtcgttcgac    180
tgcggcgagc ggaaatggct tacgaacggg gcggagattt cctggaagat gccaggaaga    240
tacttaacag ggaagtgaga gggccgcggc aaagccgttt ttccataggc tccgcccccc    300
```

tgacaagcat cacgaaatct gacgctcaaa tcagtggtgg cgaaacccga caggactata 360
aagataccag gcgtttcccc ctggcggctc cctcgtgcgc tctcctgttc ctgcctttcg 420
gtttaccggt gtcattccgc tgttatggcc gcgtttgtct cattccacgc ctgacactca 480
gttccgggta ggcagttcgc tccaagctgg actgtatgca cgaacccccc gttcagtccg 540
accgctgcgc cttatccggt aactatcgtc ttgagtccaa cccggaaaga catgcaaaag 600
caccactggc agcagccact ggtaattgat ttagaggagt tagtcttgaa gtcatgcgcc 660
ggttaaggct aaactgaaag gacaagtttt ggtgactgcg ctcctccaag ccagttacct 720
cggttcaaag agttggtagc tcagagaacc ttcgaaaaac cgccctgcaa ggcggttttt 780
tcgttttcag agcaagagat tacgcgcaga ccaaaacgat ctcaagaaga tcatcttatt 840
aatcagataa aatatttcta gatttcagtg caatttatct cttcaaatgt agcacctgaa 900
gtcagcccca tacgatataa gttgttacta gtgcttggat tctcaccaat aaaaaacgcc 960
cggcggcaac cgagcgttct gaacaaatcc agatggagtt ctgaggtcat tactggatct 1020
atcaacagga gtccaagcga gctcgatatc aaattacgcc ccgccctgcc actcatcgca 1080
gtactgttgt aattcattaa gcattctgcc gacatggaag ccatcacaga cggcatgatg 1140
aacctgaatc gccagcggca tcagcacctt gtcgccttgc gtataatatt tgcccatggt 1200
gaaaacgggg gcgaagaagt tgtccatatt ggccacgttt aaatcaaaac tggtgaaact 1260
cacccaggga ttggctgaga cgaaaaacat attctcaata aaccctttag ggaaataggc 1320
caggttttca ccgtaacacg ccacatcttg cgaatatatg tgtagaaact gccggaaatc 1380
gtcgtggtat tcactccaga gcgatgaaaa cgtttcagtt tgctcatgga aaacggtgta 1440
acaagggtga acactatccc atatcaccag ctcaccgtct ttcattgcca tacgaaactc 1500
cggatgagca ttcatcaggc gggcaagaat gtgaataaag gccggataaa acttgtgctt 1560
atttttcttt acggtcttta aaaaggccgt aatatccagc tgaacggtct ggttataggt 1620
acattgagca actgactgaa atgcctcaaa atgttcttta cgatgccatt gggatatatc 1680
aacggtggta tatccagtga tttttttctc catttttagct tccttagctc ctgaaaatct 1740
cgataactca aaaaatacgc ccggtagtga tcttatttca ttatggtgaa agttggaacc 1800
tcttacgtgc cgatcaacgt ctcattttcg ccagatatcg acgtctaaga aaccattatt 1860
atcatgacat taacctataa aaataggcgt atcacgaggc cctttcgtct tcacgaaacc 1920
attattatca tgacattaac ctataaaaat aggcgtatca cgaggccctt tcgtcttcac 1980

<210> SEQ ID NO 105
<211> LENGTH: 2077
<212> TYPE: DNA
<213> ORGANISM: Artificial Sequence
<220> FEATURE:
<223> OTHER INFORMATION: Plasmid pGV1572

<400> SEQUENCE: 105
ctagtgcttg gattctcacc aataaaaaac gcccggcggc aaccgagcgt tctgaacaaa 60
tccagatgga gttctgaggt cattactgga tctatcaaca ggagtccaag cgagctcgat 120
atcaaattac gccccgccct gccactcatc gcagtactgt tgtaattcat taagcattct 180
gccgacatgg aagccatcac agacggcatg atgaacctga atcgccagcg gcatcagcac 240
cttgtcgcct tgcgtataat atttgcccat ggtgaaaacg gggggcgaaga agttgtccat 300 attggccacg tttaaatcaa aactggtgaa actcacccag ggattggctg agacgaaaaa 360
catattctca ataaaccctt tagggaaata ggccaggttt tcaccgtaac acgccacatc 420

```
ttgcgaatat atgtgtagaa actgccggaa atcgtcgtgg tattcactcc agagcgatga    480

aaacgtttca gtttgctcat ggaaaacggt gtaacaaggg tgaacactat cccatatcac    540

cagctcaccg tctttcattg ccatacgaaa ctccggatga gcattcatca ggcgggcaag    600

aatgtgaata aaggccggat aaaacttgtg cttatttttc tttacggtct ttaaaaaggc    660

cgtaatatcc agctgaacgg tctggttata ggtacattga gcaactgact gaaatgcctc    720

aaaatgttct ttacgatgcc attgggatat atcaacggtg gtatatccag tgattttttt    780

ctccatttta gcttccttag ctcctgaaaa tctcgataac tcaaaaaata cgcccggtag    840

tgatcttatt tcattatggt gaaagttgga acctcttacg tgccgatcaa cgtctcattt    900

tcgccagata tcgacgtcta agaaaccatt attatcatga cattaaccta taaaaatagg    960

cgtatcacga ggccctttcg tcttcacctc gagaaatgtg agcggataac aattgacatt   1020

gtgagcggat aacaagatac tgagcacatc agcaggacgc actgaccggg aattcattaa   1080

agaggagaaa gtcgacatta tgcggccgcg gatccataag gaggattaat taagacttcc   1140

cgggtgatcc catggtacgc gtgctagagg catcaaataa aacgaaaggc tcagtcgaaa   1200

gactgggcct ttcgttttat ctgttgtttg tcggtgaacg ctctcctgag taggacaaat   1260

ccgccgccct agacctaggg gatatattcc gcttcctcgc tcactgactc gctacgctcg   1320

gtcgttcgac tgcggcgagc ggaaatggct tacgaacggg gcggagattt cctggaagat   1380

gccaggaaga tacttaacag ggaagtgaga gggccgcggc aaagccgttt ttccataggc   1440

tccgcccccc tgacaagcat cacgaaatct gacgctcaaa tcagtggtgg cgaaacccga   1500

caggactata aagataccag gcgtttcccc ctggcggctc cctcgtgcgc tctcctgttc   1560

ctgcctttcg gtttaccggt gtcattccgc tgttatggcc gcgtttgtct cattccacgc   1620

ctgacactca gttccgggta ggcagttcgc tccaagctgg actgtatgca cgaacccccc   1680

gttcagtccg accgctgcgc cttatccggt aactatcgtc ttgagtccaa cccggaaaga   1740

catgcaaaag caccactggc agcagccact ggtaattgat ttagaggagt tagtcttgaa   1800

gtcatgcgcc ggttaaggct aaactgaaag gacaagtttt ggtgactgcg ctcctccaag   1860

ccagttacct cggttcaaag agttggtagc tcagagaacc ttcgaaaaac cgccctgcaa   1920

ggcggttttt tcgttttcag agcaagagat tacgcgcaga ccaaaacgat ctcaagaaga   1980

tcatcttatt aatcagataa aatatttcta gatttcagtg caatttatct cttcaaatgt   2040

agcacctgaa gtcagcccca tacgatataa gttgtta                           2077
```

<210> SEQ ID NO 106
<211> LENGTH: 3135
<212> TYPE: DNA
<213> ORGANISM: Artificial Sequence
<220> FEATURE:
<223> OTHER INFORMATION: Plasmid pGV1573

<400> SEQUENCE: 106

```
ctagtgcttg gattctcacc aataaaaaac gcccggcggc aaccgagcgt tctgaacaaa     60

tccagatgga gttctgaggt cattactgga tctatcaaca ggagtccaag cgagctcgat    120

atcaaattac gccccgccct gccactcatc gcagtactgt tgtaattcat taagcattct    180

gccgacatgg aagccatcac agacggcatg atgaacctga atcgccagcg gcatcagcac    240

cttgtcgcct tgcgtataat atttgcccat ggtgaaaacg ggggcgaaga agttgtccat    300

attggccacg tttaaatcaa aactggtgaa actcacccag ggattggctg agacgaaaaa    360

catattctca ataaaccctt tagggaaata ggccaggttt tcaccgtaac acgccacatc    420
```

```
ttgcgaatat atgtgtagaa actgccggaa atcgtcgtgg tattcactcc agagcgatga    480
aaacgtttca gtttgctcat ggaaaacggt gtaacaaggg tgaacactat cccatatcac    540
cagctcaccg tctttcattg ccatacgaaa ctccggatga gcattcatca ggcgggcaag    600
aatgtgaata aaggccggat aaaacttgtg cttatttttc tttacggtct ttaaaaaggc    660
cgtaatatcc agctgaacgg tctggttata ggtacattga gcaactgact gaaatgcctc    720
aaaatgttct ttacgatgcc attgggatat atcaacggtg gtatatccag tgattttttt    780
ctccatttta gcttccttag ctcctgaaaa tctcgataac tcaaaaaata cgcccggtag    840
tgatcttatt tcattatggt gaaagttgga acctcttacg tgccgatcaa cgtctcattt    900
tcgccagata tcgacgtcta agaaaccatt attatcatga cattaaccta taaaaatagg    960
cgtatcacga ggccctttcg tcttcacctc gagaaatgtg agcggataac aattgacatt   1020
gtgagcggat aacaagatac tgagcacatc agcaggacgc actgaccggg aattcattaa   1080
agaggagaaa gtcgacatgc ccgatatgac aaacgaatct tcttctaagc cagctcaaat   1140
taacattggt atcaatggtt ttggtagaat cggtagattg gttctacgtg ctgctttgac   1200
gcacccagaa gttaaggtca gattaatcaa taatccatcc acaacaccag aatacgctgc   1260
ttatttgttc aaatacgatt ctactcacgg caagtatcgt ggtgaagttg aattcgacga   1320
tgaacgtatc atcattcaaa atgaccatgt ttcggctcat atccctctat ctcattttag   1380
ggaaccagag cgtatcccat gggcttccta caacgtcgat tatgtaattg actcaaccgg   1440
tgtcttcaag gaagtcgata cagcctctag acataaaggt gtcaaaaaag ttatcattac   1500
tgctccatca aagaccgcgc caatgtacgt ctatggtgtt aaccacgtta aatacaaccc   1560
attgacggat cacgtggtct ctaatgcctc ctgtactacc aactgtttgg ctccgttggt   1620
taaggctttg gacgatgagt tcggtatcga agaagccttg atgacaacta ttcatgcaac   1680
tactgcttct caaaagactg tcgatggtac cagttctggt ggtaaggact ggagaggcgg   1740
tagatcttgc cagggaaata tcattccttc atctactggt gcagctaagg ctgtagggaa   1800
aatcttgcct gaacttaatg gtaagatcac cggtatgtct ataagagtcc caacaattaa   1860
tatttccctg gttgacttga cattccgtac agcaaagaaa acttcttacg atgacattat   1920
gaaggcccta gaacaaagat ctcgcagcga tatgaagggt gttttgggtg ttaccaaaga   1980
cgccgttgtg tcctctgact tcacatccga ttcacgttca tctattgttg atgccaaggc   2040
cggtattgaa ttgaacgacc atttttttcaa ggtcctttct tggtatgata atgaatatgg   2100
ttactcttca agagtggttg atttatccat tttcatggct caaaaggact tcgaagctgg   2160
tgtttaagga tccataagga ggattaatta agacttcccg ggtgatccca tggtacgcgt   2220
gctagaggca tcaaataaaa cgaaaggctc agtcgaaaga ctgggccttt cgttttatct   2280
gttgtttgtc ggtgaacgct ctcctgagta ggacaaatcc gccgccctag acctagggga   2340
tatattccgc ttcctcgctc actgactcgc tacgctcggt cgttcgactg cggcgagcgg   2400
aaatggctta cgaacggggc ggagatttcc tggaagatgc caggaagata cttaacaggg   2460
aagtgagagg gccgcggcaa agccgttttt ccataggctc cgcccccctg acaagcatca   2520
cgaaatctga cgctcaaatc agtggtggcg aaacccgaca ggactataaa gataccaggc   2580
gtttccccct ggcggctccc tcgtgcgctc tcctgttcct gcctttcggt ttaccggtgt   2640
cattccgctg ttatggccgc gtttgtctca ttccacgcct gacactcagt tccgggtagg   2700
cagttcgctc caagctggac tgtatgcacg aaccccccgt tcagtccgac cgctgcgcct   2760
tatccggtaa ctatcgtctt gagtccaacc cggaaagaca tgcaaaagca ccactggcag   2820
```

```
cagccactgg taattgattt agaggagtta gtcttgaagt catgcgccgg ttaaggctaa   2880

actgaaagga caagttttgg tgactgcgct cctccaagcc agttacctcg gttcaaagag   2940

ttggtagctc agagaacctt cgaaaaaccg ccctgcaagg cggttttttc gttttcagag   3000

caagagatta cgcgcagacc aaaacgatct caagaagatc atcttattaa tcagataaaa   3060

tatttctaga tttcagtgca atttatctct tcaaatgtag cacctgaagt cagccccata   3120

cgatataagt tgtta                                                    3135
```

<210> SEQ ID NO 107
<211> LENGTH: 3069
<212> TYPE: DNA
<213> ORGANISM: Artificial Sequence
<220> FEATURE:
<223> OTHER INFORMATION: Plasmid pGV1575

<400> SEQUENCE: 107

```
ctagtgcttg gattctcacc aataaaaaac gcccggcggc aaccgagcgt tctgaacaaa     60

tccagatgga gttctgaggt cattactgga tctatcaaca ggagtccaag cgagctcgat    120

atcaaattac gccccgccct gccactcatc gcagtactgt tgtaattcat taagcattct    180

gccgacatgg aagccatcac agacggcatg atgaacctga atcgccagcg gcatcagcac    240

cttgtcgcct tgcgtataat atttgcccat ggtgaaaacg ggggcgaaga agttgtccat    300

attggccacg tttaaatcaa aactggtgaa actcacccag ggattggctg agacgaaaaa    360

catattctca ataaaccctt tagggaaata ggccaggttt tcaccgtaac acgccacatc    420

ttgcgaatat atgtgtagaa actgccggaa atcgtcgtgg tattcactcc agagcgatga    480

aaacgtttca gtttgctcat ggaaaacggt gtaacaaggg tgaacactat cccatatcac    540

cagctcaccg tctttcattg ccatacgaaa ctccggatga gcattcatca ggcgggcaag    600

aatgtgaata aaggccggat aaaacttgtg cttatttttc tttacggtct ttaaaaaggc    660

cgtaatatcc agctgaacgg tctggttata ggtacattga gcaactgact gaaatgcctc    720

aaaatgttct ttacgatgcc attgggatat atcaacggtg gtatatccag tgattttttt    780

ctccatttta gcttccttag ctcctgaaaa tctcgataac tcaaaaaata cgcccggtag    840

tgatcttatt tcattatggt gaaagttgga acctcttacg tgccgatcaa cgtctcattt    900

tcgccagata tcgacgtcta agaaaccatt attatcatga cattaaccta taaaaatagg    960

cgtatcacga ggccctttcg tcttcacctc gagaaatgtg agcggataac aattgacatt   1020

gtgagcggat aacaagatac tgagcacatc agcaggacgc actgaccggg aattcattaa   1080

agaggagaaa gtcgacatgg caaagatagc tattaatggt tttggaagaa taggaagatt   1140

agctttaaga agaattcttg aagtacctgg attggaagtt gttgcaataa acgacttaac   1200

tgatgcaaaa atgttagcac acttatttaa atatgattca tcacaaggaa gattcaatgg   1260

agaaattgaa gttaaagaag gagctttcgt agtaaacgga aaagaagtta aagttttcgc   1320

tgaagcagat cctgaaaaat taccttgggg agatcttgga atagacgttg ttcttgagtg   1380

cacaggtttc ttcacaaaga aagaaaaagc agaagctcac gtaagagcag gcgctaaaaa   1440

agttgttata tcagctccag ctggaaacga cttaaagaca atagttttca acgttaataa   1500

tgaagatctt gatggaacag aaacagttat atcaggtgca tcatgcacaa ctaactgctt   1560

agctccaatg gctaaagtat taaatgataa atttggaata gaaaaaggat tcatgactac   1620

aattcatgcg ttcactaatg accaaaacac attagatggt ccacacagaa aaggagattt   1680

aagaagagct agagctgctg ctgtaagtat catccctaac tcaactggtg ctgctaaagc   1740
```

```
tataagccaa gttattcctg acttagctgg aaaattagac ggaaacgctc aaagagttcc   1800
agttccaact ggttcaataa ctgaattagt ttcagttctt aagaaaaaag ttacagttga   1860
agaaatcaac gctgctatga aagaagctgc tgatgaatca tttggataca ctgaagatcc   1920
aatcgtttca gctgacgtag taggaatcaa ctacggatca ttatttgatg caactttaac   1980
taaaattgtt gatgttaacg gatcacaatt agttaaaaca gctgcttggt atgataatga   2040
aatgtcatac acttcacaat tagttagaac tttagcttac tttgcaaaaa tagcaaaata   2100
gggatccata aggaggatta attaagactt cccgggtgat cccatggtac gcgtgctaga   2160
ggcatcaaat aaaacgaaag gctcagtcga aagactgggc ctttcgtttt atctgttgtt   2220
tgtcggtgaa cgctctcctg agtaggacaa atccgccgcc ctagacctag ggatatatt    2280
ccgcttcctc gctcactgac tcgctacgct cggtcgttcg actgcggcga gcggaaatgg   2340
cttacgaacg gggcggagat ttcctggaag atgccaggaa gatacttaac agggaagtga   2400
gagggccgcg gcaaagccgt ttttccatag gctccgcccc cctgacaagc atcacgaaat   2460
ctgacgctca aatcagtggt ggcgaaaccc gacaggacta taaagatacc aggcgtttcc   2520
ccctggcggc tccctcgtgc gctctcctgt tcctgccttt cggtttaccg gtgtcattcc   2580
gctgttatgg ccgcgtttgt ctcattccac gcctgacact cagttccggg taggcagttc   2640
gctccaagct ggactgtatg cacgaacccc ccgttcagtc cgaccgctgc gccttatccg   2700
gtaactatcg tcttgagtcc aacccggaaa gacatgcaaa agcaccactg gcagcagcca   2760
ctggtaattg atttagagga gttagtcttg aagtcatgcg ccggttaagg ctaaactgaa   2820
aggacaagtt ttggtgactg cgctcctcca agccagttac ctcggttcaa agagttggta   2880
gctcagagaa ccttcgaaaa accgccctgc aaggcggttt tttcgttttc agagcaagag   2940
attacgcgca gaccaaaacg atctcaagaa gatcatctta ttaatcagat aaaatatttc   3000
tagatttcag tgcaatttat ctcttcaaat gtagcacctg aagtcagccc catacgatat   3060
aagttgtta                                                           3069
```

```
<210> SEQ ID NO 108
<211> LENGTH: 7093
<212> TYPE: DNA
<213> ORGANISM: Artificial Sequence
<220> FEATURE:
<223> OTHER INFORMATION: Plasmid pGV1609

<400> SEQUENCE: 108
```

```
cgatatcaaa ttacgccccg ccctgccact catcgcagta ctgttgtaat tcattaagca     60
ttctgccgac atggaagcca tcacagacgg catgatgaac ctgaatcgcc agcggcatca    120
gcaccttgtc gccttgcgta taatatttgc ccatggtgaa aacgggggcg aagaagttgt    180
ccatattggc cacgtttaaa tcaaaactgg tgaaactcac ccagggattg gctgagacga    240
aaaacatatt ctcaataaac cctttaggga aataggccag gttttcaccg taacacgcca    300
catcttgcga atatatgtgt agaaactgcc ggaaatcgtc gtggtattca ctccagagcg    360
atgaaaacgt ttcagtttgc tcatggaaaa cggtgtaaca agggtgaaca ctatcccata    420
tcaccagctc accgtctttc attgccatac gaaactccgg atgagcattc atcaggcggg    480
caagaatgtg aataaaggcc ggataaaact tgtgcttatt tttctttacg gtctttaaaa    540
aggccgtaat atccagctga acggtctggt tataggtaca ttgagcaact gactgaaatg    600
cctcaaaatg ttctttacga tgccattggg atatatcaac ggtggtatat ccagtgattt    660
ttttctccat tttagcttcc ttagctcctg aaaatctcga taactcaaaa aatacgcccg    720
```

```
gtagtgatct tatttcatta tggtgaaagt tggaacctct tacgtgccga tcaacgtctc    780
attttcgcca gatatcgacg tctaagaaac cattattatc atgacattaa cctataaaaa    840
taggcgtatc acgaggccct ttcgtcttca cctcgagaat tgtgagcgga taacaattga    900
cattgtgagc ggataacaag atactgagca catcagcagg acgcactgac cgaattcatt    960
aaagaggaga aaggtacaat gttgacaaaa gcaacaaaag aacaaaaatc ccttgtgaaa   1020
aacagagggg cggagcttgt tgttgattgc ttagtggagc aaggtgtcac acatgtattt   1080
ggcattccag gtgcaaaaat tgatgcggta tttgacgctt tacaagataa aggacctgaa   1140
attatcgttg cccggcacga acaaaacgca gcattcatgg cccaagcagt cggccgttta   1200
actggaaaac cgggagtcgt gttagtcaca tcaggaccgg gtgcctctaa cttggcaaca   1260
ggcctgctga cagcgaacac tgaaggagac cctgtcgttg cgcttgctgg aaacgtgatc   1320
cgtgcagatc gtttaaaacg gacacatcaa tctttggata atgcggcgct attccagccg   1380
attacaaaat acagtgtaga agttcaagat gtaaaaaata taccggaagc tgttacaaat   1440
gcatttagga tagcgtcagc agggcaggct ggggccgctt ttgtgagctt tccgcaagat   1500
gttgtgaatg aagtcacaaa tacgaaaaac gtgcgtgctg ttgcagcgcc aaaactcggt   1560
cctgcagcag atgatgcaat cagtgcggcc atagcaaaaa tccaaacagc aaaacttcct   1620
gtcgttttgg tcggcatgaa aggcggaaga ccggaagcaa ttaaagcggt tcgcaagctt   1680
ttgaaaaagg ttcagcttcc atttgttgaa acatatcaag ctgccggtac cctttctaga   1740
gatttagagg atcaatattt tggccgtatc ggtttgttcc gcaaccagcc tggcgattta   1800
ctgctagagc aggcagatgt tgttctgacg atcggctatg acccgattga atatgatccg   1860
aaattctgga atatcaatgg agaccggaca attatccatt tagacgagat tatcgctgac   1920
attgatcatg cttaccagcc tgatcttgaa ttgatcggtg acattccgtc cacgatcaat   1980
catatcgaac acgatgctgt gaaagtggaa tttgcagagc gtgagcagaa aatcctttct   2040
gatttaaaac aatatatgca tgaaggtgag caggtgcctg cagattggaa atcagacaga   2100
gcgcaccctc ttgaaatcgt taaagagttg cgtaatgcag tcgatgatca tgttacagta   2160
acttgcgata tcggttcgca cgccatttgg atgtcacgtt atttccgcag ctacgagccg   2220
ttaacattaa tgatcagtaa cggtatgcaa acactcggcg ttgcgcttcc ttgggcaatc   2280
ggcgcttcat tggtgaaacc gggagaaaaa gtggtttctg tctctggtga cggcggtttc   2340
ttattctcag caatggaatt agagacagca gttcgactaa aagcaccaat tgtacacatt   2400
gtatggaacg acagcacata tgacatggtt gcattccagc aattgaaaaa atataaccgt   2460
acatctgcgg tcgatttcgg aaatatcgat atcgtgaaat atgcggaaag cttcggagca   2520
actggcttgc gcgtagaatc accagaccag ctggcagatg ttctgcgtca aggcatgaac   2580
gctgaaggtc ctgtcatcat cgatgtcccg gttgactaca gtgataacat taatttagca   2640
agtgacaagc ttccgaaaga attcggggaa ctcatgaaaa cgaaagctct ctaggtcgac   2700
gaggaatcac catggctaac tacttcaata cactgaatct gcgccagcag ctggcacagc   2760
tgggcaaatg tcgctttatg ggccgcgatg aattcgccga tggcgcgagc taccttcagg   2820
gtaaaaaagt agtcatcgtc ggctgtggcg cacagggtct gaaccagggc ctgaacatgc   2880
gtgattctgg tctcgatatc tcctacgctc tgcgtaaaga agcgattgcc gagaagcgcg   2940
cgtcctggcg taaagcgacc gaaaatggtt ttaaagtggg tacttacgaa gaactgatcc   3000
cacaggcgga tctggtgatt aacctgacgc cggacaagca gcactctgat gtagtgcgca   3060
ccgtacagcc actgatgaaa gacggcgcgg cgctgggcta ctcgcacggt ttcaacatcg   3120
```

tcgaagtggg cgagcagatc cgtaaagata tcaccgtagt gatggttgcg ccgaaatgcc 3180
caggcaccga agtgcgtgaa gagtacaaac gtgggttcgg cgtaccgacg ctgattgccg 3240
ttcacccgga aaacgatccg aaaggcgaag gcatggcgat tgccaaagcc tgggcggctg 3300
caaccggtgg tcaccgtgcg ggtgtgctgg aatcgtcctt cgttgcggaa gtgaaatctg 3360
acctgatggg cgagcaaacc atcctgtgcg gtatgttgca ggctggctct ctgctgtgct 3420
tcgacaagct ggtggaagaa ggtaccgatc cagcatacgc agaaaaactg attcagttcg 3480
gttgggaaac catcaccgaa gcactgaaac agggcggcat caccctgatg atggaccgtc 3540
tctctaaccc ggcgaaactg cgtgcttatg cgctttctga acagctgaaa gagatcatgg 3600
cacccctgtt ccagaaacat atggacgaca tcatctccgg cgaattctct tccggtatga 3660
tggcggactg ggccaacgat gataagaaac tgctgacctg gcgtgaagag accggcaaaa 3720
ccgcgtttga aaccgcgccg cagtatgaag gcaaaatcgg cgagcaggag tacttcgata 3780
aaggcgtact gatgattgcg atggtgaaag cgggcgttga actggcgttc gaaaccatgg 3840
tcgattccgg catcattgaa gagtctgcat attatgaatc actgcacgag ctgccgctga 3900
ttgccaacac catcgcccgt aagcgtctgt acgaaatgaa cgtggttatc tctgataccg 3960
ctgagtacgg taactatctg ttctcttacg cttgtgtgcc gttgctgaaa ccgtttatgg 4020
cagagctgca accgggcgac ctgggtaaag ctattccgga aggcgcggta gataacgggc 4080
aactgcgtga tgtgaacgaa gcgattcgca gccatgcgat tgagcaggta ggtaagaaac 4140
tgcgcggcta tatgacagat atgaaacgta ttgctgttgc gggttaaccc ggaaggagat 4200
ataccatgcc taagtaccgt tccgccacca ccactcatgg tcgtaatatg gcgggtgctc 4260
gtgcgctgtg gcgcgccacc ggaatgaccg acgccgattt cggtaagccg attatcgcgg 4320
ttgtgaactc gttcacccaa tttgtaccgg gtcacgtcca tctgcgcgat ctcggtaaac 4380
tggtcgccga acaaattgaa gcggctggcg gcgttgccaa agagttcaac accattgcgg 4440
tggatgatgg gattgccatg ggccacgggg ggatgcttta ttcactgcca tctcgcgaac 4500
tgatcgctga ttccgttgag tatatggtca acgcccactg cgccgacgcc atggtctgca 4560
tctctaactg cgacaaaatc accccgggga tgctgatggc ttccctgcgc ctgaatattc 4620
cggtgatctt tgtttccggc ggcccgatgg aggccgggaa aaccaaactt tccgatcaga 4680
tcatcaagct cgatctggtt gatgcgatga tccagggcgc agacccgaaa gtatctgact 4740
cccagagcga tcaggttgaa cgttccgcgt gtccgacctg cggttcctgc tccgggatgt 4800
ttaccgctaa ctcaatgaac tgcctgaccg aagcgctggg cctgtcgcag ccgggcaacg 4860
gctcgctgct ggcaacccac gccgaccgta agcagctgtt ccttaatgct ggtaaacgca 4920
ttgttgaatt gaccaaacgt tattacgagc aaaacgacga aagtgcactg ccgcgtaata 4980
tcgccagtaa ggcggcgttt gaaaacgcca tgacgctgga tatcgcgatg ggtggatcga 5040
ctaacaccgt acttcacctg ctggcggcgg cgcaggaagc ggaaatcgac ttcaccatga 5100
gtgatatcga taagctttcc cgcaaggttc cacagctgtg taaagttgcg ccgagcaccc 5160
agaaatacca tatggaagat gttcaccgtg ctggtggtgt tatcggtatt ctcggcgaac 5220
tggatcgcgc ggggttactg aaccgtgatg tgaaaaacgt acttggcctg acgttgccgc 5280
aaacgctgga acaatacgac gttatgctga cccaggatga cgcggtaaaa aatatgttcc 5340
gcgcaggtcc tgcaggcatt cgtaccacac aggcattctc gcaagattgc cgttgggata 5400
cgctggacga cgatcgcgcc aatggctgta tccgctcgct ggaacacgcc tacagcaaag 5460
acggcggcct ggcggtgctc tacggtaact ttgcggaaaa cggctgcatc gtgaaaacgg 5520
caggcgtcga tgacagcatc ctcaaattca ccggcccggc gaaagtgtac gaaagccagg 5580
acgatgcggt agaagcgatt ctcggcggta aagttgtcgc cggagatgtg gtagtaattc 5640
gctatgaagg cccgaaaggc ggtccgggga tgcaggaaat gctctaccca accagcttcc 5700
tgaaatcaat gggtctcggc aaagcctgtg cgctgatcac cgacggtcgt ttctctggtg 5760
gcacctctgg tctttccatc ggccacgtct caccggaagc ggcaagcggc ggcagcattg 5820
gcctgattga agatggtgac ctgatcgcta tcgacatccc gaaccgtggc attcagttac 5880
aggtaagcga tgccgaactg gcggcgcgtc gtgaagcgca ggacgctcga ggtgacaaag 5940
cctggacgcc gaaaaatcgt gaacgtcagg tctcctttgc cctgcgtgct tatgccagcc 6000
tggcaaccag cgccgacaaa ggcgcggtgc gcgataaatc gaaactgggg ggttaaacgc 6060
gtgctagagg catcaaataa aacgaaaggc tcagtcgaaa gactgggcct ttcgttttat 6120
ctgttgtttg tcggtgaacg ctctcctgag taggacaaat ccgccgccct agacctaggg 6180
gatatattcc gcttcctcgc tcactgactc gctacgctcg gtcgttcgac tgcggcgagc 6240
ggaaatggct tacgaacggg gcggagattt cctggaagat gccaggaaga tacttaacag 6300
ggaagtgaga gggccgcggc aaagccgttt ttccataggc tccgcccccc tgacaagcat 6360
cacgaaatct gacgctcaaa tcagtggtgg cgaaacccga caggactata aagataccag 6420
gcgtttcccc ctggcggctc cctcgtgcgc tctcctgttc ctgcctttcg gtttaccggt 6480
gtcattccgc tgttatggcc gcgtttgtct cattccacgc ctgacactca gttccgggta 6540
ggcagttcgc tccaagctgg actgtatgca cgaacccccc gttcagtccg accgctgcgc 6600
cttatccggt aactatcgtc ttgagtccaa cccggaaaga catgcaaaag caccactggc 6660
agcagccact ggtaattgat ttagaggagt tagtcttgaa gtcatgcgcc ggttaaggct 6720
aaactgaaag gacaagtttt ggtgactgcg ctcctccaag ccagttacct cggttcaaag 6780
agttggtagc tcagagaacc ttcgaaaaac cgccctgcaa ggcggttttt tcgttttcag 6840
agcaagagat tacgcgcaga ccaaaacgat ctcaagaaga tcatcttatt aatcagataa 6900
aatatttcta gatttcagtg caatttatct cttcaaatgt agcacctgaa gtcagcccca 6960
tacgatataa gttgttacta gtgcttggat tctcaccaat aaaaaacgcc cggcggcaac 7020
cgagcgttct gaacaaatcc agatggagtt ctgaggtcat tactggatct atcaacagga 7080
gtccaagcga gct 7093

<210> SEQ ID NO 109
<211> LENGTH: 7112
<212> TYPE: DNA
<213> ORGANISM: Artificial Sequence
<220> FEATURE:
<223> OTHER INFORMATION: Plasmid pGV1655

<400> SEQUENCE: 109
taagaaacca ttattatcat gacattaacc tataaaaata ggcgtatcac gaggcccttt 60
cgtcttcacc tcgagaattg tgagcggata acaattgaca ttgtgagcgg ataacaagat 120
actgagcaca tcagcaggac gcactgaccg aattcattaa agaggagaaa ggtaccatgt 180
atacagtagg agattaccta ttagaccgat tacacgagtt aggaattgaa gaaatttttg 240
gagtccctgg agactataac ttacaatttt tagatcaaat tatttcccgc aaggatatga 300
aatgggtcgg aaatgctaat gaattaaatg cttcatatat ggctgatggc tatgctcgta 360
ctaaaaaagc tgccgcattt cttacaacct ttggagtagg tgaattgagt gcagttaatg 420
gattagcagg aagttacgcc gaaaatttac cagtagtaga aatagtggga tcacctacat 480

-continued

```
caaaagttca aaatgaagga aaatttgttc atcatacgct ggctgacggt gattttaaac    540
actttatgaa aatgcacgaa cctgttacag cagctcgaac tttactgaca gcagaaaatg    600
caaccgttga aattgaccga gtactttctg cactattaaa agaaagaaaa cctgtctata    660
tcaacttacc agttgatgtt gctgctgcaa aagcagagaa accctcactc cctttgaaaa    720
aagaaaactc aacttcaaat acaagtgacc aagagatctt gaacaaaatt caagaaagct    780
tgaaaaatgc caaaaaacca atcgtgatta caggacatga aataattagt tttggcttag    840
aaaaaacagt ctctcaattt atttcaaaga caaaactacc tattacgaca ttaaactttg    900
gaaaaagttc agttgatgaa gctctccctt catttttagg aatctataat ggtaaactct    960
cagagcctaa tcttaaagaa ttcgtggaat cagccgactt catcctgatg cttggagtta   1020
aactcacaga ctcttcaaca ggagccttca ctcatcattt aaatgaaaat aaaatgattt   1080
cactgaatat agatgaagga aaaatattta acgaaagcat ccaaaatttt gattttgaat   1140
ccctcatctc ctctctctta gacctaagcg aaatagaata caaaggaaaa tatatcgata   1200
aaaagcaaga agactttgtt ccatcaaatg cgcttttatc acaagaccgc ctatggcaag   1260
cagttgaaaa cctaactcaa agcaatgaaa caatcgttgc tgaacaaggg acatcattct   1320
ttggcgcttc atcaattttc ttaaaaccaa agagtcattt tattggtcaa cccttatggg   1380
gatcaattgg atatacattc ccagcagcat taggaagcca aattgcagat aaagaaagca   1440
gacacctttt atttattggt gatggttcac ttcaacttac ggtgcaagaa ttaggattag   1500
caatcagaga aaaaattaat ccaatttgct ttattatcaa taatgatggt tatacagtcg   1560
aaagagaaat tcatggacca aatcaaagct acaatgatat tccaatgtgg aattactcaa   1620
aattaccaga atcatttgga gcaacagaag aacgagtagt ctcgaaaatc gttagaactg   1680
aaaatgaatt tgtgtctgtc atgaaagaag ctcaagcaga tccaaataga atgtactgga   1740
ttgagttaat tttggcaaaa gaagatgcac caaaagtact gaaaaaaatg ggcaaactat   1800
ttgctgaaca aaataaatca taaggtcgac aggagatata ctatgcctaa atatcgcagc   1860
gcaactacta cccacggccg caacatggca ggcgcgcgtg ctctgtggcg tgcgactggt   1920
atgactgatg cggactttgg caaaccaatc attgctgtgg ttaatagctt tactcagttc   1980
gttccaggcc atgttcacct gcgtgacctg ggcaagctgg ttgcggagca gatcgaggct   2040
gcgggtggtg tggcgaagga atttaacacc atcgctgttg acgacggtat cgcgatgggt   2100
catggtggta tgctgtacag cctgccgagc cgtgagctga ttgcggacag cgtggaatac   2160
atggttaatg cgcattgtgc ggatgcgatg gtttgtatta gcaactgtga taagattact   2220
ccaggtatgc tgatggcgag cctgcgtctg aacatcccag ttattttcgt gagcggtggt   2280
ccaatggaag cgggtaagac taagctgagc gaccagatta tcaaactgga cctggtggac   2340
gctatgattc aaggtgctga tccaaaggtt agcgatagcc aatctgacca agtggagcgc   2400
agcgcttgcc caacttgtgg cagctgtagc ggtatgttca ctgcgaatag catgaattgt   2460
ctgactgagg ctctgggtct gagccaacca ggtaatggta gcctgctggc gactcatgcg   2520
gatcgcaaac aactgtttct gaacgcgggc aagcgtatcg tggagctgac taagcgctac   2580
tatgaacaga atgatgagtc cgcgctgcca cgcaacattg cgtccaaagc tgctttcgag   2640
aatgcgatga ccctggacat tgctatgggc ggtagcacca atactgttct gcatctgctg   2700
gctgctgctc aagaggctga gattgatttt actatgtccg acattgacaa actgagccgt   2760
aaagtgccgc aactgtgcaa ggtggctcca tctactcaaa agtatcacat ggaggacgtg   2820
catcgcgcgg gtggcgtgat tggcatcctg ggtgagctgg accgtgctgg tctgctgaat   2880
```

-continued

```
cgcgacgtta agaatgttct gggtctgacc ctgccacaga ccctggagca gtatgatgtg   2940
atgctgactc aagacgatgc tgttaagaac atgtttcgtg ctggtccggc gggtatccgc   3000
actacccaag cgtttagcca ggactgtcgc tgggacaccc tggatgatga ccgtgcgaac   3060
ggttgcattc gtagcctgga acatgcgtat tctaaggatg gtggtctggc tgttctgtat   3120
ggcaatttcg ctgagaatgg ttgtattgtt aagaccgcgg gtgttgacga ttctattctg   3180
aagtttactg gtccagctaa ggtttatgag tctcaagatg acgctgttga ggctatcctg   3240
ggtggcaagg tggttgcggg tgacgttgtt gttatccgtt acgagggtcc aaagggtggc   3300
ccaggtatgc aagagatgct gtatccgact tcttttctga agagcatggg cctgggtaag   3360
gcgtgcgctc tgattactga tggccgcttt agcggcggta ctagcggcct gagcattggt   3420
catgttagcc cagaggctgc gtctggtggt tctatcggtc tgatcgagga cggcgatctg   3480
attgcgattg atattccaaa tcgcggtatc caactgcaag tttctgacgc ggagctggct   3540
gctcgccgcg aggctcaaga tgcgcgtggc gataaggcgt ggaccccaaa gaaccgcgag   3600
cgccaagtta gcttcgcgct gcgcgcgtac gcctctctgg cgacttctgc ggataagggt   3660
gctgttcgtg acaagagcaa gctgggtggc taaacgcgtg ctagaggcat caaataaaac   3720
gaaaggctca gtcgaaagac tgggcctttc gttttatctg ttgtttgtcg gtgaacgctc   3780
tcctgagtag gacaaatccg ccgccctaga cctagctagg gtacgggttt tgctgcccgc   3840
aaacgggctg ttctggtgtt gctagtttgt tatcagaatc gcagatccgg cttcagccgg   3900
tttgccggct gaaagcgcta tttcttccag aattgccatg atttttttccc cacgggaggc   3960
gtcactggct cccgtgttgt cggcagcttt gattcgataa gcagcatcgc ctgtttcagg   4020
ctgtctatgt gtgactgttg agctgtaaca agttgtctca ggtgttcaat ttcatgttct   4080
agttgctttg ttttactggt ttcacctgtt ctattaggtg ttacatgctg ttcatctgtt   4140
acattgtcga tctgttcatg gtgaacagct ttaaatgcac caaaaactcg taaaagctct   4200
gatgtatcta tcttttttac accgttttca tctgtgcata tggacagttt tccctttgat   4260
atctaacggt gaacagttgt tctacttttg tttgttagtc ttgatgcttc actgatagat   4320
acaagagcca taagaacctc agatccttcc gtatttagcc agtatgttct ctagtgtggt   4380
tcgttgtttt tgcgtgagcc atgagaacga accattgaga tcatgcttac tttgcatgtc   4440
actcaaaaat tttgcctcaa aactggtgag ctgaattttt gcagttaaag catcgtgtag   4500
tgtttttctt agtccgttac gtaggtagga atctgatgta atggttgttg gtattttgtc   4560
accattcatt tttatctggt tgttctcaag ttcggttacg agatccattt gtctatctag   4620
ttcaacttgg aaaatcaacg tatcagtcgg gcggcctcgc ttatcaacca ccaatttcat   4680
attgctgtaa gtgtttaaat ctttacttat tggtttcaaa acccattggt taagcctttt   4740
aaactcatgg tagttatttt caagcattaa catgaactta aattcatcaa ggctaatctc   4800
tatatttgcc ttgtgagttt tcttttgtgt tagttctttt aataaccact cataaatcct   4860
catagagtat ttgttttcaa aagacttaac atgttccaga ttatatttta tgaatttttt   4920
taactggaaa agataaggca atatctcttc actaaaaact aattctaatt tttcgcttga   4980
gaacttggca tagtttgtcc actggaaaat ctcaaagcct ttaaccaaag gattcctgat   5040
ttccacagtt ctcgtcatca gctctctggt tgctttagct aatacaccat aagcattttc   5100
cctactgatg ttcatcatct gagcgtattg gttataagtg aacgataccg tccgttcttt   5160
ccttgtaggg ttttcaatcg tggggttgag tagtgccaca cagcataaaa ttagcttggt   5220
ttcatgctcc gttaagtcat agcgactaat cgctagttca tttgctttga aaacaactaa   5280
```

ttcagacata catctcaatt ggtctaggtg attttaatca ctataccaat tgagatgggc 5340
tagtcaatga taattactag tccttttccc gggagatctg ggtatctgta aattctgcta 5400
gacctttgct ggaaaacttg taaattctgc tagaccctct gtaaattccg ctagaccttt 5460
gtgtgttttt tttgtttata ttcaagtggt tataatttat agaataaaga aagaataaaa 5520
aaagataaaa agaatagatc ccagccctgt gtataactca ctactttagt cagttccgca 5580
gtattacaaa aggatgtcgc aaacgctgtt tgctcctcta caaaacagac cttaaaaccc 5640
taaaggctta agtagcaccc tcgcaagctc gggcaaatcg ctgaatattc cttttgtctc 5700
cgaccatcag gcacctgagt cgctgtcttt ttcgtgacat tcagttcgct gcgctcacgg 5760
ctctggcagt gaatgggggt aaatggcact acaggcgcct tttatggatt catgcaagga 5820
aactacccat aatacaagaa aagcccgtca cgggcttctc agggcgtttt atggcgggtc 5880
tgctatgtgg tgctatctga ctttttgctg ttcagcagtt cctgccctct gattttccag 5940
tctgaccact tcggattatc ccgtgacagg tcattcagac tggctaatgc acccagtaag 6000
gcagcggtat catcaacagg cttacccgtc ttactgtccc tagtgcttgg attctcacca 6060
ataaaaaacg cccggcggca accgagcgtt ctgaacaaat ccagatggag ttctgaggtc 6120
attactggat ctatcaacag gagtccaagc gagctctcga accccagagt cccgctcaga 6180
agaactcgtc aagaaggcga tagaaggcga tgcgctgcga atcgggagcg gcgataccgt 6240
aaagcacgag gaagcggtca gcccattcgc cgccaagctc ttcagcaata tcacgggtag 6300
ccaacgctat gtcctgatag cggtccgcca cacccagccg gccacagtcg atgaatccag 6360
aaaagcggcc attttccacc atgatattcg gcaagcaggc atcgccatgg gtcacgacga 6420
gatcctcgcc gtcgggcatg cgcgccttga gcctggcgaa cagttcggct ggcgcgagcc 6480
cctgatgctc ttcgtccaga tcatcctgat cgacaagacc ggcttccatc cgagtacgtg 6540
ctcgctcgat gcgatgtttc gcttggtggt cgaatgggca ggtagccgga tcaagcgtat 6600
gcagccgccg cattgcatca gccatgatgg atactttctc ggcaggagca aggtgagatg 6660
acaggagatc ctgccccggc acttcgccca atagcagcca gtcccttccc gcttcagtga 6720
caacgtcgag cacagctgcg caaggaacgc ccgtcgtggc cagccacgat agccgcgctg 6780
cctcgtcctg cagttcattc agggcaccgg acaggtcggt cttgacaaaa agaaccgggc 6840
gcccctgcgc tgacagccgg aacacggcgg catcagagca gccgattgtc tgttgtgccc 6900
agtcatagcc gaatagcctc tccacccaag cggccggaga acctgcgtgc aatccatctt 6960
gttcaatcat gcgaaacgat cctcatcctg tctcttgatc agatcttgat cccctgcgcc 7020
atcagatcct tggcggcaag aaagccatcc agtttacttt gcagggcttc ccaaccttac 7080
cagagggcgc cccagctggc aattccgacg tc 7112

<210> SEQ ID NO 110
<211> LENGTH: 7884
<212> TYPE: DNA
<213> ORGANISM: Artificial Sequence
<220> FEATURE:
<223> OTHER INFORMATION: Plasmid pGV1661

<400> SEQUENCE: 110
ctcgagtccc tatcagtgat agagattgac atccctatca gtgatagaga tactgagcac 60
atcagcagga cgcactgacc gaattcatta aagaggaaca accaaatgga tgaccagtta 120
aaacaaagtg cacttgattt ccatgaattt ccagttccag ggaaaatcca ggtttctcca 180
accaagcctc tggcaacaca gcgcgatctg gcgctggcct actcaccagg cgttgccgca 240

-continued

```
ccttgtcttg aaatcgaaaa agacccgtta aaagcctaca aatataccgc ccgaggtaac    300
ctggtggcgg tgatctctaa cggtacggcg gtgctggggt taggcaacat tggcgcgctg    360
gcaggcaaac cggtgatgga aggcaagggc gttctgttta agaaattcgc cgggattgat    420
gtatttgaca ttgaagttga cgaactcgac ccggacaaat ttattgaagt tgtcgccgcg    480
ctcgaaccaa ccttcggcgg catcaacctc gaagacatta aagcgccaga atgtttctat    540
attgaacaga aactgcgcga gcggatgaat attccggtat tccacgacga tcagcacggc    600
acggcaatta tcagcactgc cgccatcctc aacggcttgc gcgtggtgga gaaaaacatc    660
tccgacgtgc ggatggtggt ttccggcgcg ggtgccgcag caatcgcctg tatgaacctg    720
ctggtagcgc tgggtctgca aaaacataac atcgtggttt gcgattcaaa aggcgttatc    780
tatcagggcc gtgagccaaa catggcggaa accaaagccg catatgcggt ggtggatgac    840
ggcaaacgta ccctcgatga tgtgattgaa ggcgcggata ttttcctggg ctgttccggc    900
ccgaaagtgc tgacccagga aatggtgaag aaaatggctc gtgcgccaat gatcctggcg    960
ctggcgaacc cggaaccgga aattctgccg ccgctggcga aagaagtgcg tccggatgcc   1020
atcatttgca ccggtcgttc tgactatccg aaccaggtga acaacgtcct gtgcttcccg   1080
ttcatcttcc gtggcgcgct ggacgttggc gcaaccgcca tcaacgaaga gatgaaactg   1140
gcggcggtac gtgcgattgc agaactcgcc catgcggaac agagcgaagt ggtggcttca   1200
gcgtatggcg atcaggatct gagctttggt ccggaataca tcattccaaa accgtttgat   1260
ccgcgcttga tcgttaagat cgctcctgcg gtcgctaaag ccgcgatgga gtcgggcgtg   1320
gcgactcgtc cgattgctga tttcgacgtc tacatcgaca agctgactga gttcgtttac   1380
aaaaccaacc tgtttatgaa gccgattttc tcccaggctc gcaaagcgcc gaagcgcgtt   1440
gttctgccgg aaggggaaga ggcgcgcgtt ctgcatgcca ctcaggaact ggtaacgctg   1500
ggactggcga aaccgatcct tatcggtcgt ccgaacgtga tcgaaatgcg cattcagaaa   1560
ctgggcttgc agatcaaagc gggcgttgat tttgagatcg tcaataacga atccgatccg   1620
cgctttaaag agtactggac cgaatacttc cagatcatga agcgtcgcgg cgtcactcag   1680
gaacaggcgc agcgggcgct gatcagtaac ccgacagtga tcggcgcgat catggttcag   1740
cgtggggaag ccgatgcaat gatttgcggt acggtgggtg attatcatga acattttagc   1800
gtggtgaaaa atgtctttgg ttatcgcgat ggcgttcaca ccgcaggtgc catgaacgcg   1860
ctgctgctgc cgagtggtaa cacctttatt gccgatacat atgttaatga tgaaccggat   1920
gcagaagagc tggcggagat caccttgatg gcggcagaaa ctgtccgtcg ttttggtatt   1980
gagccgcgcg ttgctttgtt gtcgcactcc aactttggtt cttctgactg cccgtcgtcg   2040
agcaaaatgc gtcaggcgct ggaactggtc agggaacgtg caccagaact gatgattgat   2100
ggtgaaatgc acggcgatgc agcgctggtg gaagcgattc gcaacgaccg tatgccggac   2160
agctctttga aaggttccgc caatattctg gtgatgccga acatggaagc tgcccgcatt   2220
agttacaact tactgcgtgt ttccagctcg gaaggtgtga ctgtcggccc ggtgctgatg   2280
ggtgtggcga aaccggttca cgtgttaacg ccgatcgcat cggtgcgtcg tatcgtcaac   2340
atggtggcgc tggccgtggt agaagcgcaa acccaaccgc tgtaaggtac cattaaagag   2400
gagaaacgta gcatgaacga acaatattcc gcattgcgta gtaatgtcag tatgctcggc   2460
aaagtgctgg gagaaaccat caaggatgcg ttgggagaac acattcttga acgcgtagaa   2520
actatccgta agttgtcgaa atcttcacgc gctggcaatg atgctaaccg ccaggagttg   2580
ctcaccacct tacaaaattt gtcgaacgac gagctgctgc ccgttgcgcg tgcgtttagt   2640
```

-continued

```
cagttcctga acctggccaa caccgccgag caataccaca gcatttcgcc gaaaggcgaa   2700
gctgccagca acccggaagt gatcgcccgc accctgcgta aactgaaaaa ccagccggaa   2760
ctgagcgaag acaccatcaa aaaagcagtg gaatcgctgt cgctggaact ggtcctcacg   2820
gctcacccaa ccgaaattac ccgtcgtaca ctgatccaca aaatggtgga agtgaacgcc   2880
tgtttaaaac agctcgataa caaagatatc gctgactacg aacacaacca gctgatgcgt   2940
cgcctgcgcc agttgatcgc ccagtcatgg cataccgatg aaatccgtaa gctgcgtcca   3000
agcccggtag atgaagccaa atggggcttt gccgtagtgg aaaacagcct gtggcaaggc   3060
gtaccaaatt acctgcgcga actgaacgaa caactggaag agaacctcgg ctacaaactg   3120
cccgtcgaat ttgttccggt ccgttttact tcgtggatgg gcggcgaccg cgacggcaac   3180
ccgaacgtca ctgccgatat cacccgccac gtcctgctac tcagccgctg gaaagccacc   3240
gatttgttcc tgaaagatat tcaggtgctg gtttctgaac tgtcgatggt tgaagcgacc   3300
cctgaactgc tggcgctggt tggcgaagaa ggtgccgcag aaccgtatcg ctatctgatg   3360
aaaaacctgc gttctcgcct gatggcgaca caggcatggc tggaagcgcg cctgaaaggc   3420
gaagaactgc caaaaccaga aggcctgctg acacaaaacg aagaactgtg ggaaccgctc   3480
tacgcttgct accagtcact tcaggcgtgt ggcatgggta ttatcgccaa cggcgatctg   3540
ctcgacaccc tgcgccgcgt gaaatgtttc ggcgtaccgc tggtccgtat tgatatccgt   3600
caggagagca cgcgtcatac cgaagcgctg ggcgagctga cccgctacct cggtatcggc   3660
gactacgaaa gctggtcaga ggccgacaaa caggcgttcc tgatccgcga actgaactcc   3720
aaacgtccgc ttctgccgcg caactggcaa ccaagcgccg aaacgcgcga agtgctcgat   3780
acctgccagg tgattgccga agcaccgcaa ggctccattg ccgcctacgt gatctcgatg   3840
gcgaaaacgc cgtccgacgt actggctgtc cacctgctgc tgaaagaagc gggtatcggg   3900
tttgcgatgc cggttgctcc gctgtttgaa accctcgatg atctgaacaa cgccaacgat   3960
gtcatgaccc agctgctcaa tattgactgg tatcgtggcc tgattcaggg caaacagatg   4020
gtgatgattg gctattccga ctcagcaaaa gatgcgggag tgatggcagc ttcctgggcg   4080
caatatcagg cacaggatgc attaatcaaa acctgcgaaa aagcgggtat tgagctgacg   4140
ttgttccacg gtcgcggcgg ttccattggt cgcggcggcg cacctgctca tgcggcgctg   4200
ctgtcacaac cgccaggaag cctgaaaggc ggcctgcgcg taaccgaaca gggcgagatg   4260
atccgcttta aatatggtct gccagaaatc accgtcagca gcctgtcgct ttataccggg   4320
gcgattctgg aagccaacct gctgccaccg ccggagccga aagagagctg gcgtcgcatt   4380
atggatgaac tgtcagtcat ctcctgcgat gtctaccgcg gctacgtacg tgaaaacaaa   4440
gattttgtgc cttacttccg ctccgctacg ccggaacaag aactgggcaa actgccgttg   4500
ggttcacgtc cggcgaaacg tcgcccaacc ggcggcgtcg agtcactacg cgccattccg   4560
tggatcttcg cctggacgca aaaccgtctg atgctccccg cctggctggg tgcaggtacg   4620
gcgctgcaaa aagtggtcga agacggcaaa cagagcgagc tggaggctat gtgccgcgat   4680
tggccattct tctcgacgcg tctcggcatg ctggagatgg tcttcgccaa agcagacctg   4740
tggctggcgg aatactatga ccaacgcctg gtagacaaag cactgtggcc gttaggtaaa   4800
gagttacgca acctgcaaga agaagacatc aaagtggtgc tggcgattgc caacgattcc   4860
catctgatgg ccgatctgcc gtggattgca gagtctattc agctacggaa tatttacacc   4920
gacccgctga acgtattgca ggccgagttg ctgcaccgct cccgccaggc agaaaaagaa   4980
ggccaggaac cggatcctcg cgtcgaacaa gcgttaatgg tcactattgc cgggattgcg   5040
```

-continued

```
gcaggtatgc gtaataccgg ctaagtcgac attaaagagg agattactta tgaaagttgc   5100
tgttctgggt gctgcaggtg gtattggtca ggcactggcc ctgctgctga aaactcagct   5160
gccgagcggt tctgaactgt ccctgtacga tattgcgcct gttactccgg gtgtcgctgt   5220
agacctgtct catatcccta cggcagtaaa aatcaaaggc tttagcggtg aagatgcaac   5280
tccggcgctg gaaggtgccg acgttgtact gatctctgcg ggcgtggctc gtaaaccggg   5340
catggaccgt tctgatctgt tcaacgtgaa cgctggcatt gttaaaaatc tggtgcagca   5400
ggttgcaaaa acctgtccga aagcgtgcat tggcatcatc actaacccag ttaacaccac   5460
cgtcgcgatc gcggcagaag tcctgaagaa agcaggcgtg tacgataaaa acaaactgtt   5520
cggtgttact accctggaca tcatccgttc taatactttc gtagctgagc tgaaaggcaa   5580
acagccgggt gaagttgaag ttccggttat cggtggccac agcggtgtta ccatcctgcc   5640
tctgctgagc caggttccgg gtgtgtcttt caccgaacaa gaagtagcgg acctgaccaa   5700
acgtatccaa aacgctggca ccgaagttgt tgaagccaaa gcaggtggtg gctctgctac   5760
cctgtctatg ggtcaagcgg cagcacgctt tggcctgtct ctggttcgcg ctctgcaggg   5820
tgaacaaggt gtggtagaat gtgcttacgt tgaaggcgat ggccagtatg cacgcttctt   5880
ctcccaacct ctgctgctgg gcaaaaacgg tgttgaggaa cgtaaatcta tcggcactct   5940
gtccgcgttc gaacaaaacg cgctggaagg catgctggat actctgaaga aagatatcgc   6000
tctgggtgag gaatttgtta acaaatgacc tagggatata ttccgcttcc tcgctcactg   6060
actcgctacg ctcggtcgtt cgactgcggc gagcggaaat ggcttacgaa cggggcggag   6120
atttcctgga agatgccagg aagatactta acagggaagt gagagggccg cggcaaagcc   6180
gtttttccat aggctccgcc cccctgacaa gcatcacgaa atctgacgct caaatcagtg   6240
gtggcgaaac ccgacaggac tataaagata ccaggcgttt ccccctggcg gctccctcgt   6300
gcgctctcct gttcctgcct ttcggtttac cggtgtcatt ccgctgttat ggccgcgttt   6360
gtctcattcc acgcctgaca ctcagttccg ggtaggcagt tcgctccaag ctggactgta   6420
tgcacgaacc ccccgttcag tccgaccgct gcgccttatc cggtaactat cgtcttgagt   6480
ccaacccgga aagacatgca aaagcaccac tggcagcagc cactggtaat tgatttagag   6540
gagttagtct tgaagtcatg cgccggttaa ggctaaactg aaaggacaag ttttggtgac   6600
tgcgctcctc caagccagtt acctcggttc aaagagttgg tagctcagag aaccttcgaa   6660
aaaccgccct gcaaggcggt tttttcgttt tcagagcaag agattacgcg cagaccaaaa   6720
cgatctcaag aagatcatct tattaatcag ataaaatatt tctagatttc agtgcaattt   6780
atctcttcaa atgtagcacc tgaagtcagc cccatacgat ataagttgtt actagtgctt   6840
ggattctcac caataaaaaa cgcccggcgg caaccgagcg ttctgaacaa atccagatgg   6900
agttctgagg tcattactgg atctatcaac aggagtccaa gcgagctcga tatcaaatta   6960
cgccccgccc tgccactcat cgcagtactg ttgtaattca ttaagcattc tgccgacatg   7020
gaagccatca cagacggcat gatgaacctg aatcgccagc ggcatcagca ccttgtcgcc   7080
ttgcgtataa tatttgccca tggtgaaaac gggggcgaag aagttgtcca tattggccac   7140
gtttaaatca aaactggtga aactcaccca gggattggct gagacgaaaa acatattctc   7200
aataaaccct ttagggaaat aggccaggtt ttcaccgtaa cacgccacat cttgcgaata   7260
tatgtgtaga aactgccgga aatcgtcgtg gtattcactc cagagcgatg aaaacgtttc   7320
agtttgctca tggaaaacgg tgtaacaagg gtgaacacta tcccatatca ccagctcacc   7380
gtctttcatt gccatacgaa actccggatg agcattcatc aggcgggcaa gaatgtgaat   7440
```

aaaggccgga taaaacttgt gcttattttt ctttacggtc tttaaaaagg ccgtaatatc 7500
cagctgaacg gtctggttat aggtacattg agcaactgac tgaaatgcct caaaatgttc 7560
tttacgatgc cattgggata tatcaacggt ggtatatcca gtgatttttt tctccatttt 7620
agcttcctta gctcctgaaa atctcgataa ctcaaaaaat acgcccggta gtgatcttat 7680
ttcattatgg tgaaagttgg aacctcttac gtgccgatca acgtctcatt ttcgccagat 7740
atcgacgtct aagaaaccat tattatcatg acattaacct ataaaaatag gcgtatcacg 7800
aggccctttc gtcttcacga aaccattatt atcatgacat taacctataa aaataggcgt 7860
atcacgaggc cctttcgtct tcac 7884

<210> SEQ ID NO 111
<211> LENGTH: 4895
<212> TYPE: DNA
<213> ORGANISM: Artificial Sequence
<220> FEATURE:
<223> OTHER INFORMATION: Plasmid pGV1685

<400> SEQUENCE: 111
ctcgagtccc tatcagtgat agagattgac atccctatca gtgatagaga tactgagcac 60
atcagcagga cgcactgacc gaattcatta aagaggagaa aggtaccatg cgaattggca 120
taccaagaga acggttaacc aatgaaaccc gtgttgcagc aacgccaaaa acagtggaac 180
agctgctgaa actgggtttt accgtcgcgg tagagagcgg cgcgggtcaa ctggcaagtt 240
ttgacgataa agcgtttgtg caagcgggcg ctgaaattgt agaagggaat agcgtctggc 300
agtcagagat cattctgaag gtcaatgcgc cgttagatga tgaaattgcg ttactgaatc 360
ctgggacaac gctggtgagt tttatctggc ctgcgcagaa tccggaatta atgcaaaaac 420
ttgcggaacg taacgtgacc gtgatggcga tggactctgt gccgcgtatc tcacgcgcac 480
aatcgctgga cgcactaagc tcgatggcga acatcgccgg ttatcgcgcc attgttgaag 540
cggcacatga atttgggcgc ttctttaccg ggcaaattac tgcggccggg aaagtgccac 600
cggcaaaagt gatggtgatt ggtgcgggtg ttgcaggtct ggccgccatt ggcgcagcaa 660
acagtctcgg cgcgattgtg cgtgcattcg acacccgccc ggaagtgaaa gaacaagttc 720
aaagtatggg cgcggaattc ctcgagctgg attttaaaga ggaagctggc agcggcgatg 780
gctatgccaa agtgatgtcg gacgcgttca tcaaagcgga aatggaactc tttgccgccc 840
aggcaaaaga ggtcgatatc attgtcacca ccgcgcttat tccaggcaaa ccagcgccga 900
agctaattac ccgtgaaatg gttgactcca tgaaggcggg cagtgtgatt gtcgacctgg 960
cagcccaaaa cggcggcaac tgtgaataca ccgtgccggg tgaaatcttc actacggaaa 1020
atggtgtcaa agtgattggt tataccgatc ttccgggccg tctgccgacg caatcctcac 1080
agctttacgg cacaaacctc gttaatctgc tgaaactgtt gtgcaaagag aaagacggca 1140
atatcactgt tgattttgat gatgtggtga ttcgcggcgt gaccgtgatc cgtgcgggcg 1200
aaattacctg gccggcaccg ccgattcagg tatcagctca gccgcaggcg gcacaaaaag 1260
cggcaccgga agtgaaaact gaggaaaaat gtacctgctc accgtggcgt aaatacgcgt 1320
tgatggcgct ggcaatcatt ctttttggct ggatggcaag cgttgcgccg aaagaattcc 1380
ttgggcactt caccgttttc gcgctggcct gcgttgtcgg ttattacgtg gtgtggaatg 1440
tatcgcacgc gctgcataca ccgttgatgt cggtcaccaa cgcgatttca gggattattg 1500
ttgtcggagc actgttgcag attggccagg gcggctgggt tagcttcctt agttttatcg 1560
cggtgcttat agccagcatt aatattttcg gtggcttcac cgtgactcag cgcatgctga 1620

```
aaatgttccg caaaaattaa ggggtaacat atgtctggag gattagttac agctgcatac   1680
attgttgccg cgatcctgtt tatcttcagt ctggccggtc tttcgaaaca tgaaacgtct   1740
cgccagggta acaacttcgg tatcgccggg atggcgattg cgttaatcgc aaccattttt   1800
ggaccggata cgggtaatgt tggctggatc ttgctggcga tggtcattgg tggggcaatt   1860
ggtatccgtc tggcgaagaa agttgaaatg accgaaatgc cagaactggt ggcgatcctg   1920
catagcttcg tgggtctggc ggcagtgctg gttggcttta acagctatct gcatcatgac   1980
gcgggaatgg caccgattct ggtcaatatt cacctgacgg aagtgttcct cggtatcttc   2040
atcggggcgg taacgttcac gggttcggtg gtggcgttcg gcaaactgtg tggcaagatt   2100
tcgtctaaac cattgatgct gccaaaccgt cacaaaatga acctggcggc tctggtcgtt   2160
tccttcctgc tgctgattgt atttgttcgc acggacagcg tcggcctgca agtgctggca   2220
ttgctgataa tgaccgcaat tgcgctggta ttcggctggc atttagtcgc ctccatcggt   2280
ggtgcagata tgccagtggt ggtgtcgatg ctgaactcgt actccggctg ggcggctgcg   2340
gctgcgggct ttatgctcag caacgacctg ctgattgtga ccggtgcgct ggtcggttct   2400
tcgggggcta tcctttctta cattatgtgt aaggcgatga accgttcctt tatcagcgtt   2460
attgcgggtg gtttcggcac cgacggctct tctactggcg atgatcagga agtgggtgag   2520
caccgcgaaa tcaccgcaga agagacagcg gaactgctga aaaactccca ttcagtgatc   2580
attactccgg ggtacggcat ggcagtcgcg caggcgcaat atcctgtcgc tgaaattact   2640
gagaaattgc gcgctcgtgg tattaatgtg cgtttcggta tccacccggt cgcggggcgt   2700
ttgcctggac atatgaacgt attgctggct gaagcaaaag taccgtatga catcgtgctg   2760
gaaatggacg agatcaatga tgactttgct gataccgata ccgtactggt gattggtgct   2820
aacgatacgg ttaacccggc ggcgcaggat gatccgaaga gtccgattgc tggtatgcct   2880
gtgctggaag tgtggaaagc gcagaacgtg attgtcttta aacgttcgat gaacactggc   2940
tatgctggtg tgcaaaaccc gctgttcttc aaggaaaaca cccacatgct gtttggtgac   3000
gccaaagcca gcgtggatgc aatcctgaaa gctctgtaac ctagggatat attccgcttc   3060
ctcgctcact gactcgctac gctcggtcgt tcgactgcgg cgagcggaaa tggcttacga   3120
acggggcgga gatttcctgg aagatgccag gaagatactt aacagggaag tgagagggcc   3180
gcggcaaagc cgtttttcca taggctccgc ccccctgaca agcatcacga aatctgacgc   3240
tcaaatcagt ggtggcgaaa cccgacagga ctataaagat accaggcgtt tccccctggc   3300
ggctccctcg tgcgctctcc tgttcctgcc tttcggttta ccggtgtcat tccgctgtta   3360
tggccgcgtt tgtctcattc cacgcctgac actcagttcc gggtaggcag ttcgctccaa   3420
gctggactgt atgcacgaac cccccgttca gtccgaccgc tgcgccttat ccggtaacta   3480
tcgtcttgag tccaacccgg aaagacatgc aaaagcacca ctggcagcag ccactggtaa   3540
ttgatttaga ggagttagtc ttgaagtcat gcgccggtta aggctaaact gaaaggacaa   3600
gttttggtga ctgcgctcct ccaagccagt tacctcggtt caaagagttg gtagctcaga   3660
gaaccttcga aaaaccgccc tgcaaggcgg ttttttcgtt ttcagagcaa gagattacgc   3720
gcagaccaaa acgatctcaa gaagatcatc ttattaatca gataaaatat ttctagattt   3780
cagtgcaatt tatctcttca aatgtagcac ctgaagtcag ccccatacga tataagttgt   3840
tactagtgct tggattctca ccaataaaaa acgcccggcg gcaaccgagc gttctgaaca   3900
aatccagatg gagttctgag gtcattactg gatctatcaa caggagtcca agcgagctcg   3960
atatcaaatt acgccccgcc ctgccactca tcgcagtact gttgtaattc attaagcatt   4020
```

ctgccgacat ggaagccatc acagacggca tgatgaacct gaatcgccag cggcatcagc 4080
accttgtcgc cttgcgtata atatttgccc atggtgaaaa cgggggcgaa gaagttgtcc 4140
atattggcca cgtttaaatc aaaactggtg aaactcaccc agggattggc tgagacgaaa 4200
aacatattct caataaaccc tttagggaaa taggccaggt tttcaccgta acacgccaca 4260
tcttgcgaat atatgtgtag aaactgccgg aaatcgtcgt ggtattcact ccagagcgat 4320
gaaaacgttt cagtttgctc atggaaaacg gtgtaacaag ggtgaacact atcccatatc 4380
accagctcac cgtctttcat tgccatacga aactccggat gagcattcat caggcgggca 4440
agaatgtgaa taaaggccgg ataaaacttg tgcttatttt tctttacggt ctttaaaaag 4500
gccgtaatat ccagctgaac ggtctggtta taggtacatt gagcaactga ctgaaatgcc 4560
tcaaaatgtt ctttacgatg ccattgggat atatcaacgg tggtatatcc agtgattttt 4620
ttctccattt tagcttcctt agctcctgaa aatctcgata actcaaaaaa tacgcccggt 4680
agtgatctta tttcattatg gtgaaagttg gaacctctta cgtgccgatc aacgtctcat 4740
tttcgccaga tatcgacgtc taagaaacca ttattatcat gacattaacc tataaaaata 4800
ggcgtatcac gaggcccttt cgtcttcacg aaaccattat tatcatgaca ttaacctata 4860
aaaataggcg tatcacgagg ccctttcgtc ttcac 4895

<210> SEQ ID NO 112
<211> LENGTH: 5336
<212> TYPE: DNA
<213> ORGANISM: Artificial Sequence
<220> FEATURE:
<223> OTHER INFORMATION: Plasmid pGV1698

<400> SEQUENCE: 112
taagaaacca ttattatcat gacattaacc tataaaaata ggcgtatcac gaggcccttt 60
cgtcttcacc tcgagaattg tgagcggata acaattgaca ttgtgagcgg ataacaagat 120
actgagcaca tcagcaggac gcactgaccg aattcattaa agaggagaaa ggtacaatgt 180
tgacaaaagc aacaaaagaa caaaaatccc ttgtgaaaaa cagaggggcg gagcttgttg 240
ttgattgctt agtggagcaa ggtgtcacac atgtatttgg cattccaggt gcaaaaattg 300
atgcggtatt tgacgcttta caagataaag gacctgaaat tatcgttgcc cggcacgaac 360
aaaacgcagc attcatggcc caagcagtcg gccgtttaac tggaaaaccg ggagtcgtgt 420
tagtcacatc aggaccgggt gcctctaact tggcaacagg cctgctgaca gcgaacactg 480
aaggagaccc tgtcgttgcg cttgctggaa acgtgatccg tgcagatcgt ttaaaacgga 540
cacatcaatc tttggataat gcggcgctat tccagccgat tacaaaatac agtgtagaag 600
ttcaagatgt aaaaaatata ccggaagctg ttacaaatgc atttaggata gcgtcagcag 660
ggcaggctgg ggccgctttt gtgagctttc cgcaagatgt tgtgaatgaa gtcacaaata 720
cgaaaaacgt gcgtgctgtt gcagcgccaa aactcggtcc tgcagcagat gatgcaatca 780
gtgcggccat agcaaaaatc caaacagcaa aacttcctgt cgttttggtc ggcatgaaag 840
gcggaagacc ggaagcaatt aaagcggttc gcaagctttt gaaaaaggtt cagcttccat 900
ttgttgaaac atatcaagct gccggtaccc tttctagaga tttagaggat caatattttg 960
gccgtatcgg tttgttccgc aaccagcctg gcgatttact gctagagcag gcagatgttg 1020
ttctgacgat cggctatgac ccgattgaat atgatccgaa attctggaat atcaatggag 1080
accggacaat tatccattta gacgagatta tcgctgacat tgatcatgct taccagcctg 1140
atcttgaatt gatcggtgac attccgtcca cgatcaatca tatcgaacac gatgctgtga 1200
aagtggaatt tgcagagcgt gagcagaaaa tcctttctga tttaaaacaa tatatgcatg 1260
aaggtgagca ggtgcctgca gattggaaat cagacagagc gcaccctctt gaaatcgtta 1320
aagagttgcg taatgcagtc gatgatcatg ttacagtaac ttgcgatatc ggttcgcacg 1380
ccatttggat gtcacgttat ttccgcagct acgagccgtt aacattaatg atcagtaacg 1440
gtatgcaaac actcggcgtt gcgcttcctt gggcaatcgg cgcttcattg gtgaaaccgg 1500
gagaaaaagt ggtttctgtc tctggtgacg gcggtttctt attctcagca atggaattag 1560
agacagcagt tcgactaaaa gcaccaattg tacacattgt atggaacgac agcacatatg 1620
acatggttgc attccagcaa ttgaaaaaat ataaccgtac atctgcggtc gatttcggaa 1680
atatcgatat cgtgaaatat gcggaaagct tcggagcaac tggcttgcgc gtagaatcac 1740
cagaccagct ggcagatgtt ctgcgtcaag gcatgaacgc tgaaggtcct gtcatcatcg 1800
atgtcccggt tgactacagt gataacatta atttagcaag tgacaagctt ccgaaagaat 1860
tcggggaact catgaaaacg aaagctctct aggtcgacga ggagacaaca ttatggcgaa 1920
ttatttcaac actctgaacc tgcgtcaaca actggcgcaa ctgggtaagt gccgtttcat 1980
gggtcgtgac gagtttgcgg acggtgcttc ttatctgcaa ggcaagaagg ttgttattgt 2040
tggttgcggt gcgcaaggcc tgaatcaagg tctgaatatg cgcgacagcg gcctggacat 2100
tagctatgcg ctgcgcaagg aggctatcgc ggaaaaacgt gctagctggc gcaaggctac 2160
tgagaacggc ttcaaggttg gcacctatga ggagctgatt ccgcaagctg acctggttat 2220
caatctgacc ccagataaac aacatagcga cgttgttcgt actgttcaac cgctgatgaa 2280
ggatggtgct gctctgggtt atagccacgg ctttaacatt gttgaggtag gtgaacaaat 2340
tcgcaaggac attactgttg ttatggtggc tccaaagtgt ccgggtactg aggttcgcga 2400
ggaatataag cgcggtttg gtgttccaac cctgatcgcg gtgcatccag agaatgaccc 2460
aaagggtgag ggtatggcta tcgcgaaggc gtgggctgcg gcgactggcg gccatcgcgc 2520
tggcgttctg gagagcagct ttgtggctga ggttaagagc gatctgatgg gtgaacagac 2580
tattctgtgt ggtatgctgc aagcgggtag cctgctgtgt tttgataaac tggttgagga 2640
gggcactgac ccggcgtatg cggagaagct gatccaattt ggctgggaga ctattactga 2700
ggcgctgaag caaggtggta ttactctgat gatggatcgc ctgagcaatc cagctaagct 2760
gcgcgcgtac gctctgagcg agcaactgaa ggaaattatg gcaccgctgt ttcaaaagca 2820
catggatgat atcattagcg gtgagtttag cagcggcatg atggctgatt gggcgaatga 2880
cgacaaaaag ctgctgactt ggcgcgagga aactggtaag actgctttcg agactgctcc 2940
acaatacgag ggtaagattg gtgaacaaga atattttgac aagggtgttc tgatgatcgc 3000
tatggttaag gctggtgtgg agctggcttt tgagactatg gttgacagcg gtattatcga 3060
ggaaagcgcg tactacgaga gcctgcatga actgccactg atcgcgaata ctattgcgcg 3120
caaacgcctg tatgagatga atgttgtgat tagcgacact gcggaatatg gcaattacct 3180
gtttagctat gcgtgcgttc cactgctgaa gccattcatg gcggaactgc agccaggtga 3240
tctgggcaag gcgatcccag agggtgctgt tgacaatggt cagctgcgcg acgttaatga 3300
ggctatccgt tctcacgcta tcgaacaagt tggcaaaaag ctgcgtggtt acatgaccga 3360
catgaagcgc atcgcggtgg ctggctaacc tagggcgttc ggctgcggcg agcggtatca 3420
gctcactcaa aggcggtaat acggttatcc acagaatcag gggataacgc aggaaagaac 3480
atgtgagcaa aaggccagca aaaggccagg aaccgtaaaa aggccgcgtt gctggcgttt 3540
ttccataggc tccgcccccc tgacgagcat cacaaaaatc gacgctcaag tcagaggtgg 3600
cgaaacccga caggactata aagataccag gcgtttcccc ctggaagctc cctcgtgcgc 3660
tctcctgttc cgaccctgcc gcttaccgga tacctgtccg cctttctccc ttcgggaagc 3720
gtggcgcttt ctcatagctc acgctgtagg tatctcagtt cggtgtaggt cgttcgctcc 3780
aagctgggct gtgtgcacga accccccgtt cagcccgacc gctgcgcctt atccggtaac 3840
tatcgtcttg agtccaaccc ggtaagacac gacttatcgc cactggcagc agccactggt 3900
aacaggatta gcagagcgag gtatgtaggc ggtgctacag agttcttgaa gtggtggcct 3960
aactacggct acactagaag gacagtattt ggtatctgcg ctctgctgaa gccagttacc 4020
ttcggaaaaa gagttggtag ctcttgatcc ggcaaacaaa ccaccgctgg tagcggtggt 4080 tttttgttt gcaagcagca gattacgcgc agaaaaaaag gatctcaaga agatcctttg 4140
atcttttcta cggggtctga cgctcagtgg aacgaaaact cacgttaagg gattttggtc 4200
atgactagtg cttggattct caccaataaa aaacgcccgg cggcaaccga gcgttctgaa 4260
caaatccaga tggagttctg aggtcattac tggatctatc aacaggagtc caagcgagct 4320
cgtaaacttg gtctgacagt taccaatgct taatcagtga ggcacctatc tcagcgatct 4380
gtctatttcg ttcatccata gttgcctgac tccccgtcgt gtagataact acgatacggg 4440
agggcttacc atctggcccc agtgctgcaa tgataccgcg agacccacgc tcaccggctc 4500
cagatttatc agcaataaac cagccagccg gaagggccga gcgcagaagt ggtcctgcaa 4560
ctttatccgc ctccatccag tctattaatt gttgccggga agctagagta agtagttcgc 4620
cagttaatag tttgcgcaac gttgttgcca ttgctacagg catcgtggtg tcacgctcgt 4680
cgtttggtat ggcttcattc agctccggtt cccaacgatc aaggcgagtt acatgatccc 4740
ccatgttgtg caaaaaagcg gttagctcct tcggtcctcc gatcgttgtc agaagtaagt 4800
tggccgcagt gttatcactc atggttatgg cagcactgca taattctctt actgtcatgc 4860
catccgtaag atgcttttct gtgactggtg agtactcaac caagtcattc tgagaatagt 4920
gtatgcggcg accgagttgc tcttgcccgg cgtcaatacg ggataatacc gcgccacata 4980
gcagaacttt aaaagtgctc atcattggaa aacgttcttc ggggcgaaaa ctctcaagga 5040
tcttaccgct gttgagatcc agttcgatgt aacccactcg tgcacccaac tgatcttcag 5100
catcttttac tttcaccagc gtttctgggt gagcaaaaac aggaaggcaa aatgccgcaa 5160
aaaagggaat aagggcgaca cggaaatgtt gaatactcat actcttcctt tttcaatatt 5220
attgaagcat ttatcagggt tattgtctca tgagcggata catatttgaa tgtatttaga 5280
aaaataaaca aataggggtt ccgcgcacat ttccccgaaa agtgccacct gacgtc 5336

<210> SEQ ID NO 113
<211> LENGTH: 2289
<212> TYPE: DNA
<213> ORGANISM: Artificial Sequence
<220> FEATURE:
<223> OTHER INFORMATION: Plasmid pGV1711

<400> SEQUENCE: 113
ctagtgcttg gattctcacc aataaaaaac gcccggcggc aaccgagcgt tctgaacaaa 60
tccagatgga gttctgaggt cattactgga tctatcaaca ggagtccaag cgagctcgta 120
aacttggtct gacagttacc aatgcttaat cagtgaggca cctatctcag cgatctgtct 180
atttcgttca tccatagttg cctgactccc cgtcgtgtag ataactacga tacgggaggg 240
cttaccatct ggccccagtg ctgcaatgat accgcgagac ccacgctcac cggctccaga 300
tttatcagca ataaaccagc cagccggaag ggccgagcgc agaagtggtc ctgcaacttt 360

```
atccgcctcc atccagtcta ttaattgttg ccgggaagct agagtaagta gttcgccagt     420

taatagtttg cgcaacgttg ttgccattgc tacaggcatc gtggtgtcac gctcgtcgtt     480

tggtatggct tcattcagct ccggttccca acgatcaagg cgagttacat gatcccccat     540

gttgtgcaaa aaagcggtta gctccttcgg tcctccgatc gttgtcagaa gtaagttggc     600

cgcagtgtta tcactcatgg ttatggcagc actgcataat tctcttactg tcatgccatc     660

cgtaagatgc ttttctgtga ctggtgagta ctcaaccaag tcattctgag aatagtgtat     720

gcggcgaccg agttgctctt gcccggcgtc aatacgggat aataccgcgc cacatagcag     780

aactttaaaa gtgctcatca ttggaaaacg ttcttcgggg cgaaaactct caaggatctt     840

accgctgttg agatccagtt cgatgtaacc cactcgtgca cccaactgat cttcagcatc     900

ttttactttc accagcgttt ctgggtgagc aaaaacagga aggcaaaatg ccgcaaaaaa     960

gggaataagg gcgacacgga aatgttgaat actcatactc ttcctttttc aatattattg    1020

aagcatttat cagggttatt gtctcatgag cggatacata tttgaatgta tttagaaaaa    1080

taaacaaata ggggttccgc gcacatttcc ccgaaaagtg ccacctgacg tctaagaaac    1140

cattattatc atgacattaa cctataaaaa taggcgtatc acgaggccct ttcgtcttca    1200

cctcgagaat tgtgagcgga taacaattga cattgtgagc ggataacaag atactgagca    1260

catcagcagg acgcactgac cgaattcatt agtcgacatt atgcggccgc ggatccataa    1320

ggaggattaa ttaagacttc ccgggtgatc ccatggtacg cgtgctagag gcatcaaata    1380

aaacgaaagg ctcagtcgaa agactgggcc tttcgtttta tctgttgttt gtcggtgaac    1440

gctctcctga gtaggacaaa tccgccgccc tagacctagg cgttcggctg cggcgagcgg    1500

tatcagctca ctcaaaggcg gtaatacggt tatccacaga atcaggggat aacgcaggaa    1560

agaacatgtg agcaaaaggc cagcaaaagg ccaggaaccg taaaaaggcc gcgttgctgg    1620

cgtttttcca taggctccgc ccccctgacg agcatcacaa aaatcgacgc tcaagtcaga    1680

ggtggcgaaa cccgacagga ctataaagat accaggcgtt tccccctgga agctccctcg    1740

tgcgctctcc tgttccgacc ctgccgctta ccggatacct gtccgccttt ctcccttcgg    1800

gaagcgtggc gctttctcaa tgctcacgct gtaggtatct cagttcggtg taggtcgttc    1860

gctccaagct gggctgtgtg cacgaacccc ccgttcagcc cgaccgctgc gccttatccg    1920

gtaactatcg tcttgagtcc aacccggtaa gacacgactt atcgccactg gcagcagcca    1980

ctggtaacag gattagcaga gcgaggtatg taggcggtgc tacagagttc ttgaagtggt    2040

ggcctaacta cggctacact agaaggacag tatttggtat ctgcgctctg ctgaagccag    2100

ttaccttcgg aaaaagagtt ggtagctctt gatccggcaa acaaaccacc gctggtagcg    2160

gtggtttttt tgtttgcaag cagcagatta cgcgcagaaa aaaaggatct caagaagatc    2220

ctttgatctt ttctacgggg tctgacgctc agtggaacga aaactcacgt taagggattt    2280

tggtcatga                                                            2289
```

<210> SEQ ID NO 114
<211> LENGTH: 6416
<212> TYPE: DNA
<213> ORGANISM: Artificial Sequence
<220> FEATURE:
<223> OTHER INFORMATION: Plasmid pGV1716

<400> SEQUENCE: 114

```
taagaaacca ttattatcat gacattaacc tataaaaata ggcgtatcac gaggcccttt      60

cgtcttcacc tcgagaattg tgagcggata acaattgaca ttgtgagcgg ataacaagat     120
```

```
actgagcaca tcagcaggac gcactgaccg aattcattaa agaggagaaa ggtacaatgt    180
tgacaaaagc aacaaaagaa caaaaatccc ttgtgaaaaa cagaggggcg gagcttgttg    240
ttgattgctt agtggagcaa ggtgtcacac atgtatttgg cattccaggt gcaaaaattg    300
atgcggtatt tgacgcttta caagataaag gacctgaaat tatcgttgcc cggcacgaac    360
aaaacgcagc attcatggcc caagcagtcg gccgtttaac tggaaaaccg ggagtcgtgt    420
tagtcacatc aggaccgggt gcctctaact tggcaacagg cctgctgaca gcgaacactg    480
aaggagaccc tgtcgttgcg cttgctggaa acgtgatccg tgcagatcgt ttaaaacgga    540
cacatcaatc tttggataat gcggcgctat tccagccgat tacaaaatac agtgtagaag    600
ttcaagatgt aaaaaatata ccggaagctg ttacaaatgc atttaggata gcgtcagcag    660
ggcaggctgg ggccgctttt gtgagctttc cgcaagatgt tgtgaatgaa gtcacaaata    720
cgaaaaacgt gcgtgctgtt gcagcgccaa aactcggtcc tgcagcagat gatgcaatca    780
gtgcggccat agcaaaaatc caaacagcaa aacttcctgt cgttttggtc ggcatgaaag    840
gcggaagacc ggaagcaatt aaagcggttc gcaagctttt gaaaaaggtt cagcttccat    900
ttgttgaaac atatcaagct gccggtaccc tttctagaga tttagaggat caatattttg    960
gccgtatcgg tttgttccgc aaccagcctg gcgatttact gctagagcag gcagatgttg   1020
ttctgacgat cggctatgac ccgattgaat atgatccgaa attctggaat atcaatggag   1080
accggacaat tatccattta gacgagatta tcgctgacat tgatcatgct taccagcctg   1140
atcttgaatt gatcggtgac attccgtcca cgatcaatca tatcgaacac gatgctgtga   1200
aagtggaatt tgcagagcgt gagcagaaaa tcctttctga tttaaaacaa tatatgcatg   1260
aaggtgagca ggtgcctgca gattggaaat cagacagagc gcaccctctt gaaatcgtta   1320
aagagttgcg taatgcagtc gatgatcatg ttacagtaac ttgcgatatc ggttcgcacg   1380
ccatttggat gtcacgttat ttccgcagct acgagccgtt aacattaatg atcagtaacg   1440
gtatgcaaac actcggcgtt gcgcttcctt gggcaatcgg cgcttcattg gtgaaaccgg   1500
gagaaaaagt ggtttctgtc tctggtgacg gcggtttctt attctcagca atggaattag   1560
agacagcagt tcgactaaaa gcaccaattg tacacattgt atggaacgac agcacatatg   1620
acatggttgc attccagcaa ttgaaaaaat ataaccgtac atctgcggtc gatttcggaa   1680
atatcgatat cgtgaaatat gcggaaagct tcggagcaac tggcttgcgc gtagaatcac   1740
cagaccagct ggcagatgtt ctgcgtcaag gcatgaacgc tgaaggtcct gtcatcatcg   1800
atgtcccggt tgactacagt gataacatta atttagcaag tgacaagctt ccgaaagaat   1860
tcggggaact catgaaaacg aaagctctct aggtcgacgg atccaggaga caacattatg   1920
tctattccag aaactcaaaa agcgattatt ttctacgagt ccaacggcaa actggaacac   1980
aaagatatcc cggtgccgaa accgaagccg aacgagctgc tgattaacgt aaaatactct   2040
ggtgtgtgcc acactgatct gcacgcttgg cacggtgatt ggcctctgcc gaccaaactg   2100
ccgctggttg gtggtcatga gggtgcgggc gttgtagtag gcatgggtga aaacgtgaag   2160
ggctggaaaa tcggtgacta cgcaggtatc aagtggctga acggttcttg catggcctgc   2220
gaatactgcg agctgggtaa cgaatctaac tgcccgcacg cagacctgtc tggctatacc   2280
catgatggtt cctttcagga atacgctact gcagacgcag tgcaggctgc acatattcca   2340
cagggcaccg atctggcgga ggtagctcct attctgtgcg ctggtattac ggtttacaag   2400
gcgctgaaaa gcgccaacct gcgtgccggc cactgggcag cgatctctgg tgcggcaggc   2460
ggtctgggtt ctctggcagt ccaatatgca aaagcgatgg gttaccgcgt tctgggcatc   2520
```

-continued

```
gacggtggtc cgggtaagga ggaactgttc acttctctgg gcggcgaggt gtttatcgac   2580
ttcactaagg agaaagatat cgtttccgcg gttgttaaag cgaccaacgg tggcgcgcac   2640
ggcattatca acgtatctgt gtccgaggct gcaatcgagg cgtctactcg ttactgccgt   2700
gctaacggca ctgtggtcct ggtaggtctg ccggctggtg ctaaatgttc tagcgatgtt   2760
ttcaaccacg tagtaaaaag catcagcatc gtgggttcct acgttggcaa ccgtgcagac   2820
actcgtgagg ctctggactt cttcgcacgc ggcctggtga aatctccgat taaggttgtt   2880
ggtctgtcta gcctgccgga aatctatgag aaaatggaaa aaggtcagat tgcgggccgt   2940
tacgtggtgg acacctctaa ataagcggcc gcgtcgacga ggagacaaca ttatggcgaa   3000
ttatttcaac actctgaacc tgcgtcaaca actggcgcaa ctgggtaagt gccgtttcat   3060
gggtcgtgac gagtttgcgg acggtgcttc ttatctgcaa ggcaagaagg ttgttattgt   3120
tggttgcggt gcgcaaggcc tgaatcaagg tctgaatatg cgcgacagcg gcctggacat   3180
tagctatgcg ctgcgcaagg aggctatcgc ggaaaaacgt gctagctggc gcaaggctac   3240
tgagaacggc ttcaaggttg gcacctatga ggagctgatt ccgcaagctg acctggttat   3300
caatctgacc ccagataaac aacatagcga cgttgttcgt actgttcaac cgctgatgaa   3360
ggatggtgct gctctgggtt atagccacgg ctttaacatt gttgaggtag gtgaacaaat   3420
tcgcaaggac attactgttg ttatggtggc tccaaagtgt ccgggtactg aggttcgcga   3480
ggaatataag cgcggttttg gtgttccaac cctgatcgcg gtgcatccag agaatgaccc   3540
aaagggtgag ggtatggcta tcgcgaaggc gtgggctgcg gcgactggcg gccatcgcgc   3600
tggcgttctg gagagcagct ttgtggctga ggttaagagc gatctgatgg gtgaacagac   3660
tattctgtgt ggtatgctgc aagcgggtag cctgctgtgt tttgataaac tggttgagga   3720
gggcactgac ccggcgtatg cggagaagct gatccaattt ggctgggaga ctattactga   3780
ggcgctgaag caaggtggta ttactctgat gatggatcgc ctgagcaatc cagctaagct   3840
gcgcgcgtac gctctgagcg agcaactgaa ggaaattatg gcaccgctgt ttcaaaagca   3900
catggatgat atcattagcg gtgagtttag cagcggcatg atggctgatt gggcgaatga   3960
cgacaaaaag ctgctgactt ggcgcgagga aactggtaag actgctttcg agactgctcc   4020
acaatacgag ggtaagattg gtgaacaaga atattttgac aagggtgttc tgatgatcgc   4080
tatggttaag gctggtgtgg agctggcttt tgagactatg gttgacagcg gtattatcga   4140
ggaaagcgcg tactacgaga gcctgcatga actgccactg atcgcgaata ctattgcgcg   4200
caaacgcctg tatgagatga atgttgtgat tagcgacact gcggaatatg gcaattacct   4260
gtttagctat gcgtgcgttc cactgctgaa gccattcatg gcggaactgc agccaggtga   4320
tctgggcaag gcgatcccag agggtgctgt tgacaatggt cagctgcgcg acgttaatga   4380
ggctatccgt tctcacgcta tcgaacaagt tggcaaaaag ctgcgtggtt acatgaccga   4440
catgaagcgc atcgcggtgg ctggctaacc tagggcgttc ggctgcggcg agcggtatca   4500
gctcactcaa aggcggtaat acggttatcc acagaatcag gggataacgc aggaaagaac   4560
atgtgagcaa aaggccagca aaaggccagg aaccgtaaaa aggccgcgtt gctggcgttt   4620
ttccataggc tccgcccccc tgacgagcat cacaaaaatc gacgctcaag tcagaggtgg   4680
cgaaacccga caggactata aagataccag gcgtttcccc ctggaagctc cctcgtgcgc   4740
tctcctgttc cgaccctgcc gcttaccgga tacctgtccg cctttctccc ttcgggaagc   4800
gtggcgcttt ctcatagctc acgctgtagg tatctcagtt cggtgtaggt cgttcgctcc   4860
aagctgggct gtgtgcacga accccccgtt cagcccgacc gctgcgcctt atccggtaac   4920
```

```
tatcgtcttg agtccaaccc ggtaagacac gacttatcgc cactggcagc agccactggt   4980

aacaggatta gcagagcgag gtatgtaggc ggtgctacag agttcttgaa gtggtggcct   5040

aactacggct acactagaag gacagtattt ggtatctgcg ctctgctgaa gccagttacc   5100

ttcggaaaaa gagttggtag ctcttgatcc ggcaaacaaa ccaccgctgg tagcggtggt   5160

tttttgtttg caagcagca gattacgcgc agaaaaaaag gatctcaaga agatcctttg   5220

atcttttcta cggggtctga cgctcagtgg aacgaaaact cacgttaagg gattttggtc   5280

atgactagtg cttggattct caccaataaa aaacgcccgg cggcaaccga gcgttctgaa   5340

caaatccaga tggagttctg aggtcattac tggatctatc aacaggagtc caagcgagct   5400

cgtaaacttg gtctgacagt taccaatgct taatcagtga ggcacctatc tcagcgatct   5460

gtctatttcg ttcatccata gttgcctgac tccccgtcgt gtagataact acgatacggg   5520

agggcttacc atctggcccc agtgctgcaa tgataccgcg agacccacgc tcaccggctc   5580

cagatttatc agcaataaac cagccagccg gaagggccga gcgcagaagt ggtcctgcaa   5640

ctttatccgc ctccatccag tctattaatt gttgccggga agctagagta agtagttcgc   5700

cagttaatag tttgcgcaac gttgttgcca ttgctacagg catcgtggtg tcacgctcgt   5760

cgtttggtat ggcttcattc agctccggtt cccaacgatc aaggcgagtt acatgatccc   5820

ccatgttgtg caaaaaagcg gttagctcct tcggtcctcc gatcgttgtc agaagtaagt   5880

tggccgcagt gttatcactc atggttatgg cagcactgca taattctctt actgtcatgc   5940

catccgtaag atgcttttct gtgactggtg agtactcaac caagtcattc tgagaatagt   6000

gtatgcggcg accgagttgc tcttgcccgg cgtcaatacg ggataatacc gcgccacata   6060

gcagaacttt aaaagtgctc atcattggaa aacgttcttc ggggcgaaaa ctctcaagga   6120

tcttaccgct gttgagatcc agttcgatgt aacccactcg tgcacccaac tgatcttcag   6180

catcttttac tttcaccagc gtttctgggt gagcaaaaac aggaaggcaa aatgccgcaa   6240

aaaagggaat aagggcgaca cggaaatgtt gaatactcat actcttcctt tttcaatatt   6300

attgaagcat ttatcagggt tattgtctca tgagcggata catatttgaa tgtatttaga   6360

aaaataaaca aataggggtt ccgcgcacat ttccccgaaa agtgccacct gacgtc       6416
```

<210> SEQ ID NO 115
<211> LENGTH: 3644
<212> TYPE: DNA
<213> ORGANISM: Artificial Sequence
<220> FEATURE:
<223> OTHER INFORMATION: Plasmid pGV1720

<400> SEQUENCE: 115

```
taagaaacca ttattatcat gacattaacc tataaaaata ggcgtatcac gaggcccttt     60

cgtcttcacc tcgagaattg tgagcggata acaattgaca ttgtgagcgg ataacaagat    120

actgagcaca tcagcaggac gcactgaccg aattcattag tcgacattat gcggccgcgg    180

atccataagg aggattaatt aagacttccc gggtgatccc atggtacgcg tgctagaggc    240

atcaaataaa acgaaaggct cagtcgaaag actgggcctt tcgttttatc tgttgtttgt    300

cggtgaacgc tctcctgagt aggacaaatc cgccgcccta gacctagcta gggtacgggt    360

tttgctgccc gcaaacgggc tgttctggtg ttgctagttt gttatcagaa tcgcagatcc    420

ggcttcagcc ggtttgccgg ctgaaagcgc tatttcttcc agaattgcca tgattttttc    480

cccacgggag gcgtcactgg ctcccgtgtt gtcggcagct ttgattcgat aagcagcatc    540

gcctgtttca ggctgtctat gtgtgactgt tgagctgtaa caagttgtct caggtgttca    600
```

-continued

```
atttcatgtt ctagttgctt tgttttactg gtttcacctg ttctattagg tgttacatgc    660
tgttcatctg ttacattgtc gatctgttca tggtgaacag ctttaaatgc accaaaaact    720
cgtaaaagct ctgatgtatc tatctttttt acaccgtttt catctgtgca tatggacagt    780
tttccctttg atatctaacg gtgaacagtt gttctacttt tgtttgttag tcttgatgct    840
tcactgatag atacaagagc cataagaacc tcagatcctt ccgtatttag ccagtatgtt    900
ctctagtgtg gttcgttgtt tttgcgtgag ccatgagaac gaaccattga gatcatgctt    960
actttgcatg tcactcaaaa attttgcctc aaaactggtg agctgaattt ttgcagttaa   1020
agcatcgtgt agtgtttttc ttagtccgtt acgtaggtag gaatctgatg taatggttgt   1080
tggtattttg tcaccattca tttttatctg gttgttctca agttcggtta cgagatccat   1140
ttgtctatct agttcaactt ggaaaatcaa cgtatcagtc gggcggcctc gcttatcaac   1200
caccaatttc atattgctgt aagtgtttaa atctttactt attggtttca aaacccattg   1260
gttaagcctt ttaaactcat ggtagttatt ttcaagcatt aacatgaact taaattcatc   1320
aaggctaatc tctatatttg ccttgtgagt tttcttttgt gttagttctt ttaataacca   1380
ctcataaatc ctcatagagt atttgttttc aaaagactta acatgttcca gattatattt   1440
tatgaatttt tttaactgga aaagataagg caatatctct tcactaaaaa ctaattctaa   1500
tttttcgctt gagaacttgg catagtttgt ccactggaaa atctcaaagc ctttaaccaa   1560
aggattcctg atttccacag ttctcgtcat cagctctctg gttgctttag ctaatacacc   1620
ataagcattt tccctactga tgttcatcat ctgagcgtat tggttataag tgaacgatac   1680
cgtccgttct ttccttgtag ggttttcaat cgtggggttg agtagtgcca cacagcataa   1740
aattagcttg gtttcatgct ccgttaagtc atagcgacta atcgctagtt catttgcttt   1800
gaaaacaact aattcagaca tacatctcaa ttggtctagg tgattttaat cactatacca   1860
attgagatgg gctagtcaat gataattact agtccttttc ccgggagatc tgggtatctg   1920
taaattctgc tagacctttg ctggaaaact tgtaaattct gctagaccct ctgtaaattc   1980
cgctagacct ttgtgtgttt tttttgttta tattcaagtg gttataattt atagaataaa   2040
gaaagaataa aaaaagataa aaagaataga tcccagccct gtgtataact cactacttta   2100
gtcagttccg cagtattaca aaaggatgtc gcaaacgctg tttgctcctc tacaaaacag   2160
accttaaaac cctaaaggct taagtagcac cctcgcaagc tcgggcaaat cgctgaatat   2220
tccttttgtc tccgaccatc aggcacctga gtcgctgtct ttttcgtgac attcagttcg   2280
ctgcgctcac ggctctggca gtgaatgggg gtaaatggca ctacaggcgc cttttatgga   2340
ttcatgcaag gaaactaccc ataatacaag aaaagcccgt cacgggcttc tcagggcgtt   2400
ttatggcggg tctgctatgt ggtgctatct gactttttgc tgttcagcag ttcctgccct   2460
ctgattttcc agtctgacca cttcggatta tcccgtgaca ggtcattcag actggctaat   2520
gcacccagta aggcagcggt atcatcaaca ggcttacccg tcttactgtc cctagtgctt   2580
ggattctcac caataaaaaa cgcccggcgg caaccgagcg ttctgaacaa atccagatgg   2640
agttctgagg tcattactgg atctatcaac aggagtccaa gcgagctctc gaaccccaga   2700
gtcccgctca gaagaactcg tcaagaaggc gatagaaggc gatgcgctgc gaatcgggag   2760
cggcgatacc gtaaagcacg aggaagcggt cagcccattc gccgccaagc tcttcagcaa   2820
tatcacgggt agccaacgct atgtcctgat agcggtccgc cacacccagc cggccacagt   2880
cgatgaatcc agaaaagcgg ccattttcca ccatgatatt cggcaagcag gcatcgccat   2940
gggtcacgac gagatcctcg ccgtcgggca tgcgcgcctt gagcctggcg aacagttcgg   3000
```

ctggcgcgag cccctgatgc tcttcgtcca gatcatcctg atcgacaaga ccggcttcca 3060
tccgagtacg tgctcgctcg atgcgatgtt tcgcttggtg gtcgaatggg caggtagccg 3120
gatcaagcgt atgcagccgc cgcattgcat cagccatgat ggatactttc tcggcaggag 3180
caaggtgaga tgacaggaga tcctgccccg gcacttcgcc caatagcagc cagtcccttc 3240
ccgcttcagt gacaacgtcg agcacagctg cgcaaggaac gcccgtcgtg gccagccacg 3300
atagccgcgc tgcctcgtcc tgcagttcat tcagggcacc ggacaggtcg gtcttgacaa 3360
aaagaaccgg gcgcccctgc gctgacagcc ggaacacggc ggcatcagag cagccgattg 3420
tctgttgtgc ccagtcatag ccgaatagcc tctccaccca agcggccgga gaacctgcgt 3480
gcaatccatc ttgttcaatc atgcgaaacg atcctcatcc tgtctcttga tcagatcttg 3540
atcccctgcg ccatcagatc cttggcggca agaaagccat ccagtttact ttgcagggct 3600
tcccaacctt accagagggc gccccagctg gcaattccga cgtc 3644

<210> SEQ ID NO 116
<211> LENGTH: 6654
<212> TYPE: DNA
<213> ORGANISM: Artificial Sequence
<220> FEATURE:
<223> OTHER INFORMATION: Plasmid pGV1730

<400> SEQUENCE: 116
caggcaagtg cacaaacaat acttaaataa atactactca gtaataacct atttcttagc 60
atttttgacg aaatttgcta ttttgttaga gtcttttaca ccatttgtct ccacacctcc 120
gcttacatca acaccaataa cgccatttaa tctaagcgca tcaccaacat tttctggcgt 180
cagtccacca gctaacataa aatgtaagct ttcggggctc tcttgccttc caacccagtc 240
agaaatcgag ttccaatcca aaagttcacc tgtcccacct gcttctgaat caaacaaggg 300
aataaacgaa tgaggtttct gtgaagctgc actgagtagt atgttgcagt cttttggaaa 360
tacgagtctt ttaataactg gcaaaccgag gaactcttgg tattcttgcc acgactcatc 420
tccatgcagt tggacgatat caatgccgta atcattgacc agagccaaaa catcctcctt 480
aggttgatta cgaaacacgc caaccaagta tttcggagtg cctgaactat ttttatatgc 540
ttttacaaga cttgaaattt tccttgcaat aaccgggtca attgttctct ttctattggg 600
cacacatata atacccagca agtcagcatc ggaatctaga gcacattctg cggcctctgt 660
gctctgcaag ccgcaaactt tcaccaatgg accagaacta cctgtgaaat taataacaga 720
catactccaa gctgcctttg tgtgcttaat cacgtatact cacgtgctca atagtcacca 780
atgccctccc tcttggccct ctccttttct tttttcgacc gaattaattc ttaatcggca 840
aaaaaagaaa agctccggat caagattgta cgtaaggtga caagctattt ttcaataaag 900
aatatcttcc actactgcca tctggcgtca taactgcaaa gtacacatat attacgatgc 960
tgtctattaa atgcttccta tattatatat atagtaatgt cgttgacgtc gccggcagga 1020
gagtgaaaga gccttgttta tatatttttt tttcctatgt tcaacgagga cagctaggtt 1080
tatgcaaaaa tgtgccatca ccataagctg attcaaatga gctaaaaaaa aaatagttag 1140
aaaataaggt ggtgttgaac gatagcaagt agatcaagac accgtctaac agaaaaaggg 1200
gcagcggaca atattatgca attatgaaga aaagtactca aagggtcgga aaaatattca 1260
aacgatattt gcattaaatc ctcaattgat tgattattcc atagtaaaat accgtaacaa 1320
cacaaaattg ttctcaaatt cataaattat tcattttttc cacgagcctc atcacacgaa 1380
aagtcagaag agcatacata atcttttaaa tgcataggtt atgcattttg caaatgccac 1440

-continued

```
caggcaacaa aaatatgcgt ttagcgggcg gaatcgggaa ggaagccgga accaccaaaa   1500
actggaagct acgtttttaa ggaaggtatg ggtgcagtgt gcttatctca agaaatatta   1560
gttatgatat aaggtgttga agtttagaga taggtaaata aacgcggggt gtgtttatta   1620
catgaagaag aagttagttt ctgccttgct tgtttatctt gcacatcaca tcagcggaac   1680
atatgctcac ccagtcgcga catccaattt atagaaatca gcttgtgggt attgttcaga   1740
gaatttttca atcattggag caatcatttt acatggaccg caccaagtgg cgtagaaatc   1800
tacgacaact agcttgtctt gagcaattgc agagtcgaat tcgctggcag ttttgaattg   1860
agtaaccatt atttgtatcg aggtgtctag tcttctatta cactaatgca gtttcagggt   1920
tttggaaacc acactgttta aacagtgttc cttaatcaag gatacctctt tttttttcct   1980
tggttccact aattcatcgg ttttttttt ggaagacatc ttttccaacg aaaagaatat   2040
acatatcgtt taagagaaat tctccaaatt tgtaaagaag cggacccaga cttaagccta   2100
accaggccaa ttcaacagac tgtcggcaac ttcttgtctg gtctttccat ggtaagtgac   2160
agtgcagtaa taatatgaac caatttattt ttcgttacat aaaaatgctt ataaaacttt   2220
aactaataat tagagattaa atcgcggccg cggatcccta gagagctttc gttttcatga   2280
gttccccgaa ttctttcgga agcttgtcac ttgctaaatt aacgttatca ctgtagtcaa   2340
ccgggacatc aatgatgaca ggcccctcag cgttcatgcc ttgacgcaga acatctgcca   2400
gctggtctgg tgattctacg cgtaagccag ttgctccgaa gctttccgcg tatttcacga   2460
tatcgatatt tccgaaatcg accgcagatg tacgattata ttttttcaat tgctggaatg   2520
caaccatgtc atatgtgctg tcgttccata caatgtgtac aattggtgct tttaaacgaa   2580
ctgctgtctc taattccata gctgagaata agaaaccgcc atcaccggag actgatacta   2640
ctttttctcc cggtttcacc aatgaagcgc cgattgccca aggaagcgca acgccgagtg   2700
tttgcatacc gttactaatc attaatgtta acggctcgta gctgcggaaa taacgtgaca   2760
tccaaatcgc gtgtgaaccg atatcgcaag tcactgtaac atgatcatcg actgcgtttc   2820
gcaattcttt aacgatttca agaggatgca ctctgtctga tttccaatct gcaggcacct   2880
gctcaccctc atgcatatat tgttttaaat cagaaaggat cttctgctca cgttccgcaa   2940
agtctacttt cacagcatcg tgttcgatat gattgatcgt agatggaata tcaccgatca   3000
gttcaagatc cggctggtaa gcatgatcaa tgtcagccag aatctcgtct aaatggatga   3060
tcgtccggtc tccattgaca ttccagaatt tcggatcata ttcaattggg tcatagccga   3120
ttgtcagaac aacatcagcc tgctcaagca gcagatcgcc aggctggttg cggaataaac   3180
cgatccggcc aaaatactga tcctctaaat ctctcgtaag agtaccggca gcttgatatg   3240
tttcaacgaa tggaagctgc actttttca atagcttgcg aaccgcttta atcgcttccg   3300
gtcttccgcc cttcatgccg actaaaacga caggaagttt tgctgtttga atttttgcaa   3360
tggccatact gattgcgtca tctgctgcgg gaccaagttt tggcgctgcg acagcacgta   3420
cgttttttgt atttgtgact tcattcacaa catcttgcgg aaaactcaca aaagcggccc   3480
cagcctgccc tgctgacgct atcctaaacg catttgtaac agcttccggt atattttta   3540
catcttgaac ttctacactg tattttgtaa tcggctggaa tagcgccgca ttatccaaag   3600
attgatgtgt ccgttttaaa cgatctgcac ggatcacgtt cccagcaagc gcaacgacag   3660
ggtcaccttc agtgtttgct gtcagcagtc ctgttgccaa gttcgaagca cctggtcctg   3720
atgtgactaa cacgactccc ggttttccag ttaaacggcc gactgcttgc gccataaatg   3780
ctgcattttg ttcatgccgg gcaacgataa tttcaggccc tttatcttgt aaagcgtcaa   3840
```

```
ataccgcatc aatttttgca cctggaatgc caaatacatg tgtgacacct tgctccgcta   3900
agcaatcaac aacaagctcc gcccctctgc ttttcacaag ggatttttgt tcttttgttg   3960
cttttgtcaa catgtcgact ttatgtgatg attgattgat tgattgtaca gtttgttttt   4020
cttaatatct atttcgatga cttctatatg atattgcact aacaagaaga tattataatg   4080
caattgatac aagacaagga gttatttgct tctcttttat atgattctga caatccatat   4140
tgcgttggta gtcttttttg ctggaacggt tcagcggaaa agacgcatcg ctctttttgc   4200
ttctagaaga aatgccagca aaagaatctc ttgacagtga ctgacagcaa aaatgtcttt   4260
ttctaactag taacaaggct aagatatcag cctgaaataa agggtggtga agtaataatt   4320
aaatcatccg tataaaccta tacacatata tgaggaaaaa taatacaaaa gtgttttaaa   4380
tacagataca tacatgaaca tatgcacgta tagcgcccaa atgtcggtaa tgggatcggc   4440
gagctccagc ttttgttccc tttagtgagg gttaattgcg cgcttggcgt aatcatggtc   4500
atagctgttt cctgtgtgaa attgttatcc gctcacaatt ccacacaaca taggagccgg   4560
aagcataaag tgtaaagcct ggggtgccta atgagtgagg taactcacat taattgcgtt   4620
gcgctcactg cccgctttcc agtcgggaaa cctgtcgtgc cagctgcatt aatgaatcgg   4680
ccaacgcgcg gggagaggcg gtttgcgtat tgggcgctct tccgcttcct cgctcactga   4740
ctcgctgcgc tcggtcgttc ggctgcggcg agcggtatca gctcactcaa aggcggtaat   4800
acggttatcc acagaatcag gggataacgc aggaaagaac atgtgagcaa aaggccagca   4860
aaaggccagg aaccgtaaaa aggccgcgtt gctggcgttt ttccataggc tccgcccccc   4920
tgacgagcat cacaaaaatc gacgctcaag tcagaggtgg cgaaacccga caggactata   4980
aagataccag gcgtttcccc ctggaagctc cctcgtgcgc tctcctgttc cgaccctgcc   5040
gcttaccgga tacctgtccg cctttctccc ttcgggaagc gtggcgcttt ctcatagctc   5100
acgctgtagg tatctcagtt cggtgtaggt cgttcgctcc aagctgggct gtgtgcacga   5160
accccccgtt cagcccgacc gctgcgcctt atccggtaac tatcgtcttg agtccaaccc   5220
ggtaagacac gacttatcgc cactggcagc agccactggt aacaggatta gcagagcgag   5280
gtatgtaggc ggtgctacag agttcttgaa gtggtggcct aactacggct acactagaag   5340
gacagtattt ggtatctgcg ctctgctgaa gccagttacc ttcggaaaaa gagttggtag   5400
ctcttgatcc ggcaaacaaa ccaccgctgg tagcggtggt ttttttgttt gcaagcagca   5460
gattacgcgc agaaaaaaag gatctcaaga agatcctttg atcttttcta cggggtctga   5520
cgctcagtgg aacgaaaact cacgttaagg gattttggtc atgagattat caaaaaggat   5580
cttcacctag atccttttaa attaaaaatg aagttttaaa tcaatctaaa gtatatatga   5640
gtaaacttgg tctgacagtt accaatgctt aatcagtgag gcacctatct cagcgatctg   5700
tctatttcgt tcatccatag ttgcctgact ccccgtcgtg tagataacta cgatacggga   5760
gggcttacca tctggcccca gtgctgcaat gataccgcga gacccacgct caccggctcc   5820
agatttatca gcaataaacc agccagccgg aagggccgag cgcagaagtg gtcctgcaac   5880
tttatccgcc tccatccagt ctattaattg ttgccgggaa gctagagtaa gtagttcgcc   5940
agttaatagt ttgcgcaacg ttgttgccat tgctacaggc atcgtggtgt cacgctcgtc   6000
gtttggtatg gcttcattca gctccggttc ccaacgatca aggcgagtta catgatcccc   6060
catgttgtgc aaaaaagcgg ttagctcctt cggtcctccg atcgttgtca gaagtaagtt   6120
ggccgcagtg ttatcactca tggttatggc agcactgcat aattctctta ctgtcatgcc   6180
atccgtaaga tgcttttctg tgactggtga gtactcaacc aagtcattct gagaatagtg   6240
```

tatgcggcga ccgagttgct cttgcccggc gtcaatacgg gataataccg cgccacatag 6300
cagaacttta aaagtgctca tcattggaaa acgttcttcg gggcgaaaac tctcaaggat 6360
cttaccgctg ttgagatcca gttcgatgta acccactcgt gcacccaact gatcttcagc 6420
atcttttact ttcaccagcg tttctgggtg agcaaaaaca ggaaggcaaa atgccgcaaa 6480
aaagggaata agggcgacac ggaaatgttg aatactcata ctcttccttt ttcaatatta 6540
ttgaagcatt tatcagggtt attgtctcat gagcggatac atatttgaat gtatttagaa 6600
aaataaacaa ataggggttc cgcgcacatt tccccgaaaa gtgccacctg acgt 6654

<210> SEQ ID NO 117
<211> LENGTH: 6597
<212> TYPE: DNA
<213> ORGANISM: Artificial Sequence
<220> FEATURE:
<223> OTHER INFORMATION: Plasmid pGV1745

<400> SEQUENCE: 117
taagaaacca ttattatcat gacattaacc tataaaaata ggcgtatcac gaggcccttt 60
cgtcttcacc tcgagaattg tgagcggata acaattgaca ttgtgagcgg ataacaagat 120
actgagcaca tcagcaggac gcactgaccg aattcattag tcgacaggag aaaggtacta 180
tgcgaattgg cataccaaga gaacggttaa ccaatgaaac ccgtgttgca gcaacgccaa 240
aaacagtgga acagctgctg aaactgggtt ttaccgtcgc ggtagagagc ggcgcgggtc 300
aactggcaag ttttgacgat aaagcgtttg tgcaagcggg cgctgaaatt gtagaaggga 360
atagcgtctg gcagtcagag atcattctga aggtcaatgc gccgttagat gatgaaattg 420
cgttactgaa tcctgggaca acgctggtga gttttatctg gcctgcgcag aatccggaat 480
taatgcaaaa acttgcggaa cgtaacgtga ccgtgatggc gatggactct gtgccgcgta 540
tctcacgcgc acaatcgctg gacgcactaa gctcgatggc gaacatcgcc ggttatcgcg 600
ccattgttga agcggcacat gaatttgggc gcttctttac cgggcaaatt actgcggccg 660
ggaaagtgcc accggcaaaa gtgatggtga ttggtgcggg tgttgcaggt ctggccgcca 720
ttggcgcagc aaacagtctc ggcgcgattg tgcgtgcatt cgacacccgc ccggaagtga 780
aagaacaagt tcaaagtatg ggcgcggaat tcctcgagct ggattttaaa gaggaagctg 840
gcagcggcga tggctatgcc aaagtgatgt cggacgcgtt catcaaagcg gaaatggaac 900
tctttgccgc ccaggcaaaa gaggtcgata tcattgtcac caccgcgctt attccaggca 960
aaccagcgcc gaagctaatt acccgtgaaa tggttgactc catgaaggcg ggcagtgtga 1020
ttgttgacct ggcagcccaa aacggcggca actgtgaata caccgtgccg ggtgaaatct 1080
tcactacgga aaatggtgtc aaagtgattg gttataccga tcttccgggc cgtctgccga 1140
cgcaatcctc acagctttac ggcacaaacc tcgttaatct gctgaaactg ttgtgcaaag 1200
agaaagacgg caatatcact gttgattttg atgatgtggt gattcgcggc gtgaccgtga 1260
tccgtgcggg cgaaattacc tggccggcac cgccgattca ggtatcagct cagccgcagg 1320
cggcacaaaa agcggcaccg gaagtgaaaa ctgaggaaaa atgtacctgc tcaccgtggc 1380
gtaaatacgc gttgatggcg ctggcaatca ttctttttgg ctggatggca agcgttgcgc 1440
cgaaagaatt ccttgggcac ttcaccgttt tcgcgctggc ctgcgttgtc ggttattacg 1500
tggtgtggaa tgtatcgcac gcgctgcata caccgttgat gtcggtcacc aacgcgattt 1560
cagggattat tgttgtcgga gcactgttgc agattggcca gggcggctgg gttagcttcc 1620
ttagttttat cgcggtgctt atagccagca ttaatatttt cggtggcttc accgtgactc 1680

```
agcgcatgct gaaaatgttc cgcaaaaatt aaggggtaac atatgtctgg aggattagtt   1740
acagctgcat acattgttgc cgcgatcctg tttatcttca gtctggccgg tctttcgaaa   1800
catgaaacgt ctcgccaggg taacaacttc ggtatcgccg ggatggcgat tgcgttaatc   1860
gcaaccattt ttggaccgga tacgggtaat gttggctgga tcttgctggc gatggtcatt   1920
ggtggggcaa ttggtatccg tctggcgaag aaagttgaaa tgaccgaaat gccagaactg   1980
gtggcgatcc tgcatagctt cgtgggtctg gcggcagtgc tggttggctt taacagctat   2040
ctgcatcatg acgcgggaat ggcaccgatt ctggtcaata ttcacctgac ggaagtgttc   2100
ctcggtatct tcatcggggc ggtaacgttc acgggttcgg tggtggcgtt cggcaaactg   2160
tgtggcaaga tttcgtctaa accattgatg ctgccaaacc gtcacaaaat gaacctggcg   2220
gctctggtcg tttccttcct gctgctgatt gtatttgttc gcacggacag cgtcggcctg   2280
caagtgctgg cattgctgat aatgaccgca attgcgctgg tattcggctg gcatttagtc   2340
gcctccatcg gtggtgcaga tatgccagtg gtggtgtcga tgctgaactc gtactccggc   2400
tgggcggctg cggctgcggg ctttatgctc agcaacgacc tgctgattgt gaccggtgcg   2460
ctggtcggtt cttcgggggc tatcctttct tacattatgt gtaaggcgat gaaccgttcc   2520
tttatcagcg ttattgcggg tggtttcggc accgacggct cttctactgg cgatgatcag   2580
gaagtgggtg agcaccgcga aatcaccgca gaagagacag cggaactgct gaaaaactcc   2640
cattcagtga tcattactcc ggggtacggc atggcagtcg cgcaggcgca atatcctgtc   2700
gctgaaatta ctgagaaatt gcgcgctcgt ggtattaatg tgcgtttcgg tatccacccg   2760
gtcgcggggc gtttgcctgg acatatgaac gtattgctgg ctgaagcaaa agtaccgtat   2820
gacatcgtgc tggaaatgga cgagatcaat gatgactttg ctgataccga taccgtactg   2880
gtgattggtg ctaacgatac ggttaacccg gcggcgcagg atgatccgaa gagtccgatt   2940
gctggtatgc ctgtgctgga agtgtggaaa gcgcagaacg tgattgtctt taaacgttcg   3000
atgaacactg gctatgctgg tgtgcaaaac ccgctgttct tcaaggaaaa cacccacatg   3060
ctgtttggtg acgccaaagc cagcgtggat gcaatcctga aagctctgta acgtcgacat   3120
tatgcggccg cggatccata aggaggatta attaagactt cccgggtgat cccatggtac   3180
gcgtgctaga ggcatcaaat aaaacgaaag gctcagtcga aagactgggc ctttcgtttt   3240
atctgttgtt tgtcggtgaa cgctctcctg agtaggacaa atccgccgcc ctagacctag   3300
ctagggtacg ggttttgctg cccgcaaacg ggctgttctg gtgttgctag tttgttatca   3360
gaatcgcaga tccggcttca gccggtttgc cggctgaaag cgctatttct tccagaattg   3420
ccatgatttt ttccccacgg gaggcgtcac tggctcccgt gttgtcggca gctttgattc   3480
gataagcagc atcgcctgtt tcaggctgtc tatgtgtgac tgttgagctg taacaagttg   3540
tctcaggtgt tcaatttcat gttctagttg ctttgtttta ctggtttcac ctgttctatt   3600
aggtgttaca tgctgttcat ctgttacatt gtcgatctgt tcatggtgaa cagctttaaa   3660
tgcaccaaaa actcgtaaaa gctctgatgt atctatcttt tttacaccgt tttcatctgt   3720
gcatatggac agttttccct ttgatatcta acggtgaaca gttgttctac ttttgtttgt   3780
tagtcttgat gcttcactga tagatacaag agccataaga acctcagatc cttccgtatt   3840
tagccagtat gttctctagt gtggttcgtt gtttttgcgt gagccatgag aacgaaccat   3900
tgagatcatg cttactttgc atgtcactca aaaattttgc ctcaaaactg gtgagctgaa   3960
tttttgcagt taaagcatcg tgtagtgttt ttcttagtcc gttacgtagg taggaatctg   4020
atgtaatggt tgttggtatt ttgtcaccat tcatttttat ctggttgttc tcaagttcgg   4080
```

ttacgagatc catttgtcta tctagttcaa cttggaaaat caacgtatca gtcgggcggc 4140
ctcgcttatc aaccaccaat ttcatattgc tgtaagtgtt taaatcttta cttattggtt 4200
tcaaaaccca ttggttaagc cttttaaact catggtagtt attttcaagc attaacatga 4260
acttaaattc atcaaggcta atctctatat ttgccttgtg agttttcttt tgtgttagtt 4320
cttttaataa ccactcataa atcctcatag agtatttgtt ttcaaaagac ttaacatgtt 4380
ccagattata ttttatgaat ttttttaact ggaaaagata aggcaatatc tcttcactaa 4440
aaactaattc taatttttcg cttgagaact tggcatagtt tgtccactgg aaaatctcaa 4500
agcctttaac caaaggattc ctgatttcca cagttctcgt catcagctct ctggttgctt 4560
tagctaatac accataagca ttttccctac tgatgttcat catctgagcg tattggttat 4620
aagtgaacga taccgtccgt tctttccttg tagggttttc aatcgtgggg ttgagtagtg 4680
ccacacagca taaaattagc ttggtttcat gctccgttaa gtcatagcga ctaatcgcta 4740
gttcatttgc tttgaaaaca actaattcag acatacatct caattggtct aggtgatttt 4800
aatcactata ccaattgaga tgggctagtc aatgataatt actagtcctt ttcccgggag 4860
atctgggtat ctgtaaattc tgctagacct ttgctggaaa acttgtaaat tctgctagac 4920
cctctgtaaa ttccgctaga cctttgtgtg ttttttttgt ttatattcaa gtggttataa 4980
tttatagaat aaagaaagaa taaaaaaaga taaaaagaat agatcccagc cctgtgtata 5040
actcactact ttagtcagtt ccgcagtatt acaaaaggat gtcgcaaacg ctgtttgctc 5100
ctctacaaaa cagaccttaa aaccctaaag gcttaagtag caccctcgca agctcgggca 5160
aatcgctgaa tattcctttt gtctccgacc atcaggcacc tgagtcgctg tctttttcgt 5220
gacattcagt tcgctgcgct cacggctctg gcagtgaatg ggggtaaatg gcactacagg 5280
cgccttttat ggattcatgc aaggaaacta cccataatac aagaaaagcc cgtcacgggc 5340
ttctcagggc gttttatggc gggtctgcta tgtggtgcta tctgactttt tgctgttcag 5400
cagttcctgc cctctgattt tccagtctga ccacttcgga ttatcccgtg acaggtcatt 5460
cagactggct aatgcaccca gtaaggcagc ggtatcatca acaggcttac ccgtcttact 5520
gtccctagtg cttggattct caccaataaa aaacgcccgg cggcaaccga gcgttctgaa 5580
caaatccaga tggagttctg aggtcattac tggatctatc aacaggagtc caagcgagct 5640
ctcgaacccc agagtcccgc tcagaagaac tcgtcaagaa ggcgatagaa ggcgatgcgc 5700
tgcgaatcgg gagcggcgat accgtaaagc acgaggaagc ggtcagccca ttcgccgcca 5760
agctcttcag caatatcacg ggtagccaac gctatgtcct gatagcggtc cgccacaccc 5820
agccggccac agtcgatgaa tccagaaaag cggccatttt ccaccatgat attcggcaag 5880
caggcatcgc catgggtcac gacgagatcc tcgccgtcgg gcatgcgcgc cttgagcctg 5940
gcgaacagtt cggctggcgc gagcccctga tgctcttcgt ccagatcatc ctgatcgaca 6000
agaccggctt ccatccgagt acgtgctcgc tcgatgcgat gtttcgcttg gtggtcgaat 6060
gggcaggtag ccggatcaag cgtatgcagc cgccgcattg catcagccat gatggatact 6120
ttctcggcag gagcaaggtg agatgacagg agatcctgcc ccggcacttc gcccaatagc 6180
agccagtccc ttcccgcttc agtgacaacg tcgagcacag ctgcgcaagg aacgcccgtc 6240
gtggccagcc acgatagccg cgctgcctcg tcctgcagtt cattcagggc accggacagg 6300
tcggtcttga caaaaagaac cgggcgcccc tgcgctgaca gccggaacac ggcggcatca 6360
gagcagccga ttgtctgttg tgcccagtca tagccgaata gcctctccac ccaagcggcc 6420
ggagaacctg cgtgcaatcc atcttgttca atcatgcgaa acgatcctca tcctgtctct 6480
tgatcagatc ttgatcccct gcgccatcag atccttggcg gcaagaaagc catccagttt 6540
actttgcagg gcttcccaac cttaccagag ggcgccccag ctggcaattc cgacgtc 6597

<210> SEQ ID NO 118
<211> LENGTH: 3625
<212> TYPE: DNA
<213> ORGANISM: Artificial Sequence
<220> FEATURE:
<223> OTHER INFORMATION: Plasmid pGV1777

<400> SEQUENCE: 118
taagaaacca ttattatcat gacattaacc tataaaaata ggcgtatcac gaggcccttt 60
cgtcttcacc tcgagaattg tgagcggata acaattgaca ttgtgagcgg ataacaagat 120
actgagcaca tcagcaggac gcactgaccg aattcattaa agaggagaaa ggtacctgca 180
cgtcgacgag gagacaacat tatggcgaat tatttcaaca ctctgaacct gcgtcaacaa 240
ctggcgcaac tgggtaagtg ccgtttcatg ggtcgtgacg agtttgcgga cggtgcttct 300
tatctgcaag gcaagaaggt tgttattgtt ggttgcggtg cgcaaggcct gaatcaaggt 360
ctgaatatgc gcgacagcgg cctggacatt agctatgcgc tgcgcaagga ggctatcgcg 420
gaaaaacgtg ctagctggcg caaggctact gagaacggct tcaaggttgg cacctatgag 480
gagctgattc cgcaagctga cctggttatc aatctgaccc cagataaaca acatagcgac 540
gttgttcgta ctgttcaacc gctgatgaag gatggtgctg ctctgggtta tagccacggc 600
tttaacattg ttgaggtagg tgaacaaatt cgcaaggaca ttactgttgt tatggtggct 660
ccaaagtgtc cgggtactga ggttcgcgag gaatataagc gcggttttgg tgttccaacc 720
ctgatcgcgg tgcatccaga gaatgaccca aagggtgagg gtatggctat cgcgaaggcg 780
tgggctgcgg cgactggcgg ccatcgcgct ggcgttctgg agagcagctt tgtggctgag 840
gttaagagcg atctgatggg tgaacagact attctgtgtg gtatgctgca agcgggtagc 900
ctgctgtgtt ttgataaact ggttgaggag ggcactgacc cggcgtatgc ggagaagctg 960
atccaatttg gctgggagac tattactgag gcgctgaagc aaggtggtat tactctgatg 1020
atggatcgcc tgagcaatcc agctaagctg cgcgcgtacg ctctgagcga gcaactgaag 1080
gaaattatgg caccgctgtt tcaaaagcac atggatgata tcattagcgg tgagtttagc 1140
agcggcatga tggctgattg ggcgaatgac gacaaaaagc tgctgacttg gcgcgaggaa 1200
actggtaaga ctgctttcga gactgctcca caatacgagg gtaagattgg tgaacaagaa 1260
tattttgaca agggtgttct gatgatcgct atggttaagg ctggtgtgga gctggctttt 1320
gagactatgg ttgacagcgg tattatcgag gaaagcgcgt actacgagag cctgcatgaa 1380
ctgccactga tcgcgaatac tattgcgcgc aaacgcctgt atgagatgaa tgttgtgatt 1440
agcgacactg cggaatatgg caattacctg tttagctatg cgtgcgttcc actgctgaag 1500
ccattcatgg cggaactgca gccaggtgat ctgggcaagg cgatcccaga gggtgctgtt 1560
gacaatggtc agctgcgcga cgttaatgag gctatccgtt ctcacgctat cgaacaagtt 1620
ggcaaaaagc tgcgtggtta catgaccgac atgaagcgca tcgcggtggc tggctaacct 1680
agggcgttcg gctgcggcga gcggtatcag ctcactcaaa ggcggtaata cggttatcca 1740
cagaatcagg ggataacgca ggaaagaaca tgtgagcaaa aggccagcaa aaggccagga 1800
accgtaaaaa ggccgcgttg ctggcgtttt tccataggct ccgcccccct gacgagcatc 1860
acaaaaatcg acgctcaagt cagaggtggc gaaacccgac aggactataa agataccagg 1920
cgtttccccc tggaagctcc ctcgtgcgct ctcctgttcc gaccctgccg cttaccggat 1980

```
acctgtccgc ctttctccct tcgggaagcg tggcgctttc tcatagctca cgctgtaggt   2040
atctcagttc ggtgtaggtc gttcgctcca agctgggctg tgtgcacgaa ccccccgttc   2100
agcccgaccg ctgcgcctta tccggtaact atcgtcttga gtccaacccg gtaagacacg   2160
acttatcgcc actggcagca gccactggta acaggattag cagagcgagg tatgtaggcg   2220
gtgctacaga gttcttgaag tggtggccta actacggcta cactagaagg acagtatttg   2280
gtatctgcgc tctgctgaag ccagttacct tcggaaaaag agttggtagc tcttgatccg   2340
gcaaacaaac caccgctggt agcggtggtt tttttgtttg caagcagcag attacgcgca   2400
gaaaaaaagg atctcaagaa gatcctttga tcttttctac ggggtctgac gctcagtgga   2460
acgaaaactc acgttaaggg attttggtca tgactagtgc ttggattctc accaataaaa   2520
aacgcccggc ggcaaccgag cgttctgaac aaatccagat ggagttctga ggtcattact   2580
ggatctatca acaggagtcc aagcgagctc gtaaacttgg tctgacagtt accaatgctt   2640
aatcagtgag gcacctatct cagcgatctg tctatttcgt tcatccatag ttgcctgact   2700
ccccgtcgtg tagataacta cgatacggga gggcttacca tctggcccca gtgctgcaat   2760
gataccgcga gacccacgct caccggctcc agatttatca gcaataaacc agccagccgg   2820
aagggccgag cgcagaagtg gtcctgcaac tttatccgcc tccatccagt ctattaattg   2880
ttgccgggaa gctagagtaa gtagttcgcc agttaatagt ttgcgcaacg ttgttgccat   2940
tgctacaggc atcgtggtgt cacgctcgtc gtttggtatg gcttcattca gctccggttc   3000
ccaacgatca aggcgagtta catgatcccc catgttgtgc aaaaaagcgg ttagctcctt   3060
cggtcctccg atcgttgtca gaagtaagtt ggccgcagtg ttatcactca tggttatggc   3120
agcactgcat aattctctta ctgtcatgcc atccgtaaga tgcttttctg tgactggtga   3180
gtactcaacc aagtcattct gagaatagtg tatgcggcga ccgagttgct cttgcccggc   3240
gtcaatacgg gataataccg cgccacatag cagaacttta aaagtgctca tcattggaaa   3300
acgttcttcg gggcgaaaac tctcaaggat cttaccgctg ttgagatcca gttcgatgta   3360
acccactcgt gcacccaact gatcttcagc atcttttact ttcaccagcg tttctgggtg   3420
agcaaaaaca ggaaggcaaa atgccgcaaa aaagggaata agggcgacac ggaaatgttg   3480
aatactcata ctcttccttt ttcaatatta ttgaagcatt tatcagggtt attgtctcat   3540
gagcggatac atatttgaat gtatttagaa aaataaacaa ataggggttc cgcgcacatt   3600
tccccgaaaa gtgccacctg acgtc                                         3625
```

<210> SEQ ID NO 119
<211> LENGTH: 8870
<212> TYPE: DNA
<213> ORGANISM: Artificial Sequence
<220> FEATURE:
<223> OTHER INFORMATION: Plasmid pGV1914

<400> SEQUENCE: 119

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cataccacag cttttcaatt    420
```

caattcatca ttttttttt attctttttt ttgatttcgg tttccttgaa atttttttga 480
ttcggtaatc tccgaacaga aggaagaacg aaggaaggag cacagactta gattggtata 540
tatacgcata tgtagtgttg aagaaacatg aaattgccca gtattcttaa cccaactgca 600
cagaacaaaa acctgcagga aacgaagata aatcatgtcg aaagctacat ataaggaacg 660
tgctgctact catcctagtc ctgttgctgc caagctattt aatatcatgc acgaaaagca 720
aacaaacttg tgtgcttcat tggatgttcg taccaccaag gaattactgg agttagttga 780
agcattaggt cccaaaattt gtttactaaa aacacatgtg gatatcttga ctgatttttc 840
catggagggc acagttaagc cgctaaaggc attatccgcc aagtacaatt ttttactctt 900
cgaagacaga aaatttgctg acattggtaa tacagtcaaa ttgcagtact ctgcgggtgt 960
atacagaata gcagaatggg cagacattac gaatgcacac ggtgtggtgg gcccaggtat 1020
tgttagcggt ttgaagcagg cggcagaaga agtaacaaag gaacctagag gccttttgat 1080
gttagcagaa ttgtcatgca agggctccct atctactgga gaatatacta agggtactgt 1140
tgacattgcg aagagcgaca aagattttgt tatcggcttt attgctcaaa gagacatggg 1200
tggaagagat gaaggttacg attggttgat tatgacaccc ggtgtgggtt tagatgacaa 1260
gggagacgca ttgggtcaac agtatagaac cgtggatgat gtggtctcta caggatctga 1320
cattattatt gttggaagag gactatttgc aaagggaagg gatgctaagg tagagggtga 1380
acgttacaga aaagcaggct gggaagcata tttgagaaga tgcggccagc aaaactaaaa 1440
aactgtatta taagtaaatg catgtatact aaactcacaa attagagctt caatttaatt 1500
atatcagtta ttaccctatg cggtgtgaaa taccgcacag atgcgtaagg agaaaatacc 1560
gcatcaggaa attgtaaacg ttaatatttt gttaaaattc gcgttaaatt tttgttaaat 1620
cagctcattt tttaaccaat aggccgaaat cggcaaaatc ccttataaat caaaagaata 1680
gaccgagata gggttgagtg ttgttccagt ttggaacaag agtccactat taaagaacgt 1740
ggactccaac gtcaaagggc gaaaaaccgt ctatcagggc gatggcccac tacgtgaacc 1800
atcaccctaa tcaagttttt tggggtcgag gtgccgtaaa gcactaaatc ggaaccctaa 1860
agggagcccc cgatttagag cttgacgggg aaagccggcg aggactgcaa tagcacaaga 1920
ttaagataga atggcttcaa acagccgcct tttatacata ttggtaaaag ctcgcgaatc 1980
gcaccatatc ccttatcctg taatcaaatc gatctaggtg cagatacaga tcaattcata 2040
aaaagaaatt gaagcaccag tttatcacta ctacactatc tttttctttt ttttttttt 2100
ttgcgcagtt tcgccctttg ttcaatatca cttgataagt tgtgggcttt ttctgtcact 2160
cattcggctt aaaaagtatt cgttcttttg tgttttatga aaagggaacg tgatataaaa 2220
aaacatcctt tggtgtggga catgggcttt tgtttagaga atggttatca ctaccgcccc 2280
caccccttgaa agccacagaa aatgaaaaag tatgtgaata aggtgtgaac tctataacat 2340
tttggccaaa tgccacagcc gatctgcata ttccaatgga catgatgcaa caacaattga 2400
tgtcacattc tcttacacac ttcgattggt ccgtacgtag tactttttac ataactgact 2460
caggcgtttc cttcattgaa atgctcatct attgccaagt acatagaatc cacagtgcat 2520
aggttaacgc attgtaccca aacgacggga aacaaggaag gatgcagaat gagcacttgt 2580
tatttataaa aagacacggg agggggaatc ccgtctttcg tccgtcggag ccaaagagat 2640
gagccaaagc agaaaaacag gggacgccgc ccttcttccg tcccgtgcgt gaggggggcg 2700
cggccattcg gtttttgcaa tatgacctgt gggccaaaaa tcgaaaaaaa aaaaaaaaat 2760
aagaggcggc tgcggaattt tataagacaa gcgcagggcc aaagaaaaaa taataattga 2820

```
cgtggctgaa caacagtctc tccccacccc tttccaaaaa ggggaatgaa atacgagttc   2880
tttttcccaa ttggtagata ttcaacaaga gacgcgcagt acgtaacatg cgaattgcgt   2940
aattcacggc gataacgtag tatttagatt tagtataatt tgaaccgatg tatttatttg   3000
tctgattgat ttatgtattc aaactgtgta agtttattta tttgcaacaa taattcgttt   3060
gagtacacta ctaatggcgg ccgcttagat gccggagtcc cagtgcttgg tccactggat   3120
ggcctccagg gtgcccaagt ccagtttcca gatggctccg ttctggttca gctcgatagc   3180
cttgacgaag ttctcggcgc aggccaacga gggctgggtg ggatgagcca ggagcttctc   3240
ggcaacctga ggctcaacat ccaaccagga gttgaacgtg tgcaccaggg tggtgcgggt   3300
gatgccgggg ttcacagtgt aagccgtcac gccggtaatg gggggccagtt tcgccaggga   3360
gctggtgaag ttgaccacgg cggccttggt gccggagtag acgggcacct ggtagatggc   3420
attgaatcca gtgacggatc caatgttgca gatgatacca ccgggaccgc ccttgcgctt   3480
gtcccagaag tccagaatgg ccgtcgtggt gttgaccagg ccagtgtagt tgacggcaat   3540
ggtgcgctcg atctggtgat cgtccaggat accagctccg ttgatcagga catcgacggt   3600
cttcagctgg gcgaagatgg tcttcagcag cttggtggtc tcggcaatgg gcacggtcac   3660
atcatagggg tagaaggtga cggtcacctt tggattgatt gccttcagct cggcaatggc   3720
agccgggttc tcaatgcggt cgaggatcac caggttcttc agatcgcgct tgagcagctc   3780
cttgctggtg tccagaccaa tgcctcccag accggcaacg aaaatcacgt tcttgttggt   3840
caaagtaaac gacataccgg tatctcctag atccgtcgaa gtcgaaacta agttctggtg   3900
ttttaaaact aaaaaaaaga ctaactataa aagtagaatt taagaagttt aagaaataga   3960
tttacagaat tacaatcaat acctaccgtc tttatatact tattagtcaa gtaggggaat   4020
aatttcaggg aactggtttc aacctttttt ttcagctttt tccaaatcag agagagcaga   4080
aggtaataga aggtgtaaga aaatgagata gatacatgcg tgggtcaatt gccttgtgtc   4140
atcatttact ccaggcaggt tgcatcactc cattgaggtt gtgcccgttt tttgcctgtt   4200
tgtgcccctg ttctctgtag ttgcgctaag agaatggacc tatgaactga tggttggtga   4260
agaaaacaat attttggtgc tgggattctt ttttttctg gatgccagct taaaaagcgg   4320
gctccattat atttagtgga tgccaggaat aaactgttca cccagacacc tacgatgtta   4380
tatattctgt gtaacccgcc ccctattttg ggcatgtacg ggttacagca gaattaaaag   4440
gctaattttt tgactaaata aagttaggaa aatcactact attaattatt tacgtattct   4500
ttgaaatggc gagtattgat aatgataaac tggatcctta ggatttattc tgttcagcaa   4560
acagcttgcc cattttcttc agtaccttcg gtgcgccttc tttcgccagg atcagttcga   4620
tccagtacat acggttcgga tcggcctggg cctctttcat cacgctcaca aattcgtttt   4680
cggtacgcac aattttagac acaacacggt cctcagttgc gccgaaggac tccggcagtt   4740
tagagtagtt ccacataggg atatcgttgt aagactggtt cggaccgtgg atctcacgct   4800
caacggtgta gccgtcattg ttaataatga agcaaatcgg gttgatcttt tcacgaattg   4860
ccagacccag ttcctgtacg gtcagctgca gggaaccgtc accgatgaac agcagatgac   4920
gagattcttt atcagcgatc tgagagccca gcgctgccgg gaaagtatag ccaatgctac   4980
cccacagcgg ctgaccgata aaatggcttt tggatttcag aaagatagaa gacgcgccga   5040
aaaagctcgt accttgttcc gccacgatgg tttcattgct ctgggtcagg ttctccacgg   5100
cctgccacag gcgatcctgg gacagcagtg cgttagatgg tacgaaatct tcttgctttt   5160
tgtcaatgta tttgccttta tactcgattt cggacaggtc cagcagagag ctgatcaggc   5220
```

-continued

```
tttcgaagtc gaagttctgg atacgctcgt tgaagatttt accctcgtcg atgttcaggc   5280
taatcatttt gttttcgttc agatggtgag tgaatgcacc ggtagaagag tcggtcagtt   5340
taacgcccag catcaggatg aagtccgcag attcaacaaa ttctttcagg ttcggttcgc   5400
tcagagtacc gttgtagatg cccaggaaag acggcagagc ctcgtcaaca gaggacttgc   5460
cgaagttcag ggtggtaatc ggcagtttgg ttttgctgat gaattgggtc acggtcttct   5520
ccagaccaaa agaaatgatt tcgtggccgg tgatcacgat tggtttcttt gcgtttttca   5580
gagactcctg gattttgttc aggatttcct ggtcgctagt gttagaagtg gagttttctt   5640
tcttcagcgg caggctcggt ttttccgctt tagctgccgc aacatccaca ggcaggttga   5700
tgtaaactgg tttgcgttct ttcagcagcg cagacagaac gcggtcgatt tccacagtag   5760
cgttctctgc agtcagcagc gtacgtgccg cagtcacagg ttcatgcatt ttcatgaagt   5820
gtttgaaatc gccgtcagcc agagtgtggt ggacgaattt accttcgttc tgaactttgc   5880
tcgttgggct gcctacgatc tccaccaccg gcaggttttc ggcgtaggag cccgccagac   5940
cgttgacggc gctcagttcg ccaacaccga aagtggtcag aaatgccgcg gctttcttgg   6000
tacgtgcata accatctgcc atgtagcttg cgttcagttc gttagcgtta cccacccatt   6060
tcatgtcttt atgagagatg atctgatcca ggaactgcag attgtaatca cccggaacgc   6120
cgaagatttc ttcgataccc agttcatgca gacggtccag cagataatca ccaacagtat   6180
acatgtcgac aaacttagat tagattgcta tgctttcttt ctaatgagca agaagtaaaa   6240
aaagttgtaa tagaacaaga aaaatgaaac tgaaacttga gaaattgaag accgtttatt   6300
aacttaaata tcaatgggag gtcatcgaaa gagaaaaaaa tcaaaaaaaa aattttcaag   6360
aaaaagaaac gtgataaaaa tttttattgc ctttttcgac gaagaaaaag aaacgaggcg   6420
gtctcttttt tcttttccaa acctttagta cgggtaatta acgacaccct agaggaagaa   6480
agaggggaaa tttagtatgc tgtgcttggg tgttttgaag tggtacggcg atgcgcggag   6540
tccgagaaaa tctggaagag taaaaaagga gtagaaacat tttgaagcta tgagctccag   6600
cttttgttcc ctttagtgag ggttaattgc gcgcttggcg taatcatggt catagctgtt   6660
tcctgtgtga aattgttatc cgctcacaat tccacacaac ataggagccg gaagcataaa   6720
gtgtaaagcc tggggtgcct aatgagtgag gtaactcaca ttaattgcgt tgcgctcact   6780
gcccgctttc cagtcgggaa acctgtcgtg ccagctgcat taatgaatcg gccaacgcgc   6840
ggggagaggc ggtttgcgta ttgggcgctc ttccgcttcc tcgctcactg actcgctgcg   6900
ctcggtcgtt cggctgcggc gagcggtatc agctcactca aaggcggtaa tacggttatc   6960
cacagaatca ggggataacg caggaaagaa catgtgagca aaaggccagc aaaaggccag   7020
gaaccgtaaa aaggccgcgt tgctggcgtt tttccatagg ctccgccccc ctgacgagca   7080
tcacaaaaat cgacgctcaa gtcagaggtg gcgaaacccg acaggactat aaagatacca   7140
ggcgtttccc cctggaagct ccctcgtgcg ctctcctgtt ccgaccctgc cgcttaccgg   7200
atacctgtcc gcctttctcc cttcgggaag cgtggcgctt tctcatagct cacgctgtag   7260
gtatctcagt tcggtgtagg tcgttcgctc caagctgggc tgtgtgcacg aaccccccgt   7320
tcagcccgac cgctgcgcct tatccggtaa ctatcgtctt gagtccaacc cggtaagaca   7380
cgacttatcg ccactggcag cagccactgg taacaggatt agcagagcga ggtatgtagg   7440
cggtgctaca gagttcttga agtggtggcc taactacggc tacactagaa ggacagtatt   7500
tggtatctgc gctctgctga agccagttac cttcggaaaa agagttggta gctcttgatc   7560
cggcaaacaa accaccgctg gtagcggtgg tttttttgtt tgcaagcagc agattacgcg   7620
```

```
cagaaaaaaa ggatctcaag aagatccttt gatcttttct acggggtctg acgctcagtg   7680
gaacgaaaac tcacgttaag ggattttggt catgagatta tcaaaaagga tcttcaccta   7740
gatcctttta aattaaaaat gaagttttaa atcaatctaa agtatatatg agtaaacttg   7800
gtctgacagt taccaatgct taatcagtga ggcacctatc tcagcgatct gtctatttcg   7860
ttcatccata gttgcctgac tccccgtcgt gtagataact acgatacggg agggcttacc   7920
atctggcccc agtgctgcaa tgataccgcg agacccacgc tcaccggctc cagatttatc   7980
agcaataaac cagccagccg gaagggccga gcgcagaagt ggtcctgcaa ctttatccgc   8040
ctccatccag tctattaatt gttgccggga agctagagta agtagttcgc cagttaatag   8100
tttgcgcaac gttgttgcca ttgctacagg catcgtggtg tcacgctcgt cgtttggtat   8160
ggcttcattc agctccggtt cccaacgatc aaggcgagtt acatgatccc ccatgttgtg   8220
caaaaaagcg gttagctcct tcggtcctcc gatcgttgtc agaagtaagt tggccgcagt   8280
gttatcactc atggttatgg cagcactgca taattctctt actgtcatgc catccgtaag   8340
atgcttttct gtgactggtg agtactcaac caagtcattc tgagaatagt gtatgcggcg   8400
accgagttgc tcttgcccgg cgtcaatacg ggataatacc gcgccacata gcagaacttt   8460
aaaagtgctc atcattggaa aacgttcttc ggggcgaaaa ctctcaagga tcttaccgct   8520
gttgagatcc agttcgatgt aacccactcg tgcacccaac tgatcttcag catcttttac   8580
tttcaccagc gtttctgggt gagcaaaaac aggaaggcaa aatgccgcaa aaaagggaat   8640
aagggcgaca cggaaatgtt gaatactcat actcttcctt tttcaatatt attgaagcat   8700
ttatcagggt tattgtctca tgagcggata catatttgaa tgtatttaga aaaataaaca   8760
aataggggtt ccgcgcacat ttccccgaaa agtgccacct gacgtctaag aaaccattat   8820
tatcatgaca ttaacctata aaaataggcg tatcacgagg ccctttcgtc              8870
```

<210> SEQ ID NO 120
<211> LENGTH: 9516
<212> TYPE: DNA
<213> ORGANISM: Artificial Sequence
<220> FEATURE:
<223> OTHER INFORMATION: Plasmid pGV1936

<400> SEQUENCE: 120

```
ccagttaact gtgggaatac tcaggtatcg taagatgcaa gagttcgaat ctcttagcaa     60
ccattatttt tttcctcaac ataacgagaa cacacagggg cgctatcgca cagaatcaaa    120
ttcgatgact ggaaattttt tgttaatttc agaggtcgcc tgacgcatat accttttca    180
actgaaaaat tgggagaaaa aggaaaggtg agagcgccgg aaccggcttt tcatatagaa    240
tagagaagcg ttcatgacta aatgcttgca tcacaatact tgaagttgac aatattattt    300
aaggacctat tgttttttcc aataggtggt tagcaatcgt cttactttct aacttttctt    360
accttttaca tttcagcaat atatatatat atatttcaag gatataccat tctaatgtct    420
gcccctaaga agatcgtcgt tttgccaggt gaccacgttg gtcaagaaat cacagccgaa    480
gccattaagg ttcttaaagc tatttctgat gttcgttcca atgtcaagtt cgatttcgaa    540
aatcatttaa ttggtggtgc tgctatcgat gctacaggtg ttccacttcc agatgaggcg    600
ctggaagcct ccaagaaggc tgatgccgtt ttgttaggtg ctgtgggtgg tcctaaatgg    660
ggtaccggta gtgttagacc tgaacaaggt ttactaaaaa tccgtaaaga acttcaattg    720
tacgccaact taagaccatg taactttgca tccgactctc ttttagactt atctccaatc    780
aagccacaat ttgctaaagg tactgacttc gttgttgtca gagaattagt gggaggtatt    840
```

```
tactttggta agagaaagga agacgatggt gatggtgtcg cttgggatag tgaacaatac    900
accgttccag aagtgcaaag aatcacaaga atggccgctt tcatggccct acaacatgag    960
ccaccattgc ctatttggtc cttggataaa gctaatgttt tggcctcttc aagattatgg   1020
agaaaaactg tggaggaaac catcaagaac gaattcccta cattgaaggt tcaacatcaa   1080
ttgattgatt ctgccgccat gatcctagtt aagaacccaa cccacctaaa tggtattata   1140
atcaccagca acatgtttgg tgatatcatc tccgatgaag cctccgttat cccaggttcc   1200
ttgggtttgt tgccatctgc gtccttggcc tctttgccag acaagaacac cgcatttggt   1260
ttgtacgaac catgccacgg ttctgctcca gatttgccaa agaataaggt caaccctatc   1320
gccactatct tgtctgctgc aatgatgttg aaattgtcat tgaacttgcc tgaagaaggt   1380
aaggccattg aagatgcagt taaaaaggtt ttggatgcag gtatcagaac tggtgattta   1440
ggtggttcca acagtaccac cgaagtcggt gatgctgtcg ccgaagaagt taagaaaatc   1500
cttgcttaaa aagattctct tttttatga tatttgtaca taaactttat aaatgaaatt   1560
cataatagaa acgacacgaa attacaaaat ggaatatgtt catagggtag acgaaactat   1620
atacgcaatc tacatacatt tatcaagaag gagaaaaagg aggatgtaaa ggaatacagg   1680
taagcaaatt gatactaatg gctcaacgtg ataaggaaaa agaattgcac tttaacatta   1740
atattgacaa ggaggagggc accacacaaa aagttaggtg taacagaaaa tcatgaaact   1800
atgattccta atttatatat tggaggattt tctctaaaaa aaaaaaaata caacaaataa   1860
aaaacactca atgacctgac catttgatgg agttgccggc ttgatcgaga atggcagctc   1920
ttatatacaa gttcttttag caagcgccgc tgcattattc aagtctcatc atatgaaatt   1980
tctttcgaga gattgtcata atcaaaaaat tgcataatgc atttcttgca acacattttc   2040
tgatataatc ttaccttaat gcaggtttac gtattagttt ttctaaaaga aacgcgacct   2100
ttggatatgg aggcttttcc cataaacgca tgtagtatgc atttacgatg agaatcaatt   2160
tttttccaag ggcgcaaaaa cgcataaacg cataaagtat gcatcagaag gattctcacc   2220
tggttgcaac catacaggtg ttagcgacag taatagaaaa aaaattaaaa taatggtgtt   2280
attgttattt gctttatttc cttggccttt gttgaaggaa ttcgtatacg tattacaaat   2340
aactagtatc gaggaacttg aaagagctga aatttttgca ttcttcttcg gtgattatgc   2400
ctaagccaat gaggtcgccc caaaagaccg caatcttgtc acgaccataa gccatataat   2460
cgcgaacaaa aacccgtttt taggaaggac agaggtccat atcaatataa ttaagaaggc   2520
atgttggcct ctgtttctta atatattcta aataagatgt aaggccttgt aattcagttt   2580
gttcacaaaa ttaaaaactg tttaatgttt tttgttttgt tgtagtattc gagcattaag   2640
gataaaaaaa gcttgtgaat aaaaatcttt cgctaaaaat caatataaga aaatggtaag   2700
cagctgaaag ataataaggt atggttaaag atcacaccac cctcttcaat tagctaagat   2760
catagctaaa ggtacaaaac cgaatacgaa agtaaataaa ttaatcagca taaaattaaa   2820
taataaacca cctaaaatat tagaagctaa tctttaacct ggaagacagg acagaaaagt   2880
aattacaaga acatatgtga aaaaaaatag ttgatatttt aaaccaaatc agaaatttat   2940
tatactaaaa ctatatctat gccaattatt tacctaaaca tctataacct tcaaaagtaa   3000
aaaaatacac aaacgttgaa tcatgagttt tatgttaatt aggcggccgc ggatcttcat   3060
cctgccactg caattctttt catatcggtc atatatcctc tcagcttttt acccacctgt   3120
tctatagcat gtgaacgaat agcttcattt acgtctctca gttggccatt gtcaaccgct   3180
ccttccggaa tagccttccc caaatcacca ggttgtaact cggccatgaa gggctttaac   3240
```

-continued

```
aacgggacac atgcgtagct aaataagtaa ttaccatatt ctgcagtgtc tgatatgaca   3300
acattcatct cgtaaagtct ttttcttgca atagtatttg ctatcaaagg caattcatgc   3360
aaagactcat agtatgcaga ttcttcaatg ataccggagt caaccatagt ttcgaatgca   3420
agttctaccc ctgccttcac catagctatc atcaatactc ccttatcaaa gtattcttgt   3480
tcaccaattt taccttcgta ttgtggggct gtctcgaatg ccgtcttgcc ggtttcttct   3540
ctccacgtca ataacttttt atcatcgttt gcccaatctg ccatcattcc tgaggaaaac   3600
tcaccggaga taatatcgtc catgtgcttt tggaataatg gtgccatgat ctcttttagt   3660
tgctcagata aggcgtaggc tcttagcttg gccggatttg aaagtctatc catcatcaat   3720
gttatgccac cttgtttaag tgcctcggtg attgtctccc aaccaaattg tatcaacttt   3780
tcagcatagg caggatctgt accctcttcg accaatttat caaagcatag taaagaccct   3840
gcctgcaaca ttccgcacag aatggtttgt tcacccatta agtcactctt gacctcagct   3900
acgaaagaac tctctaacac acccgctcta tgacctccgg ttgcggctgc ccatgccttc   3960
gcaattgcca taccttcacc tttggggtca ttttcaggat gtacggcgat caatgtaggt   4020
acaccaaaac ccctcttgta ctcctctctg acttccgtac ctgggcactt tggtgcaacc   4080
attacgactg ttatatcttt tctgatctgc tcgcccactt caacgatatt aaagccatga   4140
gagtaaccta aagctgcccc atccttcatc agcggttgaa ctgttcttac tacgtctgag   4200
tgaaccttat ctggtgttag gttaatcact aaatctgcct gagggatcag ttcttcgtaa   4260
gtaccaactt tgaacccatt ttccgtcgct ttacgccagg aggccctctt ttctgcaatt   4320
gcctctttcc tcaatgcata cgaaatatcc agacctgaat ctctcatgtt taaaccttgg   4380
tttagaccct gagcaccgca gccaacaatt actactttct ttccttgcag ataagaagca   4440
ccatcagcaa actcgtccct tcccataaat ctgcacttac ccagttgagc caattgttgt   4500
ctcaaattta atgtgttaaa atagttggcc atctcgagtc gaaactaagt tctggtgttt   4560
taaaactaaa aaaaagacta actataaaag tagaatttaa gaagtttaag aaatagattt   4620
acagaattac aatcaatacc taccgtcttt atatacttat tagtcaagta ggggaataat   4680
ttcagggaac tggtttcaac cttttttttc agctttttcc aaatcagaga gagcagaagg   4740
taatagaagg tgtaagaaaa tgagatagat acatgcgtgg gtcaattgcc ttgtgtcatc   4800
atttactcca ggcaggttgc atcactccat tgaggttgtg cccgtttttt gcctgtttgt   4860
gcccctgttc tctgtagttg cgctaagaga atggacctat gaactgatgg ttggtgaaga   4920
aaacaatatt ttggtgctgg gattcttttt ttttctggat gccagcttaa aaagcgggct   4980
ccattatatt tagtggatgc caggaataaa ctgttcaccc agacacctac gatgttatat   5040
attctgtgta acccgccccc tattttgggc atgtacgggt tacagcagaa ttaaaaggct   5100
aatttttga ctaaataaag ttaggaaaat cactactatt aattatttac gtattctttg   5160
aaatggcgag tattgataat gataaactgg atcctcaagc atctaaaaca caaccgttgg   5220
aagcgttgga aaccaactta gcatacttgg atagagtacc tcttgtgtaa cgaggtggag   5280
gtgcaaccca actttgttta cgttgagcca tttccttatc agagactaat aggtcaatct   5340
tgttattatc agcatcaatg ataatctcat cgccgtctct gaccaacccg ataggaccac   5400
cttcagcggc ttcgggaaca atgtggccga ttaagaaccc gtgagaacca ccagagaatc   5460
taccatcagt caacaatgca acatctttac ccaaaccgta acccatcaga gcagaggaag   5520
gctttagcat ttcaggcata cctggtgcac ctcttggacc ttcatatctg ataacaacaa   5580
cggttttttc acccttcttg atttcacctc tttccaaggc ttcaataaag gcaccttcct   5640
```

cttcgaacac acgtgctcta cccttgaagt aagtaccttc cttaccggta attttaccca 5700
cagctccacc tggtgccaat gaaccgtaca gaatttgcaa gtgaccgttg gccttgattg 5760
ggtgggagag tggcttaata atctcttgtc cttcaggtag gcttggtgct ttctttgcac 5820
gttctgccaa agtgtcaccg gtaacagtca ttgtgttacc gtgcaacatg ttgttttcat 5880
atagatactt aatcacagat tgggtaccac caacgttaat caaatcggcc atgacgtatt 5940
taccagaagg tttgaagtca ccgatcaatg gtgtagtatc actgattctt tggaaatcat 6000
ctggtgacaa cttgacaccc gcagagtgag caacagccac caaatgcaaa acagcattag 6060
tggacccacc ggttgcaacg acataagtaa tggcgttttc aaaagcctct tttgtgagga 6120
tatcacgagg taaaataccc aattccattg tcttcttgat gtattcacca atgttgtcac 6180
actcagctaa cttctccttg gaaacggctg ggaaggaaga ggagtttgga atggtcaaac 6240
ctagcacttc agcggcagaa gccattgtgt tggcagtata cataccacca caagaaccag 6300
gacctgggca tgcatgttcc acaacatctt ctctttcttc ttcagtgaat tgcttggaaa 6360
tatattcacc gtaggattgg aacgcagaga cgatatcgat gtttttagag atcttcgaag 6420
aaccacatgt tggatgaccg ggcaagatag taccaccata taccatgatg gaaggtctgt 6480
tatgtctacc catggccatc atgacaccgg gcatgttttt gtcacatgat gggatggcga 6540
tgttagcatc gtagtgttgt gccatcatga tggtttcaaa ggagtctgca atgatttctc 6600
tactttgtaa cgagtatctc atacctttag tacccataga gataccgtct gaaacaccga 6660
tggtgttgaa ctgcatagct ttcaaacccg ctttttcaat ggattgagaa catctgttat 6720
tcaagtccaa tagatgcatg ttacatgggt taccggacca ccaacaggaa ccaaccccga 6780
cttgaggctt cttgaaatct tccttcttga aaccggtggc ataaagcatg gcctgggacg 6840
caccttggcc cttaggttca gtgatgatat acgagtactt gttgagcttc ttcatgtcga 6900
caaacttaga ttagattgct atgctttctt tctaatgagc aagaagtaaa aaaagttgta 6960
atagaacaag aaaaatgaaa ctgaaacttg agaaattgaa gaccgtttat taacttaaat 7020
atcaatggga ggtcatcgaa agagaaaaaa atcaaaaaaa aaattttcaa gaaaaagaaa 7080
cgtgataaaa atttttattg ccttttttcga cgaagaaaaa gaaacgaggc ggtctctttt 7140
ttcttttcca aacctttagt acgggtaatt aacgacaccc tagaggaaga aagaggggaa 7200
atttagtatg ctgtgcttgg gtgttttgaa gtggtacggc gatgcgcgga gtccgagaaa 7260
atctggaaga gtaaaaaagg agtagaaaca ttttgaagct atgagctcca gcttttgttc 7320
cctttagtga gggttaattg cgcgcttggc gtaatcatgg tcatagctgt ttcctgtgtg 7380
aaattgttat ccgctcacaa ttccacacaa cataggagcc ggaagcataa agtgtaaagc 7440
ctggggtgcc taatgagtga ggtaactcac attaattgcg ttgcgctcac tgcccgcttt 7500
ccagtcggga aacctgtcgt gccagctgca ttaatgaatc ggccaacgcg cggggagagg 7560
cggtttgcgt attgggcgct cttccgcttc ctcgctcact gactcgctgc gctcggtcgt 7620
tcggctgcgg cgagcggtat cagctcactc aaaggcggta atacggttat ccacagaatc 7680
aggggataac gcaggaaaga acatgtgagc aaaaggccag caaaaggcca ggaaccgtaa 7740
aaaggccgcg ttgctggcgt ttttccatag gctccgcccc cctgacgagc atcacaaaaa 7800
tcgacgctca agtcagaggt ggcgaaaccc gacaggacta taaagatacc aggcgtttcc 7860
ccctggaagc tccctcgtgc gctctcctgt tccgaccctg ccgcttaccg gatacctgtc 7920
cgcctttctc ccttcgggaa gcgtggcgct ttctcatagc tcacgctgta ggtatctcag 7980
ttcggtgtag gtcgttcgct ccaagctggg ctgtgtgcac gaaccccccg ttcagcccga 8040
ccgctgcgcc ttatccggta actatcgtct tgagtccaac ccggtaagac acgacttatc 8100
gccactggca gcagccactg gtaacaggat tagcagagcg aggtatgtag gcggtgctac 8160
agagttcttg aagtggtggc ctaactacgg ctacactaga aggacagtat ttggtatctg 8220
cgctctgctg aagccagtta ccttcggaaa aagagttggt agctcttgat ccggcaaaca 8280
aaccaccgct ggtagcggtg gtttttttgt ttgcaagcag cagattacgc gcagaaaaaa 8340
aggatctcaa gaagatcctt tgatcttttc tacggggtct gacgctcagt ggaacgaaaa 8400
ctcacgttaa gggattttgg tcatgagatt atcaaaaagg atcttcacct agatcctttt 8460
aaattaaaaa tgaagtttta aatcaatcta aagtatatat gagtaaactt ggtctgacag 8520
ttaccaatgc ttaatcagtg aggcacctat ctcagcgatc tgtctatttc gttcatccat 8580
agttgcctga ctccccgtcg tgtagataac tacgatacgg gagggcttac catctggccc 8640
cagtgctgca atgataccgc gagacccacg ctcaccggct ccagatttat cagcaataaa 8700
ccagccagcc ggaagggccg agcgcagaag tggtcctgca actttatccg cctccatcca 8760
gtctattaat tgttgccggg aagctagagt aagtagttcg ccagttaata gtttgcgcaa 8820
cgttgttgcc attgctacag gcatcgtggt gtcacgctcg tcgtttggta tggcttcatt 8880
cagctccggt tcccaacgat caaggcgagt tacatgatcc cccatgttgt gcaaaaaagc 8940
ggttagctcc ttcggtcctc cgatcgttgt cagaagtaag ttggccgcag tgttatcact 9000
catggttatg gcagcactgc ataattctct tactgtcatg ccatccgtaa gatgcttttc 9060
tgtgactggt gagtactcaa ccaagtcatt ctgagaatag tgtatgcggc gaccgagttg 9120
ctcttgcccg gcgtcaatac gggataatac cgcgccacat agcagaactt taaaagtgct 9180
catcattgga aaacgttctt cggggcgaaa actctcaagg atcttaccgc tgttgagatc 9240
cagttcgatg taacccactc gtgcacccaa ctgatcttca gcatctttta ctttcaccag 9300
cgtttctggg tgagcaaaaa caggaaggca aaatgccgca aaaaagggaa taagggcgac 9360
acggaaatgt tgaatactca tactcttcct ttttcaatat tattgaagca tttatcaggg 9420
ttattgtctc atgagcggat acatatttga atgtatttag aaaaataaac aaataggggt 9480
tccgcgcaca tttccccgaa aagtgccacc tgacgt 9516

<210> SEQ ID NO 121
<211> LENGTH: 6679
<212> TYPE: DNA
<213> ORGANISM: Artificial Sequence
<220> FEATURE:
<223> OTHER INFORMATION: Plasmid pGV2020

<400> SEQUENCE: 121
ttggatcata ctaagaaacc attattatca tgacattaac ctataaaaat aggcgtatca 60
cgaggccctt tcgtctcgcg cgtttcggtg atgacggtga aaacctctga cacatgcagc 120
tcccggagac ggtcacagct tgtctgtaag cggatgccgg gagcagacaa gcccgtcagg 180
gcgcgtcagc gggtgttggc gggtgtcggg gctggcttaa ctatgcggca tcagagcaga 240
ttgtactgag agtgcaccat accacagctt ttcaattcaa ttcatcattt ttttttatt 300 ctttttttg atttcggttt ctttgaaatt tttttgattc ggtaatctcc gaacagaagg 360
aagaacgaag gaaggagcac agacttagat tggtatatat acgcatatgg caaattaaag 420
ccttcgagcg tcccaaaacc ttctcaagca aggttttcag tataatgtta catgcgtaca 480
cgcgtctgta cagaaaaaaa agaaaaattt gaaatataaa taacgttctt aatactaaca 540
taactataaa aaaataaata gggacctaga cttcaggttg tctaactcct tccttttcgg 600

```
ttagagcgga tgtgggggga gggcgtgaat gtaagcgtga cataagaatt cttagaaaaa    660
ctcatcgagc atcaaatgaa actgcaattt attcatatca ggattatcaa taccatattt    720
ttgaaaaagc cgtttctgta atgaaggaga aaactcaccg aggcagttcc ataggatggc    780
aagatcctgg tatcggtctg cgatcccgac tcgtccaaca tcaatacaac ctattaattt    840
cccctcgtca aaaataaggt tatcaagtga gaaatcacca tgagtgacga ctgaatccgg    900
tgagaatggc aaaagcttat gcatttcttt ccagacttgt tcaacaggcc agccattacg    960
ctcgtcatca aaatcactcg cgtcaaccaa accgttattc attcgtgatt gcgcctgagc   1020
gaggcgaaat acgcgatcgc tgttaaaagg acaattacaa acaggaatcg aatgcaaccg   1080
gcgcaggaac actgccagcg catcaacaat attttcacct gaatcaggat attcttctaa   1140
tacctggaat gctgttttgc cggggatcgc agtggtgagt aaccatgcat catcaggagt   1200
acggacaaaa tgcttgatgg tcggaagagg cataaattcc gtcagccagt ttagtctgac   1260
catctcatct gcaacatcat tggcaacgct acctttgcca tgtttcagaa acaactctgg   1320
cgcatcgggc ttcccataca atcgatagat tgtcgcacct gattgcccga cattatcgcg   1380
agcccattta tacccatata aatcagcatc catgttggaa tttaatcgcg gcctcgaaac   1440
gtgagtcttt tccttaccca tactagtttt tagtttatgt atgtgttttt tgtagttata   1500
gatttaagca agaaaagaat acaaacaaaa aattgaaaaa gattgattta gaattaaaaa   1560
gaaaaatatt tacgtaagaa gggaaaatag taaatgttgc aagttcacta aactcctaaa   1620
ttatgctgcc ctttatattc cctgttacag cagccgagcc aaaggtatat aggctccttt   1680
gcattagcat gcgtaacaaa ccacctgtca gtttcaaccg aggtggtatc cgagagaatt   1740
gtgtgattgc tttaattaat ttcggagaat ctcacatgcc actgaagatt aaaaactgga   1800
tgccagaaaa ggggtgtcca ggtgtaacat caatagagga agctgaaaag tcttagaacg   1860
ggtaatcttc caccaacctg atgggttcct agatataatc tcgaagggaa taagtagggt   1920
gataccgcag aagtgtctga atgtattaag gtcctcacag tttaaatccc gctcacacta   1980
acgtaggatt attataactc aaaaaaatgg cattattcta agtaagttaa atatccgtaa   2040
tctttaaaca gcggccgcag atctctcgag tcgaaactaa gttctggtgt tttaaaacta   2100
aaaaaaagac taactataaa agtagaattt aagaagttta agaaatagat ttacagaatt   2160
acaatcaata cctaccgtct ttatatactt attagtcaag taggggaata atttcaggga   2220
actggtttca accttttttt tcagcttttt ccaaatcaga gagagcagaa ggtaatagaa   2280
ggtgtaagaa aatgagatag atacatgcgt gggtcaattg ccttgtgtca tcatttactc   2340
caggcaggtt gcatcactcc attgaggttg tgcccgtttt ttgcctgttt gtgcccctgt   2400
tctctgtagt tgcgctaaga gaatggacct atgaactgat ggttggtgaa gaaaacaata   2460
ttttggtgct gggattcttt ttttttctgg atgccagctt aaaaagcggg ctccattata   2520
tttagtggat gccaggaata aactgttcac ccagacacct acgatgttat atattctgtg   2580
taacccgccc cctattttgg gcatgtacgg gttacagcag aattaaaagg ctaatttttt   2640
gactaaataa agttaggaaa atcactacta ttaattattt acgtattctt tgaaatggcg   2700
agtattgata atgataaact ggatccgtcg acaaacttag attagattgc tatgctttct   2760
ttctaatgag caagaagtaa aaaaagttgt aatagaacaa gaaaaatgaa actgaaactt   2820
gagaaattga agaccgttta ttaacttaaa tatcaatggg aggtcatcga aagagaaaaa   2880
aatcaaaaaa aaaattttca agaaaaagaa acgtgataaa aatttttatt gccttttttcg   2940
acgaagaaaa agaaacgagg cggtctcttt tttcttttcc aaacctttag tacgggtaat   3000
```

taacgacacc ctagaggaag aaagagggga aatttagtat gctgtgcttg ggtgttttga 3060
agtggtacgg cgatgcgcgg agtccgagaa aatctggaag agtaaaaaag gagtagaaac 3120
attttgaagc tatgagctcc agcttttgtt ccctttagtg agggttaatt gcgcgcttgg 3180
cgtaatcatg gtcatagctg tttcctgtgt gaaattgtta tccgctcaca attccacaca 3240
acataggagc cggaagcata aagtgtaaag cctggggtgc ctaatgagtg aggtaactca 3300
cattaattgc gttgcgctca ctgcccgctt tccagtcggg aaacctgtcg tgccagctgc 3360
attaatgaat cggccaacgc gcggggagag gcggtttgcg tattgggcgc tcttccgctt 3420
cctcgctcac tgactcgctg cgctcggtcg ttcggctgcg gcgagcggta tcagctcact 3480
caaaggcggt aatacggtta tccacagaat caggggataa cgcaggaaag aacatgtgag 3540
caaaaggcca gcaaaaggcc aggaaccgta aaaaggccgc gttgctggcg tttttccata 3600
ggctccgccc ccctgacgag catcacaaaa atcgacgctc aagtcagagg tggcgaaacc 3660
cgacaggact ataaagatac caggcgtttc cccctggaag ctccctcgtg cgctctcctg 3720
ttccgaccct gccgcttacc ggatacctgt ccgcctttct cccttcggga agcgtggcgc 3780
tttctcatag ctcacgctgt aggtatctca gttcggtgta ggtcgttcgc tccaagctgg 3840
gctgtgtgca cgaacccccc gttcagcccg accgctgcgc cttatccggt aactatcgtc 3900
ttgagtccaa cccggtaaga cacgacttat cgccactggc agcagccact ggtaacagga 3960
ttagcagagc gaggtatgta ggcggtgcta cagagttctt gaagtggtgg cctaactacg 4020
gctacactag aaggacagta tttggtatct gcgctctgct gaagccagtt accttcggaa 4080
aaagagttgg tagctcttga tccggcaaac aaaccaccgc tggtagcggt ggtttttttg 4140
tttgcaagca gcagattacg cgcagaaaaa aaggatctca agaagatcct ttgatctttt 4200
ctacggggtc tgacgctcag tggaacgaaa actcacgtta agggattttg gtcatgagat 4260
tatcaaaaag gatcttcacc tagatccttt taaattaaaa atgaagtttt aaatcaatct 4320
aaagtatata tgagtaaact tggtctgaca gttaccaatg cttaatcagt gaggcaccta 4380
tctcagcgat ctgtctattt cgttcatcca tagttgcctg actccccgtc gtgtagataa 4440
ctacgatacg ggagggctta ccatctggcc ccagtgctgc aatgataccg cgagacccac 4500
gctcaccggc tccagattta tcagcaataa accagccagc cggaagggcc gagcgcagaa 4560
gtggtcctgc aactttatcc gcctccatcc agtctattaa ttgttgccgg gaagctagag 4620
taagtagttc gccagttaat agtttgcgca acgttgttgc cattgctaca ggcatcgtgg 4680
tgtcacgctc gtcgtttggt atggcttcat tcagctccgg ttcccaacga tcaaggcgag 4740
ttacatgatc ccccatgttg tgcaaaaaag cggttagctc cttcggtcct ccgatcgttg 4800
tcagaagtaa gttggccgca gtgttatcac tcatggttat ggcagcactg cataattctc 4860
ttactgtcat gccatccgta agatgctttt ctgtgactgg tgagtactca accaagtcat 4920
tctgagaata gtgtatgcgg cgaccgagtt gctcttgccc ggcgtcaata cgggataata 4980
ccgcgccaca tagcagaact ttaaaagtgc tcatcattgg aaaacgttct tcggggcgaa 5040
aactctcaag gatcttaccg ctgttgagat ccagttcgat gtaacccact cgtgcaccca 5100
actgatcttc agcatctttt actttcacca gcgtttctgg gtgagcaaaa acaggaaggc 5160
aaaatgccgc aaaaaaggga ataagggcga cacggaaatg ttgaatactc atactcttcc 5220
tttttcaata ttattgaagc atttatcagg gttattgtct catgagcgga tacatatttg 5280
aatgtattta gaaaaataaa caaatagggg ttccgcgcac atttccccga aaagtgccac 5340
ctgaacgaag catctgtgct tcattttgta gaacaaaaat gcaacgcgag agcgctaatt 5400
tttcaaacaa agaatctgag ctgcattttt acagaacaga aatgcaacgc gaaagcgcta 5460
ttttaccaac gaagaatctg tgcttcattt ttgtaaaaca aaaatgcaac gcgagagcgc 5520
taatttttca aacaaagaat ctgagctgca tttttacaga acagaaatgc aacgcgagag 5580
cgctatttta ccaacaaaga atctatactt cttttttgtt ctacaaaaat gcatcccgag 5640
agcgctattt ttctaacaaa gcatcttaga ttactttttt tctcctttgt gcgctctata 5700
atgcagtctc ttgataactt tttgcactgt aggtccgtta aggttagaag aaggctactt 5760
tggtgtctat tttctcttcc ataaaaaaag cctgactcca cttcccgcgt ttactgatta 5820
ctagcgaagc tgcgggtgca ttttttcaag ataaaggcat ccccgattat attctatacc 5880
gatgtggatt gcgcatactt tgtgaacaga aagtgatagc gttgatgatt cttcattggt 5940
cagaaaatta tgaacggttt cttctatttt gtctctatat actacgtata ggaaatgttt 6000
acattttcgt attgttttcg attcactcta tgaatagttc ttactacaat ttttttgtct 6060
aaagagtaat actagagata aacataaaaa atgtagaggt cgagtttaga tgcaagttca 6120
aggagcgaaa ggtggatggg taggttatat agggatatag cacagagata tatagcaaag 6180
agatactttt gagcaatgtt tgtggaagcg gtattcgcaa tattttagta gctcgttaca 6240
gtccggtgcg tttttggttt tttgaaagtg cgtcttcaga gcgcttttgg ttttcaaaag 6300
cgctctgaag ttcctatact ttctagagaa taggaacttc ggaataggaa cttcaaagcg 6360
tttccgaaaa cgagcgcttc cgaaaatgca acgcgagctg cgcacataca gctcactgtt 6420
cacgtcgcac ctatatctgc gtgttgcctg tatatatata tacatgagaa gaacggcata 6480
gtgcgtgttt atgcttaaat gcgtacttat atgcgtctat ttatgtagga tgaaaggtag 6540
tctagtacct cctgtgatat tatcccattc catgcggggt atcgtatgct tccttcagca 6600
ctacccttta gctgttctat atgctgccac tcctcaattg gattagtctc atccttcaat 6660
gctatcattt cctttgata 6679

<210> SEQ ID NO 122
<211> LENGTH: 13805
<212> TYPE: DNA
<213> ORGANISM: Artificial Sequence
<220> FEATURE:
<223> OTHER INFORMATION: Plasmid pGV2082

<400> SEQUENCE: 122
ttggatcata ctaagaaacc attattatca tgacattaac ctataaaaat aggcgtatca 60
cgaggccctt tcgtctcgcg cgtttcggtg atgacggtga aaacctctga cacatgcagc 120
tcccggagac ggtcacagct tgtctgtaag cggatgccgg gagcagacaa gcccgtcagg 180
gcgcgtcagc gggtgttggc gggtgtcggg gctggcttaa ctatgcggca tcagagcaga 240
ttgtactgag agtgcaccat accacagctt ttcaattcaa ttcatcattt ttttttttatt 300 cttttttttg atttcggttt ctttgaaatt tttttgattc ggtaatctcc gaacagaagg 360
aagaacgaag gaaggagcac agacttagat tggtatatat acgcatatgg caaattaaag 420
ccttcgagcg tcccaaaacc ttctcaagca aggttttcag tataatgtta catgcgtaca 480
cgcgtctgta cagaaaaaaa agaaaaattt gaaatataaa taacgttctt aatactaaca 540
taactataaa aaaataaata gggacctaga cttcaggttg tctaactcct tccttttcgg 600
ttagagcgga tgtgggggga gggcgtgaat gtaagcgtga cataactaat tacatgactc 660
gagcggccgc ttagatgccg gagtcccagt gcttggtcca ctggatggcc tccagggtgc 720
ccaagtccag tttccagatg gctccgttct ggttcagctc gatagccttg acgaagttct 780

-continued

```
cggcgcaggc caacgagggc tgggtgggat gagccaggag cttctcggca acctgaggct    840
caacatccaa ccaggagttg aacgtgtgca ccagggtggt gcgggtgatg ccggggttca    900
cagtgtaagc cgtcacgccg gtaatggggg ccagtttcgc cagggagctg gtgaagttga    960
ccacggcggc cttggtgccg gagtagacgg gcacctggta gatggcattg aatccagtga   1020
cggatccaat gttgcagatg ataccaccgg gaccgccctt gcgcttgtcc cagaagtcca   1080
gaatggccgt cgtggtgttg accaggccag tgtagttgac ggcaatggtg cgctcgatct   1140
ggtgatcgtc caggatacca gctccgttga tcaggacatc gacggtcttc agctgggcga   1200
agatggtctt cagcagcttg gtggtctcgg caatgggcac ggtcacatca taggggtaga   1260
aggtgacggt cacctttgga ttgattgcct tcagctcggc aatggcagcc gggttctcaa   1320
tgcggtcgag gatcaccagg ttcttcagat cgcgcttgag cagctccttg ctggtgtcca   1380
gaccaatgcc tcccagaccg gcaacgaaaa tcacgttctt gttggtcaaa gtaaacgaca   1440
tggtacctat tattgtatgt tatagtatta gttgcttggt gttatgaaag aaactaagaa   1500
aagaaaaata aaataaaaat aaaagattga gacaagggaa gaaaagatac aaaataagaa   1560
ttaattacaa ttgcgtttgc tataaatacg tttttaacaa tcaactctgg taggaagata   1620
atgctttttt tttttatata tgcttggtgc cacttgtcac atacaattct acaaccttcg   1680
acaaaaatcc aaatgatagt aagatcaaag ccagaaagca atggagaaaa aaaattaatg   1740
aaccacgatg aaccaaatga tcaatacaac caaagaaact accctagtga ggtgtatgct   1800
gacttggtat cacacttcat gaattttgca tatggcaaag tccacgaaag tgggcttcag   1860
aaaaaaggcg tgcggtgtgt agatgtatca attagtggat gccagttttg gaacgggatt   1920
ccactttccg caagttggtg cacgtcgtta gtgacataac gccgcgttca tctttgggaa   1980
gaagcagatg ctgagcgagg aggtactata gagtaaagaa ccctttctat acccgcagcc   2040
ccatggtaag tgacagtgca gtaataatat gaaccaattt atttttcgtt acataaaaat   2100
gcttataaaa ctttaactaa taattagaga ttaaatcgcg gccgcaaaag atccttagga   2160
tttattctgt tcagcaaaca gcttgcccat tttcttcagt accttcggtg cgccttcttt   2220
cgccaggatc agttcgatcc agtacatacg gttcggatcg gcctgggcct ctttcatcac   2280
gctcacaaat tcgttttcgg tacgcacaat tttagacaca acacggtcct cagttgcgcc   2340
gaaggactcc ggcagtttag agtagttcca catagggata tcgttgtaag actggttcgg   2400
accgtggatc tcacgctcaa cggtgtagcc gtcattgtta ataatgaagc aaatcgggtt   2460
gatcttttca cgaattgcca gacccagttc ctgtacggtc agctgcaggg aaccgtcacc   2520
gatgaacagc agatgacgag attctttatc agcgatctga gagcccagcg ctgccgggaa   2580
agtatagcca atgctacccc acagcggctg accgataaaa tggcttttgg atttcagaaa   2640
gatagaagac gcgccgaaaa agctcgtacc ttgttccgcc acgatggttt cattgctctg   2700
ggtcaggttc tccacggcct gccacaggcg atcctgggac agcagtgcgt tagatggtac   2760
gaaatcttct tgctttttgt caatgtattt gcctttatac tcgatttcgg acaggtccag   2820
cagagagctg atcaggcttt cgaagtcgaa gttctggata cgctcgttga agattttacc   2880
ctcgtcgatg ttcaggctaa tcattttgtt ttcgttcaga tggtgagtga atgcaccggt   2940
agaagagtcg gtcagtttaa cgcccagcat caggatgaag tccgcagatt caacaaattc   3000
tttcaggttc ggttcgctca gagtaccgtt gtagatgccc aggaaagacg gcagagcctc   3060
gtcaacagag gacttgccga agttcagggt ggtaatcggc agtttggttt tgctgatgaa   3120
ttgggtcacg gtcttctcca gaccaaaaga aatgatttcg tggccggtga tcacgattgg   3180
```

```
tttctttgcg tttttcagag actcctggat tttgttcagg atttcctggt cgctagtgtt   3240
agaagtggag ttttctttct tcagcggcag gctcggtttt tccgctttag ctgccgcaac   3300
atccacaggc aggttgatgt aaactggttt gcgttctttc agcagcgcag acagaacgcg   3360
gtcgatttcc acagtagcgt tctctgcagt cagcagcgta cgtgccgcag tcacaggttc   3420
atgcattttc atgaagtgtt tgaaatcgcc gtcagccaga gtgtggtgga cgaatttacc   3480
ttcgttctga actttgctcg ttgggctgcc tacgatctcc accaccggca ggttttcggc   3540
gtaggagccc gccagaccgt tgacggcgct cagttcgcca acaccgaaag tggtcagaaa   3600
tgccgcggct ttcttggtac gtgcataacc atctgccatg tagcttgcgt tcagttcgtt   3660
agcgttaccc acccatttca tgtctttatg agagatgatc tgatccagga actgcagatt   3720
gtaatcaccc ggaacgccga agatttcttc gatacccagt tcatgcagac ggtccagcag   3780
ataatcacca acagtataca tgtcgagctt gttttatatt tgttgtaaaa agtagataat   3840
tacttccttg atgatctgta aaaaagagaa aaagaaagca tctaagaact tgaaaaacta   3900
cgaattagaa aagaccaaat atgtatttct tgcattgacc aatttatgca agtttatata   3960
tatgtaaatg taagtttcac gaggttctac taaactaaac cacccccttg gttagaagaa   4020
aagagtgtgt gagaacaggc tgttgttgtc acacgattcg gacaattctg tttgaaagag   4080
agagagtaac agtacgatcg aacgaacttt gctctggaga tcacagtggg catcatagca   4140
tgtggtacta aacccttttcc cgccattcca gaaccttcga ttgcttgtta caaaacctgt   4200
gagccgtcgc taggaccttg ttgtgtgacg aaattggaag ctgcaatcaa taggaagaca   4260
ggaagtcgag cgtgtctggg ttttttcagt tttgttcttt ttgcaaacaa atcacgagcg   4320
acggtaattt ctttctcgat aagaggccac gtgctttatg agggtaacat caattcaaga   4380
aggagggaaa cacttccttt ttctggccct gataatagta tgagggtgaa gccaaaataa   4440
aggattcgcg cccaaatcgg catctttaaa tgcaggtatg cgatagttcc tcactctttc   4500
cttactcacg agtaattctt gcaaatgcct attatgcaga tgttataata tctgtgcgtc   4560
ttgagttgag cctagaattc ttagaaaaac tcatcgagca tcaaatgaaa ctgcaattta   4620
ttcatatcag gattatcaat accatatttt tgaaaaagcc gtttctgtaa tgaaggagaa   4680
aactcaccga ggcagttcca taggatggca agatcctggt atcggtctgc gatcccgact   4740
cgtccaacat caatacaacc tattaatttc ccctcgtcaa aaataaggtt atcaagtgag   4800
aaatcaccat gagtgacgac tgaatccggt gagaatggca aaagcttatg catttctttc   4860
cagacttgtt caacaggcca gccattacgc tcgtcatcaa aatcactcgc gtcaaccaaa   4920
ccgttattca ttcgtgattg cgcctgagcg aggcgaaata cgcgatcgct gttaaaagga   4980
caattacaaa caggaatcga atgcaaccgg cgcaggaaca ctgccagcgc atcaacaata   5040
ttttcacctg aatcaggata ttcttctaat acctggaatg ctgttttgcc ggggatcgca   5100
gtggtgagta accatgcatc atcaggagta cggacaaaat gcttgatggt cggaagaggc   5160
ataaattccg tcagccagtt tagtctgacc atctcatctg caacatcatt ggcaacgcta   5220
cctttgccat gtttcagaaa caactctggc gcatcgggct tcccatacaa tcgatagatt   5280
gtcgcacctg attgcccgac attatcgcga gcccatttat acccatataa atcagcatcc   5340
atgttggaat ttaatcgcgg cctcgaaacg tgagtctttt ccttacccat actagttttt   5400
agtttatgta tgtgtttttt gtagttatag atttaagcaa gaaaagaata caaacaaaaa   5460
attgaaaaag attgatttag aattaaaaag aaaaatattt acgtaagaag ggaaaatagt   5520
aaatgttgca agttcactaa actcctaaat tatgctgccc tttatattcc ctgttacagc   5580
```

agccgagcca aaggtatata ggctcctttg cattagcatg cgtaacaaac cacctgtcag 5640
tttcaaccga ggtggtatcc gagagaattg tgtgattgct ttaattaatt tcggagaatc 5700
tcacatgcca ctgaagatta aaaactggat gccagaaaag gggtgtccag gtgtaacatc 5760
aatagaggaa gctgaaaagt cttagaacgg gtaatcttcc accaacctga tgggttccta 5820
gatataatct cgaagggaat aagtagggtg ataccgcaga agtgtctgaa tgtattaagg 5880
tcctcacagt ttaaatcccg ctcacactaa cgtaggatta ttataactca aaaaaatggc 5940
attattctaa gtaagttaaa tatccgtaat ctttaaacag cggccgcgga tcttcatcct 6000
gccactgcaa ttcttttcat atcggtcata tatcctctca gctttttacc cacctgttct 6060
atagcatgtg aacgaatagc ttcatttacg tctctcagtt ggccattgtc aaccgctcct 6120
tccggaatag ccttccccaa atcaccaggt tgtaactcgg ccatgaaggg ctttaacaac 6180
gggacacatg cgtagctaaa taagtaatta ccatattctg cagtgtctga tatgacaaca 6240
ttcatctcgt aaagtctttt tcttgcaata gtatttgcta tcaaaggcaa ttcatgcaaa 6300
gactcatagt atgcagattc ttcaatgata ccggagtcaa ccatagtttc gaatgcaagt 6360
tctacccctg ccttcaccat agctatcatc aatactccct tatcaaagta ttcttgttca 6420
ccaattttac cttcgtattg tggggctgtc tcgaatgccg tcttgccggt ttcttctctc 6480
cacgtcaata actttttatc atcgtttgcc caatctgcca tcattcctga ggaaaactca 6540
ccggagataa tatcgtccat gtgcttttgg aataatggtg ccatgatctc ttttagttgc 6600
tcagataagg cgtaggctct tagcttggcc ggatttgaaa gtctatccat catcaatgtt 6660
atgccacctt gtttaagtgc ctcggtgatt gtctcccaac caaattgtat caacttttca 6720
gcataggcag gatctgtacc ctcttcgacc aatttatcaa agcatagtaa agaccctgcc 6780
tgcaacattc cgcacagaat ggtttgttca cccattaagt cactcttgac ctcagctacg 6840
aaagaactct ctaacacacc cgctctatga cctccggttg cggctgccca tgccttcgca 6900
attgccatac cttcaccttt ggggtcattt tcaggatgta cggcgatcaa tgtaggtaca 6960
ccaaaacccc tcttgtactc ctctctgact tccgtacctg ggcactttgg tgcaaccatt 7020
acgactgtta tatcttttct gatctgctcg cccacttcaa cgatattaaa gccatgagag 7080
taacctaaag ctgccccatc cttcatcagc ggttgaactg ttcttactac gtctgagtga 7140
accttatctg gtgttaggtt aatcactaaa tctgcctgag ggatcagttc ttcgtaagta 7200
ccaactttga acccattttc cgtcgcttta cgccaggagg ccctcttttc tgcaattgcc 7260
tctttcctca atgcatacga aatatccaga cctgaatctc tcatgtttaa accttggttt 7320
agaccctgag caccgcagcc aacaattact actttctttc cttgcagata agaagcacca 7380
tcagcaaact cgtcccttcc cataaatctg cacttaccca gttgagccaa ttgttgtctc 7440
aaatttaatg tgttaaaata gttggccatc tcgagtcgaa actaagttct ggtgttttaa 7500
aactaaaaaa aagactaact ataaaagtag aatttaagaa gtttaagaaa tagatttaca 7560
gaattacaat caatacctac cgtctttata tacttattag tcaagtaggg gaataatttc 7620
agggaactgg tttcaacctt ttttttcagc tttttccaaa tcagagagag cagaaggtaa 7680
tagaaggtgt aagaaaatga gatagataca tgcgtgggtc aattgccttg tgtcatcatt 7740
tactccaggc aggttgcatc actccattga ggttgtgccc gttttttgcc tgtttgtgcc 7800
cctgttctct gtagttgcgc taagagaatg gacctatgaa ctgatggttg gtgaagaaaa 7860
caatattttg gtgctgggat tctttttttt tctggatgcc agcttaaaaa gcgggctcca 7920
ttatatttag tggatgccag gaataaactg ttcacccaga cacctacgat gttatatatt 7980

-continued

```
ctgtgtaacc cgccccctat tttgggcatg tacgggttac agcagaatta aaaggctaat   8040
tttttgacta aataaagtta ggaaaatcac tactattaat tatttacgta ttctttgaaa   8100
tggcgagtat tgataatgat aaactggatc cgcggccgct tacagatcag taacacaccc   8160
ttccgatgca ggacgggtta atttagcgaa ttttgccaaa actcccctgg tggctttcgg   8220
agttggcttc tgataattag ctcttctctt tgcgatttct tcatcggaaa ctttcaggga   8280
tatagagttg ttgactgcat ctatctctat tatatcgtca tcttcaacta agccgattag   8340
tccaccctca acggcttcag gcacaatatg gccgacaaca aaaccgtgag tgccaccgga   8400
gaatctacca tccgtaatta acgcgcaact tttccctaaa cccgcaccaa ttaatgctga   8460
tgtaggcttc agcatttcgg gcataccagg tccgccgacg ggacctatat tcctaattac   8520
cgctacatct ccagcatgca aacgaccaga ttctatgccg tcgataaaat gttgttcacc   8580
atcaaagact ctggcagtgc ctttgaagaa ctctccttct ttaccgctaa tttttgctac   8640
ggaacccct tgagctaaat taccgtacag aatctgcaag tggccggtgg ccttgatagg   8700
attctttagt ggcctcatga tatcttgtga gtcgaaatcc aagtctaggg cagtctcgac   8760
attctcggct aatgttttac ccgtcacagt aaggcagtca ccatgcaatt ttccttcctt   8820
tagaaggtac ttaagcactg ctggcaagcc tccaatttta tgcaaatctt ccatcatata   8880
tttacctgaa ggtttaaaat cacctagtac tggagtaatg tcactaattc tttggaagtc   8940
atcctgagtt atttcgacac ctatcgcgtt agccattgca ataatatgca agacagcatt   9000
agtactaccc cccaagacca tcacaatggt aatagcgttc tcgaacgcct ccttagtcat   9060
tatatcacta ggcttgatgt ctttttccaa aagattctta atggctaatc caatctcatc   9120
acattcttct tgtttttctt gagatactgc agggttcgaa gaagaatacg gcaatgacat   9180
acctagtgtt tcgatagcgg cagctaaggt attagctgtg tacatccccc cacatgcccc   9240
ttgaccagga atagcattac aaataacacc gtgataatct tcatcagaga tattgccggt   9300
aattttctgg cctagagatt caaaagccga tacgatgttc aatttctcac ctttatattc   9360
accgtgttct attgttcctc catacaccat aatgcttggc ctattaagtc ttgccatacc   9420
aataatagaa cctggcatat ttttgtcaca acctgggatg gctacaattg catcatagta   9480
ttcagcgcca gcgttggttt caatagagtc agctataact tctctggaaa caagggagta   9540
tctcattccc aactttccat ttgctatccc atcagaaact cctatcgtat gaaattgtaa   9600
gccgatcaga ccatctgtct gatttactga gcttttaatc tttgatccaa gggttcctaa   9660
atgcatgttg catggatttc catcccagtc catcgacact atacccactt gagctttctt   9720
gaaatcttcg tctttaaacc cgatgccgta atacattgcc tgtgtggcgg gttgtgtggg   9780
atcttgtgtc aacgttttgc tgtacttatt cagttcaaca gattcaactt tgccgttata   9840
cttaaactcc atgtcgacaa acttagatta gattgctatg ctttctttct aatgagcaag   9900
aagtaaaaaa agttgtaata gaacaagaaa aatgaaactg aaacttgaga aattgaagac   9960
cgtttattaa cttaaatatc aatgggaggt catcgaaaga gaaaaaaatc aaaaaaaaaa  10020
ttttcaagaa aaagaaacgt gataaaaatt tttattgcct ttttcgacga agaaaaagaa  10080
acgaggcggt ctcttttttc ttttccaaac ctttagtacg ggtaattaac gacaccctag  10140
aggaagaaag aggggaaatt tagtatgctg tgcttgggtg ttttgaagtg gtacggcgat  10200
gcgcggagtc cgagaaaatc tggaagagta aaaaaggagt agaaacattt tgaagctatg  10260
agctccagct tttgttccct ttagtgaggg ttaattgcgc gcttggcgta atcatggtca  10320
tagctgtttc ctgtgtgaaa ttgttatccg ctcacaattc cacacaacat aggagccgga  10380
```

-continued

```
agcataaagt gtaaagcctg gggtgcctaa tgagtgaggt aactcacatt aattgcgttg  10440
cgctcactgc ccgctttcca gtcgggaaac ctgtcgtgcc agctgcatta atgaatcggc  10500
caacgcgcgg ggagaggcgg tttgcgtatt gggcgctctt ccgcttcctc gctcactgac  10560
tcgctgcgct cggtcgttcg gctgcggcga gcggtatcag ctcactcaaa ggcggtaata  10620
cggttatcca cagaatcagg ggataacgca ggaaagaaca tgtgagcaaa aggccagcaa  10680
aaggccagga accgtaaaaa ggccgcgttg ctggcgtttt tccataggct ccgcccccct  10740
gacgagcatc acaaaaatcg acgctcaagt cagaggtggc gaaacccgac aggactataa  10800
agataccagg cgtttccccc tggaagctcc ctcgtgcgct ctcctgttcc gaccctgccg  10860
cttaccggat acctgtccgc ctttctccct tcgggaagcg tggcgctttc tcatagctca  10920
cgctgtaggt atctcagttc ggtgtaggtc gttcgctcca agctgggctg tgtgcacgaa  10980
ccccccgttc agcccgaccg ctgcgcctta tccggtaact atcgtcttga gtccaacccg  11040
gtaagacacg acttatcgcc actggcagca gccactggta acaggattag cagagcgagg  11100
tatgtaggcg gtgctacaga gttcttgaag tggtggccta actacggcta cactagaagg  11160
acagtatttg gtatctgcgc tctgctgaag ccagttacct tcggaaaaag agttggtagc  11220
tcttgatccg gcaaacaaac caccgctggt agcggtggtt tttttgtttg caagcagcag  11280
attacgcgca gaaaaaaagg atctcaagaa gatcctttga tcttttctac ggggtctgac  11340
gctcagtgga acgaaaactc acgttaaggg attttggtca tgagattatc aaaaaggatc  11400
ttcacctaga tccttttaaa ttaaaaatga agttttaaat caatctaaag tatatatgag  11460
taaacttggt ctgacagtta ccaatgctta atcagtgagg cacctatctc agcgatctgt  11520
ctatttcgtt catccatagt tgcctgactc cccgtcgtgt agataactac gatacgggag  11580
ggcttaccat ctggccccag tgctgcaatg ataccgcgag acccacgctc accggctcca  11640
gatttatcag caataaacca gccagccgga agggccgagc gcagaagtgg tcctgcaact  11700
ttatccgcct ccatccagtc tattaattgt tgccgggaag ctagagtaag tagttcgcca  11760
gttaatagtt tgcgcaacgt tgttgccatt gctacaggca tcgtggtgtc acgctcgtcg  11820
tttggtatgg cttcattcag ctccggttcc caacgatcaa ggcgagttac atgatccccc  11880
atgttgtgca aaaaagcggt tagctccttc ggtcctccga tcgttgtcag aagtaagttg  11940
gccgcagtgt tatcactcat ggttatggca gcactgcata attctcttac tgtcatgcca  12000
tccgtaagat gcttttctgt gactggtgag tactcaacca agtcattctg agaatagtgt  12060
atgcggcgac cgagttgctc ttgcccggcg tcaatacggg ataataccgc gccacatagc  12120
agaactttaa aagtgctcat cattggaaaa cgttcttcgg ggcgaaaact ctcaaggatc  12180
ttaccgctgt tgagatccag ttcgatgtaa cccactcgtg cacccaactg atcttcagca  12240
tcttttactt tcaccagcgt ttctgggtga gcaaaaacag gaaggcaaaa tgccgcaaaa  12300
aagggaataa gggcgacacg gaaatgttga atactcatac tcttcctttt tcaatattat  12360
tgaagcattt atcagggtta ttgtctcatg agcggataca tatttgaatg tatttagaaa  12420
aataaacaaa taggggttcc gcgcacattt ccccgaaaag tgccacctga acgaagcatc  12480
tgtgcttcat tttgtagaac aaaaatgcaa cgcgagagcg ctaatttttc aaacaaagaa  12540
tctgagctgc atttttacag aacagaaatg caacgcgaaa gcgctatttt accaacgaag  12600
aatctgtgct tcatttttgt aaaacaaaaa tgcaacgcga gagcgctaat ttttcaaaca  12660
aagaatctga gctgcatttt tacagaacag aaatgcaacg cgagagcgct atttttacca  12720
caaagaatct atacttcttt tttgttctac aaaaatgcat cccgagagcg ctatttttct  12780
```

aacaaagcat cttagattac tttttttctc ctttgtgcgc tctataatgc agtctcttga 12840
taactttttg cactgtaggt ccgttaaggt tagaagaagg ctactttggt gtctattttc 12900
tcttccataa aaaaagcctg actccacttc ccgcgtttac tgattactag cgaagctgcg 12960
ggtgcatttt ttcaagataa aggcatcccc gattatattc tataccgatg tggattgcgc 13020
atactttgtg aacagaaagt gatagcgttg atgattcttc attggtcaga aaattatgaa 13080
cggtttcttc tattttgtct ctatatacta cgtataggaa atgtttacat tttcgtattg 13140
ttttcgattc actctatgaa tagttcttac tacaattttt ttgtctaaag agtaatacta 13200
gagataaaca taaaaaatgt agaggtcgag tttagatgca agttcaagga gcgaaaggtg 13260
gatgggtagg ttatataggg atatagcaca gagatatata gcaaagagat acttttgagc 13320
aatgtttgtg gaagcggtat tcgcaatatt ttagtagctc gttacagtcc ggtgcgtttt 13380 tggtttttttg aaagtgcgtc ttcagagcgc ttttggtttt caaaagcgct ctgaagttcc 13440
tatactttct agagaatagg aacttcggaa taggaacttc aaagcgtttc cgaaaacgag 13500
cgcttccgaa aatgcaacgc gagctgcgca catacagctc actgttcacg tcgcacctat 13560
atctgcgtgt tgcctgtata tatatataca tgagaagaac ggcatagtgc gtgtttatgc 13620
ttaaatgcgt acttatatgc gtctatttat gtaggatgaa aggtagtcta gtacctcctg 13680
tgatattatc ccattccatg cggggtatcg tatgcttcct tcagcactac cctttagctg 13740
ttctatatgc tgccactcct caattggatt agtctcatcc ttcaatgcta tcatttcctt 13800
tgata 13805

<210> SEQ ID NO 123
<211> LENGTH: 14056
<212> TYPE: DNA
<213> ORGANISM: Artificial Sequence
<220> FEATURE:
<223> OTHER INFORMATION: Plasmid pGV2227

<400> SEQUENCE: 123
ttggatcata ctaagaaacc attattatca tgacattaac ctataaaaat aggcgtatca 60
cgaggccctt tcgtctcgcg cgtttcggtg atgacggtga aaacctctga cacatgcagc 120
tcccggagac ggtcacagct tgtctgtaag cggatgccgg gagcagacaa gcccgtcagg 180
gcgcgtcagc gggtgttggc gggtgtcggg gctggcttaa ctatgcggca tcagagcaga 240
ttgtactgag agtgcaccat accacagctt ttcaattcaa ttcatcattt ttttttttatt 300 cttttttttg atttcggttt ctttgaaatt tttttgattc ggtaatctcc gaacagaagg 360
aagaacgaag gaaggagcac agacttagat tggtatatat acgcatatgg caaattaaag 420
ccttcgagcg tcccaaaacc ttctcaagca aggttttcag tataatgtta catgcgtaca 480
cgcgtctgta cagaaaaaaa agaaaaattt gaaatataaa taacgttctt aatactaaca 540
taactataaa aaaataaata gggacctaga cttcaggttg tctaactcct tccttttcgg 600
ttagagcgga tgtgggggga gggcgtgaat gtaagcgtga cataactaat tacatgactc 660
gacctaggtt atttagtaaa atcaatgacc attcggcctt caatttttcc tgccttcatt 720
tcatcaataa tatcattgat ttcttccagt ttgcgtgtcg caacaattgg ttttacctta 780
ccttctgctc caaattgaaa agcttctgcc aagtcaagtc ttgttccgac aagtgaacct 840
gcaacctcca ctccgtcaaa aacaactgtt ggaactgata aagtcatctc agtattggga 900
agtgccacag caaccatttt gcccataggt ttcaaagaag caaccgcttg ttcaaaagca 960
atccttgcaa cagcacaaac tattgcactt tgcaccccta agccgccagt tattttttta 1020
atttcatcaa ctggatttac atcaccagaa ttgataatca catcagctcc aattttttta 1080
gctaaattta atttatcttg attaatatca acagcaatta cttttgctcc aaaaacattt 1140
ttagcatatt gaattgctaa atttccaagt cctccagcac caaaaattac ttgccaatca 1200
ccaggtttta ctcctgatac tttgattgct ttgtaagttg ttactccagc acaagtaatt 1260
gagctagctt caattgggtc aagtccgtca ggaactttga cagcataatc ggcaacaaca 1320
attgcttctt cagccattcc gccatcaact gaatatcctg catttttaac ttctcgacaa 1380
aaagtttcat taccagatac acagtattca cagtgaccac atccttcaaa gaaccaagcc 1440
actgaaaccc gatcaccaac ttgaagcgag cttacatcag ctccaatttc tttgacaatt 1500
ccaattcctt catgaccaag aacagtccct gctttgttgc cataatcacc tgctgcaacg 1560
tgcaaatcgg tatgacagac tccacaatac tccatgtcaa gcaaagcttc attaggtttg 1620
attgctcgaa gttccttttc aacaaggtcc gcataaccat ctggattgtg tcttactact 1680
gctgctttca ttggtaccta ttattgtatg ttatagtatt agttgcttgg tgttatgaaa 1740
gaaactaaga aaagaaaaat aaaataaaaa taaaagattg agacaaggga agaaaagata 1800
caaaataaga attaattaca attgcgtttg ctataaatac gtttttaaca atcaactctg 1860
gtaggaagat aatgcttttt tttttatat atgcttggtg ccacttgtca catacaattc 1920
tacaaccttc gacaaaaatc caaatgatag taagatcaaa gccagaaagc aatggagaaa 1980
aaaaattaat gaaccacgat gaaccaaatg atcaatacaa ccaaagaaac taccctagtg 2040
aggtgtatgc tgacttggta tcacacttca tgaattttgc atatggcaaa gtccacgaaa 2100
gtgggcttca gaaaaaaggc gtgcggtgtg tagatgtatc aattagtgga tgccagtttt 2160
ggaacgggat tccactttcc gcaagttggt gcacgtcgtt agtgacataa cgccgcgttc 2220
atctttggga agaagcagat gctgagcgag gaggtactat agagtaaaga accctttcta 2280
tacccgcagc cccatggtaa gtgacagtgc agtaataata tgaaccaatt tatttttcgt 2340
tacataaaaa tgcttataaa actttaacta ataattagag attaaatcgc ggccgcaaaa 2400
gatccttagg atttattctg ttcagcaaac agcttgccca ttttcttcag taccttcggt 2460
gcgccttctt tcgccaggat cagttcgatc cagtacatac ggttcggatc ggcctgggcc 2520
tctttcatca cgctcacaaa ttcgttttcg gtacgcacaa ttttagacac aacacggtcc 2580
tcagttgcgc cgaaggactc cggcagttta gagtagttcc acatagggat atcgttgtaa 2640
gactggttcg gaccgtggat ctcacgctca acggtgtagc cgtcattgtt aataatgaag 2700
caaatcgggt tgatcttttc acgaattgcc agacccagtt cctgtacggt cagctgcagg 2760
gaaccgtcac cgatgaacag cagatgacga gattctttat cagcgatctg agagcccagc 2820
gctgccggga aagtatagcc aatgctaccc cacagcggct gaccgataaa atggcttttg 2880
gatttcagaa agatagaaga cgcgccgaaa aagctcgtac cttgttccgc cacgatggtt 2940
tcattgctct gggtcaggtt ctccacggcc tgccacaggc gatcctggga cagcagtgcg 3000
ttagatggta cgaaatcttc ttgctttttg tcaatgtatt tgcctttata ctcgatttcg 3060
gacaggtcca gcagagagct gatcaggctt tcgaagtcga agttctggat acgctcgttg 3120
aagattttac cctcgtcgat gttcaggcta atcattttgt tttcgttcag atggtgagtg 3180
aatgcaccgg tagaagagtc ggtcagttta acgcccagca tcaggatgaa gtccgcagat 3240
tcaacaaatt ctttcaggtt cggttcgctc agagtaccgt tgtagatgcc caggaaagac 3300
ggcagagcct cgtcaacaga ggacttgccg aagttcaggg tggtaatcgg cagtttggtt 3360
ttgctgatga attgggtcac ggtcttctcc agaccaaaag aaatgatttc gtggccggtg 3420
atcacgattg gtttctttgc gtttttcaga gactcctgga ttttgttcag gatttcctgg 3480
tcgctagtgt tagaagtgga gttttctttc ttcagcggca ggctcggttt ttccgcttta 3540
gctgccgcaa catccacagg caggttgatg taaactggtt tgcgttcttt cagcagcgca 3600
gacagaacgc ggtcgatttc cacagtagcg ttctctgcag tcagcagcgt acgtgccgca 3660
gtcacaggtt catgcatttt catgaagtgt ttgaaatcgc cgtcagccag agtgtggtgg 3720
acgaatttac cttcgttctg aactttgctc gttgggctgc ctacgatctc caccaccggc 3780
aggttttcgg cgtaggagcc cgccagaccg ttgacggcgc tcagttcgcc aacaccgaaa 3840
gtggtcagaa atgccgcggc tttcttggta cgtgcataac catctgccat gtagcttgcg 3900
ttcagttcgt tagcgttacc cacccatttc atgtctttat gagagatgat ctgatccagg 3960
aactgcagat tgtaatcacc cggaacgccg aagatttctt cgatacccag ttcatgcaga 4020
cggtccagca gataatcacc aacagtatac atgtcgagct tgttttatat ttgttgtaaa 4080
aagtagataa ttacttcctt gatgatctgt aaaaaagaga aaaagaaagc atctaagaac 4140
ttgaaaaact acgaattaga aaagaccaaa tatgtatttc ttgcattgac caatttatgc 4200
aagtttatat atatgtaaat gtaagtttca cgaggttcta ctaaactaaa ccacccccctt 4260
ggttagaaga aaagagtgtg tgagaacagg ctgttgttgt cacacgattc ggacaattct 4320
gtttgaaaga gagagagtaa cagtacgatc gaacgaactt tgctctggag atcacagtgg 4380
gcatcatagc atgtggtact aaacccttc ccgccattcc agaaccttcg attgcttgtt 4440
acaaaacctg tgagccgtcg ctaggacctt gttgtgtgac gaaattggaa gctgcaatca 4500
ataggaagac aggaagtcga gcgtgtctgg gtttttcag ttttgttctt tttgcaaaca 4560
aatcacgagc gacggtaatt tctttctcga taagaggcca cgtgctttat gagggtaaca 4620
tcaattcaag aaggagggaa acacttcctt tttctggccc tgataatagt atgagggtga 4680
agccaaaata aaggattcgc gcccaaatcg gcatctttaa atgcaggtat gcgatagttc 4740
ctcactcttt ccttactcac gagtaattct tgcaaatgcc tattatgcag atgttataat 4800
atctgtgcgt cttgagttga gcctagaatt cttagaaaaa ctcatcgagc atcaaatgaa 4860
actgcaattt attcatatca ggattatcaa taccatattt ttgaaaaagc cgtttctgta 4920
atgaaggaga aaactcaccg aggcagttcc ataggatggc aagatcctgg tatcggtctg 4980
cgatcccgac tcgtccaaca tcaatacaac ctattaattt cccctcgtca aaaataaggt 5040
tatcaagtga gaaatcacca tgagtgacga ctgaatccgg tgagaatggc aaaagcttat 5100
gcatttcttt ccagacttgt tcaacaggcc agccattacg ctcgtcatca aaatcactcg 5160
cgtcaaccaa accgttattc attcgtgatt gcgcctgagc gaggcgaaat acgcgatcgc 5220
tgttaaaagg acaattacaa acaggaatcg aatgcaaccg gcgcaggaac actgccagcg 5280
catcaacaat attttcacct gaatcaggat attcttctaa tacctggaat gctgttttgc 5340
cggggatcgc agtggtgagt aaccatgcat catcaggagt acggacaaaa tgcttgatgg 5400
tcggaagagg cataaattcc gtcagccagt ttagtctgac catctcatct gcaacatcat 5460
tggcaacgct acctttgcca tgtttcagaa acaactctgg cgcatcgggc ttcccataca 5520
atcgatagat tgtcgcacct gattgcccga cattatcgcg agcccattta tacccatata 5580
aatcagcatc catgttggaa tttaatcgcg gcctcgaaac gtgagtcttt tccttaccca 5640
tactagtttt tagtttatgt atgtgttttt tgtagttata gatttaagca agaaaagaat 5700
acaaacaaaa aattgaaaaa gattgattta gaattaaaaa gaaaaatatt tacgtaagaa 5760
gggaaaatag taaatgttgc aagttcacta aactcctaaa ttatgctgcc ctttatattc 5820

```
cctgttacag cagccgagcc aaaggtatat aggctccttt gcattagcat gcgtaacaaa   5880
ccacctgtca gtttcaaccg aggtggtatc cgagagaatt gtgtgattgc tttaattaat   5940
ttcggagaat ctcacatgcc actgaagatt aaaaactgga tgccagaaaa ggggtgtcca   6000
ggtgtaacat caatagagga agctgaaaag tcttagaacg ggtaatcttc caccaacctg   6060
atgggttcct agatataatc tcgaagggaa taagtagggt gataccgcag aagtgtctga   6120
atgtattaag gtcctcacag tttaaatccc gctcacacta acgtaggatt attataactc   6180
aaaaaaatgg cattattcta agtaagttaa atatccgtaa tctttaaaca gcggccgcgg   6240
atcttcatcc tgccactgca attcttttca tatcggtcat atatcctctc agctttttac   6300
ccacctgttc tatagcatgt gaacgaatag cttcatttac gtctctcagt tggccattgt   6360
caaccgctcc ttccggaata gccttcccca aatcaccagg ttgtaactcg gccatgaagg   6420
gctttaacaa cgggacacat gcgtagctaa ataagtaatt accatattct gcagtgtctg   6480
atatgacaac attcatctcg taaagtcttt ttcttgcaat agtatttgct atcaaaggca   6540
attcatgcaa agactcatag tatgcagatt cttcaatgat accggagtca accatagttt   6600
cgaatgcaag ttctacccct gccttcacca tagctatcat caatactccc ttatcaaagt   6660
attcttgttc accaatttta ccttcgtatt gtggggctgt ctcgaatgcc gtcttgccgg   6720
tttcttctct ccacgtcaat aactttttat catcgtttgc ccaatctgcc atcattcctg   6780
aggaaaactc accggagata atatcgtcca tgtgcttttg gaataatggt gccatgatct   6840
cttttagttg ctcagataag gcgtaggctc ttagcttggc cggatttgaa agtctatcca   6900
tcatcaatgt tatgccacct tgtttaagtg cctcggtgat tgtctcccaa ccaaattgta   6960
tcaacttttc agcataggca ggatctgtac cctcttcgac caatttatca aagcatagta   7020
aagaccctgc ctgcaacatt ccgcacagaa tggtttgttc acccattaag tcactcttga   7080
cctcagctac gaaagaactc tctaacacac ccgctctatg acctccggtt gcggctgccc   7140
atgccttcgc aattgccata ccttcacctt tggggtcatt ttcaggatgt acggcgatca   7200
atgtaggtac accaaaaccc ctcttgtact cctctctgac ttccgtacct gggcactttg   7260
gtgcaaccat tacgactgtt atatcttttc tgatctgctc gcccacttca acgatattaa   7320
agccatgaga gtaacctaaa gctgccccat ccttcatcag cggttgaact gttcttacta   7380
cgtctgagtg aaccttatct ggtgttaggt taatcactaa atctgcctga gggatcagtt   7440
cttcgtaagt accaactttg aacccatttt ccgtcgcttt acgccaggag gccctctttt   7500
ctgcaattgc ctctttcctc aatgcatacg aaatatccag acctgaatct ctcatgttta   7560
aaccttggtt tagaccctga gcaccgcagc caacaattac tactttcttt ccttgcagat   7620
aagaagcacc atcagcaaac tcgtcccttc ccataaatct gcacttaccc agttgagcca   7680
attgttgtct caaatttaat gtgttaaaat agttggccat ctcgagtcga aactaagttc   7740
tggtgtttta aaactaaaaa aaagactaac tataaaagta gaatttaaga agtttaagaa   7800
atagatttac agaattacaa tcaataccta ccgtctttat atacttatta gtcaagtagg   7860
ggaataattt cagggaactg gtttcaacct ttttttcag ctttttccaa atcagagaga   7920
gcagaaggta atagaaggtg taagaaaatg agatagatac atgcgtgggt caattgcctt   7980
gtgtcatcat ttactccagg caggttgcat cactccattg aggttgtgcc cgttttttgc   8040
ctgtttgtgc ccctgttctc tgtagttgcg ctaagagaat ggacctatga actgatggtt   8100
ggtgaagaaa acaatatttt ggtgctggga ttcttttttt ttctggatgc cagcttaaaa   8160
agcgggctcc attatattta gtggatgcca ggaataaact gttcacccag acacctacga   8220
```

```
tgttatatat tctgtgtaac ccgcccccta ttttgggcat gtacgggtta cagcagaatt   8280
aaaaggctaa ttttttgact aaataaagtt aggaaaatca ctactattaa ttatttacgt   8340
attctttgaa atggcgagta ttgataatga taaactggat ccgcggccgc ttacagatca   8400
gtaacacacc cttccgatgc aggacgggtt aatttagcga attttgccaa aactcccctg   8460
gtggctttcg gagttggctt ctgataatta gctcttctct ttgcgatttc ttcatcggaa   8520
actttcaggg atatagagtt gttgactgca tctatctcta ttatatcgtc atcttcaact   8580
aagccgatta gtccaccctc aacggcttca ggcacaatat ggccgacaac aaaaccgtga   8640
gtgccaccgg agaatctacc atccgtaatt aacgcgcaac ttttccctaa acccgcacca   8700
attaatgctg atgtaggctt cagcatttcg ggcataccag gtccgccgac gggacctata   8760
ttcctaatta ccgctacatc tccagcatgc aaacgaccag attctatgcc gtcgataaaa   8820
tgttgttcac catcaaagac tctggcagtg cctttgaaga actctccttc tttaccgcta   8880
atttttgcta cggaaccccc ttgagctaaa ttaccgtaca gaatctgcaa gtggccggtg   8940
gccttgatag gattctttag tggcctcatg atatcttgtg agtcgaaatc caagtctagg   9000
gcagtctcga cattctcggc taatgtttta cccgtcacag taaggcagtc accatgcaat   9060
tttccttcct ttagaaggta cttaagcact gctggcaagc ctccaatttt atgcaaatct   9120
tccatcatat atttacctga aggtttaaaa tcacctagta ctggagtaat gtcactaatt   9180
ctttggaagt catcctgagt tatttcgaca cctatcgcgt tagccattgc aataatatgc   9240
aagacagcat tagtactacc ccccaagacc atcacaatgg taatagcgtt ctcgaacgcc   9300
tccttagtca ttatatcact aggcttgatg tctttttcca aaagattctt aatggctaat   9360
ccaatctcat cacattcttc ttgtttttct tgagatactg cagggttcga agaagaatac   9420
ggcaatgaca tacctagtgt ttcgatagcg gcagctaagg tattagctgt gtacatcccc   9480
ccacatgccc cttgaccagg aatagcatta caaataacac cgtgataatc ttcatcagag   9540
atattgccgg taattttctg gcctagagat tcaaaagccg atacgatgtt caatttctca   9600
cctttatatt caccgtgttc tattgttcct ccatacacca taatgcttgg cctattaagt   9660
cttgccatac caataataga acctggcata tttttgtcac aacctgggat ggctacaatt   9720
gcatcatagt attcagcgcc agcgttggtt tcaatagagt cagctataac ttctctggaa   9780
acaagggagt atctcattcc caactttcca tttgctatcc catcagaaac tcctatcgta   9840
tgaaattgta agccgatcag accatctgtc tgatttactg agcttttaat ctttgatcca   9900
agggttccta aatgcatgtt gcatggattt ccatcccagt ccatcgacac tatacccact   9960
tgagctttct tgaaatcttc gtctttaaac ccgatgccgt aatacattgc ctgtgtggcg  10020
ggttgtgtgg gatcttgtgt caacgttttg ctgtacttat tcagttcaac agattcaact  10080
ttgccgttat acttaaactc catgtcgaca aacttagatt agattgctat gctttctttc  10140
taatgagcaa gaagtaaaaa aagttgtaat agaacaagaa aaatgaaact gaaacttgag  10200
aaattgaaga ccgtttatta acttaaatat caatgggagg tcatcgaaag agaaaaaaat  10260
caaaaaaaaa attttcaaga aaaagaaacg tgataaaaat ttttattgcc tttttcgacg  10320
aagaaaaaga aacgaggcgg tctctttttt cttttccaaa cctttagtac gggtaattaa  10380
cgacacccta gaggaagaaa gaggggaaat ttagtatgct gtgcttgggt gttttgaagt  10440
ggtacggcga tgcgcggagt ccgagaaaat ctggaagagt aaaaaaggag tagaaacatt  10500
ttgaagctat gagctccagc ttttgttccc tttagtgagg gttaattgcg cgcttggcgt  10560
aatcatggtc atagctgttt cctgtgtgaa attgttatcc gctcacaatt ccacacaaca  10620
```

```
taggagccgg aagcataaag tgtaaagcct ggggtgccta atgagtgagg taactcacat  10680
taattgcgtt gcgctcactg cccgctttcc agtcgggaaa cctgtcgtgc cagctgcatt  10740
aatgaatcgg ccaacgcgcg gggagaggcg gtttgcgtat tgggcgctct tccgcttcct  10800
cgctcactga ctcgctgcgc tcggtcgttc ggctgcggcg agcggtatca gctcactcaa  10860
aggcggtaat acggttatcc acagaatcag gggataacgc aggaaagaac atgtgagcaa  10920
aaggccagca aaaggccagg aaccgtaaaa aggccgcgtt gctggcgttt ttccataggc  10980
tccgcccccc tgacgagcat cacaaaaatc gacgctcaag tcagaggtgg cgaaacccga  11040
caggactata aagataccag gcgtttcccc ctggaagctc cctcgtgcgc tctcctgttc  11100
cgaccctgcc gcttaccgga tacctgtccg cctttctccc ttcgggaagc gtggcgcttt  11160
ctcatagctc acgctgtagg tatctcagtt cggtgtaggt cgttcgctcc aagctgggct  11220
gtgtgcacga accccccgtt cagcccgacc gctgcgcctt atccggtaac tatcgtcttg  11280
agtccaaccc ggtaagacac gacttatcgc cactggcagc agccactggt aacaggatta  11340
gcagagcgag gtatgtaggc ggtgctacag agttcttgaa gtggtggcct aactacggct  11400
acactagaag gacagtattt ggtatctgcg ctctgctgaa gccagttacc ttcggaaaaa  11460
gagttggtag ctcttgatcc ggcaaacaaa ccaccgctgg tagcggtggt ttttttgttt  11520
gcaagcagca gattacgcgc agaaaaaaag gatctcaaga agatcctttg atcttttcta  11580
cggggtctga cgctcagtgg aacgaaaact cacgttaagg gattttggtc atgagattat  11640
caaaaaggat cttcacctag atccttttaa attaaaaatg aagttttaaa tcaatctaaa  11700
gtatatatga gtaaacttgg tctgacagtt accaatgctt aatcagtgag gcacctatct  11760
cagcgatctg tctatttcgt tcatccatag ttgcctgact ccccgtcgtg tagataacta  11820
cgatacggga gggcttacca tctggcccca gtgctgcaat gataccgcga gacccacgct  11880
caccggctcc agatttatca gcaataaacc agccagccgg aagggccgag cgcagaagtg  11940
gtcctgcaac tttatccgcc tccatccagt ctattaattg ttgccgggaa gctagagtaa  12000
gtagttcgcc agttaatagt ttgcgcaacg ttgttgccat tgctacaggc atcgtggtgt  12060
cacgctcgtc gtttggtatg gcttcattca gctccggttc ccaacgatca aggcgagtta  12120
catgatcccc catgttgtgc aaaaaagcgg ttagctcctt cggtcctccg atcgttgtca  12180
gaagtaagtt ggccgcagtg ttatcactca tggttatggc agcactgcat aattctctta  12240
ctgtcatgcc atccgtaaga tgcttttctg tgactggtga gtactcaacc aagtcattct  12300
gagaatagtg tatgcggcga ccgagttgct cttgcccggc gtcaatacgg gataataccg  12360
cgccacatag cagaacttta aaagtgctca tcattggaaa acgttcttcg gggcgaaaac  12420
tctcaaggat cttaccgctg ttgagatcca gttcgatgta acccactcgt gcacccaact  12480
gatcttcagc atcttttact ttcaccagcg tttctgggtg agcaaaaaca ggaaggcaaa  12540
atgccgcaaa aaagggaata agggcgacac ggaaatgttg aatactcata ctcttccttt  12600
ttcaatatta ttgaagcatt tatcagggtt attgtctcat gagcggatac atatttgaat  12660
gtatttagaa aaataaacaa ataggggttc cgcgcacatt tccccgaaaa gtgccacctg  12720
aacgaagcat ctgtgcttca ttttgtagaa caaaaatgca acgcgagagc gctaattttt  12780
caaacaaaga atctgagctg cattttaca gaacagaaat gcaacgcgaa agcgctattt  12840
taccaacgaa gaatctgtgc ttcatttttg taaaacaaaa atgcaacgcg agagcgctaa  12900
tttttcaaac aaagaatctg agctgcattt ttacagaaca gaaatgcaac gcgagagcgc  12960
tattttacca acaaagaatc tatacttctt ttttgttcta caaaaatgca tcccgagagc  13020
```

```
gctatttttc taacaaagca tcttagatta cttttttttct cctttgtgcg ctctataatg  13080
cagtctcttg ataacttttt gcactgtagg tccgttaagg ttagaagaag gctactttgg  13140
tgtctatttt ctcttccata aaaaaagcct gactccactt cccgcgttta ctgattacta  13200
gcgaagctgc gggtgcattt tttcaagata aaggcatccc cgattatatt ctataccgat  13260
gtggattgcg catactttgt gaacagaaag tgatagcgtt gatgattctt cattggtcag  13320
aaaattatga acggtttctt ctattttgtc tctatatact acgtatagga aatgtttaca  13380
ttttcgtatt gttttcgatt cactctatga atagttctta ctacaatttt tttgtctaaa  13440
gagtaatact agagataaac ataaaaaatg tagaggtcga gtttagatgc aagttcaagg  13500
agcgaaaggt ggatgggtag gttatatagg gatatagcac agagatatat agcaaagaga  13560
tacttttgag caatgtttgt ggaagcggta ttcgcaatat tttagtagct cgttacagtc  13620
cggtgcgttt ttggtttttt gaaagtgcgt cttcagagcg cttttggttt tcaaaagcgc  13680
tctgaagttc ctatactttc tagagaatag gaacttcgga ataggaactt caaagcgttt  13740
ccgaaaacga gcgcttccga aaatgcaacg cgagctgcgc acatacagct cactgttcac  13800
gtcgcaccta tatctgcgtg ttgcctgtat atatatatac atgagaagaa cggcatagtg  13860
cgtgtttatg cttaaatgcg tacttatatg cgtctattta tgtaggatga aaggtagtct  13920
agtacctcct gtgatattat cccattccat gcggggtatc gtatgcttcc ttcagcacta  13980
ccctttagct gttctatatg ctgccactcc tcaattggat tagtctcatc cttcaatgct  14040
atcatttcct ttgata                                                  14056
```

<210> SEQ ID NO 124
<211> LENGTH: 7795
<212> TYPE: DNA
<213> ORGANISM: Artificial Sequence
<220> FEATURE:
<223> OTHER INFORMATION: Plasmid pGV2241

<400> SEQUENCE: 124

```
ttggatcata ctaagaaacc attattatca tgacattaac ctataaaaat aggcgtatca     60
cgaggccctt tcgtctcgcg cgtttcggtg atgacggtga aaacctctga cacatgcagc    120
tcccggagac ggtcacagct tgtctgtaag cggatgccgg gagcagacaa gcccgtcagg    180
gcgcgtcagc gggtgttggc gggtgtcggg gctggcttaa ctatgcggca tcagagcaga    240
ttgtactgag agtgcaccat accacagctt ttcaattcaa ttcatcattt ttttttttatt   300
ctttttttttg atttcggttt ctttgaaatt tttttgattc ggtaatctcc gaacagaagg   360
aagaacgaag gaaggagcac agacttagat tggtatatat acgcatatgt agtgttgaag    420
aaacatgaaa ttgcccagta ttcttaaccc aactgcacag aacaaaaacc tgcaggaaac    480
gaagataaat catgtcgaaa gctacatata aggaacgtgc tgctactcat cctagtcctg    540
ttgctgccaa gctatttaat atcatgcacg aaaagcaaac aaacttgtgt gcttcattgg    600
atgttcgtac caccaaggaa ttactggagt tagttgaagc attaggtccc aaaatttgtt    660
tactaaaaac acatgtggat atcttgactg atttttccat ggagggcaca gttaagccgc    720
taaaggcatt atccgccaag tacaattttt tactcttcga agacagaaaa tttgctgaca    780
ttggtaatac agtcaaattg cagtactctg cgggtgtata cagaatagca gaatgggcag    840
acattacgaa tgcacacggt gtggtgggcc caggtattgt tagcggtttg aagcaggcgg    900
cagaagaagt aacaaaggaa cctagaggcc ttttgatgtt agcagaattg tcatgcaagg    960
gctccctatc tactggagaa tatactaagg gtactgttga cattgcgaag agcgacaaag   1020
```

-continued

```
attttgttat cggctttatt gctcaaagag acatgggtgg aagagatgaa ggttacgatt   1080
ggttgattat gacacccggt gtgggtttag atgacaaggg agacgcattg ggtcaacagt   1140
atagaaccgt ggatgatgtg gtctctacag gatctgacat tattattgtt ggaagaggac   1200
tatttgcaaa gggaagggat gctaaggtag agggtgaacg ttacagaaaa gcaggctggg   1260
aagcatattt gagaagatgc ggccagcaaa actaaaaaac tgtattataa gtaaatgcat   1320
gtatactaaa ctcacaaatt agagcttcaa tttaattata tcagttatta ccctatgcgg   1380
tgtgaaatac cgcacagatg cgtaaggaga aaataccgca tcaggaaatt gtaaacgtta   1440
atattttgtt aaaattcgcg ttaaattttt gttaaatcag ctcatttttt aaccaatagg   1500
ccgaaatcgg caaaatccct tataaatcaa aagaatagac cgagataggg ttgagtgttg   1560
ttccagtttg gaacaagagt ccactattaa agaacgtgga ctccaacgtc aaagggcgaa   1620
aaaccgtcta tcagggcgat ggcccactac gtgaaccatc accctaatca agttttttgg   1680
ggtcgaggtg ccgtaaagca ctaaatcgga accctaaagg gagcccccga tttagagctt   1740
gacggggaaa gccggcgaac gtggcgagaa aggaagggaa gaaagcgaaa ggagcgggcg   1800
ctagggcgct ggcaagtgta gcggtcacgc tgcgcgtaac caccacaccc gccgcgctta   1860
atgcgccgct acagggcgcg tcgcgccatt cgccattcag gctgcgcaac tgttgggaag   1920
ggcgatcggt gcgggcctct tcgctattac gccagctggc gaaaggggga tgtgctgcaa   1980
ggcgattaag ttgggtaacg ccagggtttt cccagtcacg acgttgtaaa acgacggcca   2040
gtgagcgcgc gtaatacgac tcactatagg gcgaattggg taccggccgc aaattaaagc   2100
cttcgagcgt cccaaaacct tctcaagcaa ggttttcagt ataatgttac atgcgtacac   2160
gcgtctgtac agaaaaaaaa gaaaaatttg aaatataaat aacgttctta atactaacat   2220
aactataaaa aaataaatag ggacctagac ttcaggttgt ctaactcctt ccttttcggt   2280
tagagcggat gtgggggag ggcgtgaatg taagcgtgac ataactaatt acatgacgcc   2340
gcggatcctt agtggtggtg gtggtggtgt cctgccactg caattctttt catatcggtc   2400
atatatcctc tcagcttttt acccacctgt tctatagcat gtgaacgaat agcttcattt   2460
acgtctctca gttggccatt gtcaaccgct ccttccggaa tagccttccc caaatcacca   2520
ggttgtaact cggccatgaa gggctttaac aacgggacac atgcgtagct aaataagtaa   2580
ttaccatatt ctgcagtgtc tgatatgaca acattcatct cgtaaagtct ttttcttgca   2640
atagtatttg ctatcaaagg caattcatgc aaagactcat agtatgcaga ttcttcaatg   2700
ataccggagt caaccatagt ttcgaatgca agttctaccc ctgccttcac catagctatc   2760
atcaatactc ccttatcaaa gtattcttgt tcaccaattt taccttcgta ttgtggggct   2820
gtctcgaatg ccgtcttgcc ggtttcttct ctccacgtca ataacttttt atcatcgttt   2880
gcccaatctg ccatcattcc tgaggaaaac tcaccggaga taatatcgtc catgtgcttt   2940
tggaataatg gtgccatgat ctcttttagt tgctcagata aggcgtaggc tcttagcttg   3000
gccggatttg aaagtctatc catcatcaat gttatgccac cttgtttaag tgcctcggtg   3060
attgtctccc aaccaaattg tatcaacttt tcagcatagg caggatctgt accctcttcg   3120
accaatttat caaagcatag taaagaccct gcctgcaaca ttccgcacag aatggtttgt   3180
tcacccatta agtcactctt gacctcagct acgaaagaac tctctaacac acccgctcta   3240
tgacctccgg ttgcggctgc ccatgccttc gcaattgcca taccttcacc tttggggtca   3300
ttttcaggat gtacggcgat caatgtaggt acaccaaaac ccctcttgta ctcctctctg   3360
acttccgtac ctgggcactt tggtgcaacc attacgactg ttatatcttt tctgatctgc   3420
```

-continued

```
tcgcccactt caacgatatt aaagccatga gagtaaccta aagctgcccc atccttcatc   3480
agcggttgaa ctgttcttac tacgtctgag tgaaccttat ctggtgttag gttaatcact   3540
aaatctgcct gagggatcag ttcttcgtaa gtaccaactt tgaacccatt ttccgtcgct   3600
ttacgccaat cggcatcctt ttctgcaata gactctttcc tcaatgcata cgaaatatcc   3660
agacctgaat ctctcatgtt taaaccttgg tttagaccct gagcaccgca gccaacaatt   3720
actactttct ttccttgcag ataagaagca ccatcagcaa actcgtccct tcccataaat   3780
ctgcacttac ccagttgagc caattgttgt ctcaaattta atgtgttaaa atagttggcc   3840
atgtcgacaa acttagatta gattgctatg ctttctttct aatgagcaag aagtaaaaaa   3900
agttgtaata gaacaagaaa aatgaaactg aaacttgaga aattgaagac cgtttattaa   3960
cttaaatatc aatgggaggt catcgaaaga gaaaaaaatc aaaaaaaaaa ttttcaagaa   4020
aaagaaacgt gataaaaatt tttattgcct ttttcgacga agaaaaagaa acgaggcggt   4080
ctcttttttc ttttccaaac ctttagtacg ggtaattaac gacaccctag aggaagaaag   4140
aggggaaatt tagtatgctg tgcttgggtg ttttgaagtg gtacggcgat gcgcggagtc   4200
cgagaaaatc tggaagagta aaaaaggagt agaaacattt tgaagctatg agctccagct   4260
tttgttccct ttagtgaggg ttaattgcgc gcttggcgta atcatggtca tagctgtttc   4320
ctgtgtgaaa ttgttatccg ctcacaattc cacacaacat aggagccgga agcataaagt   4380
gtaaagcctg gggtgcctaa tgagtgaggt aactcacatt aattgcgttg cgctcactgc   4440
ccgctttcca gtcgggaaac ctgtcgtgcc agctgcatta atgaatcggc caacgcgcgg   4500
ggagaggcgg tttgcgtatt gggcgctctt ccgcttcctc gctcactgac tcgctgcgct   4560
cggtcgttcg gctgcggcga gcggtatcag ctcactcaaa ggcggtaata cggttatcca   4620
cagaatcagg ggataacgca ggaaagaaca tgtgagcaaa aggccagcaa aaggccagga   4680
accgtaaaaa ggccgcgttg ctggcgtttt tccataggct ccgcccccct gacgagcatc   4740
acaaaaatcg acgctcaagt cagaggtggc gaaacccgac aggactataa agataccagg   4800
cgtttccccc tggaagctcc ctcgtgcgct ctcctgttcc gaccctgccg cttaccggat   4860
acctgtccgc ctttctccct tcgggaagcg tggcgctttc tcatagctca cgctgtaggt   4920
atctcagttc ggtgtaggtc gttcgctcca agctgggctg tgtgcacgaa ccccccgttc   4980
agcccgaccg ctgcgcctta tccggtaact atcgtcttga gtccaacccg gtaagacacg   5040
acttatcgcc actggcagca gccactggta acaggattag cagagcgagg tatgtaggcg   5100
gtgctacaga gttcttgaag tggtggccta actacggcta cactagaagg acagtatttg   5160
gtatctgcgc tctgctgaag ccagttacct tcggaaaaag agttggtagc tcttgatccg   5220
gcaaacaaac caccgctggt agcggtggtt tttttgtttg caagcagcag attacgcgca   5280
gaaaaaaagg atctcaagaa gatcctttga tcttttctac ggggtctgac gctcagtgga   5340
acgaaaactc acgttaaggg attttggtca tgagattatc aaaaaggatc ttcacctaga   5400
tccttttaaa ttaaaaatga agttttaaat caatctaaag tatatatgag taaacttggt   5460
ctgacagtta ccaatgctta atcagtgagg cacctatctc agcgatctgt ctatttcgtt   5520
catccatagt tgcctgactc cccgtcgtgt agataactac gatacgggag ggcttaccat   5580
ctggccccag tgctgcaatg ataccgcgag acccacgctc accggctcca gatttatcag   5640
caataaacca gccagccgga agggccgagc gcagaagtgg tcctgcaact ttatccgcct   5700
ccatccagtc tattaattgt tgccgggaag ctagagtaag tagttcgcca gttaatagtt   5760
tgcgcaacgt tgttgccatt gctacaggca tcgtggtgtc acgctcgtcg tttggtatgg   5820
```

cttcattcag ctccggttcc caacgatcaa ggcgagttac atgatccccc atgttgtgca 5880
aaaaagcggt tagctccttc ggtcctccga tcgttgtcag aagtaagttg gccgcagtgt 5940
tatcactcat ggttatggca gcactgcata attctcttac tgtcatgcca tccgtaagat 6000
gcttttctgt gactggtgag tactcaacca agtcattctg agaatagtgt atgcggcgac 6060
cgagttgctc ttgcccggcg tcaatacggg ataataccgc gccacatagc agaactttaa 6120
aagtgctcat cattggaaaa cgttcttcgg ggcgaaaact ctcaaggatc ttaccgctgt 6180
tgagatccag ttcgatgtaa cccactcgtg cacccaactg atcttcagca tcttttactt 6240
tcaccagcgt ttctgggtga gcaaaaacag gaaggcaaaa tgccgcaaaa aagggaataa 6300
gggcgacacg gaaatgttga atactcatac tcttcctttt tcaatattat tgaagcattt 6360
atcagggtta ttgtctcatg agcggataca tatttgaatg tatttagaaa aataaacaaa 6420
taggggttcc gcgcacattt ccccgaaaag tgccacctga acgaagcatc tgtgcttcat 6480
tttgtagaac aaaaatgcaa cgcgagagcg ctaatttttc aaacaaagaa tctgagctgc 6540
atttttacag aacagaaatg caacgcgaaa gcgctatttt accaacgaag aatctgtgct 6600
tcatttttgt aaaacaaaaa tgcaacgcga gagcgctaat tttcaaaca aagaatctga 6660 gctgcatttt tacagaacag aaatgcaacg cgagagcgct attttaccaa caaagaatct 6720
atacttcttt tttgttctac aaaaatgcat cccgagagcg ctatttttct aacaaagcat 6780
cttagattac tttttttctc ctttgtgcgc tctataatgc agtctcttga taactttttg 6840
cactgtaggt ccgttaaggt tagaagaagg ctactttggt gtctattttc tcttccataa 6900
aaaaagcctg actccacttc ccgcgtttac tgattactag cgaagctgcg ggtgcatttt 6960
ttcaagataa aggcatcccc gattatattc tataccgatg tggattgcgc atactttgtg 7020
aacagaaagt gatagcgttg atgattcttc attggtcaga aaattatgaa cggtttcttc 7080
tattttgtct ctatatacta cgtataggaa atgtttacat tttcgtattg ttttcgattc 7140
actctatgaa tagttcttac tacaattttt ttgtctaaag agtaatacta gagataaaca 7200
taaaaaatgt agaggtcgag tttagatgca agttcaagga gcgaaaggtg gatgggtagg 7260
ttatataggg atatagcaca gagatatata gcaaagagat acttttgagc aatgtttgtg 7320
gaagcggtat tcgcaatatt ttagtagctc gttacagtcc ggtgcgtttt tggtttttg 7380 aaagtgcgtc ttcagagcgc ttttggtttt caaaagcgct ctgaagttcc tatactttct 7440
agagaatagg aacttcggaa taggaacttc aaagcgtttc cgaaaacgag cgcttccgaa 7500
aatgcaacgc gagctgcgca catacagctc actgttcacg tcgcacctat atctgcgtgt 7560
tgcctgtata tatatataca tgagaagaac ggcatagtgc gtgtttatgc ttaaatgcgt 7620
acttatatgc gtctatttat gtaggatgaa aggtagtcta gtacctcctg tgatattatc 7680
ccattccatg cggggtatcg tatgcttcct tcagcactac cctttagctg ttctatatgc 7740
tgccactcct caattggatt agtctcatcc ttcaatgcta tcatttcctt tgata 7795

<210> SEQ ID NO 125
<211> LENGTH: 14056
<212> TYPE: DNA
<213> ORGANISM: Artificial Sequence
<220> FEATURE:
<223> OTHER INFORMATION: Plasmid pGV2242

<400> SEQUENCE: 125
ttggatcata ctaagaaacc attattatca tgacattaac ctataaaaat aggcgtatca 60
cgaggccctt tcgtctcgcg cgtttcggtg atgacggtga aaacctctga cacatgcagc 120

-continued

```
tcccggagac ggtcacagct tgtctgtaag cggatgccgg gagcagacaa gcccgtcagg    180
gcgcgtcagc gggtgttggc gggtgtcggg gctggcttaa ctatgcggca tcagagcaga    240
ttgtactgag agtgcaccat accacagctt ttcaattcaa ttcatcattt ttttttttatt    300
ctttttttttg atttcggttt ctttgaaatt tttttgattc ggtaatctcc gaacagaagg    360
aagaacgaag gaaggagcac agacttagat tggtatatat acgcatatgg caaattaaag    420
ccttcgagcg tcccaaaacc ttctcaagca aggttttcag tataatgtta catgcgtaca    480
cgcgtctgta cagaaaaaaa agaaaaattt gaaatataaa taacgttctt aatactaaca    540
taactataaa aaaataaata gggacctaga cttcaggttg tctaactcct tccttttcgg    600
ttagagcgga tgtgggggga gggcgtgaat gtaagcgtga cataactaat tacatgactc    660
gacctaggtt atttagtaaa atcaatgacc attcggcctt caatttttcc tgccttcatt    720
tcatcaataa tatcattgat ttcttccagt ttgcgtgtcg caacaattgg ttttacctta    780
ccttctgctc caaattgaaa agcttctgcc aagtcaagtc ttgttccgac aagtgaacct    840
gcaacctcca ctccgtcaaa aacaactgtt ggaactgata aagtcatctc agtattggga    900
agtgccacag caaccatttt gcccataggt ttcaaagaag caaccgcttg ttcaaaagca    960
atccttgcaa cagcacaaac tattgcactt tgcaccccta agccgccagt tattttttta   1020
atttcatcaa ctggatttac atcaccagaa ttgataatca catcagctcc aatttttttta   1080
gctaaattta atttatcttg attaatatca acagcaatta cttttgctcc aaaaacattt   1140
ttagcatatt gaattgctaa atttccaagt cctccagcac caaaaattac ttgccaatca   1200
ccaggtttta ctcctgatac tttgattgct ttgtaagttg ttactccagc acaagtaatt   1260
gagctagctt caattgggtc aagtccgtca ggaactttga cagcataatc ggcaacaaca   1320
attgcttctt cagccattcc gccatcaact gaatatcctg catttttaac ttctcgacaa   1380
aaagtttcat taccagatac acagtattca cagtgaccac atccttcaaa gaaccaagcc   1440
actgaaaccc gatcaccaac ttgaagcgag cttacatcag ctccaatttc tttgacaatt   1500
ccaattcctt catgaccaag aacagtccct gctttgttgc cataatcacc tgctgcaacg   1560
tgcaaatcgg tatgacagac tccacaatac tccatgtcaa gcaaagcttc attaggtttg   1620
attgctcgaa gttccttttc aacaaggtcc gcataaccat ctggattgtg tcttactact   1680
gctgctttca ttggtaccta ttattgtatg ttatagtatt agttgcttgg tgttatgaaa   1740
gaaactaaga aaagaaaaat aaaataaaaa taaaagattg agacaaggga agaaaagata   1800
caaaataaga attaattaca attgcgtttg ctataaatac gtttttaaca atcaactctg   1860
gtaggaagat aatgcttttt tttttttatat atgcttggtg ccacttgtca catacaattc   1920
tacaaccttc gacaaaaatc caaatgatag taagatcaaa gccagaaagc aatggagaaa   1980
aaaaattaat gaaccacgat gaaccaaatg atcaatacaa ccaaagaaac taccctagtg   2040
aggtgtatgc tgacttggta tcacacttca tgaattttgc atatggcaaa gtccacgaaa   2100
gtgggcttca gaaaaaaggc gtgcggtgtg tagatgtatc aattagtgga tgccagtttt   2160
ggaacgggat tccactttcc gcaagttggt gcacgtcgtt agtgacataa cgccgcgttc   2220
atctttggga agaagcagat gctgagcgag gaggtactat agagtaaaga accctttcta   2280
tacccgcagc cccatggtaa gtgacagtgc agtaataata tgaaccaatt tatttttcgt   2340
tacataaaaa tgcttataaa actttaacta ataattagag attaaatcgc ggccgcaaaa   2400
gatccttagg atttattctg ttcagcaaac agcttgccca ttttcttcag taccttcggt   2460
gcgccttctt tcgccaggat cagttcgatc cagtacatac ggttcggatc ggcctgggcc   2520
```

-continued

```
tctttcatca cgctcacaaa ttcgttttcg gtacgcacaa ttttagacac aacacggtcc   2580
tcagttgcgc cgaaggactc cggcagttta gagtagttcc acatagggat atcgttgtaa   2640
gactggttcg gaccgtggat ctcacgctca acggtgtagc cgtcattgtt aataatgaag   2700
caaatcgggt tgatcttttc acgaattgcc agacccagtt cctgtacggt cagctgcagg   2760
gaaccgtcac cgatgaacag cagatgacga gattctttat cagcgatctg agagcccagc   2820
gctgccggga aagtatagcc aatgctaccc cacagcggct gaccgataaa atggcttttg   2880
gatttcagaa agatagaaga cgcgccgaaa aagctcgtac cttgttccgc cacgatggtt   2940
tcattgctct gggtcaggtt ctccacggcc tgccacaggc gatcctggga cagcagtgcg   3000
ttagatggta cgaaatcttc ttgctttttg tcaatgtatt tgcctttata ctcgatttcg   3060
gacaggtcca gcagagagct gatcaggctt tcgaagtcga agttctggat acgctcgttg   3120
aagattttac cctcgtcgat gttcaggcta atcattttgt tttcgttcag atggtgagtg   3180
aatgcaccgg tagaagagtc ggtcagttta acgcccagca tcaggatgaa gtccgcagat   3240
tcaacaaatt ctttcaggtt cggttcgctc agagtaccgt tgtagatgcc caggaaagac   3300
ggcagagcct cgtcaacaga ggacttgccg aagttcaggg tggtaatcgg cagtttggtt   3360
ttgctgatga attgggtcac ggtcttctcc agaccaaaag aaatgatttc gtggccggtg   3420
atcacgattg gtttctttgc gtttttcaga gactcctgga ttttgttcag gatttcctgg   3480
tcgctagtgt tagaagtgga gtttttctttc ttcagcggca ggctcggttt ttccgcttta   3540
gctgccgcaa catccacagg caggttgatg taaactggtt tgcgttcttt cagcagcgca   3600
gacagaacgc ggtcgatttc cacagtagcg ttctctgcag tcagcagcgt acgtgccgca   3660
gtcacaggtt catgcatttt catgaagtgt ttgaaatcgc cgtcagccag agtgtggtgg   3720
acgaatttac cttcgttctg aactttgctc gttgggctgc ctacgatctc caccaccggc   3780
aggttttcgg cgtaggagcc cgccagaccg ttgacggcgc tcagttcgcc aacaccgaaa   3840
gtggtcagaa atgccgcggc tttcttggta cgtgcataac catctgccat gtagcttgcg   3900
ttcagttcgt tagcgttacc cacccatttc atgtctttat gagagatgat ctgatccagg   3960
aactgcagat tgtaatcacc cggaacgccg aagatttctt cgatacccag ttcatgcaga   4020
cggtccagca gataatcacc aacagtatac atgtcgagct tgttttatat ttgttgtaaa   4080
aagtagataa ttacttcctt gatgatctgt aaaaaagaga aaaagaaagc atctaagaac   4140
ttgaaaaact acgaattaga aaagaccaaa tatgtatttc ttgcattgac caatttatgc   4200
aagtttatat atatgtaaat gtaagtttca cgaggttcta ctaaactaaa ccaccccctt   4260
ggttagaaga aaagagtgtg tgagaacagg ctgttgttgt cacacgattc ggacaattct   4320
gtttgaaaga gagagagtaa cagtacgatc gaacgaactt tgctctggag atcacagtgg   4380
gcatcatagc atgtggtact aaaccctttc ccgccattcc agaaccttcg attgcttgtt   4440
acaaaacctg tgagccgtcg ctaggacctt gttgtgtgac gaaattggaa gctgcaatca   4500
ataggaagac aggaagtcga gcgtgtctgg gtttttttcag ttttgttctt tttgcaaaca   4560
aatcacgagc gacggtaatt tctttctcga taagaggcca cgtgctttat gagggtaaca   4620
tcaattcaag aaggagggaa acacttcctt tttctggccc tgataatagt atgagggtga   4680
agccaaaata aaggattcgc gcccaaatcg gcatctttaa atgcaggtat gcgatagttc   4740
ctcactcttt ccttactcac gagtaattct tgcaaatgcc tattatgcag atgttataat   4800
atctgtgcgt cttgagttga gcctagaatt cttagaaaaa ctcatcgagc atcaaatgaa   4860
actgcaattt attcatatca ggattatcaa taccatattt ttgaaaaagc cgtttctgta   4920
```

atgaaggaga aaactcaccg aggcagttcc ataggatggc aagatcctgg tatcggtctg 4980
cgatcccgac tcgtccaaca tcaatacaac ctattaattt cccctcgtca aaaataaggt 5040
tatcaagtga gaaatcacca tgagtgacga ctgaatccgg tgagaatggc aaaagcttat 5100
gcatttcttt ccagacttgt tcaacaggcc agccattacg ctcgtcatca aaatcactcg 5160
cgtcaaccaa accgttattc attcgtgatt gcgcctgagc gaggcgaaat acgcgatcgc 5220
tgttaaaagg acaattacaa acaggaatcg aatgcaaccg gcgcaggaac actgccagcg 5280
catcaacaat attttcacct gaatcaggat attcttctaa tacctggaat gctgttttgc 5340
cggggatcgc agtggtgagt aaccatgcat catcaggagt acggacaaaa tgcttgatgg 5400
tcggaagagg cataaattcc gtcagccagt ttagtctgac catctcatct gcaacatcat 5460
tggcaacgct acctttgcca tgtttcagaa acaactctgg cgcatcgggc ttcccataca 5520
atcgatagat tgtcgcacct gattgcccga cattatcgcg agcccattta tacccatata 5580
aatcagcatc catgttggaa tttaatcgcg gcctcgaaac gtgagtcttt tccttaccca 5640
tactagtttt tagtttatgt atgtgttttt tgtagttata gatttaagca agaaaagaat 5700
acaaacaaaa aattgaaaaa gattgattta gaattaaaaa gaaaaatatt tacgtaagaa 5760
gggaaaatag taaatgttgc aagttcacta aactcctaaa ttatgctgcc ctttatattc 5820
cctgttacag cagccgagcc aaaggtatat aggctccttt gcattagcat gcgtaacaaa 5880
ccacctgtca gtttcaaccg aggtggtatc cgagagaatt gtgtgattgc tttaattaat 5940
ttcggagaat ctcacatgcc actgaagatt aaaaactgga tgccagaaaa ggggtgtcca 6000
ggtgtaacat caatagagga agctgaaaag tcttagaacg ggtaatcttc caccaacctg 6060
atgggttcct agatataatc tcgaagggaa taagtagggt gataccgcag aagtgtctga 6120
atgtattaag gtcctcacag tttaaatccc gctcacacta acgtaggatt attataactc 6180
aaaaaaatgg cattattcta agtaagttaa atatccgtaa tctttaaaca gcggccgcgg 6240
atcttcatcc tgccactgca attcttttca tatcggtcat atatcctctc agctttttac 6300
ccacctgttc tatagcatgt gaacgaatag cttcatttac gtctctcagt tggccattgt 6360
caaccgctcc ttccggaata gccttcccca aatcaccagg ttgtaactcg gccatgaagg 6420
gctttaacaa cgggacacat gcgtagctaa ataagtaatt accatattct gcagtgtctg 6480
atatgacaac attcatctcg taaagtcttt ttcttgcaat agtatttgct atcaaaggca 6540
attcatgcaa agactcatag tatgcagatt cttcaatgat accggagtca accatagttt 6600
cgaatgcaag ttctacccct gccttcacca tagctatcat caatactccc ttatcaaagt 6660
attcttgttc accaatttta ccttcgtatt gtggggctgt ctcgaatgcc gtcttgccgg 6720
tttcttctct ccacgtcaat aactttttat catcgtttgc ccaatctgcc atcattcctg 6780
aggaaaactc accggagata atatcgtcca tgtgcttttg gaataatggt gccatgatct 6840
cttttagttg ctcagataag gcgtaggctc ttagcttggc cggatttgaa agtctatcca 6900
tcatcaatgt tatgccacct tgtttaagtg cctcggtgat tgtctcccaa ccaaattgta 6960
tcaacttttc agcataggca ggatctgtac cctcttcgac caatttatca aagcatagta 7020
aagaccctgc ctgcaacatt ccgcacagaa tggtttgttc acccattaag tcactcttga 7080
cctcagctac gaaagaactc tctaacacac ccgctctatg acctccggtt gcggctgccc 7140
atgccttcgc aattgccata ccttcacgtt tggggtcatt ttcaggatgt acggcgatca 7200
atgtaggtac accaaaaccc ctcttgtact cctctctgac ttccgtacct gggcactttg 7260
gcgcaaccat tacgactgtt atacctttttc tgatctgctc gcccacttca acgatattaa 7320

-continued

```
agccatgaga gtaacctaaa gctgccccat ccttcatcag cggttgaact gttcttacta   7380
cgtctgagtg aaccttatct ggtgttaggt taatcactaa atctgcctga gggatcagtt   7440
cttcgtaagt accaactttg aacccatttt ccgtcgcttt acgccaatcg gcatcctttt   7500
ctgcaataga ctctttcctc aatgcatacg aaatatccag acctgaatct ctcatgttta   7560
aaccttggtt tagaccctga gcaccgcagc caacaattac tactttcttt ccttgcagat   7620
aagaagcacc atcagcaaac tcgtcccttc ccataaatct gcacttaccc agttgagcca   7680
attgttgtct caaatttaat gtgttaaaat agttggccat gtcgagtcga aactaagttc   7740
tggtgtttta aaactaaaaa aaagactaac tataaaagta gaatttaaga agtttaagaa   7800
atagatttac agaattacaa tcaataccta ccgtctttat atacttatta gtcaagtagg   7860
ggaataattt cagggaactg gtttcaacct tttttttcag ctttttccaa atcagagaga   7920
gcagaaggta atagaaggtg taagaaaatg agatagatac atgcgtgggt caattgcctt   7980
gtgtcatcat ttactccagg caggttgcat cactccattg aggttgtgcc cgtttttttgc   8040
ctgtttgtgc ccctgttctc tgtagttgcg ctaagagaat ggacctatga actgatggtt   8100
ggtgaagaaa acaatatttt ggtgctggga ttcttttttt ttctggatgc cagcttaaaa   8160
agcgggctcc attatattta gtggatgcca ggaataaact gttcacccag acacctacga   8220
tgttatatat tctgtgtaac ccgcccccta ttttgggcat gtacgggtta cagcagaatt   8280
aaaaggctaa ttttttgact aaataaagtt aggaaaatca ctactattaa ttatttacgt   8340
attctttgaa atggcgagta ttgataatga taaactggat ccgcggccgc ttacagatca   8400
gtaacacacc cttccgatgc aggacgggtt aatttagcga attttgccaa aactcccctg   8460
gtggctttcg gagttggctt ctgataatta gctcttctct ttgcgatttc ttcatcggaa   8520
actttcaggg atatagagtt gttgactgca tctatctcta ttatatcgtc atcttcaact   8580
aagccgatta gtccaccctc aacggcttca ggcacaatat ggccgacaac aaaaccgtga   8640
gtgccaccgg agaatctacc atccgtaatt aacgcgcaac ttttccctaa acccgcacca   8700
attaatgctg atgtaggctt cagcatttcg ggcataccag gtccgccgac gggacctata   8760
ttcctaatta ccgctacatc tccagcatgc aaacgaccag attctatgcc gtcgataaaa   8820
tgttgttcac catcaaagac tctggcagtg cctttgaaga actctccttc tttaccgcta   8880
atttttgcta cggaaccccc ttgagctaaa ttaccgtaca gaatctgcaa gtggccggtg   8940
gccttgatag gattctttag tggcctcatg atatcttgtg agtcgaaatc caagtctagg   9000
gcagtctcga cattctcggc taatgtttta cccgtcacag taaggcagtc accatgcaat   9060
tttccttcct ttagaaggta cttaagcact gctggcaagc ctccaatttt atgcaaatct   9120
tccatcatat atttacctga aggtttaaaa tcacctagta ctggagtaat gtcactaatt   9180
ctttggaagt catcctgagt tatttcgaca cctatcgcgt tagccattgc aataatatgc   9240
aagacagcat tagtactacc ccccaagacc atcacaatgg taatagcgtt ctcgaacgcc   9300
tccttagtca ttatatcact aggcttgatg tctttttcca aaagattctt aatggctaat   9360
ccaatctcat cacattcttc ttgtttttct tgagatactg cagggttcga agaagaatac   9420
ggcaatgaca tacctagtgt ttcgatagcg gcagctaagg tattagctgt gtacatcccc   9480
ccacatgccc cttgaccagg aatagcatta caaataacac cgtgataatc ttcatcagag   9540
atattgccgg taattttctg gcctagagat tcaaaagccg atacgatgtt caatttctca   9600
cctttatatt caccgtgttc tattgttcct ccatacacca taatgcttgg cctattaagt   9660
cttgccatac caataataga acctggcata tttttgtcac aacctgggat ggctacaatt   9720
```

```
gcatcatagt attcagcgcc agcgttggtt tcaatagagt cagctataac ttctctggaa   9780
acaagggagt atctcattcc caactttcca tttgctatcc catcagaaac tcctatcgta   9840
tgaaattgta agccgatcag accatctgtc tgatttactg agcttttaat ctttgatcca   9900
agggttccta aatgcatgtt gcatggattt ccatcccagt ccatcgacac tatacccact   9960
tgagctttct tgaaatcttc gtctttaaac ccgatgccgt aatacattgc ctgtgtggcg  10020
ggttgtgtgg gatcttgtgt caacgttttg ctgtacttat tcagttcaac agattcaact  10080
ttgccgttat acttaaactc catgtcgaca aacttagatt agattgctat gctttctttc  10140
taatgagcaa gaagtaaaaa aagttgtaat agaacaagaa aaatgaaact gaaacttgag  10200
aaattgaaga ccgtttatta acttaaatat caatgggagg tcatcgaaag agaaaaaaat  10260
caaaaaaaaa attttcaaga aaaagaaacg tgataaaaat ttttattgcc tttttcgacg  10320
aagaaaaaga aacgaggcgg tctctttttt cttttccaaa cctttagtac gggtaattaa  10380
cgacacccta gaggaagaaa gaggggaaat ttagtatgct gtgcttgggt gttttgaagt  10440
ggtacggcga tgcgcggagt ccgagaaaat ctggaagagt aaaaaaggag tagaaacatt  10500
ttgaagctat gagctccagc ttttgttccc tttagtgagg gttaattgcg cgcttggcgt  10560
aatcatggtc atagctgttt cctgtgtgaa attgttatcc gctcacaatt ccacacaaca  10620
taggagccgg aagcataaag tgtaaagcct ggggtgccta atgagtgagg taactcacat  10680
taattgcgtt gcgctcactg cccgctttcc agtcgggaaa cctgtcgtgc cagctgcatt  10740
aatgaatcgg ccaacgcgcg gggagaggcg gtttgcgtat tgggcgctct tccgcttcct  10800
cgctcactga ctcgctgcgc tcggtcgttc ggctgcggcg agcggtatca gctcactcaa  10860
aggcggtaat acggttatcc acagaatcag gggataacgc aggaaagaac atgtgagcaa  10920
aaggccagca aaaggccagg aaccgtaaaa aggccgcgtt gctggcgttt ttccataggc  10980
tccgcccccc tgacgagcat cacaaaaatc gacgctcaag tcagaggtgg cgaaacccga  11040
caggactata aagataccag gcgtttcccc ctggaagctc cctcgtgcgc tctcctgttc  11100
cgaccctgcc gcttaccgga tacctgtccg cctttctccc ttcgggaagc gtggcgcttt  11160
ctcatagctc acgctgtagg tatctcagtt cggtgtaggt cgttcgctcc aagctgggct  11220
gtgtgcacga accccccgtt cagcccgacc gctgcgcctt atccggtaac tatcgtcttg  11280
agtccaaccc ggtaagacac gacttatcgc cactggcagc agccactggt aacaggatta  11340
gcagagcgag gtatgtaggc ggtgctacag agttcttgaa gtggtggcct aactacggct  11400
acactagaag gacagtattt ggtatctgcg ctctgctgaa gccagttacc ttcggaaaaa  11460
gagttggtag ctcttgatcc ggcaaacaaa ccaccgctgg tagcggtggt ttttttgttt  11520
gcaagcagca gattacgcgc agaaaaaaag gatctcaaga agatcctttg atcttttcta  11580
cggggtctga cgctcagtgg aacgaaaact cacgttaagg gattttggtc atgagattat  11640
caaaaaggat cttcacctag atccttttaa attaaaaatg aagttttaaa tcaatctaaa  11700
gtatatatga gtaaacttgg tctgacagtt accaatgctt aatcagtgag gcacctatct  11760
cagcgatctg tctatttcgt tcatccatag ttgcctgact ccccgtcgtg tagataacta  11820
cgatacggga gggcttacca tctggcccca gtgctgcaat gataccgcga gacccacgct  11880
caccggctcc agatttatca gcaataaacc agccagccgg aagggccgag cgcagaagtg  11940
gtcctgcaac tttatccgcc tccatccagt ctattaattg ttgccgggaa gctagagtaa  12000
gtagttcgcc agttaatagt ttgcgcaacg ttgttgccat tgctacaggc atcgtggtgt  12060
cacgctcgtc gtttggtatg gcttcattca gctccggttc ccaacgatca aggcgagtta  12120
```

```
catgatcccc catgttgtgc aaaaaagcgg ttagctcctt cggtcctccg atcgttgtca  12180
gaagtaagtt ggccgcagtg ttatcactca tggttatggc agcactgcat aattctctta  12240
ctgtcatgcc atccgtaaga tgcttttctg tgactggtga gtactcaacc aagtcattct  12300
gagaatagtg tatgcggcga ccgagttgct cttgcccggc gtcaatacgg gataataccg  12360
cgccacatag cagaacttta aaagtgctca tcattggaaa acgttcttcg gggcgaaaac  12420
tctcaaggat cttaccgctg ttgagatcca gttcgatgta acccactcgt gcacccaact  12480
gatcttcagc atcttttact ttcaccagcg tttctgggtg agcaaaaaca ggaaggcaaa  12540
atgccgcaaa aaagggaata agggcgacac ggaaatgttg aatactcata ctcttccttt  12600
ttcaatatta ttgaagcatt tatcagggtt attgtctcat gagcggatac atatttgaat  12660
gtatttagaa aaataaacaa ataggggttc cgcgcacatt tccccgaaaa gtgccacctg  12720
aacgaagcat ctgtgcttca ttttgtagaa caaaaatgca acgcgagagc gctaattttt  12780
caaacaaaga atctgagctg catttttaca gaacagaaat gcaacgcgaa agcgctattt  12840
taccaacgaa gaatctgtgc ttcatttttg taaaacaaaa atgcaacgcg agagcgctaa  12900
tttttcaaac aaagaatctg agctgcattt ttacagaaca gaaatgcaac gcgagagcgc  12960
tattttacca acaaagaatc tatacttctt ttttgttcta caaaaatgca tcccgagagc  13020
gctatttttc taacaaagca tcttagatta cttttttctc cctttgtgcg ctctataatg  13080
cagtctcttg ataacttttt gcactgtagg tccgttaagg ttagaagaag gctactttgg  13140
tgtctatttt ctcttccata aaaaaagcct gactccactt cccgcgttta ctgattacta  13200
gcgaagctgc gggtgcattt tttcaagata aaggcatccc cgattatatt ctataccgat  13260
gtggattgcg catactttgt gaacagaaag tgatagcgtt gatgattctt cattggtcag  13320
aaaattatga acggtttctt ctattttgtc tctatatact acgtatagga aatgtttaca  13380
ttttcgtatt gttttcgatt cactctatga atagttctta ctacaatttt tttgtctaaa  13440
gagtaatact agagataaac ataaaaaatg tagaggtcga gtttagatgc aagttcaagg  13500
agcgaaaggt ggatgggtag gttatatagg gatatagcac agagatatat agcaaagaga  13560
tacttttgag caatgtttgt ggaagcggta ttcgcaatat tttagtagct cgttacagtc  13620
cggtgcgttt ttggtttttt gaaagtgcgt cttcagagcg cttttggttt tcaaaagcgc  13680
tctgaagttc ctatactttc tagagaatag gaacttcgga ataggaactt caaagcgttt  13740
ccgaaaacga gcgcttccga aaatgcaacg cgagctgcgc acatacagct cactgttcac  13800
gtcgcaccta tatctgcgtg ttgcctgtat atatatatac atgagaagaa cggcatagtg  13860
cgtgtttatg cttaaatgcg tacttatatg cgtctattta tgtaggatga aaggtagtct  13920
agtacctcct gtgatattat cccattccat gcggggtatc gtatgcttcc ttcagcacta  13980
ccctttagct gttctatatg ctgccactcc tcaattggat tagtctcatc cttcaatgct  14040
atcatttcct ttgata                                                  14056
```

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

-continued

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201
<211> LENGTH: 46
<212> TYPE: DNA
<213> ORGANISM: UNKNOWN
<220> FEATURE:
<223> OTHER INFORMATION: Primer XX1

<400> SEQUENCE: 201
cgcaccggtt ttctcctctt taatgaattc ggtcagtgcg tcctgc 46

<210> SEQ ID NO 202
<211> LENGTH: 36
<212> TYPE: DNA
<213> ORGANISM: UNKNOWN
<220> FEATURE:
<223> OTHER INFORMATION: Primer XX2

<400> SEQUENCE: 202
gcggccgccc tagggcgttc ggctgcggcg agcggt 36

<210> SEQ ID NO 203
<211> LENGTH: 56
<212> TYPE: DNA
<213> ORGANISM: UNKNOWN
<220> FEATURE:
<223> OTHER INFORMATION: Primer XX3

<400> SEQUENCE: 203
cgcgaattcg gatccgagga gaaaatagtt atgaacaact ttaatctgca cacccc 56

<210> SEQ ID NO 204
<211> LENGTH: 42
<212> TYPE: DNA
<213> ORGANISM: UNKNOWN
<220> FEATURE:
<223> OTHER INFORMATION: Primer XX4

<400> SEQUENCE: 204
gcgcctaggg cggccgctta gcgggcggct tcgtatatac gg 42

<210> SEQ ID NO 205
<211> LENGTH: 61
<212> TYPE: DNA
<213> ORGANISM: UNKNOWN
<220> FEATURE:
<223> OTHER INFORMATION: Primer 50

<400> SEQUENCE: 205
gcagtttcac cttctacata atcacgaccg tagtaggtat cattccgggg atccgtcgac 60
c 61

<210> SEQ ID NO 206
<211> LENGTH: 60
<212> TYPE: DNA
<213> ORGANISM: UNKNOWN
<220> FEATURE:
<223> OTHER INFORMATION: Primer 73

<400> SEQUENCE: 206
ctggcttaag taccgggtta gttaacttaa ggagaatgac gtgtaggctg gagctgcttc 60

<210> SEQ ID NO 207
<211> LENGTH: 60
<212> TYPE: DNA
<213> ORGANISM: UNKNOWN
<220> FEATURE:
<223> OTHER INFORMATION: Primer 74

<400> SEQUENCE: 207
ctcaaactca ttccaggaac gaccatcacg ggtaatcatc attccgggga tccgtcgacc 60

<210> SEQ ID NO 208
<211> LENGTH: 65
<212> TYPE: DNA
<213> ORGANISM: UNKNOWN
<220> FEATURE:
<223> OTHER INFORMATION: Primer 116

<400> SEQUENCE: 208
cagcgttcgc tttatatccc ttacgctggc cctgtactgc tggaagtgta ggctggagct 60
gcttc 65

<210> SEQ ID NO 209
<211> LENGTH: 65
<212> TYPE: DNA
<213> ORGANISM: UNKNOWN
<220> FEATURE:
<223> OTHER INFORMATION: Primer 117

<400> SEQUENCE: 209
ttcggcttgc cagaaattat cgtcaatggc ctgttgcagg gcttcattcc ggggatccgt 60
cgacc 65

<210> SEQ ID NO 210
<211> LENGTH: 26
<212> TYPE: DNA
<213> ORGANISM: UNKNOWN
<220> FEATURE:
<223> OTHER INFORMATION: Primer 350

<400> SEQUENCE: 210
cttaaattct acttttatag ttagtc 26

<210> SEQ ID NO 211

<211> LENGTH: 65
<212> TYPE: DNA
<213> ORGANISM: UNKNOWN
<220> FEATURE:
<223> OTHER INFORMATION: Primer 474

<400> SEQUENCE: 211
caaagctgcg gatgatgacg agattactgc tgctgtgcag actgaattcc ggggatccgt 60
cgacc 65

<210> SEQ ID NO 212
<211> LENGTH: 20
<212> TYPE: DNA
<213> ORGANISM: UNKNOWN
<220> FEATURE:
<223> OTHER INFORMATION: Primer 772

<400> SEQUENCE: 212
aggaaggagc acagacttag 20

<210> SEQ ID NO 213
<211> LENGTH: 64
<212> TYPE: DNA
<213> ORGANISM: UNKNOWN
<220> FEATURE:
<223> OTHER INFORMATION: Primer 868

<400> SEQUENCE: 213
cacaacatca cgaggaatca ccatggctaa ctacttcaat acacgtgtag gctggagctg 60
cttc 64

<210> SEQ ID NO 214
<211> LENGTH: 65
<212> TYPE: DNA
<213> ORGANISM: UNKNOWN
<220> FEATURE:
<223> OTHER INFORMATION: Primer 869

<400> SEQUENCE: 214
cttaacccgc aacagcaata cgtttcatat ctgtcatata gccgcattcc ggggatccgt 60
cgacc 65

<210> SEQ ID NO 215
<211> LENGTH: 45
<212> TYPE: DNA
<213> ORGANISM: UNKNOWN
<220> FEATURE:
<223> OTHER INFORMATION: Primer 1030

<400> SEQUENCE: 215
gtcggtgaac gctctcctga gtagggtgta ggctggagct gcttc 45

<210> SEQ ID NO 216
<211> LENGTH: 45
<212> TYPE: DNA
<213> ORGANISM: UNKNOWN
<220> FEATURE:
<223> OTHER INFORMATION: Primer 1031

<400> SEQUENCE: 216
gaagcagctc cagcctacac cctactcagg agagcgttca ccgac 45

<210> SEQ ID NO 217
<211> LENGTH: 69
<212> TYPE: DNA

<213> ORGANISM: UNKNOWN
<220> FEATURE:
<223> OTHER INFORMATION: Primer 1032

<400> SEQUENCE: 217
cacaacatca cgaggaatca ccatggctaa ctacttcaat acaccacgag gccctttcgt 60
cttcacctc 69

<210> SEQ ID NO 218
<211> LENGTH: 65
<212> TYPE: DNA
<213> ORGANISM: UNKNOWN
<220> FEATURE:
<223> OTHER INFORMATION: Primer 1155

<400> SEQUENCE: 218
cccaacccgc attctgtttg gtaaaggcgc aatcgctggt ttacggtgta ggctggagct 60
gcttc 65

<210> SEQ ID NO 219
<211> LENGTH: 65
<212> TYPE: DNA
<213> ORGANISM: UNKNOWN
<220> FEATURE:
<223> OTHER INFORMATION: Primer 1156

<400> SEQUENCE: 219
caatcgcggc gtcaatacgc tcatcatcgg aaccttcagt gatgtattcc ggggatccgt 60
cgacc 65

<210> SEQ ID NO 220
<211> LENGTH: 65
<212> TYPE: DNA
<213> ORGANISM: UNKNOWN
<220> FEATURE:
<223> OTHER INFORMATION: Primer 1187

<400> SEQUENCE: 220
cggataaagt tcgtgagatt gccgcaaaac tggggcgtca tgtgggtgta ggctggagct 60
gcttc 65

<210> SEQ ID NO 221
<211> LENGTH: 65
<212> TYPE: DNA
<213> ORGANISM: UNKNOWN
<220> FEATURE:
<223> OTHER INFORMATION: Primer 1188

<400> SEQUENCE: 221
cagacatcaa gtaacctttta tcgcgcagca gattaaccgc ttcgcattcc ggggatccgt 60
cgacc 65

<210> SEQ ID NO 222
<211> LENGTH: 65
<212> TYPE: DNA
<213> ORGANISM: UNKNOWN
<220> FEATURE:
<223> OTHER INFORMATION: Primer 1191

<400> SEQUENCE: 222
ggcactcacg ttgggctgag acacaagcac acattcctct gcacggtgta ggctggagct 60
gcttc 65

<210> SEQ ID NO 223
<211> LENGTH: 65
<212> TYPE: DNA
<213> ORGANISM: UNKNOWN
<220> FEATURE:
<223> OTHER INFORMATION: Primer 1192

<400> SEQUENCE: 223
gcaccagaaa ccataactac aacgtcacct ttgtgtgcca gaccgattcc ggggatccgt 60
cgacc 65

<210> SEQ ID NO 224
<211> LENGTH: 67
<212> TYPE: DNA
<213> ORGANISM: UNKNOWN
<220> FEATURE:
<223> OTHER INFORMATION: Primer 1205

<400> SEQUENCE: 224
gttatctagt tgtgcaaaac atgctaatgt agccaccaaa tccacgaggc cctttcgtct 60
tcacctc 67

<210> SEQ ID NO 225
<211> LENGTH: 42
<212> TYPE: DNA
<213> ORGANISM: UNKNOWN
<220> FEATURE:
<223> OTHER INFORMATION: Primer 1218

<400> SEQUENCE: 225
gctcactcaa aggcggtaat acgtgtaggc tggagctgct tc 42

<210> SEQ ID NO 226
<211> LENGTH: 42
<212> TYPE: DNA
<213> ORGANISM: UNKNOWN
<220> FEATURE:
<223> OTHER INFORMATION: Primer 1219

<400> SEQUENCE: 226
gaagcagctc cagcctacac gtattaccgc ctttgagtga gc 42

<210> SEQ ID NO 227
<211> LENGTH: 20
<212> TYPE: DNA
<213> ORGANISM: UNKNOWN
<220> FEATURE:
<223> OTHER INFORMATION: Primer 1220

<400> SEQUENCE: 227
cgtagaatca ccagaccagc 20

<210> SEQ ID NO 228
<211> LENGTH: 56
<212> TYPE: DNA
<213> ORGANISM: UNKNOWN
<220> FEATURE:
<223> OTHER INFORMATION: Primer 1296

<400> SEQUENCE: 228
ttttgtcgac ggatccagga gacaacatta tgtctattcc agaaactcaa aaagcg 56

<210> SEQ ID NO 229
<211> LENGTH: 46
<212> TYPE: DNA

<213> ORGANISM: UNKNOWN
<220> FEATURE:
<223> OTHER INFORMATION: Primer 1297

<400> SEQUENCE: 229
ttttgtcgac gcggccgctt atttagaggt gtccaccacg taacgg 46

<210> SEQ ID NO 230
<211> LENGTH: 20
<212> TYPE: DNA
<213> ORGANISM: UNKNOWN
<220> FEATURE:
<223> OTHER INFORMATION: Primer 1321

<400> SEQUENCE: 230
aatcatatcg aacacgatgc 20

<210> SEQ ID NO 231
<211> LENGTH: 20
<212> TYPE: DNA
<213> ORGANISM: UNKNOWN
<220> FEATURE:
<223> OTHER INFORMATION: Primer 1322

<400> SEQUENCE: 231
tcagaaagga tcttctgctc 20

<210> SEQ ID NO 232
<211> LENGTH: 20
<212> TYPE: DNA
<213> ORGANISM: UNKNOWN
<220> FEATURE:
<223> OTHER INFORMATION: Primer 1323

<400> SEQUENCE: 232
atcgatatcg tgaaatacgc 20

<210> SEQ ID NO 233
<211> LENGTH: 20
<212> TYPE: DNA
<213> ORGANISM: UNKNOWN
<220> FEATURE:
<223> OTHER INFORMATION: Primer 1324

<400> SEQUENCE: 233
agctggtctg gtgattctac 20

<210> SEQ ID NO 234
<211> LENGTH: 20
<212> TYPE: DNA
<213> ORGANISM: UNKNOWN
<220> FEATURE:
<223> OTHER INFORMATION: Primer 1341

<400> SEQUENCE: 234
tgctgaaaga gaaattgtcc 20

<210> SEQ ID NO 235
<211> LENGTH: 20
<212> TYPE: DNA
<213> ORGANISM: UNKNOWN
<220> FEATURE:
<223> OTHER INFORMATION: Primer 1342

<400> SEQUENCE: 235
tttcttgttc gaagtccaag 20

<210> SEQ ID NO 236
<211> LENGTH: 37
<212> TYPE: DNA
<213> ORGANISM: UNKNOWN
<220> FEATURE:
<223> OTHER INFORMATION: Primer 1364

<400> SEQUENCE: 236
ttttgcggcc gcttagatgc cggagtccca gtgcttg 37

<210> SEQ ID NO 237
<211> LENGTH: 22
<212> TYPE: DNA
<213> ORGANISM: UNKNOWN
<220> FEATURE:
<223> OTHER INFORMATION: Primer 1365

<400> SEQUENCE: 237
agttgttgac gcaggttcag ag 22

<210> SEQ ID NO 238
<211> LENGTH: 20
<212> TYPE: DNA
<213> ORGANISM: UNKNOWN
<220> FEATURE:
<223> OTHER INFORMATION: Primer 238

<400> SEQUENCE: 238
aaatgacgac gagcctgaag 20

<210> SEQ ID NO 239
<211> LENGTH: 20
<212> TYPE: DNA
<213> ORGANISM: UNKNOWN
<220> FEATURE:
<223> OTHER INFORMATION: Primer 1437

<400> SEQUENCE: 239
gacctgacca tttgatggag 20

<210> SEQ ID NO 240
<211> LENGTH: 21
<212> TYPE: DNA
<213> ORGANISM: UNKNOWN
<220> FEATURE:
<223> OTHER INFORMATION: Primer 1439

<400> SEQUENCE: 240
caattggcga agcagaacaa g 21

<210> SEQ ID NO 241
<211> LENGTH: 47
<212> TYPE: DNA
<213> ORGANISM: UNKNOWN
<220> FEATURE:
<223> OTHER INFORMATION: Primer 1469

<400> SEQUENCE: 241
ttttagatct aggagatacc ggtatgtcgt ttactttgac caacaag 47

<210> SEQ ID NO 242
<211> LENGTH: 21
<212> TYPE: DNA
<213> ORGANISM: UNKNOWN
<220> FEATURE:
<223> OTHER INFORMATION: Primer 1440

<400> SEQUENCE: 242
atcgtacatc ttccaagcat c 21

<210> SEQ ID NO 243
<211> LENGTH: 20
<212> TYPE: DNA
<213> ORGANISM: UNKNOWN
<220> FEATURE:
<223> OTHER INFORMATION: Primer 1441

<400> SEQUENCE: 243
aatcggaacc ctaaagggag 20

<210> SEQ ID NO 244
<211> LENGTH: 20
<212> TYPE: DNA
<213> ORGANISM: UNKNOWN
<220> FEATURE:
<223> OTHER INFORMATION: Primer 1442

<400> SEQUENCE: 244
aatgggcaag ctgtttgctg 20

<210> SEQ ID NO 245
<211> LENGTH: 20
<212> TYPE: DNA
<213> ORGANISM: UNKNOWN
<220> FEATURE:
<223> OTHER INFORMATION: Primer 1443

<400> SEQUENCE: 245
tgcagatgca gatgtgagac 20

<210> SEQ ID NO 246
<211> LENGTH: 51
<212> TYPE: DNA
<213> ORGANISM: UNKNOWN
<220> FEATURE:
<223> OTHER INFORMATION: Primer 1470

<400> SEQUENCE: 246
ttttggatcc aggaaataga tctatgatgg ctaacagaat gattctgaac g 51

<210> SEQ ID NO 247
<211> LENGTH: 36
<212> TYPE: DNA
<213> ORGANISM: UNKNOWN
<220> FEATURE:
<223> OTHER INFORMATION: Primer 1471

<400> SEQUENCE: 247
ttttgcggcc gcttaccagg cggtatggta aagctc 36

<210> SEQ ID NO 248
<211> LENGTH: 64
<212> TYPE: DNA
<213> ORGANISM: UNKNOWN
<220> FEATURE:
<223> OTHER INFORMATION: Primer 1479

<400> SEQUENCE: 248
ccgataggct tccgccatcg tcgggtagtt aaaggtggtg ttgagtgtag gctggagctg 60
cttc 64

<210> SEQ ID NO 249

<211> LENGTH: 70
<212> TYPE: DNA
<213> ORGANISM: UNKNOWN
<220> FEATURE:
<223> OTHER INFORMATION: Primer 1485

<400> SEQUENCE: 249
gcctttattg tacgcttttt actgtacgat ttcagtcaaa tctaacacga ggccctttcg 60
tcttcacctc 70

<210> SEQ ID NO 250
<211> LENGTH: 65
<212> TYPE: DNA
<213> ORGANISM: UNKNOWN
<220> FEATURE:
<223> OTHER INFORMATION: Primer 1486

<400> SEQUENCE: 250
aagtacgcag taaataaaaa atccacttaa gaaggtaggt gttacattcc ggggatccgt 60
cgacc 65

<210> SEQ ID NO 251
<211> LENGTH: 39
<212> TYPE: DNA
<213> ORGANISM: UNKNOWN
<220> FEATURE:
<223> OTHER INFORMATION: Primer 1526

<400> SEQUENCE: 251
tcgacgagga gacaacattg tgtaggctgg agctgcttc 39

<210> SEQ ID NO 252
<211> LENGTH: 39
<212> TYPE: DNA
<213> ORGANISM: UNKNOWN
<220> FEATURE:
<223> OTHER INFORMATION: Primer 1527

<400> SEQUENCE: 252
gaagcagctc cagcctacac aatgttgtct cctcgtcga 39

<210> SEQ ID NO 253
<211> LENGTH: 65
<212> TYPE: DNA
<213> ORGANISM: UNKNOWN
<220> FEATURE:
<223> OTHER INFORMATION: Primer 1539

<400> SEQUENCE: 253
ccattctgtt gcttttatgt ataagaacag gtaagcccta ccatggagaa ttgtgagcgg 60
ataac 65

<210> SEQ ID NO 254
<211> LENGTH: 42
<212> TYPE: DNA
<213> ORGANISM: UNKNOWN
<220> FEATURE:
<223> OTHER INFORMATION: Primer 1561

<400> SEQUENCE: 254
gcaatcctga aagctctgta acattccggg gatccgtcga cc 42

<210> SEQ ID NO 255
<211> LENGTH: 42
<212> TYPE: DNA

<213> ORGANISM: UNKNOWN
<220> FEATURE:
<223> OTHER INFORMATION: Primer 1562

<400> SEQUENCE: 255
ggtcgacgga tccccggaat gttacagagc tttcaggatt gc 42

<210> SEQ ID NO 256
<211> LENGTH: 70
<212> TYPE: DNA
<213> ORGANISM: UNKNOWN
<220> FEATURE:
<223> OTHER INFORMATION: Primer 1563

<400> SEQUENCE: 256
caaatcggcg gtaacgaaag aggataaacc gtgtcccgta ttattcacga ggccctttcg 60
tcttcacctc 70

<210> SEQ ID NO 257
<211> LENGTH: 22
<212> TYPE: DNA
<213> ORGANISM: UNKNOWN
<220> FEATURE:
<223> OTHER INFORMATION: Primer 1566

<400> SEQUENCE: 257
tcccacccaa tcaaggccaa cg 22

<210> SEQ ID NO 258
<211> LENGTH: 22
<212> TYPE: DNA
<213> ORGANISM: UNKNOWN
<220> FEATURE:
<223> OTHER INFORMATION: Primer 1567

<400> SEQUENCE: 258
tccacctggt gccaatgaac cg 22

<210> SEQ ID NO 259
<211> LENGTH: 24
<212> TYPE: DNA
<213> ORGANISM: UNKNOWN
<220> FEATURE:
<223> OTHER INFORMATION: Primer 1587

<400> SEQUENCE: 259
cggctgccag aactctacta actg 24

<210> SEQ ID NO 260
<211> LENGTH: 23
<212> TYPE: DNA
<213> ORGANISM: UNKNOWN
<220> FEATURE:
<223> OTHER INFORMATION: Primer 1588

<400> SEQUENCE: 260
gcgacgtcta ctggcaggtt aat 23

<210> SEQ ID NO 261
<211> LENGTH: 21
<212> TYPE: DNA
<213> ORGANISM: UNKNOWN
<220> FEATURE:
<223> OTHER INFORMATION: Primer 1595

<400> SEQUENCE: 261
caacctggtg atttggggaa g 21

<210> SEQ ID NO 262
<211> LENGTH: 20
<212> TYPE: DNA
<213> ORGANISM: UNKNOWN
<220> FEATURE:
<223> OTHER INFORMATION: Primer 1597

<400> SEQUENCE: 262
gaatgatggc agattgggca 20

<210> SEQ ID NO 263
<211> LENGTH: 22
<212> TYPE: DNA
<213> ORGANISM: UNKNOWN
<220> FEATURE:
<223> OTHER INFORMATION: Primer 1598

<400> SEQUENCE: 263
tattgtgggg ctgtctcgaa tg 22

<210> SEQ ID NO 264
<211> LENGTH: 19
<212> TYPE: DNA
<213> ORGANISM: UNKNOWN
<220> FEATURE:
<223> OTHER INFORMATION: Primer 1624

<400> SEQUENCE: 264
ccctcatgtt gtctaacgg 19

<210> SEQ ID NO 265
<211> LENGTH: 24
<212> TYPE: DNA
<213> ORGANISM: UNKNOWN
<220> FEATURE:
<223> OTHER INFORMATION: Primer 1633

<400> SEQUENCE: 265
tccgtcactg gattcaatgc catc 24

<210> SEQ ID NO 266
<211> LENGTH: 20
<212> TYPE: DNA
<213> ORGANISM: UNKNOWN
<220> FEATURE:
<223> OTHER INFORMATION: Primer 1634

<400> SEQUENCE: 266
ttcgccaggg agctggtgaa 20

<210> SEQ ID NO 267
<211> LENGTH: 21
<212> TYPE: DNA
<213> ORGANISM: UNKNOWN
<220> FEATURE:
<223> OTHER INFORMATION: Primer 1798

<400> SEQUENCE: 267
gcaaattaaa gccttcgagc g 21

<210> SEQ ID NO 268
<211> LENGTH: 39
<212> TYPE: DNA
<213> ORGANISM: UNKNOWN
<220> FEATURE:

<223> OTHER INFORMATION: Primer 1926

<400> SEQUENCE: 268
tttttgtcga cggatccagt ttatcattat caatactcg 39

<210> SEQ ID NO 269
<211> LENGTH: 45
<212> TYPE: DNA
<213> ORGANISM: UNKNOWN
<220> FEATURE:
<223> OTHER INFORMATION: Primer 1927

<400> SEQUENCE: 269
ttttgcggcc gcagatctct cgagtcgaaa ctaagttctg gtgtt 45

<210> SEQ ID NO 270
<211> LENGTH: 22
<212> TYPE: DNA
<213> ORGANISM: UNKNOWN
<220> FEATURE:
<223> OTHER INFORMATION: Primer 2091

<400> SEQUENCE: 270
cttttcttcc cttgtctcaa tc 22

<210> SEQ ID NO 271
<211> LENGTH: 39
<212> TYPE: DNA
<213> ORGANISM: UNKNOWN
<220> FEATURE:
<223> OTHER INFORMATION: Primer 2352

<400> SEQUENCE: 271
gactcgacct aggttattta gtaaaatcaa tgaccattc 39

<210> SEQ ID NO 272
<211> LENGTH: 38
<212> TYPE: DNA
<213> ORGANISM: UNKNOWN
<220> FEATURE:
<223> OTHER INFORMATION: Primer 2353

<400> SEQUENCE: 272
ctaaataacc taggtcgagt catgtaatta gttatgtc 38

<210> SEQ ID NO 273
<211> LENGTH: 30
<212> TYPE: DNA
<213> ORGANISM: UNKNOWN
<220> FEATURE:
<223> OTHER INFORMATION: Primer KARIpETfor

<400> SEQUENCE: 273
attcatatgg cgaattattt caacactctg 30

<210> SEQ ID NO 274
<211> LENGTH: 28
<212> TYPE: DNA
<213> ORGANISM: UNKNOWN
<220> FEATURE:
<223> OTHER INFORMATION: Primer KARIpETrev

<400> SEQUENCE: 274
taatctcgag gccagccacc gcgatgcg 28

<210> SEQ ID NO 275

<211> LENGTH: 16
<212> TYPE: DNA
<213> ORGANISM: UNKNOWN
<220> FEATURE:
<223> OTHER INFORMATION: Primer pETup

<400> SEQUENCE: 275
atgcgtccgg cgtaga 16

<210> SEQ ID NO 276
<211> LENGTH: 35
<212> TYPE: DNA
<213> ORGANISM: UNKNOWN
<220> FEATURE:
<223> OTHER INFORMATION: Primer seq_ilvC_pGV

<400> SEQUENCE: 276
gcggccgcgt cgacgaggag acaacattat ggcga 35

<210> SEQ ID NO 277
<211> LENGTH: 51
<212> TYPE: DNA
<213> ORGANISM: UNKNOWN
<220> FEATURE:
<223> OTHER INFORMATION: Primer pGV1994ep_for

<400> SEQUENCE: 277
cggtcttcaa tttctcaagt ttcagtttca tttttcttgt tctattacaa c 51

<210> SEQ ID NO 278
<211> LENGTH: 35
<212> TYPE: DNA
<213> ORGANISM: UNKNOWN
<220> FEATURE:
<223> OTHER INFORMATION: Primer pGV1994ep_rev

<400> SEQUENCE: 278
ctaactcctt ccttttcggt tagagcggat gtggg 35

<210> SEQ ID NO 279
<211> LENGTH: 47
<212> TYPE: DNA
<213> ORGANISM: UNKNOWN
<220> FEATURE:
<223> OTHER INFORMATION: Primer Not_in_for

<400> SEQUENCE: 279
cctctagaaa taatttgcgg ccgcgttaag aaggagatat acatatg 47

<210> SEQ ID NO 280
<211> LENGTH: 41
<212> TYPE: DNA
<213> ORGANISM: UNKNOWN
<220> FEATURE:
<223> OTHER INFORMATION: Primer AvrII_in_rev

<400> SEQUENCE: 280
ccgaacgccc taggtcagtg gtggtggtgg tggtgctcga g 41

<210> SEQ ID NO 281
<211> LENGTH: 28
<212> TYPE: DNA
<213> ORGANISM: UNKNOWN
<220> FEATURE:
<223> OTHER INFORMATION: Primer R68DK69Lfor

<400> SEQUENCE: 281

-continued tagctatgcg ctggacctgg aggctatc 28

<210> SEQ ID NO 282
<211> LENGTH: 28
<212> TYPE: DNA
<213> ORGANISM: UNKNOWN
<220> FEATURE:
<223> OTHER INFORMATION: Primer R68DK69Lrev

<400> SEQUENCE: 282
gatagcctcc aggtccagcg catagcta 28

<210> SEQ ID NO 283
<211> LENGTH: 28
<212> TYPE: DNA
<213> ORGANISM: UNKNOWN
<220> FEATURE:
<223> OTHER INFORMATION: Primer K75VR76Dfor

<400> SEQUENCE: 283
aggctatcgc ggaagttgac gctagctg 28

<210> SEQ ID NO 284
<211> LENGTH: 28
<212> TYPE: DNA
<213> ORGANISM: UNKNOWN
<220> FEATURE:
<223> OTHER INFORMATION: Primer K75VR76Drev

<400> SEQUENCE: 284
cagctagcgt caacttccgc gatagcct 28

<210> SEQ ID NO 285
<211> LENGTH: 28
<212> TYPE: DNA
<213> ORGANISM: UNKNOWN
<220> FEATURE:
<223> OTHER INFORMATION: Primer R69NNKfor
<220> FEATURE:
<221> NAME/KEY: misc_feature
<222> LOCATION: (17)..(18)
<223> OTHER INFORMATION: n is a, c, g, or t

<400> SEQUENCE: 285
tagctatgcg ctgcgcnnkg aggctatc 28

<210> SEQ ID NO 286
<211> LENGTH: 28
<212> TYPE: DNA
<213> ORGANISM: UNKNOWN
<220> FEATURE:
<223> OTHER INFORMATION: Primer R69NNKrev
<220> FEATURE:
<221> NAME/KEY: misc_feature
<222> LOCATION: (11)..(12)
<223> OTHER INFORMATION: n is a, c, g, or t

<400> SEQUENCE: 286
gatagcctcm nngcgcagcg catagcta 28

<210> SEQ ID NO 287
<211> LENGTH: 28
<212> TYPE: DNA
<213> ORGANISM: UNKNOWN
<220> FEATURE:
<223> OTHER INFORMATION: Primer K75NNKfor
<220> FEATURE:
<221> NAME/KEY: misc_feature
<222> LOCATION: (15)..(16)

<223> OTHER INFORMATION: n is a, c, g, or t

<400> SEQUENCE: 287
aggctatcgc ggaannkcgt gctagctg 28

<210> SEQ ID NO 288
<211> LENGTH: 28
<212> TYPE: DNA
<213> ORGANISM: UNKNOWN
<220> FEATURE:
<223> OTHER INFORMATION: Primer K75NNKrev
<220> FEATURE:
<221> NAME/KEY: misc_feature
<222> LOCATION: (13)..(14)
<223> OTHER INFORMATION: n is a, c, g, or t

<400> SEQUENCE: 288
cagctagcac gmnnttccgc gatagcct 28

<210> SEQ ID NO 289
<211> LENGTH: 30
<212> TYPE: DNA
<213> ORGANISM: UNKNOWN
<220> FEATURE:
<223> OTHER INFORMATION: Primer R76NNKfor
<220> FEATURE:
<221> NAME/KEY: misc_feature
<222> LOCATION: (18)..(19)
<223> OTHER INFORMATION: n is a, c, g, or t

<400> SEQUENCE: 289
aggctatcgc ggaaaaannk gctagctggc 30

<210> SEQ ID NO 290
<211> LENGTH: 30
<212> TYPE: DNA
<213> ORGANISM: UNKNOWN
<220> FEATURE:
<223> OTHER INFORMATION: Primer R76NNKrev
<220> FEATURE:
<221> NAME/KEY: misc_feature
<222> LOCATION: (12)..(13)
<223> OTHER INFORMATION: n is a, c, g, or t

<400> SEQUENCE: 290
gccagctagc mnntttttcc gcgatagcct 30

<210> SEQ ID NO 291
<211> LENGTH: 28
<212> TYPE: DNA
<213> ORGANISM: UNKNOWN
<220> FEATURE:
<223> OTHER INFORMATION: Primer R68NNK_for
<220> FEATURE:
<221> NAME/KEY: misc_feature
<222> LOCATION: (14)..(15)
<223> OTHER INFORMATION: n is a, c, g, or t

<400> SEQUENCE: 291
tagctatgcg ctgnnkaagg aggctatc 28

<210> SEQ ID NO 292
<211> LENGTH: 28
<212> TYPE: DNA
<213> ORGANISM: UNKNOWN
<220> FEATURE:
<223> OTHER INFORMATION: Primer R68NNK_rev
<220> FEATURE:
<221> NAME/KEY: misc_feature
<222> LOCATION: (14)..(15)

<223> OTHER INFORMATION: n is a, c, g, or t

<400> SEQUENCE: 292
gatagcctcc ttmnncagcg catagcta 28

<210> SEQ ID NO 293
<211> LENGTH: 33
<212> TYPE: DNA
<213> ORGANISM: UNKNOWN
<220> FEATURE:
<223> OTHER INFORMATION: Primer S78NNK_for
<220> FEATURE:
<221> NAME/KEY: misc_feature
<222> LOCATION: (16)..(17)
<223> OTHER INFORMATION: n is a, c, g, or t

<400> SEQUENCE: 293
gcggaaaaac gtgctnnktg gcgcaaggct act 33

<210> SEQ ID NO 294
<211> LENGTH: 33
<212> TYPE: DNA
<213> ORGANISM: UNKNOWN
<220> FEATURE:
<223> OTHER INFORMATION: Primer S78NNK_rev
<220> FEATURE:
<221> NAME/KEY: misc_feature
<222> LOCATION: (17)..(18)
<223> OTHER INFORMATION: n is a, c, g, or t

<400> SEQUENCE: 294
agtagccttg cgccamnnag cacgtttttc cgc 33

<210> SEQ ID NO 295
<211> LENGTH: 31
<212> TYPE: DNA
<213> ORGANISM: UNKNOWN
<220> FEATURE:
<223> OTHER INFORMATION: Primer A71NNK_for
<220> FEATURE:
<221> NAME/KEY: misc_feature
<222> LOCATION: (16)..(17)
<223> OTHER INFORMATION: n is a, c, g, or t

<400> SEQUENCE: 295
gcgctgcgca aggagnnkat cgcggaaaaa c 31

<210> SEQ ID NO 296
<211> LENGTH: 31
<212> TYPE: DNA
<213> ORGANISM: UNKNOWN
<220> FEATURE:
<223> OTHER INFORMATION: Primer A71NNK_rev
<220> FEATURE:
<221> NAME/KEY: misc_feature
<222> LOCATION: (15)..(16)
<223> OTHER INFORMATION: n is a, c, g, or t

<400> SEQUENCE: 296
gtttttccgc gatmnnctcc ttgcgcagcg c 31

<210> SEQ ID NO 297
<211> LENGTH: 31
<212> TYPE: DNA
<213> ORGANISM: UNKNOWN
<220> FEATURE:
<223> OTHER INFORMATION: Primer Gln110NNK_for
<220> FEATURE:
<221> NAME/KEY: misc_feature
<222> LOCATION: (16)..(17)

<223> OTHER INFORMATION: n is a, c, g, or t

<400> SEQUENCE: 297
ctgaccccag ataaannkca tagcgacgtt g 31

<210> SEQ ID NO 298
<211> LENGTH: 31
<212> TYPE: DNA
<213> ORGANISM: UNKNOWN
<220> FEATURE:
<223> OTHER INFORMATION: Gln110NNK_rev
<220> FEATURE:
<221> NAME/KEY: misc_feature
<222> LOCATION: (15)..(16)
<223> OTHER INFORMATION: n is a, c, g, or t

<400> SEQUENCE: 298
caacgtcgct atgmnnttta tctggggtca g 31

<210> SEQ ID NO 299
<211> LENGTH: 35
<212> TYPE: DNA
<213> ORGANISM: UNKNOWN
<220> FEATURE:
<223> OTHER INFORMATION: Primer seq_ilvC_pGV

<400> SEQUENCE: 299
gcggccgcgt cgacgaggag acaacattat ggcga 35

<210> SEQ ID NO 300
<211> LENGTH: 31
<212> TYPE: DNA
<213> ORGANISM: UNKNOWN
<220> FEATURE:
<223> OTHER INFORMATION: Primer Q110Qfor

<400> SEQUENCE: 300
gaccccagat aaacaacata gcgacgttgt t 31

<210> SEQ ID NO 301
<211> LENGTH: 31
<212> TYPE: DNA
<213> ORGANISM: UNKNOWN
<220> FEATURE:
<223> OTHER INFORMATION: Primer Q110Qrev

<400> SEQUENCE: 301
aacaacgtcg ctatgttgtt tatctggggt c 31

<210> SEQ ID NO 302
<211> LENGTH: 31
<212> TYPE: DNA
<213> ORGANISM: UNKNOWN
<220> FEATURE:
<223> OTHER INFORMATION: Primer Q110Afor

<400> SEQUENCE: 302
gaccccagat aaagcacata gcgacgttgt t 31

<210> SEQ ID NO 303
<211> LENGTH: 31
<212> TYPE: DNA
<213> ORGANISM: UNKNOWN
<220> FEATURE:
<223> OTHER INFORMATION: Primer Q110Arev

<400> SEQUENCE: 303
aacaacgtcg ctatgtgctt tatctggggt c 31

<210> SEQ ID NO 304
<211> LENGTH: 31
<212> TYPE: DNA
<213> ORGANISM: UNKNOWN
<220> FEATURE:
<223> OTHER INFORMATION: Primer Q110Vfor

<400> SEQUENCE: 304
gaccccagat aaagtacata gcgacgttgt t 31

<210> SEQ ID NO 305
<211> LENGTH: 31
<212> TYPE: DNA
<213> ORGANISM: UNKNOWN
<220> FEATURE:
<223> OTHER INFORMATION: Primer Q110Vrev

<400> SEQUENCE: 305
aacaacgtcg ctatgtactt tatctggggt c 31

<210> SEQ ID NO 306
<211> LENGTH: 30
<212> TYPE: DNA
<213> ORGANISM: UNKNOWN
<220> FEATURE:
<223> OTHER INFORMATION: Primer R68A71recombfor

<400> SEQUENCE: 306
gctatgcgct gckaaaggag dcaatcgcgg 30

<210> SEQ ID NO 307
<211> LENGTH: 30
<212> TYPE: DNA
<213> ORGANISM: UNKNOWN
<220> FEATURE:
<223> OTHER INFORMATION: Primer R68A71recombrev

<400> SEQUENCE: 307
ccgcgattgh ctcctttmgc agcgcatagc 30

<210> SEQ ID NO 308
<211> LENGTH: 30
<212> TYPE: DNA
<213> ORGANISM: UNKNOWN
<220> FEATURE:
<223> OTHER INFORMATION: Primer R76S78recombfor

<400> SEQUENCE: 308
gaaaaacgtg ctagctggcg caaggctact 30

<210> SEQ ID NO 309
<211> LENGTH: 30
<212> TYPE: DNA
<213> ORGANISM: UNKNOWN
<220> FEATURE:
<223> OTHER INFORMATION: Primer R76S78recombrev

<400> SEQUENCE: 309
agtagccttg cgccagctag cacgtttttc 30

<210> SEQ ID NO 310
<211> LENGTH: 30
<212> TYPE: DNA
<213> ORGANISM: UNKNOWN
<220> FEATURE:

<223> OTHER INFORMATION: Primer G76S78recombfor

<400> SEQUENCE: 310
gaaaaaggtg ctagctggcg caaggctact 30

<210> SEQ ID NO 311
<211> LENGTH: 30
<212> TYPE: DNA
<213> ORGANISM: UNKNOWN
<220> FEATURE:
<223> OTHER INFORMATION: Primer G76S78recombrev

<400> SEQUENCE: 311
agtagccttg cgccagctag cacctttttc 30

<210> SEQ ID NO 312
<211> LENGTH: 30
<212> TYPE: DNA
<213> ORGANISM: UNKNOWN
<220> FEATURE:
<223> OTHER INFORMATION: Primer S76S78recombfor

<400> SEQUENCE: 312
gaaaaaagtg ctagctggcg caaggctact 30

<210> SEQ ID NO 313
<211> LENGTH: 30
<212> TYPE: DNA
<213> ORGANISM: UNKNOWN
<220> FEATURE:
<223> OTHER INFORMATION: Primer S76S78recombrev

<400> SEQUENCE: 313
agtagccttg cgccagctag cacttttttc 30

<210> SEQ ID NO 314
<211> LENGTH: 30
<212> TYPE: DNA
<213> ORGANISM: UNKNOWN
<220> FEATURE:
<223> OTHER INFORMATION: Primer T76S78recombfor

<400> SEQUENCE: 314
gaaaaaactg ctagctggcg caaggctact 30

<210> SEQ ID NO 315
<211> LENGTH: 30
<212> TYPE: DNA
<213> ORGANISM: UNKNOWN
<220> FEATURE:
<223> OTHER INFORMATION: Primer T76S78recombrev

<400> SEQUENCE: 315
agtagccttg cgccagctag cagttttttc 30

<210> SEQ ID NO 316
<211> LENGTH: 30
<212> TYPE: DNA
<213> ORGANISM: UNKNOWN
<220> FEATURE:
<223> OTHER INFORMATION: Primer D76S78recombfor

<400> SEQUENCE: 316
gaaaaagatg ctagctggcg caaggctact 30

<210> SEQ ID NO 317

<211> LENGTH: 30
<212> TYPE: DNA
<213> ORGANISM: UNKNOWN
<220> FEATURE:
<223> OTHER INFORMATION: Primer D76S78recombrev

<400> SEQUENCE: 317
agtagccttg cgccagctag catctttttc 30

<210> SEQ ID NO 318
<211> LENGTH: 30
<212> TYPE: DNA
<213> ORGANISM: UNKNOWN
<220> FEATURE:
<223> OTHER INFORMATION: Unknown R76D78recombfor

<400> SEQUENCE: 318
gaaaaacgtg ctgactggcg caaggctact 30

<210> SEQ ID NO 319
<211> LENGTH: 30
<212> TYPE: DNA
<213> ORGANISM: UNKNOWN
<220> FEATURE:
<223> OTHER INFORMATION: Primer R76D78recombrev

<400> SEQUENCE: 319
agtagccttg cgccagtcag cacgtttttc 30

<210> SEQ ID NO 320
<211> LENGTH: 30
<212> TYPE: DNA
<213> ORGANISM: UNKNOWN
<220> FEATURE:
<223> OTHER INFORMATION: Primer G76D78recombfor

<400> SEQUENCE: 320
gaaaaaggtg ctgactggcg caaggctact 30

<210> SEQ ID NO 321
<211> LENGTH: 30
<212> TYPE: DNA
<213> ORGANISM: UNKNOWN
<220> FEATURE:
<223> OTHER INFORMATION: Primer G76D78recombrev

<400> SEQUENCE: 321
agtagccttg cgccagtcag cacctttttc 30

<210> SEQ ID NO 322
<211> LENGTH: 30
<212> TYPE: DNA
<213> ORGANISM: UNKNOWN
<220> FEATURE:
<223> OTHER INFORMATION: Primer S76D78recombfor

<400> SEQUENCE: 322
gaaaaaagtg ctgactggcg caaggctact 30

<210> SEQ ID NO 323
<211> LENGTH: 30
<212> TYPE: DNA
<213> ORGANISM: UNKNOWN
<220> FEATURE:
<223> OTHER INFORMATION: Primer S76D78recombrev

<400> SEQUENCE: 323
agtagccttg cgccagtcag cacttttttc 30

<210> SEQ ID NO 324
<211> LENGTH: 30
<212> TYPE: DNA
<213> ORGANISM: UNKNOWN
<220> FEATURE:
<223> OTHER INFORMATION: Primer T76D78recombfor

<400> SEQUENCE: 324
gaaaaaactg ctgactggcg caaggctact 30

<210> SEQ ID NO 325
<211> LENGTH: 30
<212> TYPE: DNA
<213> ORGANISM: UNKNOWN
<220> FEATURE:
<223> OTHER INFORMATION: Primer T76D78recombrev

<400> SEQUENCE: 325
agtagccttg cgccagtcag cagttttttc 30

<210> SEQ ID NO 326
<211> LENGTH: 30
<212> TYPE: DNA
<213> ORGANISM: UNKNOWN
<220> FEATURE:
<223> OTHER INFORMATION: Primer D76D78recombfor

<400> SEQUENCE: 326
gaaaaagatg ctgactggcg caaggctact 30

<210> SEQ ID NO 327
<211> LENGTH: 30
<212> TYPE: DNA
<213> ORGANISM: UNKNOWN
<220> FEATURE:
<223> OTHER INFORMATION: Primer D76D78recombrev

<400> SEQUENCE: 327
agtagccttg cgccagtcag catctttttc 30

<210> SEQ ID NO 328
<211> LENGTH: 56
<212> TYPE: DNA
<213> ORGANISM: UNKNOWN
<220> FEATURE:
<223> OTHER INFORMATION: Primer 1994hisrev

<400> SEQUENCE: 328
tgactcgagc ggccgcggat ccttagtggt ggtggtggtg gtgtcctgcc actgca 56

<210> SEQ ID NO 329
<211> LENGTH: 51
<212> TYPE: DNA
<213> ORGANISM: UNKNOWN
<220> FEATURE:
<223> OTHER INFORMATION: Primer pGV1994ep_for

<400> SEQUENCE: 329
cggtcttcaa tttctcaagt ttcagtttca tttttcttgt tctattacaa c 51

<210> SEQ ID NO 330
<211> LENGTH: 35
<212> TYPE: DNA
<213> ORGANISM: UNKNOWN
<220> FEATURE:

-continued

<223> OTHER INFORMATION: Primer pGV1994ep_rev

<400> SEQUENCE: 330
ctaactcctt ccttttcggt tagagcggat gtggg 35